United States Patent
Voytas et al.

(10) Patent No.: US 12,077,764 B2
(45) Date of Patent: *Sep. 3, 2024

(54) DELIVERY OF DEVELOPMENTAL REGULATORS TO PLANTS FOR THE INDUCTION OF MERISTEMATIC TISSUE WITH GENETIC ALTERATIONS

(71) Applicant: Regents of the University of Minnesota, Minneapolis, MN (US)

(72) Inventors: Daniel F. Voytas, Falcon Heights, MN (US); Ryan A. Nasti, Berkeley, CA (US); Michael F. Maher, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/178,290

(22) Filed: Mar. 3, 2023

(65) Prior Publication Data

US 2023/0265447 A1    Aug. 24, 2023

Related U.S. Application Data

(63) Continuation of application No. 17/255,305, filed as application No. PCT/US2019/039297 on Jun. 26, 2019, now Pat. No. 11,608,506.

(60) Provisional application No. 62/690,165, filed on Jun. 26, 2018.

(51) Int. Cl.
*C12N 15/82* (2006.01)
*A01H 4/00* (2006.01)
*C12Q 1/6895* (2018.01)

(52) U.S. Cl.
CPC ......... *C12N 15/8229* (2013.01); *A01H 4/008* (2013.01); *C12N 15/8213* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 7,473,822 B1 | 1/2009 | Paz et al. | |
| 8,586,363 B2 | 11/2013 | Voytas et al. | |
| 11,608,506 B2 * | 3/2023 | Voytas | A01H 4/008 |
| 2011/0145940 A1 | 6/2011 | Voytas et al. | |
| 2014/0157453 A1 | 6/2014 | Gordon-Kamm et al. | |
| 2015/0059010 A1 | 2/2015 | Cigan et al. | |
| 2015/0166980 A1 | 6/2015 | Liu et al. | |
| 2015/0166981 A1 | 6/2015 | Liu et al. | |
| 2015/0167000 A1 | 6/2015 | Voytas et al. | |
| 2016/0237451 A1 | 8/2016 | Voytas et al. | |
| 2017/0121722 A1 | 5/2017 | Anand et al. | |
| 2018/0051267 A1 | 2/2018 | Voytas et al. | |
| 2019/0177740 A1 | 6/2019 | Gou et al. | |
| 2019/0249183 A1 | 8/2019 | Humanes et al. | |
| 2021/0047652 A1 | 2/2021 | Zhang et al. | |
| 2021/0054389 A1 | 2/2021 | Cho et al. | |
| 2021/0269813 A1 | 9/2021 | Voytas et al. | |

FOREIGN PATENT DOCUMENTS

| | | |
|---|---|---|
| WO | WO 2002004649 | 1/2002 |
| WO | WO 2017112006 | 6/2017 |
| WO | WO 2017123772 | 7/2017 |
| WO | WO 2018080389 | 5/2018 |

OTHER PUBLICATIONS

Gallois, J.L. et al, Development (2002) vol. 129, pp. 3207-3217. (Year: 2002).*
Altpeter et al., "Advancing Crop Transformation in the Era of Genome Editing," Plant Cell, Jul. 2016, 28(7):1510-1520.
Altschul et al., "Gapped BLAST and PSI-BLAST: a new generation of protein database search programs," Nucl. Acids Research, Sep. 1997, 25(17):3389-3402.
Bairu et al., "Somaclonal variation in plants: causes and detection methods," Plant Growth Regulation, Mar. 2011, 63(2):147-173.
Banakar et al., "High-frequency random DNA insertions upon co-delivery of CRISPR-Cas9 ribonucleoprotein and selectable marker plasmid in rice," Sci. Reports, 9:19902, Dec. 2019, 13 pages.
Barton, "Twenty years on: The inner workings of the shoot apical meristem, a developmental dynamo," Dev. Biology, May 2010, 341(1):95-113.
Boehm (2014) (Masters Theses, Univ. Tenn.) "Molecular Marker Assisted Backcross Development and Evaluation of an Environmentally Friendly, Commercially Acceptable Low Seed Phytate Soybean".
Butler et al., "Crop improvement using genome editing," Plant Breeding Reviews, Jan. 2018, 41:55-101.
Campbell et al., "Functional analysis and development of a CRISPR/Cas9 allelic series for a CPR5 ortholog necessary for proper growth of soybean trichomes," Sci. Reports, Oct. 2019, 9:14757, 11 pages.
Čermák et al., "A Multipurpose Toolkit to Enable Advanced Genome Engineering in Plants," Plant Cell, Jun. 2017, 29(6):1196-1217.
Christian et al., "Targeting DNA Double-Strand Breaks with TAL Effector Nucleases, " Genetics, Oct. 2010, 186(2):757-761.
Ckurshumova et al., "Irrepressible MONOPTEROS/ARF5 promotes de novo shoot formation," New Phytologist, Nov. 2014, 204(3):556-566.
Cong et al., "Multiplex Genome Engineering Using CRISPR/Cas Systems," Science, Feb. 2013, 339(6121):819-823.
Curtin et al., "CRISPR/Cas9 and TALENs generate heritable mutations for genes involved in small RNA processing of Glycine max and Medicago truncatula," Plant Biotechnol. Journal, Jun. 2018, 16(6):1125-1137.

(Continued)

*Primary Examiner* — Russell Kallis
(74) *Attorney, Agent, or Firm* — Fish & Richardson P.C.

(57) ABSTRACT

Materials and methods for inducing genetic alterations in meristematic plant tissue are provided herein.

19 Claims, 50 Drawing Sheets
Specification includes a Sequence Listing.

(56) References Cited

OTHER PUBLICATIONS

Curtin et al., "Genome Engineering of Crops with Designer Nucleases," Plant Genome, Jul. 2012, 5(2):42-50.
Curtin et al., "MicroRNA Maturation and MicroRNA Target Gene Expression Regulation are Severely Disrupted in Soybean dicer-like1 Double Mutants," G3 (Bethesda), Feb. 2016, 6(2):423-433.
Curtin et al., "Targeted Mutagenesis for Functional Analysis of Gene Duplication in Legumes," Methods Mol. Biology, Aug. 2013, 1069:25-42.
Curtin et al., "Targeted Mutagenesis of Duplicated Genes in Soybean with Zinc-Finger Nucleases," Plant Physiology, Jun. 2011, 156(2):466-473.
Curtin et al., "Validating Genome-Wide Association Candidates Controlling Quantitative Variation in Nodulation," Plant Physiology, Feb. 2017, 173(2):921-931.
Demorest et al., "Direct stacking of sequence-specific nuclease-induced mutations to produce high oleic and low linolenic soybean oil," BMC Plant Biology, Oct. 2016, 16(1):225, 8 pages.
Gallois et al., "Combined Shoot Meristemless and Wuschel trigger ectopic organogenesis in *Arabidopsis*," Development, Jul. 2002, 129(13):3207-3217.
Gasiunas et al., "Cas9-crRNA ribonucleoprotein complex mediates specific DNA cleavage for adaptive immunity in bacteria," Proc. Natl. Acad. Sci. USA, Sep. 2012, 109(39):E2579-E2586.
Gelvin, "Agrobacterium-Mediated Plant Transformation: the Biology behind the 'Gene-Jockeying' Tool, " Microbiol. Mol. Biol. Reviews, Mar. 2003, 67(1):16-37.
Graham et al., "Plant Genome Editing and the Relevance of Off-Target Changes," Plant Physiology, Aug. 2020, 183(4):1453-1471.
Groß-Hardt et al., "Stem cell regulation in the shoot meristem," J. Cell Science, May 2003, 116(9):1659-1666.
Haun et al., "Improved soybean oil quality by targeted mutagenesis of the fatty acid desaturase 2 gene family," Plant Biotechnology Journal, , Sep. 2014, 12(7):934-940.
Heidstra et al., "Plant and animal stem cells: similar yet different," Nat. Rev. Mol. Cell Biology, May 2014, 15(5):301-312.
Jacoby et al., "Expanding Laglidadg endonuclease scaffold diversity by rapidly surveying evolutionary sequence space," Nucl. Acids Research, Feb. 2012, 40(11):4954-4964.
Jinek et al., "A Programmable Dual-RNA-Guided DNA Endonuclease in Adaptive Bacterial Immunity," Science, Aug. 2012, 337(6096):816-821.
Komor et al., "Programmable editing of a target base in genomic DNA without double-stranded DNA cleavage," Nature, May 2016, 533(7603):420-424.
Kumaran et al., "Yabby Polarity Genes Mediate the Repression of Knox Homeobox Genes in *Arabidopsis*," Plant Cell, , Nov. 2002, 14(11):2761-2770.
Kunkel et al., "Inducible isopentenyl transferase as a high efficiency marker for plant transformation," Nat. Biotechnology, Sep. 1999, 17(9):916-919.
Lee et al., "An Overview of Genetic Transformation of Soybean, a Comprehensive Survey of International Soybean Research," Genetics, Physiology, Agronomy and Nitrogen Relationships, Chapter 23, Jan. 2, 2013, 18 pages.
Li et al., "Generation of Targeted Point Mutations in Rice by a Modified CRISPR/Cas9 System," Molecular Plant, Mar. 2017, 10(3):526-529.
Liang et al., "Genome editing of bread wheat using biolistic delivery of CRISPR/Cas9 in vitro transcripts or ribonucleoproteins," Nat. Protocols, Mar. 2018, 13(3):413-430.
Liu et al., "Genome Editing in Soybean with CRISPR/Cas9," Methods Mol. Biology, Jan. 2019, 1917:217-234.
Liu et al., "Phenotypic novelty by CRISPR in plants," Developmental Biology, Mar. 2018, 435(2):170-175.
Lowe et al., "Morphogenic Regulators Baby boom and Wuschel Improve Monocot Transformation," Plant Cell, Sep. 2016, 28(9):1998-2015.

Makarova et al., "Evolution and classification of the CRISPR-Cas systems," Nat. Rev. Microbiology, Jun. 2011, 9(6):467-477.
Mali et al., "CAS9 transcriptional activators for target specificity screening and paired nickases for cooperative genome engineering," Nat. Biotechnology, Aug. 2013, 31:833-838.
Mali et al., "RNA-Guided Human Genome Engineering via Cas9," Science, Feb. 2013, 339(6121):823-826.
Michno et al., "CRISPR/Cas mutagenesis of soybean and Medicago truncatula using a new web-tool and a modified Cas9 enzyme," GM Crops Food, Mar. 2016, 6(4):243-252.
Mishra et al., "Genome editing technologies and their applications in crop improvement," Plant Biotechnology Reports, Jan. 2018, 12:57-68.
Mookkan et al., "Selectable marker independent transformation of recalcitrant maize inbred B73 and sorghum P898012 mediated by morphogenic regulators Baby Boom and Wuschel2," Plant Cell Reports, , Sep. 2017, 36(9):1477-1491.
PCT International Preliminary Report on Patentability in International Appln. No. PCT/US2019/039297, dated Dec. 29, 2020, 7 pages.
PCT International Search Report and Written Opinion in International Appln. No. PCT/US2019/039297, dated Oct. 9, 2019, 10 pages.
Qin et al., "Disruption of phytoene desaturase gene results in albino and dwarf phenotypes in *Arabidopsis* by impairing chlorophyll, carotenoid, and gibberellin biosynthesis," Cell Research, May 2007, 17(5):471-482.
Rodriguez-Leal et al., "Engineering Quantitative Trait Variation for Crop Improvement by Genome Editing," Cell, Oct. 2017, 171(2):470-480.
Sander et al., "Selection-free zinc-finger-nuclease engineering by context-dependent assembly (CoDA)," Nat. Methods, Jan. 2011, 8(1):67-69.
Schmidt et al., "Towards normalization of soybean somatic embryo maturation," Plant Cell Reports, Sep. 2005, 24(7):383-391.
Somers et al., "Recent Advances in Legume Transformation," Plant Physiology, Mar. 2003, 131(3):892-899.
Southern et al., "Luciferases as Reporter Genes," Methods Mol. Biol. *Arabidopsis* Protocols, 323:293-305, 2006.
Stupar et al., "All in the Family: Understanding soybean gene redundancies through genome engineering," Presented at Proceedings of Crops 2015 Conference, Huntsville, AL, May 18-21, 2015, 29 pages.
Stupar et al., "Building a better mutant: Challenges and opportunities for understanding and utilizing gene functions in soybean," Presented at Proceedings of the Université Laval Institute for Integrative and Systems Biology Seminar Series, Quebec City, Canada, Oct. 4-8, 2017, 41 pages.
Stupar et al., "Comparison of genomic structural variation associated with cultivars, mutagenized, and transgenic soybeans," Presented at Proceedings of the Plant and Animal Genome Conference, San Diego, CA, Jan. 10-14, 2015, 22 pages.
Stupar et al., "Identification of Functional Variants in Soybean Using Fast Neutron and CRISPR-Based Mutagenesis," Presented at Proceedings of the Plant and Animal Genome Conference, San Diego, CA, Jan. 13-18, 2017, 27 pages.
Stupar, "All in the Family: Understanding soybean gene redundancies through genome engineering," Presented at Proceedings of the Iowa State University Genome Editing: Foundations and Applications Meeting, Ames, IA, Apr. 9-11, 2015, 39 pages.
Stupar, "Applications of engineered nucleases," Presented at Proceedings of the Soybean Precision Genomics Workshop 2013, Columbia, MO, Jul. 7-10, 2013, 4 pages.
Stupar, "Cloudy with a chance of mutations: Gene editing and functional analyses in soybean," Presented at Proceedings of the 17th Biennial Molecular and Cellular Biology of the Soybean Conference, Athens, GA, Aug. 26-29, 2018, 20 pages.
Stupar, "Cloudy with a chance of mutations: Gene editing and functional analyses in soybean," Presented at Proceedings of the Plant and Animal Genome Conference, San Diego, CA, Jan. 12-16, 2019, 5 pages.

(56) References Cited

OTHER PUBLICATIONS

Stupar, "CRISPR/Cas-9 overview, applications and case studies," Presented at Proceedings of the Soybean Precision Genomics and Mutant Finder Workshops 2016, Columbia, MO, Aug. 3-4, 2016, 28 pages.
Stupar, "Gene Editing for Crop Improvement," Presented at Proceedings of the ASA-CSSA-SSSA 2015 International Annual Meetings Symposium, Minneapolis, MN, Nov. 15-18, 2015, 23 pages.
Stupar, "Inheritance patterns of transgenes and targeted mutations in a soybean CRISPR-based system," Presented at Proceedings of the 16th Biennial Molecular and Cellular Biology of the Soybean Conference, Columbus, OH, Aug. 7-10, 2016, 19 pages.
Stupar, "Old mutations and new biotechnology: expanding and understanding the genetic resources of soybean," Presented at Proceedings of the University of York Genomics Seminar, York, UK, Mar. 22, 2016, 63 pages.
Stupar, "Opportunities and obstacles for candidate gene validation using CRISPR/Cas in soybean," Presented at Proceedings of the ASA-CSSA-SSSA 2016 International Annual Meetings Symposium, Phoenix, AZ, Nov. 6-9, 2016, 21 pages.
Stupar, "Opportunities and Obstacles for CRISPR in Soybean: Lessons Learned from the Inheritance of Transgenes and Targeted Mutations," Presented at Proceedings of the Banbury Center Genomics-enabled Accelerated Crop Breeding Meeting, Long Island, NY, Oct. 16-19, 2016, 31 pages.
Stupar, "Opportunities and Obstacles for CRISPR in Soybean: Lessons Learned from the Inheritance of Transgenes and Targeted Mutations," Presented at Proceedings of the Donald Danforth Plant Sciences Center 18th Annual Fall Symposium, St. Louis, MO, Sep. 28-30, 2016, 30 pages.
Stupar, "Opportunities and Obstacles for CRISPR in Soybean: Lessons Learned from the Inheritance of Transgenes and Targeted Mutations," Presented at Proceedings of the National Association of Plant Breeders Annual Meeting, Raleigh, NC, Aug. 15-18, 2016, 6 pages.
Stupar, "Overcoming the bottleneck: Understanding and expanding soybean genetic diversity," Presented at the Institute of Crop Science, Chinese Academy of Agricultural Sciences, Beijing, China, Feb. 16-25, 2014, 42 pages.
Stupar, "Soybean breeding with genome-editing technology," Presented at Proceedings of the 2019 Soybean Breeders Workshop, St. Louis, MO, Feb. 11-13, 2019, 6 pages.
Stupar, "Soybean precision genomics," Presented at Proceedings of the Soybean Precision Genomics Workshop 2012, St. Paul, MN, Jul. 18-20, 2012, 23 pages.
Stupar, "The CRISPR x Genome interaction: Challenges and opportunities for understanding gene function in soybean," Presented at Proceedings of Biotechnology Havana 2017, Havana, Cuba, Dec. 3-6, 2017, 29 pages.
Stupar, "USDA-BRAG: Genomic variation associated with different soybean germplasm sources," Presented to the U.S. Department of Agriculture—Animal and Plant Health Inspection Service, Washington, DC, Sep. 2016, 23 pages.
UniProt Accession No. Q03JI6, "CRISPR-associated endonuclease Cas9 2," dated May 23, 2018, 3 pages.
UniProt Accession No. Q99ZW2, "CRISPR-associated endonuclease Cas9/Csn1," dated Jun. 20, 2018, 11 pages.
Veena et al., "Agrobacterium rhizogenes: recent developments and promising applications," In Vitro Cell. Dev. Biol.—Plant, Nov. 2007, 43(5):383-403.
Virdi et al., "Similar Seed Composition Phenotypes are Observed From CRISPR-Generated In-Frame and Knockout Alleles of a Soybean KASI Ortholog," Front. Plant Science, Jul. 2020, 11:1005, 11 pages.
Voytas, "Genome Editing and Plant Agriculture: Expression of Developmental Regulators for Accelerated Plant Gene Editing," Presentation at the Federation of American Societies for Experimental Biology Science Research Conference—Genome Engineering: Cutting Edge Research and Applications, Florence, Italy, Jun. 24-28, 2017, 26 pages.
Wu et al., "AGROBEST: an efficient Agrobacterium-mediated transient expression method for versatile gene function analyses in *Arabidopsis* seedlings," Plant Methods, 10:19, Jun. 2014, 16 pages.
Zeng et al., "Refined glufosinate selection in Agrobacterium-mediated transformation of soybean [*Glycine max* (L.) Merrill]," Plant Cell Reports, Feb. 2004, 22(7):478-482.
Aronesty, "Comparison of Sequencing Utility Programs," The Open Bioinformatics Journal, Jan. 2013, 7:1-8.
Bally et al., "The Rise and Rise of Nicotiana benthamiana: A Plant for All Reasons," Annu. Rev. Phytopathol., Aug. 2018, 56:405-426.
Baltes et al., "Conferring resistance to geminiviruses with the CRISPR-Cas prokaryotic immune system," Nat. Plants, Oct. 2015, 1(10):15145.
Baltes et al., "DNA replicons for plant genome engineering," Plant Cell, Jan. 2014, 26(1):151-163.
Bombarely et al., "A draft genome sequence of Nicotiana benthamiana to enhance molecular plant-microbe biology research," Mol. Plant Microbe Interact., Dec. 2012, 25(12):1523-1530.
Brinkman et al., "Easy quantitative assessment of genome editing by sequence trace decomposition," Nucleic Acids Res., Dec. 2014, 42(22):e168.
Clough et al., "Floral dip: a simplified method for Agrobacterium-mediated transformation of *Arabidopsis thaliana*," Plant J., Dec. 1998, 16(6):735-743.
Doyle et al., "Isolation of plant DNA from fresh tissue," Focus, 1990, 12:13-15.
Ebinuma et al., "Selection of marker-free transgenic plants using the isopentenyl transferase gene," Proc. Natl. Acad. Sci. USA, Mar. 1997, 94(6):2117-2121.
Hamada et al., "An in planta biolistic method for stable wheat transformation," Sci. Rep., Sep. 2017, 7(1):11443.
Jansing et al., "CRISPR/Cas9-mediated knockout of six glycosyltransferase genes in Nicotiana benthamiana for the production of recombinant proteins lacking ß-1,2-xylose and core α-1,3-fucose," Plant Biotechnol. J., Feb. 2019, 17(2):350-361.
Lowe et al., "Rapid genotype 'independent' *Zea mays* L. (maize) transformation via direct somatic embryogenesis," In Vitro Cell. Dev. Biol. Plant, Apr. 2018, 54(3):240-252.
Maher et al., "Plant gene editing through de novo induction of meristems," Nat. Biotechnol., Jan. 2020, 38(1):84-89.
Nelson-Vasilchik et al., "Transformation of Recalcitrant Sorghum Varieties Facilitated by Baby Boom and Wuschel2," Curr. Protoc. Plant Biol., Dec. 2018, 3(4):e20076.
Park et al., "Cas-analyzer: an online tool for assessing genome editing results using NGS data," Bioinformatics, Jan. 2017, 33(2):286-288.
Phillips et al., "Genetic instability of plant tissue cultures: breakdown of normal controls," Proc. Natl. Acad. Sci. USA, Jun. 1994, 91(12):5222-5226.
Smigocki et al., "Cytokinin gene fused with a strong promoter enhances shoot organogenesis and zeatin levels in transformed plant cells," Proc. Natl. Acad. Sci. USA, Jul. 1988, 85(14):5131-5135.
Wang et al., "Axillary meristem initiation—a way to branch out," Curr. Opin. Plant Biol., Feb. 2018, 41:61-66.
Zhang et al., "Tissue culture-induced heritable genomic variation in rice, and their phenotypic implications," PLoS One, May 2014, 9(5):e96879.

* cited by examiner

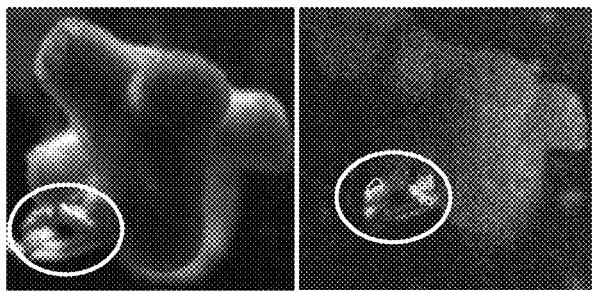
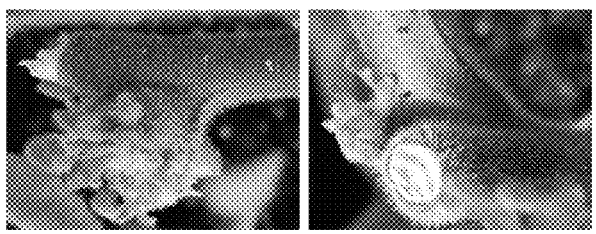
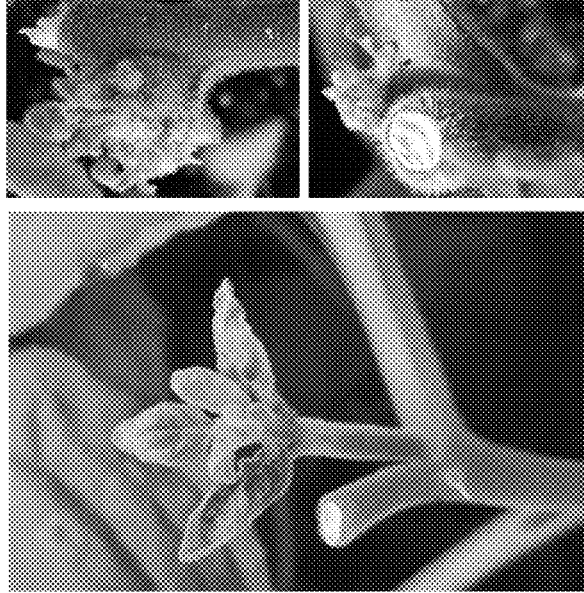

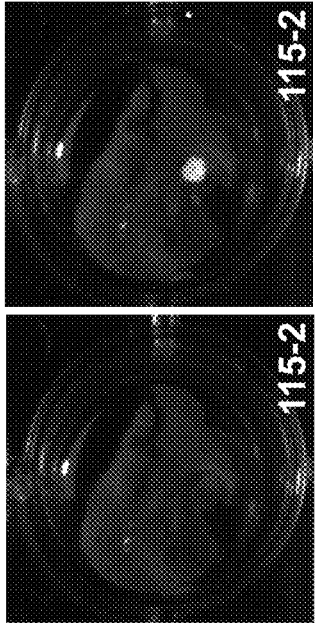
FIG. 3A
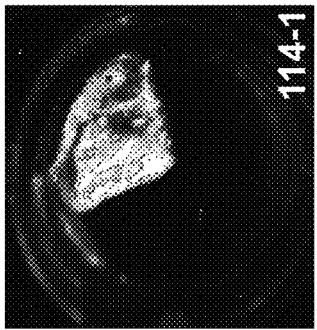
FIG. 3B
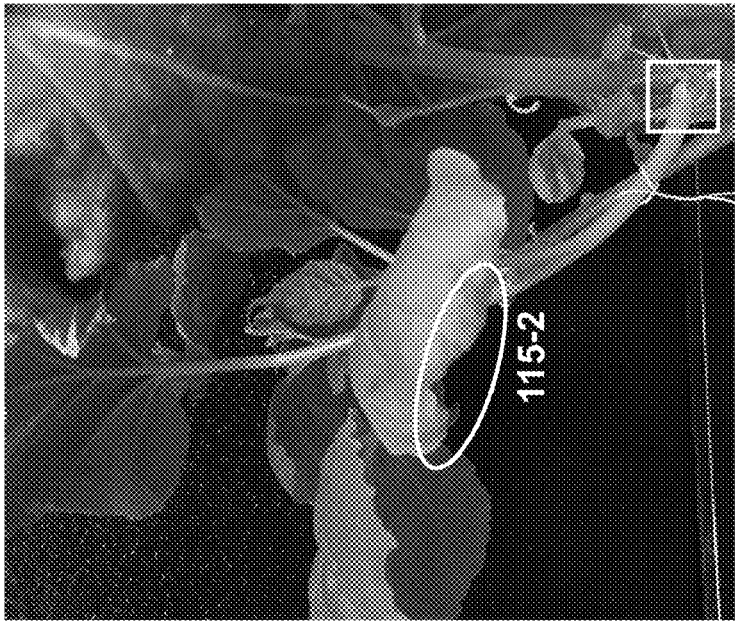
FIG. 3C
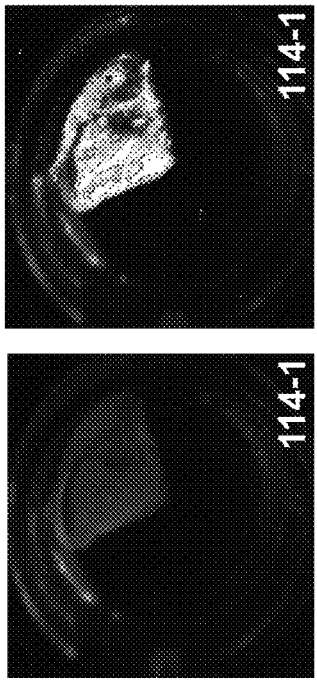
FIG. 3D
FIG. 3E
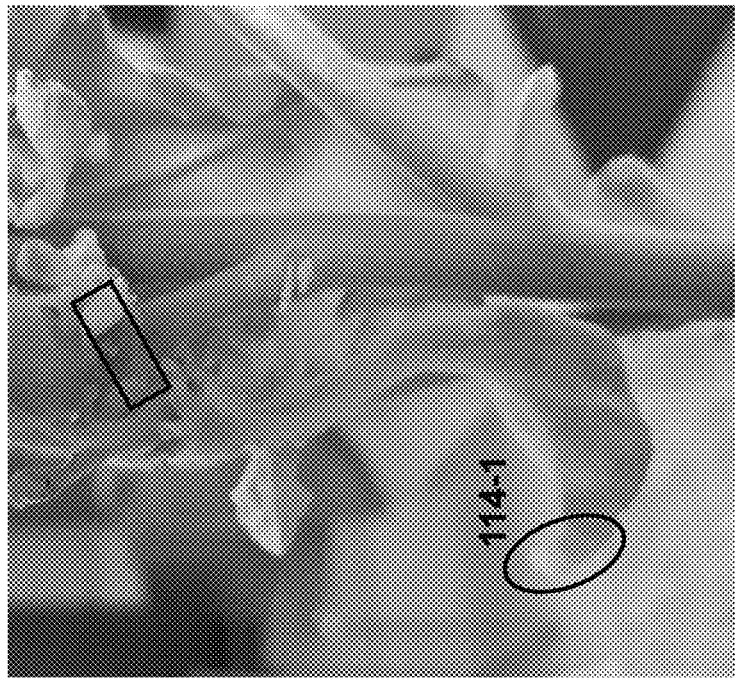
FIG. 3F

FIG. 4F

Split STM & WUS

```
GTTTTGGTAGTAGCGACTCCATGGGGCATAAGTTTTAGAAT  Reference
GTTTTGGTAGTAGCGACT-CATGGGGCATAAGTTTTAGAAT  93.43% (14997 reads)
TTTTTGGTAGTAGCGACTCCATGGGGCATAAGTTTTAGAAT  4.60% (739 reads)
GTTTTGGTAGTAGCGACTCCATGGGGCATAAGTTTTAGAAT  0.21% (34 reads)
```

FIG. 4G

WUS & IPT

```
GTTTTGGTAGTAGCGACTCCATGGGGCATAAGTTTTAGAAT  Reference
TTTTTGGTAGTAGCGACTCCATGGGGCATAAGTTTTAGAAT  96.92% (2488 reads)
GTTTTGGTAGTAGCGACT-CATGGGGCATAAGTTTTAGAAT  1.52% (39 reads)
```

FIG. 5A

| Construct | Plant designator | Sequences analyzed | Insertions | Deletions | Indel frequency | Observed mutations | Seed produced? |
|---|---|---|---|---|---|---|---|
| WUS/STM | 5-13-3-12 | 1628 | 0 | 821 | 821 (50.4%) | -1bp & WT | No |
| WUS/IPT | 7-19-2-11** | 1089 | 0 | 1072 | 1072 (98.4%) | -10bp & -29bp | No |
| WUS/IPT | 7-19-2-12** | 2431 | 0 | 2399 | 2399 (98.7%) | -10bp & -29bp | No |
| WUS/IPT | 7-19-2-13** | 528 | 0 | 493 | 493 (93.4%) | -10bp & -29bp | No |
| All Combo | 5-14-1-08 | 258 | 0 | 104 | 104 (40.3%) | -3bp & WT | Yes |
| All Combo | 1-1-5 | 1057 | 111 | 892 | 1003 (94.9%) | Chimeric: spectrum of +1bp, -3bp, -1bp or larger | No |

** Shoots derived from the same injection site had the same mutation profile, suggesting they were derived from common, edited progenitor cells.

FIG. 5B

```
                                                                                                    (SEQ ID NO:)
WT:      GGAATTTGTTATGTTTTGGTAGTAGCGACTC-CATGGGCATAAGTTTAGAATTCGTACTCCC  (99)
5-13-3-12:  GGAATTTGTTATGTTTTGGTAGTAGCGACT---CATGGGCATAAGTTTAGAATTCGTACTCCC  (100)
            GGAATTTGTTATGTTTTGGTAGTAGCGACTC-CATGGGCATAAGTTTAGAATTCGTACTCCC   (99)

7-19-2-11:  GGAATTTGTTATGTTTTGGTAG-----------ATGGGCATAAGTTTAGAATTCGTACTCCC  (101)
            GGAATTTGTTATGTTTTGGTAGCG-------------------------------ACTCCC   (102)

7-19-2-12:  GGAATTTGTTATGTTTTGGTAG-----------ATGGGCATAAGTTTAGAATTCGTACTCCC  (101)
            GGAATTTGTTATGTTTTGGTAGCG-------------------------------ACTCCC   (102)

7-19-2-13:  GGAATTTGTTATGTTTTGGTAG-----------ATGGGCATAAGTTTAGAATTCGTACTCCC  (101)
            GGAATTTGTTATGTTTTGGTAGCG-------------------------------ACTCCC   (102)

5-14-1-08:  GGAATTTGTTATGTTTTGGTAGTAGCGA----CATGGGCATAAGTTTAGAATTCGTACTCCC  (103)
            GGAATTTGTTATGTTTTGGTAGTAGCGACTC-CATGGGCATAAGTTTAGAATTCGTACTCCC   (99)

1-1-5 #1:   GGAATTTGTTATGTTTTGGTAGTAGCGA-------CATGGGCATAAGTTTAGAATTCGTACTCCC  (104)
1-1-5 #2:   GGAATTTGTTATGTTTTGGTAGTAGCGACT---CATGGGCATAAGTTTAGAATTCGTACTCCC  (100)
1-1-5 #3:   GGAATTTGTTATGTTTTGGTAGTAGCGACTCCCATGGGCATAAGTTTAGAATTCGTACTCCC  (105)
1-1-5 #4:   GGAATTTGTTATGTTTTGGTAGTAGCGACTC-CATGGGCATAAGTTTAGAATTCGTACTCCC   (99)
1-1-5 #5:   GGAATTTGTTATGTTTTGGTAGTAGCGA-------ATGGGCATAAGTTTAGAATTCGTACTCCC  (106)
1-1-5 #6:   GGAATTTGTTATGTTTTGGTAGTAGCGA----CATGGGCATAAGTTTAGAATTCGTACTCCC  (107)
1-1-5 #7:   GGAATTTGTTATGTTTTGGTAGCG-----------------------------ACTCCC  (108)
1-1-5 #8:   GGAATTTGTTATGTTTTGGTAG-------------ATGGGCATAAGTTTAGAATTCGTACTCCC  (109)
1-1-5 #9:   GGAATTTGTTATGTTTTGGTAGT------------ATGGGCATAAGTTTAGAATTCGTACTCCC  (110)
1-1-5 #10:  GGAATTTGTTATGTTTTGGTAGTAG----------ATGGGCATAAGTTTAGAATTCGTACTCCC  (111)
1-1-5 #11:  GGAATTTGTTATGTTTTGGTAGTA------------------GGGCATAAGTTTAGAATTCGTACTCCC  (112)
1-1-5 #12:  -----------------------------------ATGGGCATAAGTTTAGAATTCGTACTCCC  (113)
1-1-5 #13:  -----------------------------------------------------------
```

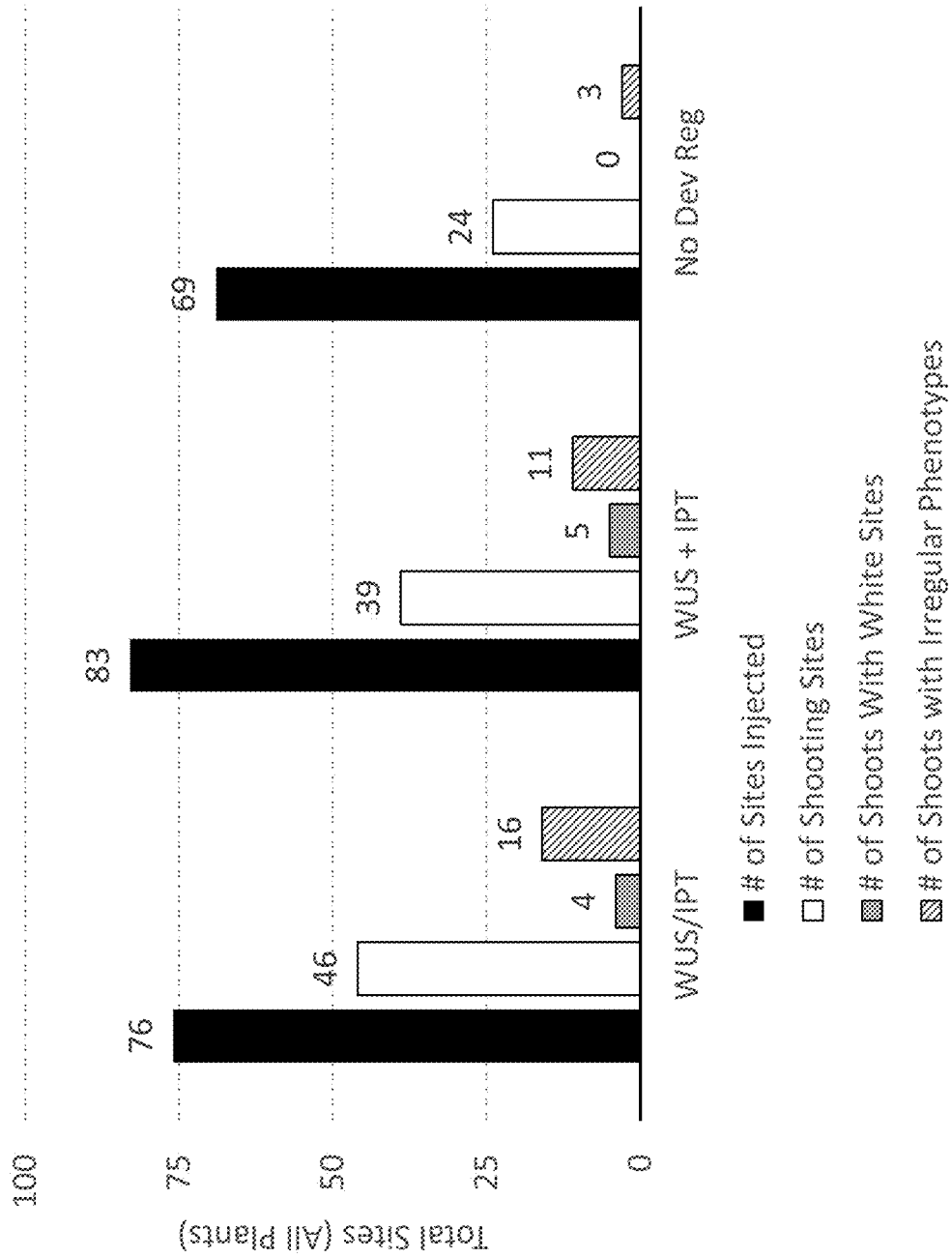

FIG. 8A

| Sample | Phenotype | PDS1* | PDS2* |
|---|---|---|---|
| Parental white tissue | White | +1 (18%) / -1 (34%) / -2 (21%) / -3 (16%) | -48 / +1 / -1 |
| Seedling 1 | White | +1 (42%) / -2 (49%) | -1 (98%) |
| Seedling 2 | White | +1 (43%) / -2 (48%) | -1 (96%) |
| Seedling 3 | White | +1 (39%) / -2 (51%) | +1 (44%) / -1 (46%) |
| Seedling 4 | White | -2 (95%) | +1 (49%) / -1 (37%) |
| Seedling 5 | White | +1 (46%) / -2 (46%) | +1 (99%) |
| Seedling 6 | White | +1 (51%) / -1 (41%) | +1 (42%) / -1 (45%) |
| Seedling 7 | White | No data | +1 (58%) / -1 (35%) |
| Seedling 8 | White | +1 (55%) / -2 (35%) | +1 (36%) / -1 (35%) |
| Seedling 9 | White | +1 (100%) | +1 (49%) / -1 (42%) |
| Seedling 10 | White | +1 (41%) / -2 (48%) | +1 (98%) |

FIG. 10A

| Sample | Phenotype | PDS1* | PDS2* |
|---|---|---|---|
| Parental green tissue | Green | -1bp (100%) | Heterozygous -48/-1 |
| Seedling 1 | Green | -1 (99%) | Heterozygous -48/-1 |
| Seedling 2 | Green | -1 (99%) | Homozygous -48 |
| Seedling 3 | Green | -1 (100%) | Heterozygous -48/-1 |
| Seedling 4 | Green | No data | No data |
| Seedling 5 | Green | -1 (100%) | Heterozygous -48/-1 |
| Seedling 6 | Green | -1 (100%) | Heterozygous -48/-1 |
| Seedling 7 | Green | -1 (100%) | Heterozygous -48 |
| Seedling 8 | Green | -1 (98%) | Heterozygous -1/-48 |
| Seedling 9 | Green | -1 (100%) | Homozygous -48 |
| Seedling 10 | Green | -1 (100%) | Heterozygous -48/-1 |
| Seedling 28 | White | -1 (100%) | Homozygous -1 |
| Seedling 29 | White | -1 (100%) | Homozygous -1 |
| Seedling 30 | White | -1 (100%) | Homozygous -1 |
| Seedling 31 | White | -1 (100%) | Homozygous -1 |
| Seedling 32 | White | -1 (100%) | Homozygous -1 |

FIG. 11

| Seedling Number | Phenotype | PDS1* | PDS2* |
|---|---|---|---|
| Parental tissue | WT | -3bp, WT | WT (100%) |
| S1 | WT | WT (100%) | WT (100%) |
| S3 | WT | WT (100%) | WT (100%) |
| S5 | WT | WT (48%), -3bp (46%) | WT (98%) |
| S7 | WT | WT (48%), -3bp (45%) | WT (99%) |
| S9 | WT | WT (100%) | WT (96%) |
| S11 | WT | WT (46%), -3bp (48%) | WT (99%) |
| S13 | WT | -3bp (99.6%) | WT (99%) |
| S15 | WT | WT (43%), -3bp (55%) | WT (97%) |
| S17 | WT | -3bp (99.4%) | WT (100%) |
| S19 | WT | -3bp (99%) | WT (98%) |

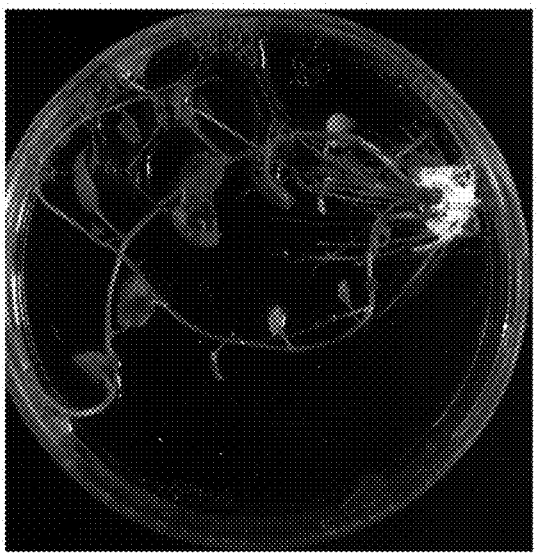
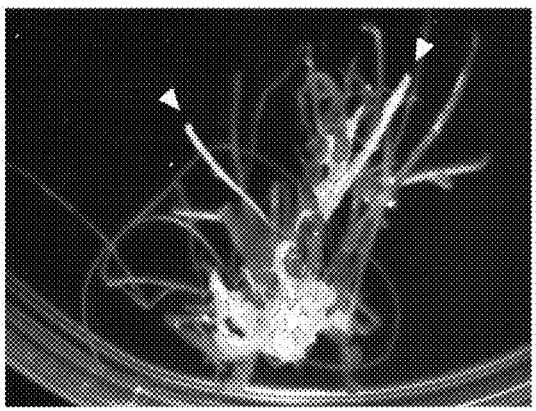
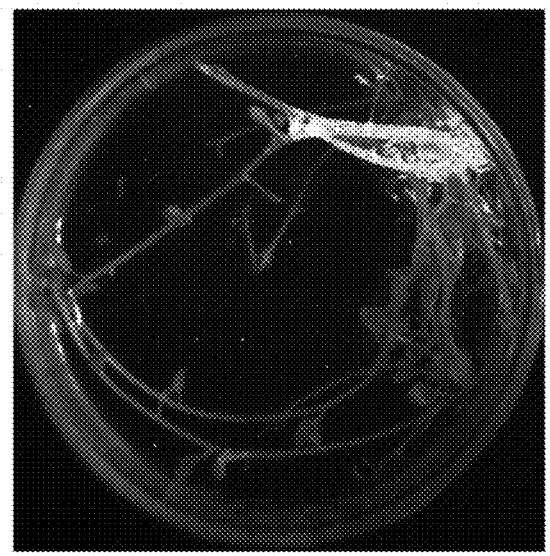
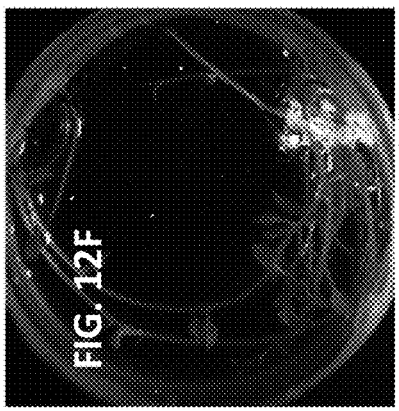

pRN114 (Nos-WUS & CmYLCV-STM, BeYDV Replicon), P1 #2
Initial Luciferase Fluorescence pRN114 (Nos-WUS & CmYLCV-STM, BeYDV Replicon), P1 #2
24 Days Post Imaging pRN119 (Nos-WUS & 35S-STM, BeYDV Replicon), P1 #7
Initial Luciferase Fluorescence pRN119 (Nos-WUS & 35S-STM, BeYDV Replicon), P1 #7
24 Days Post Imaging pRN119-4-5
Original Growth pRN119-4-5
Regenerated Plantlets pRN120-1-3
Original Growth pRN120-1-3
Regenerated Plantlets

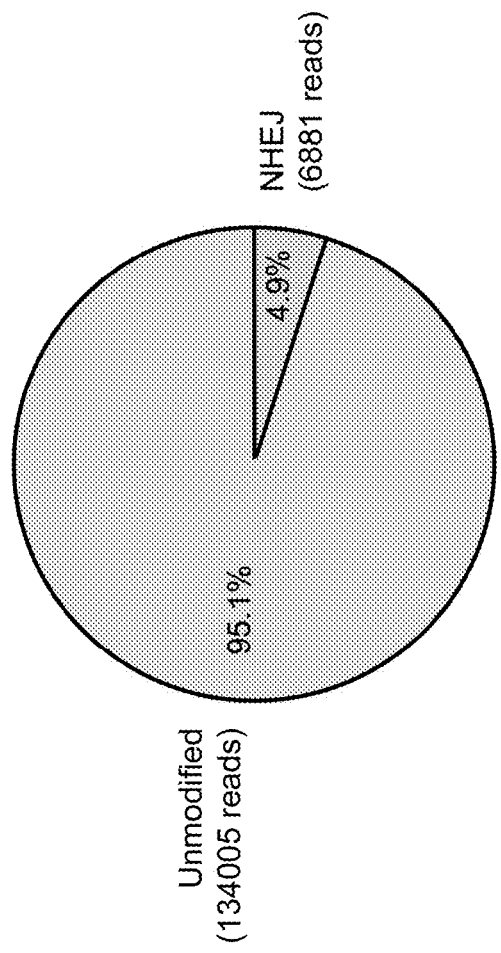

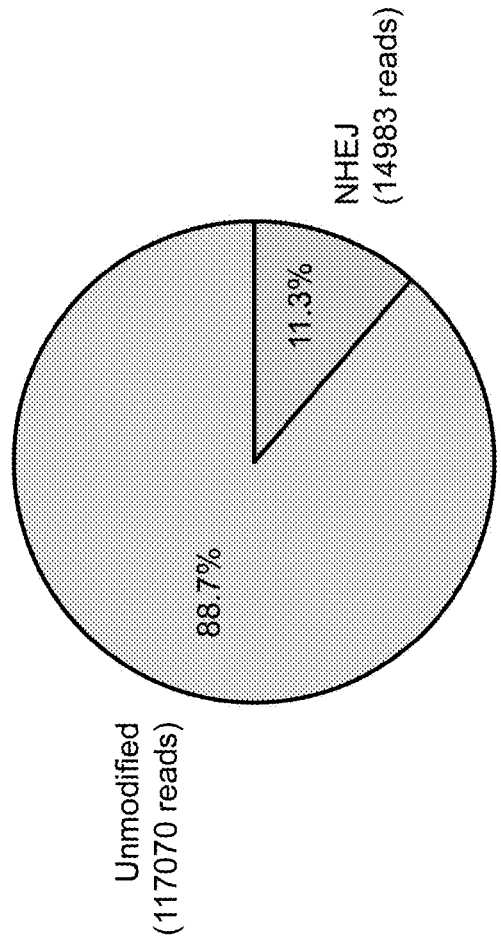

| Developmental regulator combinations | Constructs co-cultured | Starting # seedlings | Total # growths | # shoot-like growths | # white shoot-like growths | Full plants formed | # edited plants | # plants with developmental abnormalities |
|---|---|---|---|---|---|---|---|---|
| BBM | pMM146 | 24 | 0 | 0 | 0 | 0 | 0 | 0 |
| IPT | pMM134 | 24 | 0 | 0 | 0 | 0 | 0 | 0 |
| MPΔ | pMM136 | 24 | 0 | 0 | 0 | 0 | 0 | 0 |
| STM | pMM131 | 24 | 0 | 0 | 0 | 0 | 0 | 0 |
| WUS | pMM135 | 24 | 20 | 4 | 0 | 1 | 1 | 1 |
| All | pMM131, 134, 135, 136, 146 | 30 | 17 | 4 | 0 | 1 | 0 | 1 |
| BBM & IPT | pMM134, 146 | 36 | 0 | 0 | 0 | 0 | 0 | 0 |
| BBM & WUS | pMM135, 146 | 31 | 12 | 4 | 0 | 3 | 0 | 0 |
| IPT & MPΔ | pMM134, 136 | 34 | 0 | 0 | 0 | 0 | 0 | 0 |
| STM & MPΔ | pMM131, 136 | 29 | 0 | 0 | 0 | 0 | 0 | 0 |
| WUS & IPT | pMM134, 135 | 27 | 46 | 23 | 3.5 | 11 | 2 | 0 |
| WUS & STM | pMM131, 135 | 36 | 29 | 17 | 3 | 11 | 2 | 7 |

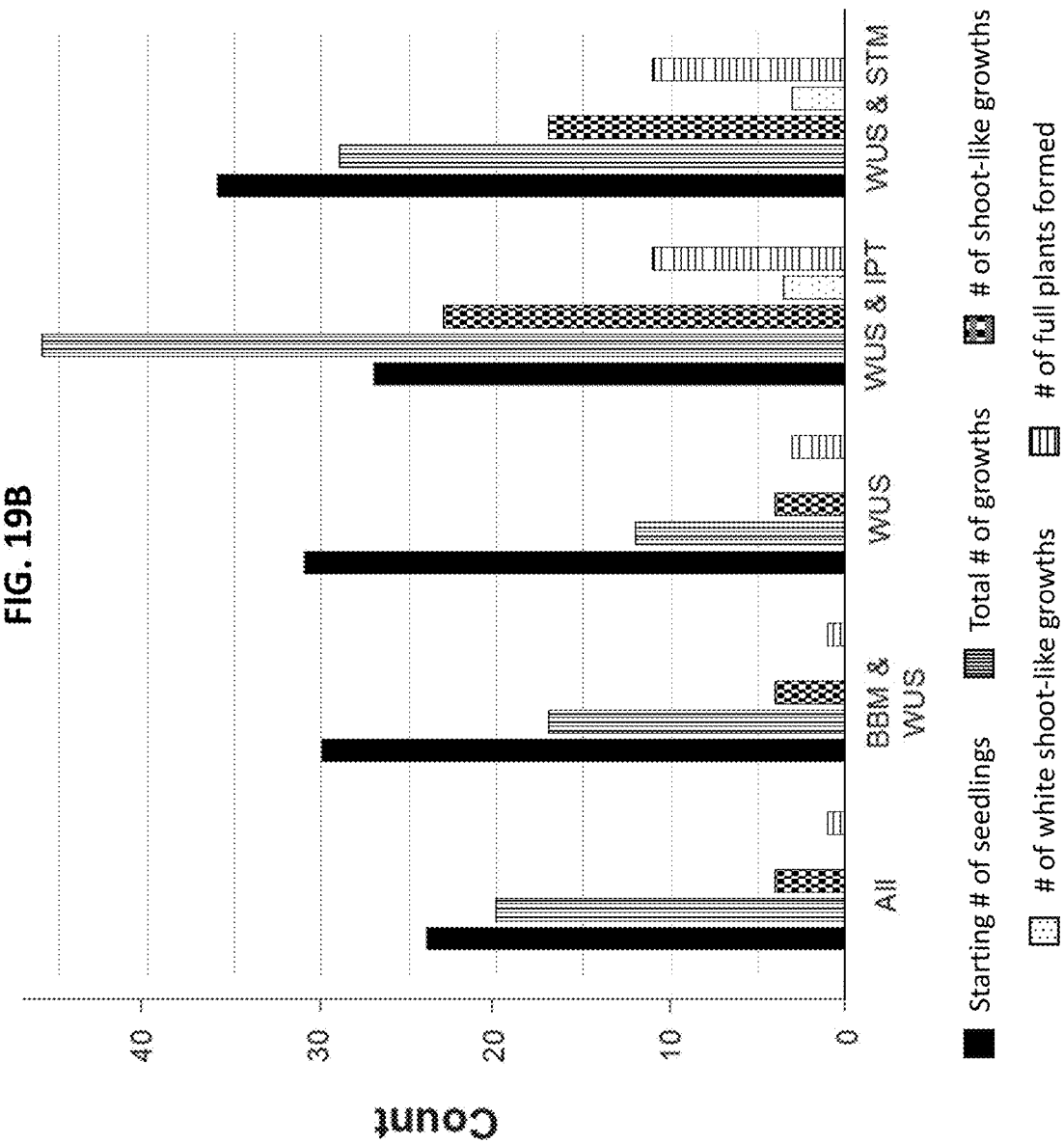

FIG. 21B

PDS1

| | | (SEQ ID NO:) |
|---|---|---|
| WT: | GGAATTTGTTATGTTTTGGTAGTAGCCGACTC\|CATGGGGCA | (114) |
| F4: #5- | GGAATTTGTTATGTTTTGGTAGTAGCCGACTCC\|CATGGGGCA | (115) |
| | GGAATTTGTTATGTTTTGGTAGTAGCCGAC\|CATGGGGCA | (116) |
| F4: #6- | GGAATTTGTTATGTTTTGGTAGTAGCCGACTCC\|CATGGGGCA | (115) |
| | GGAATTTGTTATGTTTTGGTAGTAGCCGAC\|CATGGGGCA | (116) |
| F6: #9- | GGAATTTGTTATGTTTTGGTAGTAGCCGACTCC\|CATGGGGCA | (115) |
| | GGAATTTGTTATGTTTTGGTAGTAGCCGACTCC\|CATGGGGCA | (115) |
| F6: #10- | GGAATTTGTTATGTTTTGGTAGTAGCCGACTCC\|CATGGGGCA | (115) |
| | GGAATTTGTTATGTTTTGGTAGTAGCCGAC\|CATGGGGCA | (116) |

PDS2

| | | (SEQ ID NO:) |
|---|---|---|
| WT: | GGAATTTGTTATGTTTTGGTAGTAGCCGACTC\|CATGGGGCA | (114) |
| F4: #5- | GGAATTTGTTATGTTTTGGTAGTAGCCGACTCC\|CATGGGGCA | (115) |
| | GGAATTTGTTATGTTTTGGTAGTAGCCGACT\|CATGGGGCA | (117) |
| F4: #6- | GGAATTTGTTATGTTTTGGTAGTAGCCGACT\|CATGGGGCA | (117) |
| F6: #9- | GGAATTTGTTATGTTTTGGTAGTAGCCGACTCC\|CATGGGGCA | (115) |
| | GGAATTTGTTATGTTTTGGTAGTAGCCGACT\|CATGGGGCA | (117) |
| F6: #10- | GGAATTTGTTATGTTTTGGTAGTAGCCGACT\|CATGGGGCA | (117) |
| | GGAATTTGTTATGTTTTGGTAGTAGCCGACT\|CATGGGGCA | (117) |

FIG. 22C

| Developmental Regulators | Total Seedlings | Number w/ Callus-like Growths | Number w/ Shoot-like Growths |
|---|---|---|---|
| Nos:WUS/CmYLCV:STM | 24 | 4 | 0 |
| Nos:WUS/35S:IPT | 41 | 15 | 3 |
| Nos:WUS/35S:STM | 24 | 7 | 0 |

FIG. 22J

| Constructs and DR combinations | Expt. | Starting # of seedlings | # of growths | Avg. growths per plant | # Shoot-like growths | Luc + shoot-like growths |
|---|---|---|---|---|---|---|
| WUS/IPT (MKV57) | 1 | 6 | 9 | 1.5 | 0 | 0 |
|  | 2 | 18 | 44 | 2.444444 | 3 | 3 |
| WUS & IPT (MKV58 & MKV59) | 1 | 6 | 20 | 3.333333 | 4 | 1 |
|  | 2 | 18 | 46 | 2.555556 | 7 | 3 |
| No DRs (MKV60) | 1 | 5 | 8 | 1.6 | 0 | 0 |
|  | 2 | 18 | 18 | 1 | 1 | 0 |

SEQUENCE LISTING

```
Sequence total quantity: 122
SEQ ID NO: 1              moltype = DNA  length = 842
FEATURE                   Location/Qualifiers
source                    1..842
                          mol_type = other DNA
                          organism = Cauliflower mosaic virus
SEQUENCE: 1
agatttgcct tttcaatttc agaaagaatg ctaacccaca gatggttaga gaggcttacg   60
cagcaggtat catcaagacg atctacccga gcaataatct ccaggaaatc aaataccttc  120
ccaagaaggt taaagatgca gtcaaaagat tcaggactaa ctgcatcaag aacacagaga  180
aagatatatt tctcaagatc agaagtacta ttccagtatg gacgattcaa ggcttgcttc  240
acaaaccaag gcaagtaata gagattggag tctctaaaaa ggtagttccc actgaatcaa  300
aggccatgga gtcaaagatt caaatagagg acctaacaga actcgccgta aagactggcg  360
aacagttcat acagagtctc ttacgactca atgacaagaa gaaaatcttc gtcaacatgg  420
tggagcacga cacacttgtc tactccaaaa atatcaaaga tacagtctca gaagaccaaa  480
gggcaattga gactttcaa caaagggtaa tatccggaaa cctcctcgga ttccattgcc   540
cagctatctg tcactttatt gtgaagatag tggaaaagga aggtggctcc tacaaatgcc  600
atcattgcga taaaggaaag gccatcgttg aagatgcctc tgccgacagt ggtcccaaag  660
atggacccc acccacgagg agcatcgtgg aaaaagaaga cgttccaacc acgtcttcaa   720
agcaagtgga ttgatgtgat atctccactg acgtaaggga tgacgcacaa tcccactatc  780
cttcgcaaga cccttcctct atataaggaa gttcatttca tttggagaga acacggggga  840
ct                                                                  842

SEQ ID NO: 2              moltype = DNA  length = 1327
FEATURE                   Location/Qualifiers
source                    1..1327
                          mol_type = other DNA
                          organism = Arabidopsis thaliana
SEQUENCE: 2
gtcgagctgc aggtcaacgg atcaggatat tctttgtttaa gatgttgaac tctatggagg   60
tttgtatgaa ctgatgatct aggaccggat aagttccctt cttcatagcg aacttattca   120
aagaatgttt tgtgtatcat tcttgttaca ttgttattaa tgaaaaaata ttattggtca   180
ttggactgaa cacgagtgtt aaatatggac caggcccaa ataagatcca ttgatatatg     240
aattaaataa caagaataaa tcgagtcacc aaaccacttg cctttttttaa cgagacttgt  300
tcaccaactt gatacaaaag tcattatcct atgcaaatca ataatcatac aaaaatatcc   360
aataacacta aaaaattaaa agaaatggat aatttcacaa tatgttatac gataaagaag  420
ttacttttcc aagaaattca ctgattttat aagcccactt gcattagata aatggcaaaa  480
aaaaacaaaa aggaaaagaa ataaagcacg aagaattcta gaaaatacga aatacgcttc  540
aatgcagtgg gacccacggt tcaattattg ccaattttca gctccaccgt atatttaaaa  600
aataaaacga taatgctaaa aaaatataaa tcgtaacgat cgttaaatct caacggctgg   660
atcttatgac gaccgttaga aattgtggtt gtcgacgagt cagtaataaa cggcgtcaaa  720
gtggttgcag ccggcacaca cgagtcgtgt ttatcaactc aaagcacaaa tacttttcct  780
caacctaaaa ataaggcaat tagccaaaaa caactttgcg tgtaaacaac gctcaataca   840
cgtgtcatttt tattattagc tattgcttca ccgccttagc tttctcgtga cctagtcgtc   900
ctcgtctttt cttcttcttc ttctataaaa caatacccaa agagctcttc ttcttcacaa  960
ttcagatttc aatttctcaa aatcttaaaa actttctctc aatctctct accgtgatca   1020
aggtaaattt ctgtgttcct tattctctca aaatcttcga ttttgttttc gttcgatccc   1080
aatttcgtat atgttctttg gtttagattc tgttaatctt agatcgaaca cgatttctgt   1140
ggtttgatcg ttagatatca tcttaattct cgattagggt ttcatagata tcatccgatt   1200
tgttcaaata atttgagttt tgtcgaataa ttactcttcg atttgtgatt tctatctaga   1260
tctggtgtta gtttctagtt tgtgcgatcg aatttgtcga ttaatctgag tttttctgat   1320
taacagg                                                            1327

SEQ ID NO: 3              moltype = DNA  length = 465
FEATURE                   Location/Qualifiers
source                    1..465
                          mol_type = other DNA
                          organism = Cestrum yellow leaf curling virus
SEQUENCE: 3
tggcagacat actgtcccac aaatgaagat ggaatctgta aaagaaaacg cgtgaaataa    60
tgcgtctgac aaaggttagg tcggctgcct ttaatcaata ccaaagtggt ccctaccacg   120
```

-continued

```
atggaaaaac tgtgcagtcg gtttggcttt ttctgacgaa caaataagat tcgtggccga    180
caggtggggg tccaccatgt gaaggcatct tcagactcca ataatggagc aatgacgtaa    240
gggcttacga aataagtaag ggtagtttgg gaaatgtcca ctcacccgtc agtctataaa    300
tacttagccc ctccctcatt gttaaggag caaaatctca gagagatagt cctagagaga    360
gaaagagagc aagtagccta gaagtagtca aggcggcgaa gtattcaggc acgtggccag    420
gaagaagaaa agccaagacg acgaaaacag gtaagagcta agctt                    465

SEQ ID NO: 4              moltype = DNA   length = 445
FEATURE                   Location/Qualifiers
source                    1..445
                          mol_type = other DNA
                          organism = Arabidopsis thaliana
SEQUENCE: 4
cttcgttgaa caacggaaac tcgacttgcc ttccgcacaa tacatcattt cttcttagct     60
ttttttcttc ttcttcgttc atacagtttt tttttgttta tcagcttaca ttttcttgaa    120
ccgtagcttt cgtttcttc tttttaactt tccattcgga gtttttgtat cttgtttcat    180
agtttgtccc aggattagaa tgattaggca tcgaaccttc aagaatttga ttgaataaaa    240
catcttcatt cttaagatat gaagataatc ttcaaaagcc ccctgggaat ctgaaagaag    300
agaagcaggc ccatttatat gggaaagaac aatagtattt cttatatagg cccatttaag    360
ttgaaaacaa tcttcaaaag tcccacatcg cttagataag aaaacgaagc tgagtttata    420
tacagctaga gtcgaagtag tgatt                                          445

SEQ ID NO: 5              moltype = DNA   length = 304
FEATURE                   Location/Qualifiers
source                    1..304
                          mol_type = other DNA
                          organism = Agrobacterium tumefaciens
SEQUENCE: 5
gatcatgagc ggagaattaa gggagtcacg ttatgacccc cgccgatgac gcgggacaag     60
ccgttttacg tttggaactg acagaaccgc aacgttgaag gagccactca gccgcgggtt    120
tctggagttt aatgagctaa gcacatacgt cagaaaccat tattgcgcgt tcaaaagtcg    180
cctaaggtca ctatcagcta gcaaatattt cttgtcaaaa atgctccact gacgttccat    240
aaattcccct cggtatccaa ttagagtctc atattcactc tcaatccaaa taatctgcac    300
cgta                                                                 304

SEQ ID NO: 6              moltype = DNA   length = 909
FEATURE                   Location/Qualifiers
source                    1..909
                          mol_type = other DNA
                          organism = Zea Mays
SEQUENCE: 6
atggcggcca atgcgggcgg cggtggacgg ggaggaggca gcggcagcgg cagcgtggct     60
gcgccggcgg tgtgccgccc cagcggctcg cggtggacgc cgaccgccgg acagatcagg    120
atgctgaagg agctgtacta cggctgcggg atccggtcgc ccagctcgga gcagatccag    180
cgcatcaccg ccatgctgcg gcagcacggc aagatcgagg caagaacgt cttctactgg    240
ttccagaacc acaaggcccg cgagcgccag aagccccgcc tcaccagcct cgacgtgaac    300
gtgccgccca ccggcgcggc cgacgccacc accagccaac tcggcgtcct ctcgctgtcg    360
tcgccgccgc cttcaggcgc ggcgcctccc tcgcccaccc tcggcttcta cgccgccggc    420
aatggcggcg atcggctgt gctgctggac acgagttccg actgggggcag cagcggcgct    480
gcgatggcca ccgagacatg cttcctccag gactacatgg gcgtgacgga cacgggcagc    540
tcgtcgcagt ggccacgctt ctcgtcgtcg gacacgataa tggccgtcag cgcggcgcag    600
gcggcgacga cgcggggcgcc cgagactctc cctctcttcc cgacctgcgg cgacgacggc    660
ggcagcggta gcagcagcta cttgccgttc tggggtgccg cgtccacaac tgccggcgcc    720
acttcttccg ttgcgatcca gcagcaacac cagctgcagg agcagtacag cttttacagc    780
aacagcaaca gcacccagct ggccggcacc ggcaaccaag acgtatcggc aacagcagca    840
gcagccgccg ccctggagct gagcctcagc tcatggtgct ccccttaccc tgctgcaggg    900
agtatgtga                                                            909

SEQ ID NO: 7              moltype = DNA   length = 1149
FEATURE                   Location/Qualifiers
source                    1..1149
                          mol_type = other DNA
                          organism = Arabidopsis thaliana
SEQUENCE: 7
atggagagtg gttccaacag cacttcttgt ccaatggctt ttgccgggga taatagtgat     60
ggtccgatgt gtcctatgat gatgatgatg ccgcccatca tgacatcaca tcaacatcat    120
ggtcatgatc atcaacatca acaacaagaa catgatggtt atgcatatca gtcacaccac    180
caacaaagta gttcccttt tcttcaatca ctagctcctc cccaaggaac taagaacaaa    240
gttgcttctt cttcttctcc ttcctcttgt gctcctgcct attcctaat ggagatccat    300
cataacgaaa tcgttgcagg aggaatcaac ccttgctcct cttcctcttc ttcagcctct    360
gtcaaggcca agatcatggc tcatcctcac taccaccgcc tcttggccgc ttatgtcaat    420
tgtcagaagg ttggagcacc accggaggtt gtggcgaggc tagaggaggc atgctcgtct    480
gccgcagccg ctgccgcatc tatgggacca acaggatgtc taggtgaaga tccagggctt    540
gatcaattca tggaagctta ctgtgaaatg ctcgttaagt atgacaaga gctctccaaa    600
ccttttcaagg aagctatggt cttccttcaa cgtgtcgagt gtcaattcaa atccctctct    660
ctatcctcac cttcctcttt ctccggttat ggagagacag caattgatag gaacaatat    720
gggtcatccg aggaagaagt cgatatgaac aatgaatttg tagatccaca agctgaggat    780
agagagctta aggacagct cttgcgcaag tacagtggtt acttagggag cctcaagcaa    840
gagttcatga agaagaggaa gaaaggaaag ctccctaaag aagctcgtca acaactgctt    900
```

```
gattggtgga gccgtcacta caaatggcct taccctteggg agcaacaaaa gctcgccctt  960
gcggaatcaa cggggctgga ccagaaacag ataaacaatt ggttcataaa ccagaggaaa  1020
cggcattgga agccgtcgga ggacatgcag tttgtagtaa tggacgcaac acatcctcac  1080
cattacttca tggataatgt cttgggcaat cctttcccaa tggatcacat ctcctccacc  1140
atgctttga                                                         1149

SEQ ID NO: 8           moltype = DNA  length = 1245
FEATURE                Location/Qualifiers
source                 1..1245
                       mol_type = other DNA
                       organism = Arabidopsis thaliana
SEQUENCE: 8
atgatggctt cattgtcttg tgttgaagac aagatgaaaa caagttgttt ggttaatggt   60
ggaggaacta taacaacaac aacatctcaa tctaccttgc ttgaagagat gaagctgttg  120
aaagaccagt caggtacaag aaagccggta ataaactcgg agctatggca cgcttgtgca  180
ggccctttgg tgtgtctccc tcaagttggg agcttagtgt attacttctc acaaggtcat  240
agcgagcagg ttgctgtttc aaccagaaga tcagcaacaa cacaagttcc taattatccg  300
aaccttccat ctcagttgat gtgtcaagtc cataatgtta ctcttcatgc tgacaaagac  360
agtgacgaaa tctatgctca gatgagtctt caacctgttc actctgagag agatgtgttc  420
cctgtaccag actttggaat gctgagagga agtaagcacc cgactgagtt tttctgcaaa  480
acacttactg caagtgacac aagcacacat ggaggtttct cagtgccacg tagagctgca  540
gagaagctat ttccaccatt ggactactca gcacagccgc caacgcaaga gcttgtagtt  600
cgagatcttc atgagaatac ttggacattt cgccatatct accgagggca accaaagaga  660
catctcctaa ctacaggatg gagtttgttc gttggatcga agagattgag agctggggat  720
tctgtttgt tcatcaggga tgagaagtca caacttatgg tcggtgttag gcgtgccaat  780
cgccaacaaa cagcacttcc ttcatcagtt ctctcagcgg atagtatgca catcggtgtt  840
cttgctgctg ctgctcacgc aaccgccaac cgtactcctt ttttgatatt ctataatcca  900
agagcttgtc cagcagagtt cgtgatccct ctagctaagt accgtaaggc gatatgcggg  960
tctcagctct cagttggtat gagatttgga atgatgtttg aaactgaaga ttccgggaaa  1020
cgaaggtaca tgggaactat tgttggaatc agcgatttgg atccgttgag atggcctggt  1080
tctaagtggc gtaaccttca ggtagaatgg gatgagcctg gatgtaatga taaacctact  1140
cgggtcagtc catgggatat cgaaacacct gaaagtctct tcatttttcc ttctctgacc  1200
tcaggactca aacgtcagct ccatccatct tactttgctg gtgaa              1245

SEQ ID NO: 9           moltype = DNA  length = 2133
FEATURE                Location/Qualifiers
source                 1..2133
                       mol_type = other DNA
                       organism = Zea Mays
SEQUENCE: 9
atggccactg tgaacaactg gctcgctttc tccctctccc cgcaggagct gccgccctcc   60
cagacgacga actccacact catctcggcc gccaccgccg accatgtctc cggcgatgtc  120
tgcttcaaca tcccccaaga ttggagcatg aggggatcag agctttcggc gctcgtcgcg  180
gagccgaagc tggaggactt cctcggcggg atctccttct ccgagcagca tcacaaggcc  240
aactgcaaca tgatacccag cactagcagc acagtttgct acgccagctc aggtgctagc  300
accggctacc atcaccagct gtaccaccag cccaccagct cagcgctcca cttcgcggac  360
tccgtaatgg tggcctcctc ggccggtgtc cacgacgggc gtgccatgct cagccgcggcc  420
gccgctaacg tgtcgctggg cgctgccagt gccaacggcg gcggcatcgg gctgtccatg  480
attaagaact ggctgcggag ccaaccggcg cccatgcagc cgagggtggc ggcggctgag  540
ggcgcgcagg ggctctcttt gtccatgaac atggcgggga cgaccaaggc gctgctggc  600
atgccacttc tcgctggaga gcgcgcacgg gcgcccaagg tgtatccac gtcagcacag  660
ggtggagccg tcgtcgtcac ggcgccgaag aggatagccg gtggcagcgg tgttgccggc  720
gctctagtag ccgtgagcac ggacacgggt ggcagcggcg gcgcgtcggc tgacaacacg  780
gcaaggaaga cggtggacac gttcgggcag cgcacgtcga tttaccgtgg cgtgacaagg  840
catagatgga ctgggagata tgaggcacat cttttgggata acagttgcag aagggaaggg  900
caaactcgta agggtcgtca agtctatttta ggtggctatg ataaagagga gaaagctgct  960
agggcttatg atcttgctgc tctgaagtac tggggtgcca caacaacaac aaattttcca  1020
gtgagtaact acgaaaagga gctggaggac atgaagcaca tgacaaggca ggagtttgta  1080
gcgcctctga aaggaagtc cagtggtttc tccagaggtg catccattta cagggagtg  1140
actaggcatc accaactgg aagatggcaa gcacggatgg acgagttgc agggaacaag  1200
gatctttact tgggcacctt cagcacccag gaggaggcag cggaggcta cgacatcgcg  1260
gcgatcaagt tccgcggcct caacgccgtc accaacttcg acatgagccg ctacgacgtg  1320
aagtccatcc tggacagcag cgccctcccc atcggcagcg ccgccaagcg cctcaaggag  1380
gccgagggcc ggcgtcgc gcagcaccac catgcggttg tcgtttccta tgacgttggg  1440
aggattgcca gccaactggg agatggcggt gccctcgctg cggcctatgg tgctcactat  1500
cacggtgcc cgtggccaac gattgcattc cagccgggcg cggcgtccac cggactgtac  1560
catccttacg cgcagcagcc tatgcgcggc ggtggatggt gtaaacaaga gcaagatcac  1620
gctgtgatag cagcggcaca ctccttgcag gatcttcatc atttgaatct cggagccgcc  1680
gggcccacg acttttctc ggcagggcag caggccgccg ccgctgcgat gacggttggg  1740
ggtagcatcg acagtgcgtc gctggagcac agcaccggct ccaactccgt cgtctacaac  1800
ggcggggtcg gcgacagcaa cggcgccagc gccgtcggcg gcagtggcgg tggctacatg  1860
atgccgatga gcgctgccgg agcaaccact acatcggcaa tggtgagcca cgagcaggtc  1920
catgcacggg cctacgacga agccaagcag gctgctcaga tggggtacga gagctacctg  1980
gtgaacgcgg agaacaatgg tggcggaagg atgtctgcat gggggactgt cgtgtctgca  2040
gccgcggcgc cagcagcaag cagcaacgac aacactgtgc ccgacgtggg ccacgccggc  2100
gcgcagctgt tcagtgtctg gaacgacact taa                              2133

SEQ ID NO: 10          moltype = DNA  length = 1007
FEATURE                Location/Qualifiers
```

| | | |
|---|---|---|
| source | 1..1007 | |
| | mol_type = other DNA | |
| | organism = Arabidopsis thaliana | |

SEQUENCE: 10

```
atgaactcga tgaataactg gttaggcttc tctctctctc ctcatgatca aaatcatcac   60
cgtacggatg ttgactcctc caccaccaga accgccgtag atgttgccgg agggtactgt  120
tttgatctgg ccgctccctc cgatgaatct tctgccgttc aaacatcttt tcttttctcct 180
ttcggtgtca ccctcgaagc tttcaccaga gacaataata gtcactcccg agattgggac  240
atcaatggtg gtgcatgcaa taacattaac aataacgaac aaaatggacc aaagcttgag  300
aatttcctcg gccgcaccac cacgatttac aataccaacg agaccgttgt agatggaaat  360
ggcgattgtg gaggaggaga cggtggtggt ggcggctcac taggccttttc gatgataaaa  420
acatggctga gtaatcattc ggttgctaat gctaatcatc aagacaatgg taacggtgca  480
cgaggcttgt ccctctctat gaattcatct actagtgata gcaacaacta caacaacaat  540
gatgatgtcg tccaagagaa gactattgtt gatgtcgtag aaactaccac gaagaaaact  600
attgagagtt tggacaaaag gacgtctata taccgcggtg ttacaaggca tcggtggaca  660
ggtagatacg aggcacattt atgggacaat agttgcaaaa gagaaggcca gactcgcaaa  720
ggaagacaag tttatctggg aggttatgac aaagaagaaa aagcagctag gcttacgat   780
ttagccgcac taaagtattg gggaaccacc actactacta acttccccctt gagtgaatat  840
gagaaagagg tagaagagat gaagcacatg acgaggcaag agtatgttgc ctctctgcgc  900
aggaaaagta gtggtttctc tcgtggtgca tcgatttatc gaggagtaac aaggcatcac  960
caacatgaa ggtggcaagc taggatcgga agagtcgccg gtaacaa              1007
```

| | | |
|---|---|---|
| SEQ ID NO: 11 | moltype = DNA length = 723 | |
| FEATURE | Location/Qualifiers | |
| source | 1..723 | |
| | mol_type = other DNA | |
| | organism = Agrobacterium tumefaciens | |

SEQUENCE: 11

```
atggatctgc gtctaatttt cggtccaact tgcacaggaa agacgtcgac cgcgatacgt   60
cttcccagc agactggcct tccagtcctt tcgctcgatc gggtccaatg ctgtcctcaa  120
ctgtcaaccg gaagcggacg accaacagtg gaagaactga aaggaacgac ccgtctatac  180
cttgaagatc ggcctctggt gaagggtatc atcgcagcca agcaagctca cgaaaggctg  240
atcggggaag tgtacaatta tgaggcccac ggcgggctta tcttgaggg aggatctatc  300
tcgttgctca ggtgcatggc gcaaaagcagt tattggagta ccgatttcg ttggcatatt  360
attgccaca agttagcaga cgaggagaca ttcatgaacg gccgcaaggc cagagttagg  420
cagatgttgc gccctgctgt aggcccatct attattcaag agttggttca tctttggaat  480
gagcctcggc tgaggcccat actgaaagag atcgacggat atcgatatgc catgttattt  540
gctagccaga accagatcac acccgatatg ctattgcagc ttgacccaga tatggagggt  600
gagttgattc atggaatcgc tcaggagtat ctcatccatg cgcgccggca ggagcaggaa  660
ttccctccag tgagcgtggt cgctttcgaa ggattcgaag gtccaccgtt cggaatgtgc  720
tag                                                                  723
```

| | | |
|---|---|---|
| SEQ ID NO: 12 | moltype = DNA length = 20 | |
| FEATURE | Location/Qualifiers | |
| source | 1..20 | |
| | mol_type = other DNA | |
| | organism = synthetic construct | |

SEQUENCE: 12

```
ttggtagtag cgactccatg                                                20
```

| | | |
|---|---|---|
| SEQ ID NO: 13 | moltype = DNA length = 20 | |
| FEATURE | Location/Qualifiers | |
| source | 1..20 | |
| | mol_type = other DNA | |
| | organism = synthetic construct | |

SEQUENCE: 13

```
ccattggaga ttgttattgc                                                20
```

| | | |
|---|---|---|
| SEQ ID NO: 14 | moltype = DNA length = 1457 | |
| FEATURE | Location/Qualifiers | |
| source | 1..1457 | |
| | mol_type = other DNA | |
| | organism = synthetic construct | |

SEQUENCE: 14

```
atggaagacg ccaaaaacat aaagaaaggc ccggcgccat tctatccgct ggaagatgga   60
accgctggag agcaactgca taaggctatg aagagatacg cccctggttcc tggaacaatt  120
gcttttacag atgcacatat cgaggtggac atcacttacg ctgagtactt cgaaatgtcc  180
gttcggtata acgtggcgta agtgaaacta agctttcgaa cgtgacatag tccaccgttc  240
ggttggcaga agctatgaaa cgatatgggc tgaatacaaa tcacagaatc gtcgtatgca  300
gtgaaaactc tcttcaattc tttatgccgg tgttgggcgc gttatttatc ggagttgcag  360
ttgcgcccgc gaacgacatt tataatgaac gtgaattgct caacagtatg ggcatttcgc  420
agcctaccgt ggtgttcgtt ccaaaaaggg gttgcaaaa aatttgaac gtgcaaaaaa  480
agctcccaat catccaaaaa attattatca tggattctaa aacggattac cagggatttc  540
agtcgatgta acgtcctcgtc acatctcatc tacctcccgg ttttaatgaa tacgattttg  600
tgccagagtc cttcgatagg gacaagacaa ttgcactgat catgaactcc tctggatcta  660
ctggtctgcc taaaggtgtc gctctgcctc atagaactgc ctgcgtgaga ttctcgcatg  720
ccagagatcc tatttttggc aatcaaatca ttccggatac tgcgatttta agtgttgttc  780
cattccatca cggttttgga atgtttacta cactcggata tttgatatgt ggatttcgag  840
tcgtcttaat gtatagattt gaagaagagc tgtttctgag gagccttcag gattacaaga  900
```

```
ttcaaagtgc gctgctggtg ccaaccctat tctccttctt cgccaaaagc actctgattg    960
acaaatacga tttatctaat ttacacgaaa ttgcttctgg tggcgctccc ctctctaagg   1020
aagtcgggga agcggttgcc aagaggttcc atctgccagg tatcaggcaa ggatatgggc   1080
tcactgagac tacatcagct attctgatta cacccgaggg ggatgataaa ccgggcgcgg   1140
tcggtaaagt tgttccattt tttgaagcga aggttgtgga tctggataca gggaaaacgc   1200
tgggcgttaa tcaaagaggc gaactgtgtg tgagaggtcc tatgattatg tccggtttatg   1260
taaacaatcc ggaagcgacc aacgccttga ttgacaagga tggatggcta cattctggag   1320
acatagctta ctgggacgaa gacgaacact tcttcatcgt tgaccgcctg aagtctctga   1380
ttaagtacaa aggctatcag gtggctcccg ctgaattgga atccatcttg ctccaacacc   1440
ccaacatctt cgacgct                                                 1457

SEQ ID NO: 15            moltype = DNA   length = 720
FEATURE                  Location/Qualifiers
source                   1..720
                         mol_type = other DNA
                         organism = synthetic construct
SEQUENCE: 15
atggtgagta aaggagaaga acttttcact ggagttgtcc caattcttgt tgaattagat    60
ggtgatgtta atgggcacaa attttctgtc agtggagagg gtgaaggtga tgcaacatac   120
ggaaaactta cccttaaatt tatttgcact actggaaaac tacctgttcc atggccaacc   180
ctggtcacca ccctgaccta cggcgtgcag tgcttctccc gttaccctga tcatatgaag   240
cggcacgact tcttcaagag cgccatgcct gagggatacg tgcaggagag gaccatcttc   300
ttcaaggacg acgggaacta caagacacgt gctgaagtca agtttgaggg agacaccctc   360
gtcaacagga tcgagcttaa gggaatcgat ttcaaggagg acggaaacat cctcggccac   420
aagttggaat acaactacaa ctcccacaac gtatacatca tggccgacaa gcaaaagaac   480
ggcatcaaag ccaacttcaa gacccgccac aacatcgaag acggcggcgt gcaactcgct   540
gatcattatc aacaaaatac tccaattggc gatggccctg tccttttacc agacaaccat   600
tacctgtcca cacaatctgc cctttcgaaa gatcccaacg aaaagagaga ccacatggtc   660
cttcttgagt ttgtaacagc tgctgggatt acacatggca tggatgaact atacaaataa    720

SEQ ID NO: 16            moltype = DNA   length = 8895
FEATURE                  Location/Qualifiers
variation                1..8895
                         note = n is a, c, g, or t
variation                2763..3070
                         note = n is a, c, g, or t
variation                4364
                         note = n is a, c, g, or t
variation                5293
                         note = n is a, c, g, or t
variation                5675..6605
                         note = n is a, c, g, or t
source                   1..8895
                         mol_type = other DNA
                         organism = Nicotiana benthamiana
SEQUENCE: 16
cctcaatgac ccagtaaccc aagtgggaga tgtgtgcaaa gtggtcaaat cttagaagga    60
atgagcaaag caagaaatta aaagagagag cagagaggtg ttatccatca aatgtggcta   120
tggtcggaat agccaatggt gggacagtct agccaaacat aaaggccggt ccagtgcgag   180
ttgctgcaaa ttgagttgga gtaaaaaatt aagataccat atttccagct aaatagcaaa   240
caaatgaccc accattaacg gaagtggcca aaccaccaaa ttcaggcatc tccaccaaaa   300
attagttttt tatacacgaa agattcaaca attagtattt cttttaagcct tcctaattct   360
ttgtcagggg tatctttttg tgggtaacag ccaaaccacc acaaattttc agttcccact   420
cttaactctt tttaacttca acacaacaaa ttttttgctt ttccttcttt gtttatcttg   480
tgcataacga tttcctacaa ctttagcata atcttggttt gtaatccaca acgtgaaaca   540
catcacctag gcggtttcat accgaggtaa caaatgattt tggtttcttt ggttacatca   600
gctgaatgct ttacttgaga aaagctttct cctttttccg tttaggatct tgtttatttg   660
ctttcgtttt tctactcgtt aaaatttaa cttgattttg tgggtgaatt ataactttac   720
tcatagtgcg agaacaagtt tcgtatggac tgtaaaagct aaagaatctttt ttacttttgc   780
atataaattt gtgtaataaa tgcttaagaa ccagaatatt gaaaaaacaa aggaattcta   840
catagtattt aggttcacaa gtgggacaat cttcttacag tgaaatatct ttatgtcagg   900
cttaatttac tgctatttg ttcagtaaaa tgccccaaat tggacttgtt tctgccgtta    960
atttgagagt ccaaggtaat tcagcttatc ttttggagctc gaggtcttct ttgggaactg   1020
aaagtcaaga tggtcgcttg caaaggaatt tgttatgttt tggtagtagc gactccatgg   1080
ggcataagtt tagaattcgt actcccagtg ccatgaccag aagattgaca aaggacttca   1140
atcctttaaa ggtttgtttt gaatgcgaaa gtgtgatgct gaatttatga tcacgagcat   1200
atattctcta aaataagata tcttgccatt caggtagtct gcattgatta tccaagaccg   1260
gagctagaca atacagttaa ctatttggag gcggcgttat catcatcatc atttcgtact   1320
tcctcacgcc caacaaaacc attggagatt gttattgctg gtgcaggtga ttttttccag   1380
tcatctatat ttgtagtctt catttttctt tctttggaag gaagatcatt ctattagttg   1440
tattatcact agaacattta ttgtgcattc tttttcttatt aactgttttg gaccgcaaaa   1500
ttttaagttc ttacttcttc gcctcccaac tgattagatt aggagtgatt tgaaaattag   1560
tttgtttgga gctattttg ccgtcactca tatactgttg agttgtccca atcggtgag   1620
atttgaagtc cttggtctca cctcataagt tagctttgg ggttgagtta ggcccaatat   1680
ccatttatca tagtacgaga gccaggccca tcccagttat tgttaccaat gtcgggctcc   1740
tatttatgtt gtccacgctc cagtttgcaa gcctaggcgt gggggagggg ggtgttgagt   1800
tgtcccacat ccgtgggatt tgaggtactt ggtctcctta tggtcttg dacaatccat   1860
aagctagctt tggggttga gttcggccca atgttcattt atcatatata tatatatata   1920
tatatatgtc tattctctct taccatctga gccatgataa gcgggtgaac gtgctgtcta   1980
```

```
ttggatggca tgtccgatgg atcattccga aatattggag gcagatgaac caataccttg   2040
tgcaagattg atatcactat acctataatc agagtactta gagttccaaa aatttgcaga   2100
acccattgaa aagtcaaaca agttacatat aggggttgca ctcttctaag gcttgcaatc   2160
tgtgagaaaa agatgagaag gagatcttca tatttcatct ttattaggct ggaccattga   2220
ccggttagca gttttgaact tgttcttcaa cttggcttgc atagtactgt gccgatcatt   2280
tcttttgtat tgtcatcaac tggttgatta tttgagtacc taaagaaaga atgttatgca   2340
tgatacattg tgctgtacta taaaagatat aataaagaat gctagccgag gtactacatg   2400
gccttttcag acaaatagaa gctgtagcat gattctaatt cgatttgttt tgaaatatca   2460
ggtttggggtg gcttgtctac agcaaaatat ctggcagatg ctggtcacaa accgatattg   2520
ctggaggcaa gagatgtcct aggtggaaag gtgaagaata tccaatcttt cctttaattt   2580
tattccttt tcttctgtgt ccttgcctat tggtagtccc tgttcaggaa ggcttctgtt   2640
tgttttattt aaaatcattt ttcatactct ttaaacattc agttgctcaa acaattgcaa   2700
gggtgttcac tattcctatt tttgactgtc ttactttctc tcagtttagt tttattcccc   2760
tcnnnnnnnn nnnnnnnnnn nnnnnnnnnn nnnnnnnnnn nnnnnnnnnn nnnnnnnnnn   2820
nnnnnnnnnn nnnnnnnnnn nnnnnnnnnn nnnnnnnnnn nnnnnnnnnn nnnnnnnnnn   2880
nnnnnnnnnn nnnnnnnnnn nnnnnnnnnn nnnnnnnnnn nnnnnnnnnn nnnnnnnnnn   2940
nnnnnnnnnn nnnnnnnnnn nnnnnnnnnn nnnnnnnnnn nnnnnnnnnn nnnnnnnnnn   3000
nnnnnnnnnn nnnnnnnnnn nnnnnnnnnn nnnnnnnnnn nnnnnnnnnn nnnnnnnnnn   3060
nnnnnnnnnn ccccccccct gtctctctct ctctctctgt ttttggagga aatagatctg   3120
tcctaaaaac ttccagcttt actactaata gtgttaattg tcgagaaaat attacagcat   3180
attaggtata tggaaagtat attattattc tctattattt taagattgag tcaattttac   3240
ccgtcctgtt ggttgcattt ctcacataaa cagtcttttc tgtgagatgc tatgttaatt   3300
agctgatgtt tttggtatag agcactatgt tagttttatc tttactgaag cagtcaccaa   3360
gaatctagtt gtataggcta aaagattgaa ttagcattaa tctttatgtg ttttgcacct   3420
gaatacctat acctaccttt taggtagctg catggaaaga tgatgatgga gattggtacg   3480
agactgggt gcacatattc tgtaagtttg actcctcaag aatgcatact ttaatcttct   3540
aatacaacag tttcttcaa gatctctttt ctctattaat cagatagata tcgctgtttt   3600
tgttttgtct tttgcaaata gccaattttt gtcagtcgat ctgtattctg ccttgcctat   3660
ctttttttat ctgttaattt catatggtga ctcatacaag ttggtgcatc ccctttaagt   3720
tggggcttac ccaaatatgc agaacctgtt tggagaacta gggattaacg atcggttgca   3780
gtggaaggaa cattcgatga tatttgcgat gcctaacaag ccgggggagt tcagccgctt   3840
tgatttcct gaagctcttc ctgcgccatt aaatggttag tacttaatca tgatttctcc   3900
cttctgcatt gattatccaa taaggtatga aattgattag tccattgacc attaatactc   3960
tggcacattg ctaacatcaa aagaacataa aggttcatta tgtcttgatc agaattttctg   4020
catgtagcta aagtgattga gtgtctgtgt atattttat acattgcaag cataagccag   4080
ttatgttatc tcttattttc atttctctat cgatgcgtta ttacttctac aggaatttta   4140
gccatactaa agaacaacga aatgcttaca tggcccgaaa aaatcaaatt tgctattgga   4200
ctcttgccag caatgcttgg agggcaatct tatgttgaag ctcaagacgg tttaagtgtt   4260
aaggactgga tgaaaagca agtatgtgat cgttttatct tattctttaa agttcataac   4320
cttgaggaca tagttgactt gcatgttgtt gatttaacat gttnatgtga tcgttttatc   4380
ttactcttta aagttcataa ccttgaggac atagttgact tgcatgttgt tgatttaaca   4440
tgttagaatt gtctacctgc cttttctttt ttaacaacat acatcttaca aatctcagca   4500
gcagctattt gcttaattgc ttttcagggt gtgcctgata gggtgacaga tgaggtgttc   4560
attgccatgt caaaggcact taacttcata aaccctgacg agctttcgat gcagtgcatt   4620
tgattgctt tgaacagatt tcttcaggtt agaatcctga tccaccctca aaacaaaaag   4680
agagaaaggg atataatccg accaagctgt aaatcatgtt agggacctga catattggtg   4740
caggaaactt atttgtgaac ttttccactc tgtttaactt ttctgatata tttgaattat   4800
taatctgcag gagaaacatg gttcaaaaat ggcctttta gatggtaatc ctcctgagag   4860
acttgcatg ccaattgttg aacatattga gtcaaaaggt ggccaagtca gactaaactc   4920
acgaataaaa aagattgagc tgaatgagga tggaagtgtc aaatgtttta tactgaataa   4980
tggcagtaca attaaaggag atgctttttgt gtttgccact ccaggtataa tatccattat   5040
actagtatcg atgcttccag ttttcacatt tttaatatga atgtataatt ttttgctgac   5100
ttttcattat ccgattagtg gatatcttca agcttcttt gcctgaagac tggaaagaga   5160
tcccatattt ccaaaagttg gagaagctag tgggagttcc tgtgataaat gtccatatat   5220
ggttagtgat gaaaattttg cttttcagtg tttggtcttc ctctagcata tctatgtatg   5280
tgcatgttaa tgnactttc agtgtttgtt cttcctctag catatctatg tatgtgcctg   5340
ttaatgtcta tacatacatg tttatgtggt cctccggtat tgtgttaact tcccttgagc   5400
gaggaactta tggatctacg cttttccaaa actttgattg cacacattgc aattgtctgt   5460
tcaactttga tgagcagaac taccattgtt agctattag tggctgagat tcctgctaga   5520
aagatttgta taaatttaat tgcaggtttg acagaaaact gaagaacaca tctgataatc   5580
tgctcttcag caggttcatt tttgatcaat ttattgttc cagagcagtt tctgcgtgtc   5640
catgactaca ttctcatatt agctccccc cccnnnnnn nnnnnnnnnn nnnnnnnnnn   5700
nnnnnnnnnn nnnnnnnnnn nnnnnnnnnn nnnnnnnnnn nnnnnnnnnn nnnnnnnnnn   5760
nnnnnnnnnn nnnnnnnnnn nnnnnnnnnn nnnnnnnnnn nnnnnnnnnn nnnnnnnnnn   5820
nnnnnnnnnn nnnnnnnnnn nnnnnnnnnn nnnnnnnnnn nnnnnnnnnn nnnnnnnnnn   5880
nnnnnnnnnn nnnnnnnnnn nnnnnnnnnn nnnnnnnnnn nnnnnnnnnn nnnnnnnnnn   5940
nnnnnnnnnn nnnnnnnnnn nnnnnnnnnn nnnnnnnnnn nnnnnnnnnn nnnnnnnnnn   6000
nnnnnnnnnn nnnnnnnnnn nnnnnnnnnn nnnnnnnnnn nnnnnnnnnn nnnnnnnnnn   6060
nnnnnnnnnn nnnnnnnnnn nnnnnnnnnn nnnnnnnnnn nnnnnnnnnn nnnnnnnnnn   6120
nnnnnnnnnn nnnnnnnnnn nnnnnnnnnn nnnnnnnnnn nnnnnnnnnn nnnnnnnnnn   6180
nnnnnnnnnn nnnnnnnnnn nnnnnnnnnn nnnnnnnnnn nnnnnnnnnn nnnnnnnnnn   6240
nnnnnnnnnn nnnnnnnnnn nnnnnnnnnn nnnnnnnnnn nnnnnnnnnn nnnnnnnnnn   6300
nnnnnnnnnn nnnnnnnnnn nnnnnnnnnn nnnnnnnnnn nnnnnnnnnn nnnnnnnnnn   6360
nnnnnnnnnn nnnnnnnnnn nnnnnnnnnn nnnnnnnnnn nnnnnnnnnn nnnnnnnnnn   6420
nnnnnnnnnn nnnnnnnnnn nnnnnnnnnn nnnnnnnnnn nnnnnnnnnn nnnnnnnnnn   6480
nnnnnnnnnn nnnnnnnnnn nnnnnnnnnn nnnnnnnnnn nnnnnnnnnn nnnnnnnnnn   6540
nnnnnnnnnn nnnnnnnnnn nnnnnnnnnn nnnnnnnnnn nnnnnnnnnn nnnnnnnnnn   6600
nnnnnacatg ttatgatgac catttctcca aggcatttta tccatgccac gtttcatcag   6660
ctacatgttg actatgttcc cctactttt aaatggcacc attgttggtg gagaaagatt   6720
```

```
atagatgttc ctgatacttg tatgggttcc cttgctcaat ctctctttta cttcatgcag   6780
aagcccattg ctcagtgtgt atgctgacat gtctgttaca tgtaaggtat tgactcgtct   6840
gtaccattca tactggtcta atctgttgga tatgagttgc tggtaaattg cataatgctt   6900
gttggatttg tgtgtgagtt gctgctagat ctgtgtcctg ctatatttat gtatgagttg   6960
ctgctattgt aatcttcatt taggatgctt aatgatatag gttctgtatg tatggaatag   7020
tcaggacaat gctcctgtct gtgcacaggg gctctacagg aagcaacttt cgaaggagaa   7080
gtaaagaaag tgtgatgaac agggaaagta gtttcctttta gctaccttaa ttcagtgtta   7140
cctgcaatgt tcagtgtttg gagagaggcg ataagcctac ttcttaattt tgttagaaaa   7200
tgcgtacaaa atataaatca gtagttacta aaaagtttgga gaagtagtgg gatcttttcg   7260
ctattttttaa cccagaataa gacagctatg ccatatagct ttgattatcc gttaacgttc   7320
tgtatataaa tagataattc ataataatgt cgtaatacta aagcctggag atcagactgc   7380
tttaactatc ctgagatgat tactttttact cttggattag cttaggcgag ccacaagact   7440
acattgaatc tttagaaatg agaacataaa aagggtgcag aagtggggaa gtggctgaac   7500
gatatgcata tgggagtgag tggggagtaa aattatttcc tttacttggg tacaatcaag   7560
aatgaatgac aacttagccc actatatccg ttcatgtgtt cttttagggcc ctctgatata   7620
attggtctct ctgcaggaat attacaaccc caatcagtct atgttggaat tggtatttgc   7680
acctgcagaa gagtggataa atcgtagtga ctcagaaatt attgatgcta caatgaagga   7740
actagcaagg cttttccctg acgaaatttc ggcagatcag agcaaagcaa aaatattgaa   7800
gtatcatgtt gtcaaaactc caaggccagt aatcatttgc tttcatactt gtgcaatata   7860
cgagaactgc agtccacgtg gaatctattc ctattctgaa tcctgattaa tctgcttttt   7920
ttctctcagg tctgttttata aaactgtgcc aggttgtgaa ccctgtcggc ccttgcaaag   7980
atctcctatt gagggtttt atttagctgg cgactacaca aaacagaaat acttggcttc   8040
aatgaaggt gctgtcttat caggaaagct ttgtgcccaa gctattgtac aggttagttc   8100
tcacagttgt ttttgtccac taatagtata tttgatcaaa ttttgtcatc tttgctgcgg   8160
tagaaatttt tgaagcatg gacgtcaagc atgcctctta cttataattg ctaatttgcg   8220
gaatagttct ccaaccaata tagtgttaaa ccaaaaaaat aaaattgtgc acacagatca   8280
cagagttgct caggatatct gcattttttgg agcctcagta gtagcatgat aaaatgcaga   8340
aggttatgtt tttttcattc tttattaaat ttatatctct atattttgca ggattacgag   8400
ttacttcttg gccggagcca aagaagttg gcagaagcaa gcgtagttta gcatggtgaa   8460
ctaaaatgtt gcttctctac actaaattta agatgaaggt ggccacactg aattagcgtt   8520
gtagacaaca catacaagga cagtacaaca tttaacccaa atacgagaaa tgttacacaa   8580
atatgtgctc tgctttccct ccgatttagt tcgcaagtta ctaattataa gatggaattg   8640
aatgaaacca aagacggata aagacccttaa actataagat aagtaagcct ctccagacca   8700
tacaagtgcg cgtcgagccc atgcgaaggg tttggttaag atatgccaga ttccaccaag   8760
tatacaaatg aaacctaacc atacatgtcc tccgattata taatgcaaat tgattcattc   8820
aaactaaact tttaagcgtc acagttatac tagcaaatac ctttaagaca ttaagcttca   8880
cgtcttaaaa catca                                                   8895

SEQ ID NO: 17          moltype = DNA  length = 7951
FEATURE                Location/Qualifiers
variation              1..7951
                       note = n is a, c, g, or t
variation              5069..5130
                       note = n is a, c, g, or t
variation              6277..6653
                       note = n is a, c, g, or t
source                 1..7951
                       mol_type = other DNA
                       organism = Nicotiana benthamiana
SEQUENCE: 17
gaatgagcaa agcaagaaat taaaaagaga gagaggtgct ttatccatca aatgtggcta    60
tggtaggaag agccaatggt gggacatttt tggagtgtag ccaaaacata aggaaggtc    120
cagtgcgagt tactgcaaat tgagttggga gtgaggatta agaagatag taacatattt   180
ctagctaaat agcaaacaaa tgatccgtta acagaagtgg ccaaaccacc aaattcaggc   240
atctccacca aatattagtt tttttatacac aaaagattca aacaaacag ttaagtactt   300
ctttaatcgt tcctaattct ttgttcaggg gtatcttttt gtgggtaacg gccaaaccac   360
cacaaatttt cagttcccac tcttaactct ttcaacttca acacaacaaa ttagtatttg   420
cttttccttc tttgcttatc tagtgcataa cgatttttcta caactttagc atagtccaca   480
acgtgaaaca caactccttg gcggtttata ccgaggtaag aaatgatttt ggtttctttg   540
gttacatcag ctgaatgctt tgcttgagaa aagctctctt ttccgtttt aggatcttgt    600
ttatttgctt tcgttttttct actcgtttga attttaactt gattttgtgg gtgaaggcta   660
atttttctca tagtgtaaga acaagtttca tatgtactgt aaaagctaga atctttttta   720
cttttgcata taaatttgtg taataaatgc ttaagaacca gaatatttga aaaagataag   780
gaatttgca tagtatttag gttcacaagt gggacatttt tcttacactg aaatatcttt   840
atgtcaggct taatttactg ctatcttgtt caataaaatg ccccaaattg gacttgtttc   900
tgccgttaat ttgagagtcc aaggtaattc agcttatctt tggagctcga ggtcttcgtt   960
gggaactgaa agtcaagatg tttgcttgca aaggaattttg ttatgttttg gtagtagcga  1020
ctccatgggg cataagttaa ggattcgtac tccaagtgac acgacccgaa gattgacaaa  1080
ggactttaat cctttaaagg tttgttttga atgcgaaagt ggtatgctga atttatgatc  1140
gtgggcatat atcctctaaa ataagagatg tatatcttgc cattcaggta gtctgcattg  1200
attatccaag accagagcta gacaatacag ttaactattt ggaggcggcg ttattatcat  1260
catcgtttcg tacttcctca cgcccaacta aaccattgga gattgttatt gctggtgcag  1320
gtgattttttt ccagccatct atatttgtag ttttcatttt tctttctttg gaaggaagat  1380
cattctatta gttatattat cactagaata ttttaacctga cattcttttc tgattaactg  1440
ttttggaccg caaaatttta ggttcttact tcttcgccat tttgcaacta atcagcaatt  1500
wrdaggagcg gtttgaaaac tagttttgttt tgaactattt ttgccgtcac tctatttata  1560
tactgttgaa ttgtcccaaa tcggtggaat ttgaggtcct tggtctcatc tcataagcta  1620
gcttttgggg ttgagttacc acatcggtgg gatttgaggt ccttcgtctc cttatatgtt  1680
cttggacaag cttcacctca taagctagct tttggggtta gagttaggcc caaggtccat  1740
```

-continued

```
ttatcatatg cttgtctatt ctctcttatc atctgagcca tgataagcgg gtgaacgtgc 1800
tgtctattgg gtggcatgtc caaaggatca ttctgaaata ttggaggcaa atgaaccaat 1860
accttgtgca agattgatct cactatacct ataatcagag tactgagttc caaaaatttc 1920
aaaacccatt gaaaagtcaa acgagttaca tataggggtt gcactcttct acggcttgca 1980
atatgtgaga aaaagatgag aagtcgatct tcatatttca tctttactag gctggaccat 2040
tgactggtta gcagttttga acttgttctt caacttggct tgcatggtac tgtgccgatc 2100
attttcttttg tattgtcatc agctggttga ttatctgagt acctaaagaa agaatgttat 2160
atgcatgata tattctactg tactataaaa gatataataa agaatgctag ccgaggtact 2220
gcatggcctt ttcagataaa tagaaagctgt agcatgattc taattcaatt tttttgggaa 2280
tatcaggttt gggtggtttg tctacagcaa aatatctggc agatgctggt cacaaaccga 2340
tattgctgga ggcaagagat gtcctaggtg ggaaggtgaa gaatatccaa tcttttccttt 2400
aattttattc cttttttcttt tgtgtccttc cctattgata gtcccttttc aggaaggctt 2460
ctgtttgttt tatttgaaat cattttttcat actctttaag cattcagttg ctcaaacaat 2520
tgcaaggata ttcactattc ctaatttgta ccgtcttctt ttctctcagt ttagtttttat 2580
tccctctct ttttgaagga aatagatctg tcctaaaaat ttccagcttt actactaata 2640
gtgttaattg tcgataaaat agtacatcat attaggtaaa agatatggac tgtatattat 2700
tatcattctc tattattttta aactgagtca atttttaaccg tcctgttggg tgcatttctc 2760
atataaacag tcttttctgt gagatgctat gtgaattagc tgattgttttt ggtatagagc 2820
actatgttag tcagttttat cttactgaag cagtcaccaa gagtctagtt gtataggcta 2880
gaagattgaa ttagcattaa tcttttatgtg ttctgcaccct gaatacttgt acctcccttt 2940
taggtagctg catggaaaga tgatgatgga gattggtacg agactgggtt gcacatattc 3000
tgtaagtttg actcctcaag aatgctactt taatcttcta atacagtcat agcaatttct 3060
ttcaagatct cttttattaa tcagatagct atccctgttt gtcttttgtc ttttgcaaat 3120
agccaatttt tgtcagtcga tctgtattct gccttgcctc tctttattta tctgctaact 3180
cgtatggtga ctcatacaag ttggtgcatc tcctttaagt tggggcttac ccaaatatgc 3240
agaacctgtt tggagaacta gggattgatg atcggttgca gtggaaggaa cattcaatga 3300
tatttgcgat gcctaacaag ccaggggagt tcagccgctt tgattttcct gaagctcttc 3360
ctgcgccatt aaatggtaag tacttaatca tgagtaaatt tctcccttca gcgttgatta 3420
tgcaaacttc cccaataagg tatgaaattg attagtctta ataccctggc acattgctaa 3480
catcaaaaga acataaaggt tcattacgtc ttgatcagaa tttctgcatg tagctaaagt 3540
gaatgagtgt ctgtatagat ttttacacat tgcaagcata agcctgttat gttatctctt 3600
tttttcattt ctctacctgt atctcttatt ctcatttctc tatctatgcg ttattacttc 3660
tacaggaatt ttggccatac taaagaacaa cgaaatgctt acgtggcccg agaaagtcaa 3720
atttgctatt ggactcttgc cagcaatgct tggagggcaa tcttatgttg aagctcaaga 3780
cggtttaagt gttaaggact ggatgagaaa gcaagtgcgt gatcgttta tcttattctt 3840
taaagttcat aaccttgagg acatagttga cttgcatatt gttgatttaa catgttcgaa 3900
ttgtctacct gcctttcttt ttctaacaac atagatctta caatctcagc agcagctatt 3960
tgcttaatgc ttttcaggt gtgcctgata gggtgacaga tgaggtgttc attgccatgt 4020
caaaggcact taacttcata aaccctgacg agctttcgat gcagtgcatt ttgattgctt 4080
tgaacagatt tcttcaggtt agaatcctga tccaccctca aaacaaaaag agagaaaggg 4140
atataatcct accaaagctg taaatcatgt tagggacctg acatatcggt gcaggaaact 4200
tatgagtgaa cttgtccact ctgtttaact tttctgatat atttgaatta ttaatctgca 4260
ggagaaacat ggttcaaaaa tggccttttt agatggtaac cctcctgaga gactttgcat 4320
gccgattgtg aacatattg agtcaaaagg tggccaagtc agactaaaact cacgaataaa 4380
aaagatcgag ctgaatgagg atggaagtgt caaatgtttt atactgaata atggcagtac 4440
aattaaagga gatgcttttg tgtttgccac tccaggtata atatccatta tactagtatg 4500
acgcttccag ttttcacatt ttaatatgaa tttataggtt tttgctgact tttgattatc 4560
caattagtgg atatcttgaa gcttctttttg cctgaagact ggaaagagat cccatatttc 4620
caaaagttgg agaagctagt gggagttcct gtgataaatg tccatatatg gttagtgatg 4680
aaaatttgc ttttcagtgt ttggtcttcc tctagcatat ctatgtatgt gcatgttaat 4740
gtctatacgt acatgtttat ggtcctcc cgtattgtgt ttacttccct tgaatgagga 4800
acttatggat gtacgctttt ccaactttga ttgtacacat tgcaattgtc tgttcaactt 4860
tgaggagcag aacttccatt gtttagctat tagtggctga gattcctgct gaaaagattt 4920
gtataaattt aattttgcagg tttgacagaa aactgaagaa cacatctgat aatctgctct 4980
tcagcaggtt catttttgat caatttttatt gttccagacc agtttctgcg tgtccatgac 5040
tacattctca tattagctcc cccccccnn nnnnnnnnn nnnnnnnnnn nnnnnnnnn 5100
nnnnnnnnn nnnnnnnnnn nnnnnnnnnn cccccccccc ccggtctctt ttttgccatt 5160
taaatgagac cttacaattt gtttagtact ctaccatagt ttttttaatca ataagccaaa 5220
ggggaaaaac taataaaagt gtataaaatt tcttcctgta ttagtccaat tcttttcgaa 5280
cttatattgt taattattat ttatcttttg gattgaaatg gattttgtat atctaataat 5340
ataaacaaat atatctcttc ctcttataag attttttcacc atagaaaaat gctcccataa 5400
ggtcagtcat tctggctaaa tatcccacac ttcaaccatt gagatatttt gttctttgca 5460
tccaggaata catttggcat caatagatag gaatcaatga agatatatta tcaatttcct 5520
gcaagtttct tggcactaga aacattagat ccatatcgta taaattgcct ttgttaaatt 5580
gaaggtctat gaaatttggg ttggtttgaa aaccttttgt ttttccccc cacatcccta 5640
atcgtttatt tagtcaaggt cagacctgac atgttatgat gaccatttct ccaaggcatt 5700
tataatggac tggagtatcc atgccacatt tcatcagcta catgtcgatt atgttcccct 5760
acttttaaat ggcaccattg ttggtggagc aagattatag attttcctga tacttgtatg 5820
ggttccccttg ctcaatctct cttttacttc atgcagaagc ccgttgctca gtgtgtacgc 5880
tgacatgtct gttacatgta aggtattgac tcgtctgtac cattatactg gtctaatctg 5940
ttgggtatga gttgctggta aattgcataa tgcttgttgg atttgtgtgt gagttgctgc 6000
tagatctatg tcctgctata tttatgtatg agttgctgtt gttgcaatct tcatttcgaa 6060
tgcataatga tataggttct gtatgtacgg aatagtcagg acaatgctcc tgtctgtgca 6120
cgggggctct acaggaagca acttccggag gagaagtaca gaaagtgtga tgaatcctaa 6180
ggcggttaaa gtagtttctt ttagctaaat tttgaaataa tttgaaggag gggaaaacgc 6240
tctctcagtc tgtggttgca ttggttgtgg gggggggnnn nnnnnnnnn nnnnnnnnn 6300
nnnnnnnnn nnnnnnnnnn nnnnnnnnnn nnnnnnnnnn nnnnnnnnnn nnnnnnnnn 6360
nnnnnnnnn nnnnnnnnnn nnnnnnnnnn nnnnnnnnnn nnnnnnnnnn nnnnnnnnn 6420
nnnnnnnnn nnnnnnnnnn nnnnnnnnnn nnnnnnnnnn nnnnnnnnnn nnnnnnnnn 6480
```

```
nnnnnnnnnn nnnnnnnnnn nnnnnnnnnn nnnnnnnnnn nnnnnnnnnn nnnnnnnnnn   6540
nnnnnnnnnn nnnnnnnnnn nnnnnnnnnn nnnnnnnnnn nnnnnnnnnn nnnnnnnnnn   6600
nnnnnnnnnn nnnnnnnnnn nnnnnnnnnn nnnnnnnnnn nnnnnnnnnn nnntggaggg   6660
accttaattc agtgttacct gcatataaat cagactaaag cctggagatc agacgttctg   6720
catataaata gataattaat aatgatctcg taatactcta aagcctggag atcagactgt   6780
tttaactatc ctgagatgat tacttttact ctcggattag cttaggcgag ctgcaagact   6840
acatcgaatc tttagaaatg ggaacataaa aaaggtgcga agtggggaag tggctgaaca   6900
ataggcatat gtgagtgagt ggggagtaaa attacttcct ttacttgggt acagtcaaga   6960
atggatgaca gcttagccca ctatatctgt tcatgtgttc tttagggtcc tctgatataa   7020
ctggtctctc tgcaggaata ttacaacccc aatcagtcta tgttggaatt ggtatttgca   7080
cccgcagaag agtggataaa tcgtagtgac tcagaaatta ttgatgctac aatgaaggaa   7140
ctagcgaagc ttttccctga tgaaatttcg gcagatcaga gcaaagcaaa aatattgaag   7200
tatcatgttg tcaaaacccc aaggtcagta atcattttgc tttcatagtt gtgtagtatg   7260
cgagaattac tgtccacgtg gaatctattc ctgttatgaa tcctgattaa tctgcttttt   7320
actttcaggt ctgtttataa aactgtgcca ggttgtgaac cctgtcggcc cttgcaaaga   7380
tcccctatag agggttttta tttagctggt gactacacga aacagaagta cttggcttca   7440
atggaaggtg ctgtcttatc aggaaagctt tgtgccgaag ctattgtaca ggttagctct   7500
cacattttttt tcccttccat tgatagtgta tttgattata tttgtcatc tttgctgcgg   7560
tagagaattt tagaagcatt tctcagacat tagttagcag agttactcag gatatctgca   7620
gttttggagc ttcagtagta gcatgataaa atgcagagga ttgtgttttt tcattcttta   7680
ttaaaccttg tgccaaaggt cttttggaaa caacctctct accccgaggt aggggtaagg   7740
tctgcgtaca tattaccctc cccataccec atgcgtggga ttatactggg tggttgttgt   7800
ataaacctat atctctataa tttgcaggat tacgagttac ttcttggccg agccagaag    7860
atgttggcag aagcaagcgt agttagcata gtgaactaaa atgttaattc tgtacacaaa   7920
atttaagatg aaggcggcca cgctgaatta g                                  7951

SEQ ID NO: 18          moltype = DNA   length = 10145
FEATURE                Location/Qualifiers
source                 1..10145
                       mol_type = other DNA
                       organism = synthetic construct
SEQUENCE: 18
gtaggcggtg ctacagagtt cttgaagtgg tggcctaact acggctacac tagaaggaca     60
gtatttggta tctgcgctct gctgaagcca gttaccttcg gaaaaagagt tggtagctct    120
tgatccggca aacaaaccac cgctggtagc ggtggttttt ttgtttgcaa gcagcagatt    180
acgcgcagaa aaaaggatc tcaagaagat cctttgatct tttctacggg gtctgacgct     240
cagtggaacg aaaactcacg ttaagggatt ttggtcatgc attctaggta ctaaaacaat    300
tcatccagta aaatataata tttttattttc tcccaatcag gcttgatccc cagtaagtca    360
aaaaatagct cgacatactg ttcttcccg atatcctccc tgatcgaccg gacgcagaag     420
gcaatgtcat accacttgtc cgccctgccg cttctcccaa gatcaataaa gccacttact    480
ttgccatctt tcacaaagat gttgctgtct cccaggtcgc cgtgggaaaa gacaagttcc    540
tcttcgggct tttccgtctt taaaaaatca tacagctcgc gcggatcttt aaatggagtg    600
tcttctttccc agttttcgca atccacatcg gccagatcgt tattcagtaa gtaatccaat    660
tcggctaagc ggctgtctaa gctattcgta tagggacaat ccgatatgtc gatggagtga    720
aagagcctga tgcactccgc atacagctcg ataatctttt cagggctttg ttcatcttca    780
tactcttccg agcaaaggac gccatcggcc tcactcatga gcagattgct ccagccatca    840
tgccgttcaa agtgcaggac cttgaaca ggcagctttc cttccagcca tagcatcatg     900
tccttttccc gttccacatc ataggtggtc cctttatacc ggctgtccgt cattttaaa    960
tataggtttt cattttctcc caccagctta tataccttag caggagacat tccttccgta   1020
tcttttacgc agcggtattt ttcgatcagt ttttttcaatt ccggtgatat tctcattta    1080
gccatttatt atttccttcc tctttttctac agtatttaaa gatacccaa gaagctaaa    1140
ataacaagac gaactccaat tcactgttcc ttgcattcta aaaccttaaa taccagaaaa   1200
cagcttttc aaagttgttt tcaaagttgg cgtataacat agtatcgacg agccgatttt   1260
tgaaccgcg gtgatcacag gcagcaacgc tctgtcatcg ttacaatcaa catgctaccc    1320
tccgcgagat catccgtgtt tcaaacccgg cagcttagtt gccgttcttc cgaatagcat    1380
cggtaacatg agcaaagtct gccgccttac aacggctctc ccgctgacgc cgtcccggac    1440
tgatgggctg cctgtatcga gtggtgatt tgtgccgagc tgccggtcgg ggagctgttg    1500
gctggctggt ggcaggatat attgtggtgt aaacaaattg acgcttagac aacttaataa    1560
cacattgcgg acgttttaa tgtagagctc aaagtttaac gcgttagcag aaggcatgtt    1620
gttgtgactc cgaggggttg cctcaaactc tatcttata ccggcgtgga ggcatggagg     1680
caggggtatt ttggtcattt taatagatag tggaaaatga cgtggaattt acttaaagac    1740
gaagtctttg cgacaagggg gggcccacgc cgaatttaat attaccggcg tggccccccc    1800
ttatcgcgag tgctttagca cgagcggtcc agatttaaag tagaaaattt cccgcccact    1860
agggttaaag tgttcacac tataaaagca tatacgtcgt gatggtattt gatgggacgt    1920
atattgtatc aggtatttcc gttggatacg aattattcgt acgaccctcg gtaccgatca    1980
aaagcaggtg acaagtttgt acaaaaaagc tgaacgagaa acgtaaaatg atataaaatt    2040
caatatattta aattagattt tgcataaaaa acagactaca taatactgta aaacacaaca    2100
tatccagtca ctatggcggc cgcattaggc accccaggct ttacacttta tgcttccggc    2160
tcgtataatg tgtggatttt gagttaggat ccgtcgagac tttcaggagc taaggaagct    2220
aaaatggaga aaaaaatcac tggatatacc accgttgata tatcccaatg gcatcgtaaa    2280
gaacattttg aggcatttca gtcagttgct caatgtacct ataaccagac cgttcagctg    2340
gatattacgg cctttttaaa gaccgtaaag aaaaataagc acaagtttta tccggccttt    2400
attcacattc ttgcccgcct gatgaatgct catccggaat tccgtatggc aatgaaagac    2460
ggtgagctgg tgatatggga tagtgttcac ccttgttaca cgttttcca tgagcaaact    2520
gaaacgtttt catcgctctg gagtgaatac cacgacgatt tccggcagtt tctacacata    2580
tattcgcaag atgtggcgtg ttacggtgaa aacctggcct atttccctaa agggtttatt    2640
gagaatatgt tttcgtctc agccaatccc tgggtgagtt tcaccagttt tgatttaaac    2700
gtggccaata tggacaactt cttcgccccc gttttcacca tgggcaaata ttatacgcaa    2760
ggcgacaagg tgctgatgcc gctggcgatt caggttcatc atgccgtttg tgatggcttc    2820
```

-continued

```
catgtcggca gaatgcttaa tgaattacaa cagtactgcg atgagtggca ggcggggcgt  2880
aatctagagg atccggctta ctaaaagcca gataacagta tgcgtatttg cgcgctgatt  2940
tttgcggtat aagaatatat actgatatgt atacccgaag tatgtcaaaa agaggtatgc  3000
tatgaagcag cgtattacag tgacagttga cagcgcacagc tatcagttgc tcaaggcata  3060
tatgatgtca atatctccgg tctggtaagc acaaccatgc agaatgaagc ccgtcgtctg  3120
cgtgccgaac gctggaaagc ggaaaatcag gaagggatgg ctgaggtcgc ccggtttatt  3180
gaaatgaacg gctcttttgc tgacgagaac aggggctggt gaaatgcagt ttaaggttta  3240
cacctataaa agagagagcc gttatcgtct gtttgtggat gtacagagtg atattattga  3300
cacgcccggg cgacggatgg tgatccccct ggccagtgca cgtctgctgt cagataaagt  3360
cccccgtgaa ctttacccgg tggtgcatat cggggatgaa agctggcgca tgatgaccac  3420
cgatatggcc agtgtgccgg tctccgttat cggggaagaa gtggctgatc tcagccaccg  3480
cgaaaatgac atcaaaaacg ccattaacct gatgttctgg ggaatataaa tgtcaggctc  3540
ccttatacac agccagtctg caggtcgacc atagtgactg gatatgttgt gttttacagt  3600
attatgtagt ctgttttta tgcaaaatct aatttaatat attgatattt atatcattt  3660
acgtttctcg ttcagctttc ttgtacaaag tggtcacctg caaaaagtgt ttgatcgccg  3720
gcggtaccga gtgtacttca agtcagtggg aaatcaataa aatgattatt ttatgaatat  3780
atttcattgt gcaagtagat agaaattaca tatgttacat aacacacgaa ataaacaaaa  3840
aaagacaatc caaaaacaaa caccccaaaa aaaataatca ctttagataa actcgtatga  3900
ggagaggcac gttcagtgac tcgacgattc ccgagcaaaa aaagtctccc cgtcacacat  3960
gtagtgggtg acgcaattat ctttaaagta atccttctgt tgacttgtca ttgataacat  4020
ccagtcttcg tcaggattgc aaagaattat agaagggatc ccaccttta ttttcttctt  4080
ttttccatat ttagggttga cagtgaaatc agactagcaa cctattaatt gcttccacaa  4140
tgggacgaac ttgaagggga tgtcgtcgat gatattatag gtggcgtgtt catcgtagtt  4200
ggtgaaatcg atggtaccgt tccaatagtt gtgtcgtccg agacttctag cccaggtggt  4260
ctttccggta cgagttggtc cgcagatgta gaggctgggg tgtcggattc cattccttcc  4320
attgtccttg ttaaatcggc catccattca aggtcagatt gagcttgttg gtatgagaca  4380
ggatgtatgt aagtataagc gtctatgctt acatggtata gatgggtttc cctccaggag  4440
tgtagatctt cgtggcagcg aagatctgat tctgtgaagg gcgacacata cggttcaggt  4500
tgtggaggga taaatttgtt ggctgaatat tccagccatt gaagctttgt tgcccattca  4560
tgagggaatt cttcctgat catgtcaaga tattcctcct tagacgttgc agtctggata  4620
atagttctcc atcgtgcgtc agatttgcga ggagaaacct tatgatctcg gaaatctcct  4680
ctggttttaa tatctccgtc ctttgatatg taatcaagga cttgtttaga gtttctagct  4740
ggctggatat tagggtgatt tccttcaaaa tcgaaaaag aaggatccct aatacaaggt  4800
tttttatcaa gctggagaag agcatgatag tgggtagtgc catcttgatg aagctcagaa  4860
gcaacaccaa ggaagaaaat aagaaaaggt gtgagtttct cccagagaaa ctggaataaa  4920
tcatctcttt gagatgagca cttgggatag gtaaggaaaa catatttaga ttggagtctg  4980
aagttcttac tagcagaagg catgttgttg tgactccgag gggttgcctc aaactctatc  5040
ttataaccgt cgtggaggca tggaggcagg ggtattttgg tcattttaat agatagtgga  5100
aaatgacgtg gaatttactt aaagacgaag tctttgcgac aagggggggc ccacgccgaa  5160
tttaatatta ccggcgtggc ccccccttat cgcgagtgct ttagcacgag cggtccagat  5220
ttaaagtaga aaatttcccg cccactaggg ttaaaggtgt tcacactata aaagcatata  5280
cgatgtgatg gtatttgatg gagcgtatat tgtatcaggt atttccgttg gatacgaatt  5340
attcgtacga ccctcatagt ttaaactatc agtgtttgac aggatatatt ggcgggtaaa  5400
cctaagagaa aagagcgttt attagaataa cggatattta aaaggggctg aaaaggttta  5460
tccgttcgtc catttgtatg tgcatgccaa ccacagggtt cccctcggga tcaaagtact  5520
ttgatccaac ccctccgctg ctatagtgca gtcggcttct gacgttcagt gcagccgtct  5580
tctgaaaacg acatgtcgca caagtcctaa gttacgcgac aggctgccgc cctgcccttt  5640
tcctggcgtt ttcttgtcgc gtgttttagt cgcataaagt agaatacttg cgactagaac  5700
cggagacatt acgccatgaa caagagcgcc gccgctggcc tgctgggcta tgcccgcgtc  5760
agcaccgacg accaggactt gaccaaccaa cgggccgaac tgcacgcggc cggctgcacc  5820
aagctgtttt ccgagaagat caccggcacc aggcgcgacc gcccggagct ggccaggatg  5880
cttgaccacc tacgccctgg cgacgttgtg acagtgacca ggctagaccg cctggcccgc  5940
agcacccgcg acctactgga cattgccgag cgcatccagg aggccggcgc gggcctgcgt  6000
agcctggcag agccgtgggc cgacaccacc acgccgccgc cgcatggt gttgaccgtg  6060
ttcgccggca ttgccgagtt cgagcgttcc ctaatcatcg accgcacccg gagcgggcgc  6120
gaggccgcca aggccgaggc gtgaagtttt ggccccgcc ctaccctcac cccgcacag  6180
atcgcgcacg cccgcgagct gatcgaccag gaaggccgca ccgtgaaaga gcggctgca  6240
ctgcttggcg tgcatcgctc gaccctgtac cgcgcacttg agcgcagcga ggaagtgacg  6300
cccaccgagg ccaggcggcg cggtgccttc cgtgaggacg cattgaccga ggccgacgcc  6360
ctggcggccg ccgagaatga acgccaagag gaacaagcat gaaaccgcac caggacgcc  6420
aggacgaacc gttttttcatt accgaagaga tcgaggcgga gatgatcgcg gccgggtacg  6480
tgttcgagcc gcccgcgcac ggctcaaccg tgcggctgca tgaaatcctg gccggtttgt  6540
ctgatgccaa gctggcggcc tggccggcca gcttggccgc tgaagaaacc gagcgccgcc  6600
gtctaaaaag gtgatgtgta tttgagtaaa acagcttgcg tcatgcggtc gctgcgtata  6660
tgatgcgatg agtaaataaa caaatacgca aggggaacgc atgaaggtta tcgctgtact  6720
taaccagaaa ggcgggtcag gcaagacgac catcgcaacc catctagccc gcgccctgca  6780
actcgccggg gccgatgttc tgttagtcga ttccgatccc cagggcagtg cccgcgattg  6840
gcggccgtg cgggaagatc aaccgctaac cgttgtcggc atcgaccgcc cgacgattga  6900
ccgcgacgtg aaggccatcg gccggcgcga cttcgtagtg atcgacgaag cgcccccagge  6960
ggcggacttg gctgtgtccg cgatcaaggc agccgacttc gtgctgattc cggtgcagcc  7020
aagcccttac gacatatggg ccaccgccga cctggtggag ctggttaagc agcgcattga  7080
ggtcacggat ggaaggctac aagcggcctt tgtcgtgtcg cgggcgatca aaggcacgcg  7140
catcggcggt gaggttgccg aggcgctggc cgggtacgag ctgcccattc ttgagtcccg  7200
tatcacgcag cgcgtgagct acccaggcac ttccgcaacc ttcttgaatc  7260
agaacccgag ggcgacgctg cccgcgaggt ccaggcgctg gccgctgaaa ttaaatcaaa  7320
actcatttga gttaatgagg taaagagaaa atgagcaaaa gcacaaacac gctaagtgcc  7380
ggccgtccga gcgcacgcag cagcaaggct gcaacgttgg ccagcctggc agacacgcca  7440
gccatgaagc gggtcaactt tcagttgccg cggaggatc acaccaagct gaagatgtac  7500
gcggtacgcc aaggcaagac cattaccgag ctgctatctg aatacatcgc gcagctacca  7560
```

```
gagtaaatga gcaaatgaat aaatgagtag atgaattta gcggctaaag gaggcggcat    7620
ggaaaatcaa gaacaaccag gcaccgacgc cgtggaatgc cccatgtgtg gaggaacggg    7680
cggttggcca ggcgtaagcg gctgggttgt ctgccggccc tgcaatggca ctggaacccc    7740
caagcccgag gaatcggcgt gacggtcgca aaccatccgg cccggtacaa atcggcgcgc    7800
cgctgggtga tgacctggtg gagaagttga aggccgccac cggcaacgca                7860
tcgaggcaga agcacgcccc ggtgaatcgt ggcaagcggc cgctgatcga atccgcaaag    7920
aatcccggca accgccggca gccggtgcgc cgtcgattag gaagccgccc aagggcgacg    7980
agcaaccaga ttttttcgtt ccgatgctct atgacgtggg cacccgcgat agtcgcagca    8040
tcatggacgt ggcgttttc cgtctgtcga agcgtgaccg acgagctggc gaggtgatcc    8100
gctacgagct tccagacggg cacgtagagg tttccgcagg gccggccggc atggccagtg    8160
tgtgggatta cgacctggta ctgatggcgg tttccatct aaccgaatcc atgaaccgat    8220
accgggaagg gaagggagac aagcccggcc gcgtgttccg tccacacgtt gcggacgtac    8280
tcaagttctg ccggcgagcc gatggcgaaa agcagaaaga cgacctggta gaaacctgca    8340
ttcggttaaa caccacgcac gttgccatgc agcgtacgaa gaaggccaag aacggccgcc    8400
tggtgacggt atccgagggt gaagccttga ttagccgcta caagatcgta aagagcgaaa    8460
ccgggcggcc ggagtacatc gagatcgagc tagccgattg gatgtaccgc gagatcacag    8520
aaggcaagaa cccggacgtg ctgacggttc accccgatta ctttttgatc gatcccggca    8580
tcggccgttt tctctaccgc ctggcacgcc gcgccgcagg caaggcagaa gccagatggt    8640
tgttcaagac gatctacgaa cgcagtggca gcgccggaga gttcaagaag ttctgttca    8700
ccgtgcgcaa gctgatcggg tcaaatgacc tgccggagta cgatttgaag gaggaggcgg    8760
ggcaggctgg cccgatccta gtcatgcgct accgcaacct gatcgagggc gaagcatccg    8820
ccggttccta atgtacggag cagatgctag ggcaaattgc cctagcaggg gaaaaaggtc    8880
gaaaaggcct cttttcctgtg gatagcacgt acattgggaa cccaaagccg tacattggga    8940
accggaaccc gtacattggg aacccaaagc cgtacattgg gaaccggtca cacatgtaag    9000
tgactgatat aaaagagaaa aaaggcgatt tttccgccta aaactcttta aaacttatta    9060
aaactcttaa aacccgctg gcctgtgcat aactgtctgg ccagcgcaca gccgaagagc    9120
tgcaaaaagc gcctacccctt cggtcgctgc gctccctacg ccccgccgct tcgcgtcggc    9180
ctatcgcggc cgctggccgc tcaaaaatgg ctggcctacg gccaggcaat ctaccagggc    9240
gcggacaagc cgcgccgtcg ccactcgacc gccggcgccc acatcaaggc accctgcctc    9300
gcgcgtttcg gtgatgacgg tgaaaacctc tgacacatgc agctcccgga aacggtcaca    9360
gcttgtctgt aagcggatgc cgggagcaga caagcccgtc agggcgcgtc agcgggtgtt    9420
ggcgggtgtc ggggcgcagc catgacccag tcacgtagcg atagcggagt gtatactggc    9480
ttaactatgc ggcatcagag cagattgtac tgagagtgca ccatatgcgg tgtgaaatac    9540
cgcacagatg cgtaaggaga aaataccgca tcaggcgctc ttccgcttcc tcgctcactg    9600
actcgctgcg ctcggtcgtt cggctgcggc gagcggtatc agctcactca aaggcggtaa    9660
tacggttatc cacagaatca ggggataacg caggaaagaa catgtgagca aaaggccagc    9720
aaaaggccag gaaccgtaaa aaggccgcgt tgctggcgtt tttccatagg ctccgccccc    9780
ctgacgagca tcacaaaaat cgacgctcaa gtcagaggtg gcgaaacccg acaggactat    9840
aaagatacca ggcgtttccc cctggaagct ccctcgtgcg ctctcctgtt ccgaccctgc    9900
cgcttaccgg atacctgtcc gcctttctcc cttcggaag cgtggcgctt tctcatagct    9960
cacgctgtag gtatctcagt tcggtgtagg tcgttcgctc caagctgggc tgtgtgcacg    10020
aacccccgt tcagcccgac cgctgcgcct tatccggtaa ctatcgtctt gagtccaacc    10080
cggtaagaca cgacttatcg ccactggcag cagccactgg taacaggatt agcagagcga    10140
ggtat                                                                10145
SEQ ID NO: 19          moltype = DNA  length = 12261
FEATURE                Location/Qualifiers
source                 1..12261
                       mol_type = other DNA
                       organism = synthetic construct
SEQUENCE: 19
gtaggcggtg ctacagagtt cttgaagtgg tggcctaact acggctacac tagaaggaca      60
gtatttggta tctgcgctct gctgaagcca gttaccttcg gaaaaagagt tggtagctct     120
tgatccggca aacaaccac cgctggtagc ggtggttttt tgtttgcaa gcagcagatt       180
acgcgcagaa aaaaggatc tcaagaagat cctttgatct tttctacggg gtctgacgct      240
cagtggaacg aaaactcacg ttaagggatt ttggtcatgc attctaggta ctaaaacaat     300
tcatccagta aaatataata ttttatttc tcccaatcag gcttgatccc cagtaagtca     360
aaaaatagct cgacatactg ttcttccccg atatcctccc tgatcgaccg gacgcagaag    420
gcaatgtcat accacttgtc cgccctgccg ctttctcccaa gatcaataaa gccacttact    480
ttgccatctt tcacaaagat gttgctgtct cccaggtcgc cgtgggaaaa gacaagttcc    540
tcttcgggct tttccgtctt taaaaaatca tacagctcgc gcggatcttt aaatggagtg   600
tcttcttccc agttttcgca atccacatcg gccagatcgt tattcagtaa gtaatccaat    660
tcggctaagc ggctgtctaa gctattcgta tagggacaat ccgatatgtc gatggagtga    720
aagagcctga tgcactccgc atacagctcg ataatctcg caggggctttg ttcatcttca    780
tactcttccg agcaaaggac gccatcggcc tcactcatga gcagattgct ccagccatca    840
tgccgttcaa agtgcaggac cttggaaca ggcagcttc cttccagcca tgcatcatg      900
tccttttccc gttccacatc ataggtggtc cctttatacc ggctgtccgt cattttaaa      960
tataggtttt cattttctcc caccagctta tacccttag caggagacat tccttccgta    1020
tcttttacgc agcggtattt ttcgatcagt tttttcaatt ccggtgatat tctcattta   1080
gccatttatt atttccttcc tcttttctac agtatttaaa gatacccaa gaagctaatt    1140
ataacaagac gaactccaat tcactgttcc ttgcattcta aaacctttaaa taccagaaaa   1200
cagctttttc aaagttgttt tcaaagttgg cgtataacat agtatcgacg agccgattt    1260
tgaaaccgcg gtgatcacag gcagcaacgc tctgtcatcg ttacaatcaa catgctaccc    1320
tccgcgagat catccgtgtt tcaaaccgg cagcttagtt gcgttcttc cgaatagcat    1380
cggtaacatg agcaaagtct gccgccttac aacggctctc ccgctgacgc cgtcccggac   1440
tgatgggctg cctgtatcga gtggtgattt tgtgccgagc tgccggtcgg ggagctgttg    1500
gctggctggt ggcaggatat attgtggtgt aaacaaattg acgcttagac aacttaataa    1560
cacattgcgg acgtttttaa tgtactgaat taacgccgaa ttaattcggg ggatctggat    1620
tttagtactg gattttggtt ttaggaatta gaaatttat tgatagaagt attttacaaa    1680
```

```
tacaaataca tactaagggt ttcttatatg ctcaacacat gagcgaaacc ctataggaac  1740
cctaattccc ttatctggga actactcaca cattattatg gagaaactcg agcttgtcga  1800
tcgactctag ctagaggatc gatccgaacc ccagagtccc gctcagaaga actcgtcaag  1860
aaggcgatag aaggcgatgc gctgcgaatc gggagcggcg ataccgtaaa gcacgaggaa  1920
gcggtcagcc cattcgccgc caagttcttc agcaatatca cgggtagcca acgctatgtc  1980
ctgatagcgg tccgcacac ccagccggcc acagtcgatg aatccagaaa agcggccatt  2040
ttccaccatg atattcggca agcaggcatc gccatgtgtc acgacgagat cctcgccgtc  2100
gggcatgcgc gccttgagcc tggcgaacag ttcggctggc gcgagcccct gatgttcttc  2160
gtccagatca tcctgatcga caagaccggc ttccatccga gtacgtgctc gctcgatgcg  2220
atgtttcgct tggtggtcga atgggcaggt agccggatca agcgtatgca gccgccgcat  2280
tgcatcagcc atgatggata ctttctcggc aggagcaagg tgagatgaca ggagatcctg  2340
ccccggcact tcgcccaata gcagccagtc ccttcccgct tcagtgacaa cgtcgagcac  2400
agctgcgcaa ggaacgcccg tcgtggccag ccacgatagc cgcgctgcct cgtcctggag  2460
ttcattcagg gcaccggaca ggtcggtctt gacaaaaaga accgggcgcc cctgcgctga  2520
cagccgaaac acggcggcat cagagcagcc gattgtctgt tgtgcccagt catagccgaa  2580
tagcctctcc acccaagcgg ccggagaacc tgcgtgcaat ccatcttgtt caatccccat  2640
ggtcgatcga cagatctgcg aaagctcgag agagatagat ttgtagagag agactggtga  2700
tttcagcgtg tcctctccaa atgaaatgaa cttccttata tagaggaagg tcttgcgaag  2760
gatagtggga ttgtgcgtca tcccttacgt cagtggagat atcacatcaa tccacttgct  2820
ttgaagacgt ggttggaacg tcttctttt ccacgatgct cctcgtgggt ggggtccat   2880
ctttgggacc actgtcggca gaggcatctt gaacgatagc ctttccttta tcgcaatgat  2940
ggcatttgta ggtgccacct tccttttcta ctgtcctttt gatgaagtga cagatagctg  3000
ggcaatggaa tccgaggagg tttcccgata ttaccctttg ttgaaaagtc tcaatagccc  3060
tttggtcttc tgagactgta tctttgatat tcttggagta gacgagagtg tcgtgctcca  3120
ccatgttatc acatcaatcc acttgctttg aagacgtggt tggaacgtct tcttttcca   3180
cgatgctcct cgtgggtggg ggtccatctt tgggaccact tcggcagag gcatcttgaa   3240
cgatagcctt tcctttatcg caatgatggc atttgtaggt gccaccttcc ttttctactg  3300
tccttttgat gaagtgacag atagctgggc aatggaatcc gaggaggttt cccgatatta  3360
cccttttgttt aaaagtctca atagccctt ggtcttctga gactgtatct ttgatattct  3420
tggagtagac gagagtgtcg tgctccacca tgttggcaag ctgctctagc caatacgcaa  3480
accgcctctc cccgcgcgtt ggccgattca ttaatgcagc tggcacgaca ggtttcccga  3540
ctggaaagcg ggcagtgagc gcaacgcaat taatgtgagt tagctcactc attaggcacc  3600
ccaggcttta cactttatgc ttccggctcg tatgttgtgt ggaattgtga gcggataaca  3660
atttcacaca ggaaacagct atgaccatga ttacgaattc gagctcaaag tttaacgcgt  3720
tagcagaagg catgttgttg tgactccgag gggttgcctc aaactctatc ttataacgcg  3780
cgtggaggca tggaggcagg ggtatttggt tcatttaat agatagtgga aaatgacgtg   3840
gaatttactt aaagacgaag tctttgcgac aagggggggc ccacgccgaa tttaatatta  3900
ccggcgtggc ccccccttat cgcgagtgct ttagcacgag cggtccagat ttaaagtaga  3960
aaatttcccg cccactaggg ttaaaggtgt tcacactata aaagcatata cgatgtgatg  4020
gtatttgatg gagcgtatat tgtatcaggt atttccgttg gatacgaatt attcgtacga  4080
ccctcggtac cgatcaaaag caggtgacaa gtttgtacaa aaaagctgaa cgagaaacgt  4140
aaaatgatat aaatatcaat atattaaatt agattttgca taaaaaacag actacataat  4200
actgtaaaac acaacatatc cagtcactat ggcggccgca ttaggcaccc caggctttac  4260
actttatgct tccggctcgt ataatgtgtg gattttgagt taggatccgt cgagattttc  4320
aggagctaag gaagctaaaa tggagaaaaa aatcactgga tataccaccg ttgatatatc  4380
ccaatggcat cgtaaagaac attttgaggc atttcagtca gttgctcaat gtacctataa  4440
ccagaccgtt cagctggata ttacggcctt tttaaagacc gtaaagaaaa ataagcacaa  4500
gttttatccg gcctttattc acattcttgc ccgcctgatg aatgctcatc cggaattccg  4560
tatgcaatg aaagacggtg agctggtgat atgggatagt gttcacccctt gttacaccgt   4620
tttccatgag caaactgaaa cgttttcatc gctctggagt gaataccacg acgatttccg  4680
gcagtttcta cacatatatt cgcaagatgt ggcgtgttac ggtgaaaacc tggcctattt  4740
ccctaaaggg tttattgaga atatgttttt cgtctcagcc aatccctggg tgagtttcac  4800
cagttttgat ttaaacgtgg ccaatatgga aacttcttc gcccccgttt tcaccatggg   4860
caaatattat acgcaaggcg acaaggtgct gatgccgctg gcgattcagg ttcatcatgc  4920
cgtttgtgat ggcttccatg tcggcagaat gcttaatgaa ttacaacagt actgcgatga  4980
gtggcaggcg gggcgtaatc tagaggatcc ggcttactaa aagccagata acagtatgcg  5040
tatttgcgcg ctgatttttg cggtataaga atatatactg atatgtatac ccgaagtatg  5100
tcaaaaagag gtatgctatg aagcagcgta ttacagtgac agttgacagc gacagctatc  5160
agttgctcaa ggcatatatg atgtcaatat ctccggtctg gtaagcacaa ccatgcagaa  5220
tgaagcccgt cgtctgcgtg ccgaacgctg gaaagcggaa aatcaggaag gatggctgaa  5280
ggtcgccgg tttattgaaa tgaacggctc ttttgctgac gagaacaggg gctggtgaaa  5340
tgcagtttaa ggtttacacc tataaaagag agagccgtta tcgtctgttt gtggatgtac  5400
agagtgatat tattgacacg cccgggcgac ggatggtgat cccctggcc agtgcacgtc   5460
tgctgtcaga taaagtcccc cgtgaacttt acccggtggt gcatatcaag gatgaagct   5520
ggcgcatgat gaccaccgat atggccagtg tgccggtctc cgttatcggg gaagaagtgg  5580
ctgatctcag ccaccgcgaa aatgacatca aaaacgccat taacctgatg ttctggggaa  5640
tataaatgtc aggctccctt atacacagcc agtctgcagg tcgaccatag tgactggata  5700
tgttgtgttt tacagtatta tgtagtctgt tttttatgca aaatctaatt taatatattg  5760
atatttatat cattttacgt ttctcgttca gctttcttgt acaaagtggt cacctgcaaa  5820
aagtgtttga tcgccggcgg taccgagtgt acttcaagtc agtgggaaat caataaaatg  5880
attatttat gaatatattt cattgtgcaa gtagatagaa attacatatg ttacataaca  5940
cacgaaataa acaaaaaaag acaatccaaa acaaacacc ccaaaaaaaa taatcacttt   6000
agataaaactc gtatgaggag aggcacgttc agtgactcga cgattcccga gcaaaaaaag  6060
tctcccgtc acacatgtag tgggtgacgc aattatcttt aaagtaatcc ttctgttgac  6120
ttgtcattga taacatccag tcttcgtcag gattgcaaag aattatagaa gggatcccac  6180
cttttatttt cttctttttt ccatatttag ggttgacagt gaaatcagac tggcaaccta  6240
ttaattgctt ccacaatggg acgaacttga aggggatgtc gtcgatgata ttataggtgg  6300
cgtgttcatc gtagttggtg aaatcgatgg taccgttcca atagttgtgt cgtccgagac  6360
ttctagccca ggtggtcttt ccggtacgag ttggtccgca gatgtagagg ctggggtgtc  6420
```

```
ggattccatt ccttccattg tccttgttaa atcggccatc cattcaaggt cagattgagc   6480
ttgttggtat gagacaggat gtatgtaagt ataagcgtct atgcttacat ggtatagatg   6540
ggtttccctc caggagtgta gatcttcgtg gcagcgaaga tctgattctg tgaagggcga   6600
cacatacggt tcaggttgtg gagggaataa tttgttggct gaatattcca gccattgaag   6660
ctttgttgcc cattcatgag ggaattcttc cttgatcatg tcaagatatt cctccttaga   6720
cgttgcagtc tggataatag ttctccatcg tgcgtcagat ttgcgaggag aaaccttatg   6780
atctcggaaa tctcctctgg ttttaatatc tccgtccttt gatatgtaat caaggacttg   6840
tttagagttt ctagctggct ggatattagg gtgatttcct tcaaaatcga aaaagaagg    6900
atccctaata caaggttttt tatcaagctg gagaagagca tgatagtggg tagtgccatc   6960
ttgatgaagc tcagaagcaa caccaaggaa gaaaataaga aaaggtgtga gtttctccca   7020
gagaaactgg aataaatcat ctctttgaga tgagcacttg ggataggtaa ggaaaacata   7080
tttagattgg agtctgaagt tcttactagc agaaggcatg ttgttgtgac tccgaggggt   7140
tgcctcaaac tctatcttat aaccggcgtg gaggcatgga ggcaggggta ttttggtcat   7200
tttaatagat agtggaaaat gacgtggaat ttacttaaag acgaagtctt tgcgacaagg   7260
gggggcccac gccgaattta atattaccgg cgtggccccc ccttatcgcg agtgctttag   7320
cacgagcggt ccagatttaa agtagaaaat ttcccgccca ctagggttaa aggtgttcac   7380
actataaaag catatacgat gtgatggtat ttgatggagc gtatattgta tcaggtatt    7440
ccgttggata cgaattattc gtacgaccct catagtttaa actatcagtg tttgacagga   7500
tatattggcg ggtaaaccta agagaaaaga gcgtttatta gaataacgga tatttaaaag   7560
ggcgtgaaaa ggtttatccg ttcgtccatt tgtatgtgca tgccaaccac agggttcccc   7620
tcgggatcaa agtactttga tccaaccct ccgctgctat agtgcagtcg gcttctgacg    7680
ttcagtgcag ccgtcttctg aaaacgacat gtcgcacaag tcctaagtta cgtgcagacagg 7740
tgccgccctg ccctttcct ggcgttttct tgtcgcgtgt tttagtcgca taaagtagaa    7800
tacttgcgac tagaaccgga gacattacgc catgaacaag agcgccgcc ctggcctgct    7860
gggctatgcc cgcgtcagca ccgacgacca ggacttgacc aaccaacggg ccgaactgca   7920
cgcggccggc tgcaccaagc tgttttccga gaagatcaac ggcaccaggc gcgaccgccc   7980
ggagctggcc aggatgcttg accacctacg ccctgcgac gttgtgacag tgaccaggct    8040
agaccgcctg gcccgcagca cccgcgacct actggacatt gccgagcgca tccaggaggc   8100
cggcgcgggc ctgcgtagcc tggcagagcc gtgggccgac accaccacgc cggccggccg   8160
catggtgttg accgtgttcg ccggcattgc cgagttcgag cgttccctaa tcatcgaccg   8220
cacccggagc gggcgcgagg ccgccaaggc ccgaggcgtg aagtttggcc cccgccctac   8280
cctcaccccg gcacagatcg cgcacgcccc gagctgatc gaccaggaag gccgcaccgt    8340
gaaagaggcg gctgcactgc ttggcgtgca tcgctcgacc ctgtaccgcg cacttgagcg   8400
cagcgaggaa gtgacgccca ccgaggccag gcggcgcggt gccttccgtg aggacgcatt   8460
gaccgaggcc gacgcctgg cggccgccga gaatgaacgc caagaggaac aagcatgaaa    8520
ccgcaccagg acgccagga cgaaccgttt tcattaccg aagagatcga ggcggagatg     8580
atcgcggccg ggtacgtgtt cgagccgccc gcgcacggct caaccgtgcg gctgcatgaa   8640
atcctggccg gtttgtctga tgccaagctg gcggcctggc cggccagctt ggccgctgaa   8700
gaaaccgagc gccgccgtct aaaaaggtga tgtgtatttg agtaaaacag cttgcgtcat   8760
gcggtcgctg cgtatatgat gcgatgagta aataaacaaa tacgcaaggg gaacgcatga   8820
aggttatcgc tgtacttaac cagaaaggcg ggtcaggcaa gacgaccatc gcaacccatc   8880
tagcccgcgc cctgcaactc gccggggccg atgttctgtt agtcgattcc gatccccagg   8940
gcagtcccg cgattgggcg gccgtgcggg aagatcaacc gctaaccgtt gtcggcatcg   9000
accgcccgac gattgaccgc gacgtgaagg ccatcggccg gcgcgacttc gtagtgatcg   9060
acggagcgcc caggcggcg gacttggctg tgtccgcgat caaggcagcc gacttcgtgc   9120
tgattccggt gcagccaagc ccttacgaca tatgggccac cgccgacctg gtggagctgg   9180
ttaagcagcg cattgaggtc acggatggaa ggctacaagc ggccttttgc tgtcgcgagg   9240
cgatcaaagg cacgcgcatc ggcggtgagg ttgccgaggc gctggccggg tacgagctgc   9300
ccattcttga gtcccgtatc acgcagcgcg tgagctaccc aggcactgcc gccgccggca   9360
caaccgttct tgaatcagaa cccgagggcg acgctgcccg cgaggtccag gcgctggccg   9420
ctgaaattaa atcaaaactc atttgagtta atgaggtaaa gagaaaatga gcaaaagcac   9480
aaacacgcta agtgccggcc gtccgagcgc acgcagcagc aaggctgcaa cgttggccag   9540
cctggcagac acgccagcca tgaagcgggt caactttcag ttgccggcgg aggatcacac   9600
caagctgaag atgtacgcgg tacgccaagg caagaccatt accgagctgc tatctgaata   9660
catcgcgcag ctaccagagt aaatgagcaa atgaataaat gagtagatga attttagcgg   9720
ctaaaggagg cggcatggaa aatcaagaac aaccaggcac cgacgccgtg gaatgcccca   9780
tgtgtggagg aacgggcggt tggccaggcg taagcggctg ggttgtctgc cggcctgca    9840
atggcactgg aaccccccaag cccgaggaat cggcgtgacg gtcgcaaacc atccggcccg   9900
gtacaaatcg gcgcggcgct gggtgatgac ctggtggaga agttgaaggc cgcgcaggcc   9960
gcccagcgc aacgcatcga ggcagaagca cgccccggtg aatcgtggca agcggccgct    10020
gatcgaatcc gcaaagaatc ccggcaaccg ccggcagccg gtgcgccgtc gattaggaag   10080
ccgcccaagg gcgacgagca accagatttt tcgttccga tgctctatga cgtgggcacc    10140
cgcgatagtc gcagcatcat ggacgtggcc gttttccgtc tgtcgaagcg tgaccgacga   10200
gctggcga tgatccgcta cgagcttcca gacgggacg tagaggtttc cgcagggccg      10260
gccggcatgg ccagtgtgtg gattacgac ctggtactga tggcggtttc ccatctaacc    10320
gaatccatga accgataccg ggaaggaag ggagacaagc ccggccgcgt gttccgtcca    10380
cacgttgcgc acgtactcaa gttctgccgg cgagccgatg gcgaaagca gaaagacgac   10440
ctggtagaaa cctgcattcg gttaaacacc acgcacgttg ccatgcagcg tacgaagaag   10500
gccaagaacg gccgcctggt gacggtatcc gagggtgaag ccttgattag ccgctacaag   10560
atcgtaaaga gcgaaaccgg gcggccggag tacatcgaga tcgagctagc tgattgatgc   10620
taccgcgaga tcacagaagg caagaacccg gacgtgctga cggttcaccc cgattacttt   10680
ttgatcgatc ccggcatcgg ccgttttctc taccgcctgg cacgccgcgc cgcaggcaag   10740
gcagaagcca gatggttgtt caagacgatc tacgaacgtg tggcagcgc ggagagttc     10800
aagaagttct gtttcaccgt gcgcaagctg atcggggtca atgaccgtgc ggagtacgat   10860
ttgaaggagg aggcggggca ggctgggccg atcctagtca tgcctacgg caacctgatc   10920
gagggcgaag catccgccgg ttcctaatgt acggagcaga tgctagggca aattgcccta   10980
gcaggggaaa aaggtcgaaa aggcctcttt cctgtggata gcacgtacat tgggaaccca  11040
aagccgtaca ttgggaaccg gaacccgtac attgggaacc caaagccgta cattgggaac   11100
cggtcacaca tgtaagtgac tgatataaaa gagaaaaaag gcgatttttc cgcctaaaac   11160
```

| | | | |
|---|---|---|---|
| tctttaaaac | ttattaaaac | tcttaaaacc | cgcctggcct gtgcataact gtctggccag | 11220 |
| cgcacagccc | aagagctgca | aaaagcgcct | acccttcggt cgctgcgctc cctacgcccc | 11280 |
| gccgcttcgc | gtcggcctat | cgcggccgct | ggccgctcaa aaatggctgg cctacggcca | 11340 |
| ggcaatctac | cagggcgcgg | acaagccgcg | ccgtcgccac tcgaccgccg gcgcccacat | 11400 |
| caaggcaccc | tgcctcgcgc | gtttcggtga | tgacggtgaa aacctctgac acatgcagct | 11460 |
| cccggaaacg | gtcacagctt | gtctgtaagc | ggatgccggg agcagacaag cccgtcaggg | 11520 |
| cgcgtcagcg | ggtgttggcg | ggtgtcgggg | cgcagccatg acccagtcac gtagcgatag | 11580 |
| cggagtgtat | actggcttaa | ctatgcggca | tcagagcaga ttgtactgag agtgcaccat | 11640 |
| atgcggtgtg | aaataccgca | cagatgcgta | aggagaaaat accgcatcag gcgctcttcc | 11700 |
| gcttcctcgc | tcactgactc | gctgcgctcg | gtcgttcggc tgcggcgagc ggtatcagct | 11760 |
| cactcaaagg | cggtaatacg | gttatccaca | gaatcagggg ataacgcagg aaagaacatg | 11820 |
| tgagcaaaag | gccagcaaaa | ggccaggaac | cgtaaaaagg ccgcgttgct ggcgtttttc | 11880 |
| cataggctcc | gcccccctga | cgagcatcac | aaaaatcgac gctcaagtca gaggtggcga | 11940 |
| aacccgacag | gactataaag | ataccaggcg | tttccccctg gaagctccct cgtgcgctct | 12000 |
| cctgttccga | ccctgccgct | taccggatac | ctgtccgcct ttctcccttc gggaagcgtg | 12060 |
| gcgctttctc | atagctcacg | ctgtaggtat | ctcagttcgg tgtaggtcgt tcgctccaag | 12120 |
| ctgggctgtg | tgcacgaacc | ccccgttcag | cccgaccgct gcgccttatc cggtaactat | 12180 |
| cgtcttgagt | ccaacccggt | aagacacgac | ttatcgccac tggcagcagc cactggtaac | 12240 |
| aggattagca | gagcgaggta | t | | 12261 |

SEQ ID NO: 20           moltype = DNA  length = 24
FEATURE                 Location/Qualifiers
source                  1..24
                        mol_type = other DNA
                        organism = synthetic construct
SEQUENCE: 20
tgggaactga aagtcaagat ggtc                                          24

SEQ ID NO: 21           moltype = DNA  length = 22
FEATURE                 Location/Qualifiers
source                  1..22
                        mol_type = other DNA
                        organism = synthetic construct
SEQUENCE: 21
acaataaatg ggatgggcct gg                                            22

SEQ ID NO: 22           moltype = DNA  length = 24
FEATURE                 Location/Qualifiers
source                  1..24
                        mol_type = other DNA
                        organism = synthetic construct
SEQUENCE: 22
tgggaactga aagtcaagat gttt                                          24

SEQ ID NO: 23           moltype = DNA  length = 25
FEATURE                 Location/Qualifiers
source                  1..25
                        mol_type = other DNA
                        organism = synthetic construct
SEQUENCE: 23
caaaagctag cttatgaggt gaagc                                         25

SEQ ID NO: 24           moltype = DNA  length = 4140
FEATURE                 Location/Qualifiers
source                  1..4140
                        mol_type = other DNA
                        organism = Streptococcus pyogenes
SEQUENCE: 24

| | | | |
|---|---|---|---|
| atggataaga | agtactctat | cggactcgat | atcggaacta actctgtggg atgggctgtg | 60 |
| atcaccgatg | agtacaaggt | gccatctaag | aagttcaagg ttctcggaaa caccgatagg | 120 |
| cactctatca | agaaaaacct | tatcggtgct | ctcctcttcg attctggtga aactgctgag | 180 |
| gctaccagac | tcaagagaac | cgctagaaga | aggtacacca agagaaagaa caggatctgc | 240 |
| tacctccaag | agatcttctc | taacgagatg | gctaaagtgg atgattcatt cttccacagg | 300 |
| ctcgaagagt | cattcctcgt | ggaagaagat | aagaagcacg agaggcaccc tatcttcgga | 360 |
| aacatcgttg | atgaggtggc | ataccacgag | aagtacccta ctatctacca cctcagaaag | 420 |
| aagctcgttg | attctactga | taaggctgat | ctcaggctca tctacctcgc tctcgctcac | 480 |
| atgatcaagt | tcagaggaca | cttcctcatc | gagggtgatc tcaaccctga taactctgat | 540 |
| gtggataagt | tgttcatcca | gctcgtgcag | acctacaacc agcttttcga agagaaccct | 600 |
| atcaacgctt | caggtgtgga | tgctaaggct | atcctctctg ctaggctctc taagtcaaga | 660 |
| aggcttgaga | acctcattgc | tcagctccct | ggtgagaaga gaacggact tttcggaaac | 720 |
| ttgatcgctc | tctctctcgg | actcaccct | aacttcaagt ctaacttcga tctcgctgag | 780 |
| gatgcaaagc | tccagctctc | aaaggatacc | tacgatgatg atctcgataa cctcctcgct | 840 |
| cagatcggag | atcagtacgc | tgatttgttc | ctcgctgcta gaaacctctc tgatgctatc | 900 |
| ctcctcagtg | atatcctcag | agtgaacacc | gagatctcca aggctccact ctcagcttct | 960 |
| atgatcaaga | gatacgatga | gcaccaccag | gatctcacac ttctcaaggc tcttgttaga | 1020 |
| cagcagctcc | cagagaagta | caaagagatt | ttcttcgatc agtctaagaa cggatacgct | 1080 |
| ggttacatcg | atggtggtgc | atctcaagaa | gagttctaca agttcatcaa gcctatcctc | 1140 |
| gagaagatgg | atggaaccga | ggaactcctc | gtgaagctca atagagagga tcttctcaga | 1200 |
| aagcagagga | ccttcgataa | cggatctatc | cctcatcaga tccacctcgg agagttgcac | 1260 |

```
gctatcctta gaaggcaaga ggatttctac ccattcctca aggataacag ggaaaagatt    1320
gagaagattc tcaccttcag aatcccttac tacgtgggac ctctcgctag aggaaactca    1380
agattcgctt ggatgaccag aaagtctgag gaaaccatca ccccttggaa cttcgaagag    1440
gtggtggata agggtgctag tgctcagtct ttcatcgaga ggatgaccaa cttcgataag    1500
aaccttccaa acgagaaggt gctccctaag cactcttttg tctacgagta cttcaccgtg    1560
tacaacgagt tgaccaaggt taagtacgtg accgagggaa tgaggaagcc tgctttttg    1620
tcaggtgagc aaaagaaggc tatcgttgat ctccttgttca agaccaacag aaaggtgacc    1680
gtgaagcagc tcaaagagga ttacttcaag aaaatcgagt gcttcgattc agttgagatt    1740
tctggtgttg aggataggtt caacgcatct tccggaacct accacgatct cctcaagatg    1800
attaaggata aggatttctt ggataacgag gaaaacgagg atatcttgga ggatatcgtt    1860
cttaccctca ccctctttga agatagagag atgattgaag aaaggctcaa gacctacgct    1920
catctcttcg atgataaggt gatgaagcag ttgaagagaa aagatacac tggttgggga    1980
aggctctcaa gaaagctcat taacggaatc agggataagc agtctggaaa gacaatccttt   2040
gatttcctca agtctgatgg attcgctaac agaaacttca tcgagctcat ccacgatgat   2100
tctctcacct ttaaaggaga tatccagaag gctcaggttt caggacaggg tgatagtctc    2160
catgagcata tcgctaacct cgctggatct cctgcaatca agagagggaat cctccagact    2220
gtgaaggttg tggatgagtt ggtgaaggtg atgggaaggc ataagcctga aacatcgtg    2280
atcgaaatgg ctagaagaaa ccagaccact cagaaggga agaagaactc tagggaaagg    2340
atgaagagga tcgaggaagg tatcaaagag cttggatctc agatcctcaa agagcaccct    2400
gttgagaaca ctcagctcca gaatgagaag ctctacctct actacctcca gaacgcaagg    2460
gatatgtatg tggatcaaga gttggatatc aacaggctct ctgattacga tgttgatcat    2520
atcgtgccac agtcattctt gaaggatgat tctatcgata aaaggtgct caccaggtct    2580
gataagaaca gggtaagag tgataacgtg ccaagtgaag aggttgtgaa gaaaatgaag    2640
aactattgga ggcagctcct caacgctaag ctcatcactc agagaaagtt cgataacttg    2700
actaaggctg agaggggagg actctctgaa ttggataagg caggattcat caagaggcag    2760
cttgtggaaa ccaggcagat cactaagcac gttgcacaga tcctcgattc taggatgaac    2820
accaagtacg atgagaacga taagttgatc agggaagtga aggttatcac cctcaagtca    2880
aagctcgtgt ctgatttcag aaaggatttc aattctaca aggtgaggga aatcaacaac    2940
taccaccacg ctcacgatgc ttaccttaac gctgttgttg aaccgctct catcaagaag    3000
tatcctaagc tcgagctcag agttcgtgtac ggtgattcaa aggtctacga tgtgaggaag    3060
atgatcgcta agtctgagca agagatcgga aaggctaccg ctaagatttt cttctactct    3120
aacatcatga atttcttcaa gaccgagatt accctcgcta acggtgagat cagaaagagg    3180
ccactcatcg agacaaacgg tgaaacaggt gagatcgtgt gggataaggg aagggattc    3240
gctaccgtta gaagtgtgct ctctatgcca caggtgaaca tcgttaagaa aaccgagtg    3300
cagaccggtg gattctaa agagtctatc ctccctaaga ggaactctga taagctcatt    3360
gctaggaaga aggattggga ccctaagaaa tacggtggtt tcgattctcc taccgtggct    3420
tactctgttc tcgttgtggc taaggttgag aagggaaaga gtaagaagct caagtctgtt    3480
aaggaacttc tcggaatcac tatcatggaa aggtcatctt tcgagaagaa cccaatcgat    3540
ttcctcgagg ctaagggata caaagaggt tcatcatca gctcccaaag    3600
tactcactct tcgaactcga aacggtaga aagaggatgc tcgcttctgc tggtgagctt    3660
caaaagggaa acgagcttgc tctcccatct aagtacgtta actttctta cctcgcttct    3720
cactacgaga agttgaaggg atctccagaa gataacgagc agaagcaact tttcgttgag    3780
cagcacaagc actacttgga tgagatcatc gagacgatct ctgagttctc taaaagggtg    3840
atcctcgctg atgcaaaacct cgataaggtg ttgtctgctt acaacaagca cagagataag    3900
cctatcaggg aacaggcaga gaacatcatc catctcttca cccttaccaa cctcggtgct    3960
cctgctgctt tcaagtactt cgatacaacc atcgataggga agagatacac ctctaccaaa    4020
gaagtgctcg atgctaccct catccatcag tctatcactg gactctacga gactaggatc    4080
gatctctcac agctcggtgg tgattcaagg gctgatccta agaagaagag gaaggttga    4140

SEQ ID NO: 25            moltype = DNA  length = 940
FEATURE                  Location/Qualifiers
source                   1..940
                         mol_type = other DNA
                         organism = Agrobacterium tumefaciens
SEQUENCE: 25
cctttattt tcttcttttt tccatattta gggttgacag tgaaatcaga ctggcaacct      60
attaattgct tccacaatgg gacgaacttg aaggggatgt cgtcgatgat attataggtg    120
gcgtgttcat cgtagttggt gaaatcgatg gtaccgttcc aatagttgtg tcgtccgaga    180
cttctagccc aggtggtctt tccggtacga gttggtccgc agatgtagag gctgggtgt    240
cggattccat tccttccatt gtccttgtta aatcggccat ccattcaagg tcagattgag    300
cttgttggta tgagacagga tgtatgtaag tataagcgtc tatgcttaca tggtatagat    360
gggtttccct ccaggagtgt agatcttcgt ggcagcgaag atctgattct gtgaagggcg    420
acacatacgg ttcaggttgt ggagggaata atttgttggc tgaatattcc agccattgaa    480
gctttgttgc ccattcatga gggaattctt ccttgatcat gtcaagatat tcctccttag    540
acgttgcagt ctggataata gttctccatc gtgcgtcaga tttgcgagga gaaacctat    600
gatctcggaa atctcctctg gttttaatat ctccgtcctt tgtatgtaa tcaaggactt    660
gtttagagtt tctagctggc tggatattag ggtgatttcc ttcaaaatcg aaaaagaag    720
gatccctaat acaaggtttt ttatcaagct ggagaagagc atgatagtgg gtagtgcat    780
cttgatgaag ctcagaagca acaccaagga agaaaatgga aaaggtgtg agtttctccc    840
agagaaactg gaataaatca tctctttgag atgagcactt gggataggta aggaaaacat    900
atttagattg gagtctgaag ttcttactag cagaaggcat                         940

SEQ ID NO: 26            moltype = DNA  length = 17275
FEATURE                  Location/Qualifiers
source                   1..17275
                         mol_type = other DNA
                         organism = synthetic construct
SEQUENCE: 26
gtaggcggtg ctacagagtt cttgaagtgg tggcctaact acggctacac tagaaggaca     60
```

```
gtatttggta tctgcgctct gctgaagcca gttaccttcg gaaaaagagt tggtagctct    120
tgatccggca aacaaccacc cgctggtagc ggtggttttt ttgtttgcaa gcagcagatt    180
acgcgcagaa aaaaggatc  tcaagaagat cctttgatct tttctacggg gtctgacgct    240
cagtggaacg aaaactcacg ttaagggatt ttggtcatgc attctaggta ctaaaacaat    300
tcatccagta aaatataata tttttatttc tcccaatcag gcttgatccc cagtaagtca    360
aaaaatagct cgacatactg ttcttccccg atatcctccc tgatcgaccg gacgcagaag    420
gcaatgtcat accacttgtc cgccctgccg cttctcccaa gatcaataaa gccacttact    480
ttgccatctt tcacaaagat gttgctgtct cccaggtcgc cgtgggaaaa gacaagttcc    540
tcttcgggct tttccgtctt taaaaaatca tacagctcgc gcggatcttt aaatggagtg    600
tcttcttccc agttttcgca atccacatcg gccagatcgt tattcagtaa gtaatccaat    660
tcggctaagc ggctgtctaa gctattcgta tagggacaat ccgatatgtc gatgagtga     720
aagagcctga tgcactccgc atacagctcg ataatctttt cagggctttg ttcatcttca    780
tactcttccg agcaaaggac gccatcggcc tcactcatga gcagattgct ccagccatca    840
tgccgttcaa agtgcaggac cttttggaaca ggcagctttc cttccagcca tagcatcatg    900
tcctttttccc gttccacatc ataggtggtc cctttatacc ggctgtccgt catttttaaa    960
tataggtttt cattttctcc caccagctta tataccttag caggagacat tccttccgta   1020
tcttttacgc agcggtattt ttcgatcagt ttttcaattt ccggtgatat tctcattta    1080
gccatttatt atttccttcc tcttttctac agtatttaaa gatacccaa gaagctaatt   1140
ataacaagac gaactccaat tcactgttcc ttgcattcta aaaccttaaa taccagaaaa   1200
cagcttttc aaagttgttt tcaaagttgg cgtataacat agtatcgacg gagccgattt    1260
tgaaaccgcg gtgatcacag gcagcaacgc tctgtcatcg ttacaatcaa catgctaccc   1320
tccgcgagat catccgtgtt tcaaacccgg cagcttagtt gccgttcttc cgaatagcat   1380
cggtaacatg agcaaagtct gccgccttac aacggctctc ccgctgacgc cgtcccggac   1440
tgatgggctg cctgtatcga gtggtgattt tgtgccgagc tgccggtcgg ggagctgttg   1500
gctggctggt ggcaggatat attgtggtgt aaacaaattg acgcttagac aacttaataa   1560
cacattgcgg acgtttttaa tgtactgaat taacgccgaa ttaattcggg ggatctggat   1620
tttagtactg gattttggtt ttaggaatta gaaattttat tgatagaagt attttacaaa   1680
tacaaatca  tactaagggt ttcttatatg ctcaacacat gagcgaaacc ctataggaac   1740
cctaattccc ttatctggga actactcaca cattattatg gagaaactcg agcttgtcga   1800
tcgactctag ctagaggatc gatccgaacc ccagagtccc gctcagaaga actcgtcgaa   1860
aaggcgatag aaggcgatgc gctgcgaatc gggagcggcg ataccgtaaa gcacaggaa    1920
gcggtcagcc cattcgccgc caagttcttc agcaatatca cgggtagcca acgctatgtc   1980
ctgatagcgg tccgccacac ccagccgcc  acagtcgatg aatccagaaa agcggccatt   2040
ttccaccatg atattcggca agcaggcatc gccatgtgtc acgacgagat cctcgccgtc   2100
gggcatgcgc gccttgagcc tggcgaacag ttcggctggc gcgagcccct gatgtcttc    2160
gtccagatca tcctgatcga caagaccggc ttccatccga gtacgtgctc gctcgatgcg   2220
atgtttcgct tggtggtcga atgggcaggt agccggatca agcgtatgca gccgccgcat   2280
tgcatcagcc atgatggata cttttctcggc aggagcaagg tgagatgaca ggagatcctg   2340
ccccgcact  tcgcccaata gcagccagtc ccttcccgct tcagtgacaa cgtcgagcac   2400
agctgcgcaa ggaacgcccg tcgtggccag ccacgatagc cgcgctgcct cgtcctggag   2460
ttcattcagg gcaccggaca ggtcggtctt gacaaaaaga accgggcgcc cctgcgctga   2520
cagccgaaac acggcggcat cagagcagcc gattgtctgt tgtgcccagt catagccgaa   2580
tagcctctcc acccaagcgg ccggagaacc tgcgtgcaat ccatcttgtt caatcccat    2640
ggtcgatcga cagatctgcg aaagctcgag agagatagat ttgtagagag agactggtga   2700
tttcagcgtg tcctctccaa atgaaatgaa cttccttata tagaggaagg tcttgcgaag   2760
gatagtggga ttgtgcgtca tcccttacgt cagtggagat atcacatcaa tccacttgct   2820
ttgaagacgt ggttggaacg tcttcttttt ccacgacgtg cctcgtgggt ggggtccat    2880
ctttgggacc actgtcggca gaggcatctt gaacgatagc cttttcctta tcgcaatgat   2940
ggcatttgta ggtgccacct tccttttcta ctgtcctttt gatgaagtga cagatagctg   3000
ggcaatggaa tccgaggagg tttcccgata ttaccctttg ttgaaaagtc tcaatagccc   3060
tttggtcttc tgagactgta tctttgatat tcttggagta gacgagagtg tcgtgctcca   3120
ccatgttatc acatcaatcc acttgctttg aagacgtggt tggaacgtct tcttttcca    3180
cgatgctcct cgtgggtggg ggtccatctt tgggaccact gtcggcagag gcatcttgaa   3240
cgatagcctt tccttttatcg caatgatggc atttgtaggt gccaccttcc ttttctactg   3300
tccttttgat gaagtgacag atagctgggc aatggaatcc gaggaggttt cccgatatta   3360
cccttttgttg aaaagtctca atagcccttt ggtcttctga gactgtatct ttgatattct   3420
tggagtagac gagagtgtcg tgctccacca tgttggcaag ctgctctagc caatacgcaa   3480
accgcctctc cccgcgcgtt ggccgattca ttaatgcagc tggcacgaca ggtttcccga   3540
ctggaaagcg ggcagtgagc gcaacgcaat taatgtgagt tagctcactc attaggcacc   3600
ccaggcttta cactttatgc ttccggctcg tatgttgtgt ggaattgtga gcggataaca   3660
atttcacaca ggaaacagct atgaccatga ttacgaattc gagctcaaag tttaacgcgt   3720
tagcagaagg catgttgttg tgactccgag gggttgcctc aaactctatc ttataaccgg   3780
cgtggaggca tggaggcagg ggtatttggg tcattttaat agatagtgga aaatgacgtg   3840
gaatttactt aaagacgaag tcttttgcgac aaggggggggc ccacgccgaa tttaatatta   3900
ccggcgtggc ccccccttat cgcgagtgct ttagcacgac cggtccagat ttaaagtaga   3960
aaatttcccg cccactaggg ttaaaggtgt tcacactata aaagcatata cgatgtgatg   4020
gtatttgatg gagcgtatat tgtatcaggt atttccgttg gatacgaatt attcgtacga   4080
ccctcggtac cgatcaaaag caggtgtggc gcgcagatt  tgccttttca atttcagaaa   4140
gaatgctaac ccacagatgg ttagagaggc ttacgcagca ggtatcatca agacgatcta   4200
cccgagcaat aatctccagg aaatcaaata ccttcccaag aaggttaaag atgcagtcaa   4260
aagattcagg actaactgca tcaagaacac agagaaagat atattctca  agatcagaag   4320
tactattcca gtatgggacga ttcaaggctt gcttcacaaa ccaaggcaag taatagagat   4380
tggagtctct aaaaaggtag ttcccactga atcaaaggcc atggagtcaa agattcaaat   4440
agaggaccta acagaactcg ccgtaaagac tggaacagaa ttcatacaga gtctcttacg   4500
actcaatgac aagaagaaaa tcttcgtcaa catggtggga cacgacacac ttgtctactc   4560
caaaaatatc aaagatacag tctcagaaga ccaaagggca attgacttt  tcaacaaag    4620
ggtaatatcc ggaaacctcc tcggattcca ttgcccagct atctgtcact ttattgtgaa   4680
gatagtggaa aaggaaggtg gctcctacaa atgccatcat tgcgataaag gaaaggccat   4740
cgttgaagat gcctctgccg acagtggtcc caaagatgga cccccacca  cgaggagcat   4800
```

```
cgtggaaaaa gaagacgttc caaccacgtc ttcaaagcaa gtggattgat gtgatatctc   4860
cactgacgta agggatgacg cacaatccca ctatccttcg caagacccct cctctatata   4920
aggaagttca tttcatttgg agagaacacg ggggactcct gcaggatgga agacgccaaa   4980
aacataaaga aaggcccggc gccattctat ccgctggaag atggaaccgc tggagagcaa   5040
ctgcataagg ctatgaagag atacgccctg gttcctggca caattgcttt tacagatgca   5100
catatcgagg tggacatcac ttacgctgag tacttcgaaa tgtccgttcg gttggcagaa   5160
gctatgaaac gatatgggct gaatacaaat cacagaatcg tcgtatgcag tgaaaactct   5220
cttcaattct ttatgccggt gttgggcgcg ttatttatcg gagttgcagt tgcgcccgcg   5280
aacgacattt ataatgaacg tgaattgctc aacagtatgg gcatttcgca gcctaccgtg   5340
gtgttcgttt ccaaaaaggg gttgcaaaaa attttgaacg tgcaaaaaaa gctcccaatc   5400
atccaaaaaa ttattatcat ggattctaaa acggattacc agggatttca gtcgatgtac   5460
acgttcgtca catctcatct acctcccggt tttaatgaat acgattttgt gccagagtcc   5520
ttcgataggg acaagacaat tgcactgatc atgaactcct ctggatctac tggtctgcct   5580
aaaggtgtcg ctctgcctca tagaactgcc tgcgtcgagat tctcgcatgc cagagatcct   5640
atttttggca atcaaatcat tccggatact gcgattttaa gtgttgttcc attccatcac   5700
ggttttggaa tgtttactac actcggatat ttgatatgtg gatttcgagt cgtcttaatg   5760
tatagatttg aagaagagct gtttctgagg agccttcagg attacaagat tcaaagtgcg   5820
ctgctggtgc caaccctatt ctccttcttc gccaaaagca ctctgattga caaatacgat   5880
ttatctaatt tacacgaaat tgcttctggt ggcgctcccc tctctaagga agtcggggaa   5940
gcggttgcca gaggttccca tctgccaggt atcaggcaag gatatgggct cactgagact   6000
acatcagcta ttctgattac acccgagggg gatgataaac cgggcgcggt cggtaaagtt   6060
gttccatttt ttgaagcgaa ggttgtggat ctggatacccg gaaaacgct gggcgttaat   6120
caaagaggcg aactgtgtgt gagaggtcct atgattatgt ccggttatgt aaacaatccg   6180
gaagcgacca acgccttgat tgacaaggat ggatggctac attctggaga catagcttac   6240
tgggacgaag acgaacactt cttcatcgtt gaccgcctga agtctctgat taagtacaaa   6300
ggctatcagg tggctcccgc tgaattggaa tccatcttgc tccaacaccc caacatcttc   6360
gacgctggtg tcgcaggtct tcccgacgat gacgccggtg aacttcccgc cgccgttgtt   6420
gttttggagc acggaaagac gatgacggaa aaagagatcg tggattacgt cgccagtcaa   6480
gtaacaaccg cgaaaagtt gcgcggagga gttgtgtttg tggacgaagt accgaaaggt   6540
cttaccggaa aactcgacgc aagaaaaatc agagagatcc tcataaaggc caagaagggc   6600
ggaaagatcg ccgtgtgacg tcgacgatat gaagatgaag atgaaatatt tggtgtgtca   6660
aataaaaagc ttgtgtgctt aagtttgtgt ttttttcttg gcttgttgtg ttatgaattt   6720
gtggcttttt ctaatattaa atgaatgtaa gatcacatta taatgaataa acaaatgttt   6780
ctataatcca ttgtgaatgt tttgttgaat ctcttctgca gcatataact actgtatgtg   6840
ctatggtatg gactatggaa tatgattaaa gataagccag agctctggtg acggacgcgg   6900
cgactagttt tacgtacgtt aattaacccg ggcgcgccga tcatgagcgg agaattaagg   6960
gagtcacgtt atgacccccg ccgatgacgc gggacaagcc gttttacgtt tggaactgac   7020
agaaccgcaa cgttgaagga gccactcagc cgcgggtttc tggagtttaa tgagctaagc   7080
acatacgtca gaaaccatta ttgcgcgttc aaaagtcgcc taaggtcact atcagctagc   7140
aaatatttct tgtcaaaaat gctccactga cgttccataa attcccctcg gtatccaatt   7200
agagtctcat attcactctc aatccaaata atctgcaccg tacctgcagg gtccgagcta   7260
ggtcacagaa gcgctcagga aggccgctga gatagaggca tggcggccaa tgcgggcggc   7320
ggtggagcgg gaggaggcag cggcagcggc agcgtggctg cgcggcggt gtgccgcccc   7380
agcggctcgc ggtggacgcc gacgccgagc cagatcagga tgctgaagga gctgtactac   7440
ggctgcggca tccggtcgcc cagctcggag cagatccagc gcatcaccgc catgctgcgg   7500
cagcacggca agatcgaggg caagaacgtc ttctactggt tccagaacca caaggcccgc   7560
gagcgccaga agcgccgcct caccagcctc gacgtgaacg tgcccgaagc cggcgggcgc   7620
gacgccacca ccagccaact cggcgtcctc tcgctgtcgt cgccgccgcc ttcaggcgcg   7680
gcgcctccct cgcccacccgt cggcttctac gccgccggca atggcggcgg atcggctgtg   7740
ctgctggaca cgagttccga ctggggcagc agcggcgctg cgatgccac cgagacatgc   7800
ttcctccagg actacatggg cgtgacggac acgggcagct cgtcgcagtg gccacgcttc   7860
tcgtcgtcgg acacgataat ggcgcggcc gcggcgccgg ccggcgacgac gcggcgccc   7920
gagactctcc ctctcttccc gacctgcggc gacgacggcg gcagcggtag cagcagctac   7980
ttgccgttct ggggtgccgc gtccacaact gccggcgcca cttcttccgt tgcgatccag   8040
cagcaacacc agctgcagga gcagtacagc ttttacagca acagcaacag cacccagctg   8100
gccggcaccg gcaaccaaga cgtatcggca acagcagcag cagccgccgc cctgggactg   8160
agcctcagct catggtgctc cccttaccct gctgcaggga gtatgtgaga gcaacgcgag   8220
ctgccactgc tcttcactta tgtctctgga atggaaggag gaggaagtga gcatagcgtt   8280
ggtgcgttgc tgtcattgtc ctaggttagt agctagtgcc agttactagt aagcatcagg   8340
cataggagta tgtagtagaa gcatgcacgt tgccggccag ccaggcttta gacgggaaaa   8400
gaatttggtg cagccggctg caaaacagga tgtttacagc ccccccctcg agccctagac   8460
ttgtccatct tctggattgg ccaagttaat taatgtatga aataaaagga tgcacacata   8520
gtgacatgct aatcactata atgtgggcat caaagttgtg tgttatgtgt aattactaat   8580
tatctgaata agagaaagag atcatccata ttcttaatc tcacgtgctt   8640
ttataattct ttgatgaacc agatgcattt tattaaccaa ttccatatac atataaatat   8700
taatcatata taattaatat caattgggtt agcaaaacaa atctagtcta ggtgtgtttt   8760
gctaattatt gggggatagt gcaaaagaa atctacgttc tcaataattc agatagaaaa   8820
cttaataaag tgagataatt tacatagatt gcttttatcc tttgatatat gtgaaaccat   8880
gcatgatata aggaaaatag atagagaaat aatttttac atcgttgaat atgtaaacaa   8940
tttaattcaa gaagctagga atataaatat tgaggagttt atgattagag ctctcccact   9000
aaacgtcccg ctgcagacga tactgtccca caaatgaaga tggaatctgt aaaagaaaac   9060
gcgtgaaata atgcgtctga caaaggttag gtcggctgcc tttaatcaat accaaagtgg   9120
tccctaccac gatggaaaaa ctgtgcagtc ggtttggctt tttctgacga acaaataaga   9180
ttcgtggcac acaggtgggg gtccaccatg tgaaggcatc ttcagactcc aataatggtc   9240
caatgacgta agggcttacg aaataagtaa gggtagtttg gaaatgtcc actcaccgt   9300
cagtctataa atacttagcc cctccctcat tgttaaggga gcaaaatctc agagagatag   9360
tcctagagag agaagagag caagtagcct agaagtagtc aaggcggcga agtattcagg   9420
cacgtggcca ggaagaagaa aagccaagac gacgaaaaca ggtaagagct aagcttatgg   9480
agagtggttc caacagcact tcttgtccaa tggcttttgc cggggataat agtgatggtc   9540
```

```
cgatgtgtcc tatgatgatg atgatgccgc ccatcatgac atcacatcaa catcatggtc  9600
atgatcatca acatcaacaa caagaacatg atggttatgc atatcagtca caccaccaac  9660
aaagtagttc ccttttcttt caatcactag ctcctcccca aggaactaag aacaaagttg  9720
cttcttcttc ttctccttcc tcttgtgctc ctgcctattc tctaatggag atccatcata  9780
acgaaatcgt tgcaggagga atcaaccctt gctcctcttc ctcttcttca gcctctgtca  9840
aggccaagat catggctcat cctcactacc accgcctctt ggccgcttat gtcaattgtc  9900
agaaggttgg agcaccaccg gaggttgtgg cgaggctaga ggaggcatgc tcgtctgccg  9960
cagccgctgc cgcatctatg ggaccaacag gatgtctagg tgaagatcca gggcttgatc 10020
aattcatgga agcttactgt gaaatgctcg ttaagtatga gcaagagctc tccaaacctt 10080
tcaaggaagc tatggtcttc cttcaacgtg tcgagtgtca attcaaatcc ctctctctat 10140
cctcaccttc ctctttctcc ggttatggag agacagcaat tgataggaac aataatgggt 10200
catccgagga agaagtcgat atgaacaatg aatttgtaga tccacaagct gaggatagag 10260
agcttaaagg acagctcttg cgcaagtaca gtggttactt agggagcctc aagcaagagt 10320
tcatgaagaa gaggaagaaa ggaaagctcc ctaaagaagc tcgtcaacaa ctgcttgatt 10380
ggtgagccg tcactacaaa tggccttacc cttcggagca acaaaagctc gccctgcgg  10440
aatcaacggg gctggaccag aaacagataa acaattggtt cataaccag aggaaacggc  10500
attggaagcc gtcggaggac atgcagtttg tagtaatgga cgcaacacat cctcaccatt 10560
acttcatgga taatgtcttg ggcaatcctt cccaatgga tcacatctcc tccaccatgc 10620
tttgactcga gtttctccat aataatgtgt gagtagttcc cagataaggg aattagggtt 10680
cctataggg ttcgctcatg tgttgagcat ataagaaacc cttagtatgt atttgtattt  10740
gtaaatact tctatcaata aaatttctaa ttcctaaaac caaaatccag tactaaaatc  10800
cagatccccc gaattaagtg actacacctg caaaaagtgt ttgatcgccg gcggtaccga 10860
gtgtacttca agtcagtggg aaatcaataa aatgattatt ttatgaatat atttcattgt 10920
gcaagtagat agaaattaca tatgttacat aacacacgaa ataaacaaaa aaagacaatc 10980
caaaaacaaa caccccaaaa aaaataatca ctttagataa actcgtatga ggagaggcac 11040
gttcagtgac tcgacgattc ccgagcaaaa aaagtcccc cgtcacacat gtagtgggtg 11100
acgcaattat cttaaagta atccttctgt tgacttgtca ttgataacat ccagtcttcg 11160
tcaggattgc aaagaattat agaagggatc ccacctttta ttttcttctt ttttccatat 11220
ttaggggtga cagtgaaatc agactggcaa cctattaatt gcttccacaa tgggacgaac 11280
ttgaagggga tgtcgtcgat gatattatag gtggcgtgtt catcgtagtt ggtgaaatcg 11340
atggtaccgt tccaatagtt gtgtcgtccg agacttctag cccaggtggt ctttccggta 11400
cgagttggtc cgcagatgta gaggctgggg tgtcggattc cattccttcc attgtccttg 11460
ttaaatcggc catccattca aggtcagatt gagcttgttg gtatgagaca ggatgtatgt 11520
aagtataagc gtctatgctt acatggtata gatgggttc cctccaggag tgtagatctt 11580
cgtggcagcg aagatctgat tctgtgaagg gcgacacata cggttcaggt tgtggaggga 11640
ataatttgtt ggctgaatat tccagccatt gaagctttgt tgcccattca tgagggaatt 11700
cttccttgat catgtcaaga tattcctcct tagacgttgc agtctggata atagttctcc 11760
atcgtgcgtc agatttgcga ggagaaacct tatgatctcg gaaatctcct ctggttttaa 11820
tatctccgtc ctttgatatg taatcaagga cttgtttaga gtttctagct ggctggatat 11880
tagggtgatt tccttcaaaa tcgaaaaaag aaggatccct aatacaaggt tttttatcaa 11940
gctgagaag agcatgatag tgggtagtgc catcttgatg aagctcagaa gcaacaccaa 12000
ggaagaaaat aagaaaaggt gtgagtttct cccagagaaa ctggaataaa tcatctcttt 12060
gagatgagca cttgggatag gtaaggaaaa catatttaga ttggagtctg aagttcttac 12120
tagcagaagg catgttgttg tgactccgag ggggttgcctc aaactctatc ttataaccgg 12180
cgtgaggca tggaggcagg ggtatttggg tcattttaat agatagtgga aaatgacgtg 12240
gaatttactt aaagacgaag tctttgcgac aagggggggc ccacgccgaa tttaatatta 12300
ccggcgtggc ccccccttat cgcgagtgct ttagcacgag cgtccagat ttaaagtaga 12360
aaatttcccg cccactaggg ttaaaggtgt tcacactata aaagcatata cgatgtgatg 12420
gtatttgatg gagcgtatat tgtatcaggt atttccgttg gatacgaatt attcgtacga 12480
ccctcatagt ttaaactatc agtgtttgac aggatatatt ggcgggtaaa cctaagagaa 12540
aagagcgttt attagaataa cggatattta aaagggcgtg aaaaggttta tccgttcgtc 12600
catttgtatg tgcatgccaa ccacagggtt cccctcggga tcaaagtact ttgatccaac 12660
ccctccgctg ctatagtgca gtcggcttct gacgttcagt gcagccgtct tctgaaaacg 12720
acatgtcgca caagtcctaa gttacgcgac aggctgccgc cctgcccttt tcctggcgtt 12780
ttcttgtcgc gtgttttagt cgcataaagt agaatacttg cgactagaac ggagacatt 12840
acgccatgaa caagagcgcc gccgctggcc tgctgggcta tgcccgcgtc agcaccgacg 12900
accaggactt gaccaaccaa cgggccgaac tgcacgcggc cggctgcacc aagctgttt 12960
ccgagaagat caccggcacc aggcgcgacc gcccggagct ggccaggatg cttgaccacc 13020
tacgcctctgg cgacgttgtg acagtgacca ggctagaccg cctggcccgc agcacccgcg 13080
acctactgga cattgccgag cgcatccagg aggccggcgc gggcctgcgt agcctgcag 13140
agccgtgggc cgacaccacc acgccggccg gccgcatggt gttgaccgtg ttcgccggca 13200
ttgccgagtt cgagcgttcc ctaatcatcg accgcacccg gagcgggcgc gaggccgcca 13260
aggcccgagg cgtgaagttt ggcccccgcc taccctcac cccggcacag atcgcgcacg 13320
ccggcgagct gatcgaccag gaaggccgca ccgtgaaaga ggcgctgtcg ctgttgcag 13380
tgcatcgctc gaccctgtac cgcgcacttg agcgcagcga ggaagtgacg cccaccgagg 13440
ccaggcggcg cggtgccttc cgtgaggacg cattgaccga ggccgacgcc ctggcggccg 13500
ccgagaatga acgccaagag gaacaagcat gaaaccgcac caggacggcc aggacgaacc 13560
gtttttcatt accgaagaga tcgaggcgga gatgatcgcg gccgggtacg tgttcgagcc 13620
gcccgccac ggctccaaccg tgcgcgtgca tgaaatcccg gccggtttgt ctgatgccaa 13680
gctggcggcc tggccggcca gcttggccgc tgaagaaacc gagcgccgcc gtctaaaaag 13740
gtgatgtgta tttgagtaaa acagcttgcg tcatgcggtc gctgcgtata tgatgcgatg 13800
agtaaataaa caaatacgca aggggaacgc atgaaggtta tcgctgtact taaccagaaa 13860
ggcgggtcag gcaagacgac catcgcaacc catctagccc gcgccctgca actcgccggg 13920
gccgatgttc tgttagtcga ttccgatccc caggcagtg gcgcatcagg aacactcgg 13980
cgggaagatc aaccgctaac cgttgtcggc atcgaccgcc cgacgattga ccgcgacgtg 14040
aaggccatcg gccggcgcga cttcctagtg atcgacgagg cgcccaggc ggcggacttg 14100
gctgtgtccg cgatcaaggc agccgacttc gtgctgattc cggtgcagcc aagcccttac 14160
gacatatggg ccaccgccga cctggtggag ctggttaagc agcgcattga ggtcacggat 14220
ggaaggctac aagcggcctt tgtcgtgtcg cgggcgatca aggcacgcg catcggcggt 14280
```

```
gaggtttgccg aggcgctggc cgggtacgag ctgcccattc ttgagtcccg tatcacgcag  14340
cgcgtgagct acccaggcac tgccgccgcc ggcacaaccg ttcttgaatc agaacccgag  14400
ggcgacgctg cccgcgaggt ccaggcgctg gccgctgaaa ttaaatcaaa actcatttga  14460
gttaatgagg taaagagaaa atgagcaaaa gcacaaacac gctaagtgcc ggccgtccga  14520
gcgcacgcag cagcaaggct gcaacgttgg ccagcctggc agacacgcca gccatgaagc  14580
gggtcaactt tcagttgccg gcggaggatc acaccaagct gaagatgtac gcggtacgcc  14640
aaggcaagac cattaccgag ctgctatctg aatacatcgc gcagctacca gagtaaatga  14700
gcaaatgaat aaatgagtag atgaatttta gcggctaaag gaggcggcat ggaaaatcaa  14760
gaacaaccag gcaccgacgc cgtggaatgc cccatgtgtg gaggaacggg cggttggcca  14820
ggcgtaagcg gctgggttgt ctgccggccc tgcaatggca ctggaacccc caagcccgag  14880
gaatcggcgt gacggtcgca aaccatccgc cccgtacaa atcggcgcgg cgctgggtga  14940
tgacctggtg gagaagttga aggccgcgca ggccgcccag cggcaacgca tcgaggcaga  15000
agcacgcccc ggtgaatcgt ggcaagcggc cgctgatcga atccgcaaag aatcccggca  15060
accgccggca gccggtcgcg cgtcgattag gaagccgccc aagggcgacg agcaaccaga  15120
tttttttcgtt ccgatgctct atgacgtggg caccgcgat agtcgcagca tcatggacgt  15180
ggccgttttc cgtctgtcga agcgtgaccg acgagctggc gaggtgatcc gctacgagct  15240
tccagacggg cacgtagagg tttccgcagg gccggccgga atggccagtg tgtgggatta  15300
cgacctggta ctgatggcgg tttccatct aaccgaatcc atgaaccgat accgggaagg  15360
gaagggagac aagcccggcc gcgtgttccg tccacacgtt gcggacgtac tcaagttctg  15420
ccggcgagcc gatggcggaa agcagaaaga cgacctggta gaaacctgca ttcgttaaa  15480
caccacgcac gttgccatgc agcgtacgaa gaaggccaag aacggccgcc tggtgacggt  15540
atccgaaggt gaagccttga ttagccgcta caagatcgta aagagcgaaa ccggggcgcc  15600
ggagtacatc gagatcgagc tagctgattg gatgtaccgc gagatcacag aaggcaagaa  15660
cccgacgtg ctgacggttc accccgatta cttttttgatc gatcccggca tcggccgttt  15720
tctctaccgc ctggcacgcc gcgccgcagg caaggcagaa gccagatggt tgttcaagac  15780
gatctacgaa cgcagtggca gcgccggaga gttcaagaag ttctgttca ccgtgcgcaa  15840
gctgatcggg tcaaatgacc tgccggagta cgatttgaag gaggaggcgg ggcaggctgg  15900
cccgatccta gtcatgcgct accgcaacct gatcgagggc gaagcatccc ccggttccta  15960
atgtacggag cagatgctag ggcaaattgc cctagcaggg gaaaaggtc gaaaggcct  16020
ctttcctgtg gatagcacgt acattgggaa cccaaagccg tacattggga accggaaccc  16080
gtacattggg aacccaaagc cgtacattgg gaaccggtca cacatgtaag tgactgatat  16140
aaaagagaaa aaaggcgatt tttccggcta aaactcttta aaacttatta aaactcttaa  16200
aacccgcctg gcctgtgcat aactgtctgg ccagcgcaca gccaagagc tgcaaaaagc  16260
gcctacccct cggtcgctgc gctccctacg ccccgccgct tcgcgtcggc ctatcgcggc  16320
cgctggccgc tcaaaaatgg ctggcctacg gccaggcaat ctaccagggc gcggacaagc  16380
cgcgccgtcg ccactcgacc gccggcgccc acatcaaggc accctgcctc gcgcgtttcg  16440
gtgatgacgg tgaaaacctc tgacacatgc agctcccgga aacggtcaca gcttgtctgt  16500
aagcggatgc cgggagcaga caagcccgtc agggcgcgt agcgggtgtt ggcgggtgtc  16560
ggggcgcagc catgacccag tcacgtagcg atagcggagt gtatactggc ttaactatgc  16620
ggcatcagag cagattgtac tgagagtgca ccatatgcgg tgtgaaatac cgcacagatg  16680
cgtaaggaga aaataccgca tcaggccctc ttccgcttcc tcgctcactg actcgctgcg  16740
ctcggtcgtt cggctgcggc gagcggtatc agctcactca aaggcggtaa tacggttatc  16800
cacagaatca gggaataacg caggaaagaa catgtgagca aaaggccag caaaggccag  16860
gaaccgtaaa aaggccgcgt tgctggcgtt tttccatagg ctccgccccc ctgacgagca  16920
tcacaaaaat cgacgctcaa gtcagaggtg gcgaaacccg acaggactat aaagatacca  16980
ggcgtttccc cctggaagct ccctcgtgcg ctctcctgtt ccgaccctgc cgcttaccgg  17040
atacctgtcc gcctttctcc cttcgggaag cgtggcgctt tctcatagct cacgctgtag  17100
gtatctcagt tcggtgtagg tcgttcgctc caagctgggc tgtgtgcacg aaccccccgt  17160
tcagcccgac cgctgcgcct tatccggtaa ctatcgtctt gagtccaacc cggtaagaca  17220
cgacttatcg ccactggcag cagccactgg taacaggatt agcagagcga ggtat  17275
```

SEQ ID NO: 27          moltype = DNA   length = 17263
FEATURE                Location/Qualifiers
source                 1..17263
                       mol_type = other DNA
                       organism = synthetic construct
SEQUENCE: 27
```
gtaggcggtg ctacagagtt cttgaagtgg tggcctaact acggctacac tagaaggaca    60
gtatttggta tctgcgctct gctgaagcca gttaccttcg gaaaaagagt tggtagctct   120
tgatccggca aacaaaccac cgctggtagc ggtggttttt ttgttttgcaa gcagcagatt   180
acgcgcagaa aaaaaggatc tcaagaagat cctttgatct tttctacggg gtctgacgct   240
cagtggaacg aaaactcacg ttaagggatt ttggtcatgc attctaggta ctaaaacaat   300
tcatccagta aaatataata tttttattttc tcccaatcag gcttgatccc cagtaagtga   360
aaaaatagct cgacatactg ttcttccccg atatcctccg tgatcgaccg gacgcagaag   420
gcaatgtcat accacttgtc cgccctgccg cttctcccaa gatcaataaa gccacttact   480
tgccatcttt tcacaaagat gttgctgtct cccaggtcgc cgtgggaaaa gacaagttcc   540
tcttcgggct tttccgtctt taaaaaatca tacagctcgc gcggatcttt aaatggagtg   600
tcttcttccc agttttcgca atccacatcg gccagatcgt tattcagtaa gtaatccaat   660
tcggctaagc ggctgtctaa gctattcgta tagggacaat ccgatatgtc gatggagtga   720
aagagcctga tgcactccgc atacagctcg ataatctttt cagggctttg ttcatcttca   780
tactcttccg agcaaaggac gccatcggcc tcactcatga gcagattgct ccagccatca   840
tgccgttcaa agtgcaggac ctttggaaca ggcagctttc cttccagcca tagcatcatg   900
tcctttttcc cgttccacatc ataggtggtc cctttatacc ggctgtccgt catttttaaa   960
tataggtttt catttttctcc caccagctta tatccttag caggagacat tccttccgta  1020
tcttttacgc agcggtattt ttcgatcagt ttttttcaatt ccggtgatat tctcatttta  1080
gccatttatt atttccttcc tctttttctac agtatttaaa gataccccaa gaagctaatt  1140
ataacaagac gaactccaat tcactgttcc ttgcattcta aaaccttaaa taccagaaaa  1200
cagctttttc aaagttgttt tcaaagttgg cgtataacat agtatcgacg gagccgattt  1260
tgaaaccgcg gtgatcacag gcagcaacgc tctgtcatcg ttacaatcaa catgctaccc  1320
```

```
tccgcgagat catccgtgtt tcaaacccgg cagcttagtt gccgttcttc cgaatagcat  1380
cggtaacatg agcaaagtct gccgccttac aacggctctc ccgctgacgc cgtcccggac  1440
tgatgggctg cctgtatcga gtggtgattt tgtgccgagc tgccggtcgg ggagctgttg  1500
gctggctggt ggcaggatat attgtggtgt aaacaaattg acgcttagac aacttaataa  1560
cacattgcgg acgttttaa tgtactgaat taacgccgaa ttaattcggg ggatctggat  1620
tttagtactg gattttggtt ttaggaatta gaaattttat tgatagaagt attttacaaa  1680
tacaaataca tactaagggt ttcttatatg ctcaacacat gagcgaaacc ctataggaac  1740
cctaattccc ttatctggga actactcaca cattattatg gagaaactcg agcttgtcga  1800
tcgactctag ctagaggatc gatccgaacc ccagagtccc gctcagaaga actcgtcaag  1860
aaggcgatag aaggcgatgc gctgcgaatc gggagcggcg ataccgtaaa gcacgaggaa  1920
gcggtcagcc cattcgccgc caagttcttc agcaatatca cgggtagcca acgctatgtc  1980
ctgatagcgg tccgccacac ccagccggcc acagtcgatg aatccagaaa agcggccatt  2040
ttccaccatg atattcggca agcaggcatc gccatgtgtc acgacgagat cctcgccgtc  2100
gggcatgcgc gccttgagcc tggcgaacag ttcggctggc gcgagcccct gatgttcttc  2160
gtccagatca tcctgatcga caagaccggc ttccatccga gtacgtgctc gctcgatgcg  2220
atgtttcgct tggtggtcga atgggcaggt agccggatca agcgtatgca gccgccgcat  2280
tgcatcagcc atgatggata cttctctcgg caggagcaag gtgagatgac aggagatcctg  2340
ccccggcact cgcccaata gcagccagtc cttccccgct tcagtgacaa cgtcgagcac  2400
agctgcgcaa ggaacgcccg tcgtggccag ccacgatagc cgcgctgcct cgtcctggag  2460
ttcattcagg gcaccggaca ggtcggtctt gacaaaaaga accgggcgcc cctgcgctga  2520
cagccgaaac acggcggcat cagagcagcc gattgtctgt tgtgcccagt catagccgaa  2580
tagcctctcc acccaagcgg ccggagaacc tgcgtgcaat ccatcttgtt caatcccat   2640
ggtcgatcga cagatctgcg aaagctcgag agagatagat ttgtagagag agactggtga  2700
tttcagcgtg tcctctccaa atgaaatgaa cttccttata tagaggaagg tcttgcgaag  2760
gatagtggga ttgtgcgtca tcccttacgt cagtggagat atcacatcaa tccacttgct  2820
ttgaagacgt ggttggaacg tcttctttt ccacgatgct cctcgtgggt cctgtccca   2880
ctttgggacc actgtcggca gaggcatctt gaacgatagc cttcccttta tcgcaatgat  2940
ggcatttgta ggtgccacct tcctttctca ctgtccttt gatgaagtga cagatagctg  3000
ggcaatggaa tccgaggagg tttcccgata ttaccctttg ttgaaaagtc tcaatagccc  3060
tttggtcttc tgagactgta tcttgatat tcttgggta gacgagagtg tcgtgctcca  3120
ccatgttatc acatcaatcc acttgctttg aagacgtggt tggaacgtct tctttttcca  3180
cgatgctcct cgtgggtggg ggtccatctt tgggaccact gtcggcagag gcatcttgaa  3240
cgatagcctt tcctttatcg caatgatggc atttgtaggt gccaccttcc ttttctactg  3300
tccttttgat gaagtgacag atagctgggc aatggaatcc gaggaggttt cccgatatta  3360
cccttgttg aaaagtctca atagcccttt ggtcttctga gactgtatct ttgatattct  3420
tggagtagac gagagtgtcg tgctccacca tgttggcaag ctgctctagc caatacgcaa  3480
accgcctctc cccgcgcgtt ggccgattca ttaatgcagc tggcacgaca ggtttcccga  3540
ctggaaagcg ggcagtgagc gcaacgcaat taatgtgagt tagctcactc attaggcacc  3600
ccaggcttta cactttatgc ttccggctcg tatgttgtgt ggaattgtga gcggataaca  3660
atttcacaca ggaaacagct atgaccatga ttacgaattc gagctcaaag tttaacgcgt  3720
tagcagaagg catgttgttg tgactccgag gggttgcctc aaactctatc ttataaccgg  3780
cgtggaggca tggaggcagg gtatttttgg tcatttaat agatagtgga aaatgacgtg  3840
gaatttactt aaagacgaag tctttgcgac aagggggggc ccacgccgaa tttaatatta  3900
ccggcgtggc ccccccttat cgcgagtgct ttagcacgag cggtccagat ttaaagtaga  3960
aaatttcccg cccactaggg ttaaaggtgt tcacactata aaagcatata cgatgtgatg  4020
gtatttgatg gagcgtatat tgtatcaggt atttccgttg gatacgaatt attcgtacga  4080
ccctcggtac cgatcaaaag caggtgtcat gatcggcgcg cctggcagac atactgtccc  4140
acaaatgaag atgaatctg taaaagaaaa cgcgtgaaat aatgcgtctg acaaaggtta  4200
ggtcggctgc ctttaatcaa taccaaagtg gtccctacca cgatgaaaaa actgtgcagt  4260
cggtttggct ttttctgacg aacaaataag attcgtggcc gacaggtggg ggtccaccat  4320
gtgaaggcat cttcagactc caataatgga gcaatgacgt aagggcttac gaaataagta  4380
agggtagttt gggaaatgtc cactcacccg tcagtctata aatacttagc ccctccctca  4440
ttgttaaggg agcaaaatct cagagagata gtcctagaga gagaaagaga gcaagtagcc  4500
tagaagtagt caaggcggcg aagtattcag gcacgtggcc aggaagaaga aaagccaaga  4560
cgacgaaaac aggtaagagc taagcttcct gcaggatgga agacgccaaa aacataaaga  4620
aaggcccggc gccattctat ccgctgaaag atgaaccgc tggagagcaa ctgcataagg  4680
ctatgaagag atacgccctg gttcctggaa caattgcttt tacagatgca catatcgagg  4740
tggacatcac ttacgctgag tacttcgaaa tgtccgttcg gttggcagaa gctatgaaac  4800
gatatgggct gaatacaaat cacagaatcg tcgtatgcag tgaaaactct cttcaattct  4860
ttatgccggt gttgggcgcg ttatttatcg gagttgcagt tgcgcccgcg aacgactttt  4920
ataatgaacg tgaattgctc aacagtatgg gcatttcgca gcctaccgtg gtgttcgttt  4980
ccaaaaaggg gttgcaaaaa attttgaacg tgcaaaaaaa gctcccaatc atccaaaaaa  5040
ttattatcat ggattctaaa acggattacc agggatttca gtcgatgtac acgttcgtca  5100
catctcatct acctcccggt tttaatgaat acgattttgt gccagagtcc ttcgatagga  5160
acaagacaat tgcactgatc atgaactcct ctggatctac tggtctgcct aaaggtgtcg  5220
ctctgcctca tagaactgcc tgcgtgagat tctcgcatgc cagagatcct atttttggca  5280
atcaaatcat tccggatact gcgattttaa gtgttgttcc attccatcac ggttttggaa  5340
tgtttactac actcggatat ttgatatgtg gatttcgagt cgtcttaatg tatagatttg  5400
aagaagagct gtttctgagg agccttcagg attacaagat tcaaagtgcg ctgctggtgc  5460
caaccctatt ctccttcttc gccaaaagca ctctgattga caaatacgat ttatctaatt  5520
tacacgaaat tgcttctggt ggcgctcccc tctctaagga gtcggggaa gcggttgcca  5580
agaggttcca tctgccaggt atcaggcaag atatgggct cactgagact acatcagcta  5640
ttctgattac acccgagggg gatgataaac cgggcgcggt cggtaaagtt gttccatttt  5700
ttgaagcgaa ggttgtggat ctggataccg ggaaaacgct gggcgttaat caagagcgtg  5760
aactgtgtgt gagaggtcct atgattatgt ccggttatgt aaacaatccg gaagcgacca  5820
acgcctttgat tgacaaggat ggatggctac attctggaga catagcttac tgggacgaag  5880
acgaacactt cttcatcgtt gaccgcctga agtctctgat taagtacaaa ggctatcagg  5940
tggctcccgc tgaattggaa tccatcttgc tccaacaccc caacatcttc gacgctggtg  6000
tcgcaggtct tcccgacgat gacgccggtg aacttcccgc cgccgttgtt gttttggagc  6060
```

```
acggaaagac gatgacgaaa aaagagatcg tggattacgt cgccagtcaa gtaacaaccg   6120
cgaaaaagtt gcgcggagga gttgtgtttg tggacgaagt accgaaaggt cttaccggaa   6180
aactcgacgc aagaaaaatc agagagatcc tcataaaggc caagaagggc ggaaagatcg   6240
ccgtgtgacg tcgacgatat gaagatgaag atgaaatatt tggtgtgtca aataaaaagc   6300
ttgtgtgctt aagtttgtgt tttttcttg gcttgttgtg ttatgaattt gtggcttttt    6360
ctaatattaa atgaatgtaa gatcacatta taatgaataa acaaatgttt ctataatcca   6420
ttgtgaatgt tttgttggat ctcttctgca gcatataact actgtatgtg ctatggtatg   6480
gactatggaa tatgattaaa gataagccag agctctggtg acggacggcg cgactagttt   6540
tacgtacgtt aattaacccg ggcgcgccga tcatgagcgg agaattaagg gagtcacgtt   6600
atgacccccg ccgatgacgc gggacaagcc gttttacgtt tggaactgac agaaccgcaa   6660
cgttgaagga gccactcagc cgcgggtttc tggagtttaa tgagctaagc acatacgtca   6720
gaaaccatta ttgcgcgttc aaaagtcgcc taaggtcact atcagctagc aaatatttct   6780
tgtcaaaaat gctccactga cgttccataa attccctcg gtatccaatt agagtctcat    6840
attcactctc aatccaaata atctgcaccg tacctgcagg gtccgagcta ggtcacagaa   6900
gcgctcagga aggccgctga gatagaggca tggcggccaa tgcgggcggc ggtggagcgg   6960
gaggaggcag cggcagcggc agcgtggctg cgccggcggt gtgccgcccc agcggctcgc   7020
ggtggacgcc gacgccggag cagatcagga tgctgaagga gctgtactac ggctgcggca   7080
tccggtcgcc cagctcggag cagatccagc gcatcaccgc catgctgcgg cagcacggca   7140
agatcgaggg caagaacgtc ttctactggt tccagaacca caaggcccgc gagcgccaga   7200
agcgccgcct caccagcctc gacgtgaacg tgcccgccgc cggcgcggcc gacgccacca   7260
ccagccaact cggcgtcctc tcgctgtcgt cgccgccgcc ttcaggcgcg cgcctccct    7320
cgcccaccct cggcttctac ccgccgcgcca atggcgggag atcggctgtg ctgctggaca   7380
cgagttccga ctgggcagc agcggcgctg cgatggccac cgagacatgc ttcctccaga   7440
actacatggg cgtgacggac acgggcagct cgtcgcagtg gccacgcttc tcgtcgtcgg   7500
acacgataat ggcggcggcc gcggcgcggg cggcgacgac gcgggcgccc gagactctcc   7560
ctctcttccc gacctgcggc gacgacggcg gcagcggctac cggcgctac ttgccgttct    7620
ggggtgccgc gtccacaact gccgcgcca cttcttccgt tgcgatccag cagcaacacc    7680
agctgcagga gcagtacagc ttttacagca acagcaacag cacccagctg gccggcaccg   7740
gcaaccaaga cgtatcggca acagcagcag cagccgccgc cctggagctg agcctcagct   7800
catggtgctc cccttaccct gctgcaggga gtatgtgaga gcaacgcgag ctgccactgc   7860
tcttcactta tgtctctgga atggaaggag gaggaagtga gcatagcgtt ggtgcgttgc    7920
tgtcattgtc ctaggttagt agctagtgcc agttactagt aagcatcagg cataggagta   7980
tgtagtagaa gcatgcacgt tgccggccag ccaggcttta gacgggaaaa gaatttggtg   8040
cagccggctg caaaacagga tgtttacagc ccccccctcg agccctagac ttgtccatct   8100
tctggattgg ccaagttaat taatgtatga aataaaagga tgcacacata gtgacatgct   8160
aatcactata atgtgggcat caaagttgtg tgttatgtgt aattactaat tatctgaata   8220
agagaaaaag atcatccata tttcttatcc taaatgaatg tcacgtgtct ttataattct   8280
ttgatgaacc agatgcattt tattaaccaa ttccatatac atataaatat taatcatata   8340
taattaatat caattgggtt agcaaaacaa atctagtcta ggtgtgttt gctaattatt     8400
ggggatagt gcaaaagaa atctacgttc tcaataattc agatagaaaa cttaataaag     8460
tgagataatt tacatagatt gcttttatcc tttgatatat gtgaaccat gcatgatata    8520
aggaaatag atagagaaat aatttttac atcgttgaat atgtaaacaa tttaattcaa     8580
gaagctagga atataaatat tgaggagttt atgattagag ctctcccact aaacgtcccg   8640
cagatttgcc tttcaattt cagaaagaat gctaacccac agatggttag agaggcttac     8700
gcagcaggta tcatcaagac gatctacccg agcaataatc tccaggaaat caaataacctt   8760
cccaagaagg ttaaagatgc agtcaaaaga ttcaggacta actgcatcaa gaacacagag   8820
aaagatatat ttctcaagat cagaagtact atttccagta ggaccgattca aggcttgctt   8880
cacaaaccaa ggcaagtaat agagattgga gtctctaaaa aggtagttcc cactgaatca   8940
aaggccatgg agtcaaagat tcaaatagag gacctaacag aactcgccgt aaagactggc   9000
gaacagttca tacagagtct cttacgactc aatgacaaga agaaaatctt cgtcaacatg   9060
gtggacacg acacacttgt ctactccaaa aatatcaaag atacagtctc agaagaccaa    9120
agggcaattg agacttttca acaaagggta atatccggaa acctcctcgg attccattgg   9180
ccagctatct gtcactttat tgtgaagata gtggaaaagg aagtggctc ctacaaatgc     9240
catcattgcg ataaggaaa ggccatcgtt gaagatgcct ctgccgacag tggtcccaaa    9300
gatggaccc cacccacgag gagcatcgtg gaaaaagaag acgttccaac cacgtcttca   9360
aagcaagtgg attgatgtga tatctccact gacgtaaggg atgacgcaca atcccactat    9420
ccttcgcaag acccttcctc tatataagga agttcatttc atttggagag aacacggggg   9480
actatggaga gtggttccaa cagcacttct tgtccaatgg cttttgccgg ggataatagt   9540
gatggtccga tgtgtcctat gatgatgatg atgccgccca tcatgacatc acatcaaat     9600
catggtcatg atcatcaaca tcaacaacaa gaacatgatg gttatgcata tcagtcacac   9660
caccaacaaa gtagttccct tttcttcaa tcactagctc ctcccaagg aactaagaac     9720
aaagttgctt cttcttcttc tccttcctct tgtgctcctg cctattctct aatggagatc   9780
catcataacg aaatcgttgc aggaggaatc aaccttgct cctcttcctc ttcttcagcc     9840
tctgtcaagg ccaagatcat ggctcatcct cactaccacc gctccttggc cgcttatgtc   9900
aattgtcaga aggttggagc accaccggag gttggcga ggctagagga ggcatgctcg      9960
tctgccgcag ccgctgccgc atctatggga ccaacaggat gtcaggtga agatccaggg   10020
cttgatcaat tcatggaagc ttactgtgaa atgctcgtta agtatgagca agagctctcc   10080
aaacctttca aggaagctat ggtcttcctt caacgtgtcg agtgtcaatt caaatcctcc   10140
tctctatcct caccttcctc tttctccggt tatggagaga cagcaattga taggaacaat   10200
aatgggtcat ccgaggaaga agtcgatatg aacaatgaat ttgtagatcc acaagctgag   10260
gatagagagc ttaaaggaca gctcttgcgc aagtacagtg gttacttagg gagcctcaag   10320
caagagttca tgaagaagag gaagaaagga agctcccta agaagctcg tcaacaactg     10380
cttgattggt ggagccgtca ctacaaatgg ccttacccttt cggagcaaca aaagctcgcc   10440
cttgcggaat caacggggct ggaccagaaa cagataaaca attggttcat aaaccagagg   10500
aaacggcatt ggaagccgtc ggaggacatg cagtttgtag taatgacgc aacacatcct     10560
caccattact tcatgggataa tgtcttggc aatcctttcc caatggatca catctcctcc      10620
accatgcttt gactcgagtt tctccataat aatgtgtgag tagttccag ataagggaat      10680
tagggttcct atagggtttc gctcatgtgt tgagcatata agaaaccctt agtatgtatt   10740
tgtatttgta aaatacttct atcaataaaa tttctaattc ctaaaaccaa aatccagtac   10800
```

```
taaaatccag atcccccgaa ttaagtgttt gatcgccggc ggtaccgagt gtacttcaag   10860
tcagtgggaa atcaataaaa tgattatttt atgaatatat ttcattgtgc aagtagatag   10920
aaattacata tgttacataa cacacgaaat aaacaaaaaa agacaatcca aaaacaaaca   10980
ccccaaaaaa aataatcact ttagataaac tcgtatgagg agaggcacgt tcagtgactc   11040
gacgattccc gagcaaaaaa agtctccccg tcacacatgc agtgggtgac gcaattatct   11100
ttaaagtaat ccttctgttg acttgtcatt gataacatcc agtcttcgtc aggattgcaa   11160
agaattatag aagggatccc acctttatt ttcttctttt ttccatattt agggttgaca    11220
gtgaaatcag actggcaacc tattaattgc ttccacaatg ggacgaactt gaaggggatg   11280
tcgtcgatga tattataggt ggcgtgttca tcgtagttgg tgaaatcgat ggtaccgttc   11340
caatagttgt gtcgtccgag acttctagcc caggtggtct ttccggtacg agttggtccg   11400
cagatgtaga ggctggggtg tcggattcca ttccttccat tgtccttgtt aaatcggcca   11460
tccattcaag gtcagattga gcttgttggt atgagacagg atgtatgtaa gtaaagcgt    11520
ctatgcttac atggtataga tgggtttccc tccaggagtg tagatcttcg tggcagcgaa   11580
gatctgattc tgtgaagggc gacacatacg gttcaggttg tggagggaat aatttgttgg   11640
ctgaatattc cagccattga agctttgttg cccattcatg agggaattct tccttgatca   11700
tgtcaagata ttcctcctta gacgttgcag tctggataat agttctccat cgtgcgtcag   11760
atttgcgagg agaaacctta tgatctcgga aatctcctct ggttttaata tctccgtcct   11820
ttgatatgta atcaaggact tgtttagagt ttctagctcg tggatatta gggtgatttc    11880
cttcaaaatc gaaaaagaa ggatccctaa tacaaggttt tttatcaagc tggagaagag    11940
catgatagtg ggtagtgcca tcttgatgaa gctcagaagc aacaccaagg aagaaaataa   12000
gaaaaggtgt gagtttctcc cagagaaact ggaataaatc atctctttga gatgagcact   12060
tgggataggt aaggaaaaca tatttagatt ggagtctgaa gttcttacta gcagaaggca   12120
tgttgttgtg actccgaggg gttgcctcaa actctatctt ataaccgcg tggaggcatg     12180
gaggcagggg tattttggtc attttaatag atagtggaaa atgacgtgga atttacttaa   12240
agacgaagtc tttgcgacaa ggggggggccc acgccgaatt taatattacc ggcgtggccc   12300
cccttatcg cgagtgcttt agcacgagcg gtccagattt aaagtagaaa atttcccgcc    12360
cactagggtt aaaggtgttc acactataaa agcatatacg atgtgatggt atttgatgga   12420
gcgtatattg tatcaggtat ttccgttgga tacgaattat tcgtacgacc ctcatagttt   12480
aaactatcag tgtttgacag gatatattgg cgggtaaacc taagagaaaa gagcgtttat   12540
tagaataacg gatatttaaa agggcgtaaa aaggtttatc cgttcgtcca tttgtatgtg   12600
catgccaacc acagggttcc cctcgggatc aaagtacttt gatccaaccc ctccgctgct   12660
atagtgcagt cggcttctga cgttcagtgc agccgtcttc tgaaaacgac atgtcgcaca   12720
agtcctaagt tacgcgacag gctgccgccc tgccctttc ctggcgtttt cttgtcgcgt     12780
gttttagtcg cataaagtag aatacttgcg actagaaccg gagacattac gccatgaaca   12840
agagcgccgc cgctggcctg ctgggctatg cccgcgtcag caccgacgac caggacttga   12900
ccaaccaacg ggccgaactg cacgcggccg gctgcaccaa gctgttttcc gagaagatca   12960
ccggcaccag gcgcgaccgc ccggagctgg ccaggatgct tgaccaccta cgccctggcg   13020
acgttgtgac agtgaccagg ctagaccgcc tggcccgcag cacccgcgac ctactggaca   13080
ttgccgagcg catccaggag gccggcgcgg gcctgacgga cctggcagag ccgtgggcg    13140
acaccaccac gccggccggc cgcatggtgt tgaccgtgtt cgccggcatt gccgagttcg   13200
agcgttccct aatcatcgac cgcacccgga gcgggcgcga ggccgccaag gcccgaggcg   13260
tgaagtttgg cccccgccct accctcaccc cggcacagat cgcgcacgcc cgcgagctga   13320
tcgaccagga aggccgcacc gtgaaagagg cggctgcact gcttggcgtg catcgctcga   13380
ccctgtaccg cgcacttgag cgcagcgagg aagtgacgcc caccgaggcc aggcggcgcg   13440
gtgccttccg tgaggacgca ttgaccgagg ccgacgcctt ggcggccgcc gagaatgaac   13500
gccaagagga caagcatga aaccgcacca ggacggccag gacgaaccgt ttttcattac    13560
cgaagagatc gaggcggaga tgatcgcggc cgggtacgtg ttcgagccgc ccgcgcacgg   13620
ctcaaccgtg cggctgcatg aaatcctggc cggtttgtct gatgccaagc tggcggcctg   13680
gccggccagc ttggccgctg aagaaaccga gcgccgccgt ctaaaaaggt gatgtgtatt   13740
tgagtaaaac agcttgcgtc atgcggtcgc tgcgtatatg atgcgatgag taaataaaca   13800
aatacgcaag gggaacgcat gaaggttatc gctgtactta accagaaagg cgggtcaggc   13860
aagacgacca tcgcaaccca tctagccgcg ccctgcaac tcgccggggc cgatgttctg   13920
ttagtcgatt ccgatcccca gggcagtgcc cgcgattggg cggccgtgcg gaagatcaa    13980
ccgctaaccg ttgtcggcat cgaccgcccg acgattgacc gcgacgtgaa ggccatcggc   14040
cggcgcgact tcgtagtgat gacggagctg ccccaggcgg cggacttgc tgtgtccgca    14100
atcaaggcag ccgacttcgt gctgattccg gtgcagccaa gcccttacga catatgggcc   14160
accgccgacc tggtggagct ggttaagcag cgcattgagg tcacggatgg aaggctacaa   14220
gcggcctttg tcgtgtcgcg ggcgatcaaa ggcacgcgca tcggcggtga ggttgccgag   14280
gcgctggccg ggtacgagct gcccattctt gagtcccgta tcacgcagcg cgtgagctcg   14340
ccaggcactg ccgccgccgg cacaaccgtt cttgaatcag aacccgaggg cgacgctgcc   14400
cgcgaggtcc aggcgctggc cgctgaaatt aaatcaaaac tcatttgagt taatgaggta   14460
aagagaaaat gagcaaaagc acaaacacgc taagtgccgg ccgtccgagc gcacgcagca   14520
gcaaggctgc aacgttggcc agcctggcag acacgccagc catgaagcgg gtcaactttc   14580
agttgccggc ggaggatcac accaagctga agatgtacgc ggtacgccaa gctgaagacca   14640
ttaccgagct gctatctgaa tacatcgcgc agctaccaga gtaaatgagc aaatgaataa   14700
atgagtagat gaattttagc ggctaaagga ggcggcatgg aaaatcaaga acaaccaggc   14760
accgacgccg tggaatgccc catgtgtgga ggaacgggcg gttggccagg cgtaagcggc   14820
tgggttgtct gccggccctg caatggcact ggaaccccca agcccgagga atcgcgtga    14880
cggtcgcaaa ccatccggcc cggtacaaat cggcgcggcg ctggtgatg acctggtgga    14940
gaagttgaag gccgcgcagg ccgcccagcg gcaacgcatc gaggcagaag cacgccccgg   15000
tgaatcgtgg caagcggccg ctgatcgaat ccgcaaagaa tcccggcaac cgccggcagc   15060
cggtgcgccg tcgattagga agccgcccaa gggcgacgag caaccagatt ttttcgttcc   15120
gatgctctat gacgtgggca cccgcgatag tcgcagcatc atggacgtgg ccgttttccg   15180
tctgtcgaag cgtgaccgac gagctggcga ggtgatccgc tacgagcttc cagacgggca   15240
cgtagaggtt tccgcagggc cggccggcat ggccagtgtg tgggattacg acctggtact   15300
gatgcggttt tccatctaa ccgaatccat gaaccgatac cgggaaggga agggagacaa    15360
gccccggccgc gtgttccgtc cacacgttgc ggacgtactc aagttctgcc ggcgagccga   15420
tggcggaaag cagaaagacg acctggtaga aacctgcatt cggttaaaca ccacgcacgt   15480
tgccatgcag cgtacgaaga aggccaagaa cggccgcctg gtgacggtat ccgagggtga   15540
```

```
agccttgatt agccgctaca agatcgtaaa gagcgaaacc gggcggccgg agtacatcga 15600
gatcgagcta gctgattgga tgtaccgcga gatcacagaa ggcaagaacc cggacgtgct 15660
gacggttcac cccgattact tttttgatcga tcccggcatc ggccgttttc tctaccgcct 15720
ggcacgccgc gccgcaggca aggcagaagc cagatggttg ttcaagacga tctacgaacg 15780
cagtggcagc gccggagagt tcaagaagtt ctgtttcacc gtgcgcaagc tgatcgggtc 15840
aaatgacctg ccggagtacg atttgaagga ggaggcgggg caggctggcc cgatcctagt 15900
catgcgctac cgcaacctga tcgagggcga agcatccgcc ggttcctaat gtacggagca 15960
gatgctaggg caaattgccc tagcagggga aaaaggtcga aaaggcctct ttcctgtgga 16020
tagcacgtac attgggaacc caaagccgta cattgggaac cggaacccgt acattgggaa 16080
cccaaagccg tacattggga accggtcaca catgtaagtg actgatataa aagagaaaaa 16140
aggcgatttt tccgcctaaa actctttaaa acttattaaa actcttaaaa cccgcctggc 16200
ctgtgcataa ctgtctggcc agcgcacagc ccaagagctg caaaaagcgc ctacccttcg 16260
gtcgctgcgc tccctacgcc ccgccgcttc gcgtcggcct atcgcggccg ctggccgctc 16320
aaaaatggct ggcctacggc caggcaatct accagggcgc ggacaagccg gccgtcgcc 16380
actcgaccgc cggcgcccac atcaaggcac cctgcctcgc gcgtttcggt gatgacggtg 16440
aaaacctctg acacatgcag ctcccggaaa cggtcacagc ttgtctgtaa gcggatgccg 16500
ggagcagaca agcccgtcag ggcgcgtcag cgggtgttgg cgggtgtcgg ggcgcagcca 16560
tgacccagtc acgtagcgat agcggagtgt atactggctt aactatgcgg catcagagca 16620
gattgtactg agagtgcacc atatgcggtg tgaaataccg cacagatgcg taaggagaaa 16680
ataccgcatc aggccctctt ccgcttcctc gctcactgac tcgctgcgct cggtcgttcg 16740
gctgcggcga gcggtatcag ctcactcaaa ggcggtaata cggttatcca cagaatcagg 16800
ggataacgca ggaaagaaca tgtgagcaaa aggccagcaa aaggccagga accgtaaaaa 16860
ggccgcgttg ctggcgtttt tccataggct ccgcccccct gacgagcatc acaaaaatcg 16920
acgctcaagt cagaggtggc gaaacccgac aggactataa agataccagg cgtttccccc 16980
tggaagctcc ctcgtgcgct ctcctgttcc gaccctgccg cttaccggat acctgtccgc 17040
ctttctccct tcgggaagcg tggcgctttc tcatagctcg cgctgtaggt atctcagttc 17100
ggtgtaggtc gttcgctcca agctgggctg tgtgcacgaa ccccccgttc agcccgaccg 17160
ctgcgcctta tccggtaact atcgtcttga gtccaacccg gtaagacacg acttatcgcc 17220
actggcagca gccactggta acaggattag cagagcgagg tat              17263

SEQ ID NO: 28          moltype = DNA   length = 17767
FEATURE                Location/Qualifiers
source                 1..17767
                       mol_type = other DNA
                       organism = synthetic construct
SEQUENCE: 28
gtaggcggtg ctacagagtt cttgaagtgg tggcctaact acggctacac tagaaggaca 60
gtatttggta tctgcgctct gctgaagcca gttaccttcg aaaaagagt tggtagctct 120
tgatccggca aacaaaccac cgctggtagc ggtggttttt ttgtttgcaa gcagcagatt 180
acgcgcagaa aaaaggatc tcaagaagat cctttgatct ttttctacgg gtgtcgacgct 240
cagtggaacg aaaactcacg ttaagggatt ttggtcatgc attctaggta ctaaaacaat 300
tcatccagta aaatataata ttttatttc tcccaatcag gcttgatccc cagtaagtca 360
aaaaatagct cgacatactg ttcttccccg atatcctccg tgatcgaccg gacgcagaag 420
gcaatgtcat accacttgtc cgccctgccg cttctcccaa gatcaataaa gccacttact 480
ttgccatctt tcacaaagat gttgctgtct cccaggtcgc cgtgggaaaa gacaagttcc 540
tcttcgggct tttccgtctt taaaaaatca tacagctcgc gcggatcttt aaatggagtg 600
tcttcttccc agttttcgca atccacatcg ccagattgtt tattcagtaa gtaatccaat 660
tcggctaagc ggctgtctaa gctattcgta tagggacaat ccgatatgtc gatggagtga 720
aagagcctga tgcactccgc atacagctcg ataatctttt cagggctttg ttcatcttca 780
tactcttccg agcaaaggac gccatcggcc tcactcatga gcagattgct ccagccatca 840
tgccgttcaa agtgcaggac cttttggaaca ggcactttc cttccagcca tagcatcatg 900
tcctttttccc gttccacatc ataggtggtc cctttatacc ggctgtccgt catttttaaa 960
tataggtttt catttctcc caccagctta tataccttag caggagacat tccttccgta 1020
tcttttacgc agcggtattt ttcgatcagt ttttcaatt ccggtgatat tctcatttta 1080
gccatttatt atttccttcc tcttttctac agtatttaaa gatacccaa gaagctaatt 1140
ataacaagac gaactccaat tcactgttcc ttgcattcta aaaccttaaa taccagaaaa 1200
cagcttttc aaagttgttt tcaaagttgg cgtataacat agtatcgacg gagccgattt 1260
tgaaaccgcg gtgatcacag gcagcaacgc tctgtcatcg ttacaatcaa catgctaccc 1320
tccgcgagat catccgtgtt tcaaaccccgg cagcttagtt gccgttcttc cgaatagcat 1380
cggtaacatg agcaaagtct gccgccttac aacggctctc ccgctgacgc cgtcccggac 1440
tgatgggctg cctgtatcga gtggtgattt tgtgccgagc tgccggtcgg ggagctgttg 1500
gctggctggt ggcaggatat attgtggtgt aaacaaattg acgcttagac aacttaataa 1560
cacattgcgg acgtttttaa tgtactgaat taacgccgaa ttaattcggg ggatctggat 1620
tttagtactg gatttttggtt ttaggaatta gaatttat tgatagaagt atttttacaaa 1680
tacaaataca tactaagggt ttcttatatg ctcaacacat gagcgaaacc ctataggaac 1740
cctaattccc ttatcgggga actactcaca cattattatg gagaaactcg agcttgtcga 1800
tcgactctag ctagaggatc gatccgaacc ccagagtccc gctcagaaga actcgtcaag 1860
aaggcgatag aaggcgatgc gctgcgaatc gggagcggcg ataccgtaaa gcacgaggaa 1920
gcggtcagcc cattcgccgc caagttcttc agcaatatca cgggtagcca acgctatgtc 1980
ctgatagcgg tccgccacac ccagccggcc acagtcgatg aatccagaaa agcggccatt 2040
ttccaccatg atattcggca agcaggcatc gccatgtgtc acgacgagat cctgccgtc 2100
gggcatgcgc gccttgagcc tggcgaacag ttcggctggc gcgagcccct gatgttcttc 2160
gtccagatca tcctgatcga caagaccggc ttccatccga gtacgtgctc gctcgatgcg 2220
atgtttcgct tggtggtcga atgggcaggt agccggatca agcgtatgca gccgccgcat 2280
tgcatcagcc atgatggata cttctccggc aggagcaagg tgagatgaca ggagatcctg 2340
ccccggcact cgcccaata gcagccagtc ccttcccgct tcagtgacaa cgtcgagcac 2400
agctgcgcaa ggaacgcccg tcgtggccag ccacgatagc cgcgctgcct cgtcctggag 2460
ttcattcagg gcaccggaca ggtcggtctt gacaaaaaga accgggcgcc cctgcgctga 2520
cagccgaaac acggcggcat cagagcagcc gattgtctgt tgtgcccagt catagccgaa 2580
```

```
tagcctctcc acccaagcgg ccggagaacc tgcgtgcaat ccatcttgtt caatccccat  2640
ggtcgatcga cagatctgcg aaagctcgag agagatagat ttgtagagag agactggtga  2700
tttcagcgtg tcctctccaa atgaaatgaa cttccttata tagaggaagg tcttgcgaag  2760
gatagtggga ttgtgcgtca tcccttacgt cagtggagat atcacatcaa tccacttgct  2820
ttgaagacgt ggttggaacg tcttctttt ccacgatgct cctcgtgggt gggggtccat  2880
ctttgggacc actgtcggca gaggcatctt gaacgatagc cttccttta tcgcaatgat  2940
ggcatttgta ggtgccacct tccttttcta ctgtccttt gatgaagtga cagatagctg  3000
ggcaatggaa tccgaggagg tttcccgata ttaccctttg ttgaaaagtc tcaatagccc  3060
tttggtcttc tgagactgta tcttttgatat tcttggagta gacgagagtg tcgtgctcca  3120
ccatgttatc acatcaatcc acttgctttg aagacgtggt tggaacgtct tcttttcca  3180
cgatgctcct cgtgggtggg ggtccatctt tgggaccact gtcggcagag gcatcttgaa  3240
cgatagcctt tcctttatcg caatgatggc atttgtaggt gccaccttcc ttttctactg  3300
tccttttgat gaagtgacag atagctgggc aatggaatcc gaggaggttt cccgatatta  3360
cccttgttg aaaagtctca atagccctt gtcttctga gactgtatct ttgatattct  3420
tggagtagac gagagtgtcg tgctccacca tgttggcaag ctgctctagc aatacgcaa  3480
accgcctctc cccgcgcgtt ggccgattca ttaatgcagc tggcacgaca ggtttcccga  3540
ctggaaagcg ggcagtgagc gcaacgcaat taatgtgagt tagctcactc attaggcacc  3600
ccaggcttta cactttatgc ttccggctcg tatgttgtgt ggaattgtga gcggataaca  3660
atttcacaca ggaaacagct atgaccatga ttacgaattc gagctcaaag tttaacgcgt  3720
tagcagaagg catgttgttg tgactccgag gggttgcctc aaactctatc ttataaccgg  3780
cgtggaggca tggaggcagg ggtattttgg tcatttaat agatagtgga aaatgacgtg  3840
gaatttactt aaagacgaag tctttgcgac aagggggcc ccagccgaa tttaatatta  3900
ccggcgtggc cccccttat cgcgagtgct ttagcacgag cggtccagat ttaaagtaga  3960
aaatttcccg cccactaggg ttaaaggtgt tcacactata aaagcatata cgatgtgatg  4020
gtatttgatg gagcgtatat tgtatcaggt atttccgttg gatacgaatt attcgtacga  4080
ccctcggtac cgatcaaaag caggtgtcat gatcggcgcg cctggcagac atactgtccc  4140
acaaatgaag atggaatctg taaaagaaaa cgcgtgaaat aatgcgtctg acaaaggtta  4200
ggtcggctgc ctttaatcaa taccaaagtg gtccctacca cgatgaaaaa actgtgcagt  4260
cggtttggct ttttctgacg aacaaataag attcgtggcc gacaggtggg ggtccaccat  4320
gtgaaggcat cttcagactc caataatgga gcaatgacgt aagggcttac gaaataagta  4380
agggtagttt gggaaatgtc cactcacccg tcagtctata aatacttagc ccctccctca  4440
ttgttaaggg agcaaaatct cagagagata gtcctagaga gagaaagaga gcaagtagcc  4500
tagaagtagt caaggcggcg aagtattcag gcacgtggcc aggaagaaga aaagccaaga  4560
cgacgaaaac aggtaagagc taagcttcct gcaggatgga agacgccaaa aacataaaga  4620
aaggcccggc gccattctat ccgctgaag atggaaccgc tggagagcaa ctgcataagg  4680
ctatgaagag atacgccctg gttcctggaa caattgcttt tacagatgca catatcgagg  4740
tggacatcac ttacgctgag tacttcgaaa tgtccgttcg gttggcagaa gctatgaaac  4800
gatatgggct gaatacaaat cacagaatcg tcgtatgcag tgaaaactct cttcaattct  4860
ttatgccggt gttgggcgcg ttatttatcg gagttgcagt tgcgcccgcg aacgacattt  4920
ataatgaacg tgaattgctc aacagtatgg gcatttcgca gcctaccgtg gtgttcgttt  4980
ccaaaaaggg gttgcaaaaa attttgaacg tgcaaaaaaa gctcccaatc atccaaaaaa  5040
ttattatcat ggattctaaa acggattacc agggatttca gtcgatgtac acgttcgtca  5100
catctcatct acctcccggt tttaatgaat acgattttgt accagagtcc ttcgataggg  5160
acaagacaat tgcactgatc atgaactcct ctggatctac tggtctgcct aaaggtgtcg  5220
ctctgcctca tagaactgcc tgcgtgagat tctcgcatgc cagagatcct atttttggca  5280
atcaaatcat tccggatact gcgattttaa gtgttgttcc attccatcac ggttttggaa  5340
tgtttactac actcggatat ttgatatgtg gatttcgagt cgtcttaatg tatagatttg  5400
aagaagagct gtttctgagg agccttcagg attacaagat tcaaagtgcg ctgctggtgc  5460
caacccatt ctccttcttc gccaaaagca ctctgattga caatacgat ttatctaatt  5520
tacacgaaat tgcttctggt ggcgctcccc tctctaagga agtcggggaa gcggttgcca  5580
agaggttcca tctgccaggt atcaggcaag gatatgtgca cactgagact acatcagcta  5640
ttctgattac acccgagggg gatgataaac cgggcgcggt cggtaaagtt gttccatttt  5700
ttgaagcgaa ggttgtggat ctggataccg ggaaaacgct gggcgttaat caaagaggcg  5760
aactgtgtgt gagaggtcct atgattatgt ccggttatgt aaacaatccg gaagcgacca  5820
acgccttgat tgacaaggat ggatggctac atttctgaga catagcttac tgggacgaag  5880
acgaacactt cttcatcgtt gaccgcctga agtctctgat taagtacaaa ggctatcagg  5940
tggctcccgc tgaattggaa tccatcttgc tccaacaccc caacatcttc gacgctggtg  6000
tcgcaggtct cccgacgat gacgccggtg aacttcccgc cgccgttgtt gttttggagc  6060
acggaaagac gatgacgaca aaagagatcg tggattcgc cgccagtcaa gtaacaacg  6120
cgaaaaagtt gcgcggagga gttgtgtttg tggacgaagt accgaaaggt cttaccggaa  6180
aactcgacgc aagaaaaatc agagagatcc tcataaaggc caagaagggc ggaaagatcg  6240
ccgtgtgacg tcgacgatat gaagatgaag atgaaatatt tggtgtgtca aataaaaagc  6300
ttgtgtgctt aagtttgtgt ttttttcttg gcttgttgtg ttatgaattt gtggcttttt  6360
ctaatattaa atgaatgtaa gatcacatta taatgaatta caaaatgttt ctataatcca  6420
ttgtgaatgt tttgttggat ctcttctgca gcatataact actgtatgtg ctatggtatg  6480
gactatggaa tatgattaaa gataagccag agctctggtg acggacggcg cgactagttt  6540
tacgtacgtt aattaacccg gcgcgccga tcatgagcgg agaattaagg gagtcacgtt  6600
atgacccccg ccgatgacgc gggacaagcc gttttacgtt tggaactgac agaaccgcaa  6660
cgttgaagga gccactcagc cgcgggtttc tggagtttaa tgagctaaga cacatacgtca  6720
gaaaccatta ttgcgcgttc aaaagtcgcc taaggtcact atcagctagc aaatatttct  6780
tgtcaaaaat gctccactga cgttccataa attccctcg gtatccaatt agagtctcat  6840
attcactctc aatccaaata atctgcaccg tacctgcagg gtccgagcta ggtcacgaaa  6900
gcgctcagga aggccgctga gatagaggca tggcggccaa tgcgggcggc ggtggagcgg  6960
gaggaggcag cggcagcggc agcgtggcg gccgctgacc gttgcgcccc agcgctcgc  7020
ggtgacgcc gacgccggag cagatcagga tgctgaagga gctgtactac ggctgcggca  7080
tccggtcgcc cagctcggag cagatccagc gcatcaccgc catgctgcgg cagcacggca  7140
agatcgaggg caagaacgtc ttctactggt tccagaacca caaggcccgc gagcgccaga  7200
agcgccgcct caccagcctc gacgtgaacg tgcccgccgc cggcgcggcc gacgccacca  7260
ccagccaact cggcgtcctc tcgctgtcgt cgccgccgcc ttcaggcgcg cgcctccct  7320
```

```
cgcccaccct cggcttctac gccgccggca atggcggcgg atcggctgtg ctgctggaca  7380
cgagttccga ctggggcagc agcggcgctg cgatggccac cgagacatgc ttcctccagg  7440
actacatggg cgtgacggac acgggcagct cgtcgcagtg gccacgcttc tcgtcgtcgg  7500
acacgataat ggcggcggcc gcggcgcggg cggcgacgac gcgggcgccc gagactctcc  7560
ctctcttccc gacctgccgc gacgacggcg gcagcggctac ttgccgttct  7620
ggggtgccgc gtccacaact gccggcgcca cttcttccgt tgcgatccag cagcaacacc  7680
agctgcagga gcagtacagc ttttacagca acagcaacag cacccagctg gccggcaccg  7740
gcaaccaaga cgtatcggca acagcagcag cagccgccgc cctggagctg agcctcagct  7800
catggtgctc cccttaccct gctgcaggga gtatgtgaga gcaacgcgag ctgccactgc  7860
tcttcactta tgtctctgga atggaaggag gaggaagtga gcatagcgtt ggtgcgttgc  7920
tgtcattgtc ctaggttagt agctagtgcc agttactagt aagcatcagg cataggagta  7980
tgtagtagaa gcatgcacgt tgccggccag ccaggcttta gacgggaaaa gaatttggtg  8040
cagccggctg caaaacagga tgtttacagc cccccccctcg agccctagac ttgtccatct  8100
tctggattgg ccaagttaat taatgtatga tgcacacata gtgacatgct  8160
aatcactata atgtgggcat caaagttgtg tgttatgtgt aattactaat tatctgaata  8220
agagaaagag atcatccata tttcttatcc taaatgaatg tcacgtgtct ttataattct  8280
ttgatgaacc agatgcattt tattaaccaa ttccatatac atataaatat taatcatata  8340
taattaatat caattgggtt agcaaaacaa atctagtcta ggtgtgtttt gctaattatt  8400
gggggatagt gcaaaagaa atctacgttc tcaataattc agatagaaaa cttaataaag  8460
tgagataatt tacatagatt gcttttatcc tttgatatat gtgaaaccat gcatgatata  8520
aggaaaatag atagagaaat aattttttac atcgttgaat atgtaaacaa tttaattcaa  8580
gaagctagga atataaatat tgaggagttt atgattagga ctctcccact aaacgtcccg  8640
cgtcgagctg caggtcaacg gatcaggata ttcttgttta agatgttgaa ctctatggag  8700
gtttgtatga actgatgatc taggaccgga taagttccct tcttcatagc gaacttattc  8760
aaagaatgtt ttgtgtatca ttcttgttac attgttatta atgaaaaat attattggtc  8820
attggactga acacgagtgt taaatatgga ccaggccccca aataagatcc attgatatat  8880
gaattaaata acaagaataa atcgagtcac caaaccactt gcctttttta acgagacttg  8940
ttcaccaact tgatacaaaa gtcattatcc tatgcaaatc aataatcata caaaaatatc  9000
caataacact aaaaaattaa aagaaatgga taatttcaca atatgttata cgataaagaa  9060
gttactttc caagaaattc actgattta taagcccact tgcattagat aatggcaaa  9120
aaaaaacaaa aaggaaaaga aataaagcac gaagaattct agaaaatacg aaatacgctt  9180
caatgcagtg ggaccacgg ttcaattatt gccaatttc agctccaccg tatatttaaa  9240
aaataaaacg ataatgctaa aaaaatataa atcgtaacga tcgttaaatc tcaacggctg  9300
gatcttatga cgaccgttag aaattgtggt tgtcgacgag tcagtaataa acggcgtcaa  9360
agtggttgca gccggcacac acgagtcgtg tttatcaact caaagcacaa atactttttcc  9420
tcaacctaaa aataaggcaa ttagccaaaa acaactttgc gtgtaaacaa cgctcaatac  9480
acgtgtcatt ttattattag ctattgcttc accgccttag cttttctcgtg acctagtcgt  9540
cctcgtcttt tcttcttctt cttctataaa acaatacca aagagctctt cttcttcaca  9600
attcagattt caatttctca aaatcttaaa aactttctct caattcctc taccgtagtc  9660
aaggtaaatt tctgtgttcc ttattctctc aaaatcttcg attttgtttt cgttcgatcc  9720
caatttcgta tatgttcttt ggtttagatt ctgttaatct tagatcgaac acgatttctct  9780
gggtttgatc gttagatatc atcttaattc tcgattaggg tttcatagat atcatccgat  9840
ttgttcaaat aatttgagtt ttgtcgaata attactcttc gatttttgat ttctatctag  9900
atctggtgtt agtttctagt ttgtgcgatc gaatttgtcg attaatctga gttttttctga  9960
ttaacaggat ggagagtggt tccaacagca cttcttgtcc aatggctttt gccggggata 10020
atagtgatgg tccgatgtgt cctatgatga tgatgatgcc gccatcatg acatcacatc  10080
aacatcatgg tcatgatcat caacatcaac aacaagaaca tgcaggttat gcatatcagt  10140
cacaccacca acaaagtagt tcccttttc ttcaatcact agctcctccc caaggaacta  10200
agaacaaagt tgcttcttct tcttctcctt cctcttgtgc tcctgccat tctctaatgg 10260
agatccatca taacgaaatc gttgcaggag gaatcaaccc ttgctcctct tcctcttctt  10320
cagcctctgt caaggccaag atcatggctc atcctcacta ccaccgcctc ttggccgcat  10380
atgtcaattg tcagaaggtt ggagcaccac cggaggttgt ggcgaggcta gaggaggcat  10440
gctcgtctgc cgcagccgct gccgcatcta tgggaccaac aggatgtcta ggtgaagatc  10500
cagggcttga tcaattcatg gaagcttact gtgaaatgct cgttaagtat gagcaagagc  10560
tctccaaacc tttcaaggaa gctatggtct tccttcaaca tgtcgagtgt caattcaaat  10620
ccctctctct atcctcacct tcctctttct ccggttatgg agagacagca attgatagga  10680
acaataatgg gtcatccgag gaagaagtcg atataacaa tgaatttgta gatccacaag  10740
ctgaggatag agagcttaaa ggacagctct tgcgcaagta cagtggttac ttagggagcc  10800
tcaagcaaga gttcatgaag aagaggaaga aggaaagct ccctaaagaa gctcgtcaac  10860
aactgcttga ttggtggagc cgtcactaca aatggcctta cccttcggag caacaaaagc  10920
tcgcccttgc ggaatcaacg gggctggacc agaaacagat aaacaattgg ttcataaacc  10980
agaggaaacg gcattggaag ccgtcggagg acatgcagtt tgtagtaatg gacgcaacac  11040
atcctccacca ttacttcatg gataatgtct tgggcaatca tttcccaatg gatcacatct  11100
cctccaccat gctttgactc gagtttctcc ataataatgt gtgagtagt cccagatagg  11160
ggaattaggg ttcctatagg gtttcgctca tgtgttgagc atataagaaa cccttagtat  11220
gtatttgtat ttgtaaaata cttctatcaa taaaatttct aattcctaaa accaaaatcc  11280
agtactaaaa tccagatccc ccgaattaag tgactacacc tgcaaaaagt gtttgatcgc  11340
cggcggtacc gagtgtactt caagtcagtg ggaaatcaat aaaatgattt ttttatgaat  11400
atatttcatt gtgcaagtag atagaaatta catatgttac ataacacacg aaataacaa  11460
aaaaagacaa tccaaaaaca aacaccccaa aaaaataat cactttagat aaactcgtat  11520
gaggagaggc acgttcagtg actcgacgat tcccgagcaa aaaaagtctc cccgtcacac  11580
atgtagtggg tgacgcaatt atcttaaag taatccttct gttgacttgt cattgataac  11640
atccagtctt cgtcaggatt gcaaagaatt atagaaggga tcccaccttt tatttttctc  11700
ttttttccat atttagggtt gacagtgaaa tcagactgga aacctattaa ttgcttccac  11760
aatgggacga acttgaaggg gatgtcgtcg atgatattat aggtggcgtg ttcatcgtag  11820
ttggtgaaat cgatggtacc gttccaatag ttgtgtcgtc cgagacttct agcccaggtg  11880
gtcttttccg tacgagttgg tccgcagatg tagaggctgg ggtgtcggat tccattcctt  11940
ccattgtcct tgttaaatcg gccatccatt caaggtcaga ttgagcttgt tggtatgaga 12000
caggatgtat gtaagtataa gcgtctatgc ttacatggta tagatgggtt tccctccagg 12060
```

```
agtgtagatc ttcgtggcag cgaagatctg attctgtgaa gggcgacaca tacggttcag  12120
gttgtggagg gaataatttg ttggctgaat attccagcca ttgaagcttt gttgcccatt  12180
catgagggaa ttcttccttg atcatgtcaa gatattcctc cttagacgtt gcagtctgga  12240
taatagttct ccatcgtgcg tcagatttgc gaggagaaac cttatgatct cggaaatctc  12300
ctctggtttt aatatctccg tcctttgata tgtaatcaag gacttgttta gagtttctag  12360
ctggctggat attagggtga tttccttcaa aatcgaaaaa agaaggatcc ctaatacaag  12420
gtttttatc aagctggaga agagcatgat agtgggtagt gccatcttga tgaagctcag  12480
aagcaacacc aaggaagaaa ataagaaaag gtgtgagttt ctcccagaga aactggaata  12540
aatcatctct ttgagatgag cacttgggat aggtaaggaa aacatattta gattggagtc  12600
tgaagttctt actagcagaa ggcatgttgt tgtgactccg aggggttgcc tcaaactcta  12660
tcttataacc ggcgtggagg catggaggca ggggtatttt ggtcatttta atagatagtg  12720
gaaaatgacg tggaatttac ttaaagacga agtctttgcg acaaggggggg gcccacgccg  12780
aatttaatat taccggcgtg gccccccctt atcgcgagtg ctttagcacg agcggtccga  12840
atttaaagta gaaaatttcc cgcccactag ggttaaaggt gttcacacta taaaagcata  12900
tacgatgtga tggtatttga tggagcgtat attgtatcag gtatttccgt tggatacgaa  12960
ttattcgtac gaccctcata gtttaaacta tcagtgtttg acaggatata ttggcgggta  13020
aacctaagag aaaagagcgt ttattagaat aacggatatt taaagggcg tgaaaaggtt  13080
tatccgttcg tccatttgta tgtgcatgct aaccacaggg ttcccctcgg gatcaaagta  13140
ctttgatcca accctccgc tgctatagta cagtcggctt ctgacgttca gtgcagccgt  13200
cttctgaaaa cgacatgtcg cacaagtcct aagttacgcg acaagctgcc gccctgccct  13260
tttcctggcg ttttcttgtc gcgtgtttta gtcgcataaa gtagaatact tgcgactaga  13320
accggagaca ttacgccatg aacaagagcg ccgccgctgg cctgctgggc tatgcccgcg  13380
tcagcaccga cgaccaggac ttgaccaacc aacgggccga actgcacgcg gccggctgca  13440
ccaagctgtt ttccgagaag atcaccggca ccaggcgcga ccgcccggag ctggccagga  13500
tgcttgacca cctacgccct ggcgacgttg tgacagtgac caggctagac cgcctggccc  13560
gcagcaccg cgacctactg gacattgccg agcgcatcca ggaggccggc gcgggcctg  13620
gtagcctggc agagccgtgg gccgacacca ccacgccggc cggccgcatg gtgttgaccg  13680
tgttcgccgg cattgccgag ttcgagcgtt ccctaatcat cgaccgcacc cggagcgggc  13740
gcgaggccgc caaggcccga ggcgtgaagt ttggcccccg ccctaccctc accccggcac  13800
agatccgcca cgccccgcgag ctgatcgacc aggaaggccg caccgtgaaa gaggcggctg  13860
cactgcttgg cgtgcatcgc tcgaccctgt accgcgcact tgagcgcagc gaggaagtga  13920
cgcccaccga ggccaggcgg cgcggtgcct tccgtgagga cgcattgacc gaggccgacg  13980
ccctggcggc cgccgagaat gaacgccaag aggaacaagc atgaaaccgc accaggacgg  14040
ccaggacgaa ccgttttttca ttaccgaaga gatcgaggcg gagatgatcg cggccgggta  14100
cgtgttcgag ccgccccgcgc acggctcaac cgtgcggctg catgaaatcc tggccggttt  14160
gtctgatgcc aagctggcgg cctggccggc cagcttggcc gctgaagaaa ccgagcgccg  14220
ccgtctaaaa aggtgatgtg tatttgagta aaacagcttg cgtcatgcgg tcgctgcgta  14280
tatgatgcga tgagtaaata aacaaatacg caaggggaac gcatgaaggt tatcgctgta  14340
cttaaccaga aaggcgggtc aggcaagacg accatcgcaa cccatctagc ccgcgccctg  14400
caactcgccg gggccgatgt tctgttagtc gattccgatc cccagggcag tgcccgcgat  14460
tgggcggccg tgcgggaaga tcaaccgcta accgttgtcg gcatcgaccg cccgacgatt  14520
gaccgcgacg tgaaggccat cggccggcgc gacttcgtag tgatcgacgg agcgcccag  14580
gcggcggact tggctgtgtc cgcgatcaag gcagccgact tcgtgctgat tccggtgcga  14640
ccaagccctt acgacatatg gccaccgcc gacctggtgg agctggttaa gcagcgcatt  14700
gaggtcacgg atggaaggct acaagcggcc tttgtcgtgt cgcggggcgat caaaggcacg  14760
cgcatcggcg gtgaggttgc cgaggcgctg gccgggtacg agctgcccat tcttgagtcc  14820
cgtatcacgc agcgcgtgag ctaccaggc actgccgccg ccggcacaac cgttcttgaa  14880
tcagaacccg agggcgacgc tgcccgcgag gtccaggcgc tggccgctga aattaaatca  14940
aaactcattt gagttaatga ggtaaagaga aatgagcaa aagcacaaac acgctaagtg  15000
ccggccgtcc gagcgcacgc agcagcaagg ctgcaacgtt ggccagcctg gcagacacgc  15060
cagccatgaa gcgggtcaac tttcagttgc cggcggaaga tcacaccaag ctgaagatgt  15120
acgcggtacg ccaaggcaag accattaccg agctgctatc tgaatacatc gcgcagctac  15180
cagagtaaat gagcaaatga ataaatgagt agatgaattt tagcggctaa aggaggcggc  15240
atggaaaatc aagaacaacc aggcaccgac gccgtggaat gccccatgtg tggaggaacg  15300
ggcggttggc caggcgtaag cggctgggtt gtctgccggc cctgcaattg cactggaacc  15360
cccaagcccg aggaatcggc gtgacggtcg caaaccatcc ggcccggtac aaatcggcgc  15420
ggcgctggt gatgacctgg tggagaagtt gaaggccgcg caggccgccc agcggcaacg  15480
catcgaggca gaagcacgcc ccggtgaatc gtggcaagcg gccgctgatc gaatccgcaa  15540
agaatcccgg caaccgccgc cagccggtgc gccgtcgatt aggaagccgc ccaagggcga  15600
cgagcaacca gatttttttcg ttccgatgct ctatgacgtg ggcacccgcg atagtcgcag  15660
catcatggac gtggccgtt tccgtctgtc gaagcgtgac cgacgagctg gcgaggtgat  15720
ccgctacgag cttccagacg ggcacgtaga ggtttccgca gggccggccg gcatggccag  15780
tgtgtgggat tacgacctgg tactgatggc ggtttcccat ctaaccgaat ccatgaaccg  15840
ataccgggaa gggaaggag acaagcccgg ccgcgtgttc cgtccacacg ttgcggacgt  15900
actcaagttc tgccggcgag ccgatggcgg aaagcagaaa gacgacctgg tagaaacctg  15960
cattcggtta acaccacgc acgttgccat gcagcgtacg aagaaggcca gaacggccg  16020
cctggtgacg gtatccgagg gtgaagcctt gattagccgc tacaagatcg taaagagcga  16080
aaccgggcgg ccggagtaca tcgagatcga gctagctgat tggatgtacc gcgagatcac  16140
agaaggcaag aaccccggca tgctgacggt tcaccccgat tactttttga tcgatcccga  16200
catcggccgt tttctctacc gcctggcacg ccgcgccgca ggcaaggcag aagccagatg  16260
gttgttcaag acgatctacg aacgcagtgg cagcgccgga gagttcaaga agttctgttt  16320
caccgtgcgc aagctgatcg gtcaaatga cctgccggag tacgatttga aggaggaggc  16380
ggggcaggct ggcccgatcg tagtcatgcg ctaccgcaac ctgatcgagg gcgaagcatc  16440
cgccggttcc taatgtacgg agcagatgct agggcaaatt gccctagcag gggaaaaagg  16500
tcgaaaaggc ctctttcctg tggatagcac gtacattggg aacccaaagc cgtacattgg  16560
gaaccggaac ccgtacattg gaaacccaaa gccgtacatt gggaaccggt cacacatgta  16620
agtgactgat ataaaagaga aaaaggcga ttttccgcc taaaactctt taaaacttat  16680
taaaactctt aaaacccgcc tggcctgtgc ataactgtct ggccagcgca cagcccaaga  16740
gctgcaaaaa gcgcctaccc ttcggtcgct gcgctcccta cgccccgccg cttcgcgtcg  16800
```

```
gcctatcgcg gccgctggcc gctcaaaaat ggctggccta cggccaggca atctaccagg   16860
gcgcggacaa gccgcgccgt cgccactcga ccgccggcgc ccacatcaag gcaccctgcc   16920
tcgcgcgttt cggtgatgac ggtgaaaacc tctgacacat gcagctcccg gaaacggtca   16980
cagcttgtct gtaagcggat gccgggagca gacaagcccg tcagggcgcg tcagcggtgt   17040
ttggcgggtg tcggggcgca gccatgaccc agtcacgtag cgatagcgga gtgtatactg   17100
gcttaactat gcggcatcag agcagattgt actgagagtg caccatatgc ggtgtgaaat   17160
accgcacaga tgcgtaagga gaaaataccg catcaggcgc tcttccgctt cctcgctcac   17220
tgactcgctg cgctcggtcg ttcggctgcg gcgagcggta tcagctcact caaaggcggt   17280
aatacggtta tccacagaat caggggataa gcaggaaag aacatgtgag caaaaggcca   17340
gcaaaaggcc aggaaccgta aaaaggccgc gttgctggcg ttttccata ggctccgccc   17400
ccctgacgag catcacaaaa atcgacgctc aagtcagagg tggcgaaacc cgacaggact   17460
ataaagatac caggcgtttc ccctggaag ctccctcgtg cgctcctg ttccgaccct   17520
gccgcttacc ggatacctgt ccgcctttct cccttcggga agcgtggcgc tttctcatag   17580
ctcacgctgt aggtatctca gttcggtgta ggtcgttcgc tccaagctgg gctgtgtgca   17640
cgaaccccc gttcagcccg accgctgcgc cttatccggt aactatcgtc ttgagtccaa   17700
cccggtaaga cacgacttat cgccactggc agcagccact ggtaacagga ttagcagagc   17760
gaggtat                                                             17767
```

```
SEQ ID NO: 29          moltype = DNA   length = 20340
FEATURE                Location/Qualifiers
source                 1..20340
                       mol_type = other DNA
                       organism = synthetic construct
SEQUENCE: 29
gtaggcggtg ctacagagtt cttgaagtgg tggcctaact acggctacac tagaaggaca     60
gtatttggta tctgcgctct gctgaagcca gttaccttcg gaaaaagagt tggtagctct    120
tgatccggca aacaaaccac cgctggtagc ggtggttttt ttgtttgcaa gcagcagatt    180
acgcgcagaa aaaaaggatc tcaagaagat cctttgatct tttctacggg gtctgacgct    240
cagtggaacg aaaactcacg ttaagggatt ttggtcatgc attctaggta ctaaaacaat    300
tcatccagta aaatataata tttattttc tcccaatcag gcttgatccc cagtaagtca    360
aaaaatagct cgacatactg ttcttccccg atatcctccc tgatcgaccg gacgcagaag    420
gcaatgtcat accactgtc cgccctgccg cttctcccaa gatcaataaa gccacttact    480
ttgccatctt tcacaaagat gttgctgtct cccaggtcgc cgtgggaaaa gacaagttcc    540
tcttcgggct tttccgtctt taaaaaatca tacagctcgc gcggatcttt aaatggagtg    600
tcttctttcc agttttcgca atccacatcg gccagatcgt tattcagtaa gtaatccaat    660
tcggctaagc ggctgtctaa gctattcgta tagggacaat ccgatatgtc gatggagtga    720
aagagcctga tgcactccgc atacagctcg ataatcttt cagggctttg ttcatcttca    780
tactcttccg agcaaaggac gccatcggcc tcactcatga gcagattgct ccagccatca    840
tgccgttcaa agtgcaggac cttttggaaca ggcagcttc cttccagcca tagcatcatg    900
tccttttccc gttccacatc ataggtggtc cctttatacc ggctgtccgt cattttaaaa    960
tataggtttt cattttctcc caccagctta tataccttag caggagacat tccttccgta   1020
tcttttacgc agcggtattt tcgatcagt tttttcaatt ccggtgatat tctcattta    1080
gccatttatt atttccttcc tcttttctac agtatttaaa gataccccaa gaagctaatt   1140
ataacaagac gaactccaat tcactgttcc ttgcattcta aaaccttaaa taccagaaaa   1200
cagcttttt aaagttgttt tcaaagttgg cgtataacat agtatcgacg gagccgattt   1260
tgaaaccgcg gtgatcacag gcagcaacgc tctgtcatcg ttacaatcaa catgctaccc   1320
tccgcgagat catccgtgtt tcaaacccgg cagcttagtt gccgttcttc cgaatagcat   1380
cggtaacatg agcaaagtct gccgccttac aacggctctc ccgctgacgc cgtcccggac   1440
tgatgggctg cctgtatcga gtggtgattt tgtgccgagc tgccggtcgg ggagctgttg   1500
gctggctggt ggcaggatat attgtggtgt aaacaaattg acgcttagac aacttaataa   1560
cacattgcgg acgtttttaa tgtactgaat taacgccgaa ttaattcggg ggatctgaat   1620
tttagtactg gattttggtt ttaggaatta gaaattttat tgatagaagt attttacaaa   1680
tacaaataca tactaagggt ttcttatatg ctcaacacat gagcgaaacc ctataggaac   1740
cctaattccc ttatctggga actactcaca cattattatg gagaaactcg agcttgtcga   1800
tcgactcag ctagaggatc gatccgaacc ccagagtccc gctcagaaga actcgtcaag   1860
aaggcgatag aaggcgatgc gctgcgaatc gggagcggcg ataccgtaaa gcacgaggaa   1920
gcggtcagcc cattcgccgc caagttcttc agcaatatca cgggtagcca acgctatgtc   1980
ctgatagcgg tccgccacac ccagccggcc acagtcgatg aatccagaaa agcggccatt   2040
ttccaccatg atattcggca agcaggcatc gccatgggtc acgacgagat cctcgccgtc   2100
gggcatgcgc gccttgagcc tggcgaacag ttcggctggc gcgagcccct gatgttcttc   2160
gtccagatca tcctgatcga caagaccggc ttccatccga gtacgtgctc gctcgatgcg   2220
atgtttcgct tggtggtcga atgggcaggt agccggatca agcgtatgca gccgccgcat   2280
tgcatcagcc atgatggata cttctcggc aggagcaagg tgagatgaca ggagatcctg   2340
ccccggcact tcgcccaata gcagccagtc ccttcccgct tcagtgacaa cgtcgagcac   2400
agctgcgcaa ggaacgcccg tcgtggccag ccacgatagc cgcgctgcct cgtcctggag   2460
ttcattcagg gcaccggaca ggtcggtctt gacaaaaaga accgggcgcc cctgcgctga   2520
cagccgaaac acggcggcat cagagcagcc gattgtctgt tgtgcccagt catagccgaa   2580
tagcctctcc acccaagcgg ccggagaacc tgcgtgcaat ccatcttgtt caatcccat    2640
ggtcgatcga cagatctgcg aaagctcgag agagatagt ttgtagagag agactgtga   2700
tttcagcgtg tcctctccaa atgaaatgaa cttccttata tagaggaagg tcttgcgaag   2760
gatagtggga ttgtgcgtca tcccttacgt cagtggagat atcacatcaa tccacttgct   2820
ttgaagacgt ggttggaacg tcttcttttt ccacgatgct cctcgtgggt gggggtccat   2880
ctttgggacc actgtcggca gaggcatctt gaacgatagc ctttccttta tcgcaatgat   2940
ggcatttgta ggtgccacct tccttttcta tgtcccttta gatgaagtga cagatagctg   3000
ggcaatggaa tccgaggagg tttcccgata ttaccctttg ttgaaaagtc tcaatagccc   3060
tttggtcttc tgagactgta tctttgatat tcttggagta gacgagagtg tcgtgctcca   3120
ccatgttatc acatcaatcc acttgctttg aagacgtggt tggaacgtct tctttttcca   3180
cgatgctcct cgtgggtggg ggtccatctt tggaccact gtcggcagag gcatcttgaa   3240
cgatagcctt tcctttatcg caatgatggc atttgtaggt gccaccttcc ttttctactg   3300
```

```
tccttttgat gaagtgacag atagctgggc aatggaatcc gaggaggttt cccgatatta   3360
cccttttgttg aaaagtctca atagccctttt ggtcttctga gactgtatct ttgatattct  3420
tggagtagac gagagtgtcg tgctccacca tgttggcaag ctgctctagc caatacgcaa   3480
accgcctctc cccgcgcgtt ggccgattca ttaatgcagc tggcacgaca ggtttcccga   3540
ctggaaagcg ggcagtgagc gcaacgcaat taatgtgagt tagctcactc attaggcacc   3600
ccaggcttta cactttatgc ttccggctcg tatgttgtgt ggaattgtga gcggataaca   3660
atttcacaca ggaaacagct atgaccatga ttacgaattc gagctcaaag tttaacgcgt   3720
tagcagaagg catgttgttg tgactccgag gggttgcctc aaactctatc ttataaccgg   3780
cgtggaggca tggaggcagg ggtattttgg tcattttaat agatagtgga aaatgacgtg   3840
gaatttactt aaagacgaag tctttgcgac aagggggggc ccacgccgaa tttaatatta   3900
ccggcgtggc ccccccttat cgcgagtgct ttagcacgag cggtccagat ttaaagtaga   3960
aaatttcccg cccactaggg ttaaaggtgt tcacactata aaagcatata cgatgtgatg   4020
gtatttgatg gagcgtatat tgtatcaggt atttccgttg gatacgaatt attcgtacga   4080
ccctcggtac cgatcaaaat catgatcggc gcgccagatt tgccttttca atttcagaaa   4140
gaatgctaac ccacagatgg ttagagaggc ttacgcagca ggtatcatca agacgatcta   4200
cccgagcaat aatctccagg aaatcaaata ccttcccaag aaggttaaag atgcagtcaa   4260
aagattcagg actaactgca tcaagaacac agagaaagat atatttctca agatcagaag   4320
tactattcca gtatggacga ttcaaggctt gcttcacaaa ccaaggcaag taatagagat   4380
tggagtctct aaaaaggtag ttcccactga atcaaaggcc atggagtcaa agattcaaat   4440
agaggaccta acagaactcg ccgtaaagac tggcgaacag ttcatacaga gtctcttacg   4500
actcaatgac aagaagaaaa tcttcgtcaa catggtggag cacgacacac ttgtctactc   4560
caaaaatatc aaagatacag tctcagaaga ccaaaggca attgagactt ttcaacaaag   4620
ggtaatatcc ggaaacctcc tcggattcca ttgcccagct atctgtcact ttattgtgaa   4680
gatagtggaa aaggaaggtg gctcctacaa atgccatcat tgcgataaag gaaaggccat   4740
cgttgaagat gcctctgccg acagtggtcc caaagatgga cccccaccca cgaggagcat   4800
cgtggaaaaa gaaacgttc caaccacgtc ttcaaagcaa gtggattgat gtgtatatct   4860
cactgacgta agggatgacg cacaatccca ctatccttcg caagaccctt cctctatata   4920
aggaagttca tttcatttgg agagaacacg ggggactcct gcaggtagat cgctcgtcga   4980
catggataag aagtactcta tcggactcga tatcggaact aactctgtgg gatgggctgt   5040
gatcaccgat gagtacaagg tgccatctaa gaagttcaag gttctcggaa acaccgatag   5100
gcactctatc aagaaaaacc ttatcggtgc tctcctcttc gattctggtg aaactgctga   5160
ggctaccaga ctcaagagaa ccgctagaag aaggtacacc agaagaaaga acaggatctg   5220
ctacctccaa gagatcttct ctaacgagat ggctaaagtg gatgattcat tcttccacag   5280
gctcgaagag tcattcctcg tggaagaaga taagaagcac gagaggcacc ctatcttcgg   5340
aaacatcgtt gatgaggtgg cataccacga gaagtaccct actatctacc acctcagaaa   5400
gaagctcgtt gattctactg ataaggctga tctcaggctc atctacctcg ctctcgctca   5460
catgatcaag ttcagaggac acttcctcat cgagggtgat ctcaaccctg ataactctga   5520
tgtggataag ttgttcatcc agctcgtgca gacctacaac cagcttttcg aagagaaccc   5580
tatcaacgct tcaggtgtgg atgctaaggc tatcctctct gctaggctct ctaagtcaag   5640
aaggcttgag aacctcattg ctcagctccc tggtgagaag aagaacggac ttttcggaaa   5700
cttgatcgct ctctctctcg gactcacccc taacttcaag tctaacttcg atctcgctga   5760
ggatgcaaag ctccagctct caaaggatac ctacgatgat gatctcgata acctcctcgc   5820
tcagatcgga gatcagtacg ctgatttgtt cctcgctgct aagaacctct ctgatgctat   5880
cctcctcagt gatatcctca gagtgaacac cgagatcacc aaggctccac tctcagcttc   5940
tatgatcaag agatacgatg agcaccacca ggatctcaca cttctcaagg ctcttgttag   6000
acagcagctc ccagagaagt acaaagagat tttcttcgat cagtctaaga acggatacg   6060
tggttacatc gatggtggtg catctcaaga agagttctac aagttcatca agcctatcct   6120
cgagaagatg gatggaaccg aggaactcct cgtgaagctc aatagagagg atcttctcag   6180
aaaagcagagg accttcgata acggatctat cccctcatcag atccacctcg agagttgca   6240
cgctatcctt agaaggcaag aggatttcta cccattcctc aaggataaca gggaaaagat   6300
tgagaagatt ctcaccttca gaatccctta ctacgtggga cctctcgcta gaggaaactc   6360
aagattcgct tggatgacca gaaagtctga ggaaaccatc acccccttgga acttcgaaga   6420
ggtggtggat aagggtgcta gtgctcagtc tttcatcgag aggatgacca acttcgataa   6480
gaaccttcca aacgagaagg tgctccctaa gcactctttg ctctacgagt acttccaccg   6540
gtacaacgag ttgaccaagg ttaagtacgt gaccgaggga atgaggaagc ctgctttttt   6600
gtcaggtgag caaaagaagg ctatcgttga tctcttgttc aagaccaaca gaaaggtgac   6660
cgtgaagcag ctcaaagagg attcttcaa gaaaatcgag tgcttcgatt cagttgagat   6720
ttctggtgtt gaggataggt tcaacgcatc tctcggaacc taccacgatc tcctcaagat   6780
cattaaggat aaggatttct tggataacga ggaaaacgga gatatcttgg aggatatgct   6840
tcttaccctc accctcttt aagatagaga gatgatgaa gaaaggctca agacctacgc   6900
tcatctcttc gatgataagg tgatgaagca gttgaagaga agaagataca ctggttgggg   6960
aaggctctca agaaagctca ttaacggaat cagggataag cagtctgaa agacaatcct   7020
tgatttcctc aagtctgatg gattcgctaa cagaaacttc atgcagctca tccacgatga   7080
ttctctcacc ttaaagagg atatccagaa gctcaggtc caggacagg tgtatgtct   7140
ccatgagcat atcgctaacc tcgctgatc tcctgcaatc aagaagggaa tcctccgac   7200
tgtgaaggtt gtggatgagt tggtgaaggt gatgggaagg cataagcctg agaacatcgt   7260
gatcgaaatg gctagagaga accagaccac tcagaaggga cagaagaact ctaggagaaag   7320
gatgaagagg atcgaggaag gtatcaaga gcttggatct cagatcctca aagcaccc   7380
tgttgagaac actcagctcc agaatgaaa gctctacctc tactacctcc agaacggaag   7440
ggatatgtat gtggatcaag agttggatat caacaggctc tctgattacg atgttgatca   7500
tatcgtgcca cagtcattct tgaaggatga ttctatcgat aacaaggtgc tcaccaggtc   7560
tgataagaac aggggtaaga gtgataacgt gccaagtgaa gaggttgtga agaaaatgaa   7620
gaactattgg aggcagctcc tcaacgctaa gctcatcact cagagaaagt tcgataactt   7680
gactaaggct gagaggggag gactctctga attggataga gcaggattca tcaagaggca   7740
gcttgtggaa accaggcaga tcactaagca cgttgcacag atcctcgatt ctaggatgaa   7800
caccaagtac gatgagaacg ataagttgat cagggaagtg aaggttatca ccctcaagtc   7860
aaagctcgtg tctgatttca gaaaggattt ccaattctac aaggtgaggg aaatcaacaa   7920
ctaccaccac gctcacgatg cttaccttaa cgctgttgtt ggaaccgctc tcatcaagaa   7980
gtatcctaag ctcgagtcag agttcgtgta cggtgattac aaggtgtacg atgtgaggaa   8040
```

```
gatgatcgct aagtctgagc aagagatcgg aaaggctacc gctaagtatt tcttctactc   8100
taacatcatg aatttcttca agaccgagat taccctcgct aacgtgaga  tcagaaagag   8160
gccactcatc gagacaaacg gtgaaacagg tgagatcgtg tgggataagg aagggattt    8220
cgctaccgtt agaaaggtgc tctctatgcc acaggtgaac atcgttaaga aaaccgaggt   8280
gcagaccggt ggattctcta aagagtctat cctccctaag aggaactctg ataagctcat   8340
tgctaggaag aaggattggg accctaagaa atacgtggt  ttcgattctc ctaccgtggc   8400
ttactctgtt ctcgttgtgg ctaaggttga aagggaaag  agtaagaagc tcaagtctgt   8460
taaggaactt ctcggaatca ctatcatgga aaggtcatct ttcgagaaga acccaatcga   8520
tttcctcgag gctaagggat acaaagaggt taagaaggat ctcatcatca agctcccaaa   8580
gtactcactc ttcgaactcg agaacggtag aaagaggatg ctcgcttctg ctggtgagct   8640
tcaaaaggga aacgagcttg ctctcccatc taagtacgtt aactttcttt acctcgcttc   8700
tcactacgag aagttgaagg gatctccaga agataacgag cagaagcaac ttttcgttga   8760
gcagcacaag cactacttgg atgagatcat cgagcagatc tctgagttct ctaaaagggt   8820
gatcctcgct gatgcaaacc tcgataaggt gttgtctgct tacaacaagc acagagataa   8880
gcctatcagg gaacaggcag agaacatcat ccatctcttc acccttacca acctcggtgc   8940
tcctgctgct ttcaagtact tcgatacaac catcgatagg aagagataca cctctaccaa   9000
agaagtgctc gatgctaccc tcatccatca gtctatcact ggactctacg agactaggat   9060
cgatctctca cagctcggtg gtgattcaag ggctgatcct aagaagagaa ggaaggtttg   9120
acgtcgacga tatgaagatg aagatgaaat atttggtgtg tcaaataaaa agcttgtgtg   9180
cttaagtttg tgttttttc  ttggcttgtt gtgttatgaa tttgtggctt tttctaatat   9240
taaatgaatg taagatcaca ttataatgaa taaacaaatg tttctataat ccattgtgaa   9300
tgttttgttg gatctcttct gcagcatata actactgtat gtgctatggt atggactatg   9360
gaatatgatt aaagataagc cagagctctg gtgacggacg tgggcttcgt tgaacaacgg   9420
aaaactcgact tgccttccgc acaatacatc atttcttctt agcttttttt cttcttcttc   9480
gttcatacag tttttttttg tttatcagct tacatttttct tgaaccgtag ctttcgtttt   9540
cttcttttta actttccatt cggagttttta gtatcttgtt tcatagtttg tcccaggatt   9600
agaatgatta ggcatcgaac cttcaagaat ttgattgaat aaaacatctt cattcttaag   9660
atatgaagat aatcttcaaa aggccctgg  gaatctgaaa aagagaagc  aggcccattt   9720
atatgggaaa gaacaatagt atttcttata taggcccatt taagttgaaa acaatcttca   9780
aaagtcccac atcgcttaga taagaaaacg aagctagtt  tatatacagc tagagtcgaa   9840
gtagtgattg ttggtagtag cgactccatg gtttagagc  tagaaatagc aagttaaaat   9900
aaggctagtc cgttatcaac ttgaaaagt  ggcaccgagt cggtgccag  agctctggtg   9960
acggacggcg cgactagttt tacgtacgtt aattaacccg ggcgcgccga tcatgagcgg  10020
agaattaagg gagtcacgtt atgaccccccg acaagcc    gttttacgtt             10080
tggaactgac agaaccgcaa cgttgaagga gccactcagc cgcgggtttc tggagtttaa  10140
tgagctaagc acatacgtca gaaaccatta ttgcgcgttc aaaagtcgcc taaggtcact  10200
atcagctagc aaatatttct tgtcaaaaat gctccactga cgttccataa attcccctcg  10260
gtatccaatt agagtctcat attcactctc aatccaaata atctgcaccg tacctgcagg  10320
gtccgagcta ggtcacagaa gcgctcagga aggccgctga gatagaggca tggcggccaa  10380
tgcgggcggc ggtggagcgg gaggaggcag cggcagcggc agcgtggctg cgccggcggt  10440
gtgccgcccc agcggctcgc ggtggacgcc gacgccggag cagatcagga tgctgaagga  10500
gctgtactac ggctgcggca tccggtcgcc cagctcggag cagatccagc gcatcaccgc  10560
catgctgggg cagcacggca agatcgaggg caagaacgtc ttctactggt tccagaacca  10620
caaggcccgc gagcgccaga agcgccgcct caccagcctc gacgtgaacg tgcccgccgc  10680
cggcgcggcc gacgccacca ccagccaact cggcgtcctc tcgctgtcgt cgccgccgcc  10740
ttcaggcgcg gcgcctccct cgcccaccct cggcttctac gccgccggca atggcggcgg  10800
atcggctgtg ctgctggaca cgagttccga ctggggcagc agcggcgctg cgatggccac  10860
cgagacatgc ttcctccagg actacatggg cgtgacggac acgggcagct cgtcgcagtg  10920
gccacgcttc tcgtcgtcgg acacgataat ggcggcggcc gcggcgcggg cggcgacgac  10980
gcgggcgccc gagactctcc ctctcttccc gacctgcggc gacgacggcg gcagcggtag  11040
cagcgctac  ttgccgttct ggggtgccgc tccacaact  gccggcgcca cttcttccgt  11100
tgcgatccag cagcaacacc agctgcagga gcagtacagc ttttacagca acagcaacag  11160
cacccagctg gccggcaccg gcaaccaaga cgtatcggca acagcagcag cagccgccgc  11220
cctggagctg agcctcagct catggtgctc ccttaccct  gctgcaggga gtatgtgaga  11280
gcaacgcgag ctgccactgc tcttcactta tgtctctgga atggaaggag gaggaagtga  11340
gcatagcgtt ggtgcgttgc tgtcattgtc ctaggttagt agctagtgcc agttactagt  11400
aagcatcagg cataggagta tgtagtagaa gcatgcacgt tgccggccag ccaggctta   11460
gacgggaaaa gaatttggtg cagccggctg caaaacagga tgtttacagc ccccccctcg  11520
agccctagac ttgtccatct tctgattggg ccaagttaat taatgtatga aataaaagga  11580
tgcacacata gtgacatgct aatcactata atgtgggcat caaagttgtg tgttatgtgt  11640
aattactaat tatctgaata agagaaagag atcatcccata tttcttatcc taaatgaatg  11700
tcacgtgtct ttataattct ttgatgaacc agatgcattt tattaaccaa ttccatatac  11760
atataaatat taatcatata taattaatat caattgggtt agcaaaacaa atctagtcta  11820
ggtgtgttt  gctaattatt gggggatagt gcaaaaagaa atctacgttc tcaataattc  11880
agatagaaaa cttaataaag tgagataatt tacatagatt gcttttatcc tttgatatat  11940
gtgaaaccat gcatgatata aggaaaatag atagagaaat aatttttttac atcgttgaat  12000
atgtaaacaa tttaattcaa gaagctagga atataaatat tgaggagttt atgattagag  12060
ctctcccact aaacgtcccg ctggcagaca tactgtccca caaatgaaga tggaatctgt  12120
aaaagaaaac gcgtgaaata atgcgtctga caaaggttag gtcggctgcc tttaatcaat  12180
accaaagtgg tccctaccac gatggaaaaa ctgtgcagtc ggtttggctt tttctgacga  12240
acaaatagga ttcgtggccg acaggtgggg gtccaccatg tgaaggcatc ttcagactcc  12300
aataatggag caatgacgta agggcttacg aaataagtaa gggtagtttg ggaaatgtcc  12360
actcacccgt cagtctataa atacttagcc cctccctcat tgttaaggga gcaaaatctc  12420
agagagatag tcctagagag agaaagagag caagtagct  aagggcgga  acgcggagga  12480
agtattcagg cacgtggcca ggaagaagaa aagccaagac gacgaaaaca ggtaagagct  12540
aagcttatgg agagtggttc caacagcact tcttgtccaa tggcttttgc cggggataat  12600
agtgatggtc cgatgtgtcc tatgatgatg atgatgccgc ccatcatgac atcacatcaa  12660
catcatggtc atgatcatca acatcaacaa caagaacatg atggttatgc atatcagtca  12720
caccaccaac aaagtagttc cctttttctt caatcactag ctcctcccca aggaactaag  12780
```

```
aacaaagttg cttcttcttc ttctccttcc tcttgtgctc ctgcctattc tctaatggag   12840
atccatcata acgaaatcgt tgcaggagga atcaacccct gctcctcttc ctcttcttca   12900
gcctctgtca aggccaagat catggctcat cctcactacc accgcctctt ggccgcttat   12960
gtcaattgtc agaaggttgg agcaccaccg gaggttgtgg cgaggctaga ggaggcatgc   13020
tcgtctgccg cagccgctgc cgcatctatg ggaccaacag gatgtctagg tgaagatcca   13080
gggcttgatc aattcatgga agcttactgt gaaatgctcg ttaagtatga gcaagagctc   13140
tccaaacctt tcaaggaagc tatggtcttc cttcaacgtg tcgagtgtca attcaaatcc   13200
ctctctctat cctcaccttc ctcttttctcc ggttatggag agacagcaat tgataggaac   13260
aataatgggt catccgagga agaagtcgat atgaacaatg aatttgtaga tccacaagct   13320
gaggatagag agcttaaagg acagctcttg cgcaagtaca gtggttactt agggagcctc   13380
aagcaagagt tcatgaagaa gaggaagaaa ggaaagctcc ctaaagaagc tcgtcaacaa   13440
ctgcttgatt ggtggagccg tcactacaaa tggccttacc cttcggagca acaaaagctc   13500
gcccttgcgg aatcaacggg gctggaccag aaacagataa acaattggtt cataaaccag   13560
aggaaacggc attggaagcc gtcggaggac atgcagtttg tagtaatgga cgcaacacat   13620
cctcaccatt acttcatgga taatgtcttg ggcaatcctt tcccaatgga tcacatctcc   13680
tccaccatgc tttgactcga gtttctccat aataatgtgt gagtagttcc cagataaggg   13740
aattagggtt cctataggt ttcgctcatg tgttgagcat ataagaaacc cttagtatgt   13800
atttgtattt gtaaaatact tctatcaata aaatttctaa ttcctaaaac caaaatccaa   13860
tactaaaatc cagatccccc gaattaagtg actacaaaaa agtgtttgat cgccggcggt   13920
accgagtgta cttcaagtca gtgggaaatc aataaaatga ttattttatg aatatatttc   13980
attgtgcaag tagatagaaa ttacatatgt tacataacac acgaaataaa caaaaaaaga   14040
caatccaaaa acaaacaccc caaaaaaaat aatcacttta gataaactcg tatgaggaga   14100
ggcacgttca gtgactcgac gattcccgag caaaaaaagt ctcccgtca cacatgtagt   14160
gggtgacgca attatctta aagtaatcct tctgttgact tgtcattgat aacatccagt   14220
cttcgtcagg attgcaaaga attatagaag ggatcccacc ttttattttc ttcttttttc   14280
catatttagg gttgacagtg aaatcagact ggcaacctat taattgcttc cacaatgggt   14340
cgaacttgaa ggggatgtcg tcgatgatat tataggtggc gtgttcatcg tagttggtga   14400
aatcgatggt accgttccaa tagttgtgtc gtccgagact tctagcccag gtggtctttc   14460
cggtacgagt tggtccgcag atgtagaggc tggggtgtcg gattccattc cttccattgt   14520
ccttgttaaa tcggccatcc attcaaggtc agattgaact tgttggtatg agacaggatg   14580
tatgtaagta taagcgtcta tgcttacatg gtatagatgg gtttccctcc aggagtgtag   14640
atcttcgtgg cagcgaagat ctgattctgt gaagggcgac acatacggtt caggttgtgg   14700
agggaataat ttgttggctg aatattccag ccattgaagc tttgttgccc attcatgagg   14760
gaattcttcc ttgatcatgt caagatattc ctccttagca gttgcagtct ggataatagt   14820
tctccatcgt gcgtcagatt tgcgaggaga aaccttatga tctcggaaat ctcctctggt   14880
tttaatatct ccgtcctttg atatgtaatc aaggacttgt ttagagtttc tagctggctg   14940
gatattaggg tgatttcctt caaaatcgaa aaagaagga tccctaatac aaggtttttt   15000
atcaagctgg agaagagcat gatagtgggt agtgccatct tgatgaagct cagaagcaac   15060
accaaggaag aaaataagaa aaggtgtgag tttctccacg agaaactgga ataaatcatc   15120
tctttgagat gagcacttgg gataggtaag gaaaacatat ttagattgga gtctgaagtt   15180
cttactagca gaaggcatgt tgttgtgact ccgagggggtt gcctcaaaact ctatcttata   15240
accggcgtga aggcatggag gcaggggtat tttggtcatt taatagata gtggaaaatg   15300
agtggaaatt tacttaaaga cgaagtcttt gcgacaaggg ggggcccacg ccgaatttaa   15360
tattaccggc gtggccccc cttatcgcga gtgcttagc acgagcggtc cagatttaaa   15420
gtagaaaatt tcccgcccac tagggttaaa ggtgttcaca ctataaaagc atatacgatg   15480
tgatggtatt tgatggagcg tatattgtat caggtatttc cgttggatac gaattattcg   15540
tacgaccctc atagttttaaa ctatcagtgt ttgacaggat atattggcgg gttaaacctaa   15600
gagaaaagag cgtttattag aataacggat atttaaaagg gcgtgaaaag gtttatccgt   15660
tcgtccattt gtatgtgcat gccaaccaca gggttcccct cgggatcaaa gtactttgat   15720
ccaacccctc cgctgctata gtgcagtcgg cttctgacgt tcagtgcagc cgtcttctga   15780
aaacgacatg tcgcacaagt cctaagttac gcgacaggct gccgccctgc ccttttccgg   15840
gcgtttttctt gtcgcgtgtt ttagtcgcat aaagtagaat acttgcgact agaaccggag   15900
acattacgcc atgaacaaga gcgccgccgc tggcctgctg ggctatgccc gcgtcagcac   15960
cgacgaccag gacttgacca accaacgggc cgaactgcac gcggccggct gcaccaagct   16020
gtttttccgag aagatcaccg gcaccaggcg cgaccgcccg gagctggcca ggatgcttga   16080
ccacctacgc cctggcgacg ttgtgacagt gaccaggcta gaccgcctgg ccccgcagcac   16140
ccgcgaccta ctgacattg ccgagcgcat ccaggaggcc ggcgcgggcc tgcgtagcct   16200
ggcagagccg tgggccgaca ccaccacgcc ggccggccgc atggtgttga ccgtgttcgc   16260
cggcattgcc gagttcgagc gttccctaat catcgaccgc acccggagcg ggcgcgaggc   16320
cgccaaggcc cgaggcgtga agtttgggcc ccgccctacc ctcacccgg cacagatcgc   16380
gcacgcccgc gagctgatcg accaggaagg ccgcaccgtg aaagaggcgg ctgcactgct   16440
tggcgtgcat cgctcgaccc tgtaccgcgc acttgagcgc agcgaggaag tgacgcccac   16500
cgaggccagg cggcgcggtg ccttccgtga ggacgcattg accgaggccg acgccctggc   16560
ggccgcgag aatgaacgcc aagaggaaca gcatgaaac cgccaccagga cggccaggac   16620
gaaccgtttt tcattaccga agagatcgag gcggagatga tcgcggccgg gtacgtgttc   16680
gagccgcccg cgcacggctc aaccgtgcgg ctgcatgaaa tcctgccggg tttgtctgat   16740
gccaagctgc cggcctggcc ggccagcttg gccgctgaag aaaccgagcg ccgccgtcta   16800
aaaaggtgat gtgtatttga gtaaaacagc ttgcgtcatg cggtcgctgc gtatatgatg   16860
cgatgagtaa ataaacaaat acgcaagggg aacgcatgaa ggttatcgct gtacttaacc   16920
agaaaggcgg gtcaggcaag acgaccatcg caacccatct agcccgcgcc ctgcaactcg   16980
ccggggccga tgttctgtta gtcgattccg atccccaggg cagtgccgc gattgggcgg   17040
ccgtgcggga agatcaaccg ctaaccgttg tcggcatcga ccgcccgacg attgaccgcg   17100
acgtgaaggc catcggccgg cgcgacttcg tagtgatcga cggagcgccc caggcggcgg   17160
acttcgtgt gtccggatc aaggcagcgg acttcgtgct gattccggtg cgccaagcc   17220
cttacgacat atgggccacc gccgacctgg tggagctggt taagcagcgc attgaggtca   17280
cggatggaag gctacaagcg gcctttgtcg tgtcgcgggc gatcaaggc acgcgcatcg   17340
gcggtgaggt tgccgaggcg ctggccgggt acgagctgcc cattcttgag tcccgtatca   17400
cgcagcgcgt gagctaccca ggcactgccg ccgcggcac aaccgttctt gaatcagaac   17460
ccgagggcga cgctgcccgc gaggtccagg cgctggccgc tgaaattaaa tcaaaactca   17520
```

```
tttgagttaa tgaggtaaag agaaaatgag caaaagcaca aacacgctaa gtgccggccg    17580
tccgagcgca cgcagcagca aggctgcaac gttggccagc ctggcagaca cgccagccat    17640
gaagcgggtc aactttcagt tgccggcgga ggatcacacc aagctgaaga tgtacgcggt    17700
acgccaaggc aagaccatta ccgagctgct atctgaatac atcgcgcagc taccagagta    17760
aatgacaaa tgaataaatg agtagatgaa ttttagcggc taaaggaggc ggcatggaaa    17820
atcaagaaca accaggcacc gacgccgtgg aatgccccat gtgtggagga acgggcggtt    17880
ggccaggcgt aagcggctgg gttgtctgcc ggccctgcaa tggcactgga accccaagc    17940
ccgaggaatc ggcgtgacgg tcgcaaacca tccggcccgg tacaaatcgg cgcggcgctg    18000
ggtgatgacc tggtggagaa gttgaaggcc gcgcaggccg cccagcggca acgcatcgag    18060
gcagaagcac gccccggtga atcgtggcaa gcggccgctg atcgaatccg caaagaatcc    18120
cggcaaccgc cggcagccgg tgcgccgtcg attaggaagc gcccaaggg cgacgagcaa    18180
ccagatttt cgttccgat gctctatgac gtgggcaccc gcgatagtcg cagcatcatg    18240
gacgtggccg ttttccgtct gtcgaagcgt gaccgacgag ctggcgaggt gatccgctac    18300
gagcttccag acgggcacgt agaggtttcc gcagggccgg ccggcatggc cagtgtgtgg    18360
gattacgacc tggtactgat ggcggttccc catctaaccg aatccatgaa ccgataccgt    18420
gaagggaagg gagacaagcc cggccgcgtg ttccgtccac acgttgcgga cgtactcaag    18480
ttctgccggc gagccgatgg cggaaagcag aaagacgacc tggtagaaac ctgcattcgg    18540
ttaaacacca cgcacgttgc catgcagcgt acgaagaagg ccaagaacgg ccgcctggtg    18600
acggtatccg agggtgaagc cttgattagc cgctacaaga tcgtaaagag cgaaaccggg    18660
cggccggagt acatcgagat cgagctagct gattggatgt accgcgagat cacagaaggc    18720
aagaacccgg acgtgctgac ggttcacccc gattacttt tgatcgatcc cggcatcggc    18780
cgttttctct accgcctggc acgccgcgcc gcaggcaagg cagaagccag atggttgttc    18840
aagacgatct acgaacgcag tggcagcgcc ggagagttca agaagttctg tttcaccgtg    18900
cgcaagctga tcgggtcaaa tgacctgccg gagtacgatt tgaaggagga ggcggggcag    18960
gctgcccga tcctagtcat gcgctaccgc aacctgatcg agggcgaagc atccgccggt    19020
tccctaatgta cggagcagat gctagggcaa attgccctag cgggggaaaa aggtcgaaaa    19080
ggcctctttc ctgtgatag cacgtacatt gggaacccaa agccgtacat tgggaaccgg    19140
aacccgtaca ttgggaaccc aaagccgtac attgggaacc ggtcacacat gtaagtgact    19200
gatataaaag agaaaaaagg cgattttccc gcctaaaact cttaaaact tattaaaact    19260
cttaaaaccc gcctggcctg tgcataactg tctggccagc gcacagccca agagctgcaa    19320
aaagcgccta cccttcggtc gctgcgctcc ctacgcccg ccgcttcgcg tcggcctatc    19380
gcggccgctg gccgctcaaa aatggctggc ctacggccag gcaatctacc agggcgcgga    19440
caagccgcgc cgtcgccact cgaccgccgg cgcccacatc aaggcaccct gcctcgcgcg    19500
tttcggtgat gacggtgaaa acctctgaca catgcagctc ccggaaacgg tcacagcttg    19560
tctgtaagcg gatgccggga gcagacaagc ccgtcagggc cgtcagcgga gtgttggcgg    19620
gtgtcgggc gcagccatga cccagtcacg tagcgatagc ggagtgtata ctggcttaac    19680
tatgcggcat cagagcagat tgtactgaga gtgcaccata tgcggtgtga aataccgcac    19740
agatgcgtaa ggagaaaata ccgcatcagg ccctcttccg cttcctcgct cactgactcg    19800
ctgcgctcgg tcgttcggct gcggcgagcg gtatcagctc actcaaaggc ggtaatacg    19860
ttatccacag aatcagggga taacgcagga agaacatgt gagcaaaagg ccagcaaaag    19920
gccaggaacc gtaaaaaggc cgcgttgctg gcgtttttcc ataggctccg cccccctgac    19980
gagcatcaca aaaatcgacg ctcaagtcag aggtggcgaa acccgacagg actataaaga    20040
taccaggcgt ttccccctgg aagctccctc gtgcgctctc ctgttccgac cctgccgctt    20100
accggatacc tgtccgcctt tctcccttcg ggaagcgtgg cgctttctca tagctcacgc    20160
tgtaggtatc tcagttcggt gtaggtcgtt cgctccaagc tgggctgtgt gcacgaaccc    20220
cccgttcagc ccgaccgctg cgccttatcc ggtaactatc gtcttgagtc aacccggta    20280
agacacgact tatcgccact ggcagcagcc actggtaaca ggattagcag agcgaggtat    20340
```

SEQ ID NO: 30          moltype = DNA    length = 15641
FEATURE                Location/Qualifiers
source                 1..15641
                       mol_type = other DNA
                       organism = synthetic construct
SEQUENCE: 30
```
ggcagccggt gcgccgtcga ttaggaagcc gcccaagggc gacgagcaac cagatttttt      60
cgttccgatg ctctatgacg tgggcacccg cgatagtcgc agcatcatgg acgtggccgt     120
tttccgtctg tcgaagcgtg accgacgagc tggcgaggtg atccgctacg agcttccaga    180
cgggcacgta gaggtttccg cagggccggc cggcatggcc agtgtgtggg attacgacct    240
ggtactgatg gcggtttccc atctaaccga atccatgaac cgataccggg aagggaaggg    300
agacaagccc ggccgcgtgt tccgtccaca cgttgcggac gtactcaagt tctgccggcg    360
agccgatggc ggaaagcaga aagacgacct ggtagaaacc tgcattcggt taaacaccac    420
gcacgttgcc atgcagcgta cgaagaaggc caagaacggc cgcctggtga cggtatccga    480
gggtgaagcc ttgattagcc gctacaagat cgtaaagagc gaaaccgggc ggccggagta    540
catcgagatc gagctagctg attggatgta ccgcgagatc acagaaggca agaacccgga    600
cgtgctgacg gttcacccgg attactttt gatcgatccc ggcatcggcc gttttctcta    660
ccgcctggca cgccgcgccg caggcaaggc agaagccaga tggttgttca agacgatcta    720
cgaacgcagt ggcagcgccg gagagttcaa gaagttctgt ttcaccgtgc gcaagctgat    780
cgggtcaaat gacctgccgg agtacgattt gaaggaggag gcggggcagg ctgcccgat    840
cctagtcatg cgctaccgca acctgatcga gggcgaagca tccgccggtt cctaatgtac    900
ggagcagatg ctagggcaaa ttgccctagc gggggaaaaa ggtcgaaaag gcctcttcc    960
tgtggatagc acgtacattg ggaacccaaa gccgtacatt gggaaccgga cccgtacat   1020
tgggaaccca aagccgtaca ttgggaaccg gtcacacatg taagtgactg atataaaaga   1080
gaaaaaaggc gattttccg cctaaaactc tttaaaactt attaaaactc ttaaaaccg   1140
cctggcctgt gcataactgt ctggccagcg cacagcccaa agctgcaa              1200
ccttcggtcg ctgcgctccc tacgccccgc cgcttcgcgt cggcctatcg gccgctgt   1260
ccgctcaaaa atggctggcc tacggccagg caatctacca gggcgcggac aagccgcgcc   1320
gtcgccactc gaccgccggc gcccacatca aggcaccctg cctcgcgcgt ttcggtgatg   1380
acggtgaaaa cctctgacac atgcagctcc cggaaacggt cacagcttgt ctgtaagcgg   1440
atgccggag cagacaagcc cgtcagggcg cgtcagcgga gtggcggg tgtcgggcg   1500
```

```
cagccatgac ccagtcacgt agcgatagcg gagtgtatac tggcttaact atgcggcatc   1560
agagcagatt gtactgagag tgcaccatat gcggtgtgaa ataccgcaca gatgcgtaag   1620
gagaaaatac cgcatcaggc gctcttccgc ttcctcgctc actgactcgc tgcgctcggt   1680
cgttcggctg cggcgagcgg tatcagctca ctcaaaggcg gtaatacggt tatccacaga   1740
atcaggggat aacgcaggaa agaacatgtg agcaaaaggc cagcaaaagg ccaggaaccg   1800
taaaaaggcc gcgttgctgg cgtttttcca taggctccgc cccccctgacg agcatcacaa   1860
aaatcgacgc tcaagtcaga ggtggcgaaa cccgacagga ctataaagat accaggcgtt   1920
tccccctgga agctccctcg tgcgctctcc tgttccgacc ctgccgctta ccggatacct   1980
gtccgccttt ctcccttcgg gaagcgtggc gctttctcat agctcacgct gtaggtatct   2040
cagttcggtg taggtcgttc gctccaagct gggctgtgtg cacgaacccc ccgttcagcc   2100
cgaccgctgc gccttatccg gtaactatcg tcttgagtcc aacccggtaa gacacgactt   2160
atcgccactg gcagcagcca ctggtaacag gattagcaga gcgaggtatg taggcggtgc   2220
tacagagttc ttgaagtggt ggcctaacta cggctacact agaaggacag tatttggtat   2280
ctgcgctctg ctgaagccag ttaccttcgg aaaaagagtt ggtagctctt gatccggcaa   2340
acaaaccacc gctggtagcg gtggtttttt tgtttgcaag cagcagatta cgcgcagaaa   2400
aaaaggatct caagaagatc ctttgatctt ttctacgggg tctgacgctc agtggaacga   2460
aaactcacgt taagggattt tggtcatgca ttctaggtac taaaacaatt catccagtaa   2520
aatataatat tttatttttct cccaatcagg cttgatcccc agtaagtcaa aaaatagctc   2580
gacatactgt tcttccccga tatcctcccct gatcgaccgg acgcagaagg caatgtcata   2640
ccacttgtcc gccctgccgc ttctcccaag atcaataaag ccacttactt tgccatcttt   2700
cacaaagatg ttgctgtctc ccaggtcgcc gtgggaaaaa acaagttcct cttcgggctt   2760
ttccgtcttt aaaaaatcat acagctcgcg cggatcttta aatggagtgt cttcttccca   2820
gttttcgcaa tccacatcgg ccagatcgtt attcagtaag taatccaatt cggctaagcg   2880
gctgtctaag ctattcgtat agggacaatc cgatatgtcg atggagtgaa agagcctgat   2940
gcactccgca tacagctcga taatcttttc agggctttgt tcatcttcat actcttccga   3000
gcaaaggacg ccatcggcct cactcatgag cagattcgcc cagccatcat gccgttcaaa   3060
gtgcaggacc tttggaacag gcagctttcc ttccagccat agcatcatgt ccttttcccg   3120
ttccacatca taggtggtcc ctttataccg gctgtccgtc attttaaat ataggttttc   3180
attttctccc accagcttat ataccttagc aggagacatt ccttccgtat cttttacgca   3240
gcggtatttt tcgatcagtt ttttcaattc cggtgatatt ctcattttag cattttatta   3300
tttccttcct cttttctaca gtatttaaag atacccccaag aagctaatta taacaagacg   3360
aactccaatt cactgttcct tgcattctaa aaccttaaat accagaaaac agcttttttca   3420
aagttgtttt caaagttggc gtataacata gtatcgacgg agccgatttt gaaaccgcgg   3480
tgatcacagg cagcaacgct ctgtcatcgt tacaatcaac atgctaccct ccgcgagatc   3540
atccgtgttt caaacccggc agcttagttg ccgttcttcc gaatagcatc ggtaacatga   3600
gcaaagtctg ccgccttaca acggctctcc cgctgacgcc gtcccggact gatgggctgc   3660
ctgtatcgag tggtgatttt tgtgccagct gccggtcggg gagctgttgg ctggctggtg   3720
gcaggatata ttgtggtgta aacaaattga cgcttagaca acttaataac acattgcgga   3780
cgtttttaat gtagagctca aagttaacg cgttagcaga aggcatgttg ttgtgactcc   3840
gaggggttgc ctcaaactct atcttataac cggcgtggaa gcatggaggc aggggtattt   3900
tggtcatttt aatagatagt ggaaaatgac gtggaattta cttaaagacg aagtctttgc   3960
gacaaggggg ggcccacgcc gaatttaata ttaccggcgt ggcccccccct tatcgcgagt   4020
gcttagcac gagcggttcca gatttaaagt agaaaatttc ccgcccacta gggttaaagg   4080
tgttcacact ataaaagcat atcgatgtg atggtatttg atggagcgta tattgtatca   4140
ggtatttccg ttggatacga attattcgta cgacccctcgg taccgatcgg cgcgccagat   4200
ttgcctttc aatttcagaa agaatgctaa cccacagatg gttagagagg cttacgcagc   4260
aggtatcatc aagacgatct acccgagcaa taatctccag gaaatcaaat accttcccaa   4320
gaaggttaaa gatgcagtca aaagattcag gactaactgc atcaagaaca cagagaaaga   4380
tatatttctc aagatcagaa gtactattcc agtatggacg attcaaggct tgcttcacaa   4440
accaaggcaa gtaatagaga ttggagtctc taaaaaggta gttcccactg aatcaaaggc   4500
catgagtca aagattcaaa tagaggacct aacagaactc gccgtaaaga ctggcgaaca   4560
gttcatacag agtctcttac gactcaatga caagaagaaa atcttcgtca acatggtgga   4620
gcacgacaca cttgtctact ccaaaaatat caaagataca gtctcagaag accaaagggc   4680
aattgagact tttcaacaaa gggtaatatc cggaaacctc ctcggattcc attgcccagc   4740
tatctgtcac tttattgtga agatagtgga aaaggaagtt ggctcctaca aatgccatca   4800
ttgcgataaa ggaaaggcca tcgttgaaga tgcctctgcc gacagtggtc ccaaagatgg   4860
accccaccc acgaggagca tcgtggaaaa agaagacgtt ccaaccacgt cttcaaagca   4920
agtggattga tgtgatatct ccactgacgt aagggatgac gcacaatccc actatccttc   4980
gcaagaccct tcctctatat aaggaagttc atttcatttg gagagaacac ggggactcc   5040
tgcaggatgg aagacgccaa aaacataaag aaaggcccgg cgccattcta tccgctggaa   5100
gatgaaccg ctgagagca actgcataag gctatgaaga gatacgccct ggttcctgga   5160
acaattgctt ttacagatgc acatatcgag gtggacatca cttacgctga gtacttcgaa   5220
atgtccgttc ggttggcaga agctatgaaa cgatatgggc tgaatacaaa tcacagaatc   5280
gtcgtatgca gtgaaaactc tcttcaattc tttatgccgg tgttgggcgc gttattatc   5340
ggagttgcag ttgcgcccgc gaacgacatt tataatgaac gtgaattgct caacagtatg   5400
ggcatttcgc agcctaccgt ggtgttcgtt tccaaaaagg ggttgcaaaa attttgaac   5460
gtgcaaaaaa agctcccaat catccaaaaa attattatca tggattctaa aacggattac   5520
cagggatttc agtcgatgta cacgttcgtc acatctcatc tacctcccgg ttttaatgaa   5580
tacgattttg tgccagagtc cttcgatagg gacaagacaa ttgcactgat catgaactcc   5640
tctggatcta ctggtctgcc taaaggtgtc gctctgcctc atagaactgc ctgcgtgaga   5700
ttctcgcatg ccagagatcc tatttttggc aatcaaatca ttccggatac tgcgattta   5760
agtgttgttc cattccatca cggttttgga atgtttacta cactcggata tttgatatgt   5820
ggatttcgag tcgtcttaat gtatagattt gaagaagagc tgtttctgag gagccttcag   5880
gattacaaga ttcaaagtgc gctgctggtg ccaacccatc tctccttctt cgccaaaagc   5940
actctgattg acaaatacga tttatctaat ttacacgaaa ttgcttctgg tggcgctccc   6000
ctctctaagg aagtcgggga agcggttgcc aagaggttcc atctgccagg tatcaggcaa   6060
ggatatgggc tcactgagac tacatcagct attctgatta cacccgaggg ggatgataaa   6120
ccgggcgcgg tcggtaaagt tgttccattt tttgaagcga aggttgtgga tctggatacc   6180
gggaaaacgc tgggcgttaa tcaaagaggc gaactgtgtg tgagaggtcc tatgattatg   6240
```

```
tccggttatg taaacaatcc ggaagcgacc aacgccttga ttgacaagga tggatggcta  6300
cattctggag acatagctta ctgggacgaa gacgaacact tcttcatcgt tgaccgcctg  6360
aagtctctga ttaagtacaa aggctatcag gtggctcccg ctgaattgga atccatcttg  6420
ctccaacacc ccaacatctt cgacgctggt gtcgcaggtc ttcccgacga tgacgccggt  6480
gaacttcccg ccgccgttgt tgttttggag cacggaaaga cgatgacgga aaaagagatc  6540
gtggattacg tcgccagtca agtaacaacc gcgaaaaagt tgcgcggagg agttgtgttt  6600
gtggacgaag taccgaaagg tcttaccgga aaactcgacg caagaaaaat cagagagatc  6660
ctcataaagg ccaagaaggg cggaaagatc gccgtgtgac gtcgacgata tgaagatgaa  6720
gatgaaatat ttggtgtgtc aaataaaaag cttgtgtgct taagtttgtg ttttttttctt  6780
ggcttgttgt gttatgaatt tgtggctttt tctaatatta aatgaatgta agatcacatt  6840
ataatgaata aacaaatgtt tctataatcc attgtgaatg ttttgttgga tctcttctgc  6900
agcatataac tactgtatgt gctatggtat ggactatgga atatgattaa agataagcca  6960
gagctctggt gacggaccca tggcttcgtt gaacaacgga aactcgactt gccttccgca  7020
caatacatca tttcttctta gctttttttc ttcttcttcg ttcatacagt tttttttttgt  7080
ttatcagctt acatttcttt gaaccgtagc tttcgttttc ttcttttttaa ctttccattc  7140
ggagttttg tatcttgttt catagtttgt cccaggatta gaatgattag gcatcgaacc  7200
ttcaagaatt tgattgaata aacatcttc attcttaaga tatgaagata tcttcaaaa   7260
ggcccctggg aatctgaaag aagagaagca ggcccattta tatgggaaag aacaatagta  7320
tttcttatat aggcccattt aagttgaaaa caatcttcaa aagtcccaca tcgcttagat  7380
aagaaaacga agctcgagttt atatacagct agagtcgaag tagtgattgt tggtagtagc  7440
gactccatgg ttttagagct agaaatagca agttaaaata aggctagtcc gttatcaact  7500
tgaaaaagtg gcaccagtc ggtgctttt tccccggcgg cgccgatcat gagcggagaa   7560
ttaagggagt cacgttatga cccccgccga tgacgcggga caagccgttt tacgtttgga  7620
actgacagaa ccgcaacgtt gaaggagcca ctcagccgcg ggtttctgga gtttaatgag  7680
ctaagcacat acgtcagaaa ccattattgc gcgttcaaaa gtcgcctaag gtcactatca  7740
gctagataat atttcttgtc aaaaatgctc cactgacgtt ccataaattc ccctcggtat  7800
ccaattagag tctcatattc actctcaatc caaataatct gcaccgtacc tgcagggtcc  7860
gagctaggtc acagaagcgc tcaggaaggc cgctgagata gaggcatggc ggccaatgcg  7920
ggcggcggtg gagcgggagg aggcagcggc agcggcagcg tggctgcgcc ggcggtgtgc  7980
cgccccagcg gctcgcggtg gacgccgacg ccggagcaga tcaggatgct gaaggagctg  8040
tactacggct gcggcatccg gtcgcccagc tcggagcaga tccagcgcat caccgccatg  8100
ctgcggcagc acggcaagat cgagggcaag aacgtcttct actggttcca gaaccacaag  8160
gcccgcgagc gccagaagcg ccgcctcacc agcctcgacg tgaacgtgcc cgccgccggc  8220
gcggccgacg ccaccaccag ccaactcggc gtcctctcgc tgtcgtcgcc gccgccttca  8280
ggcgcgcgc ctccctcgcc caccctcggc ttctacggcg ccggcaatgg cggcggatcg   8340
gctgtgctgc tggacacgag ttccgactgg ggcagcagcg gcgctgcgat ggccaccgag  8400
acatgcttcc tccaggacta catgggcgtg acggacacgg gcagctcgtc gcagtggcca  8460
cgcttctcgt cgtcggacac gataatggcg gcggccgcg cgcgggcggc gacgacgcgg   8520
gcgccccgaga ctctccctct cttcccgacc tgcggcgacg acggcggcag cggtagcagc  8580
agctacttgc cgttctgggg tgccgcgtcc acaactgccg gcgccacttc ttccgttgcg  8640
atccagcagc aacaccagct gcaggagcag tacagctttt acagcaacag caacagcacc  8700
cagctggccg gcaccggcaa ccaagacgta tcggcaacag cagcagcagc gccgccctg   8760
gagctggcc tcagctcatg gtgctccct tacctgcctg caggagtat gtgagagcaa    8820
cgcgagctgc cactgctctt cacttatgtc tctggaatgg aaggaggagg aagtgagcat  8880
agcgttggtg cgttgctgtc attgtcctag gttagtagct agtgccagtt actagtaagc  8940
atcaggcata ggagtatgta gtagaagcat gcacgttgcc ggccagccag gctttagacg  9000
ggaaaagaat ttggtgcagc cggctgcaaa acaggatgt tcagccccc ccctcgagcc   9060
ctagacttgt ccatcttctg gattggccaa gttaattaat gtatgaaata aaaggatgca  9120
cacatagtga catgctaatc actataatgt gggcatcaaa gttgtgtgtt atgtgtaatt  9180
actaattatc tgaataagag aaagagatca tccatatttc ttatcctaaa tgaatgtcac  9240
gtgtcttat aattctttga tgaaccagat gcatttatt aaccaattcc atatacatat     9300
aaatattaat catatataat taatatcaat tgggttagca aaacaaatct agtctaggtg  9360
tgttttgcta attattgggg gatagtcaa aaagaaatct acgttctcaa taattcagat   9420
agaaaactta ataagtgag ataatttaca tagattgctt ttatccttg atatatgtga    9480
aaccatgcat gatataagga aatatagatag agaaataatt ttttacatcg ttgaatatgt  9540
aaacaattta attcaagaag ctaggaatat aaatattgag gagtttatga ttagagctct  9600
cccgctggca gacatactgt cccacaaatg aagatggaat ctgtaaaaga aaacgcgtga  9660
aataatgcgt ctgacaaagg ttaggtcggc tgcctttaat caataccaaa gtggtcccta  9720
ccacgatgga aaaactgtgc agtcggttg gcttttctg acgaacaaat aagattcgtg   9780
gccgacaggt gggggtccac catgtgaagg catcttcaga ctccaataat ggagcaatga  9840
cgtaaggggct tacgaaataa gtaagggtag tttgggaaat gtccactcac ccgtcagtct  9900
ataaatactt agccctccc tcattgttaa gggagcaaaa tctcagagag atagtcctag    9960
agagagaaag agagcaagta gcctagaagt agtcaaggcg gcgaagtatt caggcacgtg 10020
gccaggaaga agaaaagcca agacgacgaa aacaggtaag agctaagctt atggagagtg 10080
gttccaacag cacttcttgt ccaatggctt ttgccgggga taatagtgat ggtccgatgt 10140
gtcctatgat gatgatgatg ccgcccatca tgacatcaca tcaacatcat ggtcatgatc 10200
atcaacatca caacaagaa catgatggtt atgcatatca gtcacaccac caacaaagta  10260
gttcccttt tcttcaatca ctagcctctc cccaaggaac taagaacaaa gttgcttctt  10320
ccttctctcc ttcctcttgt gctcctgcct attctctaat ggagatccat cataacgaaa 10380
tcgttcagg aggaatcaac ccttgctcct cttcctcttc ttcagcctct gtcaaggcca  10440
agatcatggc tcatcctcac taccaccgcc tcttggccgc ttatgtcaat tgtcagaagg 10500
ttggagcacc accggaggtt gtggcgaggc tagaggaggc atgctcgtct gccgcagccg 10560
ctgccgcatc tatgggacca acaggatgtc taggtgaaga tccagggctt gatcaattca 10620
tcgtgaaatg ctcgttaagt atgacgaaga gctctccaaa cctttcaagg                  10680
tggaagctta ctgtgaaatg tcgttaagt atgacgaaga gctctccaaa cctttcaagg     10680
aagctatggt cttccttcaa cgtgtcgagt gtcaattcaa atcctctctct ctatcctcac 10740
cttcctcttt ctccggttat ggagagacag caattgatag gaacaataat gggtcatccg 10800
aggaagaagt cgatatgaac aatgaatttg tagatccaca agctgaggat agagagctta 10860
aaggacagct cttgcgcaag tacagtggtt acttaggag cctcaagcaa gagttcatga  10920
agaagaggaa gaaaggaaag ctccctaaag aagctcgtca acaactgctt gattggtgga 10980
```

```
gccgtcacta caaatggcct taccctccgg agcaacaaaa gctcgcccct gcggaatcaa    11040
cggggctgga ccagaaacag ataaacaatt ggttcataaa ccagaggaaa cggcattgga    11100
agccgtcgga ggacatgcag tttgtagtaa tggacgcaac acatcctcac cattacttca    11160
tggataatgt cttgggcaat cctttcccaa tggatcacat ctcctccacc atgctttgac    11220
tcgagtttct ccataataat gtgtgagtag ttcccagata agggaattag ggttcctata    11280
gggtttcgct catgtgttga gcatataaga aacccttagt atgtatttgt atttgtaaaa    11340
tacttctatc aataaaattt ctaattccta aaaccaaaat ccagtactaa aatccagatc    11400
ccccgaatta agtgtttgat cgccggcggt accgagtgta cttcaagtca gtgggaaatc    11460
aataaaatga ttattttatg aatatatttc attgtgcaag tagatagaaa ttacatatgt    11520
tacataacac acgaaataaa caaaaaaaga caatccaaaa acaaacaccc caaaaaaaat    11580
aatcacttta gataaaactcg tatgaggaga ggcacgttca gtgactcgac gattcccgag    11640
caaaaaaagt ctccccgtca cacatgtagt gggtgacgca attatcttta aagtaatcct    11700
tctgttgact tgtcattgat aacatccagt cttcgtcagg attgcaaaga attatagaag    11760
ggatcccacc tttattttc ttctttttc catatttagg gttgacagtg aaatcagact    11820
ggcaacctat taattgcttc cacaatggga cgaacttgga gggatgtcg tcgatgatat    11880
tataggtggc gtgttcatcg tagttggtga aatcgatggt accgttccaa tagttgtgtc    11940
gtccgagact tctagcccag gtggtctttc cggtacgagt tggtccgcag atgtagaggc    12000
tggggtgtcg gattccattc cttccattgt ccttgttaaa tcggccatcc attcaaggtc    12060
agattgagct tgttggtatg agacaggatg tatgtaagta taagcgtcta tgcttacatg    12120
gtatagatgg gtttccctcc aggagtgtag atcttcgtgg cagcgaagat ctgattctgt    12180
gaagggcgac acatacggtt caggttgtgg agggaataat ttgttggctg aatattccag    12240
ccattgaagc tttgttgccc attcatgagg gaattcttcc ttgatcatgt caagatattc    12300
ctccttagac gttgcagtct ggataatagt tctccatcgt gcgtcagatt tgcgaggaga    12360
aaccttatga tctcggaaat ctcctctggt tttaatatct ccgtcctttg atatgtaatc    12420
aaggacttgt ttagagtttc tagctggctg gatattaggg tgatttcctt caaaatcgaa    12480
aaaagaagga tccctaatac aaggttttt atcaagctgg agaagagcat gatagtgggt    12540
agtgccatct tgatgaagct cagaagcaac accaaggaag aaaataagaa aaggtgtgag    12600
tttctcccag agaaactgga ataaatcatc tctttgagat gagcacttgg gataggtaag    12660
gaaaacatat ttagattgga gtctgaagtt cttactagca gaaggcatgt tgttgtgact    12720
ccgaggggtt gcctcaaact ctatcttata accggcgtgg aggcatggag gcagggggtat    12780
tttggtcatt ttaatagata gtggaaaatg acgtggaatt tacttaaaga cgaagtcttt    12840
gcgacaaggg ggggcccacg ccgaatttaa tattaccggc gtggccccccc cttatcgcga    12900
gtgctttagc acgagcggtc cagatttaaa gtagaaaatt tcccgcccac tagggttaaa    12960
ggtgttcaca ctataaaagc atatacgatg tgatggtatt tgatggagcg tatattgtat    13020
caggtatttc cgttggatac gaattattcg tacgaccctc atagtttaaa ctatcagtgt    13080
ttgacaggat atattggcgg gtaaacctaa gagaaaagag cgtttattag aataacggat    13140
atttaaaagg gcgtgaaaag gtttatccgt tcgtccattt gtatgtgcat gccaaccaca    13200
gggttcccct cgggatcaaa gtactttgat ccaacccctc cgctgctata gtgcagtcgg    13260
cttctgacgt tcagtgcagc cgtcttctga aaacgacatg tcgcacaagt cctaagttac    13320
gcgacaggct gccgccctgc cctttttcctg gcgtttcctt gtcgcgtgtt ttagtcgcat    13380
aaagtagaat acttgcgact agaaccggag acattacgcc atgaacaaga gcgccgccgc    13440
tggcctgctg ggctatgccc gcgtcagcac cgacgaccag gacttgacca accaacgggc    13500
cgaactgcac gcggccggct gcaccaagct gttttccgga aagatcaccg gcaccaggcg    13560
cgaccgcccg gagctggcca ggatgcttga ccacctacgc cctggcgacg ttgtgacagt    13620
gaccaggcta gaccgcctgg cccgcagcac ccgcgaccta ctggacattg ccgagcgcat    13680
ccaggaggcc ggcgcgggcc tgcgtagcct ggcagagccg tgggccgaca ccaccacgcc    13740
ggccgccgc atggtgttga ccgtgttcgc cggcattgcc gagttcgacg ttcctaat    13800
catcgaccgc acccggagcg ggcgcgaggc cgcaaggcc cgaggcgtga gtttggccc    13860
ccgccctacc ctcaccccgg cacagatcgc gcacgcccgc gagctgatcg accaggaagg    13920
ccgcaccgtg aaagaggcgg ctgcactgct ggcgtgcat cgctcgaccc tgtaccgcgc    13980
acttgagcgc agcgaggaag tgacgcccac cgaggccgg cggcgcggtg ccttccgttg    14040
ggacgcattg accgaggccg acgccctggc ggccgccgag aatgaacgcc aagaggaaca    14100
agcatgaaac cgcaccagga cggccaggac gaaccgtttt tcattaccga agagatcgag    14160
gcggagatga tcgcggccgg gtacgtgttc gagccgcccg cgcacggctc aaccgtgcgg    14220
ctgcatgaaa tcctggccgg tttgtctgat gccaagctgg cggcctggcc ggccagcttg    14280
gccgctgaag aaaccgagcg ccgccgtcta aaaaggtgat gtgtatttga gtaaaacagc    14340
ttgcgtcatg cggtcgctgc gtatatgatg cgatgagtaa ataaacaaat acgcaagggg    14400
aacgcatgaa ggttatcgct gtacttaacc agaaaggcgg gtcaggcaag acgaccatcg    14460
caaccatct agccccgccc ctgcaactcg ccggggccga tgttctgtta gtcgattccg    14520
atccccaggg cagtgcccgc gattgggcgg ccgtgcggga agatcaaccg ctaaccgttg    14580
tcggcatcga ccgcccgacg attgaccgcg acgtgaaggc catcggccgg cgcgacttcg    14640
tagtgatcga cggagcgccc caggcggcgg acttggctgt gtccgcgatc aaggcagccg    14700
acttcgtgct gattccggtg cagccaagcc cttacgacat atgggccacc gccgacctgg    14760
tggagctggt taagcagcgc attgaggtca cggatgaagg gctacaagcg gcctttgtcg    14820
tgtcgcgggc gatcaaggc acgcgcatcg gcggtgaggt tgccgaggcg ctggccgggt    14880
acgagctgcc cattcttgag tcccgtatca cgcagcgcgt gagctaccca ggcactgccg    14940
ccgccggcac aaccgttctt gaatcagaac ccgagggcga cgctgcccgc gaggtccagg    15000
cgctggccgc tgaaattaaa tcaaaactca tttgagttaa tgaggtaaag agaaaatgag    15060
caaaagcaca aacacgctaa gtgccggccg tccgagcgca cgcagcagca aggctgcaac    15120
gttggccagc ctggcagaca cgccagccat gaagcgggtc aactttcagt tgccggcgga    15180
ggatcacacc aagctgaaga tgtacgcggt acgccaaggc aagaccatta ccagctgct    15240
atctgaatac atcgcgcagc taccagtaa aatgagcaaa tgaataaatg agtagatgaa    15300
ttttagcggc taaaggaggc ggcatggaaa atcaagaaca accaggcacc gacgccgtgg    15360
aatgccccat gtgtggagga acgggcggtt ggccaggcgt aagcggctgg gttgtctgcc    15420
ggccctgcaa tggcactgga accccaagc cgaggaatc ggcgtgacgg tcgcaaacca    15480
tccggcccgg tacaaatcgg cgcggcgctg ggtgatgacc tggtggagaa gttgaaggcc    15540
gcgcaggccg cccagcggca acgcatcgag gcagaagcac gccccggtga atcgtggcaa    15600
gcggccgctg atcgaatccg caaagaatcc cggcaaccgc c                       15641
```

| SEQ ID NO: 31 | moltype = DNA length = 15580 |
|---|---|
| FEATURE | Location/Qualifiers |
| source | 1..15580 |
| | mol_type = other DNA |
| | organism = synthetic construct |

SEQUENCE: 31

```
cctttatttt tcttcttttt tccatattta gggttgacag tgaaatcaga ctggcaacct   60
attaattgct tccacaatgg gacgaacttg aaggggatgt cgtcgatgat attataggtg  120
gcgtgttcat cgtagttggt gaaatcgatg gtaccgttcc aatagttgtg tcgtccgaga  180
cttctagccc aggtggtctt tccggtacga gttggtccgc agatgtagag gctggggtgt  240
cggattccat tccttccatt gtccttgtta aatcggccat ccattcaagg tcagattgag  300
cttgttggta tgagacagga tgtatgtaag tataagcgtc tatgcttaca tggtatagat  360
gggtttccct ccaggagtgt agatcttcgt ggcagcgaag atctgattct gtgaagggcg  420
acacatacgg ttcaggttgt ggagggaata atttgttggc tgaatattcc agccattgaa  480
gctttgttgc ccattcatga gggaattctt ccttgatcat gtcaagatat tcctccttag  540
acgttgcagt ctggataata gttctccatc gtgcgtcaga tttgcgagga gaaaccttat  600
gatctcggaa atctcctctg gttttaatat ctccgtcctt tgatatgtaa tcaaggactt  660
gtttagagtt tctagctggc tggatattag ggtgatttcc ttcaaaatcg aaaaaagaag  720
gatccctaat acaaggtttt ttatcaagct ggagaagagc atgatagtgg gtagtgccat  780
cttgatgaag ctcagaagca acaccaagga agaaaataag aaaaggtgtg agtttctccc  840
agagaaactg gaataaatca tctctttgag atgagcactt gggataggta aggaaaacat  900
atttagattg gagtctgaag ttcttactag cagaaggcat gttgttgtga ctccgagggg  960
ttgcctcaaa ctctatctta taaccggcgt ggaggcatgg aggcaggggt attttggtca 1020
ttttaataga tagtggaaaa tgacgtggaa tttacttaaa gacgaagtct ttgcgacaag 1080
gggggggccca cgccgaattt aatattaccg gcgtggcccc cccttatcgc gagtgcttta 1140
gcacgagcgg tccagattta aagtagaaaa tttcccgacc actagggtta aaggtgttca 1200
cactataaaa gcatatacga tgtgatggta tttgatggag cgtatattgt atcaggtatt 1260
tccgttggat acgaattatt cgtacgaccc tcatagttta aactatcagt gtttgacagg 1320
atatattggc gggtaaacct aagagaaaag agcgtttatt agaataacgg atatttaaaa 1380
gggcgtgaaa aggtttatcc gttcgtccat ttgtatgtgc atgccaacca caggggttccc 1440
ctcgggatca aagtactttg atccaacccc tccgctgcta tagtgcagtc ggcttctgac 1500
gttcagtgca gccgtcttct gaaaacgaca tgtcgcacaa gtcctaagtt acgcgacagg 1560
ctgccgccct gcccttttcc tggcgttttc ttgtcgcgtg ttttagtcgc ataaagtaga 1620
atacttgcga ctagaaccgg agacattacg ccatgaacaa gagcgccgcc gctggcctgc 1680
tgggctatgc ccgcgtcagc accgacgacc aggacttgac caaccaacgg gccgaactgc 1740
acgcggccgg ctgcaccaag ctgttttccg agaagatcac cggcaccagg cgcgaccgcc 1800
cggagctggc caggatgctt gaccacctac gccctggcga cgttgtgaca gtgaccaggc 1860
tagaccgcct ggcccgcagc acccgcgacc tactggacat tgccgagcgc atccaggagg 1920
ccggcgcggg cctgcgtagc ctggcagagc cgtgggccga caccaccacg ccggccgccg 1980
gcatggtgtt gaccgtgttc gccggcattg ccgagttcga gcgttcccta atcatcgacc 2040
gcacccggag cgggcgcgag gccgccaagg cccgaggcgt gaagtttggc ccccgcccta 2100
ccctcacccc ggcacagatc gcgcacgccc gcgagctgat cgaccaggaa ggccgcaccg 2160
tgaaagaggc ggctgcactg cttggcgtgc atcgctcgac cctgtaccgc gcacttgagc 2220
gcagcgagga agtgacgccc accgaggcca ggcggcgcgg tgccttccgt gaggacgcat 2280
tgaccgagge cgacgccctg gcggccgccg agaatgaacg ccaagaggaa caagcatgaa 2340
accgcaccag gacggccagg acgaaccgtt tttcattacc gaagagatcg aggcggagat 2400
gatccgcggc gggtacgtgt tcgagccgcc gcgcacggc tcaaccgtgc ggctgcatga 2460
aatcctggcc ggtttgtctg atgccaagct ggcggcctgg ccggccagct ggccgctga 2520
agaaaccgag cgccgccgtc taaaaaggtg atgtgtattt gagtaaaaca gcttgcgtca 2580
tgcggtcgct gcgtatatga tgcgatgagt aaataaacaa atacgcaagg gaacgcatg 2640
aaggttatcg ctgtacttaa ccagaaaggc gggtcaggca agacgaccat gcaacccat 2700
ctagcccgcg ccctgcaact cgccggggcc gatgttctgt tagtcgattc cgatccccag 2760
ggcagtgccc gcgattgggc ggccgtgcgg gaagatcaac cgctaaccgt tgtcggcatc 2820
gaccgcccga cgattgaccg cgacgtgaag gccatcggcc ggcgcgactt cgtagtgatc 2880
gacggagcgc cccaggcggc ggacttggct gtgtccggaa tcaaggcagc cgacttcgtg 2940
ctgattccgg tgcagccaag cccttacgac atatgggcca ccgccgacct ggtggagctg 3000
gttaagcagc gcattgaggt cacgatgga aggctacaag cggcctttgt cgtgtcgcgg 3060
gcgatcaaag gcacgcgcat cggcggtgag gttgccgagg cgctggcgg gtacgagctg 3120
cccattcttg agtcccgtat cacgcagcgc gtgagctacc caggcactgc cgccgctggc 3180
acaaccgttc ttgaatcaga acccgagggc gacgctgccc gcgaggtcca ggcgctggc 3240
gctgaaatta aatcaaaact catttgagtt aatgaggtaa agagaaaatg agcaaagca 3300
caaacacgct aagtgccggc cgtccgagcg cacgcagcag caaggctgca acgttggcca 3360
gcctggcaga cacgccagcc atgaagcggg tcaactttca gttgccggcg gaggatcaca 3420
ccaagctgaa gatgtacgcg gtacgccaag gcaagaccat taccgagctg ctatctgaat 3480
acatcgcgca gctaccagag taaatgagca aatgaataaa tgagtagatg aattttagcg 3540
gctaaaggag gcggcatgga aaatcaagaa caaccaggca ccgacgccgt ggaatgcccc 3600
atgtgtggag gaacgggcgg ttggccaggc gtaagcggct gggttgtctg ccggccctgc 3660
aatggcactg gaaccccaa gcccgaggaa tcggcgtgac ggtcgcaaac catccggccc 3720
ggtacaaatc ggcgcggcgc tgggtgatga cctggtggag aagttgaagg ccgcgcaggc 3780
cgccagcgg caacgcatcg aggcagaagc acgcccggt gaatcgtggc aagcggccgc 3840
tgatcgaatc cgcaaagaat cccggcaacc gccggcagcc ggtgcgccgt cgattaggaa 3900
gccgcccaag ggcgacgagc aaccagattt ttcgttccg atgctctatg acgtgggcac 3960
ccgcgatagt cgcagcatca tggacgtggc cgttttccgt ctgtcgaagc gtgaccgacg 4020
agctggcgag gtgatccgct acgagcttcc agacgggcac gtagaggttt ccagggggcca 4080
ggccggcatg gccagtgtgt gggattacga cctggtactg atggcggttt ccatcctaac 4140
cgaatccatg aaccgatacc gggaagggaa gggagacaag cccggccgcg tgttccgtcc 4200
acacgttgcg gacgtactca gttctgccgg cgagccgat ggcggaaagc agaaagacga 4260
cctggtagaa acctgcattc ggttaaacac cacgcacgtt gccatgcagc gtacgaagaa 4320
ggccaagaac ggccgcctgg tgacggtatc cgagggtgaa gccttgatta ccgctacaa 4380
```

```
gatcgtaaag agcgaaaccg ggcggccgga gtacatcgag atcgagctag ctgattggat   4440
gtaccgcgag atcacagaag gcaagaaccc ggacgtgctg acggttcacc ccgattactt   4500
tttgatcgat cccggcatcg gccgttttct ctaccgcctg gcacgccgcg ccgcaggcaa   4560
ggcagaagcc agatggttgt tcaagacgat ctacgaacgc agtggcagcg ccggagagtt   4620
caagaagttc tgtttcaccg tgcgcaagct gatcgggtca aatgacctgc cggagtacga   4680
tttgaaggag gaggcggggc aggctggccc gatcctagtc atgcgctacc gcaacctgat   4740
cgagggcgaa gcatccgccg gttcctaatg tacggagcag atgctagggc aaattgccct   4800
agcagggaaa aaaggtcgaa aaggcctctt tcctgtggat agcacgtaca ttgggaaccc   4860
aaagccgtac attgggaacc ggaacccgta cattgggaac ccaaagccgt acattgggaa   4920
ccggtcacac atgtaagtga ctgatataaa agagaaaaaa ggcgattttt ccgcctaaaa   4980
ctctttaaaa cttattaaaa ctcttaaaac ccgcctggcc tgtgcataac tgtctggcca   5040
gcgcacagcc gaagagctgc aaaaagcgcc taccctccgg tcgctgcgct ccctacgccc   5100
cgccgcttcg cgtcggccta tcgcggccgc tggccgctca aaaatggctg gcctacggcc   5160
aggcaatcta ccagggcgcg gacaagccgc gccgtcgcca ctcgaccgcc ggcgcccaca   5220
tcaaggcacc ctgcctcgcg cgtttcggtg atgacggtga aaacctctga cacatgcagc   5280
tcccggaaac ggtcacagct tgtctgtaag cggatgccgg gagcagacaa gcccgtcagg   5340
gcgcgtcagc gggtgttggc gggtgtcggg gcgcagccat gacccagtca cgtagcgata   5400
gcggagtgta tactggctta actatgcggc atcagagcga attgtactga gagtgcacca   5460
tatgcggtgt gaaataccgc acagatgcgt aaggagaaaa taccgcatca ggcgctcttc   5520
cgcttcctcg ctcactgact cgctgcgctc ggtcgttcgg ctgcggcgag cggtatcagc   5580
tcactcaaag gcggtaatac ggttatccac agaatcaggg gataacgcag gaaagaacat   5640
gtgagcaaaa ggccagcaaa aggccaggaa ccgtaaaaag gccgcgttgc tggcgttttt   5700
ccataggctc cgcccccctg acgagcatca caaaaatcga cgctcaagtc agaggtggcg   5760
aaacccgaca ggactataaa gataccaggc gtttccccct ggaagctccc tcgtgcgctc   5820
tcctgttccg accctgccgc ttaccggata cctgtccgcc tttctccctt cgggaagcgt   5880
ggcgctttct catagctcac gctgtaggta tctcagttcg gtgtaggtcg ttcgctccaa   5940
gctgggctgt gtgcacgaac cccccgttca gcccgaccgc tgcgccttat ccggtaacta   6000
tcgtcttgag tccaacccgg taagacacga cttatcgcca ctggcagcag ccactggtaa   6060
caggattagc agagcgaggt atgtaggcgg tgctacagag ttcttgaagt ggtggcctaa   6120
ctacggctac actagaagga cagtatttgg tatctgcgct ctgctgaagc cagttacctt   6180
cggaaaaaga gttggtagct cttgatccgg caaacaaacc accgctggta gcggtggttt   6240
ttttgtttgc aagcagcaga ttacgcgcag aaaaaaagga tctcaagaag atcctttgat   6300
cttttctacg gggtctgacg ctcagtggaa cgaaaactca cgttaaggga ttttggtcat   6360
gcattctagg tactaaaaca attcatccag taaaatataa tatttttattt tctcccaatc   6420
aggcttgatc cccagtaagt caaaaaatag ctcgacatac tgttcttccc cgatatcctc   6480
cctgatcgac cggacgcaga aggcaatgtc ataccacttg tccgccctgc cgcttctccc   6540
aagatcaata aagccactta ctttgccatc tttcacaaag atgttgctgt ctcccaggtc   6600
gccgtgggaa aagacaagtt cctcttcggg cttttccgtc tttaaaaaat catacagtc   6660
gcgcggatct ttaaatggag tgtcttcttc ccagttttcg caatccacat cggccagatc   6720
gttattcagt aagtaatcca attcggctaa gcggctgtct aagctattcg tatagggaca   6780
atccgatatg tcgatggagt gaaagagcct gatgcactcc gcatacagct cgataatctt   6840
ttcagggctt tgttcatctt catactcttc cgagcaaagg acgccatcgg cctcactcat   6900
gagcagattg ctccagccat catgccgttc aaagtgcagg accttggaa caggcagctt   6960
tccttccagc catagcatca tgtccttttc ccgttccaca tcataggtgg tccctttata   7020
ccggctgtcc gtcattttta aatataggtt ttcattttct cccaccagct tatataccttt   7080
agcaggagac attccttccg tatctttta gcagcggtat ttttcgatca gttttttcaa   7140
ttccggtgat attctcatttt tagccatttta ttatttcctt cctcttttct acagtatttta   7200
aagataccc aagaagctaa ttataacaag acgaactcca attcactgtt ccttgcattc   7260
taaaaccctta aataccagaa aacagctttt tcaaagttgt tttcaaagtt ggcgtataac   7320
atagtatcga cggagccgat tttgaaaccg cggtgatcac aggcagcaac gctctgtcat   7380
cgttacaatc aacatgctac cctccgcgag atcatccgtg tttcaaaccc ggcagcttag   7440
ttgccgttct tccgaatagc atcggtaaca tgagcaaagt ctgccgcctt acaacggctc   7500
tcccgctgac gccgtcccgg actgatgggc tgcctgtatc gagtggtgat tttgtgccga   7560
gctgccggtc ggggagctgt tggctggctg gtggcaggat atattgtggt gtaaacaaat   7620
tgacgcttag acaacttaat aacacattgc ggacgttttt aatgtagagc tcaaagttta   7680
acgcgttagc agaaggcatg ttgttgtgac tccgaggggt tgcctcaaac tctatcttat   7740
aaccggcgtg gaggcatgga ggcaggggta ttttggtcat tttaatagat agtggaaaat   7800
gacgtggaat ttacttaaag acgaagtctt tgcgacaagg gggggcccac gccgaattta   7860
atattaccgg cgtggccccc cctttatcgcg agtgcgttag cacgagcggt ccagatttaa   7920
agtagaaaat ttcccgccca ctaggggttaa aggtgttcac actataaaag catatacgat   7980
gtgatggtat ttgatggagc gtatattgta tcaggtatttt ccgttggata cgaattattc   8040
gtacgaccct cggtaccgat cggcgcgcct ggcagacata ctgtcccaca aatgaagatg   8100
gaatctgtaa aagaaaacgc gtgaaataat gcgtctgaca aaggttaggt cggctgcctt   8160
taatcaatac caaagtggtc cctaccacga tggaaaaact gtgcagtcga tttggcttttt   8220
tctgacgaac aaataagatt cgtggccgac aggtgggggt ccaccatgtg aaggcatctt   8280
cagactccaa taatggagca atgacgtaag ggcttacgaa ataagtaagg gtagtttggg   8340
aaatgtccca tcacccgtca gtctataaat acttagcccc tccctcattg ttaagggagc   8400
aaaatctcag agagatagtc ctagagagag aaagagagca agtagcctaa aagtagtcaa   8460
ggcggcgaag tattcaggca cgtggccagg aagaagaaaa gccaagacga cgaaaacgag   8520
taagagctaa gcttcctgca ccatggaaga cgccaaaaac ataaagaaag gcccggcgcc   8580
attctatccg ctggaagatg gaaccgctgg agagcaactg cataaggcta tgaagagata   8640
cgccctggtt cctggaacaa ttgcttttac agatgcacat atcgaggtgg acatcactta   8700
cgctgagtac ttcgaaatgt ccgttcggtt ggcagaagct atgaaacgat atgggctgaa   8760
tacaaatcac agaatcgtcg tatgcagtga aaactctctt caattcttta tgccggtgtt   8820
gggcgcgtta tttatcggag ttgcagttgc gcccgcgaac gacatttata tgaacgtgaa   8880
attgctcaac agtatgggca tttcgcagcc taccgtggtg ttcgtttcca aaaagggtt   8940
gcaaaaaatt ttgaacgtgc aaaaaaagct cccaatcatc caaaaaatta ttatcatgga   9000
ttctaaaacg gattaccagg gatttcagtc gatgtacacg ttcgtcacat ctcatctacc   9060
tcccggtttt aatgaatacg attttgtgcc agagtccttt gatagggaca agacaattgc   9120
```

```
actgatcatg aactcctctg gatctactgg tctgcctaaa ggtgtcgctc tgcctcatag   9180
aactgcctgc gtgagattct cgcatgccaa agatcctatt tttggcaatc aaatcattcc   9240
ggatactgcg attttaagtg ttgttccatt ccatcacggt tttggaatgt ttactacact   9300
cggatatttg atatgtggat ttcgagtcgt cttaatgtat agatttgaag aagagctgtt   9360
tctgaggagc cttcaggatt acaagattca aagtgcgctc ctggtgccaa ccctattctc   9420
cttcttcgcc aaaagcactc tgattgacaa atacgattta tctaatttac acgaaattgc   9480
ttctggtggc gctcccctct ctaaggaagt cggggaagcg gttgccaaga ggttccatct   9540
gccaggtatc aggcaaggat atgggctcac tgagactaca tcagctattc tgattacacc   9600
cgaggggat gataaaccgg gcgcggtcgg taaagttgtt ccattttttg aagcgaaggt   9660
tgtggatctg gataccggga aaacgctggg cgttaatcaa agaggcgaac tgtgtgtgag   9720
aggtcctatg attatgtccg gttatgtaaa caatccggaa gcgaccaacg ccttgattga   9780
caaggatgga tggctacatt ctggagacat agcttactgg gacgaagacg aacacttctt   9840
catcgttgac cgcctgaagt ctctgattaa gtacaaaggc tatcaggtgg ctcccgctga   9900
attggaatcc atcttgctcc aacaccccaa catcttcgac gctggtgtcg caggtcttcc   9960
cgacgatgac gccggtgaac ttcccgccgc cgttgttgtt ttggagcacg aaagacgat   10020
gacgaaaaa gagatcgtgg attacgtcgc cagtcaagta acaaccgcga aaagttgcg   10080
cggaggagtt gtgtttgtgg acgaagtacc gaaaggtctt accggaaaac tcgacgcaag   10140
aaaaatcaga gagatcctca taaaggccga gaagggcgga aagatcgccg tgtaactcga   10200
gatatgaaga tgaagatgaa atatttggtg tgtcaaataa aaagcttgtg tgcttaagtt   10260
tgtgtttttt tcttggcttg ttgtgttatg aatttgtggc tttttctaat attaaatgaa   10320
tgtaagatca cattataatg aataaacaaa tgtttctata atccattgtg aatgttttgt   10380
tggatctctt ctgcagcata taactactgt atgtgctatg gtatggacta tggaatatga   10440
ttaaagataa ggagctccgg tgacggaccc atggcttcgt tgaacaacgg aaactcgact   10500
tgccttccgc acaatacatc atttcttctt agctttttt cttcttctc gttcatacag   10560
tttttttttg tttatcagct tacattttct tgaaccgtag ctttcgtttt cttctttta   10620
actttccatt cggagttttt gtatcttgtt tcatagtttg tcccaggatt agaatgatta   10680
ggcatcgaac cttcaagaat ttgattgaat aaaacatctt cattcttaag atatgaagat   10740
aatcttcaaa aggcccctgg gaatctgaaa gaagagaagc aggcccattt atatgggaaa   10800
gaacaatagt atttcttata taggcccatt taagttgaaa acaatcttca aaagtcccac   10860
atcgcttaga taagaaaacg aagctgagtt tatatacagc tagagtcgaa gtagtgattg   10920
ttggtagtag cgactccatg gttttagagc tagaaatagc aagttaaaat aaggctagtc   10980
cgttatcaac ttgaaaaagt ggcaccgagt cggtgcttt tttcccgggc gcgccgatca   11040
tgagcggaga attaagggag tcacgttatg acccccgccg atgacgcggg acaagccgtt   11100
ttacgttttgg aactgacaga accgcaacgt tgaaggagcc actcagccgc gggttttctgg   11160
agtttaatga gctaagcaca tacgtcagaa accattattg cgcgttcaaa agtcgcctaa   11220
ggtcactatc agctagcaaa tatttcttgt caaaaatgct ccactgacgt tccataaatt   11280
cccctcggta tccaattaga gtctcatatt cactctcaat ccaaataatc tgcaccgtac   11340
ctgcagggtc cgagctaggt cacagaagcg ctcaggaagg ccgctgagat agaggcatgg   11400
cggccaatgc gggcggcggt ggagcggcag gaggcagcgg cagccggcca gtggctgcgc   11460
cggcggtgtg ccgccccagc ggctcgcggt ggacgccgac gccggagcag atcaggatgc   11520
tgaaggagct gtactacggc tgcggcatcc ggtcgcccag ctcggagcag atccagcgca   11580
tcaccgccat gctgcggcag cacggcaaga tcgagggcaa gaacgtcttc tactggttcc   11640
agaaccacaa ggcccgcgag cgccagaagc gccgcctcac caccctcgac gtgaacgtgg   11700
ccgccgccgg cgcggccgac gccaccacca gccaactcgg cgtcctctcg ctgtcgtcgc   11760
cgccgccttc aggcgcggcg cctccctcgc ccaccctcgg cttctacgcc gccggcaatg   11820
gcggcggatc ggctgtgctg ctggacacga gttccgactg ggcagcagc ggcgctgcga   11880
tggccaccga gacatgcttc ctccaggact acatggcgat cgcagctcgt   11940
cgcagtggcc acgcttctcg tcgtcggaca cgataatggc ggcggccgcg gcgcgggcgg   12000
cgacgacgcg ggcgcccgag actctccctc tcttcccgac ctgcggcgac gacggcggca   12060
gcggtagcag cagctacttg ccgttctggg gtgccgcgtc cacaactgcc ggcgccactt   12120
cttccgttgc gatccagcag caacaccagc tgcaggacga gtacagcttt tacagcaaca   12180
gcaacagcac ccagctggcc ggcaccggca accaagacgt atcggcaaca gcagcagcag   12240
ccgccgccct ggagctgagc ctcagctcat ggtgctcccc ttaccctgct gcagggagta   12300
tgtgagagca acgcgagctg ccactgctct tcacttatgt ctctggaatg gaaggaggag   12360
gaagtgagca tagcgttggt gcgttgctgt cattgtccta ggttagtagc tagtgccagt   12420
tactagtaag catcaggcat aggagtatgt agtagaagca tgcacgttgc cggccagcca   12480
ggctttagac gggaaaagaa tttggtgcag ccggctgcaa aacaggatgt ttacagcccc   12540
cccctcgagc cctagacttg tccatcttct ggattggcca agttaattaa tgtatgaaat   12600
aaaaggatgc acacatagtg acatgctaat cactatagtg tgggcatcaa agttgtgtgt   12660
tatgtgtaat tactaattat ctgaataaga gaaagagatc atccatattt cttatcctaa   12720
atgaatgtca cgtgtcttta taattctttg atgaaccaga tgcattttat taaccaattc   12780
catatacata taaatattaa tcatatataa ttaatatcaa ttgggttagc aaaacaaatc   12840
tagtctaggt gtgttttgct aattattggg ggatagtgca aaaagaaatc tacgttctca   12900
ataattcaga tagaaaactt aataaagtga gataatttac atagattgct tttatccttt   12960
gatatatgtg aaaccatgca tgatataagg aaaatagata gagaaataat ttttacatc   13020
gttgaatatg taaacaattt aattcaagaa gctaggaata taaatattga ggagtttatg   13080
attagagctc tcccggcgcg ccagatttgc cttttcaatt tcagaaagaa tgctaaccca   13140
cagatggtta gagaggctta cgcagcaggt atcatcaaga cgatctaccc gagcaataat   13200
ctccaggaaa tcaaataccl tcccaagaag gttaaagatg cagtcaaaag attcaggact   13260
aactgcatca agaacacaga gaaagatata tttctcaaga tcagaagtac tattccagta   13320
tggacgattc aaggcttgct tcacaaacca aggcaagtaa tagagattgg agtctctaaa   13380
aaggtagttc ccactgaatc aaaggccatg gagtcaaaga ttcaaatagg gacctaaca   13440
gaactcgccg taaagactgg cgaacagttc atacagagtc tcttacgact caatgacaag   13500
aagaaaatct tcgtcaacat ggtggagcac gacacacttg tctactccaa aaatatcaaa   13560
gatacagtct cagaagacca aagggcaatt gagactttc aacaaagggt aatatccgga   13620
aacctcctcg gattccattg cccagctatc tgtcacttta ttgtgaagat agtggaaag   13680
gaaggtggct cctacaaatg ccatcattgc gataaaggaa aggccatcgt tgaagatgcc   13740
tctgccgaca gtggtcccaa agatggaccc caccccacga ggagcatcgt ggaaaaagaa   13800
gacgttccaa ccacgtcttc aaagcaagtg gattgatgtg atatctccac tgacgtaagg   13860
```

```
gatgacgcac aatcccacta tccttcgcaa gacccttcct ctatataagg aagttcattt    13920
catttggaga gaacacgggg gactcctgca ggatggatct gcgtctaatt ttcggtccaa    13980
cttgcacagg aaagacgtcg accgcgatac gtcttgccca gcagactggc cttccagtcc    14040
tttcgctcga tcgggtccaa tgctgtcctc aactgtcaac cggaagcgga cgaccaacag    14100
tggaagaact gaaaggaacg acccgtctat accttgaaga tcggcctctg gtgaagggta    14160
tcatcgcagc caagcaagct cacgaaaggc tgatcgggga agtgtacaat tatgaggccc    14220
acggcgggct tattcttgag ggaggatcta tctcgttgct caggtgcatg gcgcaaagca    14280
gttattggag taccgatttt cgttggcata ttattcgcca caagttagca gacgaggaga    14340
cattcatgaa cgcggccaag gccagagtta ggcagatgtt gcgccctgct gtaggcccat    14400
ctattattca agagttggtt catctttgga atgagcctcg gctgaggccc atactgaaag    14460
agatcgacgg atatcgatat gccatgttat ttgctagcca gaaccagatc acacccgata    14520
tgctattgca gcttgaccca gatatggagg gtgagttgat tcatgaaatc gctcaggagt    14580
atctcatcca tgcgcgccgg caggagcagg aattccctcc agtgagcgtg gtcgctttcg    14640
aaggattcga aggtccaccg ttcggaatgt gctagctcga gccctagact tgtccatctt    14700
ctggattggc caagttaatt aatgtatgaa ataaaaggat gcacacatag tgacatgcta    14760
atcactataa tgtgggcatc aaagttgtgt gttatgtgta attactaatt atctgaataa    14820
gagaaagaga tcatccatat ttcttatcct aaatgaatgt cacgtgtctt tataattctt    14880
tgatgaacca gatgcatttt attaaccaat tccatataca tataaatatt aatcatatat    14940
aattaatatc aattgggtta gcaaaacaaa tctagtctag gtgtgttttg ctaattattg    15000
ggggatagtg caaaaagaaa tctacgttct caataattca gatagaaaac ttaataaagt    15060
gagataattt acatagattg cttttatcct ttgatatatg tgaaaccatg catgatataa    15120
ggaaaataga tagagaaata attttttaca tcgttgaata tgtaaacaat ttaattcaag    15180
aagctaggaa tataaatatt gaggagttta tgattagagc tcagtgtttg atcgccggcg    15240
gtaccgagtg tacttcaagt cagtgggaaa tcaataaaat gattatttta tgaatatatt    15300
tcattgtgca agtagataga aattacatat gttacataac acacgaaata aacaaaaaaa    15360
gacaatccaa aaacaaacac cccaaaaaaa ataatcactt tagataaact cgtatgagga    15420
gaggcacgtt cagtgactcg acgattcccg agcaaaaaaa gtctccccgt cacacatgta    15480
gtgggtgacg caattatctt taaagtaatc cttctgttga cttgtcattg ataacatcca    15540
gtcttcgtca ggattgcaaa gaattataga agggatccca                          15580
```

SEQ ID NO: 32        moltype = DNA  length = 16945
FEATURE                Location/Qualifiers
source                 1..16945
                        mol_type = other DNA
                        organism = synthetic construct
SEQUENCE: 32

```
gttgaaggcc gcgcaggccg cccagcggca acgcatcgag gcagaagcac gccccggtga      60
atcgtggcaa gcggccgctg atcgaatccg caaagaatcc cggcaaccgc cggcagccgg     120
tgcgccgtcg attaggaagc cgcccaaggc cgacgagcaa ccagattttt tcgttccgat     180
gctctatgac gtgggcaccc gcgatagtcg cagcatcatg gacgtggccg ttttccgtct     240
gtcgaagcgt gaccgacgag ctggcgaggt gatccgctac gagcttccag acgggcacgt     300
agaggttttcc gcagggccgg ccggcatggc cagtgtgtgg gattacgacc tggtactgat     360
ggcggttttcc catctaaccg aatcatgaa ccgataccgg gaagggaagg ggacaagcc       420
cggccgcgtg ttccgtccac acgttgcgga cgtactcaag ttctgccggc gagccgatgg     480
cggaaagcag aaagacgacc tggtagaaac ctgcattcgg ttaaacacca cgcacgttgc     540
catgcagcgt acgaagaagg ccaagaacgg ccgcctggtg acggtatccg agggtgaagc     600
cttgattagc cgctacaaga tcgtaaagag cgaaaccggc cggccgagct acatcgagat     660
cgagctagct gattggatgt accgcgagat cacagaaggc aagaacccgg acgtgctgac     720
ggttcacccc gattactttt tgatcgatcc cggcatcggc cgtttctctt accgcctggc     780
acgccgcgcc gcaggcaagg cagaagccag atggttgttc aagacgatct acgaacgcag     840
tggcagcgcc ggagagttca agaagttctg tttcaccgtg cgcaagctga tcgggtcaaa     900
tgacctgccg gagtacgatt tgaaggagga ggcggggcag gctggcccga tcctagtcat     960
gcgctaccgc aacctgatcg agggcgaagc atccgccggt tcctaatgta cggagcagat    1020
gctagggcaa attgccctag caggggaaaa aggtcgaaaa ggcctctttc ctgtggatag    1080
cacgtacatt gggaacccaa agcccgtacat tgggaacccg aaccgtaca ttgggaaccc    1140
aaagccgtac attgggaacc ggtcacacat gtaagtgact gatataaaag agaaaaaagg    1200
cgattttttcc gcctaaaact ctttaaaact tattaaaact cttaaaaccc gcctggcctg    1260
tgcataactg tctggccagc gcacagccga agagctgcaa aaagcgccta cccttcggtc    1320
gctcgctcc ctacgcccg ccgcttcgcg tcggcctatc gcggccgctg gccgctcaaa      1380
aatggctggc ctacgccag gcaatctacc agggcgcgga caagccgcc cgtcgccact    1440
cgaccgccgg cgcccacatc aaggcaccct gcctcgcgcg tttcggtgat gacggtgaaa    1500
acctctgaca catgcagctc ccggaaacgg tcacagcttg tctgtaagcg gatgccggga    1560
gcagacaagc ccgtcagggc gcgtcagcgg gtgttggcgg gtgtcgggc gcagccatga     1620
cccagtcacg tagcgatagc ggagtgtata ctggcttaac tatgcggcat cagagcgat    1680
tgtactgaga gtgcaccata tgcggtgtga ataccgcac agatgcgtaa ggagaaaata    1740
ccgcatcagg cgctcttccg cttcctcgct cactgactcg ctgcgctcgg tcgttcggct    1800
gcggcgagcg gtatcagctc actcaaaggc ggtaatacgg ttatccacag aatcaggga    1860
taacgcagga aagaacatgt gagcaaaagg ccagcaaaag gccaggaacc gtaaaaaggc    1920
cgcgttgctg gcgtttttcc ataggctccg cccccctgac gagcatcaca aaaatcgacg    1980
ctcaagtcag aggtggcgaa acccgacagg actataaaga taccaggcgt ttccccctgg    2040
aagctccctc gtgcgctctc ctgttccgac cctgccgctt accggatacc tgtccgcctt    2100
tctcccttcg ggaagcgtgg cgcttctcta gctcacgct gtaggtatc tcagttcggt     2160
gtaggtcgtt cgctccaagc tgggctgtgt gcacgaaccc cccgttcagc ccgaccgctg    2220
cgccttatcc ggtaactatc gtcttgagtc aacccggta acacgact tatcgccact      2280
ggcagcagcc actggtaaca ggattagcag agcgaggtat gtaggcggtg ctacagagtt    2340
cttgaagtgg tggcctaact acggctacac tagaaggaca gtatttggta tctgcgctct    2400
gctgaagcca gttaccttcg gaaaaagagt ggtagctct tgatccggca aacaaaccac      2460
cgctggtagc ggtggttttt ttgtttgcaa gcagcagatt acgcgcagaa aaaaaggatc    2520
tcaagaagat cctttgatct tttctacggg gtctgacgct cagtggaacg aaaactcacg    2580
```

```
ttaagggatt ttggtcatgc attctaggta ctaaaacaat tcatccagta aaatataata  2640
ttttattttc tcccaatcag gcttgatccc cagtaagtca aaaaatagct cgacatactg  2700
ttcttcccg  atatcctccc tgatcgaccg gacgcagaag gcaatgtcat accacttgtc  2760
cgccctgccg cttctcccaa gatcaataaa gccacttact ttgccatctt tcacaaagat  2820
gttgctgtct cccaggtcgc cgtgggaaaa gacaagttcc tcttcgggct tttccgtctt  2880
taaaaaatca tacagctcgc gcggatcttt aaatggagtg tcttcttccc agttttcgca  2940
atccacatcg gccagatcgt tattcagtaa gtaatccaat tcggctaagc ggctgtctaa  3000
gctattcgta tagggacaat ccgatatgtc gatggagtga agagcctga  tgcactccgc  3060
atacagctcg ataatctttt cagggctttg ttcatcttca tactcttccg agcaaaggac  3120
gccatcggcc tcactcatga gcagattgct ccagccatca tgccgttcaa agtgcaggac  3180
ctttggaaca ggcagctttc cttccagcca tagcatcatg tccttttccc gttccacatc  3240
ataggtggtc cctttatacc ggctgtccgt catttttaaa tataggtttt catttttctcc  3300
caccagctta tataccttag caggagacat tccttccgta tctttacgc  agcggtattt  3360
ttcgatcagt tttttcaatt ccggtgatat tctcatttta gccatttatt atttccttcc  3420
tcttttctac agtatttaaa gatacccaa  gaagctaatt ataacaagac gaactccaat  3480
tcactgttcc ttgcattcta aaaccttaaa taccagaaaa cagcttttc  aaagttgttt  3540
tcaaagttgg cgtataacat agtatcgacg gagccgattt tgaaaccgcg gtgatcacag  3600
gcagcaacgc tctgtcatcg ttacaatcaa catgctaccc tccgcgagat catccgtgtt  3660
tcaaacccgg cagcttagtt gccgttcttc cgaatagcat cggtaacatg agcaaagtct  3720
gccgccttac aacggctctc ccgctgacgc cgtcccggac tgatgggctg cctgtatcga  3780
gtggtgatt  tgtgccgagc tgccggtcgg ggagctgttg gctggctggt ggcaggatat  3840
attgtggtgt aaacaaattg acgcttagac aacttaataa cacattgcgg agttttttaa  3900
tgtagagctc aaagtttaac gcgttagcag aaggcatgtt gttgtgactc cgaggggttg  3960
cctcaaactc tatcttataa ccggcgtgga ggcatggagg caggggtatt ttggtcattt  4020
taatagatag tggaaaatga cgtggaattt acttaaagac gaagtctttg cgacaagggg  4080
gggcccacgc cgaatttaat attaccggcg tggcccccccc ttatcgcgag tgctttagca  4140
cgagcggtcc agatttaaag tagaaaattt cccgcccact agggttaaag gtgttcacac  4200
tataaaagca tatcgatgt  gatggtattt gatggagcgt atattgtatc aggtatttcc  4260
gttggatacg aattattcgt acgaccctcg gtaccgatcg gcgcgcctgg cagacatact  4320
gtcccacaaa tgaagatgga atctgtaaaa gaaaacgcgt gaaataatgc gtctgacaaa  4380
ggttaggtcg gctgccttta atcaataccA aagtggtccc taccacgatg gaaaaactgt  4440
gcagtcggtt tggctttttc tgacgaacaa ataagattcg tggccgacag gtgggggtcc  4500
accatgtgaa ggcatcttca gactccaata atggagcaat gacgtaaggg cttacgaaat  4560
aagtaagggt agtttgggaa atgtccactc accccgtcagt ctataaatac ttagccccctc  4620
cctcattgtt aagggagcaa aatctcagag agatagtcct agagagagaa agagagcaag  4680
tagcctagaa gtagtcaagg cggcgaagta ttcaggcacg tggccaggaa gaagaaaagc  4740
caagacgacg aaaacaggta agagctaagc ttcctgcacc atggaagacg ccaaaaacat  4800
aaagaaaggc ccggcgccat tctatccgct ggaagatgga accgctggag agcaactgca  4860
taaggctatg aagagatacg ccctggttcc tggaacatt  gcttttacag atgcacatat  4920
cgaggtggac atcacttacg ctgagtactt cgaaatgtcc gttcggttgg cagaagctat  4980
gaaacgatat gggctgaata caaatcacag aatcgtcgta tgcagtgaaa actctcttca  5040
attctttatg ccggtgttgg gcgcgttatt tatcggagtt gcagttgcgc ccgcgaacga  5100
catttataat gaacgtgaat tgctcaacag tatgggcatt tcgcagccta ccgtggtgtt  5160
cgtttccaaa aaggggttgc aaaaaatttt gaacgtgcaa aaaaagctcc caatcatcca  5220
aaaaattatt atcatggatt ctaaaacgga ttaccaggga tttcagtcga tgtacacgtt  5280
cgtcacatct catctacctc ccggttttaa tgaatacgat tttgtgccag agtccttcga  5340
tagggacaag acaattgcac tgatcatgaa ctcctctgga tctactggtc tgcctaaagg  5400
tgtcgctctg cctcatagaa ctgcctgcgt gagattctcg catgccagag atcctatttt  5460
tggcaatcaa atcattccgg atactgcgat tttaagtgtt gttccattcc atcacggttt  5520
tggaatgttt actacactcg gatatttgat atgtggattt cgagtcgtct taatgtatag  5580
atttgaagaa gagctgtttc tgaggagcct tcaggattac agattcaaa  gtgcgctgct  5640
ggtgccaacc ctattctcct tcttcgccaa aagcactctg attgacaaat acgatttatc  5700
taatttacac gaaattgctt ctggtggcgc tcccctctct aaggaagtcg ggaagcggt  5760
tgccaagagg ttccatctgc caggtatcag gcaaggatat gggctcactg agactacatc  5820
agctattctg attacacccg aggggggatga taaaccgggc gcggtcggta aagttgttcc  5880
attttttgaa gcgaaggttg tggatctgga taccggggaaa acgctgggcg ttaatcaaag  5940
aggcgaactg tgtgtgagag gtcctatgat tatgtccggt tatgtaaaca atccggaagc  6000
gaccaacgcc ttgattgaca aggatggatg gctacattct ggagacatag cttactggga  6060
cgaagacgaa cacttcttca tcgttgaccg cctgaagtct ctgattaagt acaaaggcta  6120
tcaggtggct cccgctgaat tggaatccat cttgctccaa caccccaaca tcttcgacgc  6180
tggtgtcgca ggtcttcccg acgatgacgc cggtgaactt cccgccgccg ttgttgtttt  6240
ggagcacgga aagacgatga cggaaaaaga tcgtggatt  tacgtcgcca gtcaagtaac  6300
aaccgcgaaa aagttgcgcg gaggagttgt gtttgtggac gaagtaccga aaggtcttac  6360
cggaaaactc gacgcaagaa aaatcagaga gatcctcata aaggccaaga agggcggaaa  6420
gatcgccgtg taactcgaga tatgaagatg aagatgaaat atttggtgtg tcaaataaaa  6480
agcttgtgtg cttaagtttg tgtttttttt ttggcttgtt gtgttatgaa tttgtggctt  6540
tttctaatat taaatgaatg taagatcaca ttataatgaa taaacaaatg tttctataat  6600
ccattgtgaa tgttttgttg gatctcttct gcagcatata actactgtat gtgctatggt  6660
atggactatg gaatatgatt aaagataagg agctccggtg acggacccat ggcttcgttg  6720
aacaacggaa actcgacttg ccttccgcac aatacatcat ttcttcttag cttttttct   6780
tcttcttcgt tcatacagtt tttttttgtt tatcagctta cattttcttg aaccgtagct  6840
ttcgtttct  tcttttttaac tttccattcg gagttttttgt atcttgtttc atagtttgtc  6900
ccaggattag aatgattagg catcgaacct tcaagaattt gattgaataa aacatcttca  6960
ttcttaagat atgaagataa tcttcaaaag gccccaaaga gagaagcag   7020
gcccatttat atgggaaaga acaatagtat ttcttatata ggcccattta agttgaaaac  7080
aatcttcaaa agtcccacat cgcttagata agaaaacgaa gctgagttta tacagcta   7140
gagtcgaagt agtgattgtt ggtagtagcg actccatggt tttagagcta gaaatagcaa  7200
gttaaaataa ggctagtccg ttatcaactt gaaaagtgg  caccgagtcg gtgctttttt  7260
tcccggcgta atatggcgcg ccagatttgc cttttcaatt tcagaaagaa tgctaaccca  7320
```

```
cagatggtta gagaggctta cgcagcaggt atcatcaaga cgatctaccc gagcaataat  7380
ctccaggaaa tcaaatacct tcccaagaag gttaaagatg cagtcaaaag attcaggact  7440
aactgcatca agaacacaga gaaagatata tttctcaaga tcagaagtac tattccagta  7500
tggacgattc aaggcttgct tcacaaacca aggcaagtaa tagagattgg agtctctaaa  7560
aaggtagttc ccactgaatc aaaggccatg gagtcaaaga ttcaaataga ggacctaaca  7620
gaactcgccg taaagactgg cgaacagttc atacagagtc tcttacgact caatgacaag  7680
aagaaaatct tcgtcaacat ggtggagcac gacacacttg tctactccaa aaatatcaaa  7740
gatacagtct cagaagacca aagggcaatt gagactttc aacaaagggt aatatccgga  7800
aacctcctcg gattccattg cccagctatc tgtcactttg ttgtgaagat agtggaaaag  7860
gaaggtggct cctacaaatg ccatcattgc gataaaggaa aggccatcgt tgaagatgcc  7920
tctgccgaca gtggtcccaa agatggaccc ccacccacga ggagcatcgt ggaaaaagaa  7980
gacgttccaa ccacgtcttc aaagcaagtg gattgatgtg atatctccac tgacgtaagg  8040
gatgacgcac aatcccacta tccttcgcaa gacccttcct ctatataagg aagttcattt  8100
catttggaga gaacacgggg gactcctgca ggatgatct gcgtctaatt ttcggtccaa  8160
cttgcacagg aaagacgtcg accgcgatac gtcttgccca gcagactggc cttccagtcc  8220
tttcgctcga tcgggtccaa tgctgtcctc aactgtcaac cggaagcgga cgaccaacag  8280
tggaagaact gaaaggaacg acccgtctat accttgaaga tcggcctctg gtgaagggta  8340
tcatcgcagc caagcaagct cacgaaaggc tgatcgggga agtgtacaat tatgaggccc  8400
acggcgggct tattcttgag ggaggatcta tctcgttgct caggtgcatg gcgcaaagca  8460
gttattggag taccgatttt cgttggcata ttattcgcca caagttagca gacgaggaga  8520
cattcatgaa cgcggccaag gccagagtta ggcagatgtt gcgccctgct gtaggcccat  8580
ctattattca agagtttggt catctttgga atgagcctcg gctgaggccc atactgaaga  8640
agatcgacgg atatcgatat gccatgttat ttgctagcca gaaccagatc acacccgata  8700
tgctattgca gcttgaccca gatatggagg gtgagttgat tcatgaaatc gctcaggagt  8760
atctcatcca tgcgcgccgg caggagcagg aattccctcc agtgagcgtg gtcgctttcg  8820
aaggattcga aggtccaccg ttcggaatgt gctagctcga gccctagct tgtccatcct  8880
ctggattggc caagttaatt aatgtatgaa ataaaaggat gcacacatag tgacatgcta  8940
atcactataa tgtgggcatc aaagttgtgt gttatgtgta attactaatt atctgaataa  9000
gagaaagaga tcatccatat ttcttatcct aaatgaatgt cacgtgtctt tataattctt  9060
tgatgaacca gatgcatttt attaaccaat tccatataca tataaatatt aatcatatat  9120
aattaatatc aattgggtta gcaaaacaaa tctagtctag gtgtgttttg ctaattattg  9180
ggggatagtg caaaaagaaa tctacgttct caataattca gatagaaaac ttaataaagt  9240
gagataattt acatagattg ctttttatcct ttgatatatg tgaaaccatg catgatataa  9300
ggaaaataga tagagaaata atttttttaca tcgttgaata tgtaaacaat ttaattcaag  9360
aagctaggaa tataaatatt gaggagttta tgattagagc tctcccgcag atttgcctt  9420
tcaatttcag aaagaatgct aacccacaga tggttagaga ggcttacgca gcaggtatca  9480
tcaagacgat ctacccgagc aataatctcc aggaaatcaa atacctttccc aagaaggtta  9540
aagatgcagt caaaagattc aggactaact gcatcaagaa cacagagaaa gatatattc  9600
tcaagatcag aagtactatt ccagtatgga cgattcaagg cttgcttcac aaaccaaggc  9660
aagtaataga gattggagtc tctaaaaagg tagttcccac tgaatcaaag gccatggagt  9720
caaagattca aatagaggac ctaacagaac tcgccgtaaa gactggcgaa cagttcatac  9780
agagtctctt acgactcaat gacaagaaga aaatcttcgt caacatggtg gagcacgaca  9840
cacttgtcta ctccaaaaat atcaaagata cagtctcaga agaccaaagg gcaattgaga  9900
cttttcaaca aagggtaata tccggaaacc tcctcggatt ccattgccca gctatctgtc  9960
actttattgt gaagatagtg aaaaggaag gtggctccta caaatgccat cattgcgata  10020
aaggaaaggc catcgttgaa gatgcctctg ccgacagtgg tcccaaagat ggaccccac  10080
ccacgaggag catcgtggaa aaagaagacg ttccaaccac gtcttcaaag caagtggatt  10140
gatgtgatat ctccactgac gtaagggatg acgcacaatc ccactatcct tcgcaagacc  10200
cttcctctat ataaggaagt tcatttcatt tggagagaac acggggggact atgatggctt  10260
cattgtcttg tgttgaagac aagatgaaaa caagttgttt ggttaatggt ggaggaacta  10320
taacaacaac aacatctcaa tctaccttgc ttgaagagat gaagctgttg aaagaccagt  10380
caggtacaag aaagccggta ataaaactcgg agctatggca cgcttgtgca ggccctttgg  10440
tgtgtctccc tcaagttggg agcttagtgt attacttctc acaaggtcat agcgagcagg  10500
ttgctgtttc aaccagaaga tcagcaacaa cacaagttcc taattatccg aaccttccat  10560
ctcagttgat gtgtcaagtc cataatgtta tcttcatgc tgacaaagac agtgacgaaa  10620
tctatgctca gatgagtctt caacctgttc actctgagag agatgtgttc cctgtaccag  10680
actttgaat gctgagagga agtaagcacc cgactgagtt tttctgcaaa acacttactg  10740
caagtgacac aagcacacat ggaggtttct cagtgccacg tagagctgca gagaagctat  10800
ttccaccatt ggactactca gcacagccgc caacgcaaga gcttgtagtt cagatcttc  10860
atgagaatac ttggacattt cgccatatct accgagggca accaaagaga catctcctaa  10920
ctacaggatg gagtttgttc gttggatcga agagattgag agctggggat tctgtttttgt  10980
tcatcaggga tgagaagtca caacttatgg tcggtgttag gcgtgccaat cgccaacaaa  11040
cagcacttcc ttcatcagtt ctctcagcgg atagtatgca catcggtgtt cttgctgctg  11100
ctgctcacgc aaccgccaac cgtactcctt ttttgatatt ctataatcca agaccttgtc  11160
cagcagagtt cgtgatccct ctagctaagt accgtaaggc gatatgcggg tctcagctct  11220
cagttggtat gagatttgga atgatgtttg aaactgaaga ttccgggaaa cgaaggtaca  11280
tgggaactat tgttggaatc agcgatttgg atccgttgag atggcctggt tctagtggc  11340
gtaaccttca ggtagaatgg gatgagcctg gatgtaatga taaacctact cgggtcagtc  11400
catgggatat cgaaacacct gaaagtctct tcatttttcc ttctctgacc tcaggactca  11460
aacgtcagct ccatccatct tactttgctg gtgaaactga atgggggtagc ttgataaaac  11520
ggccacttat acgtgttcct gattccgcga atgggattat gccatatgca tctttcccta  11580
gtatggcttc ggagcagctt atgaaaatga tgatgaggcc tcacaacaac caaaatgtac  11640
catctttcat gtctgagatg cagcagaata ttgtaatggg gaatggaggt ttgctaggag  11700
atatgaagat gcagcaaccc ctgatgatga accagaaatc tgatgggtg cagccacaaa  11760
acaagctaac agtgaaccca tctgcttcta atacgagtgg ccaagaacag aatctttcac  11820
agagtatgag tgctcctgct aaacctgaga actctacact ctctggttgc agctctggta  11880
gagtccaaca tggacttgag cagtcaatgg aacaggcaag ccaggttact acatccacag  11940
tgtgtaatga ggaaaaggtt aatcagctac ttcgaaaccc gggtgcttcg tcgcctgtac  12000
aagctgatca atgtcttgac attactcatc agatttacca accacagtct gatccaataa  12060
```

```
atggattctc tttcctggaa actgatgagc tgacatcaca agtctcttcc ttccagtctc   12120
ttgccggatc atacaagcaa ccattcattc tatcctccca ggattcttca gctgttgtgt   12180
taccggattc cacaaactca ccgctgtttc atgatgtgtg ggacactcag ttgaacggtc   12240
tcaagtttga ccagttcagt cccttgatgc agcaggacct ttatgctagt cagaatatct   12300
gtatgagtaa tagcacaacc agtaacattc tagatcctcc actctcaaac acagtccttg   12360
atgacttctg tgccatcaaa gacactgatt tccagaacca cccttctggt tgtttggttg   12420
gaaacaacaa cactagcttt gctcaagatg tccagtcgca gatcacatca gctagctttg   12480
cagactcaca ggccttctct cgccaagatt ttccagataa ttctggaggc actggtacat   12540
cttcaagcaa tgttgatttt gatgattgta gtctgcggca aaatagtaaa ggctcatcat   12600
ggcagaaaat tgcgacaccc cgcgtccgaa cctactcgag tttctccata ataatgtgtg   12660
agtagttccc agataaggga attagggttc ctataggggtt tcgctcatgt gttgagcata   12720
taagaaaccc ttagtatgta tttgtatttg taaaatactt ctatcaataa aatttctaat   12780
tcctaaaacc aaaatccagt actaaaatcc agatcccccg aattaagtgt ttgatcgccg   12840
gcggtaccga gtgtacttca agtcagtggg aaatcaataa aatgattatt ttatgaatat   12900
atttcattgt gcaagtagat agaaattaca tatgttacat aacacacgaa ataaacaaaa   12960
aaagacaatc caaaaacaaa caccccaaaa aaaataatca ctttagataa actcgtatga   13020
ggagaggcac gttcagtgac tcgacgattc ccgagcaaaa aaagtctccc cgtcacacat   13080
gtagtgggtg acgcaattat cttttaaagta atccttctgt tgacttgtca ttgataacat   13140
ccagtcttcg tcaggattgc aaagaattat agaagggatc ccacctttta ttttcttctt   13200
ttttccatat ttaggggttga cagtgaaatc agactggcaa cctattaatt gcttccacaa   13260
tgggacgaac ttgaagggga tgtcgtcgat gatattatag gtggcgtgtt catcgtagtt   13320
ggtgaaatcg atggtaccgt tccaatagtt gtgtcgtccg agacttctag cccaggtggt   13380
ctttccggta cgagttggtc cgcagatgta gaggctgggg tgtcggattc cattccttcc   13440
attgtccttg ttaaatcggc catccattca aggtcagatt gagcttgttg gtatgagaca   13500
ggatgtatgt aagtataagc gtctatgctt acatggtata gatgggtttc cctccaggag   13560
tgtagatctt cgtggcaggcg aagatctgat tctgtgaagg gcgacacata cggttcaggt   13620
tgtggaggga ataattttgtt ggctaatat tccagccatt gaagctttgt tgcccattca   13680
tgagggaatt cttccttgat catgtcaaga tattcctcct tagacgttgc agtctggata   13740
atagttctcc atcgtgcgtc agatttgcga ggagaaacct tatgatctcg gaaatctcct   13800
ctggttttaa tatctccgtc ctttgatatg taatcaagga cttgtttaga gtttctagct   13860
ggctggatat tagggtgatt tccttcaaaa tcgaaaaag aaggatccct aatacaaggt   13920
tttttatcaa gctggagaag agcatgatag tgggtagtgc catcttgatg aagctcagaa   13980
gcaacaccaa ggaagaaaat aagaaaaggt gtgagtttct cccagagaaa ctggaataaa   14040
tcatctcttt gaagtgaaca cttgggatag gtaaggaaaa catatttaga ttggagtctg   14100
aagttcttac tagcagaagg catgttgttg tgactccgag gggttgcctc aaactctatc   14160
ttataaccgg cgtggaggca tggaggcagg ggtattttgg tcatttttaat agatagtgga   14220
aaatgacgtg gaatttactt aaagacgaag tctttgcgac aagggggggc ccacgccgaa   14280
tttaatatta ccggcgtggc ccccccttat cgcgagtgct ttagcacgag cggtccagat   14340
ttaaagtaga aaatttcccg cccactaggg ttaaaggtgt tcaacactaa aaagcatata   14400
cgatgtgatg gtattttgatg gagcgtatat tgtatcaggt atttccgttg gatacgaatt   14460
attcgtacga ccctcatagt ttaaactatc agtgtttgac aggatatatt ggcgggtaaa   14520
cctaagagaa aagagcgttt attagaataa cggatattta aaagggcgtg aaaaggttta   14580
tccgttcgtc catttgtatg tgcatgccaa ccacaggggt cccctcggga tcaaagtact   14640
ttgatccaac ccctccgctg ctatagtgca gtcggcttcc gacgttcagt gcagccgtct   14700
tctgaaaacg acatgtcgca caagtcctaa gttacgcgac aggctgccgc cctgcccttt   14760
tcctggcgtt ttcttgtcgc gtgttttagt cgcataaagt agaatacttg cgactagaac   14820
cggagacatt acgccatgaa caagagcgcc gccgctggcc tgctgggcta tgccccgcgtc   14880
agcaccgacg accaggactt gaccaaccaa cgggccgaac tgcacgcggc cggctgcacc   14940
aagctgtttt ccgagaagat caccggcacc aggcgcgacc gccggagct ggccaggatg   15000
cttgaccacc tacgccctgg cgacgttgtg acagtgacca ggctagaccg cctggcccgc   15060
agcaccgcg acctactgga cattgccgag cgcatccagg aggccggcgc gggcctgagc   15120
agcctggcag agccgtgggc cgacaccacc acgccggccg gccgcatggt gttgaccgtg   15180
ttcgccggca ttgccgagtt cgagcgttcc ctaatcatcg accgcacccg gagcgggcgc   15240
gaggccgcca aggcccgagg cgtgaagttt ggcccccgcc ctaccctcac cccggcacag   15300
atcgcgacg cccgcgagct gatcgaccag gaaggccgca ccgtgaaaga ggcggctgca   15360
ctgcttggcg tgcatcgctc gaccctgtac cgcgcacttg agcgcagcga ggaagtgacg   15420
cccaccgagg ccaggcggcg cggtgccttc cgtgaggacg cattgaccga ggccgacgcc   15480
ctggcggccg ccgagaatga acgccaagag gaacaagcat gaaaccgcac caggacggcc   15540
aggacgaacc gttttttcatt accgaagaga tcgaggcgga gatgatcgcg gccgggtacg   15600
tgttcgagcc gcccgcgcac ggctcaaccg tgcggctgca tgaaatcctg gccggttttgt   15660
ctgatgccaa gctggcggcc tggccggcca gcttggccgc tgaagaaacc gagcgccgcc   15720
gtctaaaaag gtgatgtgta tttgagtaaa acagcttgcg tcatgcggtc gctgcgtata   15780
tgatgcgatg agtaaataaa caaatacgca aggggaacgc atgaaggtta tcgctgtact   15840
taaccagaaa ggcgggtcag gcaagacgac catcgcaacc catctagccc gcgccctgca   15900
actcgccggg gccgatgttc tgttagtcga ttccgatccc cagggcagtg cccgcgattg   15960
gcggccgtg cgggaagatc aaccgctaac cgttgtcggc atcgaccgcc cgacgattga   16020
ccgcgacgtg aaggccatcg gccggcgcga cttcgtagtg atcgacggag cgccccaggc   16080
ggcggacttg gctgtgtccg cgatcaaggc agccgacttc gtgctgattc cggtgcagcc   16140
aagcccttac gacatatggg ccaccgccga cctgttaagc agccgcattga   16200
ggtcacggat ggaaggctac aagcggcctt tgtcgtgtcc cggccgatca aaggcacgcg   16260
catcggcggt gaggttgccg aggcgctggc cgggtacgag ctgcccattc ttgagtcccg   16320
tatcacgcag cgcgtgagct acccaggcac tgccgccgcc ggcacaaccg ttcttgaatc   16380
agaacccgag ggcgacgctg cccgcgaggt ccaggcgctg gccgctgaaa ttaaatcaaa   16440
actcatttga gttaatgagg taaagagaaa atgagcaaaa gcacaaacac gctaagtgcc   16500
ggccgtccga gcgcacgcag cagcaaggct gcaacgttgg ccagcctggc agacacgcca   16560
gccatgaagc gggtcaactt tcagttgccg cggaggatc acaccaagct gaagatgtac   16620
gcggtacgcc aaggcaagac cattaccgag ctgctatctg aatacatcgc gcagctacca   16680
gagtaaatga gcaaatgaat aaatgagtag atgaatttta gcggctaaag gaggcggcat   16740
ggaaaatcaa gaacaaccag gcaccgacgc cgtggaatgc cccatgtgtg gaggaacggg   16800
```

```
cggttggcca ggcgtaagcg gctgggttgt ctgccggccc tgcaatggca ctggaacccc   16860
caagcccgag gaatcggcgt gacggtcgca aaccatccgg cccggtacaa atcggcgcgg   16920
cgctgggtga tgacctggtg gagaa                                         16945

SEQ ID NO: 33           moltype = DNA   length = 13599
FEATURE                 Location/Qualifiers
source                  1..13599
                        mol_type = other DNA
                        organism = synthetic construct
SEQUENCE: 33
ccttttatttt tcttcttttt tccatattta gggttgacag tgaaatcaga ctggcaacct   60
attaattgct tccacaatgg gacgaacttg aaggggatgt cgtcgatgat attataggtg   120
gcgtgttcat cgtagttggt gaaatcgatg gtaccgttcc aatagttgtg tcgtccgaga   180
cttctagccc aggtggtctt tccggtacga gttggtccga agatgtagag gctggggtgt   240
cggattccat tccttccatt gtccttgtta aatcggccat ccattcaagg tcagattgag   300
cttgttggta tgagacagga tgtatgtaag tataagcgtc tatgcttaca tggtatagat   360
gggtttccct ccaggagtgt agatcttcgt ggcagcgaag atctgattct gtgaagggcg   420
acacatacgg ttcaggttgt ggagggaata atttgttggt tgaatattcc agccattgaa   480
gctttgttgc ccattcatga gggaattctt ccttgatcat gtcaagatat tcctcgttag   540
acgttgcagt ctgataata gttctccatc gtgcgtcaga tttgcgagga gaaaccttat   600
gatctcgaaa atctcctctg gttttaatat ctccgtcctt tgatatgtaa tcaaggactt   660
gtttagagtt tctagctggc tggatattag ggtgatttcc ttcaaaatcg aaaaaagaag   720
gatccctaat acaaggtttt ttatcaagct ggagaagagc atgatagtgg gtagtgccat   780
cttgatgaag ctcagaagca acaccaagga agaaaataag aaaaggtgtg agtttctccc   840
agagaaactg gaataaatca tctctttgag atgagcactt gggataggta aggaaaacat   900
atttagattg gagtctgaag ttcttactag cagaaggcat gttgttgtga ctccgagggg   960
ttgcctcaaa ctctatctta taaccggcgt ggaggcatgg aggcagggggt attttggtca   1020
ttttaataga tagtggaaaa tgacgtggaa tttacttaaa gacgaagtct ttgcgacaag   1080
gggggggccca cgccgaattt aatattaccg gcgtggcccc cccttatcgc gagtgcttta   1140
gcacgagcgg tccagattta aagtagaaaa tttcccgcc actagggtta aaggtgttca   1200
cactataaaa gcatatacga tgtgatggta tttgatggag cgtatattgt atcaggtatt   1260
tccgttggat acgaattatt cgtacgaccc tcatagttta aactatcagt gtttgacagg   1320
atatattggc gggtaaacct aagagaaaag agcgtttatt agaataacgg atatttaaaa   1380
gggcgtgaaa aggtttatcc gttcgtccat ttgtatgtgc atgccaacca cagggttccc   1440
ctcgggatca aagtactttg atccaacccc tccgctgcta tagtcgcagtc ggcttctgac   1500
gttcagtgca gccgtcttct gaaaacgaca tgtcgcacaa gtcctaagtt acgcgacagg   1560
ctgccgccct gcccttttcc tggcgttttc ttgtcgcgtg ttttagtcgc ataaagtaga   1620
atacttgcga ctagaaccgg agacattacg ccatgaacaa gagcgccgcc gctggcctgc   1680
tgggctatgc ccgcgtcagc accgacgacc aggacttgac caaccaacgg gccgaactgc   1740
acgcggccgg ctgcaccaag ctgttttccg agaagatcac cggcaccagg cgcgaccgcc   1800
cggagctggc caggatgctt gaccacctac gccctggcga cgttgtgaca gtgaccaggc   1860
tagaccgcct ggcccgcagc acccgcgacc tactggacat tgccgagcgc atccaggagg   1920
ccggcgcggg cctgcgtagc ctggcagagc gtgggcgaca caccaccgg cgccggccc   1980
gcatggtgtt gaccgtgttc gccggcattg ccgagttcga gcgttcccta atcatcgacc   2040
gcacccggag cgggcgcgag gccgccaagg cccgaggcgt gaagtttggc ccccgcccta   2100
ccctcacccc ggcacagatc gcgcacgccc gcgagctgat cgaccaggaa ggccgcaccg   2160
tgaaaaggc ggctgcactg cttggcgtgc atcgctcgac cctgtaccgc gcacttgagc   2220
gcagcgagga agtgacgccc accgaggcca ggcggcgcgg tgccttccgt gaggacgcat   2280
tgaccgaggc cgacgccctg gcggccgcg agaatgaacg ccaagaggaa caagcatgaa   2340
accgcaccag gacggccagg acgaaccgtt tttcattacc gaagagatcg aggcggagat   2400
gatcgcgccc gggtacgtgt tcgagccgcc cgcgcacgtc tcaaccgtgc ggctgcatga   2460
aatcctggcc ggtttgtctg atgccaagct ggcggcctgg ccggccagct tggccgctga   2520
agaaaccgag cgccgccgtc taaaaaggtg atgtgtattt gagtaaaaca gcttgcgtca   2580
tgcggtcgct gcgtatatga tgcgatgagt aaataaacaa atacgcaagg gaacgcatg   2640
aaggttatcg ctgtacttaa ccagaaaggc gggtcaggca agacgaccat cgcaaaccat   2700
ctagcccgcg ccctgcaact cgccggggcc gatgttctgt tagtcgattc cgatcccag   2760
ggcagtgccc gcgattgggc ggcgtcgcgg gaagatcaac cgctaaccgt tgtcggcatc   2820
gaccgcccga cgattgaccg cgacgtgaag gccatcggcc ggcgcgactt cgtagtgatc   2880
gacggagcgc cccaggcggc ggacttggct gtgtccgcga tcaaggcagc cgacttcgtg   2940
ctgattccgg tgcagccaag cccttacgac atatgggcca ccgccgacct ggtggagctg   3000
gttaagcagc gcattgaggt cacgcgatgga aggctacaag cggcctttgt cgtgtcgcgg   3060
gcgatcaaag gcacgcgcat cggcggtgag gttgccgagg cgctggccgg gtacgagctg   3120
cccattcttg agtcccgtat cacgcagcgc gtgagctacc aggcactgc cgccgccggc   3180
acaaccgttc ttgaatcaga acccgagggc gacgctgccc gcgaggtcca ggcgctggcc   3240
gctgaaatta aatcaaaact catttgagtt aatgaggtaa agagaaaatg agcaaaagca   3300
caaacacgct aagtgccggc cgtccgagcg cacgcagcag caaggctgca acgttggcca   3360
gcctggcaga cacgccagcc atgaagcggg tcaacttcca gttgccggcg gaggatcaca   3420
ccaagctgaa gatgtacgcg gtacgccaag gcaagaccat taccgagctg ctatctgaat   3480
acatcgcgca gctaccagag taaatgagca aatgaataaa tgagtagatg aatttttagcg   3540
gctaaaggag gcggcatgga aaatcaagaa caaccaggca ccgacgccgt ggaatgcccc   3600
atgtgtggag gaacgggcgg ttggccaggc gtaagcggct gggttgtctg ccggccctgc   3660
aatggcactg gaaccccaa gcccgaggaa tcggcgtgac ggtcgcaaac catccggccc   3720
ggtacaaatc ggcgcggcgc tgggtgatga cctggtggag aagttgaagg ccgcgcaggc   3780
cgcccagcgg caacgcatcg aggcagaagc acgccccggt gaatcgtggc aagcggccgc   3840
tgatcgaatc cgcaaagaat cccggcaacc gccggcagcc ggtgcgccgt cgattaggaa   3900
gccgcccaag ggcgacgagc aaccagattt tttcgttccg atgctctatg acgtgggcac   3960
ccgcgatagt cgcagcatca tggacgtggc cgttttccgt ctgtcgaagc gtgaccgacg   4020
agctggcgag gtgatccgct acgagcttcc agacgggcac gtagaggttt ccgcaggccc   4080
ggccggcatg gccagtgtgt gggattacga cctggtactg atgccggttt cccatctaac   4140
```

```
cgaatccatg aaccgatacc gggaagggaa gggagacaag cccggccgcg tgttccgtcc  4200
acacgttgcg gacgtactca agttctgccg gcgagccgat ggcggaaagc agaaagacga  4260
cctggtagaa acctgcattc ggttaaacac cacgcacgtt gccatgcagc gtacgaagaa  4320
ggccaagaac ggccgcctgg tgacggtatc cgagggtgaa gccttgatta gccgctacaa  4380
gatcgtaaag agcgaaaccg ggcggccgga gtacatcgga atcgagctag ctgattggat  4440
gtaccgcgag atcacagaag gcaagaaccc ggacgtgctg acggttcacc ccgattactt  4500
tttgatcgat cccggcatcg gccgttttct ctaccgcctg gcacgccgcg ccgcaggcaa  4560
ggcagaagcc agatggttgt tcaagacgat ctacgaacgc agtggcagcg ccggagagtt  4620
caagaagttc tgtttcaccg tgcgcaagct gatcgggtca aatgacctgc cggagtacga  4680
tttgaaggag gaggcggggc aggctggccc gatcctagtc atgcgctacc gcaacctgat  4740
cgagggcgaa gcatccgccg gttcctaatg tacggagcag atgctagggc aaattgccct  4800
agcagggaaa aaggtcgaaa aaggcctctt tcctgtggat agcacgtaca ttgggaaccc  4860
aaagccgtac attgggaacc ggaacccgta cattgggaac ccaaagccgt acattgggaa  4920
ccggtcacac atgtaagtga ctgatataaa agagaaaaaa ggcgatttt ccgcctaaaa   4980
ctctttaaaa cttattaaaa ctcttaaaac ccgcctggcc tgtgcataac tgtctggcca  5040
gcgcacagcc gaagagctgc aaaaagcgcc taccccttcgg tcgctgcgct ccctacgccc  5100
cgccgcttcg cgtcggccta tcgcggccgc tggccgctca aaaatggctg gcctacggcc  5160
aggcaatcta ccagggcgcg gacaagccgc gccgtcgcca ctcgaccgcc ggcgcccaca  5220
tcaaggcacc ctgcctcgcg cgtttcggtg atgacggtga aaacctctga cacatgcagc  5280
tcccggaaac ggtcacagct tgtctgtaag cggatgccgg gagcagacaa gcccgtcagg  5340
gcgcgtcagc gggtgttggc gggtgtcggg gcgcagccat gacccagtca cgtagcgata  5400
gcggagtgta tactggctta actatgcggc atcagagcag attgtactga gagtgcacca  5460
tatgcggtgt gaaataccgc acagatgcgt aaggagaaaa taccgcatca ggcgctcttc  5520
cgcttcctcg ctcactgact cgctgcgctc ggtcgttcgg ctgcggcgag cggtatcagc  5580
tcactcaaag gcggtaatac ggttatccac agaatcaggg gataacgcag gaaagaacat  5640
gtgagcaaaa ggccagcaaa aggccaggaa ccgtaaaaag gccgcgttgc tggcgttttt  5700
ccataggctc cgcccccctg acgagcatca caaaaatcga cgctcaagtc agaggtggcg  5760
aaacccgaca ggactataaa gataccaggc gtttccccct ggaagctccc tcgtgcgctc  5820
tcctgttccg accctgccgc ttaccggata cctgtccgcc tttctccctt cgggaagcgt  5880
ggcgctttct catagctcac gctgtaggta tctcagttcg gtgtaggtcg ttcgctccaa  5940
gctgggctgt gtgcacgaac cccccgttca gcccgaccgc tgcgccttat ccggtaacta  6000
tcgtcttgag tccaacccgg taagacacga cttatcgcca ctggcagcag ccactggtaa  6060
caggattagc agagcgaggt atgtaggcgg tgctacagag ttcttgaagt ggtggcctaa  6120
ctacggctac actagaagga cagtatttgg tatctgcgct ctgctgaagc cagttacctt  6180
cggaaaaaga gttggtagct cttgatccgg caaacaaacc accgctggta gcggtggttt  6240
ttttgtttgc aagcagcaga ttacgcgcag aaaaaaagga tctcaagaag atcctttgat  6300
cttttctacg gggtctgacg ctcagtggaa cgaaaactca cgttaaggga ttttggtcat  6360
gcattctagg tactaaaaca attcatccag taaaatataa tattttattt tctcccaatc  6420
aggcttgatc cccagtaagt caaaaaatag ctcgacatac tgttcttccc cgatatcctt  6480
cctgatcgac cggacgcaga aggcaatgtc ataccacttg tccgccctgc cgcttctccc  6540
aagatcaata aagccactta ctttgccatc tttcacaaag atgttgctgt ctcccaggtc  6600
gccgtgggaa aagacaagtt cctcttcggg cttttccgtc tttaaaaaat catacagctc  6660
gcgcggatct ttaaatggag tgtcttcttc ccagttttca caatccacat cggccagatc  6720
gttattcagt aagtaatcca attcggctaa gcggctgtct aagctattcg tatagggaca  6780
atccgatatg tcgatggagt gaaagagcct gatgcactcc gcatacagct cgataatctt  6840
ttcagggctt tgttcatctt catactcttc cgagcaaagg acgccatcgg cctcactcat  6900
gagcagattg ctccagccat catgccgttc aaagtgacag acctttggaa caggcagctt  6960
tccttccagc catagcatca tgtccttttc ccgttccaca tcataggtgg tccctttata  7020
ccggctgtcc gtcatttta aatataggtt ttcattttct cccaccagct tatatacctt  7080
agcaggagac attccttccg tatctttac gcagcggtat ttttcgatca gtttttcaa   7140
ttccggtgat atttctcattt tagccattta ttatttcctt cctcttttct acagtattta  7200
aagataccc aagaagctaa ttataacaag acgaactcca attcactgtt ccttgcattc   7260
taaaaccta aataccagaa aacagctttt tcaaagttgt tttcaaagtt ggcgtataac  7320
atagtatcga cggagccgat tttgaaaccg cggtgatcac aggcagcaac gctctgtcat  7380
cgttacaatc aacatgctac cctccgcgag atcatccgga tttcaaaccc ggcagcttag  7440
ttgccgttct tccgaatagc atcggtaaca tgagcaaagt ctgccgcctt acaacggctc  7500
tcccgctgac gccgtcccgg actgatgggc tgcctgtatc gagtggtgat tttgtgccga  7560
gctgccggtc ggggagctgt tggctggctg gtggcaggat atattgtggt gtaaacaaat  7620
tgacgcttag acaacttaat aacacattgc ggacgttttt aatgtagagc tcaaagttta  7680
acgcgttagc agaaggcatg ttgttgtgac tccgagggt tgcctcaaac tctatccttat  7740
aaccggcgtg gaggcatgga ggcagggta ttttggtcat tttaatagat agtgaaaat   7800
gacgtggaat ttacttaaag acgaagtctt tgcgacaagg ggggcccac gccgaattta   7860
atattaccgg cgtggccccc ccttatcgcg agtgctttag cacgagcggt ccagatttaa  7920
agtagaaaat ttcccgccca ctagggttaa aggtgttcac actataaaag catatacgat  7980
gtgatggtat ttgatggagc gtatattgta tcaggtattt ccgttggata cgaattattc  8040
gtacgaccct cggtaccgat cggcgcgcca gatttgcctt ttcaatttca gaaagaatgc  8100
taacccacag atggttagag aggcttacgc agcaggtatc atcaagacga tctacccgag  8160
caataatctc caggaaatca aataccttcc caagaaggtt aaagatgcag tcaaaagatt  8220
caggactaac tgcatcaaga acacagagaa agatatattt ctcaagatca gaagtactat  8280
tccagtatgg acgattcaag gcttgcttca caaaccaagg caagtaatag agattggagt  8340
ctctaaaaag gtagttccca ctgaatcaaa ggccatggag tcaaagattc aaatagagga  8400
cctaacagaa ctcgccgtaa agactggcga acagttcata cagagtctct tacgactcaa  8460
tgacaagaag aaaatcttcg tcaacatggt ggagcacgac acacttgtct actccaaaaa  8520
tatcaaagat acagtctcag aagaccaaag actttcaac aaagggtaat  8580
atccggaaac ctcctcggat tccattgccc agctatctgt cactttattg tgaagatagt  8640
ggaaaggaa ggtggctcct acaaatgcca tcattgcgat aaaggaaagg ccatcgttga  8700
agatgcctct gccgacagtg gtcccaaaga tggacccca cccacgagga gcatcgtgga  8760
aaaagaagac gttccaacca cgtcttcaaa gcaagtggat tgatgtgata tctccactga  8820
cgtaagggat gacgcacaat cccactatcc ttcgcaagac ccttcctcta tataaggaag  8880
```

```
ttcatttcat ttggagagaa cacgggggac tcctgcagga tggaagacgc caaaaacata   8940
aagaaaggcc cggcgccatt ctatccgctg gaagatggaa ccgctggaga gcaactgcat   9000
aaggctatga agagatacgc cctggttcct ggaacaattg cttttacaga tgcacatatc   9060
gaggtggaca tcacttacgc tgagtacttc gaaatgtccg ttcggttggc agaagctatg   9120
aaacgatatg ggctgaatac aaatcacaga atcgtcgtat gcagtgaaaa ctctcttcaa   9180
ttctttatgc cggtgttggg cgcgttattt atcggagttg cagttgcgcc cgcgaacgac   9240
atttataatg aacgtgaatt gctcaacagt atgggcattt cgcagcctac cgtggtgttc   9300
gtttccaaaa aggggttgca aaaaattttg aacgtgcaaa aaaagctccc aatcatccaa   9360
aaaattatta tcatggattc taaaacggat taccagggat ttcagtcgat gtacacgttc   9420
gtcacatctc atctacctcc cggtttttaat gaatacgatt ttgtgccaga gtccttcgat   9480
agggacaaga caattgcact gatcatgaac tcctctggat ctactggtct gcctaaaggt   9540
gtcgctctgc ctcatagaac tgcctgcgtg agattctcgc atgccagaga tcctattttt   9600
ggcaatcaaa tcattccgga tactgcgatt ttaagtgttg ttccattcca tcacggtttt   9660
ggaatgttta ctacactcgg atatttgata tgtggatttc gagtcgtctt aatgtataga   9720
tttgaagaag agctgtttct gaggagcctt caggattaca agattcaaag tgcgctgctg   9780
gtgccaaccc tattctcctt cttcgccaaa agcactctga ttgacaaata cgatttatct   9840
aatttacacg aaattgcttc tggtggcgct ccctctcta aggaagtcgg ggaagcggtt   9900
gccaagaggt tccatctgcc aggtatcagg caaggatatg ggctcactga gactacatca   9960
gctattctga ttacacccga gggggatgat aaaccgggcg cggtcggtaa agttgttcca  10020
ttttttgaag cgaaggttgt ggatctggat accgggaaaa cgctgggcgt taatcaaaga  10080
ggcgaactgt gtgtgagagg tcctatgatt atgtccggtt atgtaaacaa tccggaagcg  10140
accaacgcct tgattgacaa ggatggatgg ctacattctg gagacatagc ttactgggac  10200
gaagacgaac acttcttcat cgttgaccgc ctgaagtctc tgattaagta caaaggctat  10260
caggtggctc ccgctgaatt ggaatccatc ttgctccaac accccaacat cttcgacgct  10320
ggtgtcgcag gtcttcccga cgatgacgcc ggtgaacttc ccgccgccgt tgttgttttg  10380
gagcacggaa agacgatgac ggaaaaagag atcgtggatt acgtcgccag tcaagtaaca  10440
accgcgaaaa agttgcgcgg aggagttgtg tttgtggacg aagtaccgaa aggtcttacc  10500
ggaaaactcg acgcaagaaa aatcagagag atcctcataa aggccaagaa gggcggaaag  10560
atcgccgtgt gacgtcgacg atatgaagat gaagatgaaa tatttggtgt gtcaaataaa  10620
aagcttgtgt gcttaagttt gtgttttttt cttggcttgt tgtgttatga atttgtggct  10680
ttttctaata ttaaatgaat gtaagatcac attataatga ataaacaaat gtttctataa  10740
tccattgtga atgttttgtt ggatctcttc tgcagcatat aactactgta tgtgctatgg  10800
tatgactat ggaatatgat taaagataag ccagagctct ggtgacggac ccatggcttc  10860
gttgaacaac ggaaactcga cttgccttcc gcacaataca tcatttcttc ttagctttt   10920
ttcttcttct tcgttcatac agttttttt tgtttatcag cttacatttt cttgaaccgt  10980
agctttcgtt ttcttctttt taactttcca ttcggagttt ttgtatcttg tttcatagtt  11040
tgtcccagga ttagaatgat taggcatcga accttcaaga atttgattga ataaaacatc  11100
ttcattctta agatatgaag ataatcttca aaaggccct gggaatctga aagaagagaa  11160
gcaggcccat ttatatggga aagaacaata gtatttctta tataggccca tttaagttga  11220
aaacaatctt caaaagtccc acatcgctta gataagaaaa cgaagctgag tttatataca  11280
gctagagtcg aagtagtgat tgttggtagt agcgactcca tggttttaga gctagaaata  11340
gcaagttaaa ataaggctag tccgttatca acttgaaaaa gtggcaccga gtcggtgctt  11400
ttttcccggg ggcgcgccaa tatcgagctc tcccgctggc agacatactg tcccacaaat  11460
gaagatggaa tctgtaaaag aaaacgcgtg aaataatgcg tctgacaaag gttaggtcgg  11520
ctgccttttaa tcaataccaa agtggtccct accacgatgg aaaaactgtg cagtcggttt  11580
ggcttttttct gacgaacaaa taagattcgt ggccgacagg tgggggtcca ccatgtgaag  11640
gcatcttcag actccaataa tggagcaatg acgtaagggc ttacgaaata agtaagggta  11700
gtttgggaaa tgtccactca cccgtcagtc tataaatact tagcccctcc ctcattgtta  11760
agggagcaaa atctcagaga gatagtccta gagagagaaa gagagcaagt agcctagaag  11820
tagtcaaggc ggcgaagtat tcaggcacgt ggccaggaag aagaaaagcc aagacgacga  11880
aaacaggtaa gagctaagct tatggagagt ggttccaaca gcacttcttg tccaatggct  11940
tttgccgggg ataatagtga tggtccgatg tgtcctatga tgatgatgat gccgcccatc  12000
atgcacatcac atcaacatca tggtcatgat catcaacatc aacaacaaga acatgatggt  12060
tatgcatatc agtcacacca ccaacaaagt agttcccttt ttcttcaatc actagctcct  12120
ccccaaggaa ctaagaacaa agttgcttct tcttcttctc cttcctcttg tgctcctgcc  12180
tattctctaa tggagatcca tcataacgaa atcgttgcag gaggaatcaa cccttgctcc  12240
tcttcctctt cttcagcctc tgtcaaggcc aagatcatgg ctcatcctca ctaccaccgc  12300
ctcttggccg cttatgtcaa ttgtcagaag gttggagcac caccggaggt tgtggcgagg  12360
ctagaggagg catgctcgtc tgccgcagcc gctgccgcat ctatgggacc aacaggatgt  12420
ctaggtgaag ataccagggct tgatcaattc atggaagctt actgtgaaat gctcgttaag  12480
tatgagcaag agctctccaa acctttcaag gaagctatgg tcttccttca acgtgtcgag  12540
tgtcaattca aatccctctc tctatcctca ccttcctctt tctccggtta tggagagaca  12600
gcaattgata ggaacaataa tgggtcatcc gaggaagaag tcgatatgaa caatgaattt  12660
gtagatccac aagctgagga tagagagctt aaaggacagc tcttcgcaa gtacagtggt  12720
tacttaggga gcctcaagca agagttcatg aagaagagga agaaggaaa gctccctaaa  12780
gaagctcgtc aacaactgct tgattggtgg agccgtcact acaaatggcc ttaccctcg   12840
gagcaacaaa agctcgccct tgcggaatca acggggctgg accagaaaca gataaacaat  12900
tggttcataa accagaggaa acggcattgg aagcgtcgg aggacatgca gtttgtagta  12960
atggacgcaa cacatcctca ccattacttc atggataatg tcttgggcaa tccttcccca  13020
atggatcaca tctcctccac catgctttga ctcgagtttc tccataataa tgtgtgagta  13080
gttcccagat aagggaatta gggttcctat agggtttcgc tcatgtgttg agcatataag  13140
aaaccccttag tatgtatttg tatttgtaaa atacttctat caataaaatt tctaattcct  13200
aaaaccaaaa tccagtacta aaatccgat cccccgaatt aagtgtttga tcgcggcgg   13260
taccgagtgt acttcaagtc agtgggaaat caataaaatg attatttat gaatatattt  13320
cattgtgcaa gtagatagaa attacatatg ttacataaca cacgaaataa acaaaaaaag  13380
acaatccaaa aacaaacacc ccaaaaaaaa taatcacttt agataaactc gtatgaggag  13440
aggcacgttc agtgactcga cgattcccga gcaaaaaaag tctccccgtc acacatgtag  13500
tgggtgacgc aattatcttt aaagtaatcc ttctgttgac ttgtcattga taacatccag  13560
tcttcgtcag gattgcaaag aattatagaa gggatccca                        13599
```

| SEQ ID NO: 34 | moltype = DNA length = 13546 |
|---|---|
| FEATURE | Location/Qualifiers |
| source | 1..13546 |
| | mol_type = other DNA |
| | organism = synthetic construct |

SEQUENCE: 34

```
tttccgtctg tcgaagcgtg accgacgagc tggcgaggtg atccgctacg agcttccaga   60
cgggcacgta gaggtttccg cagggccggc cggcatggcc agtgtgtggg attacgacct  120
ggtactgatg gcggtttccc atctaaccga atccatgaac cgataccggg aaggaaggg   180
agacaagccc ggccgcgtgt tccgtccaca cgttgcggac gtactcaagt tctgccggcg   240
agccgatggc ggaaagcaga aagacgacct ggtagaaacc tgcattcggt taaacaccac   300
gcacgttgcc atgcagcgta cgaagaaggc caagaacggc cgcctggtga cggtatccga   360
gggtgaagcc ttgattagcc gctacaagat cgtaaagagc gaaaccggtc ggccggagta   420
catcgagatc gagctagctg attggatgta ccgcgagatc acagaaggca agaacccgga   480
cgtgctgacg gttcaccccg attacttttt gatcgatccc ggcatcggcc gttttctcta   540
ccgcctggca cgccgcgccg caggcaaggc agaagccaga tggttgttca agacgatcta   600
cgaaccgcag ttggcagccgcg gagagttcaa gaagttctgt ttcaccgtgc gcaagctgat   660
cgggtcaaat gacctgccgg agtacgattt gaaggaggag gcggggcagg ctggcccgat   720
cctagtcatg cgctaccgca acctgatcga gggcgaagca tccgccggtt cctaatgtac   780
ggagcagatg ctagggcaaa ttgccctagc aggggaaaaa ggtcgaaaag gcctcttttcc   840
tgtggatagc acgtacattg ggaacccaaa gccgtacatt gggaaccgga acccgtacat   900
tgggaaccca aagccgtaca ttgggaaccg gtcacacatg taagtgactg atataaaaga   960
gaaaaaggc gattttccg cctaaaactc tttaaaactt attaaaactc ttaaaacccg  1020
cctggcctgt gcataactgt ctggccagcg cacagccgaa gagctgcaaa aagcgcctac  1080
ccttcggtcg ctgcgctccc tacgccccgc cgcttcggtc cggcctatcg cggccgctgg  1140
ccgctcaaaa atggctggcc tacgccagg caatctacca gggcgcggac aagccgcgcg  1200
gtcgccactc gaccgccggc gcccacatca aggcaccctg cctcgcgcgt ttcggtgatg  1260
acggtgaaaa cctctgacac atgcagctcc cggaaacggt cacagcttgt ctgtaagcgg  1320
atgccgggag cagacaagcc cgtcagggcg cgtcagcggg tgttggcggg tgtcgggggg  1380
cagccatgac ccagtcacgt agcgatagcg gagtgtatac tggcttaact atgcggcatc  1440
agagcagatt gtactgagag tgcaccatat gcggtgtgaa ataccgcaca gatgcgtaag  1500
gagaaaatac cgcatcaggc gctcttccgc ttcctcgctc actgactcgc tgcgctcggt  1560
cgttcggctg cggcgagcgg tatcagctca ctcaaaggcg gtaatacggt tatccacaga  1620
atcagggat aacgcaggaa agaacatgtg agcaaaaggc cagcaaaagg ccaggaaccg  1680
taaaaaggcc gcgttgctgg cgttttttcca taggctccgc cccctgacg agcatcacaa  1740
aaatcgacgc tcaagtcaga ggtggcgaaa cccgacagga ctataaagat accaggcgtt  1800
tccccctgga agctccctcg tgcgctctcc tgttccgacc ctgccgctta ccggatacct  1860
gtccgccttt ctcccttcgg gaagcgtggc gctttctcat agctcacgct gtaggtatct  1920
cagttcggtg taggtcgttc gctccaagct gggctgtgtg cacgaacccc ccgttcagcc  1980
cgaccgctgc gccttatccg gtaactatcg tcttgagtcc aacccggtaa gacacgactt  2040
atcgccactg gcagcagcca ctggtaacag gattagcaga gcgaggtatg taggcggtgc  2100
tacagagttc ttgaagtggt ggcctaacta cggctacact agaaggacag tatttggtat  2160
ctgcgctctg ctgaagccag ttaccttcgg aaaaagagtt ggtagctctt gatccggcaa  2220
acaaaccacc gctggtagcg gtggtttttt tgtttgcaag cagcagatta cgcgcagaaa  2280
aaaaggatct caagaagatc ctttgatctt ttctacgggg tctgacgctc agtggaacga  2340
aaactcacgt taagggattt tggtcatgca ttctaggtac taaaacaatt catccagtaa  2400
aatataatat tttatttct cccaatcagg cttgatcccc agtaagtcaa aaaatagctc  2460
gacatactgt tcttccccga tatcctccct gatcgaccgg acgcagaagg caatgtcata  2520
ccacttgtcc gccctgccgc ttctcccaag atcaataaag ccacttactt tgccatcttt  2580
cacaaagatg ttgctgtctc ccaggtcgcc gtgggaaaa acaagttcct cttcgggtct  2640
ttccgtcttt aaaaaatcat acagctcgcg cggatcttta aatggagtgt cttcttccca  2700
gtttttcgcaa tccacatcgg ccagatcgtt attcagtaag taatccaatt cggctaagcg  2760
gctgtctaag ctattcgtat agggacaatc cgatatgtcg atggagtgaa agagcctgat  2820
gcactccgca tacagctcga taatcttttc agggcttttgt tcatcttcat actcttccga  2880
gcaaaggacg ccatcggcct cactcatgag cagattgctc cagccatcat gccgttcaaa  2940
gtgcaggacc tttggaacag gcagctttcc ttccagccat agcatcatgt ccttttcccg  3000
ttccacatca taggtggtcc ctttataccg gctgtccgtc atttttaaat ataggttttc  3060
attttctccc accagcttat taccttagc aggagacatt ccttccgtat ctttacgcg  3120
gcggtatttt tcgatcagtt ttttcaattc cggtgatatt ctcattttag ccatttatta  3180
tttccttcct ctttttctaca gtatttaaag atacccaag aagtaattaa taacaagacg  3240
aactccaatt cactgttcct tgcattctaa aaccttaaat accagaaaac agcttttcta  3300
aagttgtttt caaagttggc gtataacata gtatcgacgg agccgatttt gaaaccgcgg  3360
tgatcacagg cagcaacgct ctgtcatcgt tacaatcaac atgtacccct ccgcgagatc  3420
atccgtgttt caaacccggc agcttagttg ccgttcttcc gaatagcatc ggtaacatga  3480
gcaaagtctg ccgccttaca acggctctcc cgctgacgcc gtcccggact gatgggctgc  3540
ctgtatcgag tggtgatttt gtgccagctg ccggtcgggg agctgttgg ctggctggtg  3600
gcaggatata ttgtggtgta acaaattga cgcttagaca acttaatac acattgcgga  3660
cgttttaat gtagagctca agtttaacg cgttagcaga aggcatgttg ttgtgactcc  3720
gaggggttgc ctcaaactct atcttataac cggcgtggag gcatggaggc aggggtattt  3780
tggtcatttt aatagatagt ggaaaatgac gtggaattta cttaaagacg aagtctttgc  3840
gacaagggg ggcccacgcc gaatttaata ttaccggcgt ggccccccct tatcgcgagt  3900
gctttagcac gagcggtcca gatttaaagt agaaaatttc ccgcccacta gggttaaagg  3960
tgttcacact ataaaagcat atcgatgtg atggtattga tattgtatca  4020
ggtatttccg ttggatacga attattcgta cgaccctcgg taccgatcgg cgcgcctggc  4080
agacatactg tcccacaaat gaagatggaa tctgtaaaag aaaacgcgtg aaataatgcg  4140
tctgacaaag gttaggtcgg ctgcctttaa tcaataccaa gtggtccct accacgatgg  4200
aaaaactgtg cagtcggttt ggcttttctt gacgaacaaa taagattcgt ggccgacagg  4260
tgggggtcca ccatgtgaag gcatcttcag actccaataa tggagcaatg acgtaagggc  4320
```

```
ttacgaaata agtaagggta gtttgggaaa tgtccactca cccgtcagtc tataaatact   4380
tagcccctcc ctcattgtta agggagcaaa atctcagaga gatagtccta gagagagaaa   4440
gagagcaagt agcctagaag tagtcaaggc ggcgaagtat tcaggcacgt ggccaggaag   4500
aagaaaagcc aagacgacga aaacaggtaa gagctaagct tcctgcacca tggaagacgc   4560
caaaaacata aagaaaggcc cggcgccatt ctatccgctg gaagatggaa ccgctggaga   4620
gcaactgcat aaggctatga agagatacgc cctggttcct ggaacaattg cttttacaga   4680
tgcacatatc gaggtggaca tcacttacgc tgagtacttc gaaatgtccg ttcggttggc   4740
agaagctatg aaacgatatg ggctgaatac aaatcacaga atcgtcgtat gcagtgaaaa   4800
ctctcttcaa ttctttatgc cggtgttggg cgcgttattt atcggagttg cagttgcgcc   4860
cgcgaacgac atttataatg aacgtgaatt gctcaacagt atgggcattt gtcagcctac   4920
cgtggtgttc gtttccaaaa aggggttgca aaaattttg aacgtgcaaa aaagctccc    4980
aatcatccaa aaaattatta tcatggattc taaaacggat taccagggat ttcagtcgat   5040
gtacacgttc gtcacatctc atctacctcc cggttttaat gaatacgatt ttgtgccaga   5100
gtccttcgat agggacaaga caattgcact gatcatgaac tcctctgagt ctactggtct   5160
gcctaaaggt gtcgctctgc ctcatagaac tgcctgcgtg agattctcgc atgccagaga   5220
tcctattttt ggcaatcaaa tcattccgga tactgcgatt ttaagtgttg ttccattcca   5280
tcacggtttt ggaatgttta ctacactcgg atatttgata tgtggatttc gagtcgtctt   5340
aatgtataga tttgaagaag agctgtttct gaggagcctt caggattaca agattcaaag   5400
tgcgctgctg gtgccaaccc tattctcctt cttcgccaaa agcactctga ttgacaaata   5460
cgatttatct aatttacacg aaattgcttc tggtggcgct cccctctcta aggaagtcgg   5520
ggaagcggtt gccaagaggt tccatctgcc aggtatcagg caaggatatg ggctcactga   5580
gactacatca gctattctga ttacacccga ggggatgat aaaccgggcg cggtcggtaa   5640
agttgttcca ttttttgaag cgaaggttgt ggatctggat accggaaaa cgctgggcgt   5700
taatcaaaga ggcgaactgt gtgtgagagg tcctatgatt atgtccggtt atgtaaacaa   5760
tccggaagcg accaacgcct tgattgacaa ggatggatgg ctacattctg gagacatagc   5820
ttactggac gaagacgaac acttcttcat cgttgaccgc ctgaagtctc tgattaagta    5880
caaaggctat caggtggctc ccgctgaatt ggaatccatc ttgctccaac accccaacat   5940
cttcgacgct ggtgtcgcag gtcttcccga cgatgacgcc ggtgaacttc ccgccgccgt   6000
tgttgttttg gagcacggaa agacgatgac ggaaaaagag atcgtggatt acgtcgccag   6060
tcaagtaaca accgcgaaaa agttgcgcgg aggagttgtg tttgtggacg aagtaccgaa   6120
aggtcttacc ggaaaactcg acgcaagaaa aatcagagag atcctcataa aggccaagaa   6180
gggcggaaag atcgccgtgt aactcgagat atgaagatga agatgaaata tttggtgtgt   6240
caaataaaaa gcttgtgtgc ttaagtttgt gttttttct tggcttgttg tgttatgaat   6300
ttgtggcttt ttctaatatt aaatgaatgt aagatcacat tataatgaat aaacaaatgt   6360
ttctataatc cattgtgaat gttttgttgg atctcttctg cagcatataa ctactgtatg   6420
tgctatggta tggactatgg aatatgatta agataagga gctccggtga cggacccatg   6480
gcttcgttga acaacggaaa ctcgacttgc cttccgcaca atacatcatt tcttcttagc   6540
tttttttctt cttcttcgtt catacagttt ttttttgttt atcagcttac attttcttga   6600
accgtagctt tcgttttctt cttttttaact ttccattcgg agttttgta tcttgtttca   6660
tagtttgtcc caggattaga atgattaggc atcgaacctt caagaatttg attgaataaa   6720
acatcttcat tcttaagata tgaagataat cttcaaaagg ccctgggaa tctgaaagaa   6780
gagaagcagg cccatttata tgggaaagaa caatagtatt tcttatatag gcccatttaa   6840
gttgaataca atcttcaaaa gtcccacatc gcttagataa gaaaacgaag ctgagtttat   6900
atacagctag agtcgaagta gtgattgttg gtagtagcga ctccatggtt ttagagctag   6960
aaatagcaag ttaaaataag gctagtccgt tatcaacttg aaaaagtggc accgagtcgg   7020
tgcttttttt cccggcgtaa tatggcgcgc cagatttgcc ttttcaattt cagaaagaat   7080
gctaacccac agatggttag agaggcttac gcagcaggta tcatcaagac gatctacccg   7140
agcaataatc tccaggaaat caaataccgt cccaagaagg ttaaagatgc agtcaaaaga   7200
ttcaggacta actgcatcaa gaacacagag aaagatatat ttctcaagat cagaagtact   7260
attccagtat ggacgattca aggcttgctt cacaaaccaa ggcaagtaat agagattgga   7320
gtctctaaaa aggtagttcc cactgaatca aaggccatgg agtcaaagat tcaaatagag   7380
gacctaacag aactcgccgt aaagactggc gaacagttca tacagagtct cttacgactc   7440
aatgacaaga agaaaatctt cgtcaacatg gtggagcacg acacacttgt ctactccaaa   7500
aatatcaaag atacagtctc agaagaccaa agggcaattg acttttca acaaagggta   7560
atatccggaa acctcctcgg attccattgc ccagctatct gtcactttat tgtgaagata   7620
gtggaaaagg aaggtggctc tacaaatgc catcattgcg ataaaggaaa ggccatcgtt   7680
gaagatgcct ctgccgacag tggtcccaaa gatggacccc cacccacgag gagcatcgtg   7740
gaaaaagaag acgttccaac cacgtcttca agcaagtgg attgatgtga tatctccact   7800
gacgtaaggg atgacgcaca cccactat ccttcgcaag acccttcctc tatataagga   7860
agttcatttc atttggagag aacacggggg actcctgcag gatggatctg cgtctaatttt   7920
tcggtccaac ttgcacagga aagacgtcga ccgcgatacg tcttgcccag cagactggcc   7980
ttccagtcct ttcgctcgat cgggtccaat gctgtcctca actgtcaacc ggaagcggac   8040
gaccaacagt ggaagaactg aaaggaacga cccgtctata ccttgaagat cggcctctgg   8100
tgaagggtat catcgcagcc aagcaagctc acgaaaggct gatcggggaa gtgtacaatt   8160
atgaggccca cggcgggctt attcttgagg aggatctat ctcgttgctc aggtgcatgg   8220
cgcaaagcag ttattggagt accgatttc gttggcatat tattgccac aagttagcag   8280
acgaggagac attcatgaac gcggccaagg ccagagttag gcagatgttg cgccctgctg   8340
taggcccatc tattattcaa gagttggttc atctttggaa tgagcctcgg ctgaggccca   8400
tactgaaaga gatcgacgta tatgatatg ccatgttatt tgctagccag aaccagatca   8460
cacccgatat gctattgcag cttgacccag atattggagg tgagttgatt catggaatcg   8520
ctcaggagta tctcatccat gcgcgccggc aggagcagga attccctcca gtgagcgtgg   8580
tcgctttcga aggattcgaa ggtccaccgt tcggaatgtg ctagctcgag ccctagactt   8640
gtccatcttc tggattggcc aagttaatta atgtatgaaa taaaggatg cacacatagt   8700
gacatgctaa tcactataat gtgggcatca aagttgtgta ttatgtgtaa ttactaatta   8760
tctgaataag agaaagagat catccatatt tcttatccta aatgaatgtc acgtgtcttt   8820
ataattcttt gatgaaccag atgcatttta ttaaccaatt ccatatacat ataaatatta   8880
atcatatata attaatatca attgggttag caaaacaaat ctagtctagg tgtgttttgc   8940
taattattgg gggatagtgc aaaaagaaat ctacgttctc aataattcag atagaaaact   9000
taataaagtg agataattta catagattgc ttttatcctt tgatatatgt gaaaccatgc   9060
```

```
atgatataag gaaaatagat agagaaataa ttttttacat cgttgaatat gtaaacaatt  9120
taattcaaga agctaggaat ataaatattg aggagtttat gattagagct ctcccgcgc   9180
gccgatatcg agctcagtgt ttgatcgccg gcggtaccga gtgtacttca agtcagtggg  9240
aaatcaataa aatgattatt ttatgaatat atttcattgt gcaagtagat agaaattaca  9300
tatgttacat aacacacgaa ataaacaaaa aaagacaatc caaaaacaaa caccccaaaa  9360
aaaataatca ctttagataa actcgtatga ggagaggcac gttcagtgac tcgacgattc  9420
ccgagcaaaa aaagtctccc cgtcacacat gtagtgggtg acgcaattat ctttaaagta  9480
atccttctgt tgacttgtca ttgataacat ccagtcttcg tcaggattgc aaagaattat  9540
agaagggatc ccacctttta ttttcttctt ttttccatat ttaggggttga cagtgaaatc  9600
agactggcaa cctattaatt gcttccacaa tgggacgaac ttgaaggggga tgtcgtcgat  9660
gatattatag gtggcgtgtt catcgtagtt ggtgaaatcg atggtaccgt tccaatagtt  9720
gtgtcgtccg agacttctag cccaggtggt ctttccggta cgagttggtc cgcagatgta  9780
gaggctgggg tgtcggattc cattccttcc attgtccttg ttaaatcggc catccattca  9840
aggtcagatt gagcttgttg gtatgagaca ggatgtatgt aagtataagc gtctatgctt  9900
acatggtata gatgggtttc cctccaggag tgtagatctt cgtggcagcg aagatctgat  9960
tctgtgaagg gcgacacata cggttcaggt tgtggaggga ataatttgtt ggctgaatat 10020
tccagccatt gaagctttgt tgcccattca tgagggaatt cttccttgat catgtcaaga 10080
tattcctcct tagacgttgc agtctggata atagttctcc atcgtgcgtc agatttgcga 10140
ggagaaacct tatgatctcg gaaatctcct ctggtttttaa tatctccgtc ctttgatatg 10200
taatcaagga cttgtttaga gtttctagct ggctggatat tagggtgatt tccttcaaaa 10260
tcgaaaaaag aaggatccct aatacaaggt ttttatcaa gctggagaag agcatgatag 10320
tgggtagtgc catcttgatg aagctcagaa gcaacaccaa ggaagaaaat aagaaaaggt 10380
gtgagtttct cccagagaaa ctggaataaa tcatctcttt gagatgagca cttgggatag 10440
gtaaggaaaa catatttaga ttggagtctg aagttcttac tagcagaagg catgttgttg 10500
tgactccgag gggttgcctc aaactctatc ttataaccgg cgtggaggca tggaggcagg 10560
ggtattttgg tcattttaat agatagtgga aaatgacgtg gaatttactt aaagacgaag 10620
tctttgcgac aaggggggggc ccacgccgaa tttaatatta ccggcgtggc cccccccttat 10680
cgcgagtgct ttagcacgag cggtccagat ttaaagtaga aaatttcccg cccactaggg 10740
ttaaaggtgt tcacactata aaagcatata cgatgtgatg gtatttgatg gagcgtatat 10800
tgtatcaggt atttccgttg gatacgaatt attcgtacga ccctcatagt ttaaactatc 10860
agtgtttgac aggatatatt ggcgggtaaa cctaagagaa aagagcgttt attagaataa 10920
cggatattta aaagggcgtg aaaaggttta tccgttcgtc catttgtatg tgcatgccaa 10980
ccacagggtt cccctcggga tcaaagtact ttgatccaac ccctccgctg ctatagtgca 11040
gtcggcttct gacgttcagt gcagccgtc tctgaaaacg acatgtcgca caagtcctaa 11100
gttacgcgac aggctgccgc cctgcccttt tcctggcgtt ttcttgtcgc gtgttttagt 11160
cgcataaagt agaatacttg cgactagaac cggagacatt acgccatgaa caagagcgcc 11220
gccgctggcc tgctgggcta tgcccgcgtc agcaccgacg accaggactt gaccaaccaa 11280
cgggccgaac tgcacgcggc cggctgcacc aagctgtttt ccgagaagat caccggcacc 11340
aggcgcgacc gcccggagct ggccaggatg cttgaccacc tacgccctgg cgacgttgtg 11400
acagttgacca ggctagaccg cctggcccgc agcaccgcg acctactgga cattgccgag 11460
cgcatccagg aggccggcgc gggcctgcgt agcctggcag agccgtgggc cgacaccacc 11520
acgccggccg gccgcatggt gttgaccgtg ttcgccggca ttgccgagtt cgagcgttcc 11580
ctaatcatcg accgcacccg gagcggggcg gaggccgcaa aggcccggag cgtgaagttt 11640
ggccccccgcc ctaccctcac cccggcacag atcgcgcacg cccgcgagct gatcgaccag 11700
gaaggccgca ccgtgaaaga gcggctgca ctgcttggcg tgcatcgctc gaccctgtac 11760
cgcgcacttg agcgcagcga ggaagtgacg cccaccgagg ccaggcggcg cggtgccttc 11820
cgtgaggacg cattgaccga ggccgacgc ctggcgcca ccgagaatga acgccaagag 11880
gaacaagcat gaaaccgcac caggacggcc aggacgaacc gttttttcatt accgaagaga 11940
tcgaggcgga gatgatcgcg gccgggtacg tgttcgagcc gcccgcgcac ggctcaaccg 12000
tgcggctgca tgaaatcctg gccggtttgt ctgatgccaa gctggcggcc tggccggcca 12060
gcttggccgc tgaagaaacc gagcgccgcc gtctaaaaag gtgatgtgta tttgagtaaa 12120
acagcttgcg tcatgcggtc gctgcgtata tgatgcgatg agtaaataaa caaatacgaa 12180
aggggaacgc atgaaggtta tcgctgtact taaccagaaa ggcgggtcag gcaagacgac 12240
catcgcaacc catctagccc gcgccctgca actcgccggg gccgatgttc tgttagtcga 12300
ttccgatccc cagggcagtg cccgcgattg ggcgccgtcg cgggaagatc aaccgctaac 12360
cgttgtcggc atcgaccgcc cgacgattga ccgcgacgtg aaggccatcg gccggcgcga 12420
cttcgtagtg atcgacggag cgccccaggc ggcggacttg gctgtgtccg cgatcaaggc 12480
agccgacttc gtgctgattc cggtgcagcc aagcccttac gacatatggg ccaccgccga 12540
cctggtggag ctggttaagc agcgcattga ggtcacggat ggaaggctac aagcggcctt 12600
tgtcgtgtcg cgggcgatca aaggcacgcg catcggcggt gaggttgccg aggcgctgc 12660
cgggtacgag ctgcccattc ttgagtcccg tatcacgcag cgcgtgagct acccaggcac 12720
tgccgccgcc ggcacaaccg ttcttgaatc agaacccgag ggcgacgctg cccgcgaggt 12780
ccaggcgctg gccgctgaaa ttaaatcaaa actcatttga gttaatgagg taaagagaaa 12840
atgagcaaaa gcacaaacac gctaagtgcc ggccgtccga gcgcacgcag cagcaaggct 12900
gcaacgttgg ccagcctggc agacacgcca gccatgaagc gggtcaactt tcagttgccg 12960
gcggaggatc acaccaagct gaagatgtac gcggtacgcc aaggcaagac cattaccgag 13020
ctgctatctg aatacatcgc gcagctacca gagtaaatga gcaaatgaat aaatgagtag 13080
atgaattta gcggctaaag gaggcggcat ggaaaatcaa gaacaaccag gcaccgacgc 13140
cgtggaatgc cccatgtgtg gaggaacggg cggttggcca gcgtaagcg gctgggttg 13200
ctgccggccc tgcaatggca ctggaacccc caagcccgag gaatcggcgt gacggtcgca 13260
aaccatccgg cccggtacaa atcgcgcgg cgctgggtga tgacctggtg gagaagttga 13320
aggccgcgca ggccgcccag cggcaacgca tcgaggcaga agcacgcccc ggtgaatcgt 13380
ggcaagcggc cgctgatcga atccgcaaag aatcccggca accgccggca ccggtgcgc 13440
cgtcgattag gaagccgccc aagggcgacg agcaaccaga tttttttcgtt ccgatgctct 13500
atgacgtggg cacccgcgat agtcgcagca tcatggacgt ggccgt          13546

SEQ ID NO: 35        moltype = DNA  length = 13472
FEATURE              Location/Qualifiers
source               1..13472
``` mol_type = other DNA
organism = synthetic construct

SEQUENCE: 35

```
ttgcgtcatg cggtcgctgc gtatatgatg cgatgagtaa ataaacaaat acgcaagggg   60
aacgcatgaa ggttatcgct gtacttaacc agaaaggcag gtcaggcaag acgaccatcg  120
caacccatct agcccgcgcc ctgcaactcg ccggggccga tgttctgtta gtcgattccg  180
atccccaggg cagtgcccgc gattgggcgg ccgtgcggga agatcaaccg ctaaccgttg  240
tcggcatcga ccgcccgacg attgaccgcg acgtgaaggc catcggccgg cgcgacttcg  300
tagtgatcga cggagcgccc caggcggcgg acttggctgt gtccgcgatc aaggcagccg  360
acttcgtgct gattccggtg cagccaagcc cttacgacat atgggccacc gccgacctgg  420
tggagctggt taagcagcgc attgaggtca cggatggaag gctacaagcg gcctttgtcg  480
tgtcgcgggc gatcaaaggc acgcgcatcg gcggtgaggt tgccgaggcg ctggccgggt  540
acgagctgcc cattcttgag tcccgtatca cgcagcgcgt gagctaccca ggcactgccg  600
ccgccggcac aaccgttctt gaatcagaac ccgagggcga cgtccccgc gaggtccaag  660
cgctggccgc tgaaattaaa tcaaaactca tttgagttaa tgaggtaaag agaaaatgag  720
caaaagcaca aacacgctaa gtgccggccg tccgagcgca cgcagcagca aggctgcaac  780
gttggccagc ctggcagaca cgccagccat gaagcgggtc aactttcagt tgccggcgga  840
ggatcacacc aagctgaaga tgtacgcggt acgccaaggc aagaccatta ccgagctgct  900
atctgaatac atcgcgcagc taccagagta aatgagcaaa tgaataaatg agtagatgaa  960
ttttagcggc taaaggaggc ggcatggaaa atcaagaaca accaggcacc gacgccgtgg 1020
aatgccccat gtgtggagga acgggcggtt ggccaggcgt aagcggctgg gttgtctgcc 1080
ggccctgcaa tggcactgga accccaagc ccgaggaatc ggcgtgacgg tcgcaaacca 1140
tccggcccgg tacaaatcgg cgcggcgctg ggtgatgacc tggtggagaa gttgaaggcc 1200
gcgcaggccg cccagcggca acgcatcgag gcagaagcac gccccggtga atcgtggcaa 1260
gcggccgctg atcgaatccg caaagaatcc cggcaaccgc cggcagccgg tgcgccgtcg 1320
attaggaagc cgcccaaggg cgacgagcaa ccagattttt tcgttccgat gctctatgac 1380
gtgggcaccc gcgatagtcg cagcatcatg gacgtggccg ttttccgtct gtcgaagcgt 1440
gaccgacgag ctggcgaggt gatccgctac gagcttccag acgggcacgt agaggtttcc 1500
gcagggccgg ccggcatggc cagtgtgtgg gattacgacc tggtactgat ggcggttttcc 1560
catctaaccg aatccatgaa ccgataccgg gaagggaagg gagacaagcc cggccgcgtg 1620
ttccgtccac acgttgcgga cgtactcaag ttctgccggc gagccgatgg cggaaagcag 1680
aaagacgacc tggtagaaac ctgcattcgg ttaaacacac gcacgttgc catgcagcgt 1740
acgaagaagg ccaagaacgg ccgcctggtg acggtatccg agggtgaagc cttgattagc 1800
cgctacaaga tcgtaaagag cgaaaccggg cggccggagt acatcgagat cgagctagct 1860
gattggatgt accgcgagat cacagaaggc aagaacccgg acgtgctgac ggttcacccc 1920
gattactttt tgatcgatcc cggcatcggc cgttttctct accgcctggc acgccgcgcc 1980
gcaggcaagg cagaagccag atggttgttc aagacgatct acgaacgcag tggcagcgcc 2040
ggagagttca agaagttctg tttcaccgtg cgcaagctga tcgggtcaaa tgacctgccg 2100
gagtacgatt tgaaggagga ggcggggcag gctggcccga tcctagtcat gcgctaccgc 2160
aacctgatcg agggcgaagc atccgccggt tcctaatgta cggagcagat gctagggcaa 2220
attgccctag caggggaaaa aggtcgaaaa ggcctctttc ctgtggatag cacgtacatt 2280
gggaacccaa agccgtacat tgggaaccgg aacccgtaca ttgggaaccc aaagccgtac 2340
attgggaacc ggtcacacat gtaagtgact gatataaaag agaaaaaggc gcatttttcg 2400
gcctaaaact cttttaaaact tattaaaact cttaaaaccc gcctggcctg tgcataactg 2460
tctgccagc gcacagccga agagctgcaa aaagcgccta cccttcggtc gctgcgctcc 2520
ctacgccccg ccgcttcgcg tcggcctatc gcggccgctg gccgctcaaa aatggctggc 2580
ctacggccag gcaatctacc agggcgcgga caagccgcc cgtcgccact cgaccgccgg 2640
cgcccacatc aaggcaccct gcctcgcgcg tttcggtgat gacggtgaaa acctctgaca 2700
catgcagctc ccggaaacgg tcacagcttg tctgtaagcg gatgccggga gcagacaagc 2760
ccgtcagggc gcgtcagcgg gtgttggcgg gtgtcggggc gcagccatga cccagtcacg 2820
tagcgatagc ggagtgtata ctggcttaac tatgcggcat cagagcagat tgtactgaga 2880
gtgcaccata tgcggtgtga ataccgcac agatgcgtaa ggagaaaata ccgcatcagg 2940
cgctcttccg cttcctcgct cactgactcg ctgcgctcgg tcgttcggct gcggcgagcg 3000
gtatcagctc actcaaaggc ggtaatacgg ttatccacag aatcagggga taacgcagga 3060
aagaacatgt gagcaaaagg ccagcaaaag gccaggaacc gtaaaaaggc cgcgttgctg 3120
gcgtttttcc ataggctccg ccccctgac gagcatcaca aaaatcgacg ctcaagtcag 3180
aggtggcgaa acccgacagg actataaaga taccaggcgt ttcccctgg aagctccctc 3240
gtgcgctctc ctgttccgac cctgccgctt accggatacc tgtccgcctt tctcccttcg 3300
ggaagcgtgg cgctttctca tagctcacgc tgtaggtatc tcagttcggt gtaggtcgtt 3360
cgctccaagc tgggctgtgt gcacgaaccc ccgttcagc ccgaccgctg cgccttatcc 3420
ggtaactatc gtcttgagtc aacccggta agacacgact tatcgccact ggcagcagcc 3480
actggtaaca ggattagcag agcgaggtat gtaggcggtg ctacagagtt cttgaagtgg 3540
tggcctaact acggctacac tagaaggaca gtatttggta tctgcgctct gctgaagcca 3600
gttaccttcg gaaaaagagt tggtagctct tgatccggca aacaaaccac cgctggtagc 3660
ggtggttttt ttgtttgcaa gcagcagatt acgcgcagaa aaaaaggatc tcaagaagat 3720
cctttgatct tttctacggg gtctgacgct cagtggaacg aaaactcacg ttaagggatt 3780
ttggtcatga ttctaggta ctaaacaat tcatccagta aaatataata ttttattttc 3840
tcccaatcag gcttgatccc cagtaagtca aaaatagct cgacatactg ttcttccccg 3900
atatcctccc tgatcgaccg gacgcagaag gcaatgtcat accacttgtc cgccctgtcg 3960
cttctcccaa gatcaataaa gccacttact ttgccatctt tcacaaagat gttgctgtct 4020
cccaggtcgc cgtgggaaaa gacaagttcc tcttcgggct tttccgtctt taaaaaatca 4080
tacagctcgc gcggatcttt aaatggagtg tcttcttccc agttttcgca atccacatcg 4140
gccagatcgt tattcagtaa gtaatccaat tcggctaagc ggctgtctaa gctattcgta 4200
tagggacaat ccgatatgtc gatggagtga aagagcctga atacagctcg 4260
ataatctttt cagggctttg ttcatcttca tactcttccg agcaaaggac gccatcggcc 4320
tcactcatga gcagattgct ccagccatca tgccgttcaa agtgcaggac ctttggaaca 4380
ggcagctttc cttccagcca tagcatcatg tccttttccc gttccacatc ataggtggtc 4440
cctttatacc ggctgtccgt catttttaaa tataggtttt cattttctcc caccagctta 4500
tataccttag caggagacat tccttccgta tcttttacgc agcggatttt ttcgatcagt 4560
```

```
tttttcaatt ccggtgatat tctcatttta gccatttatt atttccttcc tcttttctac 4620
agtatttaaa gataccccaa gaagctaatt ataacaagac gaactccaat tcactgttcc 4680
ttgcattcta aaaccttaaa taccagaaaa cagcttttc aaagttgttt tcaaagttgg 4740
cgtataacat agtatcgacg gagccgattt tgaaaccgcg gtgatcacag gcagcaacgc 4800
tctgtcatcg ttacaatcaa catgctaccc tccgcgagat catccgtgtt tcaaacccgg 4860
cagcttagtt gccgttcttc cgaatagcat cggtaacatg agcaaagtct gccgccttac 4920
aacggctctc ccgctgacgc cgtcccggac tgatgggctg cctgtatcga gtggtgattt 4980
tgtgccgagc tgccggtcgg ggagctgttg gctggctggt ggcaggatat attgtggtgt 5040
aaacaaattg acgcttagac aacttaataa cacattgcgg acgtttttaa tgtagagctc 5100
aaagtttaac gcgttagcag aaggcatgtt gttgtgactc cgagggggttg cctcaaactc 5160
tatcttataa ccggcgtgga ggcatggagg caggggtatt ttggtcattt taatagatag 5220
tggaaaatga cgtggaattt acttaaagac gaagtctttg cgacaagggg gggcccacgc 5280
cgaatttaat attaccggcg tggccccccc ttatcgcgag tgctttagca cgagcggtcc 5340
agatttaaag tagaaaattt cccgcccact agggttaaag gtgttcacac tataaaagca 5400
tatacgatgt gatggtattt gatggagcgt atattgtatc aggtatttcc gttggataca 5460
aattattcgt acgaccctcg gtaccgatcg gcgcgcctgg cagacatact gtcccacaaa 5520
tgaagatgga atctgtaaaa gaaaacgcgt gaaataatgc gtctgacaaa ggttaggtcg 5580
gctgcccttta atcaatacca aagtggctccc taccacgatg gaaaaactgt gcagtcggtt 5640
tggcttttc tgacgaacaa ataagattcg tggccgacag gtgggggtcc accatgtgaa 5700
ggcatcttca gactccaata atggagcaat gacgtaaggg cttacgaaat aagtaagggt 5760
agtttgggaa atgtccactc acccgtcagt ctataaaatac ttagcccctc cctcattgtt 5820
aagggagcaa aatctcagag agatagtcct agagagagaa agagagcaag tagcctagaa 5880
gtagtcaagg cggcgaagta ttcaggcacg tggccaggaa gaagaaaagc caagacgacg 5940
aaaacaggta agagctaagc ttcctgcacc atggaagacg ccaaaaacat aaagaaaggc 6000
ccggcgccat tctatccgct ggaagatgga accgctggag agcaactgca taaggctatg 6060
aagagatacg ccctggttcc tggaacaatt gcttttacag atgcacatat cgaggtggac 6120
atcacttacg ctgagtactt cgaaatgtcc gttcggttgg cagaagctat gaaacgatat 6180
gggctgaata caaatcacag aatcgtcgta tgcagtgaaa actctcttca attctttatg 6240
ccggtgttgg gcgcgttatt tatcggagtt gcagttgcgc ccgcgaacga catttataat 6300
gaacgtgaat tgctcaacag tatgggcatt tcgcagccta ccgtggtgtt cgtttccaaa 6360
aaggggttgc aaaaaatttt gaacgtgcaa aaaaagctcc caatcatcca aaaaattatt 6420
atcatggatt ctaaaacgga ttaccaggga tttcagtcga tgtacacgtt cgtcacatct 6480
catctacctc ccggttttaa tgaatacgat tttgtgccag agtccttcga tagggacaag 6540
acaattgcac tgatcatgaa ctcctctgga tctactggtc tgcctaaagg tgtcgctctg 6600
cctcatagaa ctgcctgcgt gagattctcg catgccagag atcctatttt tggcaatcaa 6660
atcattccgg atactgcgat tttaagtgtt gttccattcc atcacggttt tggaatgttt 6720
actacactcg gatatttgat atgtggattt cgagtcgtct taatgtatag atttgaagaa 6780
gagctgtttc tgaggagcct tcaggattac aagattcaaa gtgcgctgct ggtgccaacc 6840
ctattctcct tcttgccaa aagcactctg attgacaaat acgatttatc taatttacac 6900
gaaattgctt ctggtggcgc tcccctctct aaggaagtcg gggaagcggt tgccaagagg 6960
ttccatctgc caggtatcag gcaaggatat gggctcactg agactacatc agctattctg 7020
attacacccg aggggatga taaaccgggc gcggtcggta agttgttcc attttttgaa 7080
gcgaaggttg tggatctgga taccgggaaa acgctgggcg ttaatcaaag aggcgaactg 7140
tgtgtgagag gtcctatgat tatgtccggt tatgtaaaca atccggaagc gaccaacgcc 7200
ttgattgaca aggatggatg gctacattct ggagacatag cttactggga cgaagacgaa 7260
cacttcttca tcgttgaccg cctgaagtct ctgattaagt acaaaggcta tcaggtggct 7320
cccgctgaat tggaatccat cttgctccaa caccccaaca tcttcgacgc aggtgtcgca 7380
ggtcttcccg acgatgacgc cggtgaactt cccgccgccg ttgttgtttt ggagcacgga 7440
aagacgatga cggaaaaaga tcgtggat tacgtcgcca gtcaagtaac aaccgcgaaa 7500
aagttgcgcg gaggagttgt gtttgtggac gaagtaccga aaggtcttac cggaaaactc 7560
gacgcaagaa aaatcagaga gatcctcata aaggccaaga agggcggaaa gatcgccgtg 7620
taactcgaga tatgaagatg aagatgaaat atttggtgtg tcaaataaaa agcttgtgtg 7680
cttaagtttg tgtttttttc ttggcttgtt gtgttatgaa tttgtggctt tttctaatat 7740
taaatgaatg taagatcaca ttataatgaa taaacaaatg tttctataat ccattgtgaa 7800
tgttttgttg gatctcttct gcagcatata actactgtat gtgctatggt atggactatg 7860
gaatatgatt aaagataagg agctccggtg acgacccat ggcttcgttg aacaacggaa 7920
actcgacttg ccttccgcac aatacatcat ttcttcttag cttttttct tcttcttcgt 7980
tcatacagtt tttttttgtt tatcagctta catttcttg aaccgtagct ttcgttttct 8040
tcttttaac tttccattcg gagttttgt atcttgtttc ccaggattag 8100
aatgattagg catcgaacct tcaagaattt gattgaataa aacatcttca ttccttaagat 8160
atgaagataa tcttcaaaag gccctggga atctgaaaga agagaagcag gcccatttat 8220
atgggaagaa acaatagtat ttcttatata ggcccattta agttgaaaac aatcttcaaa 8280
agtcccacat cgcttagata agaaaacgaa gctgagttta tatacagcta gagtcgaagt 8340
agtgattgtt ggtagtagcg actccatggt tttagagtca gaaatagcaa gttaaaataa 8400
ggctagtccg ttatcaactt gaaaaagtgg caccgagtcg gtgctttttt tcccgggcgc 8460
gccgatcatg agcggagaat taagggagtc acgttatgac ccccgccgat gacgcgggac 8520
aagccgtttt acgtttggaa ctgacagaac cgcaacgttg aaggagccac tcagccgcgg 8580
gtttctggag tttaatgagc taagcacata cgtcagaaac cattattgcg cgttcaaaag 8640
tcgcctaagg tcactatcag tagcaaata tttcttgtca aaaatgctcc actgacgttc 8700
cataaattcc cctcggtatc caattagagt ctcatattca ctctcaatcc aaataatctg 8760
caccgtacct gcagggtccg agctaggtca cagaagcgct caggaaggcc gctgagatag 8820
aggcatggcg gccaatgcgg gcggcggtgg agcgggagga ggcagcggca gcggcagcgt 8880
ggctgcgccg gcggtgtgcc gccccagcgg ctcgcggtgc acgccgacgc cggagcagat 8940
caggatgctg aaggagctgt actacgcgtg cggcatccgt gcccagatc cggagcagat 9000
ccagcgcatc accgccatgc tgcggcagca cggcaagatc gagggcaaga acgtcttcta 9060
ctggttccag aaccacaagg cccgcagcg ccagaagcgc cgcctcacca gcctcgacgt 9120
gaacgtgccc gccgccggcg cggccgacgc caccaccagc caactcggcg tcctctcgct 9180
gtcgtcgccg ccgccttcag gcgcggcgcc tccctcgccc accctcggct tctacgccgc 9240
cggcaatggc ggcggatcgg ctgtgctgct ggacacgagt tccgactggg gcagcagcgg 9300
```

```
cgctgcgatg gccaccgaga catgcttcct ccaggactac atgggcgtga cggacacggg   9360
cagctcgtcg cagtgccac  gcttctcgtc gtcggacacg ataatggcgg cggccgcggc   9420
gcgggcggcg acgacgcggg cgcccgagac tctccctctc ttcccgacct gcggcgacga   9480
cggcggcagc ggtagcagca gctacttgcc gttctggggt gccgcgtcca caactgccgg   9540
cgccacttct tccgttgcga tccagcagca acaccaggtc caggagcagt acagcttttta  9600
cagcaacagc aacagcaccc agctggccgg caccggcaac caagacgtat cggcaacagc   9660
agcagcagcc gccgccctgg agctgagcct cagctcatgg tgctccccctt accctgctgc  9720
agggagtatg tgagagcaac gcgagctgcc actgctcttc acttatgtct ctggaatgga   9780
aggaggagga agtgagcata gcgttggtgc gttgctgtca ttgtcctagg ttagtagcta   9840
gtgccagtta ctagtaagca tcaggcatag gagtatgtag tagaagcatg cacgttgccg   9900
gccagccagg ctttagacgg gaaaagaatt tggtgcagcc ggctgcaaaa caggatgttt   9960
acagcccccc cctcgagccc tagacttgtc catcttctgg attggccaag ttaattaatg  10020
tatgaaataa aaggatgcac acatagtgac atgctaataa ctataatgtg ggcatcaaag  10080
ttgtgtgtta tgtgtaatta ctaattatct gaataagaga aagagatcat ccatatttct  10140
tatcctaaat gaatgtcacg tgtctttata attctttgat gaaccagatg catttttatta 10200
accaattcca tatacatata aatattaatc atatataatt aatatcaatt gggttagcaa  10260
aacaaatcta gtcaggtgt  gttttgctaa ttattggggg atagtgcaaa aagaaatcta  10320
cgttctcaat aattcagata gaaaacttaa taaagtgaga taatttacat agattgcttt  10380
tatcctttga tatatgtgaa accatgcatg atataaggaa aatagataga gaaataattt   10440
tttacatcgt tgaatatgta aacaatttaa ttcaagaagc taggaatata aatattgagg   10500
agtttatgat tagagctctc ccggcgcgcc gatatcgagc tcagtgtttg atcgccggcg   10560
gtaccgagtg tacttcaagt cagtgggaaa tcaataagaa gattatttta tgaatatatt   10620
tcattgtgca agtagataga aattacatat gttacataac acacgaaata aacaaaaaaa   10680
gacaatccaa aaacaaacac cccaaaaaaa ataatcactt tagataaact cgtatgagga   10740
gaggcacgtt cagtgactcg acgattcccg agcaaaaaaa gtctcccgt  cacacatgta   10800
gtgggtgacg caattatctt taaagtaatc cttcgttga  cttgtcattg ataacatcca   10860
gtcttcgtca ggattgcaaa gaattataga agggatccca ccttttattt tcttcttttt    10920
tccatattta gggttgacag tgaaatcaga ctggcaacct attaattgct tccacaatgg   10980
gacgaacttg aaggggatgt cgtcgatgat attataggtg gcgtgttcat cgtagttggt   11040
gaaatcgatg gtaccgttcc aatagttgtg tcgtccgaga cttctagccg aggtggtctt   11100
tccggtacga gttggtccgc agatgtagag gctggggtgt cggattccat tccttccatt   11160
gtccttgtta aatcggccat ccattcaagg tcagattgag cttgttggta tgagacagga   11220
tgtatgtaag tataagcgtc tatgcttaca tggtatagat gggtttccct ccaggagtgt   11280
agatcttcgt ggcagcgaag atctgattct gtgaagggcg acacatacgg ttcaggttgt   11340
ggagggaata atttgttggc tgaatattcc agccattgaa gctttgttgc ccattcatga   11400
gggaattctt ccttgatcat gtcaagatat tcctccttag acgttgcagt ctggataata   11460
gttctccatc gtgcgtcaga tttgcgagga gaaaccttat gatctcggaa atctcctctg   11520
gttttaatat ctccgtcctt tgatatgtaa tcaaggactt gtttagagtt tctagctggc   11580
tggatattag ggtgatttcc ttcaaaatcg aaaaagaag gatccctaat acaaggtttt   11640
ttatcaagct ggagaagagc atgatagtgg gtagtgccat cttgatgaag ctcagaagca   11700
acaccaagga agaaaataag aaaaggtgtg agtttctccc agagaaactg gaataaatca   11760
tctctttgag atgagcactt gggataggta aggaaaacat atttagattg gagtctgaag   11820
ttcttactag cagaaggcat gttgttgtga ctccgaggg  ttgcctcaaa tctctatctta  11880
taaccggcgt ggaggcatgg aggcaggggt attttggtca ttttaataga tagtggaaaa   11940
tgacgtggaa tttacttaaa gacgaagtct ttgcgacaag ggggggccca cgccgaattt   12000
aatattaccg gcgtggcccc cccttatcgc gagtgcttta gcacgagcgg tccagattta   12060
aagtagaaaa tttcccgccc cactaggtta aaggtgttca cactataaaa gcatatacga   12120
tgtgatggta tttgatggag cgtatattgt atcaggtatt tccgttggat acgaattatt   12180
cgtacgaccc tcatagttta aactatcagt gtttgacagg atatattggc gggtaaacct   12240
aagagaaaag agcgtttatt agaataacgg atatttaaaa gggcgtgaaa aggttatcc    12300
gttcgtccat ttgtatgtgc atgccaacca cagggttccc ctcgggatca aagtactttg   12360
atccaacccc tccgctgcta tagtgcagtc ggcttctgac gttcagtgca gccgtcttct   12420
gaaaacgaca tgtcgcacaa gtcctaagtt acgcgacagg ctgccgccct gccctttcc    12480
tggcgttttc ttgtcgcgtg tttttagtcg ataaagtaga atacttgcga ctagaaccgg   12540
agacattacg ccatgaacaa gagcgccgcc gctggcctgc tgggctatgc ccgcgtcagc   12600
accgacgacc aggacttgac caaccaacg  gccgaactgc acgcggccgg ctgcaccaag   12660
ctgttttccg agaagatcac cggcaccagg cgcgaccgcc cggagctgg  caggatgctt   12720
gaccacctac gccctggcga cgttgtgaca gtgaccaggc tagaccgcct ggcccgcagc   12780
acccgcgacc tactggacat tgccgagcgc atccaggagg ccggcgcggg cctgcgtagc   12840
ctggcagagc cgtgggccga caccaccacg ccggccccga gcatggtgtt gaccgtgttc   12900
gccggcattg ccgagttcga gcgttcccta atcatcgacc gcaccggag  cgggcgcgag   12960
gccgccaagg cccgaggcgt gaagtttggc ccccgcccta ccctcacccc ggcacagatc   13020
gcgcacgccc gcgagctgat cgaccaggaa ggccgcaccg tgaagaggc  ggctgcactg   13080
cttggcgtgc atcgctcgac cctgtaccgc gcacttgagc gcagcgagga agtgacgccc   13140
accgaggcca ggcggcgcgg tgccttccgt gaggacgcat tgaccgaggc cgacgccctg   13200
gcggccgccg agaatgaacg ccaagaggaa caagcatgaa accgccagc  gacggccagg   13260
acgaaccgtt tttcattacc gaagagatcg aggcggagat gatcgcggcc gggtacgtgt   13320
tcgagccgc  cgcgcacggc tcaaccgtgc ggctgcatga atcctggcc  ggtttgtctg   13380
atgccaagct ggcggcctgg ccggccagct tggccgctga gaaaccgag  cgccgccgtc   13440
taaaaggtg  atgtgtattt gagtaaaaca gc                                  13472
```

SEQ ID NO: 36        moltype = DNA   length = 14829
FEATURE              Location/Qualifiers
source               1..14829
                     mol_type = other DNA
                     organism = synthetic construct
SEQUENCE: 36
gcagccggtg cgccgtcgat taggaagccg cccaagggcg acgagcaacc agatttttc    60
gttccgatgc tctatgacgt gggcacccgc gatagtcgca gcatcatgga cgtggccgtt  120

```
ttccgtctgt cgaagcgtga ccgacgagct ggcgaggtga tccgctacga gcttccagac   180
gggcacgtag aggtttccgc agggccggcc ggcatggcca gtgtgtggga ttacgacctg   240
gtactgatgg cggtttccca tctaaccgaa tccatgaacc gataccggga agggaaggga   300
gacaagcccg gccgcgtgtt ccgtccacac gttgcggacg tactcaagtt ctgccggcga   360
gccgatggcg gaaagcagaa agacgacctg gtagaaacct gcattcggtt aaacaccacg   420
cacgttgcca tgcagcgtac gaagaaggcc aagaacggcc gcctggtgac ggtatccgag   480
ggtgaagcct tgattagccg ctacaagatc gtaaagagcg aaaccgggcg gccggagtac   540
atcgagatcg agctagctga ttggatgtac cgcgagatca cagaaggcaa gaacccggac   600
gtgctgacgg ttcacccga ttactttttg atcgatcccg gcatcggccg tttctctca    660
cgcctggcac gccgcgccgc aggcaaggca gaagccagat ggttgttcaa gacgatctac   720
gaacgcagtg gcagcgccgg agagttcaag aagttctgtt tcaccgtgcg caagctgatc   780
gggtcaaatg acctgccgga gtacgatttg aaggaggagg cggggcaggc tggcccgatc   840
ctagtcatgc gctaccgcaa cctgatcgag ggcgaagcat ccgccggttc ctaatgtacg   900
gagcagatgc tagggcaaat tgccctagca ggggaaaaag gtcgaaaagg cctctttcct   960
gtggatagca cgtacattgg gaacccaaag ccgtacattg gaaccggaa ccgtacatt    1020
gggaacccaa agccgtacat tgggaaccgg tcacacatgt aagtgactga tataaaagag  1080
aaaaaggcg attttttccgc ctaaaactct ttaaaactta ttaaaactct taaaccccgc  1140
ctggcctgtg cataactgtc tggccagcgc acagccgaaa agctgcaaaa agcgcctacc  1200
cttcggtcgc tgcgctccct acgccccgcc gcttcgcgtc ggcctatcgc ggccgctggc  1260
cgctcaaaaa tggctggcct acggccaggc aatctaccag ggcgcggaca agccgcgccg  1320
tcgccactcg accgccggcg cccacatcaa ggcaccctgc ctcgcgcgtt tcggtgatga  1380
cggtgaaaac ctctgcacaca tgcagctccc ggaaacgtc acagcttgtc tgtaagcgga  1440
tgccgggagc agacaagccc gtcagggcgc gtcagcgggt gttggcgggt gtcggggcgc  1500
agccatgacc cagtcacgta gcgatagcgg agtgtatact ggcttaacta tgcggcatca  1560
gagcagattg tactgagagt gcaccatatg cggtgtgaaa taccgcacag atgcgtaagg  1620
agaaaatacc gcatcaggcg ctcttccgct tcctcgctca ctgactcgct gcgctcggtc  1680
gttcggctgc ggcgagcggt atcagctcac tcaaaggcgg taatacggtt atccacagaa  1740
tcaggggata acgcaggaaa gaacatgtga gcaaaaggcc agcaaaaggc caggaaccgt  1800
aaaaaggccg cgttgctggc gttttttccat aggctccgcc cccctgacga gcatcacaaa  1860
aatcgacgct caagtcagag gtggcgaaac ccgacaggac tataaagata ccaggcgttt  1920
ccccctggaa gctccctcgt gcgctctcct gttccgaccc tgccgcttac cggatacctg  1980
tccgcctttc tcccttcggg aagcgtggcg ctttctcata gctcacgctg taggtatctc  2040
agttcggtgt aggtcgttcg ctccaagctg ggctgtgtgc acgaaccccc cgttcagccc  2100
gaccgctgcg ccttatccgg taactatcgt cttgagtcca acccggtaag acacgactta  2160
tcgccactgg cagcagccac tggtaacagg attagcagag cgaggtatgt aggcggtgct  2220
acagagttct tgaagtggtg gcctaactac ggctacacta aaggacagt atttggtatc   2280
tgcgctctgc tgaagccagt taccttcgga aaaagagttg gtagctcttg atccggcaaa  2340
caaaccaccg ctggtagcgg tggtttttttt gtttgcaagc agcagattac gcgcagaaaa  2400
aaaggatctc aagaagatcc tttgatcttt tctacgggt ctgacgctca gtggaacgaa   2460
aactcacgtt aagggatttt ggtcatgcat tctaggtact aaaacaattc atccagtaaa  2520
atataatatt ttatttctc ccaatcaggc ttgatcccca gtaagtcaaa aaatagctcg   2580
acatactgtt cttccccgat atcctccctg atcgaccgga gcagaaggc aatgtcatac    2640
cacttgtccg ccctgccgct tctcccaaga tcaataaagc cacttacttt gccatcttc   2700
acaaagatgt tgctgtctcc caggtcgccg tgggaaaaga caagttcctc ttcgggcttt  2760
tccgtcttta aaaaatcata cagctcgcgc ggatctttaa atggagtgtc ttcttcccag  2820
ttttcgcaat ccacatcggc cagatcgtta ttcagtaagt aatccaattc ggctaagcgg  2880
ctgtctaagc tattcgtata gggacaatcc gatatgtcga ttggagtgaa gagcctgatg  2940
cactccgcat acagctcgat aatcttttca gggcttttgt catcttcata ctcttccgag  3000
caaaggacgc catcggcctc actcatgagc agattgctcc agccatcatg ccgttcaaag  3060
tgcaggacct ttggaacagg cagctttcct tccagccata gcatcatgtc ctttttccgt   3120
tccacatcat aggtggtccc tttataccgg ctgtccgtca ttttttaaata taggttttca  3180
ttttctccca ccagcttata taccttagca ggagacattc cttccgtatc ttttacgcag  3240
cggtattttt cgatcagttt tttcaattcc ggtgatattc tcattttagc catttattat  3300
ttccttcctc ttttctacag tatttaaaga tacccccaaga agctaattat aacaagacga  3360
actccaattc actgttcctt gcattctaaa accttaaata ccagaaaaca gcttttttcaa  3420
agttgttttc aaagttggcg tataacatag tatcgacgag gccgattttg aaaccgcggt   3480
gatcacaggc agcaacgctc tgtcatcgtt acaatcaaca tgctaccctc cgcgagatca  3540
tccgtgtttc aaaacccggca gcttagttgc cgttcttccg aatagcatcg gtaacatgag  3600
caaagtcgc cgccttacaa cggctctccc gctgacgccg tcccggactg atgggctgcc   3660
tgtatcgagt ggtgattttg tgccgagctg ccggtcgggg agctgttggc tggctggtgg  3720
caggatatat tgtggtgtaa acaaattgac gcttagacaa cttaataaca cattgcggac  3780
gttttttaatg tagagctcaa agtttaacgc gttagcagaa ggcatgttgt tgtgactccg  3840
agggggttgcc tcaaactcta tcttataacc ggcgtggagg catggaggca gggtatttt   3900
ggtcatttta atagatagtg gaaaatgacg tggaatttac ttaaagacga agtcttttgcg  3960
acaaggggg gcccacgccg aatttaatat taccggcgtg gcccccccctt atcgcgagtg  4020
ctttagcacg agcggtccag atttaaagta gaaaatttcc cgcccactag ggttaaaggt  4080
gttcacacta taaagcata tacgatgtga tggtatttga tggagcgtat attgtatcag  4140
gtatttccgt tggatacgaa ttattcgtac gaccctcggt accgatcggc gcgcctggca  4200
gacatactgt cccacaaatg aagatgaat ctgtaaaaga aaacgcgtga aataatgcgt   4260
ctgacaaagg ttaggtcggc tgcctttaat caataccaaa gtggtcccta ccacgatgg   4320
aaaactgtgc agtcggttttg gctttttctg acgaacaaat aagattcgtg gccgacaggt  4380
gggggtccac catgtgaagg catcttcaga ctccaataat ggagcaatga cgtaagggct  4440
tacgaaataa gtaaggggtag tttgggaaat gtccactcac ccgtcagtct ataaatactt  4500
agcccctccc tcattgttaa gggagcaaaa tctcagaagg atagtcctag agagagaaag  4560
agagcaagta gcctgaaagt agtcaaggcg gcgaagtatt caggcacgtg gccaggaaga   4620
agaaaagcca agacgacgaa aacaggtaag agctaagctt cctgcaccat ggaagacgcc  4680
aaaaacataa agaaggccc ggcgccattc tatccgctgg aagatggaac cgctggagag   4740
caactgcata aggctatgaa gagatacgcc ctggttcctg gaacaattgc ttttacagat  4800
gcacatatcg aggtggacat cacttacgct gagtacttcg aaatgtccgt tcggttggca  4860
```

```
gaagctatga aacgatatgg gctgaataca aatcacagaa tcgtcgtatg cagtgaaaac  4920
tctcttcaat tctttatgcc ggtgttgggc gcgttattta tcggagttgc agttgcgccc  4980
gcgaacgaca tttataatga acgtgaattg ctcaacagta tgggcatttc gcagcctacc  5040
gtggtgttcg tttccaaaaa gggttgcaa aaattttga acgtgcaaaa aaagctccca   5100
atcatccaaa aaattattat catgggattct aaaacggatt accagggatt tcagtcgatg  5160
tacacgttcg tcacatctca tctacctccc ggtttaatg aatacgattt tgtgccagag   5220
tccttcgata gggacaagac aattgcactg atcatgaact cctctggatc tactggtctg  5280
cctaaaggtg tcgctctgcc tcatagaact gcctgcgtga gattctcgca tgccagagat  5340
cctattttg gcaatcaaat cattccggat actgcgattt taagtgttgt tccattccat  5400
cacggttttg gaatgtttac tacactcgga tatttgatat gtggatttcg agtcgtctta  5460
atgtatagat ttgaagaaga gctgtttctg aggagcttc aggattacaa gattcaaagt   5520
gcgctgctgg tgccaaccct attctccttc ttcgccaaaa gcactctgat tgacaaatac  5580
gatttatcta atttacacga aattgcttct ggtggcgctc ccctctctaa ggaagtcggg   5640
gaagcggttg ccaagaggtt ccatctgcca ggtatcaggc aaggatatgg gctcactgag  5700
actacatcag ctattctgat tacacccgag ggggatgata aaccgggcgc ggtcggtaaa  5760
gttgttccat tttttgaagc gaaggttgtg gatctcgata ccgggaaaac gctgggcgtt  5820
aatcaaagag gcgaactgtg tgtgagaggt cctatgatta tgtccggtta tgtaaacaat  5880
ccggaagcga ccaacgcctt gattgacaag gatggatggc tacattctgg agacatagct  5940
tactgggacg aagacgaaca cttcttcatc gttgaccgcc tgaagtctct gattaagtac  6000
aaaggctatc aggtggctcc cgctgaattg gaatccatct tgctccaaca ccccaacatc  6060
ttcgacgctg tgtcgcagg tcttcccgac gatgacgccg tgaacttcc cgccgccgtt   6120
gttgttttgg agcacggaaa gacgatgacg gaaaaagagt tgttggatta cgtcgccagt  6180
caagtaacaa ccgcgaaaaa gttgcgcgga ggagttgtgt ttgtggacga agtaccgaaa  6240
ggtcttaccg gaaaactcga cgcaagaaaa atcagagaga tcctcataaa ggccaagaag  6300
ggcggaaaga tcgccgtgta actcgagata tgaagatgaa gatgaaatat ttggtgtgtc  6360
aaataaaaag cttgtgtgct taagtttgt ttttttctt ggcttgttgt gttatgaatt    6420
tgtggctttt tctaatatta aatgaatgta agatcacatt ataatgaata aacaaatgtt  6480
tctataatcc attgtgaatg ttttgttgga tctcttctgc agcatataac tactgtatgt  6540
gctatggtat ggactatgga atatgattaa agataaggag ctccggtgac ggacccatgg  6600
cttcgttgaa caacgaaac tcgacttgcc ttccgcacaa tacatcattt cttcttagct   6660
ttttttcttc ttcttcgttc atacagtttt tttttgttta tcagcttaca ttttcttgaa  6720
ccgtagcttt cgttttcttc ttttttaactt tccattcgga gttttgtat cttgtttcat   6780
agtttgtccc aggattagaa tgattaggca tcgaaccttc aagaatttga ttgaataaaa  6840
catcttcatt cttaagatat gaagataatc ttcaaaaggc ccctgggaat ctgaaagaag  6900
agaagcaggc ccatttatat gggaaagaac aatagtattt cttatatagg cccatttaag  6960
ttgaaaacaa tcttcaaaag tcccacatcg cttagataag aaaacgaagc tgagtttata  7020
tacagctaga gtcgaagtag tgattgttgg tagtagcgac tccatggttt tagagctaga  7080
aatagcaagt taaaataagg ctagtccgtt atcaacttga aaaatggca ccgagtcggt   7140
gcttttttc ccggggcgcg ccgatatcga gctctcccgc agatttgcct tttcaatttc   7200
agaaagaatg ctaacccaca gatggttaga gaggcttacg cagcaggtat catcaagacg  7260
atctacccga gcaataatct ccaggaaatc aaataccttc caagaaggt taaagatgca   7320
gtcaaaagat tcaggactaa ctgcatcaag aacacagaga aagatatatt tctcaagatc  7380
agaagtacta ttccagtatg gacgattcaa ggcttgcttc acaaaccaag gcaagtaata  7440
gagattggag tctctaaaaa ggtagttccc actgaatcaa aggccatgga gtcaaagatt  7500
caaatagagg acctaacaga actgccgta aagactggcg aacagttcat acagagtctc   7560
ttacgactca atgacaagaa gaaaatcttc gtcaacatgg tggagcacga cacacttgtc  7620
tactccaaaa atatcaaata tacagtctca gaagaccaaa gggcaattga gacttttcaa  7680
caaagggtaa tatccggaaa cctcctcgga ttcattgcc cagctatctg tcactttatt   7740
gtgaagatag tggaaaagga aggtggctcc tacaaatgcc atcattgcga taaggaaag   7800
gccatcgttg aagatgcctc tgccgacagt ggtcccaaag atggacccc acccacgagg   7860
agcatcgtgg aaaaagaaga cgttccaacc acgtcttcaa agcaagtgga ttgatgtgat  7920
atctccactg acgtaaggga tgacgcacaa tcccactatc cttcgcaaga cccttcctct  7980
atataaggaa gttcatttca tttggagaga acacggggga ctatgatggc ttcattgtct   8040
tgtgttgaag acaagatgaa aacaagttgt ttggttaatg gtggaggaac tataacaaca  8100
acaacatctc aatctacctt gcttgaagag atgaagctgt tgaaagacca gtcaggtaca  8160
agaaagccgg taataaactc ggagctatgg cacgcttgtg caggcccttt ggtgtgtctc  8220
cctcaagttg ggagcttagt gtattactc tcaaaggtc atagcgagca ggttgctgtt   8280
tcaaccagaa gatcagcaac aacacaagtt cctaattatc cgaaccttcc atctcagttg  8340
atgtgtcaag tccataatgt tactcttcat gctgacaaag acagtgacga aatctatgct  8400
cagatgagtc ttcaacctgt tcactctgag agagatgtgt tccctgtacc agactttgga  8460
atgctgagag gaagtaagca cccgactgag ttttctgca aaacacttac tgcaagtgac   8520
acaagcacac atggaggttt ctcagtgcca cgtagagctg cagagaagct atttccacca  8580
ttggactact cagcacagcc gccaacgcaa gagcttgtag ttcgagatct tcatgagaat  8640
acttggacat ttcgccatat ctaccgaggg caaccaaaga gacatctcct aactacagga  8700
tggagtttgt tcgttggatc gaagagattg agagctgggg attctgtttt gttcatcagg  8760
gatgagaagt cacaacttat ggtcggtgtt aggcgtgcca atgccaaca aacagcactt   8820
ccttcatcag ttctctcagc ggatagtatg cacatcggtg ttcttgctgc tgctgctcac  8880
gcaaccgcca accgtactcc tttttgata ttctataatc caagagcttg tccagcagag   8940
ttcgtgatcc ctctagctaa gtaccgtaag gcgatatgcg ggtctgcct ctcagttgt    9000
atgagatttg gaatgatgtt tgaaactgaa gattccggga aacgaaggta catgggaact  9060
attgttggaa tcagcgattt ggatccgttg agatggcctg gttctaagtg gcgtaacctt  9120
caggtagaat gggatgagcc tggatgtaat gataaaccta ctcgggtcag tccatggat   9180
atcgaaacac ctgaaagtct cttcattttt ccttctctga cctcaggact caaacgtcag  9240
ctccatccat cttactttgc tggtgaaact gaatggggta gcttgataaa acggccactt  9300
atacgtgttc ctgattccgc gaatgggatt atgccatatg catctttccc tagtatggct  9360
tcggagcagc ttatgaaaat gatgatgagg cctcacaaca accaaaatgt accatctttc  9420
atgtctgaga tgcagcagaa tattgtaatg gggaatggag gtttgctagg agatatgaag  9480
atgcagcaac ccctgatgat gaaccagaaa tctgagatgg tgcagccaca aaacaagcta  9540
acagtgaacc catctgcttc taatacgagt ggccaagaac agaatctttc acagagtatg  9600
```

```
agtgctcctg ctaaacctga gaactctaca ctctctggtt gcagctctgg tagagtccaa   9660
catggacttg agcagtcaat ggaacaggca agccaggtta ctacatccac agtgtgtaat   9720
gaggaaaagg ttaatcagct acttcagaaa ccgggtgctt cgtcgcctgt acaagctgat   9780
caatgtcttg acattactca tcagatttac caaccacagt ctgatccaat aaatggattc   9840
tctttcctgg aaactgatga gctgacatca caagtctcct ccttccagtc tcttgccgga   9900
tcatacaagc aaccattcat tctatcctcc caggattctt cagctgttgt gttaccggat   9960
tccacaaact caccgctgtt tcatgatgtg tgggacactc agttgaacgg tctcaagttt  10020
gaccagttca gtcccttgat gcagcaggac ctttatgcta gtcagaatat ctgtatgagt  10080
aatagcacaa ccagtaacat tctagatcct ccactctcaa acacagtcct tgatgacttc  10140
tgtgccatca aagacactga tttccagaac caccccttctg gttgtttggt tggaaacaac  10200
aacactagct ttgctcaaga tgtccagtcg cagatcacat cagctagctt tgcagactca  10260
caggccttcc ctcgccaaga ttttccagat aattctggag gcactggtac atcttcaagc  10320
aatgttgatt ttgatgattg tagtctgcgg caaaatagta aaggctcatc atggcagaaa  10380
attgcgacac cccgcgtccg aacctactcg agtttctcca taataatgtg tgagtagttc  10440
ccagataagg gaattagggt tcctataggg tttcgctcat gtgttgagca tataagaaac  10500
ccttagtatg tatttgtatt tgtaaaatac ttctatcaat aaaatttcta attcctaaaa  10560
ccaaaatcca gtactaaaat ccagatcccc cgaattaagt gtttgatcgc cggcggtacc  10620
gagtgtactt caagtcagtg ggaaatcaat aaaatgatta ttttatgaat atatttcatt  10680
gtgcaagtag atagaaatta catatgttac ataacacacg aaataaacaa aaaaagacaa  10740
tccaaaaaca aacaccccaa aaaaaataat cactttagat aaactcgtat gaggagaggc  10800
acgttcagtg actcgacgat tcccgagcaa aaaaagtctc cccgtcacac atgtagtggg  10860
tgacgcaatt atctttaaag taatccttct gttgacttgt cattgataac atccagtctt  10920
cgtcaggatt gcaaagaatt ataagaggga tcccaccttt tattttcttc ttttttccat  10980
atttagggtt gacagtgaaa tcagactggc aacctattaa ttgcttccac aatgggacga  11040
acttgaaggg gatgtcgtcg atgatattat aggtggcgtg ttcatcgtag ttggtgaaat  11100
cgatgtacc gttccaatag ttgtgtcgtc cgagacttct agcccaggtg gtctttccgg  11160
tacgagttgg tccgcagatg tagaggctgg ggtgtcggat tccattcctt ccattgtcct  11220
tgttaaatcg gccatccatt caaggtcaga ttgagcttgt tggtatgaga caggatgtat  11280
gtaagtataa gcgtctatgc ttacatggta tagatgggtt tccctccagg agtgtagatc  11340
ttcgtggcag cgaagatctg attctgtgaa gggcgacaca tacggttcag gttgtggagg  11400
gaataaatttg ttggctgaat attccagcca ttgaagcttt gttgcccatt catgagggaa  11460
ttcttccttg atcatgtcaa gatattcctc cttagacgtt gcagtctgga taatagttct  11520
ccatcgtgcg tcagatttgc gaggagaaac cttatgatct cggaaatctc ctctggtttt  11580
aatatctccg tcctttgata tgtaatcaag gacttgttta gagtttctag ctggctggat  11640
attagggtga tttccttcaa aatcgaaaaa agaaggatcc ctaatacaag gttttttatc  11700
aagctggaga agagcatgat agtgggtagt gccatcttga tgaagctcag aagcaacacc  11760
aaggaagaaa ataagaaaag gtgtgagttt ctcccagaga aactggaata aatcatctct  11820
ttgagatgag cacttgggat aggtaaggaa aacatatttta gattggagtc tgaagttctt  11880
actagcagaa ggcatgttgt tgtgactccg aggggttgcc tcaaactcta tcttataacc  11940
ggcgtggagg catggaggca ggggtatttt ggtcatttta atagatagtg gaaaatgacg  12000
tggaatttac ttaaagacga agtctttgcg acaaggggggg gcccacgccg aatttaatat  12060
taccggcgtg gccccccctt atcgcgagtg ctttagcacg agcggtccag atttaaagta  12120
gaaaatttcc cgcccactag ggttaaaggt gttcacacta taaagcata tacgatgtga  12180
tggtatttga tggagcgtat attgtatcag gtatttccgt tggatacgaa ttattcgtac  12240
gaccctcata gtttaaacta tcagtgtttg acaggatata ttggcgggta aacctaagag  12300
aaaagagcgt ttattagaat aacggatatt taaaaggggcg tgaaaaggtt tatccgttcg  12360
tccatttgta tgtgcatgcc aaccacaggg ttccctccgg gatcaaagta ctttgatcca  12420
accctccgc tgctatagtg cagtcggctt ctgacgttca gtgcagccgt cttctgaaaa  12480
cgacatgtcg cacaagtcct aagttacgcg acaggctgcc gccctgccct tttcctggcg  12540
ttttcttgtc gcgtgtttta gtcgcataaa gtagaatact tgcgactaga accggagaca  12600
ttacgccatg aacaagagcg ccgccgctgg cctgctgatg cccgcg tcagcaccga     12660
cgaccaggac ttgaccaacc aacgggccga actgcacgcg gccggctgca ccaagctgtt  12720
ttccgagaag atcaccggca ccaggcgcga ccgcccggag ctggccagga tgcttgacca  12780
cctacgccct ggcgacgttg tgacagtgac caggctagac cgcctggccc gcagcacccg  12840
cgacctactg gacattgccg agcgcatcca ggaggccggc gcggggcctgc gtagcctggc  12900
agagccgtgg gccgacacca ccacgccggc cggccgcatg gtgttgaccg tgttcgccga  12960
cattgccgag ttcgagcgtt ccctaatcat cgaccgcacc cggagcgggc gcgaggccgc  13020
caaggcccga ggcgtgaagt ttggcccccg ccctaccctc accccggcac agatcgcgca  13080
cgcccgcgag ctgatcgacc aggaaggccg caccgtgaaa gaggcggctg cactgcttgg  13140
cgtgcatcgc tcgaccctgt accgcgcact tgagcgcagc gaggaagtga gcgccaccga  13200
ggccaggcgg cgcggtgcct tccgtgagga cgcattgacc gaggccgacg ccctggcggc  13260
cgccgagaat gaacgccaag aggaacaagc atgaaaccgc accaggacgg ccaggacgaa  13320
ccgtttttca ttaccgaaga gatcgaggcg gagatgatcg cggccgggta cgtgttcgag  13380
ccgcccgcc acggctcaac cgtgcggctg catgaaatcc tggccggttt gtctgatgcc  13440
aagctggcgg cctggccggc cagcttggcc gctgaagcaa ccgagcgccg ccgtctaaaa  13500
aggtgatgtg tatttgagta aaacagcttg cgtcatgcgg tcgctgcgta tatgatgcga  13560
tgagtaaata aacaaatacg caaggggaac gcatgaaggt tatcgctgta cttaaccaga  13620
aaggcgggtc aggcaagacg accatcgcaa cccatctagc ccgcgccctg caactcgccg  13680
gggccgatgt tctgttagtc gattccgatc ccagggcagg ccgcgat tgggcggcg    13740
tgcgggaaga tcaaccgcta accgttgtcg gcatcgaccg cccgacgatt gaccgcgacg  13800
tgaaggccat cggccggcgc gacttcgtag tgatcgacgg agccccag gcggcggact   13860
tggctgtgtc cgcgatcaag gcagccgact tcgtgctgat tccggtgcag ccaagccctt  13920
acgacatatg gcaccgcc gacctggtgg agctggttaa gcagcgcatt gaggtcacgg    13980
atggaaggct acaagcggcc tttgtcgtgt cgcgggcgat caaggctgac cgcatcgtgg  14040
gtgaggttgc cgaggcgctg gccgggtacg agctgcccat tcttgagtcc cgtatcacgc  14100
agcgcgtgag ctaccaaggc actgccgccg ccggcacaac cgttcttgaa tcagaacccg  14160
agggcgacgc tgcccgcgag gtccaggcgc tggccgctga aattaaatca aaactcatttt  14220
gagttaatga ggtaaagaga aaatgagcaa agcacaaac acgctaagtg ccggccgtcc  14280
gagcgcacgc agcagcaagg ctgcaacgtt ggccagcctg gcagacacgc cagccatgaa  14340
```

```
gcgggtcaac tttcagttgc cggcggagga tcacaccaag ctgaagatgt acgcggtacg    14400
ccaaggcaag accattaccg agctgctatc tgaatacatc gcgcagctac cagagtaaat    14460
gagcaaatga ataaatgagt agatgaattt tagcggctaa aggaggcggc atggaaaatc    14520
aagaacaacc aggcaccgac gccgtggaat gccccatgtg tggaggaacg ggcggttggc    14580
caggcgtaag cggctgggtt gtctgccggc cctgcaatgg cactggaacc cccaagcccg    14640
aggaatcggc gtgacggtcg caaaccatcc ggcccgtac aaatcggcgc ggcgctgggt     14700
gatgacctgg tggagaagtt gaaggccgcg caggccgccc agcggcaacg catcgaggca    14760
gaagcacgcc ccggtgaatc gtggcaagcg gccgctgatc gaatccgcaa agaatcccgg    14820
caaccgccg                                                            14829

SEQ ID NO: 37              moltype = DNA   length = 16222
FEATURE                    Location/Qualifiers
source                     1..16222
                           mol_type = other DNA
                           organism = synthetic construct
SEQUENCE: 37
atggccagtg tgtgggatta cgacctggta ctgatggcgg tttcccatct aaccgaatcc     60
atgaaccgat accgggaagg gaagggagac aagcccggcc gcgtgttccg tccacacgtt    120
gcggacgtac tcaagttctg ccggcgagcc gatggcggaa agcagaaaga cgacctggta    180
gaaacctgca ttcggttaaa caccacgcac gttgccatgc agcgtacgaa gaaggccaag    240
aacggccgcc tggtgacggt atccgagggt gaagccttga ttagccgcta caagatcgta    300
aagagcgaaa ccgggcggcc ggagtacatc gagatcgaac tcgttgattg gatgtaccgc    360
gagatcacag aaggcaagaa cccggacgtg ctgacggttc accccgatta cttttttgatc   420
gatcccggca tcgccgtttt tctctaccgc ctggcacgcc gcgccgcagg caaggcagaa    480
gccagatggt tgttcaagac gatctacgaa cgcagtggca gcgccggaga gttcaagaag    540
ttctgtttca ccgtgcgcaa gctgatcggg tcaaatgacc tcgccgagta cgatttgaag    600
gaggaggcgg ggcaggctgg cccgatccta gtcatgcgct accgcaacct gatcgagggc    660
gaagcatccg ccgttcctta atgtacgagg cagatgctag ggcaaattgc cctagcaggg    720
gaaaaggtc gaaaggcct cttcctgtg gatagcacgt acattgggaa cccaaagccg      780
tacattggga accggaaccc gtacattggg aacccaaagc cgtacattgg gaaccggtca    840
cacatgtaag tgactgatat aaaagagaaa aaaggcgatt tttccgccta aaactcttta    900
aaacttatta aaactcttaa aacccgcctg gcctgtgcat aactgtctgg ccagcgcaca    960
gccgaagagc tgcaaaaagc gcctaccctt cggtcgctgc gctccctacg ccccgccgct   1020
tcgcgtcggc ctatcgcggc cgctggccgc tcaaaaatgg ctggcctgca gccaggcaat   1080
ctaccaggcc gcggacaagc cgcgccgtcg ccactcgacc gccggcgccc acatcaaggc   1140
accctgcctc gcgcgtttcg gtgatgacgg tgaaaacctc tgacacatgc agctcccgga   1200
aacggtcaca gcttgtctgt aagcggatgc cgggagcaga caagcccgtc agggcgcgtc   1260
agcgggtgtt ggcgggtgtc ggggcgcagc catgacccag tcacgtagcg atagcggagt   1320
gtatactggc ttaactatgc ggcatcagag cagattgtac tgagagtgca ccatatgcgg   1380
tgtgaaatac cgcacagatg cgtaaggaga aataccgca tcaggcgctc ttccgcttcc     1440
tcgctcactg actcgctgcg ctcggtcgtt cggctgcggc gagcggtatc agctcactca   1500
aaggcggtaa tacggttatc cacagaatca ggggataacg caggaaagaa catgtgagca   1560
aaaggccagc aaaaggccag gaaccgtaaa aaggccgcgt tgctggcgtt tttccatagg   1620
ctccgccccc ctgacgagca tcacaaaaat cgacgctcaa gtcagaggtg gcgaaacccg   1680
acaggactat aaagatacca ggcgtttccc cctggaagct ccctcgtgcg ctctcctgtt   1740
ccgaccctgc cgcttaccgg atacctgtcc gcctttctcc cttcgggaag cgtggcgctt   1800
tctcatagct cacgctgtag tatctcagt tcggtgtagg tcgttcgctc caagctgggc    1860
tgtgtgcacg aaccccccgt tcagcccgac cgctgcgcct tatccggtaa ctatcgtctt   1920
gagtccaacc cggtaagaca cgacttatcg ccactggcag cagccactgg taacaggatt   1980
agcagagcga ggtatgtagg cggtgctaca gagttcttga agtggtggcc taactacggc   2040
tacactagaa ggacagtatt tggtatctgc gctctgctga agccagttac cttcggaaaa   2100
agagttggta gctcttgatc cggcaaacaa accaccgctg gtagcggtgg ttttttttgtt   2160
tgcaagcagc agattacgcg cagaaaaaaa ggatctcaag aagatccttt gatcttttct   2220
acggggtctg acgctcagtg gaacgaaaac tcacgttaag ggattttggt catgcattct   2280
aggtactaaa acaattcatc cagtaaaata ataatttta ttttctccca atcaggcttg    2340
atccccagta agtcaaaaaa tagctcgaca tactgttctt ccccgatatc ctccctgatc   2400
gaccggacgc agaaggcaat gtcataccac ttgtccgccc tgccgcttct cccaagatca   2460
ataaagccaa ttactttgcc atctttcaca agatgttgc tgtctcccag gtcgccgtgg    2520
gaaaagacaa gttcctcttc gggcttttcc gtctttaaaa aatcatacag ctcgcgcgga   2580
tctttaaatg gagtgtcttc ttcccagttt tcgcaatcca catcggccag atcgttattc   2640
agtaagtaat ccaattcggc taagcggctg tctaagctat tcgtataggg acaatccgat   2700
atgtcgatga agtgaaagag cctgatgcac tccgcataca gctcgataat cttttcaggg   2760
ctttgttcat cttcatactc ttccgagcaa aggacgccat cggcctcact catgagcaga   2820
ttgctccagc catcatgccg ttcaaagtgc aggaccttg gaacaggcag cttctcttcc    2880
agccatagca tcatgtcctt ttcccgttcc acatcatagg tggtccctt ataccggctg    2940
tccgtcattt ttaaatatag gttttcattt tctcccacca gctatatac cttagcagga    3000
gacattcctt ccgtatcttt tacgcagcgg tattttcga tcagttttt caattccggt     3060
gatattctca ttttagccat ttattatttc cttcctcttt tctacagtat ttaaagatac   3120
cccaagaagc taattataac aagacgaact ccaattcact gttccttgca ttctaaaacc   3180
ttaaatacca gaaaacagct tttttcaaagt tgtttcaaa gttggcgtat aacatagtat   3240
cgacggagcc gatttgaaa ccgcggtgat cacaggcagc aacgtctgt catcgttaca     3300
atcaacatgc taccctccgc gagatcatcc gtgtttcaaa cccggcagct tagttgccgt   3360
tcttccgaat agcatcggta acatgagcaa agtctgccgc cttacaacgg ctctcccgct   3420
gacgccgtcc cggactgatg gctgcctgtt atcgagtggt gattttgtgc cgagctgccg   3480
gtcgggagc tgttggctgg ctggtggcag gatatattgt ggtgtaaaca aattgacgct   3540
tagacaactt aataacacat gcggacgttt ttaatgtag agctcaaagt ttaacgcgtt   3600
agcagaaggc atgttgttgt gactccgagg ggttgcctca aactctatct tataaccggc    3660
gtggaggcat ggaggcaggg gtattttggt catttaata gatagtggaa aatgacgtgg   3720
aatttactta aagacgaagt ctttgcgaca aggggggggc cacgccgaat taatattac    3780
```

```
cggcgtggcc ccccccttatc gcgagtgctt tagcacgagc ggtccagatt taaagtagaa   3840
aatttcccgc ccactagggt taaaggtgtt cacactataa aagcatatac gatgtgatgg   3900
tatttgatgg agcgtatatt gtatcaggta tttccgttgg atacgaatta ttcgtacgac   3960
cctcggtacc gatcggcgcg cctggcagac atactgtccc acaaatgaag atggaatctg   4020
taaaagaaaa cgcgtgaaat aatgcgtctg acaaaggtta ggtcggctgc ctttaatcaa   4080
taccaaagtg gtccctacca cgatggaaaa actgtgcagt cggtttggct ttttctgacg   4140
aacaaataag attcgtggcc gacaggtggg ggtccaccat gtgaaggcat cttcagactc   4200
caataatgga gcaatgacgt aagggcttac gaaataagta agggtagttt gggaaatgtc   4260
cactcacccg tcagtctata aatacttagc ccctccctca ttgttaaggg agcaaaatct   4320
cagagagata gtcctagaga gagaaagaga gcaagtagcc ttgaagtagt caaggcggcg   4380
aagtattcag gcacgtggcc aggaagaaga aaagccaaga cgacgaaaac aggtaagagc   4440
taagcttcct gcaccatgga agacgccaaa aacataaaga aaggcccggc gccattctat   4500
ccgctggaag atggaaccgc tggagagcaa ctgcataagg ctatgaagag atacgccctg   4560
gttcctggaa caattgcttt tacagatgca catatcgagg tggacatcac ttacgctgag   4620
tacttcgaaa tgtccgttcg gttggcagaa gctatgaaac gatatgggct gaatacaaat   4680
cacagaatcg tcgtatgcag tgaaaactct cttcaattct ttatgccggt gttgggcgcg   4740
ttatttatcg gagttgcagt tgcgcccgcg aacgacattt ataatgaacg tgaattgctc   4800
aacagtatgg gcatttcgca gcctaccgtg gtgttcgtt ccaaaaaggg gttgcaaaaa   4860
attttgaacg tgcaaaaaaa gctcccaatc atccaaaaaa ttattatcat ggattctaaa   4920
acggattacc agggatttca gtcgatgtac acgttcgtca catctcatct acctcccggt   4980
tttaatgaat acgattttgt gccagagtcc ttcgataggg acaagacaat tgcactgatc   5040
atgaactcct ctggatctac tggtctgcct aaaggtgtcg ctctgcctca tagaactgcc   5100
tgcgtgagat tctcgcatgc cagagatcct atttttggca atcaaatcat tccggatact   5160
gcgattttaa gtgttgttcc attccatcac ggttttggaa tgtttactac actcggatat   5220
ttgatatgtg gatttcgagt cgtcttaatg tatagatttg aagaagagct gtttctgagg   5280
agccttcagg attacaagat tcaaagtgcg ctgctggtgc caaccctatt ctccttcttc   5340
gccaaaagca ctctgattga caaatacgat ttatctaatt tacacgaaat tgcttctggt   5400
ggcgctcccc tctctaagga agtcggggaa gcggttgcca agaggttcca tctgccaggt   5460
atcaggcaag gatatgggct cactgagact acatcagcta ttctgattac acccgagggg   5520
gatgataaac cgggcgcggt cggtaaagtt gttccatttt ttgaagcgaa ggttgtggat   5580
ctggataccg ggaaaacgct gggcgttaat caaagaggcg aactgtgtgt gagaggtcct   5640
atgattatgt ccggttatgt aaacaatccg gaagcgacca acgccttgat tgacaaggat   5700
ggatggctac attctggaga catagcttac tgggacgaag acgaacactt cttcatcgtt   5760
gaccgcctga agtctctgat taagtacaaa ggctatcagg tggctcccgc tgaattggaa   5820
tccatcttgc tccaacaccc caacatcttc gacgctggtg tcgcaggtct tcccgacgat   5880
gacgccggtg aacttcccgc cgccgttgtt gttttggagc acggaaagac gatgacggaa   5940
aaagagatcg tggattacgt cgccagtcaa gtaacaaccg cgaaaagtt gcgcggagga   6000
gttgtgtttg tggacgaagt accgaaaggt cttaccggaa aactcgacgc aagaaaaatc   6060
agagagatcc tcataaaggc caagaagggc ggaaagatcg ccgtgtaact cgagatatga   6120
agatgaagat gaaatatttg gtgtgtcaaa taaaaagctt gtgtgcttaa gtttgtgttt   6180
ttttcttggc ttgttgtgtt atgaatttgt ggcttttttct aatattaaat gaatgtaaga   6240
tcacattata atgaataaac aaatgtttct ataatccatt gtgaatgttt tgttggatct   6300
cttctgcagc ataaactac tgtatgtgct atggtatgga ctatgaata tgattaaaga   6360
taaggagctc cggtgacgga cccatggctt cgttgaacaa cggaaactcg acttgccttc   6420
cgcacaatac atcatttctt cttagctttt ttcttcttc ttcgttcata cagtttttt   6480
ttgtttatca gcttacattt tcttgaaccg tagctttcgt tttcttcttt ttaactttcc   6540
attcggagtt tttgtatctt gtttcatagt ttgtcccagg attagaatga ttaggcatcg   6600
aaccttcaag aatttgattg aataaaacat cttcattctt aagatatgaa gataatcttc   6660
aaaaggcccc tgggaatctg aaagaagaga agcaggccca tttatatggg aaagaacaat   6720
agtatttctt atataggccc attttaagttg aaaacaatct tcaaaagtcc cacatcgctt   6780
agataagaaa acgaagctga gtttatatac agctagagtc gaagtagtga ttgttgggat   6840
tagcgactcc atggttttag agctagaaat agcaagttaa aataaggcta gtccgttatc   6900
aacttgaaaa agtggcaccg agtcggtgct ttttttcccg gggcgcgccc atatcgagct   6960
ctcccggcgc gcctgcagtg cagcgtgacc cggtcgtgcc cctctctaga gataatgagc   7020
attgcatgtc taagttataa aaaattacca catattttt ttgtcacact tgtttgaagt   7080
gcagtttatc tatctttata catatattta aactttactc tacgaataat ataatctata   7140
gtactacaat aatatcagtg ttttagaaa tcatataaat gaacagttag acatggtcta   7200
aaggacaatt gagtatttg acaacaggac tctacagttt tatcttttta gtgtgcatgt   7260
gttctccttt ttttttgcaa atagcttcac ctatataata cttcatccat tttattagta   7320
catccattta gggtttaggg ttaatgtttt ttatagacta attttttag tacatctatt   7380
ttattctatt ttagcctcta aattaagaaa actaaaactc tattttagtt tttttattta   7440
ataatttaga tataaaatag aataaaataa agtgactaaa aattaaacaa atacccttta   7500
agaaattaaa aaaactaagg aaacatttt cttgtttcga gtagataatg ccagcctgtt   7560
aaacgccgtc gacgagtcta acggacacca accagcgaac cagcagcgtc gcgtcgggcc   7620
aagcgaagca gacggcacgg catctctgtc gctgcctctg gacccctctc gagagttccg   7680
ctccaccgtt ggacttgctc cgctgtcgga atccagaaat gcgtggcgg agcggcagac   7740
gtgagccgga acgcaggcg gcctcctcct cctctcacgg caccggcagc tacggggat   7800
tccttcccca ccgctccttc gctttccctt cctcgcccg cgtaataaat agacaccccc   7860
tccacccct ctttcccca actctcgtgt tg ttcggagcgc acacacacac aaccagatct   7920
ccccaaatc cacccgtcgg cacctccgct tcaaggtacg ccgctcgtcc tccccccccc   7980
ccctctctac cttctctaga tcggcgttcc ggtccatggt tagggccggg tagttctact   8040
tctgttcatg tttgtgttag atccgtgttt tgttagatc cgtgctgcta gcgttcgtac   8100
acggatgcga cctgtacgtc agacacgttc tgattgctaa cttgccagtg tttctctttg   8160
gggaatgtg ggatggctct agccgttccg cagacggat cgattcatg atttttttg   8220
tttcgttgca tagggtttgg tttgcccttt tcctttattt caatatatgc cgtgcacttg   8280
tttgtcgggt catcttttca tgctttttt tgtcttggtt gtgatgatgt ggtctggttg   8340
ggcggtcgtt ctagatcgga gtagaattaa ttctgtttca aactacctgg tggatttatt   8400
aattttggat ctgtatgtgt gtgccataca tattcatagt tacgaattga agatgatgga   8460
tggaaatatc gatctaggat aggtatacat gttgatgcgg gttttactga tgcatataca   8520
```

```
gagatgctttt tgttcgcttg gttgtgatga tgtggtgtgg ttgggcggtc gttcattcg   8580
ttctagatcg gagtgaatac tgtttcaaac tacctggtgt atttattaat tttggaact   8640
gtatgtgtgt gtcatacatc ttcatagtta cgagtttaag atggatggaa atatcgatct   8700
aggataggta tacatgttga tgtgggtttt actgatgcat atacatgatg gcatatgcag   8760
catctattca tatgctctaa ccttgagtac ctatctatta taataaacaa gtatgtttta   8820
taattatttt gatcttgata tacttggatg atggcatatg cagcagctat atgtggattt   8880
ttttagccct gccttcatac gctatttatt tgcttggtac tgtttctttt gtcgatgctc   8940
accctgttgt ttggtgttac ttcctgcagg cttccctaac ctttgcactg tccaaaatgg   9000
cttcctgatc ccctcacttc ctcgaatcaa tctaagaaga aactcaagcc gcaaccatta   9060
ggggcagatt aattgctgca ctttcagata atcaagcatg gccactgtga acaactggct   9120
cgctttctcc ctctccccgc aggagctgcc gccctcccag acgacggact ccacactcat   9180
ctcggccgcc accgccgacc atgtctccgg cgatgtctgc ttcaacatcc cccaagattg   9240
gagcatgagg ggatcagagc tttcggcgct cgtcgcggag ccgaagctgg aggacttcct   9300
cggcggcatc tccttctccg agcagcatca caaggccaac tgcaacatga tacccagcac   9360
tagcagcaca gtttgctacg ccagctcagg tgctagcacc ggctaccatc accagctgta   9420
ccaccagccc accagctcag cgctccactt cgcggactcc gtaatggtgg cctcctcggc   9480
cggtgtccac gacggcggtg ccatgctcag cgcggccgcc gctaacggtg tcgctggcgc   9540
tgccagtgcc aacggcggcg gcatcggcgct gtccatgatt aagaactggc tgcggagcca   9600
accggcgccc atgcagccga gggtggcggc ggctgagggc gcgcaggggc tctctttgtc   9660
catgaacatg gcggggacga cccaaggcgc tgctggcatg ccacttctcg ctggagagcg   9720
cgcacgggcc cccgagagtg tatccacgtc agcacagggt ggagccgtcg tcgtcacggc   9780
gccgaaggag gatagcggtg gcagcggtgt tgccggcgct ctagtagccg tgagcacgga   9840
cacgggtggc agcggcggcg cgtcggctga caacacggca aggaagacgg tggacacgtt   9900
cgggcagcgc acgtcgattt accgtggcgt gacaaggcat agatggactg ggagatatga   9960
ggcacatctt tgggataaca gttgcagaag ggaagggcaa actcgtaagg gtcgtcaagt  10020
ctatttaggt ggctatgata aagaggagaa agctgctagc gcttatgatc ttgctgctct  10080
gaagtactgg ggtgccacaa caacaacaaa ttttccagtg agtaactacg aaaaggagct  10140
ggaggacatg aagcacatga caaggcagga gtttgtagcg cctctgagaa ggaagtccag  10200
tggtttctcc agaggtgcat ccatttacag gggagtgact aggcatcacc aacatggaag  10260
atggcaagca cggattggac gagttgcagg gaacaaggat ctttacttgg gcaccttcag  10320
cacccaggag gaggcagcgg aggcgtacga catcgcggcg atcaagttcc gcggcctcaa  10380
cgccgtcacc aacttcgaca tgagccgcta cgacgtgaag tccatcctgg acagcagcgc  10440
cctccccatc ggcagcgccg ccaagcgcct caaggaggcc gaggccgcag cgtccgcgca  10500
gcaccaccat gcgggtgtcg tttcctatga cgttgggagg attgccagcc aactgggaag  10560
tggcggtgcc ctcgctgcgg cctatggtgc tcactatcac ggtgccgcgt ggccaacgat  10620
tgcattccag ccgggcgcgg cgtccaccgg actgtaccat ccttacgcgc agcagcctat  10680
gcgcggcggt ggatggtgta aacaagagca agatcacgct gtgatagcag cggcacactc  10740
cttgcaggat cttcatcatt tgaatctcgg agccgccggg gccacgact ttttctcggc  10800
agggcagcag gccgccgccg ctgcgatgca cggcctgggt agcatcgaca gtgcgtcgct  10860
ggagcacagc accggctcca actccgtcgt ctacaacggc ggggtcggcg acagcaacgg  10920
cgccagcgcc gtcggcggca gtggcggtgg ctacatgatg ccgatgagcg ctgccggagc  10980
aaccactaca tcggcaatgg tgagccacga gcaggtccat gcacgggcct acgacgaagc  11040
caagcaggct gctcagatgg ggtacgagag ctacctggtg aacgcggaga acaatggttag  11100
cggaaggatg tctgcatggg ggactgtcgt gtctgcagcc gcggcggcag cagcaagcag  11160
caacgacaac atggccgccg acgtgggcca cggcggcgcg cagctgttca gtgtctggaa  11220
cgacacttaa ctcgagccct agacttgtcc atcttctgga ttggccaagt taattaatgt  11280
atgaaataaa aggatgcaca catagtgaca tgctaatcac tataatggtg gcatcaaagt  11340
tgtgtgttat gtgtaattac taattatctg aataagagaa agagatcatc catatttctt  11400
atcctaaatg aatgtcacgt gtctttataa ttcctttgatg aaccagatgc atttttattaa  11460
ccaattccat atacatataa atattaatca tatataatta atatcaattg ggttagcaaa  11520
acaaatctag tctaggtgtg ttttgctaat tattggggga tagtgcaaaa agaaatctac  11580
gttctcaata attcagatag aaaacttaat aaagtgagat aatttacata gattgctttt  11640
atcctttgat atatgtgaaa ccatgcatga tataagaaa atagatagag aaataatttt  11700
ttacatcgtt gaatatgtaa acaatttaat tcaagaagct aggaatataa atattgagga  11760
gtttatgatt agagctcagt gttttgatcgc cggcggtacc gatgtactt caagtcagtg  11820
ggaaatcaat aaaatgatta ttttatgaat atatttcatt gtgcaagtag atagaaatta  11880
catatgttac ataacacacg aaataaacaa aaaagacaa tccaaaaaca aacacccccaa  11940
aaaaaataat cactttagat aaactcgtat gaggagaggc acgttcagtg actcgacgat  12000
tcccgagcaa aaaagtctc cccgtcacac atgtagtggg tgacgcaatt atctttaaag  12060
taatccttct gttgacttgt cattgataac atccagtctt cgtcaggatt gcaaagaatt  12120
atagaaggga tcccaccttt tattttcttc ttttttccat atttagggtt gacagtgaaa  12180
tcagactggc aacctattaa ttgcttccac aatgggacga acttgaaggg gatgtcgtcg  12240
atgatattat aggtggcgtg ttcatcgtag ttggtgaaat cgatggtacc gttccaatag  12300
ttgtcgtc cgagacttct agcccaggtg gtcttccggg tacgagttgg tccgcagatg  12360
tagaggctgg ggtgtcggat tccattcctt ccattgtcct tgttaaatcg gccatccatt  12420
caaggtcaga ttgagcttgt tggtatgaga caggatgtat gtaagtataa gcgtctatgc  12480
ttacatggta tagatgggtt tccctccagg agtgtagatc ttcgtggcag cgaagatctg  12540
attctgtgaa gggcgacaca tacggttcag gttgtggagg gaataaatttg ttggctgaat  12600
attccagcca ttgaagcttt gttgcccatt catgagggaa ttcttccttg atcatgtcaa  12660
gatattcctc cttagacgtt gcagtctgga taatagttct ccatcgtgcg tcagatttgc  12720
gaggagaaac cttatgatct cggaaatctc ctctggtttt aatatctccg tcctttgata  12780
tgtaatcaag gacttgttta gagtttctag ctggctggat attagggtga tttccttcaa  12840
aatcgaaaaa agaaggatcc ctaatacaag gtttttttatc aagctggaga agagcatgat  12900
agtgggtagt gccatcttga tgaagctcag aagcaaccac aaggaagaaa ataagaaaag  12960
gtgtgagttt ctcccagaga aactggaata aatcatctct ttgagatgag cacttgggat  13020
aggtaaggaa aacatattta gattggagtc tgaagttctt actagcagaa ggcatgttgt  13080
tgtgactccg aggggttgcc tcaaactcta tcttataacc ggcgtggagg catggaggca  13140
ggggtatttt ggtcatttta atagatagtg gaaaatgacg tggaatttac ttaaagacga  13200
agtctttgcg acaagggggg gcccacgccg aatttaatat taccggcgtg gccccccctt  13260
```

```
atcgcgagtg ctttagcacg agcggtccag atttaaagta gaaaatttcc cgcccactag   13320
ggttaaaggt gttcacacta taaaagcata tacgatgtga tggtatttga tggagcgtat   13380
attgtatcag gtatttccgt tggatacgaa ttattcgtac gaccctcata gtttaaacta   13440
tcagtgtttg acaggatata ttggcgggta aacctaagag aaaagagcgt ttattagaat   13500
aacggatatt taaaagggcg tgaaaaggtt tatccgttcg tccatttgta tgtgcatgat   13560
aaccacaggg ttccctcgg gatcaaagta ctttgatcca accctccgc tgctatagtg   13620
cagtcggctt ctgacgttca gtgcagccgt cttctgaaaa cgacatgtcg cacaagtcct   13680
aagttacgcg acaggctgcc gccctgccct tttcctggcg ttttcttgtc gcgtgtttta   13740
gtcgcataaa gtagaatact tgcgactaga accggagaca ttacgccatg aacaagagcg   13800
ccgccgctgg cctgctgggc tatgcccgcg tcagcaccga cgaccaggac ttgaccaacc   13860
aacgggccga actgcacgcg gccggctgca ccaagctgtt ttccgagaag atcaccggca   13920
ccaggcgcga ccgcccggag ctggccagga tgcttgacca cctacgccct ggcgacgttg   13980
tgacagtgac caggctagac cgcctggccc gcagcacccg cgacctactg gacattgccg   14040
agcgcatcca ggaggccggc gcgggcctgc gtagcctggc agagccgtgg gccgacacca   14100
ccacgccggc cggccgcatg gtgttgaccg tgttcgccgg cattgccgag ttcgagcgtt   14160
ccctaatcat cgaccgcacc cggagcgggc gcgaggccgc caaggcccga ggcgtgaagt   14220
ttggccccg ccctacccctc accccggcac agatcgcgca cgcccgcgag ctgatcgacc   14280
aggaaggccg caccgtgaaa gaggcggctg cactgcttgg cgtgcatcgc tcgaccctgt   14340
accgcgcact tgagcgcagc gaggaagtga cgcccaccga ggccaggcgg cgcggtgcct   14400
tccgtgagga cgcattgacc gaggccgacg ccctggcggc cgccgagaat gaacgccaag   14460
aggaacaagc atgaaaccgc accaggacgg ccaggacgaa ccgttttca ttaccgaaga   14520
gatcgaggcg gagatgatcg cggccgggta cgtgttcgga ccgcccgcc acggctcaac   14580
cgtgcggctg catgaaatcc tggccggttt gtctgatgcc aagctggcgg cctggccgg   14640
cagcttggcc gctgaagaaa ccgagcgccg ccgtctaaaa aggtgatgtg tatttgagta   14700
aaacagcttg cgtcatgcgg tcgctgcgta tatgatgcga tgagtaaata aacaaatacg   14760
caagggaac gcatgaaggt tatcgctgta cttaaccaga aaggcgggtc aggcaagacg   14820
accatcgcaa cccatctagc ccgcgccctg caactcgccg gggccgatgt tctgttagtc   14880
gattccgatc cccagggcag tgcccgcgat tgggcggccg tgcgggaaga tcaaccgcta   14940
accgttgtcg gcatcgaccg cccgacgatt gaccgcgacg tgaaggccat cggccggcgc   15000
gacttcgtag tgatcgacgg agcgccccag gcggcgact tcgtgtgtc cgcgatcaag   15060
gcagccgact tcgtgctgat tccggtgcag ccaagccctt acgacatatg ggccaccgcc   15120
gacctggtgg agctggttaa gcagcgcatt gaggtcacgg atggaaggct acaagcggcc   15180
tttgtcgtgt cgcggggcgat caaaggcacg cgcatcggcg gtgaggttgc cgaggcgctg   15240
gccgggtacg agctgcccat tcttgagtcc cgtatccgcg agcgcgtgag ctacccaggc   15300
actgccgccg ccggcacaac cgttcttgaa tcagaacccg agggcgacgc tgccgcgacg   15360
gtccaggcgc tggccgctga aattaaatca aaactcattt gagttaatga ggtaaagaga   15420
aaatgagcaa aagcacaaac acgctaagtg ccggccgtcc gagcgcacgc agcagcaagg   15480
ctgcaacgtt ggccagcctg gcagacacgc cagccatgaa gcgggtcaac tttcagttgc   15540
cggcggagga tcacaccaag ctgaagatgt acgcggtacg ccaaggcaag accattaccg   15600
agctgctatc tgaatacatc gcgcagctac cagagtaaat gagcaaatga ataaatgagt   15660
agatgaattt tagcggctaa aggaggcggc atggaaaatc aagaacaacc aggcaccgac   15720
gccgtggaat gcccccatgtg tggaggaacg ggcggttggc caggcgtaag cggctgggtt   15780
gtctgccgc cctgcaatgg cactggaacc cccaagcccg aggaatcggc gtgacggtcg   15840
caaaccatcc ggcccggtac aaatcggcgc ggcgctgggt gatgacctgg tggagaagtt   15900
gaaggccgcg caggccgccc agcggaacgc catcgaggca gaagcacgcc ccggtgaatc   15960
gtggcaagcg gccgctgatc gaatccgcaa agaatcccgg caaccgccgg cagccggtgc   16020
gccgtcgatt aggaagccgc ccaagggcga gcagcaacca gatttttttcg ttccgatgct   16080
ctatgacgtg gcacccgcg atagtcgcag catcatggac gtggccgttt tccgtctgtc   16140
gaagcgtgac cgacgagctg gcgaggtgat ccgctacgag cttccagacg gcacgtaga   16200
ggtttccgca gggccggccg gc                                            16222

SEQ ID NO: 38         moltype = DNA  length = 40
FEATURE               Location/Qualifiers
source                1..40
                      mol_type = other DNA
                      organism = Nicotiana benthamiana
SEQUENCE: 38
gttttggtag tagcgactcc atggggcata agtttagaat                         40

SEQ ID NO: 39         moltype = DNA  length = 39
FEATURE               Location/Qualifiers
source                1..39
                      mol_type = other DNA
                      organism = synthetic construct
SEQUENCE: 39
gttttggtag tagcgactca tggggcataa gtttagaat                          39

SEQ ID NO: 40         moltype = DNA  length = 40
FEATURE               Location/Qualifiers
source                1..40
                      mol_type = other DNA
                      organism = synthetic construct
SEQUENCE: 40
ttttggtagt agcgactccc atggggcata agtttagaat                         40

SEQ ID NO: 41         moltype = DNA  length = 33
FEATURE               Location/Qualifiers
source                1..33
                      mol_type = other DNA
```

```
                                    organism = synthetic construct
SEQUENCE: 41
gttttggtag tagatggggc ataagtttag aat                              33

SEQ ID NO: 42           moltype = DNA  length = 31
FEATURE                 Location/Qualifiers
source                  1..31
                        mol_type = other DNA
                        organism = synthetic construct
SEQUENCE: 42
gttttggtag tatggggcat aagtttagaa t                                31

SEQ ID NO: 43           moltype = DNA  length = 38
FEATURE                 Location/Qualifiers
source                  1..38
                        mol_type = other DNA
                        organism = synthetic construct
SEQUENCE: 43
gttttggtag tagcgactat ggggcataag tttagaat                         38

SEQ ID NO: 44           moltype = DNA  length = 40
FEATURE                 Location/Qualifiers
source                  1..40
                        mol_type = other DNA
                        organism = synthetic construct
SEQUENCE: 44
gttttggtag tagcgactcc aatggggcat aagtttagaa                       40

SEQ ID NO: 45           moltype = DNA  length = 37
FEATURE                 Location/Qualifiers
source                  1..37
                        mol_type = other DNA
                        organism = synthetic construct
SEQUENCE: 45
gttttggtag tagcgacatg gggcataagt ttagaat                          37

SEQ ID NO: 46           moltype = DNA  length = 19
FEATURE                 Location/Qualifiers
source                  1..19
                        mol_type = other DNA
                        organism = synthetic construct
SEQUENCE: 46
tggggcataa gtttagaat                                              19

SEQ ID NO: 47           moltype = DNA  length = 38
FEATURE                 Location/Qualifiers
source                  1..38
                        mol_type = other DNA
                        organism = synthetic construct
SEQUENCE: 47
gttttggtag tagcgactct ggggcataag tttagaat                         38

SEQ ID NO: 48           moltype = DNA  length = 36
FEATURE                 Location/Qualifiers
source                  1..36
                        mol_type = other DNA
                        organism = synthetic construct
SEQUENCE: 48
gttttggtag tagcgaatgg ggcataagtt tagaat                           36

SEQ ID NO: 49           moltype = DNA  length = 15
FEATURE                 Location/Qualifiers
source                  1..15
                        mol_type = other DNA
                        organism = synthetic construct
SEQUENCE: 49
gttttggtag tagcg                                                  15

SEQ ID NO: 50           moltype = DNA  length = 34
FEATURE                 Location/Qualifiers
source                  1..34
                        mol_type = other DNA
                        organism = synthetic construct
SEQUENCE: 50
gttttggtag tagcatgggg cataagttta gaat                             34

SEQ ID NO: 51           moltype = DNA  length = 20
FEATURE                 Location/Qualifiers
source                  1..20
```

```
                            mol_type = other DNA
                            organism = synthetic construct
SEQUENCE: 51
gttttggtag tagcgactcc                                               20

SEQ ID NO: 52               moltype = DNA   length = 20
FEATURE                     Location/Qualifiers
source                      1..20
                            mol_type = other DNA
                            organism = synthetic construct
SEQUENCE: 52
atggggcata agtttagaat                                               20

SEQ ID NO: 53               moltype = DNA   length = 28
FEATURE                     Location/Qualifiers
source                      1..28
                            mol_type = other DNA
                            organism = synthetic construct
SEQUENCE: 53
gttttggtat ggggcataag tttagaat                                      28

SEQ ID NO: 54               moltype = DNA   length = 40
FEATURE                     Location/Qualifiers
source                      1..40
                            mol_type = other DNA
                            organism = synthetic construct
SEQUENCE: 54
gttttggtag tagcgactcc tatggggcat aagtttagaa                         40

SEQ ID NO: 55               moltype = DNA   length = 34
FEATURE                     Location/Qualifiers
source                      1..34
                            mol_type = other DNA
                            organism = synthetic construct
SEQUENCE: 55
cttctggtca tggcatgggg cataagttta gaat                               34

SEQ ID NO: 56               moltype = DNA   length = 31
FEATURE                     Location/Qualifiers
source                      1..31
                            mol_type = other DNA
                            organism = synthetic construct
SEQUENCE: 56
gttttggtag tagcgggcat aagtttagaa t                                  31

SEQ ID NO: 57               moltype = DNA   length = 23
FEATURE                     Location/Qualifiers
source                      1..23
                            mol_type = other DNA
                            organism = synthetic construct
SEQUENCE: 57
gttttggggc ataagtttag aat                                           23

SEQ ID NO: 58               moltype = DNA   length = 39
FEATURE                     Location/Qualifiers
source                      1..39
                            mol_type = other DNA
                            organism = synthetic construct
SEQUENCE: 58
tcaatcatag tgcgagaaca tcggtgagat ttgtcatgt                          39

SEQ ID NO: 59               moltype = DNA   length = 21
FEATURE                     Location/Qualifiers
source                      1..21
                            mol_type = other DNA
                            organism = synthetic construct
SEQUENCE: 59
catggggcat aagtttagaa t                                             21

SEQ ID NO: 60               moltype = DNA   length = 16
FEATURE                     Location/Qualifiers
source                      1..16
                            mol_type = other DNA
                            organism = synthetic construct
SEQUENCE: 60
gttttggtag tagaat                                                   16

SEQ ID NO: 61               moltype = DNA   length = 36
FEATURE                     Location/Qualifiers
```

```
source                  1..36
                        mol_type = other DNA
                        organism = synthetic construct
SEQUENCE: 61
gttttggtag tagcgcatgg ggcataagtt tagaat                              36

SEQ ID NO: 62           moltype = DNA   length = 13
FEATURE                 Location/Qualifiers
source                  1..13
                        mol_type = other DNA
                        organism = synthetic construct
SEQUENCE: 62
gttttggtag aat                                                       13

SEQ ID NO: 63           moltype = DNA   length = 35
FEATURE                 Location/Qualifiers
source                  1..35
                        mol_type = other DNA
                        organism = synthetic construct
SEQUENCE: 63
gttttggtag tagcgatggg gcataagttt agaat                               35

SEQ ID NO: 64           moltype = DNA   length = 34
FEATURE                 Location/Qualifiers
source                  1..34
                        mol_type = other DNA
                        organism = synthetic construct
SEQUENCE: 64
gttttggtag tagcgactgg cataagttta gaat                                34

SEQ ID NO: 65           moltype = DNA   length = 39
FEATURE                 Location/Qualifiers
source                  1..39
                        mol_type = other DNA
                        organism = synthetic construct
SEQUENCE: 65
gttttggtag tagcgactcc tggggcataa gtttagaat                           39

SEQ ID NO: 66           moltype = DNA   length = 15
FEATURE                 Location/Qualifiers
source                  1..15
                        mol_type = other DNA
                        organism = synthetic construct
SEQUENCE: 66
gcataagttt agaat                                                     15

SEQ ID NO: 67           moltype = DNA   length = 40
FEATURE                 Location/Qualifiers
source                  1..40
                        mol_type = other DNA
                        organism = synthetic construct
SEQUENCE: 67
gttttggtag tagcgactct atggggcata agtttagaat                          40

SEQ ID NO: 68           moltype = DNA   length = 40
FEATURE                 Location/Qualifiers
source                  1..40
                        mol_type = other DNA
                        organism = synthetic construct
SEQUENCE: 68
ttttggtagt agcgactcac atggggcata agtttagaat                          40

SEQ ID NO: 69           moltype = DNA   length = 30
FEATURE                 Location/Qualifiers
source                  1..30
                        mol_type = other DNA
                        organism = synthetic construct
SEQUENCE: 69
gttttggtag tagcgacata agtttagaat                                     30

SEQ ID NO: 70           moltype = DNA   length = 40
FEATURE                 Location/Qualifiers
source                  1..40
                        mol_type = other DNA
                        organism = synthetic construct
SEQUENCE: 70
gttttggtag tagcgactcc atggggcata agtgtagaat                          40

SEQ ID NO: 71           moltype = DNA   length = 40
```

```
FEATURE                 Location/Qualifiers
source                  1..40
                        mol_type = other DNA
                        organism = synthetic construct
SEQUENCE: 71
gttttggtag tagcgactcc atggggcata agtttagaag                              40

SEQ ID NO: 72           moltype = DNA   length = 40
FEATURE                 Location/Qualifiers
source                  1..40
                        mol_type = other DNA
                        organism = synthetic construct
SEQUENCE: 72
gttttggtag tagcgactcc atggggcata agttgagaat                              40

SEQ ID NO: 73           moltype = DNA   length = 30
FEATURE                 Location/Qualifiers
source                  1..30
                        mol_type = other DNA
                        organism = synthetic construct
SEQUENCE: 73
gttttggtag atggggcata agtttagaat                                         30

SEQ ID NO: 74           moltype = DNA   length = 40
FEATURE                 Location/Qualifiers
source                  1..40
                        mol_type = other DNA
                        organism = synthetic construct
SEQUENCE: 74
gttttggtag tagcgactcc aatagtatgg ccgtatactt                              40

SEQ ID NO: 75           moltype = DNA   length = 23
FEATURE                 Location/Qualifiers
source                  1..23
                        mol_type = other DNA
                        organism = synthetic construct
SEQUENCE: 75
gttttggggc ataagtttag aat                                                23

SEQ ID NO: 76           moltype = DNA   length = 29
FEATURE                 Location/Qualifiers
source                  1..29
                        mol_type = other DNA
                        organism = synthetic construct
SEQUENCE: 76
gttttggtag tagcgactcc gtttagaat                                          29

SEQ ID NO: 77           moltype = DNA   length = 40
FEATURE                 Location/Qualifiers
source                  1..40
                        mol_type = other DNA
                        organism = synthetic construct
SEQUENCE: 77
gttttggtag tagcgaatcc atggggcata agtttagaat                              40

SEQ ID NO: 78           moltype = DNA   length = 57
FEATURE                 Location/Qualifiers
source                  1..57
                        mol_type = other DNA
                        organism = synthetic construct
SEQUENCE: 78
acactctttc cctacacgac gctcttccga tctcaattgc cgttaatttg agagtcc           57

SEQ ID NO: 79           moltype = DNA   length = 57
FEATURE                 Location/Qualifiers
source                  1..57
                        mol_type = other DNA
                        organism = synthetic construct
SEQUENCE: 79
acactctttc cctacacgac gctcttccga tctcgtttgc cgttaatttg agagtcc           57

SEQ ID NO: 80           moltype = DNA   length = 57
FEATURE                 Location/Qualifiers
source                  1..57
                        mol_type = other DNA
                        organism = synthetic construct
SEQUENCE: 80
acactctttc cctacacgac gctcttccga tcttttcctgc cgttaatttg agagtcc          57
```

```
SEQ ID NO: 81              moltype = DNA   length = 57
FEATURE                    Location/Qualifiers
source                     1..57
                           mol_type = other DNA
                           organism = synthetic construct
SEQUENCE: 81
acactctttc cctacacgac gctcttccga tctgtcgtgc cgttaatttg agagtcc        57

SEQ ID NO: 82              moltype = DNA   length = 57
FEATURE                    Location/Qualifiers
source                     1..57
                           mol_type = other DNA
                           organism = synthetic construct
SEQUENCE: 82
acactctttc cctacacgac gctcttccga tctgatttgc cgttaatttg agagtcc        57

SEQ ID NO: 83              moltype = DNA   length = 56
FEATURE                    Location/Qualifiers
source                     1..56
                           mol_type = other DNA
                           organism = synthetic construct
SEQUENCE: 83
gactggagtt cagacgtgtg ctcttccgat cttgctatgc tcgtgatcat aaattc         56

SEQ ID NO: 84              moltype = DNA   length = 56
FEATURE                    Location/Qualifiers
source                     1..56
                           mol_type = other DNA
                           organism = synthetic construct
SEQUENCE: 84
gactggagtt cagacgtgtg ctcttccgat ctatagatgc tcgtgatcat aaattc         56

SEQ ID NO: 85              moltype = DNA   length = 56
FEATURE                    Location/Qualifiers
source                     1..56
                           mol_type = other DNA
                           organism = synthetic construct
SEQUENCE: 85
gactggagtt cagacgtgtg ctcttccgat ctccccatgc tcgtgatcat aaattc         56

SEQ ID NO: 86              moltype = DNA   length = 56
FEATURE                    Location/Qualifiers
source                     1..56
                           mol_type = other DNA
                           organism = synthetic construct
SEQUENCE: 86
gactggagtt cagacgtgtg ctcttccgat cttgaaatgc tcgtgatcat aaattc         56

SEQ ID NO: 87              moltype = DNA   length = 56
FEATURE                    Location/Qualifiers
source                     1..56
                           mol_type = other DNA
                           organism = synthetic construct
SEQUENCE: 87
gactggagtt cagacgtgtg ctcttccgat ctcgctatgc tcgtgatcat aaattc         56

SEQ ID NO: 88              moltype = DNA   length = 19658
FEATURE                    Location/Qualifiers
source                     1..19658
                           mol_type = other DNA
                           organism = synthetic construct
SEQUENCE: 88
ggaaagcaga aagacgacct ggtagaaacc tgcattcggt taaacaccac gcacgttgcc      60
atgcagcgta cgaagaaggc caagaacggc cgcctggtga cggtatccga gcacgttgcc     120
ttgattagcc gctacaagat cgtaaagagc gaaaccgggc ggccggagta catcgagatc     180
gagctagctg attggatgta ccgcgagatc acagaaggca agaacccgga cgtgctgacg     240
gttcaccccg attactttt gatcgatccc ggcatcggcc gttttctcta ccgcctggca     300
cgccgcgccg caggcaaggc agaagccaga tggttgttca agacgattca cgaacgcagt     360
ggcagcgccg agagttcaa gaagttctgt ttcaccgtgc gcaagctgat cgggtcaaat     420
gacctgccgg agtacgattt gaaggaggag gcgggcgcagg ctggcccgat cctagtcatg     480
cgctaccgca acctgatcga gggcgaagca tccgccggtt cctaatgtac ggagcagatg     540
ctagggcaaa ttgccctagc aggggaaaaa ggtcgaaaag gcctctttcc tgtggatagc     600
acgtacattg gaaccccaaa gccgtacatt gggaaccgga accgtacat tgggaaccca     660
aagccgtaca ttgggaaccg gtcacacatg taagtgactg atatataaag gaaaaaaggc     720
gatttttccg cctaaaactc tttaaaactt attaaaactc ttaaaacccg cctggccgtgt     780
gcataactgt ctgccagcg cacagccgaa gagctgcaaa aagcgcctac ccttcggtcg     840
ctgcgctccc tacgccccgc cgcttcgcgt cggcctatcg cggccgctgg ccgctcaaaa     900
atggctggca tacggccagg caatctacca gggcgcggac aagccgcgcc gtcgccactc     960
gaccgccggc gcccacatca aggcaccctg cctcgcgcgt ttcggtgatg acggtgaaaa    1020
```

```
cctctgacac atgcagctcc cggaaacggt cacagcttgt ctgtaagcgg atgccgggag   1080
cagacaagcc cgtcagggcg cgtcagcggg tgttggcggg tgtcgggcg cagccatgac    1140
ccagtcacgt agcgatagcg gagtgtatac tggcttaact atgcggcatc agagcagatt   1200
gtactgagag tgcaccatat gcggtgtgaa ataccgcaca gatgcgtaag gagaaaatac   1260
cgcatcaggc gctcttccgc ttcctcgctc actgactcgc tgcgctcggt cgttcggctg   1320
cggcgagcgg tatcagctca ctcaaaggcg gtaatacggt tatccacaga atcaggggat   1380
aacgcaggaa agaacatgtg agcaaaaggc cagcaaaagg ccaggaaccg taaaaaggcc   1440
gcgttgctgg cgtttttcca taggctccgc cccctgacg agcatcacaa aaatcgacgc    1500
tcaagtcaga ggtggcgaaa cccgacagga ctataaagat accaggcgtt tccccctgga   1560
agctccctcg tgcgctctcc tgttccgacc ctgccgctta ccggatacct gtccgccttt   1620
ctcccttcgg gaagcgtggc gctttctcat agctcacgct gtaggtatct cagttcggtg   1680
taggtcgttc gctccaagct gggctgtgtg cacgaacccc ccgttcagcc cgaccgctgc   1740
gccttatccg gtaactatcg tcttgagtcc aacccggtaa gacacgactt atcgccactg   1800
gcagcagcca ctggtaacag gattagcaga gcgaggtatg taggcggtgc tacagagttc   1860
ttgaagtggt ggcctaacta cggctacact agaaggacag tatttggtat ctgcgctctg   1920
ctgaagccag ttaccttcgg aaaaagagtt ggtagctctt gatccggcaa acaaaccacc   1980
gctggtagcg gtggtttttt tgtttgcaag cagcagatta cgcgcagaaa aaaggatct    2040
caagaagatc ctttgatctt ttctacgggg tctgacgctc agtggaacga aaactcacgt   2100
taagggattt tggtcatgca ttctaggtac taaaacaatt catccagtaa aatataaat    2160
tttattttct cccaatcagg cttgatcccc agtaagtcaa aaaatagctc gacatactgt   2220
tcttcccga tatcctccct gatcgaccgg acgcagaagg caatgtcata ccacttgtcc    2280
gccctgccgc ttctcccaag atcaataaag ccacttactt tgccatctct cacaaagatg   2340
ttgctgtctc ccaggtcgcc gtgggaaaag acaagttcct cttcgggctt ttccgtcttt   2400
aaaaaatcat acagctcgcg cggatcttta aatggagtgt cttcttccca gttttcgcaa   2460
tccacatcgg ccagatcgtt attcagtaag taatccaatt cggctaagcg gctgtctaag   2520
ctattcgtat agggacaatc cgatatgtcg atggagtgaa agagcctgat gcactccgca   2580
tacagctcga taatctttc agggctttgt tcatcttcat actcttccga gcaaaggacg    2640
ccatcggcct cactcatgag cagattgctc cagccatcat gccgttcaaa gtgcaggacc   2700
tttggaacag gcagctttcc ttccagccat agcatcatgt ccttttcccg ttccacatca   2760
taggtggtcc ctttataccg gctgtccgtc attttttaaat ataggttttc atttttctccc  2820
accagcttat ataccttagc aggagacatt ccttccgtat cttttacgca gcggtatttt   2880
tcgatcagtt ttttcaattc cggtgatatt ctcattttag ccatttatta tttccttcct   2940
cttttctaca gtatttaaag atacccccaag aagctaatta taacaagacg aactccaatt   3000
cactgttcct tgcattctaa aaccttaaat accagaaaac agcttttttca aagttgttt    3060
caaagttggc gtataacata gtatcgacgg agccgatttt gaaaccgcgg tgatcacagg   3120
cagcaacgct ctgtcatcgt tacaatcaac atgctaccct ccgcgagatc atccgtgttt   3180
caaaccggc agcttagttg ccgttcttcc gaatagcatc ggtaacatga gcaaagtctg    3240
ccgccttaca acggctctcc cgctgacgcc gtcccggact gatgggctgc ctgtatcgag   3300
tggtgatttt gtgccgagct gccggtcggg gagctgttgg ctggctggtg gcaggatata   3360
ttgtggtgta aacaaattga cgcttagaca acttaataac acattgcgga cgttttaat    3420
gtagagctca aagtttaacg cgttagcaga aggcatgttg ttgtgactcc gaggggttgc   3480
ctcaaactct atcttataac cggcgtggag gcatggaggc aggggtattt tggtcatttt   3540
aatagatagt ggaaaatgac gtggaattta cttaaagacg aagtctttgc gacaagggg    3600
ggcccacgcc gaatttaata ttaccggcgt ggcccccct tatcgcgagt gctttagcac    3660
gagcggtcca gatttaaagt agaaaatttc ccgcccacta gggttaaagg tgttcacact   3720
ataaaagcat atacgatgtg atggtatttg atggagcgta tattgtatca ggtatttccg   3780
ttggatacga attattcgta cgaccctcgg taccgatcgg cgccagat ttgccttttc     3840
aatttcagaa agaatgctaa cccacagatg gttagagagg cttacgcagc aggtatcatc   3900
aagacgatct acccgagcaa taatctccag gaaatcaaat accttcccaa gaaggttaaa    3960
gatgcagtca aaagattcag gactaactgc atcaagaaca cagagaaaga tatttctc     4020
aagatcagaa gtactattcc agtatggacg attcaaggct tgcttcacaa accaaggcaa   4080
gtaatagaga ttggagtctc taaaaaggta gttcccactg aatcaaaggc catggagtca   4140
aagattcaaa tagaggacct aacagaactc gccgtaaaga ctggcgaaca gttcatacag   4200
agtctcttac gactcaatga caagaagaaa atcttcgtca acatggtgga gcacgacaca   4260
cttgtctact ccaaaaatat caaagataca gtctcagaag accaaagggc aattgagact   4320
tttcaacaaa gggtaatatc cggaaacctc ctcggattcc attgcccagc tatctgtcac   4380
tttattgtga aatagtgga aaggaaggt ggctcctaca aatgccatca ttgcgataaa     4440
ggaaaggcca tcgttgaaga tgcctctgcc gacagtggtc ccaaagatgg accccacccc    4500
acgaggacga tcgtggaaaa agaagacgtt ccaaccacgt cttcaaagca agtggattga   4560
tgtgatatct ccactgacgt aagggatgac gcacaatccc actatccttc gcaagaccct   4620
tcctctatat aaggaagttc atttcatttg gagagaacac ggggggactcc tgcaggtaga  4680
tcgctcgtcg acatggataa gaagtactct atcggactcg atatcggaac taactctgtg   4740
ggatgggctg tgataccga tgagtacaag gtgccatcta agaagttcaa ggttctcgga    4800
aacaccgata ggcactctat caagaaaaac cttatcgtgc ctctcctctt cgattctgag   4860
gaaactgctg aggctaccag actcaagaga accgctagaa gaaggtacac cagaagaaag   4920
aacaggatct gctacctcca agagatcttc tctaacgaga tggctaaagt ggatgattca   4980
ttcttccaca ggctcgaaga gtcattcctc gtggaagaag ataagaagca cgagaggcac   5040
cctatcttcg gaaacatcgt tgatgaggtg gcataccacg agaagtaccc tactatctac   5100
cacctcagaa agaagctcgt tgattctact gataaggctg atctcaggct catctctccc   5160
gctctcgctc acatgatcaa gttcagagga cacttcctca tcgagggtga tctcaaccct   5220
gataactctg atgtggataa gttgttcatc cagctcgtgc agacctacaa ccagttttc    5280
gaagagaacc ctatcaacgc ttcaggtgtg atgctaagg ctatcctctc tgctaggctc    5340
tctaagtcaa gaaggcttga gaacctcatt gctcagctcc ctggtgagaa gaagaacgga   5400
cttttcggaa acttgatcgc tctctctctc ggactcaccc ctaacttcaa gtctaacttc   5460
gatctcgctg aggatgcaaa gctccagctc tcaaaggata cctacgatga tgatctcgat   5520
aacctcctcg ctcagatcgg agatcagtac gctgatttgt tcctcgctgc taagaacctc   5580
tctgatgcta tcctcctcag tgatatcctc agagtgaaca ccgagatcac caaggctcca   5640
ctctcagctt ctatgatcaa gagatacgat gagcaccacc aggatctcac acttctcaag   5700
gctcttgtta gacagcagct cccagagaag tacaaagaga ttttcttcga tcagtctaag   5760
```

```
aacggatacg ctggttacat cgatggtggt gcatctcaag aagagttcta caagttcatc   5820
aagcctatcc tcgagaagat ggatggaacc gaggaactcc tcgtgaagct caatagagag   5880
gatcttctca gaaagcagag gaccttcgat aacggatcta tccctcatca gatccacctc   5940
ggagagttgc acgctatcct tagaaggcaa gaggatttct acccattcct caaggataac   6000
agggaaaaga ttgagaagat tctcaccttc agaatccctt actacgtggg acctctcgct   6060
agaggaaact caagattcgc ttggatgacc agaaagtctg aggaaaccat caccccttgg   6120
aacttcgaag aggtggtgga taagggtgct agtgctcagt ctttcatcga gaggatgacc   6180
aacttcgata agaaccttcc aaacgagaag gtgctcccta agcactcttt gctctacgag   6240
tacttcaccg tgtacaacga gttgaccaag gttaagtacg tgaccgaggg aatgaggaag   6300
cctgcttttt tgtcaggtga gcaaaagaag gctatcgttg atctcttgtt caagaccaac   6360
agaaaggtga ccgtgaagca gctcaaagag gattacttca agaaaatcga gtgcttcgat   6420
tcagttgaga tttctggtgt tgaggatagg ttcaacgcat ctctcggaac ctaccacgat   6480
ctcctcaaga tcattaagga taaggatttc ttggataacg aggaaaacga ggatatcttg   6540
gaggatatcg ttcttaccct caccctcttt gaagatagag agatgattga agaaaggctc   6600
aagacctacg ctcatctctt cgatgataag gtgatgaagc agttgaagag aagaagatac   6660
actggttggg gaaggctctc aagaaagctc attaacggaa tcaggataag gcagtctgga   6720
aagacaatcc ttgatttcct caagtctgat ggattcgcta cagaaacttc atgcagctc   6780
atccacgatg attctctcac ctttaaagag gatatccaga aggctcaggt ttcaggacag   6840
ggtgatagtc tccatgagca tatcgctaac ctcgctggat ctcctgcaat caagaaggga   6900
atcctccaga ctgtgaaggt tgtcgatgag ttggtgaagg tgatgggaag gcataagcct   6960
gagaacatcg tgatcgaaat ggctagagag aaccagacca ctcagaaggg acagaagaac   7020
tctagggaaa ggatgaagag gatcgagaaa ggtatcaaga agcttggatc tcagatcctc   7080
aaagagcacc ctgttgagaa cactcagctc cagaatgaga agctctacct ctactacctc   7140
cagaacggaa gggatatgta tgtggatcaa gagttggata tcaacaggct ctctgattac   7200
gatgttgatc atatcgtgcc acagtcattc ttgaaggatg attctatcga taacaaggtg   7260
ctcaccaggt ctgataagaa caggggtaag agtgataacg tgccaagtga aggggttgtg   7320
aagaaaatga gaactattg gaggcagctc ctcaacgcta agctcatcac tcagagaaag   7380
ttcgataact tgactaaggc tgagagggga ggactctctg aattggataa ggcaggattc   7440
atcaagaggc agcttgtgga aaccaggcag atcactaagc acgttgcaca gatcctcgat   7500
tctaggataa acaccaagta cgatgagaac gataagttga tcagggaagt gaaggttatc   7560
accctcaagt caaagctcgt gtctgatttc agaaaggatt tccaattcta caaggtgagg   7620
gaaatcaaca actaccacca cgctcacgat gcttacctta acgctgttgt tggaaccgct   7680
ctcatcaaga gtatcctaa gctcgagtca gagttcgtgt acggtgatta caaggtgtac   7740
gatgtgagaa agatgatcgc taagtctgag caagagatcg gaaaggctac cgctaagtat   7800
ttcttctact ctaacatcat gaatttcttc aagaccgaga ttaccctcgc taacggtgag   7860
atcagaaaga ggccactcat cgagacaaac ggtgaaacag gtgagatcgt gtgggataag   7920
ggaagggatt tcgctaccgt tagaaaggtg ctctctatgc cacaggtgaa catcgttaag   7980
aaaaccgagg tgcagaccgg tggattctct aaagagtcta tcctccctaa gaggaactct   8040
gataagctca ttgctaggaa gaaggattgg gaccctaaga aatacggtgg tttcgattct   8100
cctaccgtgg cttactctgt tctcgttgtg gctaaggttg agaagggaaa gagtaagaag   8160
ctcaagtctg ttaaggaact tctcggaatc actatcatgg aaaggtcatc tttcgagaag   8220
aacccaatcg atttcctcga ggctaaggga tacaaagagg ttaagaagga tctcatcatc   8280
aagctcccaa agtactcact cttcgaactc gagaacggta gaaagaggat gctcgcttct   8340
gctggtgagc ttcaaaaggg aaacgagctt gctctcccat ctaagtacgt taactttctt   8400
tacctcgctt ctcactacga gaagttgaag ggatctccag aagataacga gcagaagcaa   8460
cttttcgttg agcagcacaa gcactacttg gatgagatca tcgagcagat ctctgagttc   8520
tctaaaaggg tgatcctcgc tgatgcaaac ctcgataagg tgttgtctgc ttacaacaag   8580
cacagagata agcctatcag ggaacaggca gagaacatca tccatctctt cacccttacc   8640
aacctcggtg ctcctgctgc tttcaagtac ttcgatacaa ccatcgatag gaagagatac   8700
acctctacca agaagtgct cgatgctacc ctcatccatc agtctatcac tggactctac   8760
gagactagga tcgatctctc acagctcggt ggtgattcaa gggctgatcc taagaagaag   8820
aggaaggttt gacgtcgacg atatgaagat gaagatgaaa tatttggtgt gtcaaataaa   8880
aagcttgtgt gcttaagttt gtgtttttt cttggcttgt tgtgttatga atttgtggct   8940
ttttctaata ttaaatgaat gtaagatcac attataatga ataaacaaat gtttctaaa   9000
tccattgtga atgttttgtt ggatctcttc tgcagcatat aactactgta tgtgctatgg   9060
tatggactat ggaatatgat taaagataag ccagagctct ggtgacggac ccatggcttc   9120
gttgaacaac ggaaactcga cttgccttcc gcacaataca tcatttcttc ttagctttt   9180
ttcttcttct tcgttcatac agttttttt tgtttatcag cttacatttt cttgaaccgt   9240
agcttttcgtt ttcttctttt taacttttcca ttcggagttt ttgtatcttg tttcatagtt   9300
tgtcccagga ttagaatgat taggcatcga accttcaaga atttgattga ataaacatc   9360
ttcattctta agatatgaag ataatcttca aaaggcccct gggaatctga agaagagaa   9420
gcaggcccat ttatatggga aagaacaata gtatttctta tataggccca tttaagttga   9480
aaacaatctt caaaagtccc acatcgctta gataagaaaa cgaagctgag tttatataca   9540
gctagagtcg aagtagtgat tgcctacttg ggctgttgca ggtttagag ctagaaatag   9600
caagttaaaa taaggctagt ccgttatcaa cttgaaaaag tggcaccgag tcggtgcttt   9660
ttttcccggg cgcgccgatc atgagcggag aattaaggga gtcacgttat gaccccgcc   9720
gatgacgcgg gacaagccgt tttacgtttg gaactgacag aaccgcaacg ttgaaggagc   9780
cactcagccg cgggtttctg gagtttaatg agctaagcac atacgtcaga aaccattatt   9840
gcgcgttcaa aagtcgccta aggtcactat cagctagcaa atatttcttg tcaaaaatgc   9900
tccactgacg ttccataaat tcccctcggt atccaattag agtctcatat tcactctcaa   9960
tccaaataat ctgcaccgta cctgcagggt ccgagctagg tcacagaagc gctcaggaag  10020
gccgctgaga tagaggcatg gcggccaatg cgggcggcgg tggagcggga ggaggcagcg  10080
gcagcggcag cgtggctgcg ccggcggtgt gccgcccag cggctcgcgg tggacgccga  10140
cgccgggaca gatcaggatg ctgaaggagc tgtactacgg cggtcgccca  10200
gctcggagca gatccagcgc atcaccgcca tgctgcggca gcacggcaag atcgagggca  10260
agaacgtctt ctactggttc cagaaccaca aggcccgcga gcgccagaag cgccgcctca  10320
ccagcctcga cgtgaacgtg cccgcgccg gcgcggccga cgccaccacc agccaactcg  10380
gcgtcctctc gctgtcgtcg ccgccgcctt caggcgcggc gcctccctcg cccacccctcg  10440
gcttctacgc cgccggcaat ggcggcggat cggctgtgct gctggacacg agttccgact  10500
```

```
ggggcagcag cggcgctgcg atggccaccg agacatgctt cctccaggac tacatgggcg  10560
tgacggacac gggcagctcg tcgcagtggc cacgcttctc gtcgtcggac acgataatgg  10620
cggcggccgc ggcgcgggcg gcgacgacgc gggcgcccga gactctccct ctcttcccga  10680
cctgcggcga cgacggcggc agcggtagca gcagctactt gccgttctgg ggtgccgcgt  10740
ccacaactgc cggcgccact tcttccgttg cgatccgaca gcaacaccag ctgcaggagc  10800
agtacagctt ttacagcaac agcaacagca cccagctggc cggcaccggc aaccaagacg  10860
tatcggcaac agcagcagca gccgccgccc tggagctgag cctcagctca tggtgctccc  10920
cttaccctgc tgcagggagt atgtgagagc aacgcgagct gccactgctc ttcacttatg  10980
tctctggaat ggaaggagga ggaagtgagc atagcgttgg tgcgttgctg tcattgtcct  11040
aggttagtag ctagtgccag ttactagtaa gcatcaggca taggagtatg tagtagaagc  11100
atgcacgttg ccggccagcc aggctttaga cgggaaaaga atttggtgca gccggctgca  11160
aaacaggatg tttacagccc cccctcgag ccctagactt gtccatcttc tggattggcc  11220
aagttaatta atgtatgaaa taaaaggatg cacacatagt gacatgctaa tcactataat  11280
gtgggcatca aagttgtgtg ttatgtgtaa ttactaatta tctgaataag agaaagagat  11340
catccatatt tcttatccta aatgaatgtc acgtgtcttt ataattcttt gatgaaccag  11400
atgcatttta ttaaccaatt ccatatacat ataatatta tcatatata attaatatca  11460
attgggttag caaaacaaat ctagtctagg tgtgttttgc taattattgg gggatagtgc  11520
aaaaagaaat ctacgttctc aataattcag atagaaaact taataaagtg agataattta  11580
catagattgc ttttatcctt tgatatatgt gaaaccatgc atgatataag gaaaatagat  11640
agagaaataa tttttacat cgttgaatat gtaaacaatt taattcaaga agctaggaat  11700
ataaatattg aggagtttat gattagagct ctcccggcgc gccctatgtc gagctgcagg  11760
tcaacggatc aggatattct tgtttaagat gttgaactct atggaggttt gtatgaactg  11820
atgatctagg accggataag ttcccttctt catagcgaac ttattcaaag aatgttttgt  11880
gtatcattct tgttacattg ttattaatga aaaaatatta ttggtcattg gactgaacac  11940
gagtgttaaa tatggaccag gccccaaata agatccattg atatatgaat taaataacaa  12000
gaataaatcg agtcaccaaa ccacttgcct tttttaacga gacttgttca ccaacttgat  12060
acaaaagtca ttatcctatg caaatcaata atcatacaaa aatatccaat aacactaaaa  12120
aattaaaaga aatggataat ttcacaatat gttatacgat aaagaagtta ctttttccaag  12180
aaattcactg attttataag cccacttgca ttagataaat ggcaaaaaaa aacaaaaagg  12240
aaaaagaaata aagcacgaag aattctagaa aatacgaaat acgcttcaat gcagtgggac  12300
ccacggttca attattgcca atttttcagct ccaccgtata tttaaaaaat aaaacgataa  12360
tgctaaaaaa atataaatcg taacgatcgt taaatctcaa cggctggatc ttatgacgac  12420
cgttagaaat tgtggttgtc gacgagtcag taataaacgg cgtcaaagtg gttgcagccg  12480
gcacacacga gtcgtgttta tcaactcaaa gcacaaatac ttttcctcaa cctaaaaata  12540
aggcaattag ccaaaaacaa ctttgcgtgt aaacaacgct caatacacgt gtcattttat  12600
tattagctat tgcttcaccg ccttagcttt ctcgtgacct agtcgtcctc gtcttttctt  12660
cttcttcttc tataaaacaa tacccaaaga gctcttcttc ttcacaattc agatttcaat  12720
ttctcaaaat cttaaaaact ttctctcaat tctctctacc gtgatcaagg taaatttctg  12780
tgttccttat tctctcaaaa tcttcgattt tgttttcgtt cgatcccaat ttcgtatatg  12840
ttctttggtt tagattctgt taatcttaga tcgaacacga ttttctgggt ttgatcgtta  12900
gatatcatct taattctcga ttagggtttc atagatatca tccgatttgt tcaaataatt  12960
tgagttttgt cgaataatta ctcttcgatt tgtgatttct atctagatct ggtgttagtt  13020
tctagtttgt gcgatcgaat ttgtcgatta atctgagttt ttctgattaa caggcctgca  13080
ggatggaaga cgccaaaaac ataaagaaag gcccggcgcc attctatccg ctggaagatg  13140
gaaccgctgg agagcaactg cataaggcta tgaagagata cgcccctggtt cctgaacaa  13200
ttgcttttac agatgcacat atcgaggtgg acatcactta cgctgagtac ttcgaaatgt  13260
ccgttcggtt ggcagaagct atgaaacgat atgggctgaa tacaaatcac agaatcgtcg  13320
tatgcagtga aaactctctt caattcttta tgccggtgtt gggcgcgtta tttatcggag  13380
ttgcagttgc gcccgcgaac gacatttata atgaacgtga attgctcaac agtatgggca  13440
tttcgcagcc taccgtggtg ttcgtttcca aaaagggggt gcaaaaaatt ttgaacgtgc  13500
aaaaaaagct cccaatcatc caaaaaatta ttatcatgga ttctaaaacg gattaccagg  13560
gatttcagtc gatgtacacg ttcgtcacat ctcatctacc tcccggtttt aatgaatacg  13620
attttgtgcc agagtccttc gatagggaca agacaattgc actgatcatg aactcctctg  13680
gatctactgg tctgcctaaa ggtgtcgctc tgcctcatag aactgcctgc gtgagattct  13740
cgcatgccag agatcctatt tttggcaatc aaatcattcc ggatactgcg attttaagtg  13800
ttgttccatt ccatcacggt tttggaatgt ttactacact cggatatttg atatgtggat  13860
ttcgagtcgt cttaatgtat agatttgaag aagagctgtt tctgaggagc ttcaggatt  13920
acaagattca aagtgcgctg ctggtgccaa cctattctc cttcttcgcc aaaagcactc  13980
tgattgacaa atacgattta tctaatttac acgaaattgc ttctggtggc gctccctct  14040
ctaaggaagt cggggaagcg gttgccaaga ggttccatct gccaggtatc aggcaaggat  14100
atgggctcac tgagactaca tcagctattc tgattacacc cgagggggat gataaaccgg  14160
gcgcggtcgg taaagttgtt ccatttttg aagcgaaggt tgtggatctg gataccggga  14220
aaacgctggg cgttaatcaa agaggcgaac tgtgtgtgag aggtcctatg attatgtccg  14280
gttatgtaaa caatccggaa gcgaccaacg ccttgattga caaggatgg tggctacatt  14340
ctggagacat agcttactgg gacgaagacg aacacttctt catcgttgac cgcctgaagt  14400
ctctgattaa gtacaaaggc tatcaggtgg ctcccgctga attggaatcc atcttgctcc  14460
aacaccccaa catcttcgac gctggtgtcg caggtcttcc cgacgatgac gccggtgaac  14520
ttcccgccgc cgttgttgtt ttggagcacg gaaagacgat gacgaaaaa gagatcgtgg  14580
attacgtcgc cagtcaagta acaaccgcga aaagttgcg cggaggagtt gtgtttgtgg  14640
acgaagtacc gaaaggtctt accggaaaac tcgacgcaag aaaatcaga gatcctca  14700
taaaggccaa gaagggcgga agatcgccg tgtgactcga ggttcagta ttatggcatt  14760
gggaaaactg ttttttcttgt accatttgtt gtgcttgtaa tttactgtgt tttttattcg  14820
gttttcgcta tcgaactgtg aaatggaaat ggatggagaa gagttaatga atgatatggt  14880
ccttttgttc attctcaaat taatattatt tgttttttct cttatttgtt gtgtgttgaa  14940
tttgaaatta taagagatat gcaaacattt tgtttttgagt aaaaatgtgt caaatcgtgg  15000
cctctaatga ccgaagttaa tatgaggagt aaaacacttg tagttgtgtt agagctcagt  15060
gtttgatcgc cggcggtacc gagtgtactt caagtcagtg ggaaatcaat aaaatgatta  15120
ttttatgaat atatttcatt gtgcaagtag atagaaatta catatgttac ataacacacg  15180
aaataaacaa aaaagacaa tccaaaaaca aacaccccaa aaaaataat cactttagat  15240
```

```
aaactcgtat gaggagaggc acgttcagtg actcgacgat tcccgagcaa aaaaagtctc    15300
cccgtcacac atgtagtggg tgacgcaatt atctttaaag taatccttct gttgacttgt    15360
cattgataac atccagtctt cgtcaggatt gcaaagaatt atagaaggga tcccacctttt   15420
tatttctttc ttttttccat atttaggggtt gacagtgaaa tcagactggc aacctattaa   15480
ttgcttccac aatgggacga acttgaaggg gatgtcgtcg atgatattat aggtggcgtg    15540
ttcatcgtag ttggtgaaat cgatggtacc gttccaatag ttgtgtcgtc cgagacttct    15600
agcccaggtg gtctttccgg tacgagttgg tccgcagatg tagaggctgg ggtgtcggat    15660
tccattcctt ccattgtcct tgttaaatcg gccatccatt caaggtcaga ttgagcttgt    15720
tggtatgaga caggatgtat gtaagtataa gcgtctatgc ttacatggta tagatgggtt    15780
tccctccagg agtgtagatc ttcgtggcag cgaagatctg attctgtgaa gggcgacaca    15840
tacggttcag gttgtggagg gaataaatttg ttggctgaat attccagcca ttgaagcttt    15900
gttgcccatt catgagggaa ttcttccttg atcatgtcaa gatattcctc cttagacgtt    15960
gcagtctgga taatagttct ccatcgtgcg tcagatttgc gaggagaaac cttatgatct    16020
cggaaatctc ctctggttttt aatatctccg tcctttgata tgtaatcaag gacttgttta   16080
gagtttctag ctggctggat attagggtga tttccttcaa aatcgaaaaa agaaggatcc    16140
ctaatacaag gttttttatc aagctggaga agagcatgat agtgggtagt gccatcttga    16200
tgaagctcag aagcaacacc aaggaagaaa ataagaaaag gtgtgagttt ctcccagaga    16260
aactggaata aatcatctct ttgagatgag cacttgggat aggtaaggaa aacatattta    16320
gattggagtc tgaagttctt actagcagaa ggcatgttgt tgtgactccg agggggttgcc   16380
tcaaactcta tcttataacc ggcgtggagg catggaggca ggggtatttt ggtcatttta    16440
atagatagtg gaaaatgacg tggaatttac ttaaagacga agtctttgcg acaaggggggg   16500
gcccacgccg aatttaatat taccgacgtg gccccccctt atcgcgagtg ctttagcacg    16560
agcggtccag atttaaagta gaaaatttcc cgcccactag ggttaaaggt gttcacacta    16620
taaaagcata tacgatgtga tggtatttga tggagcgtat attgtatcag gtatttccgt    16680
tggatacgaa ttattcgtac gaccctcata gtttaaacta tcagtgtttg acaggatata    16740
ttggcgggta aacctaagag aaaagagcgt ttattagaat aacggatatt taaaagggcg    16800
tgaaaaggtt tatccgttcg tccatttgta tgtgcatgcc aaccacaggg ttcccctcgg    16860
gatcaaagta ctttgatcca accccctccgc tgctatagtg cagtcggctt ctgacgttca   16920
gtgcagccgt cttctgaaaa cgacatgtcg cacaagtcct aagttacgcg acaggctgcc    16980
gccctgccct tttcctggcg ttttcttgtc gcgtgttttta gtcgcataaa gtagaatact   17040
tgcgactaga accggagaca ttacgccatg aacaagagcg ccgccgctgg cctgctgggc    17100
tatgcccgcg tcagcaccga cgaccaggac ttgaccaacc aacgggccga actgcacgcg    17160
gccggctgca ccaagctgtt ttccgagaag atcaccggca ccaggcgcga ccgcccggag    17220
ctggccagga tgcttgacca cctacgccct ggcgacgttg tgacagtgac caggctagac    17280
cgcctggccc gcagcacccg cgacctactg gacattgccg agcgcatcca ggaggccggc    17340
gcgggcctgc gtagcctggc agagccgtgg gccgacacca ccacgccggc cggccgcatg    17400
gtgttgaccg tgttcgccgg cattgccgag ttcgagcgtt ccctaatcat cgaccgcacc    17460
cggagcgggc gcgaggccgc caaggcccga ggcgtgaagt ttggcccccg ccctaccctc    17520
accccgcacc agatcgcgca cgcccgcgag ctgatcgacc aggaaggccg caccgtgaaa    17580
gaggcggctg cactgcttgg cgtgcatcgc tcgaccctgt accgcgcact tgagcgcagc    17640
gaggaagtga cgcccaccga ggccaggcgg cgcggtgcct tccgtgagga cgcattgacc    17700
gaggccgacg ccctggcggc cgccgagaat gaacgccaag aggaacaagc atgaaaccgc    17760
accaggacgg ccaggacgaa ccgttttttca ttaccgaaga gatcgaggtc gagatgatcg    17820
cggccgggta cgtgttcgag ccgcccgcgc acggctcaac cgtgcggctg catgaaatcc    17880
tggccggttt gtctgatgcc aagctggcgg cctggccggc cagcttggcc gctgaagaaa    17940
ccgagcgccg ccgtctaaaa aggtgatgtg tatttgagta aaacagcttg cgtcatgcgg    18000
tcgctcgtta tatgatcga tgagtaaata aacaaatacg caaggggaac gcatgaaggt    18060
tatcgctgta cttaaccaga aaggcgggtc aggcaagacg accatcgcaa cccatctagc    18120
ccgcgccctg caactcgccg gggccgatgt tctgttagtc gattccgatc cccagggcag    18180
tgcccgcgat tgggcggccg tgcgggaaga tcaaccgcta accgttgtcg gcatcgaccg    18240
cccgacgatt gaccgcgacg tgaaggccat cggccggtag gacttcgtag tgatcgacgg    18300
agcgcccccag gcggcggact tggctgtgtc cgcgatcaag gcagccgact tcgtgctgat    18360
tccggtgcag ccaagccctt acgacatatg ggccaccgcc gacctggtgg agctggttaa    18420
gcagcgcatt gaggtcacgg atggaaggct acaagcggcc tttgtcgtgt cgcgggcgat    18480
caaaggcacg cgcatcggcg gtgaggttgc cgaggcgctg gccgggtacg agctgcccat    18540
tcttgagtcc cgtatcacgc agcgcgtgag ctaccaggac actgccgccg ccggcacaac    18600
cgttcttgaa tcagaacccg agggcgacgc tgcccgcgag gtccaggcgc tggccgctga    18660
aattaaatca aaactcatttt gagttaatga ggtaaagaga aaatgagcaa aagcacaaac    18720
acgctaagtg ccggccgtcc gagcgcacgc agcagcaagg ctgcaacgtt ggccagcctg    18780
gcagacacgc cagccatgaa gcgggtcaac tttcagttgc cggcggagga tcacaccaag    18840
ctgaagatgt acgcggtacg ccaaggcaag accattaccg agctgctatc tgaatacatc    18900
gcgcagctac cagagtaaat gagcaaatga ataaatgagt agatgaattt tagcggctaa    18960
aggaggcggc atggaaaatc aagaacaacc aggcaccgac gccgtggaat gccccatgtg    19020
tggaggaacg ggcggttggc caggcgtaag cggctggttt gtctgccggc cctgcaattgg   19080
cactggaacc cccaagcccg aggaatcggc gtgacggtcg caaaccatcc ggcccggtac    19140
aaatcggcgc ggcgctgggt gatgacctgg tggagaagtt gaaggccgcg caggccgccc    19200
agcggcaacg catcgaggca gaagcacgcc ccggtgaatc gtggcaagcg gccgctgatc    19260
gaatccgcaa agaatcccgg caaccgccgg cagccggtgc gccgtcgatt aggaagccgc    19320
ccaaggcgca cgagcaacca gatttttttcg ttccgatgct ctatgacgtg ggcacccgcg    19380
atagtcgcag catcatggac gtggccgttt tccgtctgtc gaagcgtgac cgacgagctg    19440
gcgaggtgat ccgctacgag cttccagacg gcacgtaga ggtttccgca gggccggccg     19500
gcatggccag tgtgtgggat tacgacctgg tactgatggc ggtttcccat ctaaccgaat    19560
ccatgaaccg ataccgggaa gggaagggag acaagcccgg ccgcgtgttc cgtccacacg    19620
ttgcggacgt actcaagttc tgccggcgag ccgatggc                            19658

SEQ ID NO: 89           moltype = DNA   length = 19732
FEATURE                 Location/Qualifiers
source                  1..19732
                        mol_type = other DNA
```

```
                  organism = synthetic construct
SEQUENCE: 89
aagacgacct ggtagaaacc tgcattcggt taaacaccac gcacgttgcc atgcagcgta   60
cgaagaaggc caagaacggc cgcctggtga cggtatccga gggtgaagcc ttgattagcc  120
gctacaagat cgtaaagagc gaaaccgggc ggccggagta catcgagatc gagctagctg  180
attggatgta ccgcgagatc acagaaggca agaacccgga cgtgctgacg gttcaccccg  240
attactttt gatcgatccc ggcatcggcc gttttctcta ccgcctggca cgccgcgccg  300
caggcaaggc agaagccaga tggttgttca agacgatcta cgaacgcagt ggcagcgccg  360
gagagttcaa gaagttctgt ttcaccgtgc gcaagctgat cgggtcaaat gacctgccgg  420
agtacgattt gaaggaggag gcggggcagg ctggccccgat cctagtcatg cgctaccgca  480
acctgatcga gggcgaagca tccgccggtt cctaatgtac ggagcagatg ctagggcaaa  540
ttgccctagc aggggaaaaa ggtcgaaaag gcctctttcc tgtggatagc acgtacattg  600
ggaacccaaa gccgtacatt gggaaccgga acccgtacat tgggaaccca aagccgtaca  660
ttgggaaccg gtcacacatg taagtgactg atataaaaga gaaaaaggc gattttccg  720
cctaaaactc tttaaaactt attaaaactc ttaaaacccg cctggcctgt gcataactgt  780
ctggccagcg cacagccgaa gagctgcaaa aagcgcctac ccttcggtcg ctgcgctccc  840
tacgccccgc cgcttcgcgt cggcctatcg cggccgctgg ccgctcaaaa atggctggcc  900
tacggccagg caatctacca gggcgcggac aagccgcgcc gtcgccactc gaccgccggc  960
gcccacatca aggcaccctg cctcgcgcgt ttcggtgatg acggtgaaaa cctctgacac 1020
atgcagctcc cggaaacggt cacagcttgt ctgtaagcgg atgccgggag cagacaagcc 1080
cgtcagggcg cgtcagcggg tgttggcggg tgtcggggcg cagccatgac ccagtcacgt 1140
agcgatagcg gagtgtatac tggcttaact atgcggcatc agagcagatt gtactgagag 1200
tgcaccatat gcggtgtgaa ataccgcaca gatgcgtaag gagaaaatac cgcatcaggc 1260
gctcttccgc ttcctcgctc actgactcgc tgcgctcggt cgttcggctg cggcgagcgg 1320
tatcagctca ctcaaaggcg gtaatacggt tatccacaga atcaggggat aacgcaggaa 1380
agaacatgtg agcaaaaggc cagcaaaagg ccaggaaccg taaaaaggcc gcgttgctgg 1440
cgttttttcca taggctccgc ccccctgacg agcatcacaa aaatcgacgc tcaagtcaga 1500
ggtggcgaaa cccgacagga ctataaagat accaggcgtt tccccctgga agctccctcg 1560
tgcgctctcc tgttccgacc ctgccgctta ccggatacct gtccgccttt ctcccttcgg 1620
gaagcgtggc gctttctcat agctcacgct gtaggtatct cagttcggtg taggtcgttc 1680
gctccaagct gggctgtgtg cacgaacccc ccgttcagcc cgaccgctgc gccttatccg 1740
gtaactatcg tcttgagtcc aacccggtaa gacacgactt atcgcactg gcagcagcca 1800
ctggtaacag gattagcaga gcgaggtatg taggcggtgc tacagagttc ttgaagtggt 1860
ggcctaacta cggctacact agaaggacag tatttggtat ctgcgctctg ctgaagccag 1920
ttaccttcgg aaaaagagtt ggtagctctt gatccggcaa acaaaccacc gctggtagcg 1980
gtggtttttt tgtttgcaag cagcagatta cgcgcagaaa aaaaggatct caagaagatc 2040
ctttgatctt ttctacgggg tctgacgctc agtggaacga aaactcacgt taagggattt 2100
tggtcatgca ttctaggtac taaaacaatt catccagtaa aatataatat tttattttct 2160
cccaatcagg cttgatcccc agtaagtcaa aaaatagctc gacatactgt tcttcccga 2220
tatcctccct gatcgaccgg acgcagaagg caatgtcata ccacttgtcc gccctgccgc 2280
ttctcccaag atcaataaag ccacttactt tgccatcttt cacaaagatg ttgctgtctc 2340
ccaggtcgcc gtgggaaaag acaagttcct cttcgggctt ttccgtcttt aaaaaatcat 2400
acagctcgg cggatcttta aatggagtgt cttcttccca gttttcgcaa tccacatcgg 2460
ccagatcgtt attcagtaag taatccaatt cggctaagcg gctgtctaag ctattcgtat 2520
agggacaatc cgatatgtcg atggagtgaa agagcctgat gcactccgca tacagctcga 2580
taatcttttc agggctttgt tcatcttcat actcttccga gcaaaggacg ccatcggcct 2640
cactcatgag cagattgctc cagccatcat gccgttcaga gtgcaggaac tttggaacag 2700
gcagcttttcc ttccagccat agcatcatgt cctttttccg ttccacatca taggtggtcc 2760
ctttataccg gctgtccgtc attttaaat ataggttttc attttctccc accagcttat 2820
ataccttagc aggagacatt ccttccgtat cttttacgca gcggtatttt tcgatcagtt 2880
ttttcaattc cggtgtatt ctcattttag ccatttatta tttccttcct cttttctaca 2940
gtatttaaag ataccccaag aagctaatta taacaagacg aactccaatt cactgttcct 3000
tgcattctaa aaccttaaat accagaaaac agcttttca aagttgtttt caaagttggc 3060
gtataacata gtatcgacgg agccgatttt gaaaccgcgg tgatcacagg cagcaacgct 3120
ctgtcatcgt tacaatcaac atgctaccct ccgcgagatc atccgtgttt caaacccggc 3180
agcttagttg ccgttcttcc gaatagcatc ggtaacatga gcaaagtctg ccgccttaca 3240
acggctctcc cgctgacgcc gtccggact gatgggctgc ctgtatcgag tggtgatttt 3300
gtgccgagct gccggtcggg gagctgttgg ctggctggtg gcaggatata ttgtggtgta 3360
aacaaattga cgcttagaca acttaataac acattgcgga cgttttttaat gtagagctca 3420
aagtttaacg cgttagcaga aggcatgttg ttgtgactcc gaggggttgc ctcaaactct 3480
atcttataac cggcgtggag gcatggaggc aggggtattt tggtcatttt aatagatagt 3540
ggaaaatgac gtgaatttta cttaaagacg aagtctttgc gacaagggg gcccacgcc 3600
gaatttaata ttaccggcgt ggccccccct tatcgcgagt gctttagcac gagcggtcca 3660
gatttaagt agaaaatttc ccgcccacta gggttaaagg tgttcacact ataaagcat 3720
atacgatgtg atggtatttg atggagcgta tattgtatca ggtatttccg ttggatacga 3780
attattcgta cgaccctcgg taccgatcgg cgcgccagat ttgccttttc aatttcagaa 3840
agaatgctaa cccacagatg gttagagagg cttacgcagc aggtatcatc aagacgatct 3900
acccgagcaa taatcctcag gaaatcaaat accttcccaa gaaggttaaa gatgcagtca 3960
aaagattcag gactaactgc atcaagaaca cagagaaaga tatatttctc aagatcagaa 4020
gtactattcc agtatggacg attcaaggct tgcttcacaa accaaggcaa gtaatagaga 4080
ttggagtctc taaaaaggta gttcccactg aatcaaaggc catggagtca aagattcaaa 4140
tagaggacct aacagaactc gccgtaaaga ctggcgaaca gttcatacag agtctcttac 4200
gactcaatga caagaagaaa atcttcgtca acatggtgga gcacgacaca cttgtctact 4260
ccaaaaatat caaagataca gtctcagaag accaaagggc aattgagact tttcaacaaa 4320
gggtaatatc cggaaacctc ctcggattcc attgcccagc tatctgtcac tttattgtga 4380
agatagtgga aaggaaggt ggctcctaca atgccatca ttgcgataaa ggaaaggcca 4440
tcgttgaaga tgcctctgcc gacagtggtc caaagatgg accccaccc acgaggagca 4500
tcgtggaaaa agaagacgtt ccaaccacgt cttcaaagca agtggattga tgtgatatct 4560
ccactgacgt aagggatgac gcacaatccc actatccttc gcaagaccct tcctctatat 4620
```

```
aaggaagttc atttcatttg gagagaacac gggggactcc tgcaggtaga tcgctcgtcg   4680
acatggataa gaagtactct atcggactcg atatcggaac taactctgtg ggatgggctg   4740
tgatcaccga tgagtacaag gtgccatcta agaagttcaa ggttctcgga aacaccgata   4800
ggcactctat caagaaaaac cttatcggtg ctctcctctt cgattctggt gaaactgctg   4860
aggctaccag actcaagaga accgctagaa gaaggtacac cagaagaaag aacaggatct   4920
gctacctcca agagatcttc tctaacgaga tggctaaagt ggatgattca ttcttccaca   4980
ggctcgaaga gtcattcctc gtggaagaag ataagaagca cgagaggcac cctatcttcg   5040
gaaacatcgt tgatgaggtg gcataccacg agaagtaccc tactatctac cacctcagaa   5100
agaagtcgt tgattctact gataaggctg atctcaggct catctacctc gctctcgctc   5160
acatgatcaa gttcagagga cacttcctca tcgagggtga tctcaaccct gataactctg   5220
atgtggataa gttgttcatc cagctcgtgc agacctacaa ccagcttttc gaagagaacc   5280
ctatcaacgc ttcaggtgtg gatgctaagg ctatcctctc tgctaggctc tctaagtcaa   5340
gaaggcttga gaacctcatt gctcagctcc tggtgagaa gaagaacgga ctttcggaa   5400
acttgatcgc tctctctctc ggactcaccc ctaacttcaa gtctaacttc gatctcgctg   5460
aggatgcaaa gctccagctc tcaaaggata cctacgatga tgatctcgat aacctcctcg   5520
ctcagatcgg agatcagtac gctgatttgt tcctcgctgc taagaacctc tctgatgcta   5580
tcctcctcag tgatatcctc agagtgaaca ccgagatcac caaggctcca ctctcagctt   5640
ctatgatcaa gagatacgat gagcaccacc aggatctcac acttctcaag gctcttgtta   5700
gacagcagct cccagagaag tacaaagaga ttttcttcga tcagtctaag aacgggatacg   5760
ctggttacat cgatggtggt gcatctcaag aagagttcta caagttcatc aagcctatcc   5820
tcgagaagat ggatggaacc gaggaactcc tcgtgaagct caatagagag gatcttctca   5880
gaaagcagag gaccttcgat aacggatcta tccctcatca gatccacctc ggagagttgc   5940
acgctatcct tagaaggcaa gaggatttct acccattcct caaggataac agggaaaga   6000
ttgagaagat tctcacctt agaatccctt actacgtggg acctcgct agaggaaact    6060
caagattcgc ttgatgacc agaaagtctg aggaaaccat caccccttgg aacttcgaag   6120
aggtggtgga taagggtgct agtgctcagt ctttcatcga gggatgacc aacttcgata   6180
agaaccttcc aaacgagaag gtgctcccta agcactcttt gctctacgta cttccaccg    6240
tgtacaacga gttgaccaag gttaagtacg tgaccgaggg aatgaggaag cctgctttt   6300
tgtcaggtga gcaaagaag gctatcgttg atctcttgtt caagaccaac agaaaggtga   6360
ccgtgaagca gctcaaagga gattacttca agaaaatcga gtgcttcgat tcagttgaga   6420
tttctggtgt tgaggatagg ttcaacgcat ctctccggaac ctaccacgat ctccctcaaga  6480
tcattaagga taaggatttc ttggataacg aggaaaacga ggatatcttg gaggatatcg   6540
ttcttaccct caccctcttt gaagatagag agatgattga agaaaggctc aagacctacg   6600
ctcatctctt cgatgataag gtgatgaagc agttgaagag aagaagatac actggttggg   6660
gaaggctctc aagaaagctc attaacggaa tcagggataa gcagtctgga aagacaatcc   6720
ttgatttcct caagtctgat ggattcgcta acagaaactt catgcagctc atccacgatg   6780
attctctcac ctttaaagag gatatccaga aggctcaggt tcaggacag ggtgatagtc    6840
tccatgagca tatcgctaac ctcgctggat ctcctgcaat caagaaggga atcctccaga   6900
ctgtgaaggt tgtggatgag ttggtgaagg tgatggaag gcataagcct gagaactacg   6960
tgatcgaaat ggctagagag aaccagacca ctcagaaggg acagaagaac tctagggaaa   7020
ggatgaagag gatcgaggaa ggtatcaaag agcttggatc tcagatcctc aaagagcacc   7080
ctgttgagaa cactcagctc cagaatgaga agctctacct ctactacctc cagaacggaa   7140
gggatatgta tgtggatcaa gagttggata tcaacagcct ctctgattac gatgttgatc   7200
atatcgtgcc acagtcattc ttgaaggatg attctatcga taacaaggtg ctcaccaggt   7260
ctgataagaa caggggtaag agtgataacg tgccaagtga agaggttgtg aagaaaatga   7320
agaactattg gaggcagctc ctcaacgcta agctcatcac tcagagaaag ttcgataact   7380
tgactaaggc tgagagggga ggactctctg aattggataa ggcaggattc atcaagaggc   7440
agcttgtgga aaccaggcag atcactaagc acgttgcaca gatcctcgat tctaggatga   7500
acaccaagta cgatgagaac gataagttga tcagggaagt gaaggttatc accctcaagt   7560
caaagctcgt gtctgatttc agaaaggatt tccaattcta caaggtgagg gaaatcaaca   7620
actaccacca cgctcacgat gcttaccta acgctgttgt tggaaccgct ctcatcaaga   7680
agtatcctaa gctcgagtca gagttcgtgt acggtgatta caaggtgtac gatgtgagga   7740
agatgatcgc taagtctgag caagagatcg gaaaggctac cgctaagtat ttcttctact   7800
ctaacatcat gaatttcttc aagaccgaga ttaccctcgc taacggtgag atcagaaaga   7860
ggccactcat cgagacaaac ggtgaaacag gtgagatcgt gtgggataag ggagagggatt   7920
tcgctaccgt tagaaaggtg ctctctatgc cacaggtgaa catcgttaag aaaaccgagg   7980
tgcagaccgg tggattctct aaagagtcta tcctccctaa gaggaactct gataagctca   8040
ttgctaggaa gaaggattgg gaccctaaga aatacggtgg tttcgattct cctaccgtgg   8100
cttactctgt tctccgttgt gctaaggttg agaagggaaa gagtaagaag ctcaagtctg   8160
ttaaggaact tctcggaatc actatcatgg aaaggtcatc tttcgagaag aacccaatcg   8220
atttcctcga ggctaaggga tacaaagagg ttaagaagga tctcatcatc aagctcccaa   8280
agtactcact cttcgaactc gagaacggta gaaagaggat gctcgcttct gctggtgagc   8340
ttcaaaaggg aaacgagctt gctctcccat ctaagtacgt taactttctt tacctcgctt   8400
ctcactacga gaagttgaag ggatctccag aagataacga gcaagaacaa cttttcgttg   8460
agcagcacaa gcactacttg gatgagatca tcgagcagat ctctgagttc tctaaaaggg   8520
tgatcctcgc tgatgcaaac ctcgataagg tgttgtctgc ttacaacaag cacagagata   8580
agcctatcag ggaacaggca gagaacatca tccatctctt caccttacc aacctcggtgt   8640
ctcctgctgc tttcaagtac ttcgatacaa ccatcgatag gaagagatac acctctacca   8700
aagaagtgct cgatgctacc ctcatccatc agtctatcac tggactctac gagactagga   8760
tcgatctctc acagtcggt ggtgattcaa gggctgatcc taagaagaag aggaaggttt   8820
gacgtcgacg atatgaagat gaagatgaaa tatttggtgt gtcaaataaa aagcttgtgt   8880
gcttaagttt gtgtttttt cttggcttgt tgtgttatga atttgtggct ttttctaata   8940
ttaaatgaat gtaagatcac attataatga ataaacaaat gtttctataa tccattgtga   9000
atgttttgtt ggatctcttc tgcagcatat aactactgta tgtctatgg tatgactat    9060
ggaatatgat taaagataag ccagagctct ggtgacggaa ccatggcttc gttgaacaac   9120
ggaaactcga cttgccttcc gcacaataca tcatttcttc ttagcttttt ttcttcttct   9180
tcgttcatac agtttttttt tgtttatcag cttacatttt cttgaaccgt agcttttcgtt   9240
ttcttctttt taactttcca ttcggagttt ttgtatcttg tttcatagtt tgtcccagga   9300
ttagaatgat taggcatcga accttcaaga atttgattga ataaaacatc ttcattctta   9360
```

```
agatatgaag ataatcttca aaaggccccc gggaatctga aagaagagaa gcaggcccat    9420
ttatatggga aagaacaata gtatttctta tataggccca tttaagttga aaacaatctt    9480
caaaagtccc acatcgctta gataagaaaa cgaagctgag tttatataca gctagagtcg    9540
aagtagtgat tgcctacttg ggctgttgca ggttttagag ctagaaatag caagttaaaa    9600
taaggctagt ccgttatcaa cttgaaaaag tggcaccgag tcggtgcttt ttttcccggc    9660
gtaaatggc gcgccagatt tgccttttca atttcagaaa gaatgctaac ccacagatgg    9720
ttagagaggc ttacgcagca ggtatcatca agacgatcta cccgagcaat aatctccagg    9780
aaatcaaata ccttcccaag aaggttaaag atgcagtcaa aagattcagg actaactgca    9840
tcaagaacac agagaaagat atatttctca agatcagaag tactattcca gtatggacga    9900
ttcaaggctt gcttcacaaa ccaaggcaag taatagagat tggagtctct aaaaaggtag    9960
ttcccactga atcaaaggcc atggagtcaa agattcaaat agaggaccta acagaactcg   10020
ccgtaaagac tggcgaacag ttcatacaga gtctcttacg actcaatgac aagaagaaaa   10080
tcttcgtcaa catggtggag cacgacacac ttgtctactc caaaaatatc aaagatacag   10140
tctcagaaga ccaaagggca attgagactt ttcaacaaag ggtaatatcc ggaaacctcc   10200
tcggattcca ttgcccagct atctgtcact ttattgtgaa gatagtggaa aaggaaggtg   10260
gctcctacaa atgccatcat tgcgataaag gaaaggccat cgttgaagat gcctctgccg   10320
acagtggtcc caaagatgga ccccaccca cgaggagcat cgtggaaaaa gaagacgttc   10380
caaccacgtc ttcaaagcaa gtggattgat gtgatatctc cactgacgta agggatgacg   10440
cacaatccca ctatccttcg caagacccTT cctctatata aggaagttca tttcatttgg   10500
agagaacacg ggggactcct gcaggatgga tctgcgtcta attttcggtc caacttgcac   10560
aggaaagacg tcgaccgcga tacgtcttgc ccagcagact ggccttccag tccttcgct    10620
cgatcgggtc caatgctgtc ctcaactgtc aaccggaagc ggacgaccaa cagtggaaga   10680
actgaaagga acgacccgtc tataccttga agatcggcct ctggtgaagg gtatcatcgc   10740
agccaagcaa gctcacgaaa ggctgatcgg ggaagtgtac aattatgagg cccacgcgg    10800
gcttattctt gagggaggat ctatctcgtt gctcaggtgc atggcgcaaa gcagttattg   10860
gagtaccgat tttcgttggc atattattcg ccacaagtta gcagacgagg agacattcat   10920
gaacgcggcc aaggcagag ttaggcagat gttgcgccct gctgtaggcc catctattat    10980
tcaagagttg gttcatcttt ggaatgagcc tcggctgagg cccatactga aagagatcga   11040
cggatatcga tatgccatgt tatttgctag ccagaaccag atcacacccg atatgctatt   11100
gcagcttgac ccagatatgg agggtgagtt gattcatgga atcgctcagg agtatctcat   11160
ccatgcgcgc cggcaggagc aggaattccc tccagtgagc gtggtcgctt tcgaaggatt   11220
cgaaggtcca ccgttcggaa tgtgctagct cgagccctag acttgtccat cttctggatt   11280
ggccaagtta attaatgtat gaaataaaag gatgcacaca tagtgacatg ctaatcacta   11340
taatgtgggc atcaaagttg tgtgttatgt gtaattacta attatctgaa taagagaaag   11400
agatcatcca tatttcttat cctaaatgaa tgtcacgtgt ctttataatt ctttgatgaa   11460
ccagatgcat tttattaacc aattccatat acatataaat attaatcata tataattaat   11520
atcaattggg ttagcaaaac aaatctagtc taggtgtgtt ttgctaatta ttgggggata   11580
gtgcaaaaag aaatctacgt tctcaataat tcagataaga aacttaataa agtgagataa   11640
tttacataga ttgcttttat cctttgatat atgtgaaacc atgcatgata taaggaaaat   11700
agatagagaa ataatttttt acatcgttga atatgtaaac aatttaattc aagaagctag   11760
gaatataaat attgaggagt ttatgattag agctctcccg gcgcgcccta tgtcgagctg   11820
caggtcaacg gatcaggata ttcttgttta agatgttgaa ctctatggag gtttgtatga   11880
actgatgatc taggaccgga taagttccct tcttcatagc gaacttattc aaagaatgtt   11940
ttgtgtatca ttccttgttac attgttatta atgaaaaat attattgtc attggactga   12000
acacgagtgt taaatatgga ccaggcccca aataagatcc attgatatat gaattaaata   12060
acaagaataa atcgagtcac caaaccactt gcctttttta acgagacttg ttcaccaact   12120
tgatacaaaa gtcattatcc tatgcaaatc aataatcata caaaaatatc caataacact   12180
aaaaaattaa aagaaatgga taatttcaca atatgttata cgataaagaa gttactttc    12240
caagaaattc actgattta taagcccact tgcattagat aaatggcaaa aaaaaacaaa    12300
aaggaaaaga aataaagcac gaagaattct agaaaatacg aaatacgctt caatgcagtg   12360
ggaccacggg ttcaattatt gccaatttc agctccaccg tatattaaa aataaaacg     12420
ataatgctaa aaaatataa atcgtaacga tcgttaaatc tcaacggctg gatcttatga    12480
cgaccgttag aaattgtggt tgtcgacgag tcagtaataa acggcgtcaa agtggttgca    12540
gccggcacac acgagtcgtg tttatcaact caaagcacaa atacttttcc tcaacctaaa   12600
aataaggcaa ttagccaaaa acaactttgc gtgtaaacaa cgctcaaatc acgtgtcatt   12660
ttattattag ctattgcttc accgcctag ctttctcgtg acctagtcgt cctcgtcttt    12720
tcttcttctt cttctataaa acaatccca aagagctctt cttctcaca attcagattt     12780
caatttctca aaatcttaaa aactttctct caattctctc taccgtgatc aaggtaaatt   12840
tctgtgttcc ttattctctc aaaatcttcg attttgtttt cgttcgatcc caatttcgta   12900
tatgttcttt ggtttagatt ctgttaatct tagatcgaac acgattttct gggtttgatc   12960
gttagatatc atcttaattc tcgattaggg tttcatagat atcatccgat ttgttcaaat   13020
aatttgagtt ttgtcgaata attactttc gatttgtgat ttctatctag atctggtgtt    13080
agtttctagt ttgtgcgatc gaatttgtcg attaatctga gtttttctga ttaacaggcc   13140
tgcaggatgg aagacgccaa aaacataaag aaaggcccgg cgccattcta tccgctgaa    13200
gatggaaccg ctggagagca actgcataag gctatgaaga gatacgccct ggttcctgga   13260
acaattgctt ttacagatgc acatatcgag gtggacatca cttacgctga gtacttcgaa   13320
atgtccgttc ggttggcaga agctatgaaa cgatatgggc tgaatacaaa tcacagaatc   13380
gtcgtatgca gtgaaaactc tcttcaattc tttatgccgg tgttgggcgc gttatttatc   13440
ggagttgcag ttgcgcccgc gaacgacatt tataatgaac gtgaattgct caacagtatg   13500
ggcatttcgc agcctaccgt ggtgttcgtt tccaaaaagg ggttgcaaaa aatttttgaac   13560
gtgcaaaaaa agctcccaat catccaaaaa attattatca tggattctaa aacggattac    13620
cagggatttc agtcgatgta cacgttcgtc acatctcatc tacctcccgg ttttaatgaa   13680
tacgatttg tgccagagtc cttcgatagg gacaagacaa ttgcactgat catgaactcc    13740
tctggatcta ctggtctgcc taaaggtgtc gctctgcctc atagaactgc ctgcgtgaga   13800
ttctcgcatg ccagagatcc tatttttggc aatcaaatca ttccggatac tgcgatttta   13860
agtgttgttc cattccatca cggttttgga atgtttacta cactcggata tttgatatgt   13920
ggatttcgag tcgtcttaat gtatagattt gaagaagagc tgtttctgag gagccttcag   13980
gattacaaga ttcaaagtgc gctgctggtg ccaaccctat tctccttctt cgccaaaagc   14040
actctgattg acaaatacga tttatctaat ttacacgaaa ttgcttctgg tggcgctccc   14100
```

```
ctctctaagg aagtcgggga agcggttgcc aagaggttcc atctgccagg tatcaggcaa    14160
ggatatgggc tcactgagac tacatcagct attctgatta cacccgaggg ggatgataaa    14220
ccgggcgcgg tcggtaaagt tgttccattt tttgaagcga aggttgtgga tctggatacc    14280
gggaaaacgc tgggcgttaa tcaaagaggc gaactgtgtg tgagaggtcc tatgattatg    14340
tccggttatg taaacaatcc ggaagcgacc aacgccttga ttgacaagga tggatggcta    14400
cattctggag acatagctta ctgggacgaa gacgaacact tcttcatcgt tgaccgcctg    14460
aagtctctga ttaagtacaa aggctatcag gtggctcccg ctgaattgga atccatcttg    14520
ctccaacacc ccaacatctt cgacgctggt gtcgcaggtc ttcccgacga tgacgccggt    14580
gaacttcccg ccgccgttgt tgttttggag cacggaaaga cgatgacgga aaaagagatc    14640
gtggattacg tcgccagtca agtaacaacc gcgaaaaagt tgcgcggagg agttgtgttt    14700
gtggacgaag taccgaaagg tcttaccgga aaactcgacg caagaaaaat cagagagatc    14760
ctcataaagg ccaagaaggg cggaaagatc gccgtgtgac tcgaggttcg agtattatgg    14820
cattgggaaa actgttttc ttgtaccatt tgttgtgctt gtaatttact gtgttttta    14880
ttcggttttc gctatcgaac tgtgaaatgg aaatggatgg agaagagtta atgaatgata    14940
tggtcctttt gttcattctc aaattaatat tatttgtttt ttctcttatt tgttgtgtgt    15000
tgaatttgaa attataagag atatgcaaac attttgtttt gagtaaaaat gtgtcaaatc    15060
gtggcctcta atgaccgaag ttaatatgag gagtaaaaca cttgtagttg tgttagagct    15120
cagtgtttga tcgccggcgg taccgagtgt acttcaagtc agtgggaaat caataaaatg    15180
attattttat gaatatattt cattgtgcaa gtagatagaa attacatatg ttacataaca    15240
cacgaaataa acaaaaaaag acaatccaaa aacaaacacc ccaaaaaaaa taatcacttt    15300
agataaactc gtatgaggag aggcacgttc agtgactcga cgattcccga gcaaaaaaag    15360
tctcccccgtc acacatgtag tgggtgacgc aattatctt aaagtaatcc ttctgttgac    15420
ttgtcattga taacatccag tcttcgtcag gattgcaaag aattatagaa gggatcccac    15480
cttttatttt cttctttttt ccatatttag ggttgacagt gaaatcagac tggcaaccta    15540
ttaattgctt ccacaatggg acgaacttga aggggatgtc gtcgatgata ttataggtgg    15600
cgtgttcatc gtagttggtg aaatcgatgg taccgttcca atagttgtgt cgtccgagac    15660
ttctagccca ggtggtcttt ccggtacgag ttggtccgca gatgtagagg ctgggggtgtc    15720
ggattccatt ccttccattg tccttgttaa atcggccatc cattcaaggt cagattgagc    15780
ttgttggtat gagacaggat gtatgtaagt ataagcgtct atgcttacat ggtatagatg    15840
ggtttccctc caggagtgta gatcttcgtg gcagcgaaga tctgattctg tgaagggcga    15900
cacatacggt tcaggttgtg gagggaataa tttgttggct gaatattcca gccattgaag    15960
ctttgttgcc cattcatgag ggaattcttc cttgatcatg tcaagatatt cctccttaga    16020
cgttgcagtc tggataatag ttctccatcg tgcgtcagat ttgcgaggag aaaccttatg    16080
atctcggaaa tctccctctgg ttttaatatc tccgtccttt gatatgtaat caaggacttg    16140
tttagagttt ctagctggct ggatattagg gtgatttcct tcaaaatcga aaaaagaagg    16200
atccctaata caaggttttt tatcaagctg gagaagagca tgatagtggg tagtgccatc    16260
ttgatgaagc tcagaagcaa caccaaggaa gaaaataaga aaaggtgtga gtttctccca    16320
gagaaactgg aataaatcat ctctttgaga tgagcacttg ggataggtaa ggaaaaacata    16380
tttagattgg agtctgaagt tcttactagc agaaggcatg ttgttgtgac tccgagggt    16440
tgcctcaaac tctatcttat aaccggcgtg gaggcatgga ggcaggggta ttttggtcat    16500
tttaatagat agtggaaaat gacgtggaat ttacttaaag acgaagtctt tgcgacaagg    16560
gggggcccac gccgaattta atattaccgg cgtggccccc ccttatcgcg agtgctttag    16620
cacgagcggt ccagatttaa atagaaaat ttcccgccca ctagggttaa aggtgttcac    16680
actataaaag catatacgat gtgatggtat ttgatggagc gtatattgta tcaggtattt    16740
ccgttggata cgaattattc gtacgaccct catagtttaa actatcagtg tttgacagga    16800
tatattggcg ggtaaaccta agagaaaaga gcgtttatta gaataacgga tatttaaaag    16860
ggcgtgaaaa ggtttatccg ttcgtccatt tgtatgtgca tgccaaccac agggttcccc    16920
tcgggatcaa agtactttga tccaacccct ccgctgctat agtgcagtcg gcttctgacg    16980
ttcagtgcag ccgtcttctg aaaacgacat gtcgcacaag tcctaagtta cgcgacaggc    17040
tgccgccctg ccctttttcct ggcgtttttct tgtcgcgtgt tttagtcgca taaagtagaa    17100
tacttgcgac tagaaccgga gacattacgc catgaacaag agcgccgccg ctggcctgct    17160
gggctatgcc cgcgtcagca ccgacgacca ggacttgacc aaccaacggg ccgaactgca    17220
cgcggccggc tgcaccaagc tgttttccga gaagatcacc ggcaccaggc gcgaccgccc    17280
ggagctggcc aggatgcttg accacctacg ccctggcgac gttgtgacag tgaccaggct    17340
agaccgcctg gcccgcagca cccgcgacct actggacatt gccgagcgca tccaggaggc    17400
cggcgcgggc ctgcgtagcc tggcagagcc gtgggccgac accaccacgc cggccggccg    17460
catggtgttg accgtgttcg ccggcattgc cgagttcgag cgttcccttaa tcatcgaccg    17520
cacccggagc gggcgcgagg ccgccaaggc ccgaggcgtg aagtttggcc cccgccctac    17580
cctcaccccg gcacagatcg cgcacgcccg cgagctgatc gaccaggaag gccgcaccgt    17640
gaaagaggcg gctgcactgc ttggcgtgca tcgctcgacc ctgtaccgcg cacttgagcg    17700
cagcgaggaa gtgacgccca ccgaggccag gcggcgcggt gccttccgtg aggacgcatt    17760
gaccgaggcc gacgccctgg cggccgccga gaatgaacgc caagaggaac aagcatgaaa    17820
ccgcaccagg acggccagga cgaaccgttt ttcattaccg aagagatcga ggcggagatg    17880
atcgcggccg ggtacgtgtt cgagccgccc gcgcacggct caaccgtgcg gctgcatgaa    17940
atcctggccg gtttgtctga tgccaagctg gcggcctggc cggccagctt ggccgctgaa    18000
gaaaccgagc gccgccgtct aaaaaggtga tgtgtatttg agtaaaacag cttgcgtcat    18060
gcggtcgctg cgtatatgat gcgatgagta aataaacaaa tacgcaaggg gaacgcatga    18120
aggttatcgc tgtacttaac cagaaaggcg ggtcaggcaa gacgaccatc gcaacccatc    18180
tagcccgcgc cctgcaactc gccggggccg atgttctgtt agtcgattcc gatccccagg    18240
gcagtgcccg cgattgggcg gccgtgcggg aagatcaacc gctaaccgtt gtcggcatcg    18300
accgcccgac gattgaccgc gacgtgaagg ccatcggccg gcgcgacttc gtagtgatcg    18360
acggagcgcc ccaggcggcg gacttggctg tgtccgcgat caaggcagcc gacttcgtgc    18420
tgattccggt gcagccaagc ccttacgaca tatgggccac cgccgacctg gtggagctgg    18480
ttaagcagtc cattgaggtc acggatgaa ggctacaagc ggcctttgtc gtgtcgggag    18540
cgatcaaagg cacgcgcatc ggcggtgagg ttgccgagge gctggccggg tacgagctgc    18600
ccattcttga gtcccgtatc acgcagcgcg tgagctaccc aggcactgcc gccgccggca    18660
caaccgttct tgaatcagaa cccgagggcg acgctgcccg cgaggccag gcgctggccg    18720
ctgaaattaa atcaaaactc atttgagtta atgaggtaaa gagaaaatga gcaaaagcac    18780
aaacacgcta agtgccggcc gtccgagcgc acgcagcagc aaggctgcaa cgttggccag    18840
```

-continued

```
cctggcagac acgccagcca tgaagcgggt caacttttcag ttgccggcgg aggatcacac    18900
caagctgaag atgtacgcgg tacgccaagg caagaccatt accgagctgc tatctgaata    18960
catcgcgcag ctaccagagt aaatgagcaa atgaataaat gagtagatga attttagcgg    19020
ctaaaggagg cggcatggaa aatcaagaac aaccaggcac cgacgccgtg gaatgcccca    19080
tgtgtggagg aacgggcggt tggccaggcg taagcggctg ggttgtctgc cggccctgca    19140
atggcactgg aaccccaag cccgaggaat cggcgtgacg gtcgcaaacc atccggcccg    19200
gtacaaatcg gcgcggcgct gggtgatgac ctggtggaga agttgaaggc cgcgcaggcc    19260
gcccagcggc aacgcatcga ggcagaagca cgccccggtg aatcgtgcca gcggccgct    19320
gatcgaatcc gcaaagaatc ccggcaaccg ccggcagccg gtgcgccgtc gattaggaag    19380
ccgcccaagg gcgacgagca accagatttt ttcgttccga tgctctatga cgtgggcacc    19440
cgcgatagtc gcagcatcat ggacgtggcc gtttttccgtc tgtcgaagcg tgaccgacga    19500
gctggcgagg tgatccgcta cgagcttcca gacgggcacg tagaggtttc cgcagggccg    19560
gccggcatgg ccagtgtgtg ggattacgac ctggtactga tggcggtttc ccatctaacc    19620
gaatccatga accgataccg ggaagggaag ggagacaagc ccggccgcgt gttccgtcca    19680
cacgttgcgg acgtactcaa gttctgccgg cgagccgatg gcgaaagca ga             19732

SEQ ID NO: 90           moltype = DNA  length = 21015
FEATURE                 Location/Qualifiers
source                  1..21015
                        mol_type = other DNA
                        organism = synthetic construct
SEQUENCE: 90
accttccaaa cgagaaggtg ctccctaagc actctttgct ctacgagtac ttcaccgtgt    60
acaacgagtt gaccaaggtt aagtacgtga ccgagggaat gaggaagcct gcttttttgt   120
caggtgagca aaagaaggct atcgttgatc tcttgttcaa gaccaacaga aaggtgaccg   180
tgaagcagct caaagaggat tacttcaaga aaatgaaggc cttcgattca gttgagattt   240
ctggtgttga ggataggttc aacgcatctc tcggaaccta ccacgatctc ctcaagatca   300
ttaaggataa ggatttcttg gataacgagg aaaacgagga tatcttggag gatatcgttc   360
ttaccctcac cctcttttgaa gatagagaga tgattgaaga aaggctcaag acctacgctc   420
atctcttcga tgataaggtg atgaagcagt tgaagagaa aagatacact ggttgggaa    480
ggctctcaag aaagctcatt aacgaatca gggataagca gtctggaaag acaatcttg    540
atttcctcaa gtctgatgga ttcgctaaca gaaacttcat gcagctcatc cacgatgatt    600
ctctcacctt taaagaggat atccagaagg ctcaggttc aggacagggt gatagtctcc    660
atgagcatat cgctaacctc gctggatctc ctgcaatcaa gaaggggaatc ctccagactg    720
tgaaggttgt ggatgagttg gtgaaggtga tgggaaggca taagcctgag aacatcgtga    780
tcgaaatggc tagagagaac cagaccactc agaagggaca gaagaactct agggaaagga    840
tgaagaggat cgaggaaggt atcaaaggc ttggatctca gatcctcaaa gagcaccctg    900
ttgagaacac tcagctccag aatgagaagc tctacctcta ctacctccag aacgggaaagg    960
atatgtatgt ggatcaagag ttggatatca acaggctctc tgattacgat gttgatcata   1020
tcgtgccaca gtcattcttg aaggatgatt ctatcgaata caaggtgctc accaggtctg   1080
ataagaacag gggtaagagt gataacgtgc caagtgaaga ggttgtgaag aaaatgaaga   1140
actattggag gcagctcctc aacgctaagc tcatcactca gagaaagttc gataacttga   1200
ctaaggctga gagggagga ctctctgaat tggataaggc aggattcatc aagaggcagc   1260
ttgtggaaac caggcagatc actaagcacg ttgcacagat cctcgattct aggatgaaca   1320
ccaagtcga tgaaacgat aagttgatca gggaagtgaa ggttatcacc ctcaagtcaa   1380
agctcgtgtc tgatttcaga aaggatttcc aattctacaa ggtgagggaa atcaacaact   1440
accaccaacgc tcacgatgct taccttaacg ctgttgttgg aaccgctctc atcaagaagt   1500
atcctaagct cgagtcagag ttcgtgtacg gtgattacaa ggtgtacgat gtgaggaaga   1560
tgatcgctaa gtctgagcaa gagatcgaa aggctaccgc taagtatttc ttctactcta   1620
acatcatgaa ttttcttcaag accgagatta ccctcgctaa cggtgagatc agaaagaggc   1680
cactcatcga gacaaacggt gaaacaggtg agatcgttg ggataaggga agggattcg   1740
ctaccgttag aaaggtgctc tctatgccac aggtgaacat cgttaagaaa accgaggtgc   1800
agaccggtgg attctctaaa gagtctatcc tccctaagag gaactctgat aagctcattg   1860
ctaggaagaa ggattgggac cctaagaaat acggtggttt cgattctcct accgtggctt   1920
actctgttct cgttgtggct aaggttgaga agggaaagag taagaagtca agtctgtta   1980
aggaacttct cggaatcact atcatgaaa ggtcatcttt cgagaagaac ccaatcgatt   2040
tcctcgaggc taagggatac aaagaggtta agaaggatct catcatcaag ctcccaaagt   2100
actcactctt cgaactcgag aacggtagaa agaggatgc cgcttctgct ggtgagcttc   2160
aaaagggaa cgagcttgct ctcccatcta agtacgttaa cttcttttac ctcgcttctc   2220
actacgagaa gttgaaggga tctccagaag ataacgagca gaagcaactt ttcgttgagc   2280
agcacaagca ctacttggat gagatcatcg agcagatctc tgagttctct aaaagggtga   2340
tcctcgctga tgcaaacctc gataaggtgt gtctgctta caacaagcac agagataagc   2400
ctatcaggga acaggcagag aacatcatcc atctcttcac ccttaccaac ctcggtgctc   2460
ctgctgcttt caagtacttc gatacaacca tcgataggaa cagatactct accaccaaag   2520
aagtgctcga tgctaccctc atccatcagt ctatcactgg actctacgag actaggatcg   2580
atctctcaca gctcggtggt gattcaaggg ctgatcctaa gaagaagagg aaggtttgac   2640
gtcgacgata tgaagatgaa gatgaaatat ttggtgtgtc aaataaaag cttgtgtgct   2700
taagtttgtg ttttttttctt ggcttgttgt gttatgaatt tgtggctttt tctaatatta   2760
aatgaatgta agatcacatt ataatgaata aacaaatgtt tctataatcc attgtgaatg   2820
ttttgttgga tctcttctgc agcatataac tactgtatgt gctatggtat ggactatgga   2880
atatgattaa agataagcca gagctctggt gacggaccca tggcttcgtt gaacaacgga   2940
aactcgactt gccttccgca caatacatca tttcttctta gcttttttc ttcttcttcg   3000
ttcatacagt ttttttttgt ttatcagctt acatttttctt gaaccgtagc tttcgttttc   3060
ttctttttaa ctttccattc ggagttttga tatcttgtc catgtttgt cccaggatta   3120
gaatgattag gcatcgaacc ttcaagaatt tgattgaata aaacatcttc attcttaaga   3180
tatgaagata atcttcaaaa ggcccctggg aatctgaaag aagagaagca ggcccattta   3240
tatgggaaag aacaatagta ttccttatat aggcccattt aagttgaaaa caatcttcaa   3300
aagtcccaca tcgcttagat aagaaaacga agctgagttt atatacagct agagtcgaag   3360
tagtgattgc ctacttgggc tgttgcaggt tttagagcta gaaatagcaa gttaaaataa   3420
```

```
ggctagtccg ttatcaactt gaaaaagtgg caccgagtcg gtgctttttt tcccggggcg 3480
cgccctatgt cgagctgcag gtcaacggat caggatattc ttgtttaaga tgttgaactc 3540
tatggaggtt tgtatgaact gatgatctag gaccggataa gttcccttct tcatagcgaa 3600
cttattcaaa gaatgttttg tgtatcattc ttgttacatt gttattaatg aaaaaatatt 3660
attggtcatt ggactgaaca cgagtgttaa atatggacca ggcccaaat aagatccatt 3720
gatatatgaa ttaaataaca agaataaatc gagtcaccaa accacttgcc ttttttaacg 3780
agacttgttc accaacttga tacaaaagtc attatcctat gcaaatcaat aatcatacaa 3840
aaatatccaa taacactaaa aaattaaaag aaatggataa tttcacaata tgttatacga 3900
taaagaagtt acttttccaa gaaattcact gattttataa gcccacttgc attagataaa 3960
tggcaaaaaa aaacaaaaag gaaaagaaat aaagcacgaa gaattctaga aaatacgaaa 4020
tacgcttcaa tgcagtggga cccacggttc aattattgcc aattttcagc tccaccgtat 4080
atttaaaaaa taaaacgata atgctaaaaa aatataaatc gtaacgatcg ttaaatctca 4140
acggctggat cttatgacga ccgttagaaa ttgtggttgt cgacgagtca gtaatcaaacg 4200
gcgtcaaagt ggttgcagcc ggcacacacg agtcgtgttt atcaactcaa agcacaaata 4260
cttttcctca acctaaaaat aaggcaatta gccaaaaaca actttgcgtg taaacaacgc 4320
tcaatacacg tgtcatttta ttattagcta ttgcttcacc gccttagctt tctcgtgacc 4380
tagtcgtcct cgtctttttct tcttcttctt ctataaaaca atacccaaag agctcttctt 4440
cttcacaatt cagatttcaa tttctcaaaa tcttaaaaac tttctctcaa ttctctctac 4500
cgtgatcaag gtaaatttct gtgttcctta ttctctcaaa atcttcgatt ttgttttcgt 4560
tcgatcccaa tttcgtatat gttctttggt ttagattctg ttaatcttag atcgaacacg 4620
attttctggg tttgatcgtt agatatcatc ttaattctcg attagggttt catagatatc 4680
atccgatttg ttcaaataat ttgagttttg tcgaataatt actcttcgat ttgtgatttc 4740
tatctagatc tggtgttagt ttctagtttg tgcgatcgaa tttgtcgatt aatctgagtt 4800
tttctgatta acaggcctgc aggatggaag acgccaaaaa cataagaaa ggcccggcgc 4860
cattctatcc gctggaagat ggaaccgctg gagagcaact gcataaggct atgaagagat 4920
acgccctggt tcctggaaca attgctttta cagatgccaa tatcagcactt 4980
acgctgagta cttcgaaatg tccgttcggt tggcagaagc tatgaaacga tatgggctga 5040
atacaaatca cagaatcgtc gtatgcagtg aaaactctct tcaattcttt atgccggtgt 5100
tgggcgcgtt atttatcgga gttgcagttg cgcccgcgaa cgacatttat aatgaacgtg 5160
aattgctcaa cagtatgggc atttcgcagc ctaccgtggt gttcgtttcc aaaaaggggt 5220
tgcaaaaaat tttgaacgtg caaaaaaagc tcccaatcat ccaaaaaatt attatcatgg 5280
attctaaaac ggattaccag ggatttcagt cgatgtacac gttcgtcaca tctcatctac 5340
ctcccggttt taatgaatac gattttgtgc cagagtcctt cgataggga agacaattg 5400
cactgatcat gaactcctct ggatctactg gtctgcctaa aggtgtcgct ctgcctcata 5460
gaactgcctg cgtgagattc tcgcatgcca gagatcctat ttttggcaat caaatcattc 5520
cggatactgc gattttaagt gttgttccat tccatcacgg ttttggaatg tttactacac 5580
tcggatattt gatatgtgga tttcgagtcg tcttaatgta tagatttgaa gaagagctgt 5640
ttctgaggag ccttcaggat tacaagattc aaagtgcgct gctggtgcca acctattct 5700
ccttcttcgc caaagcact ctgattgaca aatacgattt atctaattta cacgaaattg 5760
cttctggtgg cgctccccte tctaaggaag tcggggaagc ggttgccaag aggttccatc 5820
tgccaggtat caggcaagga tatgggctca ctgagactac atcagctatt ctgattacac 5880
ccgaggggga tgataaaccg ggcgcggtcg gtaaagttgt tccattttt gaagcgaagg 5940
ttgtggatct ggataccggg aaaacgctgg gcgttaatca aagaggcgaa ctgtgtgtga 6000
gaggtcctat gattatgtcc ggttatgtaa acaatccgga agcgaccaac gccttgattg 6060
acaaggatgg atggctacat tctggagaca tagcttactg ggacgaagac gaacacttct 6120
tcatcgttga ccgcctgaag tctctgatta gtacaaagg ctatcaggtg gctcccgctg 6180
aattggaatc catcttgctc caacaccca acatcttcga cgctggtgtc gcaggtcttc 6240
ccgacgatga cgccggtgaa cttcccgccg ccgttgttgt tttggagcac ggaaagacga 6300
tgacggaaaa agagatcgtg gattacgtcg ccagtcaagt aacaaccgcg aaaaagttgc 6360
gcggaggagt tgtgtttgtg gacgaagtac cgaaaggtct taccggaaaa ctcgacgcaa 6420
gaaaaatcag agagatcctc ataaaggcca agaagggcga aagatcgcc gtgtgactcg 6480
aggttcgagt attatggcat tgggaaaact gttttctg taccatttgt tgtgcttgta 6540
atttactgtg ttttttattc ggttttgct atcgaactgt gaaatggaaa tggatggaga 6600
agagttaatg aatgatatgg tccttttgtt cattctcaaa ttaatattat ttgtttttc 6660
tcttatttgt tgtgtgttga attttgaaatt ataagagata tgcaaacatt ttgtttttgag 6720
taaaaatgtg tcaaatcgtg gcctctaatg accgaagtta atatgaggag taaaacactt 6780
gtagttgtgt tagagctctc ccgcagattt gccttttcaa tttcagaaag aatgctaacc 6840
cacagatggt tagagaggct tacgcagcag gtatcatcaa gacgatctac ccgagcaata 6900
atctccagga aatcaaatac cttcccaaga aggttaaaga tgcagtcaaa agattcagga 6960
ctaactgcat caagaacaca gagaaagata tatttctcaa gatcagaagt actattccag 7020
tatggacgat tcaaggcttg cttcacaaac caaggcaagt aatagagatt ggagtctcta 7080
aaaaggtagt tcccactgaa tcaaaggcca tggagtcaaa gattcaaata gaggacctaa 7140
cagaactcgc cgtaaagact ggcgaacagt tcatacagag tctcttacga ctcaatgaca 7200
agaagaaaat cttcgtcaac atggtgtgagc acgacacact tgtctactcc aaaaatatca 7260
aagatacagt ctcagaagac caagggcaa ttgagacttt tcaacaaagg gtaatatccg 7320
gaaacctcct cggattccat tgcccagcta tctgtcactt tattgtgaag atagtggaaa 7380
aggaaggtgg ctcctacaaa tgccatcatt gcgataaagg aaaggccatc gttgaagatg 7440
cctctgccga cagtggtccc aaagatggac cccaccca gaggagcatc gtggaaaaag 7500
aagacgttcc aaccacgtct tcaaagcaag tggattgatg tgatatctcc actgacgtaa 7560
gggatgacgc acaatcccac tatccttcgc aagaccctttc ctctatataa ggaagttcat 7620
ttcatttgga gagaacacgg gggactatga tggcttcatt gtcttgtgtt gaagacaaga 7680
tgaaacaag ttgtttggtt aatggtggag gaactataac aacaacaaca tctcaatcta 7740
ccttgcttga agagatgaag ctgttgaaag accagtcagg tacaagaaag ccggtaataa 7800
actcggagct atggcacgct tgtgcaggcc ctttggtgtg tctccctcaa gttgggagct 7860
tagtgtatta cttctcacaa ggtcatagcg agcaggttgc tgtttcaacc agaagatcag 7920
caacaacaca agttcctaat tatccgaacc ttccatctca gttgatgtgt caagtccata 7980
atgttactct tcatgctgac aaagacagtg acgaaatcta tgctcagatg agtcttcaac 8040
ctgttcactc tgagagagat gtgttccctg taccagactt tggaatgctg agaggaagta 8100
agcacccgac tgagttttc tgcaaaacac ttactgcaag tgacacaagc acacatggag 8160
```

```
gtttctcagt gccacgtaga gctgcagaga agctatttcc accattggac tactcagcac 8220
agccgccaac gcaagagctt gtagttcgag atcttcatga gaatacttgg acatttcgcc 8280
atatctaccg agggcaacca aagagacatc tcctaactac aggatggagt ttgttcgttg 8340
gatcgaagag attgagagct ggggattctg ttttgttcat cagggatgag aagtcacaac 8400
ttatggtcgg tgttaggcgt gccaatcgcc aacaaacagc acttccttca tcagttctct 8460
cagcggatag tatgcacatc ggtgttcttg ctgctgctgc tcacgcaacc gccaaccgta 8520
ctccttttt gatattctat aatccaagag cttgtccagc agagttcgtg atccctctag 8580
ctaagtaccg taaggcgata tgcgggtctc agctctcagt tggtatgaga tttggaatga 8640
tgtttgaaac tgaagattcc gggaaacgaa ggtacatgga aactattgtt ggaatcagcg 8700
atttggatcc gttgagatgg cctggttcta agtggcgtaa ccttcaggta gaatgggatg 8760
agcctggatg taatgataaa cctactcggg tcagtccatg ggatatcgaa acacctgaaa 8820
gtctcttcat ttttccttct ctgacctcag gactcaaacg tcagctccat ccatcttact 8880
ttgctggtga aactgaatgg ggtagcttga taaaacggcc acttatacgt gttcctgatt 8940
ccgcgaatgg gattatgcca tatgcatctt tccctagtat ggcttcggag cagcttatga 9000
aaatgatgat gaggcctcac aacaaccaaa atgtaccatc tttcatgtct gagatgcagc 9060
agaatattgt aatggggaat ggaggtttgc taggagatat gaagatgcag caacccctga 9120
tgatgaacca gaaatctgag atggtgcagc cacaaaacaa gctaacagtg aacccatctg 9180
cttctaatac gagtggccaa gaacagaatc tttcacagag tatgagtgct cctgctaaac 9240
ctgagaactc tacactctct ggttgcagct ctggatagagt ccaacatgga cttgagcagt 9300
caatggaaca ggcaagccag gttactacat ccacagtgtg taatgaggaa aaggttaatc 9360
agctacttca gaaaccgggt gcttcgtcgc ctgtacaagc tgatcaatgt cttgacatta 9420
ctcatcagat ttaccaacca cagtcgatc caataaatg attctcttc ctggaaactg 9480
atgagctgac atcacaagtc tcttccttcc agtctcttgc cggatcatac aagcaaccat 9540
tcattctatc ctcccaggat tcttcagctg ttgtgttacc ggattccaca aactcaccgc 9600
tgtttcatga tgtgtgggac actcagttga acggtctcaa gtttgaccag ttcagtccct 9660
tgatgcagca ggacctttat gctagtcaga atatctgtat gagtaatagc acaaccagta 9720
acattctaga tcctccactc tcaaacacag tccttgatga cttctgtgcc atcaaagaca 9780
ctgatttcca gaaccaccct tctgttgtt tggttggaaa caacaacact agctttgctc 9840
aagatgtcca gtcgcagatc acatcagcta gctttgcaga ctcacaggcc ttctctcgcc 9900
aagattttcc agataattct ggaggcactg gtacatcttc aagcaatgtt gattttgatg 9960
attgtagtct gcggcaaaat agtaaaggct catcatggca gaaaattgcg acaccccgcg 10020
tccgaaccta ctcgagtttc tccataataa tgtgtgagta gttcccagat aagggaatta 10080
gggttcctat agggtttcgc tcatgtgttg agcatataag aaacccttag tatgtatttg 10140
tatttgtaaa atacttctat caataaaatt tctaattcct aaaaccaaaa tccagtacta 10200
aaatccagat ccccgaatt aagtgtttga tcgccggcgg taccgagtgt acttcaagtc 10260
agtgggaaat caataaaatg attattttat gaatatattt cattgtgcaa gtagatagaa 10320
attacatatg ttacataaca cacgaaataa acaaaaaaag acaatccaaa acaaacaccc 10380
ccaaaaaaaa taatcacttt agataaactc gtatgaggag aggcacgttc agtgactcga 10440
cgattcccga gcaaaaaaag tctccccgtc acacatgtag tgggtgacgc aattatcttt 10500
aaagtaatcc ttctgttgac ttgtcattga taacatccag tcttcgtcag gattcgaaag 10560
aattatagaa gggatcccac cttttatttt cttctttttt ccatatttag ggttgacagt 10620
gaaatcgcac tggcaacta ttaattgctt ccacaatggg acgaacttga aggggatgtc 10680
gtcgatgata ttataggtgg cgtgttcatc gtagttggtg aaatcgatgg taccgttcca 10740
atagttgtgt cgtccgagac ttctagccca ggtggtcttt ccggtacgag ttggtccgca 10800
gatgtagagg ctggggtgtc ggattccatt ccttccattg tccttgttaa atcggccatc 10860
cattcaaggt cagattgagc ttgttggtat gagacaggat gtatgtaagt ataagcgtct 10920
atgcttacat ggtatagatg ggtttccctc caggagtgga gatcttcgtg gcagcgaaga 10980
tctgattctg tgaagggcga cacatacggt tcaggtgtg gagggaataa tttgttggct 11040
gaatattcca gccattgaag cttttgttgcc cattcatgag ggaattcttc cttgatcatg 11100
tcaagatatt cctccttaga cgttgcagtc tggataatag ttctccatcg tgcgtcagat 11160
ttgcgaggag aaaccttatg atctcggaaa tctcctctgg ttttaatatc tccgtccttt 11220
gatatgtaat caaggacttg tttagagttt ctagctggct ggatattagg gtgatttcct 11280
tcaaaatcga aaaagaagg atccctaata caaggttttt tatcaagctg gagaagagca 11340
tgatagtggg tagtgccatc ttgatgaagc tcagaagcaa caccaaggaa gaaaataaga 11400
aaaggtgtga gtttctccca gagaaactgg aataaatcat ctctttgaga tgagcacttg 11460
ggataggtaa ggaaaacata tttagattgg agtctgaagt tcttactagc agaaggcatg 11520
ttgttgtgac tccgagggt tgcctcaaac tctatcttat aaccggcgtg gaggcatgga 11580
ggcagggta ttttggtcat tttaatagat agtggaaaat gacgtggaat ttacttaaag 11640
acgaagtctt tgcgacaagg gggggcccac gccgaattta atattaccgg cgtggccccc 11700
ccttatcgcg agtgctttag cacgacggat ccagatttaa agtagaaaat ttcccgccca 11760
ctagggttaa aggtgttcac actataaaag catatacgat gtgatggtat ttgatggagc 11820
gtatattgta tcaggtattt ccgttggata cgaattattc gtacgaccct catagtttaa 11880
actatcagtg tttgacagga tatattgcg ggtaaaccta agagaaaaga gcgtttatta 11940
gaataacgga tatttaaaag ggcgtgaaaa ggtttatccg ttcgtccatt tgtatgtgca 12000
tgccaaccac agggttcccc tcgggatcaa agtactttga tccaacccct ccgctgctat 12060
agtgcagtcg gcttctgacg ttcagtgcag ccgtcttctg aaaacgacat gtcgcacaag 12120
tcctaagtta cgcgacaggc tgccgcctg ccctttttcct ggcgttttct tgtcgcgtgt 12180
tttagtcgca taaagtagaa tacttgcgac tagaaccgga gacattacgc catgaacaag 12240
agcgccgccg ctggcctgct gggctatgcc gcgtcagca ccgacgacca ggacttgacc 12300
aaccaacggg ccgaactgca cgcggccggc tgcaccaagc tgttttccga agatcacc 12360
ggcaccaggc gcgaccgccc ggagctggcc aggatgcttg accacctacg ccctggcgac 12420
gttgtgcagg tgaccaggct agaccgcctg gcccgcagca cccgcgaccct actggacatt 12480
gccgagcgca tccaggaggc cggcgcgggc ctgcgtagcc tggcagagcc gtgggccgac 12540
accaccaccg cggcccg catggtgttg accgtgttgcc cggcattgcc cgagttcgag 12600
cgttccctaa tcatcgaccg cacccggagc gggcgcgagg ccgccaaggc ccgaggcgtg 12660
aagtttggcc cccgccctac cctcaccccg gcacagatcg cgcacgcccg cgagctgatc 12720
gaccaggaag gccgcaccgt gaaagaggcg gctgcactgc ttggcgtgca tcgctcgacc 12780
ctgtaccgcg cacttgagcg cagcgaggaa gtgacgccca ccgaggccag gcggcgcggt 12840
gccttccgtg aggacgcatt gaccgaggcc gacgccctgg cggccgccga gaatgaacgc 12900
```

```
caagaggaac aagcatgaaa ccgcaccagg acggccagga cgaaccgttt tcattaccg    12960
aagagatcga ggcggagatg atcgcggccg ggtacgtgtt cgagccgccc gcgcacggct   13020
caaccgtgcg gctgcatgaa atcctggccg gtttgtctga tgccaagctg gcggcctggc   13080
cggccagctt ggccgctgaa gaaaccgagc gccgccgtct aaaaaggtga tgtgtatttg   13140
agtaaaacag cttgcgtcat gcggtcgctg cgtatatgat gcgatgagta aataaacaaa   13200
tacgcaaggg gaacgcatga aggttatcgc tgtacttaac cagaaaggcg ggtcaggcaa   13260
gacgaccatc gcaacccatc tagcccgcgc cctgcaactc gccggggccg atgttctgtt   13320
agtcgattcc gatccccagg gcagtgcccg cgattgggcg gccgtgcggg aagatcaacc   13380
gctaaccgtt gtcggcatcg accgcccgac gattgaccgc gacgtgaagg ccatcggccg   13440
gcgcgacttc gtagtgatcg acggagcgcc ccaggcggcg gacttggctg tgtccgcgat   13500
caaggcagcc gacttcgtgc tgattccggt gcagccaagc ccttacgaca tatgggccac   13560
cgccgacctg gtggagctgg ttaagcagcg cattgaggtc acggatggaa ggctacaagc   13620
ggcctttgtc gtgtcgcggg cgatcaaagg cacgcgcatc ggcggtgagg ttgccgaggc   13680
gctggccgg tacgagctgc ccattcttga gtcccgtatc acgcagccgc tgagctaccc   13740
aggcactgcc gccgcggca caaccgttct tgaatcagaa cccgagggcg acgctgcccg   13800
cgaggtccag gcgctggccg ctgaaattaa atcaaaactc atttgagtta atgaggtaaa   13860
gagaaaatga gcaaaagcac aaaacacgcta agtgccggcc gtccgagcgc acgcagcagc   13920
aaggctgcaa cgttggccag cctgcagac acgccagaca tgaagcgggt caactttcag   13980
ttgccggcgg aggatcacac caagctgaag atgtacgcgg tacgccaagg caagaccatt   14040
accgagctgc tatctgaata catcgcgcag ctaccagagt aaatgagcaa atgaataaat   14100
gagtagatga attttagcgg ctaaaggagg cggcatggaa aatcaagaac aaccaggcac   14160
cgacgccgtg gaatgcccca tgtgtggagg aacgggcgt tggccaggcg taagcggctg   14220
ggttgtctgc cggccctgca atggcactgg aaccccaag cccgaggaat cggcgtgacg   14280
gtcgcaaacc atccggcccg gtacaaatcg gcgcggcgct gggtgatgac ctggtggaga   14340
agttgaaggc cgcgcaggcc gcccagcggc aacgcatcga ggcagaagca cgccccggtg   14400
aatcgtgca agccgccgct gatcgaatcc gcaaagaatc ccggcaaccg ccggcagccg   14460
gtgcgccgtc gattaggaag ccgcccaagg gcgacgagca accagatttt tcgttccga   14520
tgctctatga cgtgggcacc cgcgatagtc gcagcatcat ggacgtggcc gttttccgtc   14580
tgtcgaagcg tgaccgacga gctggcgagg tgatccgcta cgagcttcca gacgggcacg   14640
tagaggtttc cgcaggggcg gccggcatgg ccagtgtgtg ggattacgac ctggtactga   14700
tggcggtttc ccatctaacc gaatccatga accgataccg ggaagggaag ggagacaagc   14760
ccggccgcgt gttccgtcca cacgttgcgg acgtactcaa gttctgccgg cgagccgatg   14820
gcggaaagca gaaagacgac ctggtagaaa cctgcattcg gttaaacacc acgcacgttg   14880
ccatgcagcg tacgaagaag gccaagaacg gccgcctggt gacgctgtcc gagggtgaag   14940
ccttgattag ccgctacaag atcgtaaaga gcgaaaccgg gcggccggag tacatcgaga   15000
tcgagctagc tgattggatg taccgcgaga tcacagaagg caagaacccg gacgtgctga   15060
cggttcaccc cgattacttt ttgatcgatc ccggcatcgg ccgttttctc taccgcctgg   15120
cacgccgcgc cgcaggcaag gcagaagcca gatggttgtt caagacgatc tacgaacgca   15180
gtggcagcgc cggagagttc aagaagttct gtttcaccgt gcgcaagctg atcgggtcaa   15240
atgacctgcc ggagtacgat ttgaaggagg aggcggggca ggctggcccg atcctagtca   15300
tgcgctaccg caacctgatc gagggcgaag catccgccgg ttcctaatgt acggagcaga   15360
tgctagggca aattgcccta gcaggggaaa aaggtcgaaa aggcctcttt cctgtggata   15420
gcacgtacat tgggaaccca aagccgtaca ttgggaaccg gaaccgtac attgggaacc   15480
caaagccgta cattgggaac cggtcacaca tgtaagtgac tgatataaaa gagaaaaaag   15540
gcgatttttc cgcctaaaac tctttaaaac ttattaaaac tcttaaaacc cgcctggcct   15600
gtgcataact gtctggccag cgcacagccg aagagctgca aaaagcgcct acccttcggt   15660
cgctgcgctc cctacgcccc gccgcttcgc gtcggcctat ggccgctcaa   15720
aaatggctgg cctacggcca ggcaatctac cagggcgcgg acaagccgcg ccgtcgccac   15780
tcgaccgccg gcgcccacat caaggcaccc tgcctcgcgc gtttcggtga tgacggtgaa   15840
aacctctgac acatgcagct cccggaaacg gtcacagctt gtctgtaagc ggatgccggg   15900
agcagacaag cccgtcaggg cgcgtcagcg ggtgttgggg ggtgtcgggg cgcagccatg   15960
acccagtcac gtagcgatag cggagtgtat actggcttaa ctatgcggca tcagagcaga   16020
ttgtactgag agtgcaccat atgcggtgtg aaataccgca cagatgcgta aggagaaaat   16080
accgcatcag gcgctcttcc gcttcctcgc tcactgactc gctgcgctcg gtcgttcggc   16140
tgcggcgagc ggtatcagct cactcaaagg cggtaatacg gttatccaca gaatcagggg   16200
ataacgcagg aaagaacatg tgagcaaaag gccagcaaaa ggccaggaac cgtaaaaagg   16260
ccgcgttgct ggcgtttttc cataggctcc gcccccctga cgagcatcac aaaaatcgac   16320
gctcaagtca gaggtggcga aacccgacag gactataaag ataccaggcg tttcccctg   16380
gaagctccct cgtgcgctct cctgttccga cctgccgct taccggatac ctgtccgcct   16440
ttctcccttc gggaagcgtg gcgctttctc atagctcacg ctgtaggtat ctcagttcgg   16500
tgtaggtcgt tcgctccaag ctgggctgtg tgcacgaacc ccccgttcag cccgaccgct   16560
gcgccttatc cggtaactat cgtcttgagt ccaacccggt aagacacgac ttatcgccac   16620
tggcagcagc cactggtaac aggattagca gagcgaggta tgtaggcggt gctacagagt   16680
tcttgaagtg gtggcctaac tacggctaca ctagaaggac agtatttggt atctgcgctc   16740
tgctgaagcc agttaccttc ggaaaaagag ttggtagctc ttgatccggc aaacaaacca   16800
ccgctggtag cggtggtttt tttgttgca agcagcagat tacgcgcaga aaaaaggat   16860
ctcaagaaga tcctttgatc ttttctacgg gtctgacgc tcagtggaac gaaaactcac   16920
gttaagggat tttggtcatg cattctaggt actaaaacaa ttcatccagt aaaatataat   16980
atttatttt ctcccaatca ggcttgatcc ccagtaagtc aaaaaatage tcgacatact   17040
gttcttcccc gatatcctcc ctgatcgacc ggacgcagaa ggcaatgtca taccacttgt   17100
ccgccctgcc gcttctccca agatcaataa agccacttac tttgcatctt tcacaaaga   17160
tgttgctgtc tcccaggtcg ccgtgggaaa agacaagttc tcttcgggc ttttccgtct   17220
ttaaaaaatc atacagctcg gcggatctt taaatggagt gtcttcttcc cagttttcgc   17280
aatccacatc ggccagatc ttattcagta agaatccaa ttcggctaag cggctgctca   17340
agctattcgt ataggaggaa tccgatatgt cgatggagtg aaagagcctg atgcactccg   17400
catacagctc gataatcttt tcagggctt gttcatcttc atactcttcc gagcaaagga   17460
cgccatcggc ctcactcatg agcagattgc tccagccatc atgccgttca aagtgcagga   17520
cctttggaac aggcagcttt ccttccagcc atagcatcat gtccttttcc cgttccacat   17580
cataggtggt cccttatac cggctgtccg tcatttttta atataggttt tcattttctc   17640
```

```
ccaccagctt atatacctta gcaggagaca ttccttccgt atcttttacg cagcggtatt    17700
tttcgatcag ttttttcaat tccggtgata ttctcatttt agccatttat tatttccttc    17760
ctctttcta cagtatttaa agataccca agaagctaat tataacaaga cgaactccaa     17820
ttcactgttc cttgcattct aaaaccttaa ataccagaaa acagctttt caaagttgtt    17880
ttcaaagttg gcgtataaca tagtatcgac ggagccgatt ttgaaaccgc ggtgatcaca    17940
ggcagcaacg ctctgtcatc gttacaatca acatgctacc ctccgcgaga tcatccgtgt    18000
ttcaaacccg gcagcttagt tgccgttctt ccgaatagca tcggtaacat gagcaaagtc    18060
tgccgcctta caacggctct cccgctgacg ccgtccgga ctgatgggct gcctgtatcg     18120
agtggtgatt ttgtgccgag ctgccggtcg gggagctgtt ggctggctgg tggcaggata    18180
tattgtggtg taaacaaatt gacgcttaga caacttaata acacattgcg gacgtttta    18240
atgtagagct caaagtttaa cgcgttagca gaaggcatgt tgttgtgact ccgaggggtt    18300
gcctcaaact ctatcttata accggcgtgg aggcatggag gcaggggtat tttggtcatt    18360
ttaatagata gtgaaaatg acgtggaatt tacttaaaga cgaagtcttt gcgacaaggg     18420
ggggcccacg ccgaatttaa tattaccggc gtggccccc cttatcgcga gtgctttagc     18480
acgagcggtc cagattaaa gtagaaaatt tcccgcccac tagggttaaa ggtgttcaca    18540
ctataaaagc atacgatg tgatggtatt tgatggagcg tatattgtat caggtatttc     18600
cgttggatac gaattattcg tacgaccctc ggtaccgatc ggcgcgccag atttgccttt    18660
tcaatttcag aaagaatgct aacccacaga tggttagaaa ggcttacgca gcaggtatca    18720
tcaagacgat ctacccgagc aataatctcc aggaaatcaa ataccttccc aagaaggtta    18780
aagatgcagt caaagattc aggactaact gcatcaagaa cacagagaaa gatatatttc     18840
tcaagatcag aagtactatt ccagtatgga cgattcaagg cttgcttcac aaaccaaggc    18900
aagtaataga gattggagtc tctaaaaagg tagttcccac tgaatcaaag ggccatggag    18960
caaagattca aatagaggac ctaacagaac tcgccgtaaa gactggcgaa cagttcatac    19020
agagtctctt acgactcaat gacaagaaga aaatcttcgt caacatggtg gagcacgaca    19080
cacttgtcta ctccaaaaat atcaaagata cagtctcaga agaccaaagg gcaattgaga    19140
cttttcaaca aagggtaata tccggaaacc tcctcggatt ccattgccca gctatctgtc    19200
actttattgt gaagatagtg gaaaggaag gtgctccta caaatgccat cattgcgata      19260
aaggaaaggc catcgttgaa gatgcctctg ccgacagtgg tcccaaagat ggaccccac    19320
ccacgaggag catcgtggaa aaagaagacg ttccaaccac gtcttcaaag caagtggatt    19380
gatgtgatat ctccactgac gtaagggatg acgcacaatc ccactatcct tcgcaagacc    19440
cttcctctat ataaggaagt tcatttcatt tggagagaac acggggact cctgcaggta     19500
gatcgctcgt cgacatggat aagaagtact ctatcggact cgatatcgga actaactctg    19560
tgggatgggc tgtgatcacc gatgagtaca aggtgccatc taagaagttc aaggttctcg    19620
gaaacaccga taggcactct atcaagaaaa accttatcgg tgctctcctc ttcgattctg    19680
gtgaaactgc tgaggctacc agactcaaga gaaccgctag aagaaggtac accagaagaa    19740
agaacaggat ctgctacctc caagagatct tctctaacga gatggctaaa gtggatgatt    19800
cattcttcca caggctcgaa gagtcattcc tcgtggaaga agataagaag cacgagaggc    19860
accctatctt cggaaacatc gttgatgagg tggcatacca cgagaagtac cctactatct    19920
accaccctcag aaagaagctc gttgattcta ctgataaggc tgatctcagg ctcatctacc    19980
tcgctctcgc tcacatgatc aagttcagag acactcct catcgagggt gatctcaacc     20040
ctgataactc tgatgtggat aagttgttca tccagctcgt gcagacctac aaccagcttt    20100
tcgaagaaa ccctatcaac gcttcaggtg tggatgctaa ggctatcctc tctgctaggc     20160
tctctaagtc aagaaggctt gagaacctca tgctcagct ccctggtgag aagaagaacg      20220
gactttcgg aaacttgatc gctctctctc tcggactcac ccctaacttc aagtctaact    20280
tcgatctcgc tgaggatgca aagctccagc tctcaaagga tacctacgat gatgatctcg    20340
ataacctcct cgctcagatc ggagatcagt acgctgattt gttcctcgct gctaagaacc    20400
tctctgatgc tatcctcctc agtgatatcc tcagagtgaa caccgagatc accaaggctc    20460
cactctcagc ttctatgatc aagagatacg atgagcacca ccaggatctc acacttctca    20520
aggctcttgt tagacagcag ctcccagaga agtacaaaga gattttcttc gatcagtcta    20580
agaacggata cgctggttac atcgatggtg gtgcatctca agaagagttc tacaagttca    20640
tcaagcctat cctcgagaag atggatggaa ccgaggaacct cgtgaag ctcaatagag      20700
aggatcttct cagaaagcag aggaccttcg ataacggatc tatccctcat cagatccacc    20760
tcggagagtt gcacgctatc cttagaaggc aagaggattt ctaccattc tcaaggata     20820
acagggaaa gattgagaag attctcacct tcagaatccc ttactacgtg ggaccctctcg    20880
ctagaggaaa ctcaagattc gcttggatga ccagaaagtc tgaggaaacc atcacccctt    20940
ggaacttcga agaggtggtg gataagggtg ctagtgctca gtctttcatc gagaggatga    21000
ccaacttcga taaga                                                     21015
```

SEQ ID NO: 91        moltype = DNA  length = 19780
FEATURE             Location/Qualifiers
source              1..19780
                     mol_type = other DNA
                     organism = synthetic construct
SEQUENCE: 91

```
ggcatggcca gtgtgtggga ttacgacctg gtactgatgg cggtttccca tctaaccgaa     60
tccatgaacc gataccggga agggaaggga gacaagcccg gccgcgtgtt ccgtccacac    120
gttgcggacg tactcaagtt ctgccggcga gccgatggcg gaaagcagaa agacgacctg    180
gtagaaacct gcattcggtt aaacaccacg cacgttgcca tgcagcgtac gaagaaggcc    240
aagaacggcc gcctggtgac ggtatccgag ggtgaagcct tgattagccg ctacaagatc    300
gtaaagagcg aaaccgggcg gccggagtac atcgagatcg agctagctga ttggatgtac    360
cgcgagatca cagaaggcaa gaacccggac gtgctgacga ttcaccccga ttactttttg    420
atcgatcccg gcatcggccg ttttctctac cgcctggcac gccgcgccgc aggcaaggca    480
gaagccagat ggttgttcaa gacgatctac gaacgcagtg gcagcgccgg agagttcaag    540
aagttctgtt tcaccgtgcg caagctgatc ggtcaaatg acctgccgga gtacgatttg    600
aaggaggagg cggggcaggc tggcccgatc ctagtcatgc gctaccgcaa cctgatcgag    660
ggcgaagcat ccgccggttc ctaatgtacg gagcagatgc tagggcaaat tgccctagca    720
ggggaaaaag gtcgaaaagg cctctttcct gtggatagca cgtacattgg gaacccaaag    780
ccgtacattg ggaaccggaa cccgtacatt gggaacccaa agccgtacat gggaaccgg    840
tcacacatgt aagtgactga tataaaagag aaaaaaggcg attttttccgc ctaaaactct    900
```

```
ttaaaactta ttaaaactct taaaaccegc ctggcctgtg cataactgtc tggccagcgc  960
acagccgaag agctgcaaaa agcgcctacc cttcggtcgc tgcgctccct acgcccgcc  1020
gcttcgcgtc ggcctatcgc ggcgctggc cgctcaaaaa tggctggcct acggccaggc  1080
aatctaccag ggcgcggaca agccgcgccg tcgccactcg accgcggcg cccacatcaa  1140
ggcaccctgc ctcgcgcgtt tcggtgatga cggtgaaaac tctgacaca tgcagctccc  1200
ggaaacggtc acagcttgtc tgtaagcgga tgccgggagc agacaagccc gtcagggcgc  1260
gtcagcgggt gttggcgggt gtcggggcgc agccatgacc cagtcacgta gcgatagcgg  1320
agtgtatact ggcttaacta tgcggcatca gagcagattg tactgagagt gcaccatatg  1380
cggtgtgaaa taccgcacag atgcgtaagg agaaaatacc gcatcaggcg ctcttccgct  1440
tcctcgctca ctgactcgct gcgctcggtc gttcggctgc ggcgagcggt atcagctcac  1500
tcaaaggcgg taatacggtt atccacagaa tcagggata acgcaggaaa gaacatgtga  1560
gcaaaaggcc agcaaaaggc caggaaccgt aaaaaggccg cgttgctggc gttttccat  1620
aggctccgcc cccctgacga gcatcacaaa aatcgacgct caagtcagag gtggcgaaac  1680
ccgacaggac tataaagata ccaggcgttt ccccctgaa gctccctcgt gcgctctcct  1740
gttccgaccc tgccgcttac cggatacctg tccgcctttc tcccttcggg aagcgtggcg  1800
ctttctcata gctcacgctg taggtatctc agttcggtgt aggtcgttcg ctccaagctg  1860
ggctgtgtgc acgaaccccc cgttcagccc gaccgctgcg ccttatccgg taactatcgt  1920
cttgagtcca acccggtaag acacgactta tcgccactgg cagcagccac tggtaacagg  1980
attagcagag cgaggtatgt aggcggtgct acagagttct tgaagtggtg gcctaactac  2040
ggctacacta aaggacagt atttggtatc tgcgctctgc tgaagccagt taccttcgga  2100
aaaagagttg gtagctcttg atccggcaaa caaaccaccg ctggtagcgg tggtttttt  2160
gtttgcaagc agcagattac gcgcagaaaa aaaggatctc aagaagatcc tttgatcttt  2220
tctacggggt ctgacgctca gtggaacgaa aactcacgtt aagggatttt ggtcatgcat  2280
tctaggtact aaaacaattc atccagtaaa atataatatt ttattttctc ccaatcaggc  2340
ttgatcccca gtaagtcaaa aaatagctcg acatactgtt cttccccgat atcctccctg  2400
atcgaccgga cgcagaaggc aatgtcatac cacttgtccg ccctgcccgct tctcccaaga  2460
tcaataaagc cacttacttt gccatctttc acaaagatgt tgctgtctcc caggtcgccg  2520
tgggaaaaga caagttcctc ttcgggcttt tccgtcttta aaaaatcata cagctcgcgc  2580
ggatctttaa atggagtgtc ttcttccag ttttcgcaat ccacatcggc cagatcgtta  2640
ttcagtaagt aatccaattc ggctaagcgg ctgtctaagc tattcgtata gggacaatcc  2700
gatatgtcga tggagtgaaa gagcctgatg cactccgcat acagctcgat aatcttttca  2760
gggctttgtt catcttcata ctcttccgag caaaggacgc catcggcctc actcatgagc  2820
agattgctcc agccatcatg ccgttcaaag tgcaggacct ttgaacagg cagctttcct  2880
tccagccata gcatcatgtc cttttcccgt tccacatcat aggtggtccc tttataccgg  2940
ctgtccgtca tttttaaata taggttttca ttttctccca ccagcttata taccttagca  3000
ggagacattc cttccgtatc ttttacgcag cggtatttt cgatcagttt tttcaattcc  3060
ggtgatattc tcattttagc catttattat ttccttcctc ttttctacag tatttaaaga  3120
taccccaaga agctaattat aacaagacga actccaattc actgttcctt gcattcaaa  3180
accttaaata ccagaaaaca gctttttcaa agttgtttc aaagttggcg tataacatag  3240
tatcgacgga gccgattttg aaaccgcggt gatcacaggc agcaacgctc tgtcatcgtt  3300
acaatcaaca tgctacccte cgcgagatca tccgtgtttc aaacccggca gcttagttgc  3360
cgttcttccg aatagcatcg gtaacatgag caaagtctgc cgccttacaa cggctctccc  3420
gctgacgccg tcccggactg atgggctgcc tgtatcgagt ggtgatttg tgccgagctg  3480
ccggtcgggg agctgttggc tggctggtgg caggatatat tgtggtgtaa acaaattgac  3540
gcttagacaa cttaataaca cattgcggac gtttttaatg tagagctcaa agttaacgc  3600
gttagcagaa ggcatgttgt tgtgactccg aggggttgcc tcaaactcta tcttataacc  3660
ggcgtgaagc catggaggca ggggtatttt ggtcatttta atagatagtg gaaaatgacg  3720
tggaatttac ttaaagacga agtctttgcg acaaggggg gcccacgccg aatttaatat  3780
taccggcgtg gccccccctt atcgcgagtg ctttagcacg agcggtccag atttaaagta  3840
gaaaatttcc cgcccactag ggttaaaggt gttcacacta taaagcata tacgatgtga  3900
tggtatttga tggagcgtat attgtatcag gtatttccgt tggatacgaa ttattcgtac  3960
gaccctcggt accgatcggc gcgccagatt tgccttttca atttcagaaa gaatgctaac  4020
ccacagatgg ttagagaggc ttacgcagca ggtatcatca agacgatcta cccgagcaat  4080
aatctccagg aaatcaaata ccttcccaag aaggttaaag atgcagtcaa aagattcagg  4140
actaactgca tcaagaacac agagaaagat atatttctca agtcagaag tactattcca  4200
gtatggacga ttcaaggctt gcttcacaaa ccaaggcaag taatagagat tggagtctct  4260
aaaaaggtag ttcccactga atcaaaggcc atggagtcaa agattcaaat agaggaccta  4320
acagaactcg ccgtaaagac tggcgaacag ttcatacaga gtctcttacg actcaatgac  4380
aagaagaaaa tcttcgtcaa catggtggag cacgacacac ttgtctactc caaaaatatc  4440
aaagatacag tctcagaaga ccaaagggca attgagactt ttcaacaaag ggtaatatcc  4500
ggaaacctcc tcggattcca ttgcccagct atctgtcact ttattgtgaa gatagtggaa  4560
aaggaaggtg gctcctacaa atgccatcat gcgataaag gaaggccat cgttgaagat  4620
gcctctgccg acagtggtcc caaagatgga cccccaccca cgaggagcat cgtggaaaaa  4680
gaagacgttc caaccacgtc ttcaaagcaa gtggattgat gtgatatctc cactgacgta  4740
agggatgacg cacaatccca ctatccttcg caagaccctt cctctatata aggaagttca  4800
tttcatttgg agaaacacg gggactcct gcagtgtagt cgctcgtcga catggataag  4860
aagtactcta tcggactcga tatcggaact aactctgtgg gatgggctgt gataccgat  4920
gagtacaagg tgccatctaa gaagttcaag gttccggaa acaccgatag gcactctatc  4980
aagaaaaacc ttatcggtgc tctcctcttc gattctggtg aaactgctga gctaccaga  5040
ctcaagagaa ccgctagaag aaggtacacc agaagaaaga acaggatctg ctacctccaa  5100
gagatcttct ctaacgagat ggctaaagtg atgattcat tcttccacag gctcgaagag  5160
tcattcctcg tggaagaaga taagaagcac gagaggcacc ctatcttcgg aaacatcgtt  5220
gatgaggtgg catacaccga gaagtaccct actatctacc acctcagaaa gaagctcgtt  5280
gattctactg ataaggctga tctcaggctc atctacctcg ctctggctca catgatcaag  5340
ttcagaggac acttcctcat cgagggtgat ctcaacccgg ataactctga tgtggataag  5400
ttgttcatcc agctcgtgca gacctacaac cagcttttcg aagagaaccc tatcaacgct  5460
tcaggtgtga atgctaaggc tatcctctct gctaggctct caagtcaag aaggcttgag  5520
aacctcattg ctcagctccc tggtgagaag aagaacggac ttttcggaaa cttgatcgct  5580
ctctctctcg gactcacccc taacttcaag tctaacttcg atctcgctga ggatgcaaag  5640
```

```
ctccagctct caaaggatac ctacgatgat gatctcgata acctcctcgc tcagatcgga   5700
gatcagtacg ctgatttgtt cctcgctgct aagaacctct ctgatgctat cctcctcagt   5760
gatatcctca gagtgaacac cgagatcacc aaggctccac tctcagcttc tatgatcaag   5820
agatacgatg agcaccacca ggatctcaca cttctcaagg ctcttgttag acagcagctc   5880
ccagagaagt acaaagagat tttcttcgat cagtctaaga acggatacgc tggttacatc   5940
gatggtggtg catctcaaga agagttctac aagttcatca agcctatcct cgagaagatg   6000
gatggaaccg aggaactcct cgtgaagctc aatagagagg atcttctcag aaagcagagg   6060
accttcgata acgatctat ccctcatcag atccacctcg gagagttgca cgctatcctt   6120
agaaggcaag aggatttcta cccattcctc aaggataaag gggaaaagat tgaagaagtt   6180
ctcaccttca gaatcccta ctacgtggga cctctcgcta gaggaaactc aagattcgct   6240
tggatgacca gaaagtctga ggaaaccatc accccttgga acttcgaaga ggtggtggat   6300
aagggtgcta gtgctcagtc tttcatcgag aggatgacca acttcgataa gaaccttcca   6360
aacgagaagg tgctccctaa gcactctttg ctctacgagt acttcaccgt gtacaacgag   6420
ttgaccaagg ttaagtacgt gaccgaggga atgaggaagc ctgcttttt gtcaggtgag   6480
caaaagaagg ctatcgttga tctcttgttc aagaccaaca gaaaggtgac cgtgaagcag   6540
ctcaaagagg attacttcaa gaaaatcgag tgcttcgatt cagttgagat ttctggtgtt   6600
gaggataggt tcaacgcatc tctcggaacc taccacgatc tcctcaagat cattaaggat   6660
aaggatttct tggataacga ggaaaacgag gatatcttgg aggatatcgt tcttaccctc   6720
accctctttg aagatagaga gatgattgaa gaaaggctca agacctacgc tcatctcttc   6780
gatgataagg tgatgaagca gttgaagaga agaagataca ctggttgggg aaggctctca   6840
agaaagctca ttaacggaat cagggataag cagtctggaa agacaatcct tgatttcctc   6900
aagtctgatg gattcgctaa cagaaacttc atgcagctca tccacgatga ttctctcacc   6960
tttaaagagg atatccagaa ggctcaggtt tcaggacagg gtgatagtct ccatgagcat   7020
atcgctaacc tcgctggatc tcctgcaatc aagaagggaa tcctccagac tgtgaaggtt   7080
gtggatgagt tggtgaaggt gatgggaagg cataagcctg agaacatcgt gatcgaaatg   7140
gctagagaga accagaccac tcagaaggga cagaagaact ctagggaaag gatgaagagg   7200
atcgaggaag gtatcaaaga gcttggatct cagatcctca agagcaccc tgttgagaac   7260
actcagctcc agaatgagaa gctctacctc tactacctcc agaacggaag ggatatgtat   7320
gtggatcaag agttggatat caacaggctc tctgattacg atgttgatca tatcgtgcca   7380
cagtcattct tgaaggatga ttctatcgat aacaaggtgt tcaccaggtc tgataagaac   7440
aggggtaaga gtgataacgt gccaagtgaa gaggttgtga agaaaatgaa gaactattgg   7500
aggcagctcc tcaacgctaa gctcatcact cagagaaagt tcgataactt gactaaggct   7560
gagaggggag gactctctga attggataag gcaggattca tcaagaggca gcttgtggaa   7620
accaggcaga tcactaagca cgttgcacag atcctcgatt ctaggatgaa caccaagtac   7680
gatgagaacg ataagttgat cagggaagtg aaggttatca ccctcaagtc aaagctcgtg   7740
tctgatttca gaaaggattt ccaattctac aaggtgaggg aaatcaacaa ctaccaccac   7800
gctcacgatg cttaccttaa cgctgttgtt ggaaccgctc tcatcaagaa gtatcctaag   7860
ctcgagtcag agttcgtgta cggtgattac aaggtgtacg atgtgaggaa gatgatcgct   7920
aagtctgagc aagagatcgg aaaggctacc gctaagtatt tcttctactc taacatcatg   7980
aatttcttca agaccgagat taccctcgct aacggtgaga tcagaaagag gccactcatc   8040
gagacaaacg gtgaaacagg tgagatcgtg tgggataagg gaagggattt cgctaccgtt   8100
agaaaggtgc tctctatgcc acaggtgaac atcgttaaga aaaccgaggt gcagaccggt   8160
ggattctcta aagagtctat cctccctaag aggaactctg ataagctcat tgctaggaag   8220
aaggattggg accctaagaa atacggtggt ttcgattctc ctaccgtggc ttactctgtt   8280
ctcgttgtgg ctaaggttga aagggaaag agtaagaagc tcaagtctgt taaggaactt   8340
ctcggaatca ctatcatgga aaggtcatct ttcgagaaga cccaaatcga tttcctcgag   8400
gctaagggat acaaagaggt taagaaggat ctcatcatca agctcccaaa gtactcactc   8460
ttcgaactcg agaacggtag aaagaggatg ctcgcttctg ctggtgagct tcaaaaggga   8520
aacgagcttg ctctcccatc taagtacgtt aactttcttt acctcgcttc tcactacgag   8580
aagttgaagg gatctccaga agataacgag cagaagcaac ttttcgttga gcagcacaag   8640
cactacttgg atgagatcat cgagcagatc tctgagttct ctaaaagggt gatcctcgct   8700
gatgcaaacc tcgataaggt gttgtctgct tacaacaagc acagagataa gcctatcagg   8760
gaacaggcag agaacatcat ccatctcttc accttaccaa acctcggtgc tcctgctgct   8820
ttcaagtact tcgatacaac catcgatagg aagagataca cctctaccaa gaagtgctct   8880
gatgctaccc tcatccatca gtctatcact ggactctacg agactaggat cgatctctca   8940
cagctcggtg gtgattcaag ggctgatcct aagaagaaga ggaaggtttg acgtcgacga   9000
tatgaagatg aagatgaaat attggtgtg tcaaataaaa agcttgtgtg cttaagtttg   9060
tgtttttttc ttggcttgtt gtgttatgaa tttgtggctt tttctaatat taaatgaatg   9120
taagatcaca ttataatgaa taaacaaatg tttctataat ccattgtgaa tgtttttgttg   9180
gatctcttct gcagcatata actactgtat gtgctatggt atggactatg aatatgatt   9240
aaagataagc cagagctctg gtgacggacc catggcttcg ttgaacaacg gaaactcgac   9300
ttgccttccg cacaatacat catttcttct tagctttttt tcttcttctt cgttcataca   9360
gttttttttt gtttatcagc ttacatttc ttgaaccgta gctttcgttt tcttcttttt   9420
aactttccat tcggagtttt tgtatcttgt ttcatagttt gtcccaggat tagaatgatt   9480
aggcatcgaa ccttcaagaa tttgattgaa taaaacatct tcattcttaa gatatgaaga   9540
taatcttcaa aaggccctg ggaatctgaa agaagagaag cagccccatt tatatgggaa   9600
agaacaatag tatttcttat ataggcccat ttaagttgaa acaatcttc aaaagtccca   9660
catcgcttag ataagaaaac gaagctgagt ttatatacag ctagagtcga agtagtgatt   9720
gcctacttgg gctgttgcag gttttagagc tagaaatagc aagttaaaat aaggctagtc   9780
cgttatcaac ttgaaaaagt ggcaccgagt cggtgctttt tttcccgggg cgcgccctat   9840
gtcgagctgc aggtcaacgg atcaggatat tcttgtttaa gatgttgaac tctatggagg   9900
tttgtatgaa ctgatgatct aggaccggat aagtcccctt cttcatagcg aacttattca   9960
aagaatgttt tgtgtatcat tcttgttaca ttgttattaa tgaaaaaata ttattggtca  10020
ttggactgaa cacgagtgtt aaatatggac caggcccaa ataagatcca ttgatatatg  10080
aattaaaataa caagaataaa tcgagtcacc aaaccacttg ccttttttaa cgagacttgt  10140
tcaccaactt gatacaaaag tcattatcct atgcaaatca ataatcatac aaaaatatcc  10200
aataacacta aaaattaaa agaaatggat aatttcacaa tatgttatac gataaagaag  10260
ttactttcc aagaaattca ctgatttat aagcccactt gcattagata aatggcaaaa  10320
aaaacaaaa aggaaagaa ataaagcacg aagaattcta gaaaatacga aatacgcttc  10380
```

```
aatgcagtgg gacccacggt tcaattattg ccaattttca gctccaccgt atatttaaaa    10440
aataaaacga taatgctaaa aaaatataaa tcgtaacgat cgttaaatct caacggctgg    10500
atcttatgac gaccgttaga aattgtggtt gtcgacgagt cagtaataaa cggcgtcaaa    10560
gtggttgcag ccggcacaca cgagtcgtgt ttatcaactc aaagcacaaa tacttttcct    10620
caacctaaaa ataaggcaat tagccaaaaa caacttttgc tgtaaacaac gctcaataca    10680
cgtgtcattt tattattagc tattgcttca ccgccttagc tttctcgtga cctagtcgtc    10740
ctcgtctttt cttcttcttc ttctataaaa caatacccaa agagctcttc ttcttcacaa    10800
ttcagatttc aatttctcaa aatcttaaaa actttctctc aattctctct accgtgatca    10860
aggtaaattt ctgtgttcct tattctctca aaatcttcga ttttgttttc gttcgatccc    10920
aatttcgtat atgttctttg gtttagattc tgttaatctt agatcgaaca cgattttctg    10980
ggtttgatcg ttagatatca tcttaattct cgattagggt ttcatagata tcatccgatt    11040
tgttcaaata atttgagttt tgtcgaataa ttactcttcg atttgtgatt tctatctaga    11100
tctggtgtta gtttctagtt tgtgcgatcg aatttgtcga ttaatctgag tttttctgat    11160
taacaggcct gcaggatgga agacgccaaa aacataaaga aaggcccggc gccattctat    11220
ccgctggaag atggaaccgc tggagagcaa ctgcataagg ctatgaagag atacgccctg    11280
gttcctggaa caattgcttt tacagatgca catatcgagg tggacatcac ttacgctgag    11340
tacttcgaaa tgtccgttcg gttggcagaa gctatgaaac gatatgggct gaatacaaat    11400
cacagaatcg tcgtatgcag tgaaaactct cttcaattct ttatgccggt gttgggcgcg    11460
ttatttatcg gagttgcagt tgcgcccgcg aacgacattt ataatgaacg tgaattgctc    11520
aacagtatgg gcatttcgca gcctaccgtg gtgttcgttt ccaaaaaggg gttgcaaaaa    11580
attttgaacg tgcaaaaaaa gctcccaatc atccaaaaaa ttattatcat ggattctaaa    11640
acggattacc agggatttca gtcgatgtac acgttcgtca catctcatct acctcccggt    11700
tttaatgaat acgattttgt gccagagtcc ttcgataggg acaagacaat tgcactgatc    11760
atgaactcct ctggatctac tggtctgcct aaaggtgtcg ctctgcctca tagaactgcc    11820
tgcgtgagat tctcgcatgc cagagatcct attttttggca atcaaatcat tccggatact    11880
gcgattttaa gtgttgttcc attccatcac ggttttggaa tgtttactac actcggatat    11940
ttgatatgtg gatttcgagt cgtcttaatg tatagatttg aagaagagct gtttctgagg    12000
agccttcagg attacaagat tcaaagtgcg ctgctggtgc caaccctatt ctccttcttc    12060
gccaaaagca ctctgattga caaatacgat ttatctaatt tacacgaaat tgcttctggt    12120
ggcgctcccc tctctaagga agtcggggaa gcggttgcca agaggttcca tgccaagt     12180
atcaggcaag gatatgggct cactgagact acatcagcta ttctgattac acccgagggg    12240
gatgataaac cgggcgcggt cggtaaagtt gttccatttt ttgaagcgaa ggttgtggat    12300
ctggataccg ggaaaacgct gggcgttaat caaagaggcg aactgtgtgt gagaggtcct    12360
atgattatgt ccggttatgt aaacaatccg gaagcgacca acgccttgat tgacaaggat    12420
ggatggctac attctggaga catagcttac tgggacgaag acgaacactt cttcatcgtt    12480
gaccgcctga agtctctgat taagtacaaa ggctatcagg tggctcccgc tgaattggaa    12540
tccatcttgc tccaacaccc caacatcttc gacgctggtg tcgcaggtct tcccgacgat    12600
gacgccggtg aacttcccgc cgccgttgtt gttttggagc acggaaagac gatgacggaa    12660
aaagagatcg tggattacgt cgccagtcaa gtaacaaccg cgaaaagtt gcgcggagga    12720
gttgtgtttg tggacgaagt accgaaaggt cttaccggaa aactcgacgc aagaaaaatc    12780
agagagatcc tcataaaggc caagaagggc ggaaagatcg ccgtgtgact cgaggttcga    12840
gtattatggc attgggaaaa ctgttttct tgtaccattt gttgtgcttg taatttactg    12900
tgtttttat tcggttttcg ctatcgaact gtgaaatgga aatggatgga gaagagttaa    12960
tgaatgatat ggtccttttg ttcattctca aattaatatt atttgttttt tctcttattt    13020
gttgtgtgtt gaatttgaaa ttataagaga tatgcaaaca ttttgttttg agtaaaaatg    13080
tgtcaaatcg tggcctctaa tgaccgaagt taatatgagg agtaaaacac ttgtagttgt    13140
gttagagctc tcccgcagat ttgccttttc aatttcagaa agaatgctaa cccacagatg    13200
gttagagagg cttacgcagc aggtatcatc aagacgatct acccgagcaa taatctccag    13260
gaaatcaaat accttcccaa gaaggttaaa gatgcagtca aaagattcag gactaactgc    13320
atcaagaaca cagagaaaga tatatttctc aagatcagaa gtactattcc agtatggacg    13380
attcaaggct tgcttcacaa accaaggcaa gtaatagaaa ttggagtctc taaaaaggta    13440
gttcccactg aatcaaaggc catgagtca aagattcaaa tagaggacct aacagaactc    13500
gccgtaaaga ctgggcgaaca gttcatacag agtctcttac gactcaatga caagaagaaa    13560
atcttcgtca acatggtgga gcacgacaca cttgtctact ccaaaaatat caaagataca    13620
gtctcagaag accaaagggc aatttgagact tttcaacaaa gggtaatatc cggaaacctc    13680
ctcggattcc attgcccagc tatctgtcac tttattgtga agatagtgga aaaggaaggt    13740
ggctcctaca aatgccatca ttgcgataaa ggaaaggcca tcgttgaaga tgcctctgcc    13800
gacagtggtc ccaaagatgg acccccaccc acgaggagca tcgtgaaaaa agaagacgtt    13860
ccaaccacgt cttcaaagca agtggattga tgtgatatct ccactgacgt aagggatgac    13920
gcacaatccc actatccttc gcaagaccct tcctctatat aaggaagttc atttcatttg    13980
gagagaacac gggggactat ggagagtggt tccaacagca cttcttgtcc aatgcttttt    14040
gccgggggata atagtgatgg tccgatgtgt cctatgatga tgatgatgcc gcccatcatg    14100
acatcacatc aacatcatgg tcatgatcat caacatcaac aacaagaaca tgatggttat    14160
gcatatcagt cacaccacca acaaagtagt tcccttttc ttcaatcact agctcctccc    14220
caaggaacta agaacaaagt tgcttcttct tcttctcctt cctcttgtgc tcctgcctat    14280
tctctaatgg agatccatca taacgaaatc gttgcaggag gaatcaaccc ttgctcctct    14340
tcctcttctt cagcctctgt caaggccaag atcatggctc atcctcacta ccaccgcctc    14400
ttggccgctt atgtcaattg tcagaaggtt ggagcaccac cggaggttgt ggcgaggcta    14460
gaggaggcat gctcgtctgc cgcagccgct ccgcatcta tgggaccaac aggatgtcta    14520
ggtgaagatc cagggcttga tcaattcatg gaagcttact gtgaaatgct cgttaagtat    14580
gagcaagagc tctccaaacc tttcaaggaa gctatggtct tccttcaacg tgtcgagtgt    14640
caattcaaat ccctctctct atcctcacct tcctcttct ccggttatgg agagacagca    14700
attgataggaa acaataatgg gtcatccgag gaagaagtcg atatgaacaa tgaatttgta    14760
gatccacaag ctgaggatag agagcttaaa ggacagcta tgcgcaagta cagtggttac    14820
ttagggagcc tcaagcaaga gttcatgaag aagaggaaga aaggaaagct ccctaaagaa    14880
gctcgtcaac aactgcttga ttggtggagc cgtcactaca aatggcctta cccttcggag    14940
caacaaaagc tcgcccttgc ggaatcaacg gggctggacc agaaacagat aaacaattgg    15000
ttcataaacc agaggaaacg gcattggaag ccgtcggagg acatgcagtt tgtagtaatg    15060
gacgcaacac atcctcacca ttacttcatg gataatgtct gggcaatcc tttcccaatg    15120
```

```
gatcacatct cctccaccat gctttgactc gagtttctcc ataataatgt gtgagtagtt    15180
cccagataag ggaattaggg ttcctatagg gtttcgctca tgtgttgagc atataagaaa    15240
cccttagtat gtatttgtat ttgtaaaata cttctatcaa taaaatttct aattcctaaa    15300
accaaaatcc agtactaaaa tccagatccc ccgaattaag tgtttgatcg ccggcggtac    15360
cgagtgtact tcaagtcagt gggaaatcaa taaaatgatt attttatgaa tatatttcat    15420
tgtgcaagta gatagaaatt acatatgtta cataacacac gaaataaaca aaaaaagaca    15480
atccaaaaac aaacacccca aaaaaaataa tcactttaga taaactcgta tgaggagagg    15540
cacgttcagt gactcgacga ttcccgagca aaaaaagtct ccccgtcaca catgtagtgg    15600
gtgacgcaat tatctttaaa gtaatccttc tgttgacttg tcattgataa catccagtct    15660
tcgtcaggat tgcaaagaat tatagaaggg atcccaccct ttatttctct ctttttttcca   15720
tatttagggt tgacagtgaa atcagactgg caacctatta attgcttcca caatgggacg    15780
aacttgaagg ggatgtcgtc gatgatatta taggtggcgt gttcatcgta gttggtgaaa    15840
tcgatggtac cgttccaata gttgtgtcgt ccgagacttc tagcccaggt ggtctttccg    15900
gtacgagttg gtccgcagat gtagaggctg gggtgtcgga ttccattcct tccattgtcc    15960
ttgttaaatc ggccatccat tcaaggtcag attgagcttg ttggtatgag acaggatgta    16020
tgtaagtata agcgtctatg cttacatggt atagatgggt ttccctccag gagtgtagat    16080
cttcgtggca gcgaagatct gattctgtga agggcgacac atacggttca ggttgtggag    16140
ggaataattt gttggctgaa tattccagcc attgaagctt tgttgcccat tcatgaggga    16200
attcttcctt gatcatgtca agatattcct ccttagacgt tgcagtctgg ataatagttc    16260
tccatcgtgc gtcagatttg cgaggagaaa ccttatgatc tcggaaatct cctctggttt    16320
taatatctcc gtcctttgat atgtaatcaa ggacttgttt agagtttcta gctggctgga    16380
tattagggtg atttccttca aaatcgaaaa aagaaggatc cctaatacaa ggtttttttat   16440
caagctggag aagagcatga tagtgggtag tgccatcttg atgaagctca gaagcaacac    16500
caaggaagaa aataagaaaa ggtgtgagtt tctcccagag aaactggaat aaatcatctc    16560
tttgagatga gcacttggga taggtaagga aaacatattt agattggagt ctgaagttct    16620
tactagcaga aggcatgttg ttgtgactcc gaggggttgc ctcaaactct atcttataac    16680
cggcgtggag gcatggaggc agggtatttt tggtcatttt aatagatagt ggaaaatgac    16740
gtggaattta cttaaagacg aagtctttgc gacaaggggg ggcccacgcc gaatttaata    16800
ttaccggcgt ggcccccct tatcgcgagt gctttagcac gagcggtcca gatttaaagt     16860
agaaaatttc ccgcccacta gggttaaagg tgttcacact ataaaagcat atacgatgtg    16920
atggtatttg atggagcgta tattgtatca ggtatttccg ttggatacga attattcgta    16980
cgaccctcat agtttaaact atcagtgttt gacaggatat attggcgggt aaacctaaga    17040
gaaaagagcg tttattagaa taacggatat ttaaagggc gtgaaaaggt ttatccgttc      17100
gtccatttgt atgtgcatgc caaccacagg gttccctcg ggatcaaagt actttgatcc      17160
aaccccctccg ctgctatagt gcagtcggct tctgacgttc gcccctgccc ttttcctggc   17220
acgacatgtc gcacaagtcc taagttacgc gacaggctgc cgccctgccc ttttcctggc    17280
gttttcttgt cgcgtgtttt agtcgcataa agtagaatac ttgcgactag aaccggagac    17340
attacgccat gaacaagagc gccgccgctg gcctgctggg ctatgcccgc gtcagcaccg    17400
acgaccagga cttgaccaac caacgggccg aactgcacgc ggccggctgc accaagctgt    17460
tttccgagaa gatcaccggc accaggcgcg accgcccgga gctggccagg atgcttgacc    17520
acctacgccc tggcgacgtt gtgacagtga ccaggctaga ccgcctggcc cgcagcaccc    17580
gcgacctact ggacattgcc gagcgcatcc aggaggccgg cgcgggcctg cgtagcctgg    17640
cagacgcgtg ggccgacacc accacgccgg ccggccgcat ggtgttgacc gtgttcgccg    17700
gcattgccga gttcgagcgt tccctaatca tcgaccgcac ccggagcggg cgcgaggccg    17760
ccaaggcccg aggcgtgaag tttggccccc gccctaccct caccccgca cagatcgcgc     17820
acgcccgcga gctgatcgac caggaaggcc gcaccgtgaa agaggcggct gcactgcttg    17880
gcgtgcatcg ctcgaccctg taccgcgcac ttgagcgcag cgaggaagtg acgcccaccg    17940
aggccaggcg gcgcggtgcc ttccgtgagg acgcattgac cgaggccgac gccctggcgg    18000
ccgccgagaa tgaacgccaa gaggaacaag catgaaaccg caccaggacg gccaggacga    18060
accgtttttc attaccgaag agatcgaggc ggagatgatc gcggccgggt acgtgttcga    18120
gccgccgcg cacggctcaa ccgtgcggct gcatgaaatc ctggccggtt tgtctgatgc      18180
caagctggcg gcctggccgg ccagcttggc cgctgaagaa accgagcgcc gccgtctaaa    18240
aaggtgatgt gtatttgagt aaaacagctt cgctcatgcg gtcgctgcgt atatgatgcg    18300
atgagtaaat aaacaaatac gcaaggggaa cgcatgaagg ttatcgctgt acttaaccag    18360
aaaggcgggt caggcaagac gaccatcgca acccatctag cccgcgccct gcaactcgcc    18420
ggggccgatg ttctgttagt cgattccgat ccccagggca gtgcccgcga ttgggcggcc    18480
gtgcggaag atcaaccgct aaccgttgtc ggcatcgacc gcccgacgat tgaccgcgac     18540
gtgaaggcca tcgccggcg cgacttcgta gtgatcgacg agcgcccca ggcggcggac      18600
ttggctgtgt ccgcgatcaa ggcagccgac ttcgctgctg ttccggtgca gccaagcct    18660
tacgacatat gggccaccgc cgacctggtg gagtcgggtta agcacgcat tgaggtcacg    18720
gatggaaggc tacaagcggc ctttgtcgtg tcgcgggcga tcaaaggcac gcgcatcggc    18780
ggtgaggttg ccgaggcgct ggccgggtac gagctgccca ttcttgagtc ccgtatcacg    18840
cagcgcgtga gctacccagg cactgccgcc gccggcacaa ccgttcttga atcagaaccc    18900
gagggcgacg ctgcccgcga ggtccaggcg ctggccgctt aaattaaatc aaaactcatt    18960
tgagttaatg aggtaaagag aaaatgagca aaagcacaaa cacgctaagt gccggccgtc    19020
cgagcgcacg cagcagcaag gctgcaacgt tggccagcct ggcagacacg ccagccatga    19080
agcgggtcaa ctttcagttg ccggcggagg atcacaccaa gctgaagatg tacgcggtac    19140
gccaaggcaa gaccattacc gagctgctat ctgaatacat cgcgcagctac ccagagtaaa    19200
tgagcaaatg aataaatgag tagatgaatt ttagcggcta aaggaggcgg catggaaaat    19260
caagaacaac caggcaccga cgccgtggaa tgccccatgt gtggaggaac gggcggttgg    19320
ccaggcgtaa gcggctgggt tgtctgccgg ccctgcaatg gcactggaac ccccaagccc    19380
gaggaatcgg cgtgacggtc gcaaaccatc cggcccggta caaatcggcg cggcgctggg    19440
tgatgacctg gtggagaagt tgaaggccgc gcaggccgcc cagcggcaac gcatcgaggc    19500
agaagcacgc cccggtgaat cgtggcaagc ggccgctgat cgaatccgca aagaatcccg    19560
gcaaccgccg gcagccggtg cgccgtcgat taggaagccg cccaagggcg acgagcaacc    19620
agattttttc gttccgatgc tctatgacgt gggcacccgc gatagtcgca gcatcatgga    19680
cgtggccgtt ttccgtctgt cgaagcgtga ccgacgagct ggcgaggtga tccgctacga    19740
gcttccagac gggcacgtag aggtttccgc agggccggcc                          19780
```

SEQ ID NO: 92          moltype = DNA    length = 20871
FEATURE                Location/Qualifiers
source                 1..20871
                       mol_type = other DNA
                       organism = synthetic construct
SEQUENCE: 92
gatccgctac gagcttccag acgggcacgt agaggtttcc gcagggccgg ccggcatggc    60
cagtgtgtgg gattacgacc tggtactgat ggcggtttcc catctaaccg aatccatgaa   120
ccgataccgg gaagggaagg gagacaagcc cggccgcgtg ttccgtccac acgttgcgga   180
cgtactcaag ttctgccggc gagccgatgg cggaaagcag aaagacgacc tggtagaaac   240
ctgcattcgg ttaaacacca cgcacgttgc catgcagcgt acgaagaagg ccaagaacgg   300
ccgcctggtg acggtatccg agggtgaagc cttgattagc cgctacaaga tcgtaaagag   360
cgaaaccggg cggccggagt acatcgagat cgagctagct gattggatgt accgcgagat   420
cacagaaggc aagaaccggg acgtgctgac ggttcacccc gattactttt tgatcgatcc   480
cggcatcggc cgttttctct accgcctggc acgccgcgcc gcaggcaagg cagaagccag   540
atggttgttc aagacgatct acgaacgcag tggcagcgcc ggagagttca agaagttctg   600
tttcaccgtg cgcaagctga tcgggtcaaa tgacctgccg gagtacgatt tgaaggagga   660
ggcggggcag gctggcccga tcctagtcat gcgctaccgc aacctgatcg agggcgaagc   720
atccgccggt tcctaatgta cggagcagat gctagggcaa attgccctag caggggaaaa   780
aggtcgaaaa ggcctctttc ctgtggatag cacgtacatt gggaacccaa agccgtacat   840
tgggaaccgg aacccgtaca ttgggaaccc aaagccgtac attgggaacc ggtcacacat   900
gtaagtgact gatataaaag agaaaaaagg cgattttttc gcctaaaact ctttaaaact   960
tattaaaact cttaaaaccc gcctggcctg tgcataactg tctggccagc gcacagccga  1020
agagctgcaa aaagccccta cccttcggtc gctgcgctcc ctacgccccg ccgcttcgcg  1080
tcggcctatc gcggccgctg gccgctcaaa aatggctggc ctacgccagg caatctacc   1140
agggcggga caagccgcgc cgtcgccact cgaccgccgg cgcccacatc aaggcaccct  1200
gcctcgcgcg tttcggtgat gacggtgaaa acctctgaca catgcagctc ccggaaacgg  1260
tcacagcttg tctgtaagcg gatgccggga gcagacaagc ccgtcagggc gcgtcagcgg  1320
gtgttggcgg gtgtcgggc gcagccatga cccagtcacg tagcgatagc ggagtgtata  1380
ctggcttaac tatgcggcat cagagcagat tgtactgaga gtgcaccata tgcggtgtga  1440
aataccgcac agatgcgtaa ggagaaaata ccgcatcagg cgctcttccg cttcctcgct  1500
cactgactcg ctgcgctcgg tcgttcggct gcggcgagcg gtatcagctc actcaaaggc  1560
ggtaatacgg ttatccacag aatcagggga taacgcagga agaacatgt gagcaaaagg  1620
ccagcaaaag gccaggaacc gtaaaaaggc cgcgttgctg gcgtttttcc ataggctccg  1680
cccccctgac gagcatcaca aaaatcgacg ctcaagtcag aggtggcgaa acccgacagg  1740
actataaaga taccaggcgt ttccccctgg aagctccctc gtgcgctctc ctgttccgac  1800
cctgccgctt accggatacc tgtccgcctt tctcccttcg ggaagcgtgg cgctttctca  1860
tagctcacgc tgtaggtatc tcagttcggt gtaggtcgtt cgctccaagc tgggctgtgt  1920
gcacgaaccc cccgttcagc ccgaccgctg cgccttatcc ggtaactatc gtcttgagtc  1980
caacccggta agacacgact tatcgccact ggcagcagcc actggtaaca ggattagcag  2040
agcgaggtat gtaggcggtg ctacagagtt cttgaagtgg tggcctaact acggctacac  2100
tagaaggaca gtatttggta tctgcgctct gctgaagcca gttaccttcg gaaaaagagt  2160
tggtagctct tgatccggca aacaaaccac cgctggtagc ggtggttttt ttgtttgcaa  2220
gcagcagatt acgcgcagaa aaaaaggatc tcaagaagat cctttgatct ttttctacgg  2280
gtctgacgct cagtggaacg aaaactcacg ttaagggatt ttggtcatgc attctaggta  2340
ctaaaacaat tcatccagta aaatataata ttttattttc tcccaatcag gcttgatccc  2400
cagtaagtca aaaaatagct cgacatactg ttcttccccg atatcctccc tgatcgaccg  2460
gacgcagaag gcaatgtcat accacttgtc cgccctgccg cttctcccaa gatcaataaa  2520
gccacttact ttgccatctt tcacaaagat gttgctgtct cccaggtcgc cgtgggaaaa  2580
gacaagttcc tcttcgggct tttccgtctt taaaaaatca tacagctcgc gcggatcttt  2640
aaatggagtg tcttcttccc agttttcgca atccacatcg gccagatcgt tattcagtaa  2700
gtaatccaat tcggctaagc ggctgtctaa gctattcgta tagggacaat ccgatatgtc  2760
gatggagtga agagcctga tgcactccgc atacagctcg ataatctttt cagggctttg  2820
ttcatcttca tactcttccg agcaaaggac gccatcggcc tcactcatga gcagattgct  2880
ccagccatca tgccgttcaa agtgcaggac ctttggaaca ggcagcttc cttccagcca  2940
tagcatcatg tcctttttcc gttccacatc ataggtggtc cctttatacc ggctgtccgt  3000
cattttaaa tataggtttt cattttctcc caccagctta taccttag caggagacat   3060
tccttccgta tcttttacgc agcggtattt ttcgatcagt tttttcaatt ccggtgatat  3120
tctcatttta gccatttatt atttccttcc tcttttctac agtatttaaa gatacccccaa  3180
gaagctaatt ataacaagac gaactccaat tcactgttcc ttgcattcta aaaccttaaa  3240
taccagaaaa cagcttttc aaagttgttt tcaaagttgg cgtataacat agtatcgacg  3300
gagccgattt tgaaaccgcg gtgatcacag gcagcaacgc tctgtcatcg ttacaatcaa  3360
catgctaccc tccgcgagat catccgtgtt tcaaacccgg cagcttagtt gccgttcttc  3420
cgaatagcat cggtaacatg agcaaagtct gccgccttac acaggctctc ccgctgacgc  3480
cgtcccggac tgatgggctg cctgtatcga gtggtgattt tgtccgagc tgccggtcgg  3540
ggagctgttg gctggctggt ggcaggatat atttgtggtgt aaacaaattg acgcttagac  3600
aacttaataa cacattgcgg acgtttttaa tgtagagctc aaagtttaac gcgttagcag  3660
aaggcatgtt gttgtgactc cgaggggttg cctcaaactc tatcttataa ccggcgtgta  3720
ggcatggagg caggggtatt ttggtcattt taatagatag tggaaatga cgtggaattt  3780
acttaaagac gaagtctttg cgacaagggg gggcccacgc cgaatttaat attaccggcg  3840
tggcccccc ttatcgcgag tgctttagca cgagcggtcc agatttaaag tagaaaattt  3900
cccgcccact agggttaaag gtgttcacac tataaaagca tatcgatgt gatggtatt   3960
gatggagcgt atattgtatc aggtatttcc gttggatacg aattattcgt acgaccctcg  4020
gtaccgatcg gcgcgcagag tttgccttt caattcgta agaatgcta acccacagat   4080
ggttagagag gcttacgcag caggtatcat caagacgatc tacccgagca ataatctcca  4140
ggaaatcaaa taccttccca gaaggttaa agatcagtc aaaagattca ggactaactg   4200
catcaagaac acagagaaag atatatttct caagatcaga agtactattc cagtatggac  4260
gattcaaggc ttgcttcaca aaccaaggca agtaatagag attggagtct ctaaaaaggt  4320
agttcccact gaatcaaagg ccatggagtc aaagattcaa atagaggacc taacagaact  4380

```
cgccgtaaag actggcgaac agttcataca gagtctctta cgactcaatg acaagaagaa    4440
aatcttcgtc aacatggtgg agcacgacac acttgtctac tccaaaaata tcaaagatac    4500
agtctcagaa gaccaaaggg caattgagac ttttcaacaa agggtaatat ccggaaacct    4560
cctcggattc cattgcccag ctatctgtca ctttattgtg aagatagtgg aaaaggaagg    4620
tggctcctac aaatgccatc attgcgataa aggaaaggcc atcgttgaag atgcctctgc    4680
cgacagtggt cccaaagatg acccccacc cacgaggagc atcgtggaaa aagaagacgt    4740
tccaaccacg tcttcaaagc aagtggattg atgtgatatc tccactgacg taagggatga    4800
cgcacaatcc cactatcctt cgcaagaccc ttcctctata taaggaagtt catttcattt    4860
ggagagaaca cgggggactc ctgcaggtag atcgctcgtc gacatggata agaagtactc    4920
tatcggactc gatatcggaa ctaactctgt gggatgggct gtgatcaccg atgagtacaa    4980
ggtgccatct aagaagttca aggttctcgg aaacaccgat aggcactcta tcaagaaaaa    5040
ccttatcggt gctctcctct tcgattctgg tgaaactgct gaggctacca gactcaagag    5100
aaccgctaga agaaggtaca ccagaagaaa gaacaggatc tgctacctcc aagagatctt    5160
ctctaacgag atggctaaag tggatgattc attcttccac aggctcgaag agtcattcct    5220
cgtggaagaa gataagaagc acgagaggca ccctatcttc ggaaacatcg ttgatgaggt    5280
ggcataccac gagaagtacc ctactatcta ccacctcaga aagaagctcg ttgattctac    5340
tgataaggct gatctcaggc tcatctacct cgctctcgct cacatgatca agttcagagg    5400
acacttcctc atcgagggtg atctcaaccc tgataactct gatgtggata agttgttcat    5460
ccagctcgtg cagacctaca accagctttt cgaagagaac cctatcaacg cttcaggtgt    5520
ggatgctaag gctatcctct ctgctaggct ctctaagtca agaaggcttg agaacctcat    5580
tgctcagctc cctggtgaga agaagaacgg acttttcgga aacttgatcg ctctctctct    5640
cggactcacc cctaacttca gtctaactt cgatctcgct gaggatgcaa agctccagct    5700
ctcaaaggat acctacgatg atgatctcga taacctcctc gctcagatcg agatcagta    5760
cgctgatttg ttcctcgctg ctaagaacct ctctgatgct atcctcctca gtgatatcct    5820
cagagtgaac accgagatca ccaaggctcc actctcagct tctatgatca agagatacga    5880
tgagcaccac caggatctca cacttctcaa ggctcttgt agacagcagc tcccagagaa    5940
gtacaaagag attttcttcg atcagtctaa gaacggatac gctggttaca tcgatggtgg    6000
tgcatctcaa gaagagttct acaagttcat caagcctatc ctcgagaaga tggatggaac    6060
cgaggaactc ctcgtgaagc tcaatagaga ggatcttctc agaaagcaga ggaccttcga    6120
taacggatct atccctcatc agatccacct cggagagttg cacgctatcc ttagaaggca    6180
agaggatttc tacccattcc tcaaggataa cagggaaaga attgagaaga ttctcacctt    6240
cagaatccct tactacgtgg gacctctcgc tagaggaaac tcaagattcg cttggatgac    6300
cagaaagtct gaggaaacca tcaccccttg gaacttcgaa gaggtggtgg ataagggtgc    6360
tagtgctcag tcttcatcg agaggatgac caacttcgat aagaaccttc caaacgaga    6420
ggtgctccct aagcactctt tgctctacga gtacttcacc gtgtacaacg agttgaccaa    6480
ggttaagtac gtgaccgagg aatgaggaa gcctgctttt ttgtcaggtg agcaaaagaa    6540
ggctatcgtt gatctcttgt tcaagaccaa cagaaaggtg accgtgaagc agctcaaaga    6600
ggattacttc aagaaaatcg agtgcttcga ttcagttgag atttctggtg ttgaggatag    6660
gttcaacgca tctctcggaa cctaccacga tcattaagg ataaggattt    6720
cttggataac gaggaaaacg aggatatctt ggaggatatc gttcttaccc tcaccctctt    6780
tgaagataga gagatgattg aagaaaggct caagacctac gctcatctct tcgatgataa    6840
ggtgatgaag cagttgaaga gaagaagata cactggttgg ggaaggctct caagaaagct    6900
cattaacgga atcagggata agcagtctgg aaagacaatc cttgatttcc tcaagtctga    6960
tggattcgct aacagaaact tcatgcagct catccacgat gattctctca cctttaaaga    7020
ggatatccag aaggctcagg tttcaggaca gggtgatagt ctccatgagc atatcgctaa    7080
cctcgctgga tctcctgcaa tcaagaaggg aatcctccag actgtgaagg ttgtggatga    7140
gttggtgaag gtgatgggaa ggcataagcc tgagaacatc gtgatcgaaa tggctagaga    7200
gaaccagacc actcagaagg gacagaagaa ctctagggaa aggatgaaga ggatccgagga    7260
aggtatcaaa gagcttggat ctcagatcct caaagagcac cctgttgaga acactcagct    7320
ccagaatgag aagctctacc tctactacct ccagaacgga agggatatgt atgtggatca    7380
agagttggat atcaacaggc tctctgatta cgatgttgat catatcgtgc cacagtcatt    7440
cttgaaggat gattctatcg ataacaaggt gctcaccagg tctgataaga acaggggtaa    7500
gagtgataac gtgccaagtg aagaggttgt gaagaaaatg aagaactatt ggaggcagct    7560
cctcaacgct aagctcatca ctcagagaaa gttcgataac ttgactaagg ctgagagggg    7620
aggactctct gaattggata aggcaggatt catcaagagg cagcttgtgg aaaccaggca    7680
gatcactaag cacgttgcac agatcctcga ttctaggatg aacaccaagt acgatgagaa    7740
cgataagttg atcagggaag tgaaggttat caccctcaag tcaaagctcg tgtctgattt    7800
cagaaaggat ttccaattct acaaggtgag ggaaatcaac aactaccacc acgctcacga    7860
tgcttacctt aacgctgttg ttggaaccgc tctcatcaag aagtatccta agctcgagtc    7920
agagttcgtg tacggtgatt acaaggtgta cgatgtgagg aagatgatcg ctaagtctga    7980
gcaagagatc ggaaaggcta ccgctaagta tttcttctac tctaacatca tgaatttctt    8040
caagaccgag attaccctcg ctaacggtga gatcagaaag aggccactca tcgagacaaa    8100
cggtgaaaca ggtgagatcg tgtgggataa gggaaggat ttcgctaccg ttagaaaggt    8160
gctctctatg ccacaggtga acatcgttaa gaaaaccgag gtgcagaccg gtggattctc    8220
taaagagtct atcctcccta gaggaactc tgataagctc attgctagga gaaggattg    8280
ggaccctaag aaatacgtg gtttgattc tcctaccgtg gcttactctg ttctcgttgt    8340
ggctaaggtt gagaagggaa agagtaagaa gctcaagtct gttaaggaac ttctcggaat    8400
cactatcatg gaaaggtcat ctttcgagaa gaacccaatc gatttcctcg aggctaaggg    8460
atacaaagag gttaagaagg atctcatcat caagctccca aagtactcca tcttcgaact    8520
cgagaacgta gaaagagga tgctcgcttc tgctggtgag cttcaaaagg gaaacgagct    8580
tgctctccca tctaagtacg ttaactttct ttacctcgct tctcactacg agaagttgaa    8640
gggatctcca gaagataacg agcagaagca acttttcgtt gagcagcaca agcactactt    8700
ggatgagatc atcgagcaga tctctgagtt ctctaaaagg gtgatcctcg ctgatgcaaa    8760
cctcgataag gtgttgtctg cttacaacaa gcacagagat aaggcctatc gggaacaggc    8820
agagaacatc atccatctct tcaccccttac caacctcggt gctcctgctg cttttcaagta    8880
cttcgataca accatcgata ggaagagata caccctctac aaagaagtgc tcgatgctac    8940
cctcatccat cagtctatca ctggactcta cgagactagg atcgatctct cacagctcgg    9000
tggtgattca agggctgatc ctaagaagaa gaggaaggt tgacgtcgac gatatgaaga    9060
tgaagatgaa atatttggtg tgtcaaataa aaagcttgtg tgcttaagtt tgtgtttttt    9120
```

```
tcttggcttg ttgtgttatg aatttgtggc tttttctaat attaaatgaa tgtaagatca   9180
cattataatg aataaacaaa tgtttctata atccattgtg aatgttttgt tggatctctt   9240
ctgcagcata taactactgt atgtgctatg gtatggacta tggaatatga ttaaagataa   9300
gccagagctc tggtgacgga cccatggctt cgttgaacaa cggaaactcg acttgccttc   9360
cgcacaatac atcatttctt cttagctttt tttcttcttc ttcgttcata cagttttttt   9420
ttgtttatca gcttacatt tcttgaaccg tagctttcgt ttccttcttt ttaactttcc     9480
attcggagtt tttgtatctt gtttcatagt ttgtcccagg attagaatga ttaggcatcg   9540
aaccttcaag aatttgattg aataaaacat cttcattctt aagatatgaa gataatcttc   9600
aaaaggcccc tgggaatctg aaagaagaga agcaggccca tttatatggg aaagaacaat   9660
agtatttctt atataggccc atttaagttg aaaacaatct tcaaaagtcc cacatcgctt   9720
agataagaaa acgaagctga gtttatatac agctagagtc gaagtagtga ttgcctactt   9780
gggctgttgc aggttttaga gctagaaata gcaagttaaa ataaggctag tccgttatca   9840
acttgaaaaa gtggcaccga gtcggtgctt tttttcccgg ggcgcgccct atgtcgagct   9900
gcaggtcaac ggatcaggat attcttgttt aagatgttga actctatgga ggtttgtatg   9960
aactgatgat ctaggaccgg ataagttccc ttcttcatag cgaacttatt caaagaatgt   10020
tttgtgtatc attcttgtta cattgttatt aatgaaaaaa tattattggt cattggactg   10080
aacacgagtg ttaaatatgg accaggcccc aaataagatc cattgatata tgaattaaat   10140
aacaagaata aatcgagtca ccaaaccact tgccttttt aacgagactt gttcaccaac    10200
ttgatacaaa agtcattatc ctatgcaaat caataatcat acaaaaatat ccataacac    10260
taaaaaatta aagaaatgg ataatttcac aatatgttat acgataaaga agttactttt    10320
ccaagaaatt cactgatttt ataagcccac ttgcattaga taaatggcaa aaaaaaacaa   10380
aaaggaaaag aaaaaagca cgaagaattc tagaaaatac gaaaatacgt tcaatgcagt   10440
gggacccacg gttcaattat tgccaatttt cagctccacc gtatatttaa aaaataaaac   10500
gataatgcta aaaaaatata aatcgtaacg atcgttaaat ctcaacggct ggatcttatg   10560
acgaccgtta gaaattgtgg ttgtcgacga gtcagtaata aacggcgtca aagtggttgc   10620
agccggcaca cacgagtcgt gtttatcaac tcaaagcaca aatactttc ctcaacctaa    10680
aaataaggca attagccaaa aacaactttg cgtgtaaaca acgctcaata cacgtgtcat   10740
tttattatta gctattgctt caccgcctta gctttctcgt gacctagtcg tcctcgtctt   10800
ttcttcttct tcttctataa aacaatacc aaagagctct tcttcttcac aattcagatt    10860
tcaatttctc aaaatcttaa aaactttctc tcaattctct ctaccgtgat caaggtaaat   10920
ttctgtgttc cttattctct caaaatcttc gatttgttt tcgttcgatc ccaatttcgt    10980
atatgttctt tggtttagat tctgttaatc ttagatcgaa cacgattttc tgggtttgat   11040
cgttagatat catcttaatt ctcgattagg gtttcataga tatcatccga tttgttcaaa   11100
taatttgagt tttgtcgaat aattactctt cgatttgtga tttctatcta gatctggtat   11160
tagtttctag tttgtgcgat cgaatttgtc gattaatctg agtttttctg attaacaggc   11220
ctgcaggatg gaagacgcca aaaacataaa gaaaggcccg cgccattct atccgctgga   11280
agatggaacc gctggagagc aactgcataa ggctatgaag agatacgccc tggttcctgg   11340
aacaattgct tttacagatg cacatatcga ggtggacatc acttacgctg agtacttcga   11400
aatgtccgtt cggttggcag aagctatgaa acgatatggg ctgaatacaa atcacagat    11460
cgtcgtatgc agtgaaaact ctcttcaatt ctttatgccg gtgttgggcg cgttatttat   11520
cggagttgca gttgcgcccg cgaacgacat ttataatgaa cgtgaattgc tcaacagtat   11580
gggcatttcg cagcctaccg tggtgttcgt ttccaaaaag gggttgcaaa aattttgaa    11640
cgtgcaaaaa aagctcccaa tcatccaaaa aattattatc atggattcta aaacggatta   11700
ccagggattt cagtcgatgt acacgttcgt cacatctcat ctacctcccg gttttaatga   11760
atacgatttt gtgccagagt ccttcgatag ggacaagaca attgcactga tcatgaactc   11820
ctctggatct actggtctgc ctaaaggtgt cgctctgcct catagaactg cctgcgtgag   11880
attctcgcat gccagagatc ctatttttgg caatcaaatc attccggata ctgcgatttt   11940
aagtgttgtt ccattccatc acggttttgg aatgtttact acactcggat atttgatatg   12000
tggatttcga gtcgtcttaa tgtatagatt tgaagaagag ctgtttctga ggagccttca   12060
ggattacaag attcaaagtg cgctgctggt gccaacccta ttctccttct tcgccaaaag   12120
cactctgatt gacaaatacg atttatctaa tttacacgaa attgcttctg gtggcgctcc   12180
cctctctaag gaagtcgggg aagcggttgc caagaggttc catctgccag gtatcaggca   12240
aggatatggg ctcactgaga ctacatcagc tattctgatt acacccgagg ggatgataa    12300
accgggcgcg gtcggtaaag ttgttccatt ttttgaagcg aaggttgtgg atctggatac   12360
cgggaaaacg ctgggcgtta atcaaagagg cgaactgtgt gtgagaggtc ctatgattat   12420
gtccggttat gtaaacaatc cggaagcgac caacgccttg attgacaagg atggatggct   12480
acattctgga gacatagctt actgggacga agacgaacac ttcttcatcg ttgaccgcct   12540
gaagtctctg attaagtaca aaggctatca ggtggctccc gctgaattgg aatccatctt   12600
gctccaacac cccaacatct tcgacgctgg tgtcgcaggt cttcccgacg atgacgccgg   12660
tgaacttccc gccgccgttg ttgttttgga gcacggaaag acgatgacgg aaaaagagat   12720
cgtggattac gtcgccagtc aagtaacaac cgcgaaaaag ttgcgcggag gagttgtgtt   12780
tgtggacgaa gtaccgaaag gtcttaccgg aaaactcgac gcaagaaaaa tcagagagat   12840
cctcataaag gccaagaagg gcggaaagat cgccgtgtga ctcgaggttc gagtattatg   12900
gcattgggaa aactgttttt cttgtaccat tgttgtgctt gtaatttac tgtgttttgt   12960
attcggtttt cgctatcgaa ctgtgaaatg gaaatggatg agaagagtt aatgaatgat    13020
atggtccttt tgttcattct caaattaata ttatttgttt tttctcttat tgttgtgtg    13080
ttgaatttga aattataaga gatatgcaaa catttttgttt tgagtaaaaa tgtgtcaaat   13140
cgtggcctct aatgaccgaa gttaatatga ggagtaaaac acttagtt gtgttagagc     13200
tctcccgcgt cgagctgcag gtcaacggat caggatattc ttgtttaaga tgttgaactc   13260
tatggaggtt tgtatgaact gatgatctag gaccggataa gttcccttct tcatagcgaa   13320
cttattcaaa gaatgttttg tgtatcattc ttgttacatt gttattaatg aaaaaatatt   13380
attggtcatt ggactgaaca cgagtgttaa atatggacca ggcccaaat aagatccatt    13440
gatatatgaa ttaaataaca agaataatc gagtcaccaa accacttgcc ttttttaacg    13500
agacttgttc accaacttga tacaaaagtc attatcctat gcaaatcaat aatcatacaa   13560
aaatatccaa taacactaaa aaattaaaag aaatggataa tttcacaata tgttatacga   13620
taaagaagtt acttttccaa gaaattcact gattttataa gcccacttgc attagataaa   13680
tggcaaaaaa aacaaaaag gaaagaaat aaagcacgaa gaattctaga aaatacgaaa    13740
tacgcttcaa tgcagtggga cccacggttc aattattgcc aattttcagc tccaccgtat   13800
atttaaaaaa taaaacgata atgctaaaaa aatataaatc gtaacgatcg ttaaatctca   13860
```

```
acggctggat cttatgacga ccgttagaaa ttgtggttgt cgacgagtca gtaataaacg    13920
gcgtcaaagt ggttgcagcc ggcacacacg agtcgtgttt atcaactcaa agcacaaata    13980
cttttcctca acctaaaaat aaggcaatta gccaaaaaca actttgcgtg taaacaacgc    14040
tcaatacacg tgtcatttta ttattagcta ttgcttcacc gccttagctt tctcgtgacc    14100
tagtcgtcct cgtcttttct tcttcttctt ctataaaaca atacccaaag agctcttctt    14160
cttcacaatt cagatttcaa tttctcaaaa tcttaaaaac tttctctcaa ttctctctac    14220
cgtgatcaag gtaaatttct gtgttcctta ttctctcaaa atcttcgatt ttgttttcgt    14280
tcgatcccaa tttcgtatat gttctttggt ttagattctg ttaatcttag atcgaacacg    14340
attttctggg tttgatcgtt agatatcatc ttaattctcg attagggttt catagatatc    14400
atccgatttg ttcaaataat ttgagttttg tcgaataatt actcttcgat ttgtgatttc    14460
tatctagatc tggtgttagt ttctagtttg tgcgatcgaa tttgtcgatt aatctgagtt    14520
tttctgatta acagggatga actcgatgaa taactggtta ggcttctctc tctctcctca    14580
tgatcaaaat catcaccgta cggatgttga ctcctccacc accagaaccg ccgtagatgt    14640
tgccggaggg tactgttttg atctggccgc tcctccgat gaatcttctg ccgttcaaac    14700
atcttttctt tctcctttcg gtgtcaccct cgaagctttc accagagaca ataatagtca    14760
ctcccgagat tgggacatca atggtggtgc atgcaataac attaacaata acgaacaaaa    14820
tggaccaaag cttgagaatt tcctcggccg caccaccacg atttacaata ccaacgagac    14880
cgttgtagat ggaaatggcg attgtggagg aggagacggt ggtggtggcg gctcactagg    14940
cctttcgatg ataaaaacat ggctgagtaa tcattcggtt gctaatgcta atcatcaaga    15000
caatggtaac ggtgcacgag gcttgtccct ctctatgaat tcatctacta gtgatagcaa    15060
caactacaac aacaatgatg atgtcgtcca agagaagact attgttgatg tcgtagaaac    15120
tacaccgaag aaaactattg agagtttttgg acaaaggacg tctatatacc gcggtgttac    15180
aaggcatcgg tggacaggta gatacgaggc acatttatgg gacaatagtt gcaaaagaga    15240
aggccagact cgcaaaggaa gacaagttta tctgggaggt tatgacaaag aagaaaaagc    15300
agctagggct tacgatttag ccgcactaaa gtattgggga accaccacta ctactaactt    15360
ccccttgagt gaatatgaga aagaggtaga agagatgaga cacatgacga ggcaaagta    15420
tgttgcctct ctgcgcagga aaagtagtgg tttctctcgt ggtgcatcga tttatcgagg    15480
agtaacaagg catcaccaac atggaaggtg gcaagctagg atcggaagag tcgccggtaa    15540
caaagacctc tacttgggaa ctttcggcac acaggaagag gctgctgagg cttatgacat    15600
tgcagccatt aaattcagag gattaagcgc agtgactaac ttcgacatga acagataaca    15660
tgttaaagca atcctcgaga gcccgagtct acctattggt agttctgcga aacgtctcaa    15720
ggacgttaat aatccggttc cagctatgat gattagtaat aacgtttcag agagtgcaaa    15780
taatgttagc ggttggcaaa acactgcgtt tcagcatcat cagggaatgg atttgagctt    15840
attgcagcaa cagcaggaga ggtacgttgg ttattacaat ggaggaaact tgtctaccga    15900
gagtactagg gttgtgtttса aacaagagga ggaacaacaa cacttcttga gaaactcgcc    15960
gagtcacatg actaatgttg atcatcatag ctcgacctct gatgattctg ttaccgtttg    16020
tggaaatgtt gttagttatg tggttatca aggattcgca atccctgttg gaacatcggt    16080
taattacgat ccctttactg ctgctgagat tgcttacaac gcaagaaatc attattacta    16140
tgctcagcat cagcaacaac agcagattca gcagtcgccg ggaggagatt ttccggtggc    16200
gatttcgaat aaccatagct ctaacatgta ctttcacggg gaaggtggtg gagaaggggc    16260
tccaacgttt tcagtttgga acgacactta gctcgagttt ctccataata atgtgtgagt    16320
agttcccaga taagggaatt agggttccta tagggtttcg ctcatgtgtt gagcatataa    16380
gaaaccctta gtatgtattt gtatttgtaa aatacttcta tcaataaaat ttctaattcc    16440
taaaaccaaa atccagtact aaaatccaga tcccccgaat aagtgtttga tcgccggcgg    16500
taccgagtgt acttcaagtc agtgggaaat caataaaatg attattttat gaatatattt    16560
cattgtgcaa gtagatagaa attacatatg ttacataaca cacgaaataa acaaaaaaag    16620
acaatccaaa aacaaacacc ccaaaaaaaa taatcacttt agataaactc gtatgaggag    16680
aggcacgttc agtgactcga cgattcccga gcaaaaaaag tctccccgtc acacatgtag    16740
tgggtgacgc aattatcttt aaagtaatcc ttctgttgac ttgtcattga taacatccag    16800
tcttcgtcag gattgcaaag aattatagaa gggatcccac cttttatttt cttctttttt    16860
ccatatttag ggttgacagt gaaatcagac tggcaaccta ttaattgctt ccacaatggg    16920
acgaacttga aggggatgtc gtcgatgata ttataggtgg cgtgttcatc gtagttggtg    16980
aaatcgatgt taccgttcca atagttgtgt cgtccgagac ttctagccca ggtggtcttt    17040
ccggtacgag ttggtccgca gatgtagagg ctggggtgtc ggattccatt ccttccattg    17100
tccttgttaa atcggccatc cattcaaggt cagattgagc ttgttggtat gagacaggat    17160
gtatgtaagt ataagcgtct atgcttacat ggtatagatg ggtttccctc caggagtgta    17220
gatcttcgtg gcagcgaaga tctgattctg tgaagggcga cacatacggt tcaggttgtg    17280
gagggaataa tttgttggct gaatattcca gccattgaag ctttgttgcc cattcatgag    17340
ggaattcttc cttgatcatg tcaagatatt cctccttaga cgttgcagtc tggataatag    17400
ttctccatcg tgcgtcagat ttgcgaggag aaaccttatg atctcggaaa tctcctctgg    17460
ttttaatatc tccgtccttt gatatgtaat caaggacttg tttagagttt ctagctggct    17520
ggatattagg gtgatttcct tcaaaatcga aaaagaagg atccctaata caaggttttt    17580
tatcaagctg gagaagagca tgatagtggg tagtgccatc ttgatgaagc tcagaagcaa    17640
caccaaggaa gaaaataaga aaaggtgtga gtttctccca aataaatcat    17700
ctctttgaga tgagcacttg ggataggtaa ggaaaacata tttagattgg agtctgaagt    17760
tcttactagc agaaggcatg ttgttgtgac tccgaggggt tgcctcaaac tctatcttat    17820
aaccggcgtg gaggcatgga ggcagggta ttttggtcat tttaatagat agtggaaaat    17880
gacgtggaat ttacttaaag acgaagtctt tgcgacaagg ggggcccac gccgaattta    17940
atattaccgg cgtggccccc cctatcgcg agtgctttag cacgagcggt ccagatttaa    18000
agtagaaaat ttcccgccca ctaggsgttaa aggtgttcac actataaaag catatacgat    18060
gtgatggtat ttgatggagc gtatattgta tcaggtattt ccgttggata cgaattattc    18120
gtacgaccct catagtttaa actatcagtg tttgacagga tatattggcg ggtaaaccta    18180
agagaaaaga gcgtttatta gaataacgga tatttaaaag ggcgtgaaaa ggtttatccg    18240
ttcgtccatt tgtatgtgca tgccaaccac aggggttccc tcgggatcaa agtactttga    18300
tccaacccct ccgctgctat agtgcagtcg gcttctgacg ttcagtcag ccgtcttctg    18360
aaaacgacat gtcgcacaag tcctaagtta cgcgacaggc tgccgcccctg cccttttcct    18420
ggcgttttct tgtcgcgtgt tttagtcgca taaagtagaa tacttgcgac tagaaccgga    18480
gacattacgc catgaacaag agcgccgccg ctggcctgct gggctatgcc cgcgtcagca    18540
ccgacgacca ggacttgacc aaccaacggg ccgaactgca cgcggccggc tgcaccaagc    18600
```

```
tgttttccga gaagatcacc ggcaccaggc gcgaccgccc ggagctggcc aggatgcttg  18660
accacctacg ccctggcgac gttgtgacag tgaccaggct agaccgcctg gcccgcagca  18720
cccgcgacct actggacatt gccgagcgca tccaggaggc cggcgcgggc ctgcgtagcc  18780
tggcagagcc gtgggccgac accaccacgc cggccggccg catggtgttg accgtgttcg  18840
ccggcattgc cgagttcgag cgttccctaa tcatcgaccg cacccggagc gggcgcgagg  18900
ccgccaaggc ccgaggcgtg aagtttggcc cccgccctac cctcaccccg gcacagatcg  18960
cgcacgcccg cgagctgatc gaccaggaag gccgcaccgt gaaagaggcg gctgcactgc  19020
ttggcgtgca tcgctcgacc ctgtaccgcg cacttgagcg cagcgaggaa gtgacgccca  19080
ccgaggccag gcggcgcggt gccttccgtg aggacgcatt gaccgaggcc gacgccctgg  19140
cggccgccga gaatgaacgc caagaggaac aagcatgaaa ccgcaccagg acggccagga  19200
cgaaccgttt ttcattaccg aagagatcga ggcggagatg atcgcggccg ggtacgtgtt  19260
cgagccgccc gcgcacggct caaccgtgcg gctgcatgaa atcctggccg gtttgtctga  19320
tgccaagctg gcggcctggc cggccagctt ggccgctgaa gaaaccgagc gccgccgtct  19380
aaaaaggtga tgtgtatttg agtaaaacag cttgcgtcat gcggtcgctg cgtatatgat  19440
gcgatgagta aataaacaaa tacgcaaggg gaacgcatga aggttatcgc tgtacttaac  19500
cagaaaggcg ggtcaggcaa gacgaccatc gcaacccatc tagcccgcgc cctgcaactc  19560
gccggggccg atgttctgtt agtcgattcc gatccccagg gcagtgcccg cgattgggcg  19620
gccgtgcggg aagatcaacc gctaaccgtt gtcggcatcg accgcccgac gattgaccgc  19680
gacgtgaagg ccatcggccg gcgcgacttc gtagtgatcg acggagcgcc ccaggcggcg  19740
gacttggctg tgtccgcgat caaggcagcc gacttcgtgc tgattccggt gcagccaagc  19800
ccttacgaca tatgggccac cgccgacctg gtggagctgg ttaagcagcg cattgaggtc  19860
acggatggaa ggctacaagc ggcctttgtc gtgtcgcggg cgatcaaagg cacgcgcatc  19920
ggcggtgagg ttgccgaggc gctgccgggg tacgagctgc ccattcttga gtcccgtatc  19980
acgcagcgcg tgagctaccc aggcactgcc gccgccggca caaccgttct gaatcagaa   20040
cccgagggcg acgctgcccg cgaggtccag gcgctggccg ctgaaattaa atcaaaactc  20100
atttgagtta atgaggtaaa gagaaaatga gcaaaagcac aaacacgcta agtgccggcc  20160
gtccgagcgc acgcagcagc aaggctgcaa cgttggccag cctggcagac acgccagcca  20220
tgaagcgggt caactttcag ttgccggcgg aggatcacac caagctgaag atgtacgcgg  20280
tacgccaagg caagaccatt accgagctgc tatctgaata catcgcgcag ctaccagagt  20340
aaatgagcaa atgaataaat gagtagatga attttagcg ctaaaggagg cggcatggaa  20400
aatcaagaac aaccaggcac cgacgccgtg gaatgcccca tgtgtggagg aacgggcggt  20460
tggccaggcg taagcggctg ggttgtctgc cggccctgca atggcactgg aaccccaag   20520
cccgaggaat cggcgtgacg gtcgcaaacc atccggcccg gtacaaatcg cgcggcgct   20580
gggtgatgac ctggtggaga agttgaaggc cgcgcaggcc gcccagcggc aacgcatcga  20640
ggcagaagca cgccccggtg aatcgtggca agcggccgct gatcgaatcc gcaaagaatc  20700
ccggcaaccg ccggcagccg gtgcgccgtc gattaggaag ccgcccaagg cgacgagca   20760
accagatttt tcgttccga tgctctatga cgtgggcacc cgcgatagtc gcagcatcat   20820
ggacgtggcc gttttccgtc tgtcgaagcg tgaccgacga gctggcgagg t           20871
```

SEQ ID NO: 93        moltype = DNA  length = 17616
FEATURE                Location/Qualifiers
source                 1..17616
                         mol_type = other DNA
                         organism = synthetic construct
SEQUENCE: 93

```
tgcagcgtac gaagaaggcc aagaacggcc gcctggtgac ggtatccgag ggtgaagcct    60
tgattagccg ctacaagatc gtaaagagcg aaaccggcg gccgagtac atcgagatcg    120
agctagctga ttggatgtac cgcgagatca cagaaggcaa gaacccggac gtgctgacgg   180
ttcaccccga ttactttttg atcgatcccg gcatcggccg ttttctctac cgcctggcac   240
gccgcgccga aggcaaggca gaagccgat ggttgttcaa gacgatctac gaacgcagtg    300
gcagcgccgg agagttcaag aagttctgtt tcaccgtgca caagctgatc gggtcaaatg   360
acctgccgga gtacgatttg aaggaggagg cggggcaggc tggcccgatc ctagtcatgc   420
gctaccgcaa cctgatcgag ggcgaagcat ccgccggttc ctaatgtacg gagcagatgc   480
tagggcaaat tgccctagca ggggaaaaag gtcgaaaagg cctctttcct gtggatagca   540
cgtacattgg gaacccaaag ccgtacattg gaaccgtaca cccgtacatt gggaacccaa   600
agccgtacat tgggaaccgg tcacacatgt aagtgactga tataaaagag aaaaaaggcg   660
attttttccgc ctaaaactct ttaaaactta ttaaaactct aaaaccgc ctggcctgtg    720
cataactgtc tggccagcgc acagccgaag agctgcaaaa agcgcctacc cttcggtcgc   780
tgcgctccct acgccccgcc gcttcgcgtc ggcctatcgc ggccgctggc cgctcaaaaa   840
tggctggcct acggccaggc aatctaccag ggcgcggaca agccgcgccg tcgccactcg   900
accgccggcg cccacatcaa ggcaccctgc ctcgcgcgtt tcggtgatga cggtgaaaac   960
ctctgacaca tgcagctccc ggaaacggtc acagcttgtc tgtaagcgga tgccgggagc   1020
agacaagccc gtcagggcgc gtcagcgggt gttggcgggt gtcggggcgc agccatgacc   1080
cagtcacgta gcgatagcgg agtgtatact ggcttaacta tgcggcatca gagcagattg   1140
tactgagagt gcaccatatg cggtgtgaaa taccgcacag atgcgtaagg agaaaatacc   1200
gcatcaggcg ctcttccgct tcctcgctca ctgactcgct gcgctcggtc gttcggctgc   1260
ggcgagcggt atcagctcac tcaaaggcgg taatacggtt atccacagaa tcaggggata   1320
acgcaggaaa gaacatgtga gcaaaaggcc agcaaaaggc caggaaccgt aaaaaggccg   1380
cgttgctggc gtttttccat aggctccgcc ccctgacga gcatcacaaa aatcgacgct   1440
caagtcagag gtggcgaaac ccgacaggac tataaagata ccaggcgttt ccccctggaa   1500
gctccctcgt gcgctctcct gttccgaccc tgccgcttac cggatacctg tccgcctttc   1560
tcccttcgg aagcgtggcg ctttctcata gctcacgctg taggtatctc agttcggtgt    1620
aggtcgttcg ctccaagctg ggctgtgtgc acgaaccccc cgttcagccc gaccgctgcg   1680
ccttatccgg taactatcgt cttgagtcca acccggtaag acacgactta tcgccactgg   1740
cagcagccac tggtaacagg attagcagag cgaggtatgt aggcggtgct acagagttct   1800
tgaagtggtg gcctaactac ggctacacta aggacagt atttggtatc tgcgctctgc     1860
tgaagccagt taccttcgga aaagagttg gtagctcttg atccggcaaa caaccaccg    1920
ctggtagcgg tggttttttt gtttgcaagc agcagattac gcgcagaaaa aaggatctc    1980
aagaagatcc tttgatcttt tctacggggt ctgacgctca gtggaacgaa aactcacgtt   2040
```

```
aagggattttt ggtcatgcat tctaggtact aaaacaattc atccagtaaa atataatatt    2100
ttattttctc ccaatcaggc ttgatcccca gtaagtcaaa aaatagctcg acatactgtt    2160
cttcccgat atcctccctg atcgaccgga cgcagaaggc aatgtcatac cacttgtccg     2220
ccctgccgct tctcccaaga tcaataaagc cacttacttt gccatctttc acaaagatgt    2280
tgctgtctcc caggtcgccg tgggaaaaga caagttcctc ttcgggcttt tccgtcttta    2340
aaaaatcata cagctcgcgc ggatctttaa atggagtgtc ttcttcccag ttttcgcaat    2400
ccacatcggc cagatcgtta ttcagtaagt aatccaattc ggctaagcgg ctgtctaagc    2460
tattcgtata gggacaatcc gatatgtcga tggagtgaaa gagcctgatg cactccgcat    2520
acagctcgat aatcttttca gggctttgtt catcttcata ctcttccgag caaaggacgc    2580
catcggcctc actcatgagc agattgctcc agccatcatg ccgttcaaag tgcaggacct    2640
ttggaacagg cagctttcct tccagccata gcatcatgtc cttttcccgt tccacatcat    2700
aggtggtccc tttataccgg ctgtccgtca tttttaaata taggttttca ttttctccca    2760
ccagcttata taccttagca ggagacattc cttccgtatc ttttacgcag cggtattttt    2820
cgatcagttt tttcaattcc ggtgatattc tcattttagc catttattat ttccttcctc    2880
ttttctacag tatttaaaga taccccaaga agctaattat aacaagacga actccaattc    2940
actgttcctt gcattctaaa accttaaata ccagaaaaca gctttttcaa agttgttttc    3000
aaagttggcg tataacatag tatcgacgga gccgattttg aaaccgcggt gatcacaggc    3060
agcaacgctc tgtcatcgtt acaatcaaca tgctaccctc cgcgagatca tccgtgtttc    3120
aaacccggca gcttagttgc cgttcttccg aatagcatcg gtaacatgag caaagtctgc    3180
cgccttacaa cggctctccc gctgacgccg tcccggactg atgggctgcc tgtatcgagt    3240
ggtgattttg tgccgagctg ccggtcgggg agctgttggc tggctggtgg caggatatat    3300
tgtggtgtaa acaaattgac gcttagacaa cttaataaca cattgcggac gttttttaatg    3360
tagagctcaa agtttaacgc gttagcagaa ggcatgttgt tgtgactccg aggggttgcc    3420
tcaaactcta tcttataacc ggcgtggagg catggaggca ggggtatttt ggtcattta    3480
atagatagtg gaaaatgacg tggaatttac ttaaagacga agtctttgcg acaagggggg    3540
gcccacgccg aatttaatat taccggcgtg gccccccctt atcgcgagtg ctttagcacg    3600
agcggtccag atttaaagta gaaaattttcc cgcccactag ggttaaaggt gttcacacta    3660
taaaagcata tacgatgtga tggtatttga tggagcgtat attgtatcag gtatttccgt    3720
tggatacgaa ttattcgtac gaccctcggt accgatcggc gcgccagatt tgccttttca    3780
atttcagaaa gaatgctaac ccacagatgg ttagagacgc ttacgcagca ggtatcatca    3840
agacgatcta cccgagcaat aatctccagg aaatcaaata ccttcccaag aaggttaaag    3900
atgcagtcaa aagattcagg actaactgca tcaagaacac agagaaagat atatttctca    3960
agatcagaag tactattcca gtatggacga ttcaaggctt gcttcacaaa ccaaggcaag    4020
taatagagat tggagtctct aaaaaggtag ttcccactga atcaaaggcc atggagtcaa    4080
agattcaaat agaggaccta acagaactcg ccgtaaagac tggcgaacag ttcatacaga    4140
gtctcttacg actcaatgac aagaagaaaa tcttcgtcaa catggtggag cacgacacac    4200
ttgtctactc caaaaatatc aaagatacag tctcagaaga ccaaagggca attgagactt    4260
ttcaacaaag ggtaatatcc ggaaacctcc tcggattcca ttgcccagct atctgtcact    4320
ttattgtgaa gatagtggaa aaggaaggtg gctcctacaa atgccatcat tgcgataaag    4380
gaaaggccat cgttgaagat gcctctgccg acagtggtcc caaagatgga cccccaccca    4440
cgaggagcat cgtggaaaaa gaagacgttc caaccacgtc ttcaaagcaa gtggattgat    4500
gtgatatctc cactgacgta agggatgacg cacaatccca ctatccttcg caagacccctt   4560
cctctatata aggaagttca tttcatttgg agagaacacg gggactcct gcaggtagat    4620
cgctcgtcga catggataag aagtactcta tcggactcga tatcggaact aactctgtgg    4680
gatgggctgt gatcaccgat gagtacaagg tgccatctaa gaagttcaag gttctcggaa    4740
acaccgatag gcactctatc aagaaaaacc ttatcggtgc tctcctcttc gattctggtg    4800
aaactgctga ggctaccaga ctcaagagaa ccgctagaag aagtacacc agaagaaaga    4860
acaggatctg ctacctccaa gagatcttct ctaacgagat ggctaaagtg gatgattcat    4920
tcttccacag gctcgaagag tcattcctcg tggaagaaga taagaagcac gagaggcacc    4980
ctatcttcgg aaacatcgtt gatgaggtgg cataccacga gaagtaccct actatctacc    5040
acctcagaaa gaagctcgtt gattctactg ataaggctga ttccaggctc atctacctcg    5100
ctctcgctca catgatcaag ttcagaggac acttcctcat cgagggtgat ctcaaccctg    5160
ataactctga tgtggataag ttgttcatcc agctcgtgca gacctacaac cagcttttcg    5220
aagagaaccc tatcaacgct tcaggtgtgg atgctaaggc tatcctctct gctaggctct    5280
ctaagtcaag aaggcttgag aacctcattg ctcagctccc tggtgagaag aagaacggac    5340
ttttcggaaa cttgatcgct ctctctctcg gactcacccc taacttcaag tctaacttcg    5400
atctcgctga ggatgcaaag ctccagctct caaaggatac ctacgatgat gatctcgata    5460
acctcctcgc tcagatcgga gatcagtacg ctgatttgtt cctcgctgct aagaacctct    5520
ctgatgctat cctcctcagt gatatcctca gagtgaacac cgagatcacc aaggctccac    5580
tctcagcttc tatgatcaag agatacgatg agcaccacca ggatctcaca cttctcaagg    5640
ctcttgttag acagcagctc ccagagaagt acaaagagat tttcttcgat cagtctaaga    5700
acggatacgc tggttacatc gatggtggtg catctcaaga agagttctac aagttcatca    5760
agcctatcct cgagaagatg gatggaaccg aggaactcct cgtgaagctc aatagagagg    5820
atcttctcag aaagcagagg accttcgata acggatctat ccctcatcag atccatctcg    5880
gagagttgca cgctctacctt agaaggcaag aggatttcta cccattcctc aaggataaca    5940
gggaaaagat tgagaagatt ctcacttcca gaatcccta ctacgtggga cctctcgcta    6000
gaggaaactc aagattcgct tggatgacca gaaagtctga ggaaaccatc accccttgga    6060
acttcgaaga ggtggtggat aagggtgcta gtgctcagtc tttcatcgag aggatgacca    6120
acttcgataa gaaccttcca aacgagaagg tgctccccaa cgactctttg ctctacgagt    6180
acttcaccgt gtacaacgag ttgaccaagg ttaagtacgt gaccgagggg atgaggaagc    6240
ctgctttttt gtcaggtgag caaaagaagg ctatcgttga tctcttgttc aagaccaaca    6300
gaaaggtgac cgtgaagcag ctcaagagag attacttcaa gaaaatcgag tgcttcgatt    6360
cagttgagat ttctggtgtt gaggataggt caacgcatc tctcggaacc taccacgatc    6420
tcctcaagat cattaaggat aagggattttct tggatagcgag gaaaacgag gatatcttgg    6480
aggatatccgt tcttaccctc accctctttg aagatagaga gatgattgaa gaaaggctca    6540
agacctacgc tcatctcttc gatgataagg tgatgaagca gttgaagaga agaagataca    6600
ctggttgggg aaggctctca agaaagctca ttaacgaat cagggataag cagtctggaa    6660
agacaatcct tgatttcctc aagtctgatg gattcgctaa cagaaacttc atgcagctca    6720
tccacgatga ttctctcacc tttaaagagg atatccagaa ggctcaggtt tcaggacagg    6780
```

```
gtgatagtct ccatgagcat atcgctaacc tcgctggatc tcctgcaatc aagaagggaa  6840
tcctccagac tgtgaaggtt gtggatgagt tggtgaaggt gatgggaagg cataagcctg  6900
agaacatcgt gatcgaaatg gctagagaga accagaccac tcagaaggga cagaagaact  6960
ctagggaaag gatgaagagg atcgaggaag gtatcaaaga gcttggatct cagatcctca  7020
aagagcaccc tgttgagaac actcagctcc agaatggaag gctctacctc tactacctcc  7080
agaacgaaag ggatatgtat gtggatcaag agttggatat caacaggctc tctgattacg  7140
atgttgatca tatcgtgcca cagtcattct tgaaggatga ttctatcgat aacaaggtgc  7200
tcaccaggtc tgataagaac aggggtaaga gtgataacgt gccaagtgaa gaggttgtga  7260
agaaaatgaa gaactattgg aggcagctcc tcaacgctaa gctcatcact cagagaaagt  7320
tcgataactt gactaaggct gagaggggag gactctctga attggataag gcaggattca  7380
tcaagaggca gcttgtggaa accaggcaga tcactaagca cgttgcacag atcctcgatt  7440
ctaggatgaa caccaagtac gatgagaacg ataagttgat cagggaagtg aaggttatca  7500
ccctcaagtc aaagctcgtg tctgatttca gaaaggattt ccaattctac aaggtgaggg  7560
aaatcaacaa ctaccaccac gctcacgatg cttaccttaa cgctgttgtt ggaaccgctc  7620
tcatcaagaa gtatcctaag ctcgagtcag agttcgtgta cggtgattac aaggtgtacg  7680
atgtgaggaa gatgatcgct aagtctgagc aagagatcgg aaaggctacc gctaagtatt  7740
tcttctactc taacatcatg aatttcttca agaccgagat taccctcgct aacggtgaga  7800
tcagaaagag gccactcatc gagacaaacg gtgaaacagg tgagatcgtg tgggataagg  7860
gaagggattt cgctaccgtt agaaaggtgc tctctatgcc acaggtgaac atcgttaaga  7920
aaaccgaggt gcagaccggt ggattctcta aagagtctat cctccctaag aggaactctg  7980
ataagctcat tgctaggaag aaggattggg accctaagaa atacgtggt ttcgattctc  8040
ctaccgtggc ttactctgtt ctcgttgtgg ctaaggttga gaagggaaag agtaagaagc  8100
tcaagtctgt taaggaactt ctcggaatca ctatcatgaa aggtcatct ttcgagaaga  8160
acccaatcga tttcctcgag gctaagggat acaagagagt taagaaggat ctcatcatca  8220
agctcccaaa gtactcactc ttcgaactcg agaacggtag aaagaggatg ctcgcttctg  8280
ctggtgagct tcaaaaggga aacgagctgt ctctcccatc taagtacgtt aactttcttt  8340
acctcgcttc tcactacgag aagttgaagg atctccaga agataacgag cagaagcaac  8400
ttttcgttga gcagcacaag cactacttgg atgagatcat cgagcagatc tctgagttct  8460
ctaaaagggt gatcctcgct gatgcaaacc tcgataaggt gttgtctgct tacaacaagc  8520
acagagataa gcctatcagg gaacaggcag agaacatcat ccatctcttc accccttacca  8580
acctcggtgc tcctgctgct ttcaagtact tcgatacaac catcgatagg aagagataca  8640
cctctaccaa agaagtgctc gatgctaccc tcatccatca gtctatcact ggactctacg  8700
agactaggat cgatctctca cagctcggtg gtgattcaag ggctgatcct aagaagaaga  8760
ggaaggtttg acgtcgacga tatgaagatg aagatgaaat atttggtgtg tcaaataaaa  8820
agcttgtgtg cttaagtttg tgtttttttc ttggcttgtt gtgttagaa tttgtggctt  8880
tttctaatat taaatgaatg taagatcaca ttataatgaa taaacaaatg tttctataat  8940
ccattgtgaa tgttttgttg gatctcttct gcagcatata actactgtat gtgctatggt  9000
atggactatg gaatatgatt aaagataagc cagagctctg gtgacggacc catgcttcg  9060
ttgaacaacg gaaactcgac ttgccttccg cacaatacat cattcttct tagctttttt  9120
tcttcttctt cgttcataca gttttttttt gtttatcagc ttacatttct ttgaaccgta  9180
gctttcgttt tcttctttt aacttttccat tcggagtttt tgtatcttgt ttcatagttt  9240
gtcccaggat tagaatgatt aggcatcgaa ccttcaagaa tttgattgaa taaaacatct  9300
tcattcttaa gatatgaaga taatcttcaa aaggccccttg ggaatctgaa agaagagaag  9360
caggcccatt tatatgggaa agaacaatag tatttcttat ataggcccat ttaagttgaa  9420
aacaatcttc aaaagtccca catcgcttag ataaaaaac gaagctgagt ttatatacag  9480
ctagagtcga agtagtgatt gcctacttgg gctgttgcag gttttagagc tagaaatagc  9540
aagttaaaat aaggctagtc cgttatcaac ttgaaaaagt ggcaccgagt cggtgctttt  9600
tttcccgggg cgcgccctat gtcgagctgc aggtcaacgg atcaggatat tcttgtttaa  9660
gatgttgaac tctatggagg tttgtatgaa ctgatgatct aggaccggat aagttccctt  9720
cttcatagcg aacttattca aagaatgttt tgtgtatcat tcttgttaca ttgttattaa  9780
tgaaaaaata ttattggtca ttggactgaa cacgagtgtt aaatatggac caggccccaa  9840
ataagatcca ttgatatatg aattaaataa caagaataaa tcgagtcacc aaaccacttg  9900
cctttttttaa cgagacttgt tcaccaactt gatacaaaag tcattatcct atgcaaatca  9960
ataatcatac aaaatatcc aataacacta aaaattaaa agaaatggat aatttcacaa 10020
tatgttatac gataaagaag ttactttttcc aagaaattca ctgattttat aagcccactt 10080
gcattagata aatggcaaaa aaaaacaaa aggaaaagaa ataagcacg aagaattcta 10140
gaaaatacga aatacgcttc aatgcagtgg gacccacggt tcaattattg ccaattttca 10200
gctccaccgt atatttaaaa aataaaacga taatgctaaa aaaatataaa tcgtaacgat 10260
cgttaaatct caacggctcg atcttatgac gaccgttaga aattgtggt gtcgacagt 10320
cagtaataaa cggcgtcaaa gtggttgcag ccggcacaca cgagtcgtgt ttatcaactc 10380
aaagcacaaa tacttttcct caacctaaaa ataaggcaat tagccaaaaa caactttgcg 10440
tgtaaacaac gctcaataca cgtgtcattt tattattagc tattgcttca ccgccttagc 10500
tttctcgtga cctagtcgtc ctcgtcttt cttcttcttc ttctataaaa caatacccaa 10560
agagctcttc ttcttcacaa ttcagatttc aattcttcaa aatcttaaaa acttctctc 10620
aattctctct accgtgatca aggtaaattt ctgtgttcct tattctctca aaatcttcga 10680
ttttgttttc gttcgatccc aatttcgtat atgttctttg gttagattc tgttaatctt 10740
agatcgaaca cgattttctg ggtttgatcg ttagatatca tcttaattct cgattagggt 10800
ttcatagata tcatccgatt tgttcaaata atttgagttt tgtcgaataa ttactcttcg 10860
atttgtgatt tctatctaga tctggtgtta gtttcgagt tgtgcgatcg aatttgtcga 10920
ttaatctgag ttttttctgat taacaggcct gcaggatgga agacgccaaa acataaaga 10980
aaggcccggc gccattctat ccgctggaag atggaaccgc tggagagcaa ctgcataagg 11040
ctatgaagag atacgccctg gttcctggaa caattgcttt tacagatgca catatcgagg 11100
tggacatcac ttacgctgag tacttcgaaa tgtccgttcg gttggcagaa gctatgaaac 11160
gatatgggct gaatacaaat cacagaatcg tcgtatgcag tgaaaactct cttcaattct 11220
ttatgccgat gttgggcgcg ttatttatcg gagttgcagt tgcgcccgcg aacgacttt 11280
ataatgaacg tgaattgctc aacagtatgg gcatttcgca gcctaccgtg gtgttcgttt 11340
ccaaaaggg gttgcaaaaa attttgaacg tgcaaaaaaa gctcccaatc atccaaaaaa 11400
ttattatcat ggattctaaa acggattacc agggatttca gtcgatgtac acgttcgtca 11460
catctcatct acctcccggt tttaatgaat acgattttgt gccagagtcc ttcgatgggg 11520
```

```
acaagacaat tgcactgatc atgaactcct ctggatctac tggtctgcct aaaggtgtcg  11580
ctctgcctca tagaactgcc tgcgtgagat tctcgcatgc cagagatcct attttttggca 11640
atcaaatcat tccggatact gcgattttaa gtgttgttcc attccatcac ggttttggaa  11700
tgtttactac actcggatat ttgatatgtg gatttcgagt cgtcttaatg tatagatttg  11760
aagaagagct gtttctgagg agccttcagg attacaagat tcaaagtcg ctgctggtgc   11820
caaccctatt ctccttcttc gccaaaagca ctctgattga caaatacgat ttatctaatt  11880
tacacgaaat tgcttctggt ggcgctcccc tctctaagga agtcggggaa gcggttgcca  11940
agaggttcca tctgccaggt atcaggcaag gatatgggct cactgagact acatcagcta  12000
ttctgattac acccgagggg gatgataaac cgggcgcggt cggtaaagtt gttccatttt  12060
ttgaagcgaa ggttgtggat ctggataccg ggaaaacgct gggcgttaat caaagaggcg  12120
aactgtgtgt gagaggtcct atgattatgt ccgttatgt aaacaatccg gaagcgacca   12180
acgccttgat tgacaaggat ggatggctac attctggaga catagcttac tgggacgaag  12240
acgaacactt cttcatcgtt gaccgcctga agtctctgat taagtacaaa ggctatcagg  12300
tggctcccgc tgaattggaa tccatcttgc tccaacaccc caacatcttc gacgctgtg   12360
tcgcaggtct tcccgacgat gacgccggtg aacttcccgc cgccgttgtt gttttggagc  12420
acggaaagac gatgacggaa aaagagatcg tggattacgt cgccagtcaa gtaacaaccg  12480
cgaaaaagtt gcgcggagga gttgtgtttg tggacgaagt accgaaaggt cttaccggaa  12540
aactcgacgc aagaaaaatc agagagatcc tcataaagga caagaaggc ggaaagatcg   12600
ccgtgtgact cgaggttcga gtattatggc attgggaaaa ctgttttct tgtaccattt    12660
gttgtgcttg taatttactg tgttttttat tcggttttcg ctatcgaact gtgaaatgga  12720
aatggatgga gaagagttaa tgaatgatat ggtccttttg ttcattctca aattaatatt  12780
attttgttttt tctcttattt gttgtgtgtt gaatttgaaa ttataagaga tatgcaaaca  12840
ttttgttttg agtaaaaatg tgtcaaatcg tggcctctaa tgaccgaagt taatatgagg  12900
agtaaaacac ttgtagttgt gttagagctc tcccggcgcg ccgatatcga gctcagtgtt  12960
tgatcgccgg cggtaccgag tgtacttcaa gtcagtggga aatcaataaa atgattattt  13020
tatgaatata tttcattgtg caagtagata gaaattacat atgttacata acacacgaaa  13080
taaacaaaaa aagacaatcc aaaaacaaac accccaaaaa aataatcac tttagataaa   13140
ctcgtatgag gagaggcacg ttcagtgact cgacgattcc cgagcaaaaa aagtctcccc  13200
gtcacacatg tagtgggtga cgcaattatc tttaaagtaa tccttctgtt gacttgtcat  13260
tgataacatc cagtcttcgt caggattgca aagaattata gaagggatcc caccttttat  13320
tttcttcttt tttccatatt tagggttgac agtgaaatca gactggcaac ctattaattg  13380
cttccacaat gggacgaact tgaagggat gtcgtcgatg atattatagg tggcgtgttc    13440
atcgtagttg tgaaatcga tggtaccgtt ccaatagttg tgtcgtccga gacttctagc   13500
ccaggtggtc tttccggtac gagttggtcc gcagatgtag aggctgggg gtcggattcc    13560
attccttcca ttgtccttgt taaatcggcc atccattcaa ggtcagattg agcttgttgg  13620
tatgagacag gatgtatgta agtataagcg tctatgctta catggtatag atgggtttcc  13680
ctccaggagt gtagatcttc gtggcagcga agatctgatt ctgtgaaggg cgacacatac  13740
ggttcaggtt gtggagggaa taatttgttg gctgaatatt ccagccattg aagctttgtt  13800
gcccattcat gagggaattc ttccttgatc atgtcaagat attcctcctt agacgttgtc  13860
gtctggataa tagttctcca tcgtgcgtca gatttgcgag gagaaacctt atgatctcgg  13920
aaatctcctc tggttttaat atccgtcc tttgatatgt aatcaaggac ttgtttagag    13980
tttctagctg gctggatatt agggtgattt ccttcaaaat cgaaaaaga aggatcccta   14040
atacaaggtt ttttatcaag ctgggagaaga gcatgatagt gggtagtgcc atcttgatga  14100
agctcagaag caacaccaag gaagaaaata agaaaaggtg tgagtttctc ccagagaaac  14160
tggaataaat catctctttg agatgagcac ttgggatagg taaggaaaac atatttagat  14220
tggagtctga agttcttact agcagaaggc atgttgttgt gactccgagg ggttgcctca  14280
aactctatct tataaccggc gtggaggcat ggaggcaggg gtattttggt cattttaata  14340
gatagtggaa aatgacgtgg aatttactta aagacgaagt ctttgcgaca aggggggggcc  14400
cacgccgaat taatattac cggcgtggcc ccccttatc gcgagtgctt tagcacgagc     14460
ggtccagatt taaagtagaa aatttcccgc ccactagggt taaaggtgtt cacactataa  14520
aagcatatac gatgtgatgg tatttgatgg agctgtatt gtatcaggta tttccgttgg    14580
atacgaatta ttcgtacgac cctcatagtt taaactatca gtgtttgaca ggatatattg  14640
gcgggtaaac ctaagagaaa agagcgttta ttagaataac ggatatttaa aagggcgtga  14700
aaaggtttat ccgttcgtcc atttgtatgt gcatgccaac cacagggttc ccctcgggat  14760
caaagtactt tgatccaacc cctccgctgc tatagtgcag tcggcttctg acgttcagtg  14820
cagccgtctt ctgaaaacga catgtcgcac aagtcctaag ttacgcgaca ggctgccgcc  14880
ctgccctttt cctggcgttt tcttgtcgcg tgttttagtc gcataaagta gaatacttgc  14940
gactagaacc ggagacatta cgccatgaac aagagcgccg ccgctggcct gctgggctat  15000
gcccgcgtca gcaccgacga ccaggacttg accaaccaac gggcgaact gcacgcggtc    15060
ggctgcacca agctgttttc cgagaagatc accggcacca ggcgcgaccg cccggagctg  15120
gccaggatgc ttgaccacct acgccctggc gacgttgtga cagtgaccag gctagaccgc  15180
ctggcccgca gcacccgcga cctactggac attgccgagc gcatccagga ggccggcgcg  15240
ggcctgcgta gcctggcaga gccgtgggcc gacaccacca gcggccgg ccgcatggt    15300
ttgaccgtgt tcgccggcat tgccgagttc agcgttccc taatcatcga ccgcaccgcc    15360
agcgggcgcg aggccgccaa ggccgaggc gtgaagtttg gccccgccc taccctcacc    15420
ccggcacaga tcgcgcacgc ccgcgagctg atcgaccagg aaggccgcac cgtgaaagag  15480
gcggctcac tgcttggcgt gcatcgctcg accctgtacc gcgcacttga gcgcagcgag  15540
gaagtgacgc ccaccgaggc caggcggcgc ggtgccttcc gtgaggacag attgaccgag  15600
gccgacgcc tggccgcgc cgagaatgaa cgccaagagg aacaagcatg aaaccgcacc  15660
aggacgccca ggacgaaccg ttttttcatta ccgaagagat cgaggcggag atgatcgcgg  15720
ccgggtacgt gttcgagccg cccgcgcacg ctcaaccgt gcggctgcat gaaatcctgg  15780
ccggtttgtc tgatgccaag ctggcggcct ggccggccag cttggccgct gaagaaaccg  15840
agcgccgccg tctaaaaagg tgatgtgtat ttgagtaaaa cagcttgcgt catgcggtcg  15900
ctgcgtatat gatgcgatga gtaaataaac aaatacgcaa ggggaacgca tgaaggttat  15960
cgctgtactt aaccagaaag gcgggtcagg caagacgacc atcgcaaccc atctagcccg  16020
cgccctgcaa ctcgccgggg ccgatgttct gttagtcgat tccgatcccc agggcagtgc  16080
ccgcgattgg gcggccgtgc gggaagatca accgctaacc gttgtcggca tcgaccgccc  16140
gacgattgac cgcgacgtga aggccatcgg ccggcgcgac ttcgtagtga tcgacggagc  16200
gccccaggcg gcggacttgg ctgtgtccgc gatcaaggca gccgacttcg tgctgattcc  16260
```

```
ggtgcagcca agcccttacg acatatgggc caccgccgac ctggtggagc tggttaagca   16320
gcgcattgag gtcacggatg gaaggctaca agcggccttt gtcgtgtcgc gggcgatcaa   16380
aggcacgcgc atcggcggtg aggttgccga ggcgctggcc gggtacgagc tgcccattct   16440
tgagtcccgt atcacgcagc gcgtgagcta cccaggcact gccgccgccg cacaaccgt    16500
tcttgaatca gaacccgagg gcgacgctgc ccgcgaggtc caggcgctgg ccgctgaaat   16560
taaatcaaaa ctcatttgag ttaatgaggt aaagagaaaa tgagcaaaag cacaaacacg   16620
ctaagtgccg gccgtccgag cgcacgcagc agcaaggctg caacgttggc cagcctggca   16680
gacacgccag ccatgaagcg ggtcaacttt cagttgccgg cggaggatca caccaagctg   16740
aagatgtacg cggtacgcca aggcaagacc attaccgagc tgctatctga atacatcggt   16800
cagctaccag agtaaatgag caaatgaata aatgagtcga tgaattttag cggctaaagg   16860
aggcggcatg gaaaatcaag aacaaccagg caccgacgcc gtggaatgcc ccatgtgtgg   16920
aggaacgggc ggttggccag gcgtaagcgg ctgggttgtc tgccggccct gcaatggcac   16980
tggaacccc aagcccgagg aatcggcgtg acggtcgcaa accatccggc ccggtacaaa    17040
tcggcgcggc gctgggtgat gacctggtgg agaagttgaa ggccgcgcag gccgcccagc   17100
ggcaacgcat cgaggcagaa gcacgccccg tgaatcgtg gcaagcggcc gctgatcgaa    17160
tccgcaaaga atcccggcaa ccgccggcag ccggtcgcgc gtcgattagg aagccgccca   17220
agggcgacga gcaaccagat ttttcgttc cgatgctcta tgacgtgggc acccgcgata    17280
gtcgcagcat catggacgtg gccgttttcc gtctgtcgaa gcgtgaccga cgagctgggg   17340
aggtgatccg ctacgagctt ccagacgggc acgtagaggt ttccgcaggg ccggccggca   17400
tggccagtgt gtgggattac gacctggtac tgatggcggt ttcccatcta accgaatcca   17460
tgaaccgata ccgggaaggg aagggagaca agcccggccg cgtgttccgt ccacacgttg   17520
cggacgtact caagttctgc cggcgagccg atggcggaaa gcagaaagac gacctggtag   17580
aaacctgcat tcggttaaac accacgcacg ttgcca                              17616

SEQ ID NO: 94        moltype = DNA  length = 15986
FEATURE              Location/Qualifiers
source               1..15986
                     mol_type = other DNA
                     organism = synthetic construct
SEQUENCE: 94
tttgatcgcc ggcggtaccg agtgtacttc aagtcagtgg gaaatcaata aaatgattat   60
tttatgaata tatttcattg tgcaagtaga tagaaattac atatgttaca taacacacga   120
aataaacaaa aaagacaat ccaaaaacaa acacccaaa aaaataatc actttagata       180
aactcgtatg aggagaggca cgttcagtga ctcgacgatt cccgagcaaa aaaagtccta   240
ccgtcacaca tgtagtgggt gacgcaatta tcttaaagt aatccttctg ttgacttgtc    300
attgataaca tccagtcttc gtcaggattg caaagaatta tagaagggat cccacccttt   360
atttcttct ttttccata tttagggttg acagtgaaat cagactggca acctattaat     420
tgcttccaca atgggacgaa cttgaagggg atgtcgtcga tgatattata ggtggcgtgt   480
tcatcgtagt tggtgaaatc gatgtaccg tccaatagt tgtgtcgtcc gagacttcta    540
gcccaggtgg tctttccggt acgagttggt ccgcagatgt agaggctggg gtgtcggatt   600
ccattccttc cattgtcctt gttaaatcgg ccatccattc aaggtcagat tgagcttgtt   660
ggtatgagac aggatgtatg taagtataag cgtctatgct tacatggtat agatgggttt   720
ccctccagga gtgtagatct tcgtggcagc gaagatctga ttctgtgaag ggcgacacat   780
acggttcagg ttgtggaggg aataatttgt tggctgaata ttccagccat tgaagctttg   840
ttgcccattc atgagggaat tcttccttga tcatgtcaag atattcctcc ttagacgttg   900
cagtctggat aatagttctc catcgtgcgt cagatttgcg aggagaaacc ttatgatctc   960
ggaaatctcc tctggtttta atatctccgt cctttgtatt gtaatcaagg acttgtttag   1020
agtttctagc tggctggata ttagggtgat ttccttcaaa atcgaaaaaa gaaggatccc   1080
taatacaagg ttttttatca agctggagaa gagcatgata gtgggtagtg ccatcttgat   1140
gaagctcaga agcaacacca aggaagaaaa taagaaaagg tgtgagtttc tcccagagaa   1200
actggaataa atcatctctt tgagatgagc acttgggata ggtaaggaaa acatatttag   1260
attggagtct gaagttctta ctagcagaag gcatgttgtt gtgactccga ggggttgcct   1320
caaactctat cttataaccg gcgtggaggc atggaggcag gggtattttg gtcatttaa    1380
tagatagtgg aaaatgacgt ggaatttact taaagacgaa gtctttgcga caagggggg    1440
cccacgccga atttaatatt accggcgtgg ccccccctta tcgcgagtgc tttagcacga   1500
gcggtccaga tttaaagtag aaaatttcc gcccactagg gttaaaggtg ttcacactat    1560
aaaagcatat acgatgtgat ggtattgat ggagcgtata ttgtatcagg tattccgtt     1620
ggatacgaat tattcgtacg accctcatag ttttaactat cagtgtttga caggatatat    1680
tggcgggtaa acctaagaga aaagagcgtt tattagaata acggatattt aaaagggcgt   1740
gaaaaggttt atccgttcgt ccatttgtat gtgcatgcca accacagggt tccctcggg    1800
atcaaagtac tttgatccaa cccctccgct gctatagtgc agtcggcttc tgacgttcag   1860
tgcagccgtc ttctgaaaac gacatgtcgc acaagtccta agttacgcga caggctgccg   1920
ccctgccctt ttcctggcgt tttcttgtcg cgtgttttag tcgcataaag tagaatactt   1980
gcgactagaa ccggagacat tacgccatga acaagagcgc cgccgctgcc ctgctcggtg   2040
atgcccgcgt cagcaccgac gaccaggact tgaccaacca acgggccgaa ctgcacgcgg   2100
ccggctgcac caagctgttt ccgagaagaa tcaccggcac caggcgcgac cgcccggagc   2160
tggccaggat gcttgaccac ctacgccctg gcgacgttgt gacagtgacc aggctagacc   2220
gcctggcccg cagcacccgc gacctactgg acattgccga gcgcatccag gaggccggcg   2280
cgggcctgcg tagcctggca gagccgtggg ccgacaccac cacgccggcc ggccgcatgg   2340
tgttgaccgt gttcgccggc attgccgagt tcgagcgttc cctaatcatc gaccgcaccc   2400
ggagcgggcg cgaggccgcc aaggcccgag gcgtgaagtt tggcccccgc cctaccctca   2460
ccccggcaca gatcgcgcac gcccgcgagc tgatcgacca ggaaggccgc accgtgaaag   2520
aggcggctgc actgcttggc gtgcatgct cgaccctgta ccgcgcactt gagcgcagcg   2580
aggaagtgac gcccaccgag gccaggcggc gcggtgcctt ccgtgaggac gcattgaccg   2640
aggccgacgc cctggcggcc gccgagaatg aacgccaaga ggaacaagca tgaaaccgca   2700
ccaggacggc caggacgaac gttttcat taccgaagag atcgaggcgg agatgatcgc   2760
ggccgggtac gtgttcgagc cgcccgcgca cggctcaacc gtgcggctgc atgaaatcct   2820
ggccggtttg tctgatgcca agctggcggc ctggccggcc agcttggccg ctgaagaaac   2880
cgagcgccgc cgtctaaaaa ggtgatgtgt atttgagtaa aacagcttgc gtcatgcggt   2940
```

```
cgctgcgtat atgatgcgat gagtaaataa acaaatacgc aaggggaacg catgaaggtt  3000
atcgctgtac ttaaccagaa aggcgggtca ggcaagacga ccatcgcaac ccatctagcc  3060
cgcgccctgc aactcgccgg ggccgatgtt ctgttagtcg attccgatcc ccagggcagt  3120
gcccgcgatt gggcggccgt gcgggaagat caaccgctaa ccgttgtcgg catcgaccgc  3180
ccgacgattg accgcgacgt gaaggccatc ggccggccgg acttcgtagt gatcgacgga  3240
gcgcccagg cggcggactt ggctgtgtcc gcgatcaagg cagccgactt cgtgctgatt  3300
ccggtgcagc caagcccta cgacatatgg gccaccgccg acctggtgga gctggttaag  3360
cagcgcattg aggtcacgga tggaaggcta caagcggcct ttgtcgtgtc gcgggcgatc  3420
aaaggcacgc gcatcggcgg tgaggttgcc gaggcgctgg ccgggtacga gctgcccatt  3480
cttgagtccc gtatcacgca gcgcgtgagc tacccaggca ctgccgccgc cggcacaacc  3540
gttcttgaat cagaacccga gggcgacgct gcccgcgagg tccaggcgct ggccgctgaa  3600
attaaatcaa aactcatttg agttaatgag gtaaagagaa aatgagcaaa agcacaaaca  3660
cgctaagtgc cggccgtccg agcgcacgca gcagcaaggc tgcaacgttg gccagcctgg  3720
cagacacgcc agccatgaag cgggtcaact ttcagttgcc ggcggaggat cacaccaagc  3780
tgaagatgta cgcggtacgc caaggcaaga ccattaccga gctgctatct gaatacatcg  3840
cgcagctacc agagtaaatg agcaaatgaa taaatgagta gatgaatttt agcggctaaa  3900
ggaggcggca tggaaaatca agaacaacca ggcaccgacg ccgtggaatg ccccatgtgt  3960
ggaggaacgg gcggttggcc aggcgtaagc ggctgggttg tctgccggcc ctgcaatgcg  4020
actggaaccc ccaagcccga ggaatcggcg tgacggtcgc aaaccatccg gcccggtaca  4080
aatcggcgcg cgctgggtg atgacctggt ggagaagttg aaggccgcgc aggccgccca  4140
gcggcaacgc atcgaggcag aagcacgccc cggtgaatcg tggcaagcgg ccgctgatcg  4200
aatccgcaaa gaatcccggc aaccgccggc agccggtgcg ccgtcgatta ggaagccgcc  4260
caagggcgac gagcaaccag attttttcgt tccgatgctc tatgacgtgg gcacccgcga  4320
tagtcgcagc atcatggacg tggccgtttt ccgtctgtcg aagcgtgacc gacgagctgg  4380
cgaggtgatc cgctacagc ttccagacgg gcacgtagag gtttccgcag ggccggccgg  4440
catggccagt gtgtgggatt acgacctggt actgatggcg gtttcccatc taaccgaatc  4500
catgaaccga taccgggaag ggaagggaga caagcccggc cgcgtgttcc gtccacacgt  4560
tgcggacgta ctcaagttct gccggcgagc cgatggcgga aagcagaaag acgacctggt  4620
agaaacctgc attcggttaa acaccacgca cgttgccatg cagcgtacga agaaggccaa  4680
gaacgggccg ctggtgacgg tatccgaggg tgaagccttg attagccgct acaagatcgt  4740
aaagagcgaa accggggcggc cggagtacat cgagatcgag ctagctgatt ggatgtaccg  4800
cgagatcaca gaaggcaaga acccggacgt gctgacggtt cacccgatt acttttgat  4860
cgatcccggc atcggccgtt ttctctaccg cctggcacgc cgcgccgcag gcaaggcaga  4920
agccagatgg ttgttcaaga cgatctacga acgcagtggc agcgccggag agttcaagaa  4980
gttctgtttc accgtgcgca agctgatcgg gtcaaatgac ctgccggagt acgatttgaa  5040
ggaggaggcg gggcaggctg gcccgatcct agtcatgcgc taccgcaacc tgatcgaggg  5100
cgaagcatcc gccggttcct aatgtacgga gcagatgcta gggcaaattg ccctagcagg  5160
ggaaaaaggt cgaaaaggcc tctttcctgt ggatagcacg tacattggga acccaaagcc  5220
gtacattggg aaccggaacc cgtacattgg gaacccaaca ccgtacattg ggaaccggtc  5280
acacatgtaa gtgactgata taaagagaa aaaggcgat ttttccgcct aaaactcttt  5340
aaaacttatt aaaactctta aaacccgcct ggcctgtgca taactgtctg gccagcgcac  5400
agccgaagag ctgcaaaaag cgcctaccct tcggtcgctg cgctcctac gccccgccgc  5460
ttcgcgtcgg cctatgcgg ccgctggccg ctcaaaaatg ggtcctac ggccaggcaa  5520
tctaccaggg cgcggacaag ccgcgccgtc gccactcgac cgccggcgcc cacatcaagg  5580
cacccctgcct cgcgcgtttc ggtgatgacg gtgaaaacct ctgacacatg cagctcccgg  5640
aaacggtcac agcttgtctg taagcggatg ccgggagcag acaagcccgt cagggcgcgt  5700
cagcgggtgt tggcgggtgt cggggcgcag ccatgaccca gtcacgtagc gatagcggag  5760
tgtatactgg cttaactatg cggcatcaga gcagattgta ctgagagtgc accatatgcg  5820
gtgtgaaata ccgcacagat gcgtaaggag aaaataccgc atcaggcgct cttccgcttc  5880
ctcgctcact gactcgctgc gctcggtcgt tcggctgcgg cgagcggtat cagctcactc  5940
aaaggcggta atacggttat ccacagaatc agggataac gcaggaaaga acatgtgtag  6000
aaaaggccag caaaaggcca ggaaccgtaa aaaggccgcg ttgctggcgt ttttccatag  6060
gctccgcccc cctgacgagc atcacaaaaa tcgacgctca agtcagaggt ggcgaaaccc  6120
gacaggacta taaagatacc aggcgtttcc ccctggaagc tccctcgtgc gctctcctgt  6180
tccgaccctg ccgcttaccg gatacctgtc cgcctttctc ccttcgggaa gcgtggcgct  6240
ttctcatagc tcacgctgta ggtatctcag ttcggtgtag tcgttcgct ccaagctggg  6300
ctgtgtgcac gaaccccccg ttcagcccga ccgctgcgcc ttatccggta actatcgtct  6360
tgagtccaac ccggtaagac acgacttatc gccactggca gcagccactg gtaacaggat  6420
tagcagagcg aggtatgtag cggtgctac agagttcttg aagtggtggc ctaactacgg  6480
ctacactaga aggacagtat ttggtatctg cgctctgctg aagccagtta ccttcggaaa  6540
aagagttggt agctcttgat ccggcaaaca aaccaccgct ggtagcggtg gttttttgt  6600
ttgcaagcag cagattacgc gcagaaaaaa aggatctcaa gaagatcctt tgatctttc  6660
tacggggtct gacgctcagt ggaacgaaaa ctcacgttaa gggattttgg tcatgcattc  6720
taggtactaa aacaattcat ccagtaaaat ataatattt ctccc aatcaggctt  6780
gatcccag aagtcaaaaa atagctcgac atactgttct tccccgatat cctccctgat  6840
cgaccggacg cagaaggcaa tgtcatacca cttgtccgcc ctgccgcttc tcccaagatc  6900
aataaagcca cttactttgc catctttcac aaagatgttg ctgtctccca ggtcgccgtg  6960
ggaaaagaca gttcctcttt cgggcttttc cgtctttaaa aaatcataca gctcgcgcgg  7020
atcttaaat ggagtgtctt cttcccagtt ttcgcaatcc acatcggtcc gatcgttatt  7080
cagtaagtaa tccaattcgg ctaagcggct gtctaagcta ttcgtatagg acaatccga  7140
tatgtcgatg gagtgaaaga gcctgatgca ctccgcatac agctcgataa tcttttcagg  7200
gctttgttca tcttcatact cttccgagca aaggacgcca tcggcctcac tcatgagcag  7260
attgctccag ccatcatgcc gttcaaagtg caggaccttt ggaacaggca gctttccttc  7320
cagccatagc atcatgtcct ttccccgttc cacatcatag gtgtccctt tataccgctt  7380
gtccgtcatt tttaaatata ggttttcatt ttctcccacc agcttatata ccttagcagg  7440
agacattcct tccgtatctt ttacgcagcg tatttttcg atcagttttt tcaattccgg  7500
tgatattctc attttagcca tttattattt ccttcctctt ttctacagta tttaaagata  7560
ccccaagaag ctaattataa caagacgaac tccaattcac tgttccttgc attctaaaac  7620
cttaaatacc agaaaacagc ttttttcaaag ttgttttcaa agttggcgta taacatagta  7680
```

```
tcgacggagc cgattttgaa accgcggtga tcacaggcag caacgctctg tcatcgttac   7740
aatcaacatg ctaccctccg cgagatcatc cgtgtttcaa acccggcagc ttagttgccg   7800
ttcttccgaa tagcatcggt aacatgagca aagtctgccg ccttacaacg gctctcccgc   7860
tgacgccgtc ccggactgat gggctgcctg tatcgagtgg tgattttgtg ccgagctgcc   7920
ggtcggggag ctgttggctg gctggtggca ggatatattg tggtgtaaac aaattgacgc   7980
ttagacaact taataacaca ttgcggacgt ttttaatgta gagctcaaag tttaacgcgt   8040
tagcagaagg catgttgttg tgactccgag ggggttgcctc aaactctatc ttataaccgg   8100
cgtggaggca tggaggcagg ggtattttgg tcatttttaat agatagtgga aaatgacgtg   8160
gaatttacttt aaagacgaag tctttgcgac aaggggggggc ccacgccgaa tttaatatta   8220
ccggcgtggc cccccttat cgcgagtgct ttagcacgag cggtccagat ttaaagtaga   8280
aaatttcccg cccactaggg ttaaaggtgt tcacactata aaagcatata cgatgtgatg   8340
gtatttgatg gagcgtatat tgtatcaggt atttccgttg gatacgaatt attcgtacga   8400
ccctcggtac cgatcggcgc gcgcggccgc acagagattt aaatagctcc ggtgacggac   8460
ggcgcgccct atgtcgagct gcaggtcaac ggatcaggat attcttgttt aagatgttga   8520
actctatgga ggtttgtatg aactgatgat ctaggaccgg ataagttccc ttcttcatag   8580
cgaacttatt caaagaatgt tttgtgtatc attcttgtta cattgttatt aatgaaaaaa   8640
tattattggt cattggactg aacacgagtg ttaaatatgg accaggcccc aaataagatc   8700
cattgatata tgaattaaat aacaagaata aatcgagtca ccaaaccaat tgcctttttt   8760
aacgagactt gttcaccaac ttgatacaaa agtcattatc ctatgcaaat caataatcat   8820
acaaaaatat ccaataacac taaaaaatta aagaaatgg ataatttcac aatatgttat   8880
acgataaaga agttactttt ccaagaaatt cactgatttt ataagcccac ttgcattaga   8940
taaatggcaa aaaaaaacaa aaaggaaaag aaataaagca cgaagaattc tagaaaatac   9000
gaaatacgct tcaatgcagt gggacccacg gttcaattat tgccaatttt cagctccacc   9060
gtatatttaa aaaataaaac gataatgcta aaaaaatata aatcgtaacg atcgttaaat   9120
ctcaacggct ggatcttatg acgaccgtta gaaattgtgt tgtcgacga gtcagtaata   9180
aacggcgtca aagtggttgc agccggcaca cacgagtcgt gtttatcaac tcaaagcaca   9240
aatactttc ctcaacctaa aaataaggca attagccaaa aacaactttg cgtgtaaaca   9300
acgctcaata cacgtgtcat tttattatta gctattgctt caccgcctta gctttctcgt   9360
gacctagtcg tcctcgtctt ttcttcttct tcttctataa aacaataccc aaagagctct   9420
tcttcttcac aattcagatt tcaatttctc aaaatcttaa aaactttctc tcaattctct   9480
ctaccgtgat caaggtaaat ttctgtgttc cttattctct caaaatcttc gattttgttt   9540
tcgttcgatc ccaatttcgt atatgttctt tggtttagat tctgttaatc ttagatcgaa   9600
cacgattttc tgggtttgat cgttagatat catcttaatt ctcgattagg gtttcataga   9660
tatcatccga tttgttcaaa taatttgagt tttgtcgaat aattactctt cgattttgtga   9720
tttctatcta gatctggtgt tagtttctag tttgtgcgat cgaatttgtc gattaatctg   9780
agttttctg attaacaggc ctgcaggatg gaagacgcca aaaacataaa gaaaggcccg   9840
gcgccattct atccgctgga agatggaacc gctggagagc aactgcataa ggctatgaag   9900
agatacgccc tggttcctgg aacaattgct tttacagatg cacatatcga ggtggacatc   9960
acttacgctg agtacttcga aatgtccgtt cggttggcag aagctatgaa acgatatgtg   10020
ctgaatacaa atcacagaat cgtcgtatgc agtgaaaact ctcttcaatt ctttatgccg   10080
gtgttgggcg cgttatttat cggagttgca gttgcgcccg cgaacgacat ttataatgaa   10140
cgtgaattgc tcaacagtat gggcatttcg cagcctaccg tggtgttcgt ttccaaaaag   10200
gggttgcaaa aaattttgaa cgtgcaaaaa aagctccaaa tcattattatc   10260
atggattcta aaacggatta ccagggattt cagtcgatgt acacgttcgt cacatctcat   10320
ctacctcccg gttttaatga atacgatttt gtgccagagt ccttcgatag ggacaagaca   10380
attgcactga tcatgaactc ctctggatct actggtctgc ctaaaggtgt cgctctgcct   10440
catagaactg cctgcgtgag atttctcgcat gccagagatc ctattttttgg caatcaaatc   10500
attccggata ctgcgatttt aagtgttgtt ccattccatc acggttttgg aatgtttact   10560
acactcggat atttgatatg tggatttcga gtcgtcttaa tgtatagatt tgaagaagag   10620
ctgtttctga ggagccttca ggattacaag attcaaagtg cgctgctggt gccaacccta   10680
ttctccttct tcgccaaaag cactctgatt gacaaatacg atttatctaa tttacacgaa   10740
attgcttctg gtggcgctcc cctctctaag gaagtcgggg aagcggttgc caagaggttc   10800
catctgccag gtatcaggca aggatatggg ctcactgaga ctacatcagc tattctgatt   10860
acacccgagg gggatgataa accgggcgcg gtcggtaaag ttgttccatt ttttgaagcg   10920
aaggttgtgg atctggatac cgggaaaacg ctgggcgtta atcaaagagg cgaactgtgt   10980
gtgagaggtc ctatgattat gtccggttat gtaaacaatc cggaagcgac caacgccttg   11040
attgacaagg atggatggct acattctgga gacatagctt actgggacga agacgaacac   11100
ttcttcatcg ttgaccgcct gaagtctctg attaagtaca aaggctatca ggtggctccc   11160
gctgaattgg aatccatctt gctccaacac cccaacatct tcgacgctgg tgtcgcaggt   11220
cttcccgacg atgacgccgg tgaacttccc gccgccgttg ttgttttgga gcacggaaag   11280
acgatgacg aaaaagagat cgtggattac gtcgccagtc aagtaacaac cgcgaaaaag   11340
ttgcgcggag gagttgtgtt tgtggacgaa gtaccgaaag gtcttaccgg aaaactcgac   11400
gcaagaaaaa tcagagagat cctcataaag gccaagaagg gcggaaagat cgccgtgtga   11460
cgtcgacggt tcgagtatta tggcattggg aaaactgttt tcttgtacc atttgttgtg   11520
cttgtaattt actgtgtttt ttattcggtt ttcgctatcc aactgtgaaa tggaaatgga   11580
tggagaagag ttaatgaatg atatggtcct tttgttcatt ctcaaattaa tattatttgt   11640
tttttctctt atttgttgtg tgttgaattt gaaattataa agatatgca aacatttgt   11700
tttgagtaaa aatgtgcaa atcgtggcct ctaatgaccg aagttaatat gaggagtaaa   11760
acacttgtag ttgtgttaga tcctccgggc gcgccatcc tgagcggaga attaagggag   11820
tcacgttatg acccccgccg atgacgcggg acaagccgtt ttacgtttgg aactgacaga   11880
accgcaacgt tgaaggagcc actcagccgc gggtttctgg agtttaatga gctaagcaca   11940
tacgtcagaa accattattg cgcgttcaaa agtcgcctaa ggtcactatc agctagcaaa   12000
tatttcttgt caaaaatgct ccactgacgt tccataaatt cccctcggta tccaattaga   12060
gtctcatatt cactctcaat tcaaataatc tgcaggtgtc gcagcggcgg ggagcggcgg t   12120
cacagaagcg ctcaggaagg ccgctgagat agaggcatgg cggccaatgc ggagcggcgg t   12180
ggagcgggag gaggcagcgg cagcggcagc gtggctgcgc cggcggtgtg ccgcccage  12240
ggctcgcggt ggacgccgac gccggagcag atcaggatgc tgaaggagct gtactacggc  12300
tgcggcatcc ggtcgcccag ctcggagcag atccagcgca tcaccgccat gctgcggcag  12360
cacggcaaga tcgagggcaa gaacgtcttc tactggttcc agaaccacaa ggcccgcgag  12420
```

```
cgccagaagc gccgcctcac cagcctcgac gtgaacgtgc ccgccgccgg cgcggccgac   12480
gccaccacca gccaactcgg cgtcctctcg ctgtcgtcgc cgccgccttc aggcgcggcg   12540
cctccctcgc ccaccctcgg cttctacgcc gccggcaatg gcggcggatc ggctgtgctg   12600
ctggacacga gttccgactg gggcagcagc ggcgctgcga tggccaccga gacatgcttc   12660
ctccaggact acatgggcgt gacggacacg ggcagctcgt gcagtggcc acgcttctcg   12720
tcgtcggaca cgataatggc ggcggccgcg gcgcggcgg cgacgacgcg ggcgcccgag   12780
actctccctc tcttcccgac ctgcggcgac gacggcggca gcggtagcag cagctacttg   12840
ccgttctggg gtgccgcgtc cacaactgcc ggcgccactt cttccgttgc gatccagcag   12900
caacaccagc tgcaggagca gtacagcttt tacagcaaca gcaacagcac ccagctggcc   12960
ggcaccggca accaagacgt atcccgcaaca gcagcagcag ccgccgccct ggagctgagc   13020
ctcagctcat ggtgctcccc ttaccctgct gcagggagta tgtgagagca acgcgagctg   13080
ccactgctct tcacttatgt ctctggaatg aaggaggag gaagtgagca tagcgttggt   13140
gcgttgctgt cattgtccta ggttagtagc tagtgccagt tactagtaag catcaggcat   13200
aggagtatgt agtagaagca tgcacgttgc cggccagcca ggcttagcc gggaaaagaa   13260
tttggtgcag ccggctgcaa aacaggatgt ttacagcccc ccctcgagc cctagacttg   13320
tccatcttct ggattggcca agttaattaa tgtatgaaat aaaggatgc acacatagtg   13380
acatgctaat cactataatg tgggcatcaa agttgtgtgt tatgtgtaat tactaattat   13440
ctgaataaga gaaagagatc atccatattt cttatcctaa gcaatgtca cgtgtctta   13500
taattctttg atgaaccaga tgcatttat taaccaattc catatacata taaatattaa   13560
tcatatataa ttaatatcaa ttgggttagc aaaacaaatc tagtctaggt gtgttttgct   13620
aattattggg ggatagtgca aaagaaatc tacgttctca ataattcaga tagaaaactt   13680
aataaagtga gataattac atagattgct tttatccttt gatatatgtg aaaccatgca   13740
tgatataagg aaaatagata gagaaataat tttttacatc gttgaatatg taaacaattt   13800
aattcaagaa gctaggaata taaatattga ggagtttatg attagagctc tcccggcgcg   13860
ccagatttgc cttttcaatt tcagaaagaa tgctaaccca cagatggtta gagaggctta   13920
cgcagcaggt atcatcaaga cgatctaccc gagcaataat ctccaggaaa tcaaatacct   13980
tcccaagaag gttaaagatg cagtcaaaag attcaggact aactgcatca agaacacaga   14040
gaaagatata tttctcaaga tcagaagtac tattccagta tggacgattc aaggcttgct   14100
tcacaaacca aggcaagtaa tagagattgg agtctctaaa aaggtagttc ccactgaatc   14160
aaaggccatg gagtcaaaga ttcaaataga ggacctaaca ggcttagac gaagactgg   14220
cgaacagttc atacagagtc tcttacgact caatgacaag aagaaaatct tcgtcaacat   14280
ggtggagcac gacacacttg tctactccaa aaatatcaaa gatacagtct cagaagacca   14340
aagggcaatt gagactttc aacaaagggg aatatccgga aacctcctcg gattccattg   14400
cccagctatc tgtcacttta ttgtgaagat agtggaaag gaaggtggct cctacaaatg   14460
ccatcattgc gataaggaa aggcatcgt tgaagatgcc tctgccgaca gtggtcccaa   14520
agatggaccc ccaccacga ggagcatcgt ggaaaagaa gacgttccaa ccacgtcttc   14580
aaagcaagtg gattgatgtg atatctccac tgacgtaagg gatgacgcac aatcccacta   14640
tccttcgcaa gacccttcct ctatataagg aagttcattt cattggaga gaacacgggg   14700
gactccgtga ggatggatct gcgtctaatt ttcggtccaa ccttgcacagg aaagacgtcg   14760
accgcgatac gtcttgccca gcagactggc cttccagtcc tttcgctcga tcgggtccaa   14820
tgctgtcctc aactgtcaac cggaagcgga cgaccaacag tggaagaact gaaaggaacg   14880
acccgtctat accttgaaga tcggcctctg gtgaaggggta tcatcgcagc caagcaagct   14940
cacgaaaggc tgatcgggga agtgtacaat tatgaggccc acgcggggct tattcttgag   15000
ggaggatcta tctcgttgct caggtgcatg gcgcaaagca gttattggag taccgatttt   15060
cgttggcata ttattcgcca caagttagca gacgaggaga cattcatgaa cgcggccaag   15120
gccagagtta ggcagatgtt gcgccctgct gtaggcccat ctattattca agagttggtt   15180
catctttgga atgagcctcg gctgaggccc atactgaagg agatcgacgg atatcgatat   15240
gccatgttat ttgctagcca gaaccagatc acacccgata tgctattgca gcttgaccca   15300
gatatggagg gtgagttgat tcatggaatc gctcaggagt atctcatcca tgcgcgccgg   15360
caggagcagg aattccctcc agtgagcgtg gtcgctttcg aaggattcga aggtccaccg   15420
ttcggaatgt gctagctcga gccctagact tgtccatctt ctggattgac caagttaatt   15480
aatgtatgaa ataaaaggat gcacacatag tgacatgcta atcactataa tgtgggcatc   15540
aaagttgtgt gttatgtgta attactaatt atctgaataa gagaaagaga tcatccatat   15600
ttcttatcct aaatgaatgt cacgtgtctt tataattctt tgatgaacca gatgcattt   15660
attaaccaat tccatataca tataaatatt aatcatatat aattaatatc aattgggtta   15720
gcaaaacaaa tctagtctag gtgtgttttg ctaattattg ggggatagtg caaaagaaa   15780
tctacgttct caataattca gatagaaaac ttaataaagt gagataattt acatagattg   15840
cttttatcct tgatatatg tgaaaccatg catgatataa ggaaaataga tagagaaata   15900
attttttaca tcgttgaata tgtaaacaat ttaattcaag aagctaggaa tataaatatt   15960
gaggagttta tgattagagc tcagtg                                        15986

SEQ ID NO: 95        moltype = DNA   length = 15986
FEATURE              Location/Qualifiers
source               1..15986
                     mol_type = other DNA
                     organism = synthetic construct
SEQUENCE: 95
cagctcgata atcttttcag ggctttgttc atcttcatac tcttccgagc aaaggacgcc    60
atcggcctca ctcatgagca ggattgctcca gccatcatgc cgttcaaagt gcaggaccttt  120
tggaacaggc agctttcctt ccagccatag catcatgtcc ttttcccgtt ccacatcata   180
ggtggtccct ttataccggc tgtccgtcat tttaaatat aggttttcat tttctcccac   240
cagcttatat accttagcag gagacattcc ttccgtatct tttacgcagc ggtatttttc   300
gatcagtttt ttcaattccg gtgatattct cattttagcc atttattatt tccttcctct   360
tttctacagt atttaaagat accccaagaa gctaattaca acaagacgaa ctccaattca   420
ctgttccttg cattctaaaa ccttaaatac cagaaaacag ctttttcaaa gttgttttca   480
aagttggcgt ataacatagt atcgacggag ccgattttga aaccgcgtg atcacaggca   540
gcaacgctct gtcatcgtta caatcaacat gctaccctcc gcgagatcat ccgtgtttca   600
aacccggcag cttagttgcc gttcttccga atagcatcgg taacatgagc aaagtctgcc   660
gccttacaac ggctctcccg ctgacgccgt cccggactga tgggctgcct gtatcgagtg   720
```

```
gtgattttgt gccgagctgc cggtcgggga gctgttggct ggctggtggc aggatatatt    780
gtggtgtaaa caaattgacg cttagacaac ttaataacac attgcggacg tttttaatgt    840
agagctcaaa gtttaacgcg ttagcagaag gcatgttgtt gtgactccga ggggttgcct    900
caaactctat cttataaccg gcgtggaggc atggaggcag gggtattttg gtcattttaa    960
tagatagtgg aaaatgacgt ggaatttact taaagacgaa gtctttgcga caaggggggg   1020
cccacgccga atttaatatt accggcgtgg cccccccctta tcgcgagtgc tttagcacga   1080
gcggtccaga tttaaagtag aaaatttccc gcccactagg gttaaaggtg ttcacactat   1140
aaaagcatat acgatgtgat ggtatttgat ggagcgtata ttgtatcagg tatttccgtt   1200
ggatacgaat tattcgtacg accctcggta ccgatcggcg cgcgcggccg cacagagatt   1260
taaatagctc cggtgacgga cggcgcgccc tatgtcggca tgcaggtcaa cggatcagga   1320
tattcttgtt taagatgttg aactctatgg aggtttgtat gaactgatga tctaggaccg   1380
gataagttcc cttcttcata gcgaacttat tcaaagaatg ttttgtgtat cattcttgtt   1440
acattgttat taatgaaaaa atattattgg tcattggact gaacacgagt gttaaatatg   1500
gaccaggccc caaataagat ccattgatat atgaattaaa taacaagaat aaatcgagtc   1560
accaaaccac ttgccttttt taacgagact tgttcaccaa cttgataacaa aagtcattat   1620
cctatgcaaa tcaataatca tacaaaaata tccaataaca ctaaaaaatt aaaagaaatg   1680
gataaatttca caatatgtta tacgataaag aagttacttt tccaagaaat tcactgtttt   1740
tataagccca cttgcattag ataaatggca aaaaaaaaca aaaggaaaa gaaataaagc   1800
acgaagaatt ctagaaaata cgaaatacgc ttcaatgcag tgggacccac ggttcaatta   1860
ttgccaattt tcagctccac cgtatatttta aaaaataaaa cgataatgct aaaaaaaatat   1920
aaatcgtaac gatcgttaaa tctcaacggc tggatcttat gacgaccgtt agaaattgtg   1980
gttgtcgacg agtcagtaat aaacggcgtc aaagtggttg cagccggcac acacgagtcg   2040
tgtttatcaa ctcaaagcac aaatacttt cctcaaccta aaaataaggc aattagccaa   2100
aaacaacttt gcgtgtaaac aacgctcaat acacgtgtca ttttattatt agctattgct   2160
tcaccgcctt agctttctcg tgacctagtc gtcctcgtct tttcttcttc ttcttctata   2220
aaacaatacc caagagctc ttcttcttca caattcagat ttcaattttct caaaatctca   2280
aaacttttct ctcaattctc tctaccgtga tcaaggtaaa tttctgtgtt cttattctc    2340
tcaaaatctt cgatttgtt ttcgttgat cccaatttcg tatatgttct ttggtttaga    2400
ttctgttaat cttagatcga acacgatttt ctggggttga tcgttagata tcatcttaat   2460
tctcgattag ggttcatag atatcatccg atttgttcaa ataatttgg ttttgtcgaa    2520
taattactct tcgatttgtg atttctatct agatctggtg ttagtttcta gtttgtgcga   2580
tcgaatttgt cgattaatct gagttttttct gattaacagg cctgcaggat ggaagacgcc   2640
aaaaacataa agaaggccc ggcgccattc tatccgctgg aagatggaac cgctggagag   2700
caactgcata aggctatgaa gagatacgcc ctggttcctg gaacaattgc ttttacagat   2760
gcacatatcg aggtggacat cacttacgct gagtacttcg aaatgtccgt tcggttggca   2820
gaagctatga aacgatatgg gctgaataca aatcacagaa tcgtcgtatg cagtgaaaac   2880
tctcttcaat tctttatgcc ggtgttgggc gcgttattta tcggagttgc agttgcgccc   2940
gcgaacgaca tttataatga acgtgaattg ctcaacagta tgggcatttc gcagcctacc   3000
gtggtgttcg tttccaaaaa gggttgcaa aaattttga acgtgcaaaa aagctccca    3060
atcatccaaa aaattattat catggattct aaaacggatt accagggatt tcagtcgatg   3120
tacacgttcg tcacatctca tctacctccc ggttttaatg aatacgattt tgtgccagag   3180
tccttcgata gggacaagac aattgcactg atcatgaact cctctggatc tactggtctg   3240
cctaaaggtg tcgctctgcc tcatagaact gcctgcgtga gattctgcgca tgccagagat   3300
cctatttttg gcaatcaaat cattccggat actgcgattt aagtgttgt tccattccat   3360
cacggttttg gaatgtttac tacactcgga tatttgatat gtggatttcg agtcgtctta   3420
atgtatagat ttgaagaaga gctgtttctg aggagcttc aggattacaa gattcaaagt   3480
gcgctgctgg tgccaaccct attctccttc ttcgccaaaa gcactctgat tgacaaatac   3540
gatttatcta atttacacga aattgcttct ggtggcgctc ccctctcaa ggaagtcggg   3600
gaagcggttg ccaagaggtt ccatctgcca ggtatcaggc aaggatatgg gctcactgag   3660
actacatcag ctattctgat tacacccgag ggggatgata aaccgggcgc ggtcggtaaa   3720
gttgttccat tttttgaagc gaaggttgtg gatctggata ccgggaaaac gctgggcgtt   3780
aatcaaagag gcgaactgtg tgtgagaggt cctatgatta tgtccggtta tgtaaacaat   3840
ccggaagcga ccaacgcctt gattgacaag gatggatggc tacattctgg agacatagct   3900
tactgggacg aagacgaaca cttcttcatc gttgaccgcc tgaagtctct gattaagtac   3960
aaaggctatc aggtggctcc cgctgaattg gaatccaaca tgctccaaca ccccaacatc   4020
ttcgacgctg gtgtcgcagg tcttcccgac gatgacgccg gtgaacttcc cgccgccgtt   4080
gttgttttgg agcacggaaa gacgatgacg gaaaagagat cgtggatta cgtcgccagt   4140
caagtaacaa ccgcgaaaaa gttgcgcgga ggagttgtgt ttgtggacga agtaccgaaa   4200
ggtcttaccg gaaaactcga caagaaaa atcagaga tcctcataaa ggccaagaag   4260
ggcggaaaga tcgccgtgtg acgtcgacgg ttcgagtatt atggcattgg gaaaactgtt   4320
tttcttgtac catttgttgt gcttgtaatt tactgtgttt tttattcggt tttcgctatc   4380
gaactgtgaa atggaaatgg atggagaaga gttaatgaat gatatggtcc ttttgttcat   4440
tctcaaatta atattttg tttttctct tatttgttgt gtgttgaatt tgaaattata   4500
agagatatgc aaacattttg ttttgagtaa aaatgtggca aatcgtggcc tctaatgacc   4560
gaagttaata tgaggagtaa aacacttgta gttgtgttag agctcccggg cgcgccgatc   4620
atgagcggag aattaaggga gtcacgttat gaccccgcc gatgacgcgg gacaagccgt   4680
tttacgtttg gaactgacag aaccgcaacg ttgaaggagc cactcagccg cgggtttctg   4740
gagtttaatg agctaagcac atacgtcaga aaccattatt gcgcgttcaa aagtcgctca   4800
aggtcactat cagctagcaa atatttcttg tcaaaatgc tccactgacg ttccataaat   4860
tcccctcggt atccaattag agtctctat tcactctcaa tccaaataat ctgcaccgta   4920
cctgcagggt ccgagctagg tcacagaagc gctcaggaag gccgctgaga tagaggcatg   4980
gcggccaatg cgggcggcgg tggagcggga ggaggcagcg gcagcggcag cgtggctgcg   5040
ccggcggtgt gccgcccag cggctcgcgg tggacgccga cgccggagca gatcaggatg   5100
ctgaaggagc tgtactacgg ctgcgcatc cggtcgccca gctccgactc gatccagctg   5160
atcaccgcca tgctgcggca gcacggcaag atcgagggcg agaacgtctt ctactggttc   5220
cagaaccaca aggcccgcga gcgccagaag cgccgcctca ccagcctcga cgtgaacgtg   5280
cccgccgccg cgcggccga cgccaccacc agccaactcg gcgtcctctc gctgtcgtcg   5340
ccgccgcctt caggcgcggc gcctccctcg cccacccctcg cgttctacgc cgccggcaat   5400
ggcggcggat cggctgtgct gctggacacg agttccgact ggggcagcag cggcgctgcg   5460
```

```
atggccaccg agacatgctt cctccaggac tacatgggcg tgacggacac gggcagctcg   5520
tcgcagtggc cacgcttctc gtcgtcggac acgataatgg cggcggccgc ggcgcgggcg   5580
gcgacgacgc gggcgcccga gactctccct ctcttcccga cctgcggcga cgacggcggc   5640
agcggtagca gcagctactt gccgttctgg ggtgccgcgt ccacaactgc cggcgccact   5700
tcttccgttg cgatccagca gcaacaccag ctgcaggagc agtacagctt ttacagcaac   5760
agcaacagca cccagctggc cggcaccggc aaccaagacg tatcggcaac agcagcagca   5820
gccgccgccc tggagctgag cctcagctca tggtgctccc cttaccctgc tgcagggagt   5880
atgtgagagc aacgcgagct gccactgctc ttcacttatg tctctggaat ggaaggagga   5940
ggaagtgagc atagcgttgg tgcgttgctg tcattgtcct aggttagtag ctagtgcoag   6000
ttactagtaa gcatcaggca taggagtatg tagtagaagc atgcacgttg ccggccagcc   6060
aggctttaga cgggaaaaga atttggtgca gccggctgca aaacaggatg tttacagccc   6120
cccctcgag ccctagactt gtccatcttc tggattggcc aagttaatta atgtatgaaa   6180
taaaaggatg cacacatagt gacatgctaa tcactataat gtgggcatca aagttgtgtg   6240
ttatgtgtaa ttactaatta tctgaataag agaaagagat catccatatt tcttatccta   6300
aatgaatgtc acgtgtcttt ataattcttt gatgaaccag atgcatttta ttaaccaatt   6360
ccatatacat ataaatatta atcatatata attaatatca attgggttag caaaacaaat   6420
ctagtctagg tgtgttttgc taattattgg gggatagtgt aaaaagaaat ctacgttctc   6480
aataattcag atagaaaact taataaagtg agataattta catagattgc ttttatcctt   6540
tgatatatgt gaaaccatgc atgatataag gaaaatagat agagaaataa ttttttacat   6600
cgttgaatat gtaaacaatt taattcaaga agctaggaat ataaatattg aggagtttat   6660
gattagagct ctccccggcgc gccagatttg ccttttcaat ttcagaaaga atgctaaccc   6720
acagatggtt agagaggctt acgcagcagg tatcatcaag acgatctacc cgagcaataa   6780
tctccaggaa atcaaatacc ttcccaagaa ggttaaagat gcagtcaaaa gattcaggac   6840
taactgcatc aagaacacag agaaagatat atttctcaag atcagaagta ctattccagt   6900
atggacgatt caaggcttgc ttcacaaacc aaggcaagta atagagattg gagtctctaa   6960
aaaggtagtt cccactgaat caaaggccat ggagtcaaga attcaaatag aggacctaac   7020
agaactcgcc gtaaagactg gcgaacagtt catacagagt ctcttacgac tcaatgacaa   7080
gaagaaaatc ttcgtcaaca tggtggagca cgacacactt gtctactcca aaaatatcaa   7140
agatacagtc tcagaagacc aaagggcaat tgagactttt caacaaaggg taatatccgg   7200
aaacctcctc ggattccatt gcccagctat ctgtcacttt atttgtgaaga tagtggaaaa   7260
ggaaggtggc tcctacaaat gccatcattg cgataaagga aaggccatcg ttgaagatgc   7320
ctctgccgac agtggtccca aagatggacc cccacccacg aggagcatcg tggaaaaaga   7380
agacgttcca accacgtctt caaagcaagt ggattgatgt gatatctcca ctgacgtaag   7440
ggatgacgca caatcccact atccttcgca agacccttcc tctatataag gaagttcatt   7500
tcatttggag agaacacggg ggactcctgc aggatggatc tgcgtctaat tttcggtcca   7560
acttgcacag gaaagacgtc gaccgcgata cgtcttgccc agcagactgg ccttccagtc   7620
cttcgctcg atcgggtcca atgctgtcct caactgtcaa ccggaagcgg acgaccaaca   7680
gtggaagaac tgaaaggaac gacccgtcta taccttgaag atcggcctct ggtgaaggt    7740
atcatcgcag ccaagcaagc tcacgaaagg ctgatcgggg aagtgtacaa ttatgaggcc   7800
cacggcgggc ttattcttga ggaggatcc atctcgttgc tcaggtgcat ggcgcaaagc   7860
agttattgga gtaccgattt tcgttggcat attattcgcc acaagttagc agacgaggag   7920
acattcatga acgcggccaa ggccagagtt aggcagatgt tgccgcctgc tgtaggccca   7980
tctattattc aagagttggt tcatctttgg aatgagcctc ggctgaggcc catactgaaa   8040
gagatcgacg gatatcgata tgccatgtta tttgctagcc agaaccagat cacacccgat   8100
atgctattgc agcttgaccc agatatggag ggtgagttga ttcatggaat cgctcaggag   8160
tatctcatcc atgcgcgccg gcaggagcag gaattccctc cagtgagcgt ggtcgctttc   8220
gaaggattcg aaggtccacc gttcggaatg tgctagctcg agccctagac ttgtccatct   8280
tctggattgg ccaagttaat taatgtatga aataaaagga tgcacacata gtgacatgct   8340
aatcactata atgtgggcat caaagttgtg tgttatgtgt aattactaat tatctgaata   8400
agagaaagag atcatccata tttcttatcc taaatgaatg tcacgtgtct ttataattct   8460
ttgatgaacc agatgcattt tattaaccaa ttccatatac atataaatat taatcatata   8520
taattaatat caattgggtt agcaaaacaa atctagtcta ggtgtgtttt gctaattatt   8580
ggggatagt gcaaaagaa atctacgttc tcaataattc agatagaaaa cttaataaag   8640
tgagataatt tacatagatt gcttttatcc tttgatatat gtgaaaccat gcatgatata   8700
aggaaaatag atagagaaat aatttttttac atcgttgaat atgtaaacaa tttaattcaa   8760
gaagctagga atataaatat tgaggagttt atgattagag ctcagtgttt gatcgccggc   8820
ggtaccgagt gtacttcaag tcagtgggaa atcaataaaa tgattatttt atgaatatat   8880
ttcattgtgc aagtagatag aaattacata tgttacataa cacacgaaat aaacaaaaaa   8940
agacaatcca aaaacaaaca cccccaaaaaa aataatcact ttagataaac tcgtatgagg   9000
agaggcacgt tcagtgactc gacgattccc gagcaaaaaa agtctccccg tcacacatgt   9060
agtgggtgac gcaattatct ttaaagtaat ccttctgttg acttgtcatt gataacatcc   9120
agtcttcgtc aggattgcaa agaattatag aagggatccc accttttatt ttcttctttt   9180
ttccatattt agggttgaca gtgaaatcag actggcaacc tattaattgc ttccacaatg   9240
ggacgaactt gaaggggatg tcgtcgatga tattatggtg ggctgttca tcgtagttgg   9300
tgaaatcgat ggtaccgttc caatagttgt gtcgtccgag acttctagcc caggtggtct   9360
ttccggtacg agttggtccg cagatgtaga ggctggggtg tcggattcca ttccttccat   9420
tgtccttgtt aaatcggcca tccattcaag gtcagattga gcttgttggt atgagacagg   9480
atgtatgtaa gtataagcgt ctatgcttac atggtataga tgggtttccc tccaggagtg   9540
tagatcttcg tggcagcgaa gatcgattc tgtgaaggc gacacatacg gttcaggttg   9600
tggagggaat aatttgttgg ctgaatattc cagccattga agctttgttg cccattcatg   9660
agggaattct tccttgatca tgtcaagata ttcctcctta gacgttgcag tctgaataat   9720
agttctccat cgtgcgtcag atttgcgagg agaaccttta gatctccgga aatctccctct   9780
ggttttaata tctccgtcct ttgatatgta atcaaggact tgtttagagt ttctagctgg   9840
ctggatatta gggtgatttc cttcaaaatc gaaaaagaa gatcccttaa tacaaggttt   9900
tttatcaagc tggagaagag catgatagtg ggtagtgcca tcttgatgaa gctcagaagc   9960
aacaccaagg aagaaaataa gaaaaggtgt gagtttctcc cagagaaact ggaataaatc   10020
atctctttga gatgagcact tgggataggt aaggaaaaca tatttagatt ggagtctgaa   10080
gttcttacta gcagaaggca tgttgttgtg actccgaggg gttgcctcaa actctatctt   10140
ataaccggcg tggaggcatg gaggcagggg tattttggtc attttaatag atagtggaaa   10200
```

```
atgacgtgga atttacttaa agacgaagtc tttgcgacaa ggggggggccc acgccgaatt    10260
taatattacc ggcgtggccc cccccttatcg cgagtgcttt agcacgacgcg gtccagattt    10320
aaaagtagaaa atttcccgcc cactagggtt aaaggtgttc acactataaa agcatatacg    10380
atgtgatggt atttgatgga gcgtatattg tatcaggtat ttccgttgga tacgaattat    10440
tcgtacgacc ctcatagttt aaactatcag tgtttgacag gatatattg cgggtaaacc    10500
taagagaaaa gagcgtttat tagaataacg gatatttaaa agggcgtgaa aaggtttatc    10560
cgttcgtcca tttgtatgtg catgccaacc acagggttcc cctcgggatc aaagtacttt    10620
gatccaaccc ctccgctgct atagtgcagt cggcttctga cgttcagtgc agccgtcttc    10680
tgaaaacgac atgtcgcaca agtcctaagt tacgcgacag gctgccgccc tgcccttttc    10740
ctggcgtttt cttgtcgcgt gttttagtcg cataaagtag aatacttgcg actagaaccg    10800
gagacattac gccatgaaca agagcgccgc cgctggcctg ctgggctatg cccgcgtcag    10860
caccgacgac caggacttga ccaaccaacg ggccgaactg cacgcggccg gctgcaccaa    10920
gctgttttcc gagaagatca ccggcaccag gcgcgaccgc ccggagctgg ccaggatgct    10980
tgaccaccta cgccctggcg acgttgtgac agtgaccagg ctagaccgcc tggcccgcag    11040
cacccgcgac ctactggaca ttgccgagcg catccaggag gccggcgcgg gcctgcgtag    11100
cctggcagag ccgtgggccg acaccaccac gccggccggc cgcatggtgt tgaccgtgtt    11160
cgccggcatt gccgagttcg agcgttccct aatcatcgac cgcacccgga gcgggcgcga    11220
ggccgccaag gcccgaggcg tgaagtttgg cccccgccct accctcaccc cggcacagat    11280
cgcgcacgcc cgcgagctga tcgaccagga aggccgcacc gtgaaagagg cggctgcact    11340
gcttggcgtg catcgctcga ccctgtaccg cgcacttgag cgcagcgagg aagtgacgcc    11400
caccgaggcc aggcggcgcg gtgccttccg tgaggacgca ttgaccgagg ccgacgccct    11460
ggcggccgcc gagaatgaac gccaagagga acaagcatga aaccgcacca ggacggccag    11520
gacgaaccgt ttttcattac cgaagagatc gaggcggaga tgatcgcggc cgggtacgtg    11580
ttcgagccgc ccgcgcacgg ctcaaccgtg cggctgcatg aaatcctggc cggttttgtct    11640
gatgccaagc tggcggcctg gccggccagc ttggccgctg aagaaccgga cgccgccgt    11700
ctaaaaaggt gatgtgtatt tgagtaaaac agcttgcgtc atgcggtcgc tgcgtatatg    11760
atgcgatgag taaataaaca aatacgcaag gggaacgcat gaaggttatc gctgtactta    11820
accagaaagg cgggtcaggc aagacgacca tcgcaaccca tctagccgc gccctgcaac    11880
tcgccggggc cgatgttctg ttagtcgatt ccgatcccca gggcagtgcc cgcgattggg    11940
cggccgtgcg ggaagatcaa ccgctaaccg ttgtcggcat cgaccgcccg acgattgacc    12000
gcgacgtgaa ggccatcggc cggcgcgact tcgtagtgat cgacgagcg ccccaggcgg    12060
cggacttggc tgtgtccgcg atcaaggcag ccgacttcgt gctgattccg gtgcagccaa    12120
gcccttacga catatgggcc accgccgacc tggtggagct ggttaagcag cgcattgagg    12180
tcacggatgg aaggctacaa gcggcctttg tcgtgtcgcg ggcgatcaaa ggcacgcgca    12240
tcggcggtga ggttgccgag gcgctggccg ggtacgagct gcccattctt gagtccgta    12300
tcacggcagcg cgtgagctac ccaggcactg ccgccgccgg cacaaccgtt cttgaatcag    12360
aacccgaggg cgacgctgcc cgcgaggtcc aggcgctggc cgctgaaatt aaatcaaaac    12420
tcatttgagt taatgaggta aagagaaaat gagcaaaagc acaaacacgc taagtgccgg    12480
ccgtccgagc gcacgcagca gcaaggctgc aacgttggcc agcctggcag acacgccagtc    12540
catgaagcgg gtcaactttc agttgccggc ggaggatcac accaagctga agatgtacgc    12600
ggtacgccaa ggcaagacca ttaccgagct gctatctgaa tacatcgcgc agctaccaga    12660
gtaaatgagc aaatgaataa atgagtagat gaatttttagc ggctaaagga ggcggcatgg    12720
aaaatcaaga acaaccaggc accgacgccg tggaatgccc catgtgtgga ggaacgggcg    12780
gttggccagg cgtaagcggc tgggttgtct gccggcctg caatggcact ggaaccccca    12840
agcccgagga atcggcgtga cggtcgcaaa ccatccggcc cggtacaaat cggcgcggcg    12900
ctgggtgatg acctggtgga gaagttgaag gccgcgcagg ccgcccagcg gcaacgcatc    12960
gaggcagaag cacgccccgg tgaatcgtgg caagcggccg ctgatcgaat cgcaaagaa    13020
tcccggcaac cgccggcagc cggtgcgccg tcgattagga agccgcccaa gggcgacgag    13080
caaccagatt ttttcgttcc gatgctctat gacgtgggca cccgcgatag tcgcagcatc    13140
atggacgtgg ccgttttccg tctgtcgaag cgtgaccgac gagctggcga ggtgatccgc    13200
tacgacttc cagacgggca cgtagaggtt tccgcagggc cggccgcat ggccagtgtg    13260
tgggattacg acctggtact gatgcgcgtt tccatctaa ccgaatccat gaaccgatac    13320
cgggaaggga agggagacaa gccggccgc gtgttccgtc cacacgttgc ggacgtactc    13380
aagttctgcc ggcgagccga tggcggaaag cagaaagacg acctggtaga aacctgcatt    13440
cggttaaaca ccacgcacgt tgccatgcag cgtacgaaga aggccaagaa cggccgcctg    13500
gtgacggtat ccgagggtga agccttgatt agccgctaca agatcgtaaa gagcgaaacc    13560
gggcggccgg agtacatcga gatcgagcta gctgattgga tgtaccgcga gatcacagaa    13620
ggcaagaacc cggacgtgct gacggttcac ccgattact ttttgatcga tcccggcatc    13680
ggccgttttc tctaccgcct ggcacgccgc gccgcaggca aggcagaagc cagatggttg    13740
ttcaagacga tctacgaacg cagtggcagc gccggagagt tcaagaagtt ctgtttcacc    13800
gtgcgcaagc tgatcgggtc aaatgacctg ccggagtacg atttgaagga ggaggcgggg    13860
caggctggcc cgatcctagt catgcgctac cgcaacctga tcgagggcga agcatccgcc    13920
ggttcctaat gtacggagca gatgctaggg caaattgccc tagcagggga aaaaggtcga    13980
aaaggcctct ttcctgtgga tagcacgtac attgggaacc caaagccgta cattgggaac    14040
cggaacccgt acattgggaa cccaaagccg tacattggga accggtcaca catgtaagtg    14100
actgatataa aagagaaaaa aggcgatttt tccgcctaaa actctttaaa acttattaaa    14160
actcttaaaa cccgcctggc ctgtgcataa ctgtctggcc agcgcacagc cgaagagctg    14220
caaaaagcgc ctacccttcg gtcgctcgc tccctacgcc ccgccgcttc gcgtcggcct    14280
atcgcggccg ctggccgctc aaaaatggct ggcctacggc caggcaatct accagggcgc    14340
ggacaagccg cgccgtcgcc actcgaccgc cggcgcccac atcaaggcac cctgcctcgc    14400
gcgtttcggt gatgacggtg aaaacctctg acacatgcag ctcccggaaa cggtcacagc    14460
ttgtctgtaa gcggatgccg ggagcagaca agcccgtcag ggcgcgtcag cgggtgttgg    14520
cgggtgtcgg ggcgcagcca tgacccagtc acgtagcgat agcggagtgt atactggctt    14580
aactatgcgg catcagagca gattgtactg agagtgcacc atatgcggtg tgaaataccg    14640
cacagatgcg taaggagaaa ataccgcatc aggcgctctt ccgcttcctc gctcactgac    14700
tcgctgcgct cggtcgttcg gctgcggcga gcggtatcag ctcactcaaa ggcggtaata    14760
cggttatcca cagaatcagg ggataacgca ggaaagaaca tgtgagcaaa aggccagcaa    14820
aaggccagga accgtaaaaa ggccgcgttg ctggcgtttt tccataggct ccgcccccct    14880
gacgagcatc acaaaaatcg acgctcaagt cagaggtggc gaaacccgac aggactataa    14940
```

```
agataccagg cgtttccccc tggaagctcc ctcgtgcgct ctcctgttcc gaccctgccg   15000
cttaccggat acctgtccgc ctttctccct tcgggaagcg tggcgctttc tcatagctca   15060
cgctgtaggc atctcagttc ggtgtaggtc gttcgctcca agctgggctg tgtgcacgaa   15120
cccccgttc agcccgaccg ctgcgcctta tccgtaact atcgtcttga gtccaacccg    15180
gtaagacacg acttatcgcc actggcagca gccactgtta acaggattag cagagcgagg   15240
tatgtaggcg gtgctacaga gttcttgaag tggtggccta actacggcta cactagaagg   15300
acagtatttg gtatctgcgc tctgctgaag ccagttacct tcggaaaaag agttggtagc   15360
tcttgatccg gcaaacaaac caccgctggt agcggtggtt ttttgtttg caagcagcag    15420
attacgcgca gaaaaaaagg atctcaagaa gatcctttga tcttttctac ggggtctgac   15480
gctcagtgga acgaaaactc acgttaaggg attttggtca tgcattctag gtactaaaac   15540
aattcatcca gtaaaatata atatttatt ttctcccaat caggcttgat ccccagtaag    15600
tcaaaaaata gctcgacata ctgttcttcc ccgatatcct ccctgatcga ccggacgcag   15660
aaggcaatgt cataccactt gtccgccctg ccgcttctcc caagatcaat aaagccactt   15720
actttgccat cttttcacaaa gatgttgctg tctcccaggt cgccgtggga aaagacaagt   15780
tcctcttcgg gcttttccgt cttttaaaaa tcatacagct cgcgcggatc tttaaatgga   15840
gtgtcttctt cccagttttc gcaatccaca tcggccagat cgttattcag taagtaatcc   15900
aattcggcta agcggctgtc taagctattc gtataggac aatccgatat gtcgatggag    15960
tgaaagagcc tgatgcactc cgcata                                         15986
```

SEQ ID NO: 96            moltype = DNA   length = 13942
FEATURE                  Location/Qualifiers
source                   1..13942
                         mol_type = other DNA
                         organism = synthetic construct
SEQUENCE: 96

```
cggtaatacg gttatccaca gaatcagggg ataacgcagg aaagaacatg tgagcaaaag   60
gccagcaaaa ggccaggaac cgtaaaaagg ccgcgttgct ggcgttttc cataggctcc    120
gccccctga cgagcatcac aaaaatcgac gctcaagtca gaggtggcga acccgacag     180
gactataaag ataccaggcg tttccccctg gaagctccct cgtgcgctct cctgttccga   240
cctgccgct taccggatac ctgtccgcct ttctccctt cgggaagcgt ggcgctttct    300
atagctcacg ctgtaggtat ctcagttcgg tgtaggtcgt tcgctccaag ctgggctgtg   360
tgcacgaacc ccccgttcag cccgaccgct gcgccttatc cggtaactat cgtcttgagt   420
ccaacccggt aagacacgac ttatcgccac tggcagcagc cactggtaac aggattagca   480
gagcgaggta tgtaggcggt gctacagagt tcttgaagtg gtggcctaac tacggctaca   540
ctagaaggac agtatttggt atctgcgctc tgctgaagcc agttaccttc ggaaaaagag   600
ttggtagctc ttgatccggc aaacaaacca ccgctggtag cggtggtttt tttgtttgca   660
agcagcagat tacgcgcaga aaaaaggat ctcaagaaga tcctttgatc ttttctacgg    720
ggtctgacgc tcagtggaac gaaaactcac gttaaggat tttggtcatg cattctaggt    780
actaaacaa ttcatccagt aaaatataat atttattt ctcccaatca ggcttgatcc     840
ccagtaagtc aaaaaatagc tcgacatact gttcttcccc gatatcctcc ctgatcgacc   900
ggacgcagaa ggcaatgtca taccacttgt ccgccctgcc gcttctccca agatcaataa   960
agccacttac tttgccatct ttcacaaaga tgttgctgtc tcccaggtcg ccgtgggaaa   1020
agacaagttc ctcttcgggc ttttccgtct taaaaaatc atacagctcg cgcggatctt   1080
taatggagt gtcttcttcc agttttcgc aatccacatc ggccagatcg ttattcagta    1140
agtaatccaa ttcggctaag cggctgtcta agctattcgt ataggacaa tccgatatgt    1200
cgatggagtg aaagagcctg atgcactccg catacagctc gataatcttt tcagggcttt   1260
gttcatcttc atactcttcc gagcaaagga cgccatcggc ctcactcatg agcagattgc   1320
tccagccatc atgccgttca agtgcagga cctttggaac aggcagcttt ccttccagcc   1380
atagcatcat gtccttttcc cgttccacat cataggtggt ccctttatac cggctgtccg   1440
tcattttaa atataggttt tcattttctc ccaccagctt atataccta gcaggagaca    1500
ttccttccgt atcttttacg cagcggtatt tttttgatcg tttttcaat tccggtgata   1560
ttctcatttt agccatttat tatttccttc ctcttttcta cagtatttaa agataccca    1620
agaagctaat tataacaaga cgaactccaa ttcactgttc cttgcattct aaaaccttaa   1680
ataccagaaa acagctttt caagttgtt ttcaaagttg cgtataaca tagtatcgac     1740
ggagccgatt ttgaaaccgc ggtgatcaca ggcagcaacg ctctgtcatc gttacaatca   1800
acatgctacc ctccgcgaga tcatccgtgt ttcaaacccg gcagcttagt tgccgttctt   1860
ccgaatagca tcggtaacat gagcaaagtc tgccgcctta aacggctct cccgctgacg    1920
ccgtcccgga ctgatgggct gcctgtatcg agtggtgatt ttgtgccgag ctgccggtcg   1980
gggagctgtt ggctggctgg tggcaggata tattgtggtg taaacaaatt gacgcttaga   2040
caacttaata acacattgcg gacgttttta atgtagagcat caaagtttaa cgcgttagca   2100
gaaggcatgt tgttgtgact ccgaggggtt gcctcaaact ctatcttata accggcgtgg   2160
aggcatggag gcagggtat tttggtcatt taatagata gtgaaaatg acgtggaatt     2220
tacttaaaga cgaagtcttt gcgacaaggg ggggcccacg ccgaatttaa tattaccggc   2280
gtggcccccc cttatcgcga gtgctttagc acgagcggtc cagattaaga gtagaaaatt   2340
tcccgcccac tagggttaaa ggtgttcaca ctataaagc atatacgatg tgatggtatt    2400
tgatgccagcg tatattgtat caggtatttc cgttggatac gaattattcg tacgaccctc   2460
ggtaccgatc ggcgcgcgcg ccgcacaga gatttaaata gctccggtga cggacggcgc    2520
gccctatgtc gagctgcagg tcaacggatc aggatattct tgtttaagat gttgaactct   2580
atggagtttt gtatgaactg atgatctagg accggataag ttccctatct catgcgaac    2640
ttattcaaag aatgttttgt gtatcattct tgttacattg ttattaatga aaaaatatta   2700
ttggtcattg gactgaacac gagtgttaaa tatggaccag gccccaaata agatccattg   2760
atatatgaat taaataacaa gaataatcg agtcaccaaa ccacttgcct ttttaacga    2820
gacttgttca ccaacttgat acaaagtca ttatcctatg caaatcaata atcatacaaa    2880
aatactaaaa aacactaaaa aattaaaaga aatggataat ttcacatat gttatacgat   2940
aaagaagtta ctttttccaag aaattcactg attttataag cccacttgca ttagataaat   3000
ggcaaaaaaa aacaaaaagg aaaagaaata agcacgaag aattctagaa aatacgaat     3060
acgcttcaat gcagtgggac ccacggttca attattgcca attttcagct ccaccgtata   3120
tttaaaaaat aaaacgataa tgctaaaaaa atataaatcg taacgatcgt taatctcaa    3180
cggctggatc ttatgacgac cgttagaaat tgtggttgtc gacgagtcag taataaacgg   3240
```

```
cgtcaaagtg gttgcagccg gcacacacga gtcgtgttta tcaactcaaa gcacaaatac   3300
ttttcctcaa cctaaaaata aggcaattag ccaaaaacaa ctttgcgtgt aaacaacgct   3360
caatacacgt gtcattttat tattagctat tgcttcaccg ccttagcttt ctcgtgacct   3420
agtcgtcctc gtcttttctt cttcttcttc tataaaacaa tacccaaaga gctcttcttc   3480
ttcacaattc agatttcaat ttctcaaaat cttaaaaact ttctctcaat tctctctacc   3540
gtgatcaagg taaatttctg tgttccttat tctctcaaaa tcttcgattt tgttttcgtt   3600
cgatcccaat ttcgtatatg ttctttggtt tagattctgt taatcttaga tcgaacacga   3660
ttttctgggt ttgatcgtta gatatctct taattctcga ttagggtttc atagatatca    3720
tccgatttgt tcaaataatt tgagttttgt cgaataatta ctcttcgatt tgtgatttct   3780
atctagatct ggtgttagtt tctagtttgt gcgatcgaat ttgtcgatta atctgagttt   3840
ttctgattaa caggcctgca ggatggaaga cgccaaaaac ataaagaaag gcccggcgcc   3900
attctatccg ctggaagatg gaaccgctgg agagcaactg cataaggcta tgaagagata   3960
cgccctggtt cctggaacaa ttgcttttac agatgcacat atcgaggtgg acatcactta   4020
cgctgagtac ttcgaaatgt ccgttcggtt ggcagaagct atgaaacgat atgggctgaa   4080
tacaaatcac agaatcgtcg tatgcagtga aaactctctt caattcttta tgccggtgtt   4140
gggcgcgtta tttatcggag ttgcagttgc ccccgcgaac gacatttata tgaacgtga    4200
attgctcaac agtatgggca tttcgcagcc taccgtggtg ttcgttttcca aaaaggggtt   4260
gcaaaaaatt ttgaacgtgc aaaaaaagct cccaatcatc caaaaaatta ttatcatgga   4320
ttctaaaacg gattaccagg gatttcagtc gatgtacacg ttcgtcacat ctcatctacc   4380
tcccggtttt aatgaatacg attttgtgcc agagtcctcc gatagggaca agacaattgc   4440
actgatcatg aactcctctg gatctactgg tctgcctaaa ggtgtcgctc tgcctcatag   4500
aactgcctgc gtgagattct cgcatgccag agatcctatt tttggcaatc aaatcattcc   4560
ggatactgcg atttaagtg ttgttccatt ccatcacggt tttggaatgt ttactacact    4620
cggatatttg atatgtggat ttcgagtcgt cttaatgtat agatttgaag aagagctgtt   4680
tctgaggagc cttcaggatt acaagattca aagtgcgctg ctggtgccaa ccctattctc   4740
cttcttcgcc aaaagcactc tgattgacaa atacgatttt tctaatttac acgaaattgc   4800
ttctggtggc gctccctct caaggaagt cggggaagcg gttgccaaga ggttccatct    4860
gccaggtatc aggcaaggat atgggctcac tgagactaca tcagctattc tgattacacc   4920
cgaggggat gataaaccgg gcgcggtcgg taaagttgtt ccatttttttg aagcgaaggt   4980
tgtggatctg gataccggga aaacgctggg cgttaatcaa agaggcgaac tgtgtgtgag   5040
aggtcctatg attatgtccg gttatgtaaa caatccggaa gcgaccaacg ccttgattga   5100
caaggatgga tggctacatt ctggagacat agcttactgg gacgaagacg aacacttctt   5160
catcgttgac cgcctgaagt ctctgattaa gtacaaaggc tatcaggtgg ctcccgctga   5220
attggaatcc atcttgctcc aacacccaa catctcgac gctggtgtcg caggtcttcc    5280
cgacgatgac gccggtgaac ttcccgccgc cgttgttgtt ttggagcacg gaaagacgat   5340
gacgggaaaaa gagatcgtgg attacgtcgc cagtcaagta acaaccgcga aaaagttgcg   5400
cggaggagtt gtgtttgtgg acgaagtacc gaaaggtctt accggaaaac tcgacgcaag   5460
aaaaatcaga gagatcctca taaaggccaa gaagggcgga aagtcgccg tgtgactcga    5520
ggttcgagta ttatggcatt gggaaaactg ttttcttgt accatttgtt gtgcttgtaa    5580
tttactgtgt tttttattcg gttttcgcta tcgaactgtg aaatgaaat ggatggagaa    5640
gagttaatga atgatatggt ccttttgttc attctcaaat taatattatt tgttttttct   5700
cttatttgtt gtgtgttgaa tttgaaatta taagagatat gcaaacattt tgttttgagt   5760
aaaaatgtgt caaatcgtgg cctctaatga ccgaagttaa tatgaggagt aaaacactta   5820
tagttgtgtt agagctcccg gggcgcgccg atatcgagct ctcccggcgc gccagatttg   5880
ccttttcaat ttcagaaaga atgctaaccc acagatggtt agagaggctt acgcagcagg   5940
tatcatcaag acgatctacc cgagcaataa tctccaggaa atcaaatacc ttcccaagaa   6000
ggttaaagat gcagtcaaaa gattcaggac taactgcatc agaacacag agaaagatat    6060
atttctcaag atcagaagta ctattccagt atggacgatt caaggcttgc ttcacaaacc   6120
aaggcaagta atagagattg gagtctctaa aaggtagtt cccactgaat caaaggccat     6180
ggagtcaaag attcaaatag aggacctaac agaactcgcc gtaaagactg gcgaacagtt   6240
catacagagt ctcttacgac tcaatgacaa gaagaaaatc ttcgtcaaca tggtggagag   6300
cgacacactt gtctactcca aaaatatcaa agatacagtc tcagaagacc aaagggcaat   6360
tgagactttt caacaaaggg taatatccgg aaacctcctc ggattccatt gcccagctat   6420
ctgtcacttt attgtgaaga tagtggaaaa ggaaggtggc tcctacaaat gccatcattg   6480
cgataaagga aaggccatcg ttgaagatgc ctctgccgac agtggtccca aagatggacc   6540
cccacccacg aggagcatcg tggaaaaaga agacgttcca accacgtctt caaagcaagt   6600
ggattgatgt gatatctcca ctgacgtaag ggatgacgca caatcccact atccttcgca   6660
agacccttcc tctatataag gaagttcatt tcatttggag agaacacggg ggactcctgc   6720
aggatgatc tgcgtctaat tttcggtcca acttgcacag gaaagacgtc gaccgcgata   6780
cgtcttgccc agcagactgg ccttccagtc ctttcgctcg atcgggtcca atgctgtcct   6840
caactgtcaa ccggaagcgg acgaccaaca gtgaagaac tgaaaggaac gacccgtcta   6900
taccttgaag atcggcctct ggtgaagggt atcatcgcag ccaagcaagc tcacgaaagg   6960
ctgatcgggg aagtgtacaa ttatgaggcc cacgcgggc ttattcttga gggaggatct    7020
atctcgttgc tcaggtgcat ggcgcaaagc agttattgga gtaccgattt tcgttggcat   7080
attattcgcc acaagttagc agacgaggag acattcatga acgcggccaa ggccagagtt   7140
aggcagatgt tgcgccctgc tgtaggccca tctattattc aagagttggt tcatctttgg   7200
aatgagcctc ggctgaggcc catactgaaa agatcgacg gatatcgata tgccatgtta   7260
tttgctagcc agaaccagat cacacccgat atgcttattgc agcttgaccc agatatggag   7320
ggtgagttga ttcatggaat cgctcaggag tatctcatcc atcgcgccg gcaggagcag   7380
gaattccctc cagtgagcgt ggtcgctttc gaaggattcg aagtccacc gttcggaatg    7440
tgctagctcg agcccctagac ttgtccatct tctggattgg ccaagttaat taatgtatga   7500
aataaaagga tgcacacata gtgacatgct aatcactata atgtgggcat caaagttgtg   7560
tgttatgtgt aattactaat tatctgaata agagaaagag atcatccata tttcttatcc   7620
taaatgaatg tcacgtgtct ttataattct ttgatgaacc tatgaatgag tattaaccaa   7680
ttccatatac atataaatat taatcatata taattaatat caattgggtt agcaaaacaa   7740
atctagtcta ggtgtgtttt gctaattatt ggggatagt gcaaaagaa atctacgttc    7800
tcaataattc agatagaaaa cttaataaag tgagataatt tacatagatt gcttttatcc   7860
tttgatatat gtgaaaccat gcatgatata aggaaaatag atagagaaat aatttttttac   7920
atcgttgaat atgtaaacaa tttaattcaa gaagctagga atataaatat tgaggagttt   7980
```

```
atgattagag ctcagtgttt gatcgccggc ggtaccgagt gtacttcaag tcagtgggaa    8040
atcaataaaa tgattatttt atgaatatat ttcattgtgc aagtagatag aaattacata    8100
tgttacataa cacacgaaat aaacaaaaaa agacaatcca aaaacaaaca ccccaaaaaa    8160
aataatcact ttagataaac tcgtatgagg agaggcacgt tcagtgactc gacgattccc    8220
gagcaaaaaa agtctccccg tcacacatgt agtgggtgac gcaattatct ttaaagtaat    8280
ccttctgttg acttgtcatt gataacatcc agtcttcgtc aggattgcaa agaattatag    8340
aagggatccc accttttatt ttcttctttt ttccatattt agggttgaca gtgaaatcag    8400
actggcaacc tattaattgc ttccacaatg ggacgaactt gaaggggatg tcgtcgatga    8460
tattataggt ggcgtgttca tcgtagttgg tgaaatcgat ggtaccgttc caatagttgt    8520
gtcgtccgag acttctagcc caggtggtct ttccggtacg agttggtccg cagatgtaga    8580
ggctggggtg tcggattcca ttccttccat tgtccttgtt aaatcggcca tccattcaag    8640
gtcagattga gcttgttggt atgagacagg atgtatgtaa gtataagcgt ctatgcttac    8700
atggtataga tgggtttccc tccaggagtg tagatcttcg tggcagcgaa gatctgattc    8760
tgtgaagggc gacacatacg gttcaggttg tggagggaat aatttgttgg ctgaatattc    8820
cagccattga agctttgttg cccattcatg agggaattct tccttgatca tgtcaagata    8880
ttcctcctta gacgttgcag tctggataat agttctccat cgtgcgtcag atttgcgagg    8940
agaaaccttg tgatctcgga aatctcctct ggttttaata tctccgtcct ttgatatgta    9000
atcaaggact tgtttagagt ttctagctgg ctggatatta gggtgatttc cttcaaaatc    9060
gaaaaaagaa ggatccctaa tacaaggttt tttatcaagc tggagaagag catgatagtg    9120
ggtagtgcca tcttgatgaa gctcagaagc aacaccaagg aagaaaataa gaaaaggtgt    9180
gagtttctcc cagagaaact ggaataaatc atctctttga gatgagcact tgggataggt    9240
aaggaaaaca tatttagatt ggagtctgaa gttcttacta cagaaggca tgttgttgtg    9300
actccgaggg gttgcctcaa actctatctt ataaccggcg tggaggcatg gaggcagggg    9360
tattttggtc attttaatag atagtggaaa atgacgtgga atttacttaa agacgaagtc    9420
tttgcgacaa ggggggggccc acgccgaatt taatattacc ggcgtggccc cccctttatcg    9480
cgagtgcttt agcacgagcg gtccagattt aaagtagaaa atttcccgcc cactaggtt    9540
aaaggtgttc acactataaa agcatatacg atgtgatggt atttgatgga gcgtatattg    9600
tatcaggtat ttccgttgga tacgaattat tcgtacgacc ctcatagttt aaactatcag    9660
tgtttgacag gatatattgg cgggtaaacc taagagaaaa gagcgtttat tagaataacg    9720
gatattttaaa agggcgtgaa aagttttatc cgttcgttgt tttgtatgtg catgccaacc    9780
acaggggttcc cctcgggatc aaagtacttt gatccaaccc ctccgctgct atagtgcagt    9840
cggcttctga cgttcagtgc agccgtcttc tgaaaacgac atgtcgcaca agtcctaagt    9900
tacgcgacag gctgccgccc tgcccttttc ctggcgtttt cttgtcgcgt gttttagtcg    9960
cataaagtag aatacttgcg actagaaccg gagacattac gccatgaaca agagcgcgtc   10020
cgctggcctg ctgggctatg cccgcgtcag caccgacgac caggacttga ccaaccaacg   10080
ggccgaactg cacgcggccg gctgcaccaa gctgttttcc gagaagatca ccggcaccag   10140
gcgcgaccgc ccggagctgg ccaggatgct tgaccaccta cgccctggcg acgttgtgac   10200
agtgaccagg ctagaccgcc tggcccgcag cacccgcgac ctactggaca ttgccgagcg   10260
catccggag gccggagcgg gcctgcgtag cctggcagga ccgtgggccg acaccaccag   10320
gccggccggc cgcatggtgt tgaccgtgtt cgcggcatt gccgagttcg agcgttccct   10380
aatcatcgac cgcacccgga gcgggcgcga ggccgccaag gcccgaggcg tgaagtttgg   10440
cccccgccct accctcaccc cggcacagat cgcgcacgcc cgcgagctga tcgaccagga   10500
aggccgcacc gtgaaagagg cggctgcact gcttggcgtg catcgctgga ccctgtaccg   10560
cgcacttgag cgcagcgagg aagtgacgcc caccgaggcc aggcggcgcg gtgccttccg   10620
tgaggacgca ttgaccgagg ccgaccgcct ggcggccgcc gagaatgaac gccaagagga   10680
acaagcatga aaccgcacca ggacggccag gacgaaccgt ttttcattac cgaagagatc   10740
gaggcggaga tgatcgcggc cgggtacgtg ttcgagccgc ccgcgcacgg ctcaaccgtg   10800
cggctgcatg aaatcctggc cggtttgtct gatgccaagc tggcggcctg gccggccagc   10860
ttggccgctg aagaaaccga gcgccgccgt ctaaaaaggt gatgtgtatt tgagtaaaac   10920
agcttgcgtc atgcggtcgc tgcgtatatg atgcgatgag taaataaaca aatacgcaag   10980
gggaacgcat gaaggttatc gctgtactta accagaaagg cgggtcaggc aagacgacca   11040
tcgcaaccca tctagcccgc gccctgcaac tcgccggggc cgatgttctg ttagtcgatt   11100
ccgatcccca gggcagtgcc cgcgattggg cggccgtgcg gaagatcaa ccgctaaccg   11160
ttgtcggcat cgaccgcccg acgattgacc gcgacgtgaa ggccatcggc cggcgcgact   11220
tcgtagtgat cgacggagcc cccaggcgg cggcttggc tgtgtccgcg atcaaggcag   11280
ccgacttcgt gctgattccg gtgcagccaa gcccttacga catatgggcc accgccgacc   11340
tggtggagct ggttaagcag cgcattgagg tcacggatgg aaggctacaa gcggcctttg   11400
tcgtgtcgcg ggcgatcaaa ggcacgcgca tcggcggtga ggttgccgag gcgctggccg   11460
ggtacgagct gcccattctt gagtcccgta tcacgcagcg cgtgagctac ccaggcactg   11520
ccgccgccgg cacaaccgtt cttgaatcag aacccgcgg cgacgctgcc cgcgaggtcc   11580
aggcgctggc cgctgaaatt aaatcaaaac tcatttgagt taatgaggta aagagaaaat   11640
gagcaaaagc acaaacacgc taagtgccgg ccgtccgagc gcacgcagca gcaaggctgc   11700
aacgttggcc agcctggcag acacgccagc catgaagcgg gtcaactttc agttgccggc   11760
ggaggatcac accaagctga agatgtacgc ggtacgccaa ggcaagacca ttaccgagct   11820
gctatctgaa tacatcgcgc agctaccaga gtaaatgagc aaatgaataa atgagtagat   11880
gaattttagc ggctaaagga ggcggcatgg aaaatcaaga acaaccaggc accgacgccg   11940
tggaatgccc catgtgtgga ggaacgggcg gttggccagg cgtaagcggc tgggttgtct   12000
gccggccctg caatggcact ggaaccccca agcccgagga atcgcgtga cggtcgcaaa   12060
ccatccgccc cggtacaaat cggcgcggcg ctgggtgatg acctggtgga agttgaag   12120
gccgcgcagg ccgcccagcg gcaacgcatc gaggcagaag cacgccccgg tgaatcgtgg   12180
caagcggccg ctgatcgaat ccgcaaagaa tcccggcaac cgccgcagc cggtgcgccg   12240
tcgattagga agccgcccaa gggcgacgag caaccagatt ttttcgttcc gatgctctat   12300
gacgtgggca cccgcgatag tcgcagcatc atggacgtgg ccgttttccg tctgtcgaag   12360
cgtgaccgac gagctggcga ggtgatccgc tacgagcttc cagacgggca cgtagaggtt   12420
tccgcagggc cggccggcat ggccagtgtg tgggattacg acctggtact gatgcgggtt   12480
tcccatctaa ccgaatccat gaaccgatac cggaaggga agggagacaa gcccggccgc   12540
gtgttccgtc cacacgttgc ggacgtactc aagttctgcc ggcgagccga tggcggaaag   12600
cagaaagacg acctggtaga aacctgcatt cggttaaaca ccacgcacgt tgccatgcag   12660
cgtacgaaga aggccaagaa cggccgcctg gtgacggtat ccgagggtga agccttgatt   12720
```

-continued

```
agccgctaca agatcgtaaa gagcgaaacc gggcggccgg agtacatcga gatcgagcta  12780
gctgattgga tgtaccgcga gatcacagaa ggcaagaacc cggacgtgct gacggttcac  12840
cccgattact ttttgatcga tcccggcatc ggccgttttc tctaccgcct ggcacgccgc  12900
gccgcaggca aggcagaagc cagatggttg ttcaagacga tctacgaacg cagtggcagc  12960
gccggagagt tcaagaagtt ctgtttcacc gtgcgcaagc tgatcgggtc aaatgacctg  13020
ccggagtacg atttgaagga ggaggcgggg caggctggcc cgatcctagt catgcgctac  13080
cgcaacctga tcgagggcga agcatccgcc ggttcctaat gtacgagca gatgctaggg  13140
caaattgccc tagcagggga aaaaggtcga aaaggcctct ttcctgtgga tagcacgtac  13200
attgggaacc caaagccgta cattgggaac cggaacccgt acattgggaa cccaaagccg  13260
tacattggga accggtcaca catgtaagtg actgatataa aagagaaaaa aggcgatttt  13320
tccgcctaaa actctttaaa acttattaaa actcttaaaa cccgcctggc ctgtgcataa  13380
ctgtctggcc agcgcacagc cgaagagctg caaaaagcgc ctaccctctcg gtcgctgcgc  13440
tccctacgcc ccgccgcttc gcgtcggcct atcgcggccg ctggccgctc aaaaatggct  13500
ggcctacggc caggcaatct accagggcgc ggacaagccg cgccgtcgcc actcgaccgc  13560
cggcgcccac atcaaggcac cctgcctcgc gcgtttcggt gatgacggtg aaaacctctg  13620
acacatgcag ctcccggaaa cggtcacagc ttgtctgtaa gcggatgccg ggagcagaca  13680
agcccgtcag ggcgcgtcag cgggtgttgg cgggtgtcgg ggcgcagcca tgacccagtc  13740
acgtagcgat agcggagtgt atactggctt aactatgcgg catcagagca gattgtactg  13800
agagtgcacc atatgcggtg tgaaataccg cacagatgcg taaggagaaa ataccgcatc  13860
aggcgctctt ccgcttcctc gctcactgac tcgctgcgct cggtcgttcg gctgcggcga  13920
gcggtatcag ctcactcaaa gg                                          13942

SEQ ID NO: 97           moltype = DNA  length = 11836
FEATURE                 Location/Qualifiers
source                  1..11836
                        mol_type = other DNA
                        organism = synthetic construct
SEQUENCE: 97
tcgaggcaga agcacgcccc ggtgaatcgt ggcaagcggc cgctgatcga atccgcaaag   60
aatcccggca accgccggca gccggtgcgc cgtcgattag gaagccgccc aagggcgacg  120
agcaaccaga ttttttcgtt ccgatgctct atgacgtggg cacccgcgat agtcgcagca  180
tcatggacgt ggccgttttc cgtctgtcga agcgtgaccg acgagctggc gaggtgatcc  240
gctacgagct tccagacggg cacgtagagg ttttccgcag gccggccggc atggccagtg  300
tgtgggatta cgacctggta ctgatggcgg tttcccatct aaccgaatcc atgaaccgat  360
accgggaagg gaagggagac aagcccggcc gcgtgttccg tccacacgtt gcggacgtac  420
tcaagttctg ccggcgagcc gatggcgaa agcagaaaga cgacctggta gaaacctgca  480
ttcgttaaaa caccacgcac gttgccatgc agcgtacgaa gaaggccaag aacgccgcc   540
tggtgacggt atccgagggt gaagccttga ttagccgcta caagatcgta aagagcgaaa  600
ccggggcggcc ggagtacatc gagatcgagc tagctgattg gatgtaccgc gagatcacag  660
aaggcaagaa cccggacgtg ctgacggttc accccgatta cttttttgatc gatcccggca  720
tcggccgttt tctctaccgc ctggcacgcc gcgccgcagg caaggcagaa gccagatggt  780
tgttcaagac gatctacgaa cgcagtggca gcgccggaga gttcaagaag ttctgtttca  840
ccgtgcgcaa gctgatcggg tcaaatgacc tgccggaata cgatttgaag gaggaggcgg  900
ggcaggctgg cccgatccta gtcatgcgct accgcaacct gatcgagggc aagcatccg   960
ccggttccta atgtacgag cagatgctag ggcaaattgc cctagcaggg aaaaaggtc   1020
gaaaaggcct ctttcctgtg gatagcacgt acattgggaa cccaaagccg tacattggga  1080
accggaacccaaagc cgtacattgg gaaccggtca cacatgtaag                   1140
tgactgatat aaaagagaaa aaaggcgatt tttccgccta aaactcttta aaacttatta  1200
aaactcttaa aacccgcctg gcctgtgcat aactgtctgg ccagcgcaca gccgaagagc  1260
tgcaaaaagc gcctaccctt cggtcgctgc gctcccctacg ccccgccgct tcgcgtcggc  1320
ctatcgcggc cgctggccgc tcaaaaatgg ctggcctacg gccaggcaat ctaccagggc  1380
gcggacaagc cgcgccgtcg ccactcgacc gccggcgccc acatcaaggc acctgcctc  1440
gcgcgtttcg gtgatgacgg tgaaaacctc tgacacatgc agctcccgga aacggtcaca  1500
gcttgtctgt aagcggatgc cgggagcaga caagcccgtc agggcgcgtc agcgggtgtt  1560
ggcgggtgtc ggggcgcagc catgacccag tcacgtagcg atagcggagt gtatactggc  1620
ttaactatgc ggcatcagag cagattgtac tgagagtgca ccatatgcgg tgtgaaatac  1680
cgcacagatg cgtaaggaga aaataccgca tcaggcgctc ttccgcttcc tcgctcactg  1740
actcgctgcg ctcggtcgtt cggctgcggc gagcggtatc agctcactca aaggcggtaa  1800
tacggttatc cacagaatca ggggataacg caggaaagaa catgtgagca aaaggccagc  1860
aaaaggccag gaaccgtaaa aaggccgcgt tgctggcgtt tttccatagg ctccgccccc  1920
ctgacgagca tcacaaaaat cgacgctcaa gtcagaggtg gcgaaacccg acaggactat  1980
aaagatacca ggcgtttccc cctggaagct ccctcgtgcg ctctcctgtt ccgaccctgc  2040
cgcttaccgg atacctgtcc gcctttctcc cttcgggaag cgtggcgctt tctcatagct  2100
cacgctgtag gtatctcagt tcggtgtagg tcgttcgctc caagctgggc tgtgtgcacg  2160
aaccccccgt tcagcccgac cgctgcgcct tatccggtaa ctatcgtctt gagtccaacc  2220
cggtaagaca cgacttatcg ccactggcag cagccactgg taacaggatt agcagagcga  2280
ggtatgtagg cggtgctaca gagttcttga agtggtggcc taactacggc tacactagaa  2340
ggacagtatt tggtatctgc gctctgctga agccagttac cttcggaaaa agagttggta  2400
gctcttgatc cggcaaacaa accaccgctg gtagcggtgg tttttttgtt tgcaagcagc  2460
agattacgcg cagaaaaaaa ggatctcaag aagatccttt gatcttttct acggggtctg  2520
acgctcagtg gaacgaaaac tcacgttaag ggattttggt catgcattct aggtactaaa  2580
acaattcatc cagtaaaata taatatttta ttttctccca atcaggcttg atccccagta  2640
agtcaaaaaa tagctcgaca tactgttctt ccccgatatc ctccctgatc gaccggacgc  2700
agaaggcaat gtcataccac ttgtccgccc tgccgcttct cccaagatca ataagcaac  2760
ttactttgcc atctttcaca aagatgttgc tgtctcccag gtcgccgtgg gaaaagacaa  2820
gttcctcttc gggcttttcc gtctttaaaa aatcatacag ctcgcgcgga tctttaaatg  2880
gagtgtcttc ttcccagttt tcgcaatcca catcggccag atcgttattc agtaagtaat  2940
ccaattcggc taagcggctg tctaagctat tcgtataggg acaatccgat atgtcgatgg  3000
agtgaaagag cctgatgcac tccgcataca gctcgataat cttttcaggg ctttgttcat  3060
```

```
cttcatactc ttccgagcaa aggacgccat cggcctcact catgagcaga ttgctccagc   3120
catcatgccg ttcaaagtgc aggacctttg gaacaggcag cttccttcc  agccatagca   3180
tcatgtcctt ttcccgttcc acatcatagg tggtcccttt ataccggctg tccgtcattt   3240
ttaaatatag gttttcattt tctcccacca gcttatatac cttagcagga gacattcctt   3300
ccgtatcttt tacgcagcgg tattttcga  tcagttttt  caattccggt gatattctca   3360
ttttagccat ttattatttc cttcctcttt tctacagtat ttaaagatac cccaagaagc   3420
taattataac aagacgaact ccaattcact gttccttgca ttctaaaacc ttaaatacca   3480
gaaaacagct ttttcaaagt tgttttcaaa gttggcgtat aacatagtat cgacggagcc   3540
gattttgaaa ccgcggtgat cacaggcagc aacgctctgt catcgttaca atcaacatgc   3600
taccctccgc gagatcatcc gtgtttcaaa cccggcagct tagttgccgt tcttccgaat   3660
agcatcggta acatgagcaa agtctgccgc cttacaacgg ctctcccgct gacgccgtcc   3720
cggactgatg ggctgcctgt atcgagtggt gattttgtgc cgagctgccg gtcggggagc   3780
tgttggctgg ctggtggcag gatatattgt ggtgtaaaca aattgacgct tagacaactt   3840
aataacacat tgcggacgtt tttaatgtag agctcaaagt ttaacgcgtt agcagaaggc   3900
atgttgttgt gactccgagg ggttgcctca aactctatct tataaccggc gtggaggcat   3960
ggaggcaggg gtattttggt cattttaata gatagtggaa aatgacgtgg aatttactta   4020
aagacgaagt ctttgcgaca aggggggggcc cacgccgaat ttaatattac cggcgtggcc   4080
cccccttatc gcgagtgctt tagcacgagc ggtccagatt taaagtagaa aatttcccgc   4140
ccactagggt taaaggtgtt cacactataa aagcatatac gatgtgatgg tatttgatgg   4200
agcgtatatt gtatcaggta tttccgttgg atacgaatta ttcgtacgac cctcggtacc   4260
gatcggcgcg cgcggccgca cagagattta aatagctccg gtgacggacg gcgcgcccta   4320
tgtcgagctg caggtcaacg gatcaggata ttccttgttta agatgttgaa ctctatggag   4380
gtttgtatga actgatgatc taggaccgga taagttccct tcttcatagc gaacttattc   4440
aaagaatgtt ttgtgtatca ttcttgttac attgttatta atgaaaaaat attattggtc   4500
attggactga acacgagtgt taaatatgga ccaggcccca aataagatcc attgatatat   4560
gaattaaata acaagaataa atcgagtcac caaaccactt gccttttta  acgagacttg   4620
ttcaccaact tgatacaaaa gtcattatcc tatgcaaatc aataatcata caaaaatatc   4680
caataacact aaaaaattaa aagaaatgga taatttcaca atatgttata cgataaagaa   4740
gttacttttc caagaaattc actgatttta taagcccact tgcattagat aaatggcaaa   4800
aaaaaacaaa aaggaaaaga aataaagcac gaagaattct agaaaatacg aaatacgctt   4860
caatgcagtg ggacccacgg ttcaattatt gccaattttc agctccaccg tatatttaaa   4920
aaataaaacg ataatgctaa aaaaatataa atcgtaacga tcgttaaatc tcaacggctg   4980
gatcttatga cgaccgttag aaattgtggt tgtcgacgag tcagtaataa acggcgtcaa   5040
agtggttgca gccggcacac acgagtcgtg tttatcaact caaagcacaa atactttttcc  5100
tcaacctaaa aataaggcaa ttagccaaaa acaactttgc gtgtaaacaa cgctcaatac   5160
acgtgtcatt ttattattag ctattgcttc accgccttag cttttctgtg acctagtcgt   5220
cctcgtcttt tcttcttctt cttctataaa acaatacccca aagagctctt cttcttcaca   5280
attcagattt caatttctca aaatcttaaa aacttttctct caattctctc taccgtgatc   5340
aaggtaaatt tctgtcgttcc ttattctctc aaaatcttcg atttttgttt cgttcgatcc   5400
caatttcgta tatgttcttt ggtttagatt ctgttaatct tagatcgaac acgatttttct  5460
gggtttgatc gttagatatc atcttaattc tcgattaggg tttcatagat atcatccgat   5520
ttgttcaaat aatttgagtt ttgtcgaata attactcttc gatttgtgat ttctatctag   5580
atctggtgtt agtttctagt ttgtgcgatc gaatttgtcg attaatctga gttttttctga  5640
ttaacaggcc tgcaggatgg aagacgccaa aaacataaag aaaggcccgg cgccattcta   5700
tccgctggaa gatggaaccg ctggagagca actgcataag gctatgaaga gatacgccct   5760
ggttcctgga acaattgctt ttacagatgc acatatcgag gtggacatca cttacgctga   5820
gtacttcgaa atgtccgttc ggttggcaga agctacgaaa cgatatgggc tgaatacaaa   5880
tcacagaatc gtcgtatgca gtgaaaactc tcttcaattc tttatgccgg tgttgggcgc   5940
gttatttatc ggagttgcag ttgcgcccgc gaacgacatt tataatgaac gtgaattgct   6000
caacagtatg ggcatttcgc agcctaccgt ggtgttcgtt tccaaaaagg ggttgcaaaa   6060
aattttgaac gtgcaaaaaa agctcccaat catccaaaaa attattatca tggattctaa   6120
aacggattac cagggatttc agtcgatgta cacgttcgtc acatctcatc tacctcccgg   6180
ttttaatgaa tacgattttg tgccagagtc cttcgatagg gacaagacaa ttgcactgat   6240
catgaactcc tctggatcta ctggtctgcc taaaggtgtc gctctgcctc atagaactgc   6300
ctgcgtgaga ttctcgcatg ccagagatcc tatttttggc aatcaaatca ttccggatac   6360
tgcgatttta agtgttgttc cattccatca cggttttgga atgtttacta cactcggata   6420
tttgatatgt ggatttcgag tcgtcttaat gtatagattt gaagaagagc tgtttctgag   6480
gagccttcag gattacaaga ttcaaagtgc gctgctggtg ccaacccctat tctccttctt   6540
cgccaaaagc actctgattg acaaatacga tttatctaat ttacacgaaa ttgcttctgg   6600
tggcgctccc ctctctaagg aagtcgggga agcggttgcc aagaggttcc atctgccaga   6660
tatcaggcaa ggatatgggc tcactgagac tacatcagct attctgatta cacccgaggg   6720
ggatgataaa ccgggcgcgg tcggtaaagt tgttccattt tttgaagcga aggttgtgga   6780
tctggatacc gggaaaacgc tgggcgttaa tcaaagaggc gaactgtgtg tgagaggtcc   6840
tatgattatg tccggttatg taaacaatcc ggaagcgacc aacgccttga ttgacaagga   6900
tggatggcta cattctggag acatagctta ctgggacgaa gacgaacact tcttcatcgt   6960
tgaccgcctg aagtctctga ttaagtacaa aggctatcag gtggctcccg ctgaattgga   7020
atccatcttg ctccaacacc ccaacatctt cgacgctggt gtcgcaggtc ttcccgacga   7080
tgacgccggt gaacttcccg ccgccgttgt tgttttggag cacggaaaga cgatgacgga   7140
aaaagagatc gtggattacg tcgccagtca gtaacaccc  gcgaaaagt  tgccggagag   7200
agttgtgttt gtggacgaag taccgaaagg tcttaccgga aaactcgacg caagaaaaat   7260
cagagagatc ctcataaagg ccaagaaggg cggaaagatc gccgtgtgac gtcgacggtt   7320
cgagtattat ggcattggga aaactgtttt tcttgtacca tttgttgtgc ttgtaattta   7380
ctgtgttttt tattcggttt tcgctatcga actgtgaaat ggaaatggat ggagaagagt   7440
taatgaatga tatggttcctt ttgttcattc tcaaattatt ttttctctta   7500
tttgttgtgt gttgaatttg aaattataag agatatgcaa acattttgtt ttgagtaaaa   7560
atgtgtcaaa tcgtggcctc taatgaccga agttaatatg aggagtaaaa cacttgtagt   7620
tgtgttagag ctcccggggc gcgccgatat cgagctctcc cggcgcgccg atatcgagct   7680
cagtgttga  tcgccggcgg taccgagtgt acttcaagtc agtgggaaat caataaaatg   7740
attattttat gaatatattt cattgtgcaa gtagatagaa attacatatg ttacataaca   7800
```

```
cacgaaataa acaaaaaaag acaatccaaa aacaaacacc ccaaaaaaaa taatcacttt    7860
agataaactc gtatgaggag aggcacgttc agtgactcga cgattcccga gcaaaaaaag    7920
tctcccgtc acacatgtag tgggtgacgc aattatcttt aaagtaatcc ttctgttgac     7980
ttgtcattga taacatccag tcttcgtcag gattgcaaag aattatagaa gggatcccac    8040
ctttttatttt ctttctttttt ccatatttag ggttgacagt gaaatcagac tggcaaccta  8100
ttaattgctt ccacaatggg acgaacttga aggggatgtc gtcgatgata ttataggtg     8160
cgtgttcatc gtagttggtg aaatcgatgg taccgttcca atagttgtgt cgtccgagac    8220
ttctagccca ggtggtcttt ccggtacgag ttggtccgca gatgtagagg ctggggtgtc    8280
ggattccatt ccttccattg tccttgttaa atcggccatc cattcaaggt cagattgagc    8340
ttgttggtat gagacaggat gtatgtaagt ataagcgtct atgcttacat ggtatagatg    8400
ggtttccctc caggagtgta gatcttcgtg gcagcgaaga tctgattctg tgaagggcga    8460
cacatacggt tcaggttgtg gagggaataa tttgttggct gaatattcca gccattgaag    8520
cttgtgttgcc cattcatgag ggaattcttc cttgatcatg tcaagatatt cctccttaga   8580
cgttgcagtc tggataatag ttctccatcg tgcgtcagat ttgcgaggag aaaccttatg    8640
atctcggaaa tctcctctgg ttttaatatc tccgtccttt gatatgtaat caaggacttg    8700
tttagagttt ctagctggct ggatattagg gtgatttcct tcaaaatcga aaaaagaagg    8760
atccctaata caaggttttt tatcaagctg gagaagagca tgatagtggg tagtgccatc    8820
ttgatgaagc tcagaagcaa caccaaggaa gaaaataaga aaaggtgtga gtttctccca    8880
gagaaactgg aataaatcat ctctttgaga tgagcacttg ggataggtaa ggaaaacata    8940
tttagattgg agtctgaagt tcttactagc agaaggcatg ttgttgtgac tccgaggggt    9000
tgcctcaaac tctatcttat aaccggcgtg gaggcatgga ggcaggggta ttttggtcat    9060
tttaatagat attggaaaat gacgtggaat ttacttaaag acgaagtctt tgcgacaagg    9120
gggggcccac gccgaattta atattaccgg cgtggccccc ccttatcgcg agtgcttag    9180
cacgagcggt ccagatttaa agtagaaaat ttcccgccca ctagggttaa aggtgttcac    9240
actataaaag catatacgat gtgatggtat ttgatggagc gtatattgta tcaggtattt    9300
ccgttggata cgaattattc gtacgaccct catagtttaa actatcagtg tttgacagga    9360
tatattggcg ggtaaaccta agagaaaaga gcgtttatta gaataacgga tatttaaaag    9420
ggcgtgaaaa ggtttatccg ttcgtccatt tgtatgtgca tgccaaccac agggttcccc    9480
tcgggatcaa agtactttga tccaacccct ccgctgctat agtgcagtcg gcttctgacg    9540
ttcagtgcag ccgtcttctg aaaacgacat gtcgcacaag tcctaagtta cgcgacaggc    9600
tgccgccctg ccctttttcct ggcgttttct tgtcgcgtgt tttagtcgca taaagtagaa    9660
tacttgcgac tagaaccgga gacattacgc catgaacaag agcgccgccg ctggcctgct    9720
gggctatgcc cgcgtcagca ccgacgacca ggacttgacc aaccaacggg ccgaactgca    9780
cgcggccggc tgcaccaagc tgttttccga gaagatcacc ggcaccaggc gcgaccgccc    9840
ggagctgcgg aggatgcttg accacctacg ccctggcgac gttgtgacag tgaccaggct    9900
agaccgcctg gcccgcagca cccgcgacct actggacatt gccgagcgca tccaggaggc    9960
cggcgcgggc ctgcgtagcc tggcagagcc gtgggccgac accaccacgc cggccggccg   10020
catggtgttg accgtgttcg ccggcattgc cgagttcgag cgttcctaa tcatcgaccg    10080
cacccggagc gggcgcgagg ccgcaaggc cgaggcgtg aagtttggcc cccgccctac     10140
cctcaccccg gcacagatcg cgcacgcccc cgagctgatc gaccaggaag gccgcaccgt   10200
gaaagaggcg gctgcactgc ttggcgtgca tcgctcgacc ctgtaccgcg cacttgagcg   10260
cagcgaggaa gtgacgccca ccgaggccag gcggcgcggt gccttccgtg aggacgcatt   10320
gaccgagccg gacgccctgg cggccgccga gaatgaaccgc aagaggaacc aagcatgaaa   10380
ccgcaccagg acggccagga cgaaccgttt tcattaccg aagagatcga ggcggagatg   10440
atcgcggccg ggtacgtgtt cgagccgccc gcgcacggct caaccgtgcg gctgcatgaa   10500
atcctggccg gtttgtctga tgccaagctg gcggcctggc cggccagctt ggccgctgaa   10560
gaaaccgagc gccgccgtct aaaaaggtga tgtgtatttg agtaaaacag cttgcgtcat   10620
gcggtcgctg cgtatatgat gcgatgagta aataaacaaa tacgcaaggg gaacgcatga   10680
aggttatcgc tgtacttaac cagaaaggcg ggtcaggcaa gacgaccatc gcaacccatc   10740
tagcccgcgc cctgcaactc gccggggccg atgttctgtt agtcgattcc gatccccagg   10800
gcagtcgccg cgattgggcg gccgtgcggg aagatcaacc gctaaccgtt gtcggcatcg   10860
accgcccgac gattgaccgc gacgtgaagg ccatcggccg gcgcgacttc gtagtgatcg   10920
acggagcgcc caggcggcg gacttggctg tgtccgcgat caaggcagcc gacttcgtgc    10980
tgattccggt gcagcaagc ccttacgaca tatgggccac cgccgacctg gtggagctgg   11040
ttaagcagcg cattgaggtc acggatggaa ggctacaagg ccttttgtc gtgtcgcggg    11100
cgatcaaagg cacgcgcatc ggcggtgagg ttgccgaggc gctggccggg tacgagctgc   11160
ccattcttga gtcccgtatc acgcagcgcg tgagctaccc aggcactgcc gccgccggca   11220
caaccgttct tgaatcagaa cccgagggcg acgctgcccg cgaggtccag gcgctggccg   11280
ctgaaattaa atcaaaactc atttgagtta atgaggtaaa gagaaaatga gcaaaagcac   11340
aaacacgcta agtgccggcc gtccgagcgc acgcagcagc aaggctgcaa cgttggccag   11400
cctggcagac acgccagcca tgaagcgggt caactttcag ttgccggcgg aggatcacac   11460
caagctgaag atgtacgcgg tacgccaagg caagaccatt accgagctgc tatctgaata   11520
catcgcgcag ctaccagagt aaatgagcaa atgaataaat gagtagatga attttagcgg   11580
ctaaaggagg cggcatgaa aatcaagaac aaccaggcac cgacgccgtg gaatgcccca   11640
tgtgtggagg aacgggcggt tggccaggcg taagcggctg ggttgtctgc cggccctgca   11700
atggcactgg aaccccaag cccgaggaat cggcgtgacg gtcgcaaacc atccggcccg   11760
gtacaaatcg cgcggcgcct gggtgatgac ctggtggaga agttgaaggc cgcgcaggcc   11820
gcccagcggc aacgca                                                   11836

SEQ ID NO: 98        moltype = DNA   length = 11812
FEATURE              Location/Qualifiers
source               1..11812
                     mol_type = other DNA
                     organism = synthetic construct
SEQUENCE: 98
ccttttatttt tcttcttttt tccatatttta gggttgacag tgaaatcaga ctggcaacct    60
attaattgct tccacaatgg gacgaacttg aaggggatgt cgtcgatgat attaggtgt      120
gcgtgttcat cgtagttggt gaaatcgatg gtaccgttcc aatagttgtg tcgtccgaga    180
cttctagccc aggtggtctt tccggtacga gttggtccgc agatgtagag gctggggtgt    240
```

```
cggattccat tccttccatt gtccttgtta aatcggccat ccattcaagg tcagattgag    300
cttgttggta tgagacagga tgtatgtaag tataagcgtc tatgcttaca tggtatagat    360
gggtttccct ccaggagtgt agatcttcgt ggcagcgaag atctgattct gtgaagggcg    420
acacatacgg ttcaggttgt ggagggaata atttgttggc tgaatattcc agccattgaa    480
gctttgttgc ccattcatga gggaattctt ccttgatcat gtcaagatat tcctccttag    540
acgttgcagt ctggataata gttctccatc gtgcgtcaga tttgcgagga gaaacccttat   600
gatctcggaa atctcctctg gttttaatat ctccgtcctt tgatatgtaa tcaaggactt    660
gtttagagtt tctagctggc tggatattag ggtgatttcc ttcaaaatcg aaaaagaag     720
gatccctaat acaaggtttt ttatcaagct ggagaagagc atgatagtgg gtagtgccat    780
cttgatgaag ctcagaagca acaccaagga agaaaataag aaaaggtgtg agtttctccc    840
agagaaactg gaataaatca tctctttgag atgagcactt gggataggta aggaaaacat    900
atttagattg gagtctgaag ttcttactag cagaaggcat gttgttgtga ctccgagggg    960
ttgcctcaaa ctctatctta taaccggcgt ggaggcatgg aggcaggggt attttggtca   1020
ttttaataga tagtggaaaa tgacgtggaa tttacttaaa gacgaagtct ttgcgacaag   1080
gggggggccca cgccgaattt aatattaccg gcgtggcccc cccttatcgc gagtgcttta   1140
gcacgagcgg tccagattta aagtagaaaa tttcccgccc actagggtta aaggtgttca   1200
cactataaaa gcatatacga tgtgatggta tttgatggag cgtatattgt atcaggtatt   1260
tccgttggat acgaattatt cgtacgaccc tcatagttta aactatcagt gtttgacagg   1320
atatattggc gggtaaacct aagagaaaag agcgtttatt agaataacgg atatttaaaa   1380
gggcgtgaaa aggtttatcc gttcgtccat ttgtatgtgc atgccaacca cagggttccc   1440
ctcgggatca aagtactttg atccaacccc tccgctgcta tagtgcagtc ggcttctgac   1500
gttcagtgca gccgtcttct gaaaacgaca tgtcgcacaa gtcctaagtt acgcgacagg   1560
ctgccgccct gccctttttcc tggcgttttc ttgtcgcgtg ttttagtcgc ataaagtaga   1620
atacttgcga ctagaaccgg agacattacg ccatgaacaa gagcgccgcc gctggcctgc   1680
tgggctatgc ccgcgtcagc accgacgacc aggacttgac caaccaacgg gccgaactgc   1740
acgcgccgg ctgcaccaag ctgttttccg agaagatcac cggcaccagg tgcgaccgcc   1800
cggagctggc caggatgctt gaccaccta gccctggcga cgttgtgaca gtgaccaggc   1860
tagaccgcct ggcccgcagc acccgcgacc tactggacat tgccgagcgc atccaggagg   1920
ccggcgcggg cctgcgtagc ctggcagagc cgtgggccga caccaccacg ccggccggcc   1980
gcatggtgtt gaccgtgttc gccggcattg ccgagttcga gcgttcccta atcatcgacc   2040
gcacccggag cgggcgcgag gccgccaagg ccctgaggcgt gaagtttggc ccccgcccta   2100
ccctcacccc ggcacagatc gcgcacgccc gcgagctgat cgaccaggaa ggccgcaccg   2160
tgaaagaggc ggctgcactg cttggcgtgc atcgctcgac cctgtaccgc gcacttgagc   2220
gcagcgagga agtgacgccc accgaggcca ggcggcgcgg tgccttccgt gaggacgcat   2280
tgaccgaggc cgacgcccctg gcgggcgccg caagatgaacg ccaagaggaa caagcatgaa   2340
accgcaccag gacggccagg acgaaccgtt tttcattacc gaagagatcg aggcggagat   2400
gatcgcggcc gggtacgtgt tcgagccgcc cgcgcacggc tcaaccgtgc ggctgcatga   2460
aatcctggcc ggtttgtctg atgccaagct ggcggcctgg ccggcagct tggccgctga   2520
agaaaccgag cgccgccgtc taaaaaggtg atgtgtattt gagtaaaaca gcttgcgtca   2580
tgcggtcgct gcgtatatga tgcgatgagt aaataaacaa atacgcaagg ggaacgcatg   2640
aaggttatcg ctgtacttaa ccagaaaggc gggtcaggca agacgaccat cgcaacccat   2700
ctagcccgcg ccctgcaact cgccggggcc gatgttctgt tagtcgattc cgatccccag   2760
ggcagtgccc gcgattgggc ggcgtcgcgg gaagatcaac cgctaacgct tgtcggcac    2820
gaccgcccga cgattaccg cgacgtgaag gccatcggcc ggcgacgtt cgtagtgatc    2880
gacgagcgc cccaggcggc ggacttgct gtgtccgcga tcaaggcagc cgacttcgtg    2940
ctgattccgg tgcagccaag cccttacgac atatgggcca ccgccgacct ggtggagctg   3000
gttaagcagc gcattgaggt cacggatgga aggctacaag aggcctttgt cgtgtcgcgg   3060
gcgatcaaag gcacgcgcat cggcggtgag gttgccgagg cgctggccgg gtacgagctg   3120
cccattcttg agtcccgtat cacgcagcgc gtgagctacc caggcactgc cgccgccggc   3180
acaaccgttc ttgaatcaga acccgagggc gacgctgccc gcgaggtcca ggcgctggcc   3240
gctgaaatta aatcaaaact catttgagtt aatgaggtaa agagaaaatg agcaaaagca   3300
caaacacgct aagtgccggc cgtccgagcc cacgcagcag caaggctgca acgttggcca   3360
gcctggcaga cacgccagcc atgaagcggg tcaactttca gttgccggcg gaggatcaca   3420
ccaagctgaa gatgtacgcg gtacgccaag gcaagaccat taccgagctg ctatctgaat   3480
acatcgcgca gctaccagag taaatgagca aatgaataaa tgagtagatg aattttagcg   3540
gctaaaggag gcggcatgga aaatcaagaa caaccaggca ccgacgccgt ggaatgcccc   3600
atgtgtggag gaacgggcgg ttggccaggc gtaagcggct gggttgtctg ccggccctgc   3660
aatggcactg gaaccccaa gcccgaggaa tcggcgtgac ggtcgcaaac catccggccc   3720
ggtacaaatc ggcgcggcgc tgggtgatga cctggtggag aagttgaagg ccgcgaggc    3780
cgcccagcgg caacgcatcg aggcagaagc acgccccggt gaatcgtgca agcggccgc    3840
tgatcgaatc cgcaaagaat cccggcaacc gccggcagcc ggtgcgccgt cgattaggaa   3900
gccgcccaag ggcgacgagc aaccagattt ttcgttccg atgctctatg acgtgggcac    3960
ccgcgatagt cgcagcatca tggacgtggc cgttttccgt ctgtcgaagc gtgaccacg    4020
agctgccggg tgatccgct acgagcttcc agacgggacg ctagaggtt ccgcagggcc    4080
ggccggcatg gccagtgtgt gggattacga cctggtactg atgcggtttt ccatctaac    4140
cgaatccatg aaccgatacc gggaagggaa gggagacaag cccggccgcg tgttccgtcc   4200
acacgttgcg gactactca gttctgccgg cgagccgat ggcggaaagc agaaagacga    4260
cctggtagaa acctgcattc ggttaaacac cacgcacgtt gccatgcagc gtacgaagaa   4320
ggccaagaac ggccgcctgg tgacggtatc cgagggtgaa gccttgatta gccgctacaa   4380
gatcgtaaag agcgaaaccg gcggccgga gtacatcgag atcgagctag ctgattggat   4440
gtaccgcgag atcacagaag gcaagaaccc ggacgtgctg acggttaccc cgattacttt   4500
tttgatcgat cccggcatcg gccgttttct ctaccgcctg gcacgccgcg ccgcaggcaa   4560
ggcagaagcc agatggttgt tcaagacgat ctacgaacgc agtggcagcg ccggagagtt   4620
caagaagttc tgtttcaccg tgcgcaagct gatcgggtca aatgacctgc cggagtacga   4680
tttgaaggag gaggcgggcc aggctggccc gatcctagtc atgcgctacc gcaacctgat   4740
cgagggcgaa gcatccgccg gttcctaatg tacggagcag atgctagggc aaattgccct   4800
agcagggaa aaggtcgaa aaggcctctt tcctgtggat agcacgtaca ttgggaaccc    4860
aaagccgtac attgggaacc ggaacccgta cattgggaac ccaaagccgt acattgggaa   4920
ccggtcacac atgtaagtga ctgatataaa agagaaaaaa ggcgattttt ccgcctaaaa   4980
```

```
ctctttaaaa cttattaaaa ctcttaaaac ccgcctggcc tgtgcataac tgtctggcca   5040
gcgcacagcc gaaagagctgc aaaaagcgcc taccccttcgg tcgctgcgct ccctacgccc  5100
cgccgcttcg cgtcggccta tcgcggccgc tggccgctca aaaatggctg gcctacggcc   5160
aggcaatcta ccagggcgcg gacaagccgc gccgtcgcca ctcgaccgcc ggcgcccaca   5220
tcaaggcacc ctgcctcgcg cgtttcggtg atgacggtga aaacctctga cacatgcagc   5280
tcccggaaac ggtcacagct tgtctgtaag cggatgccgg gagcagacaa gcccgtcagg   5340
gcgcgtcagc gggtgttggc gggtgtcggg gcgcagccat gacccagtca cgtagcgata   5400
gcggagtgta tactggctta actatgcggc atcagagcag attgtactga gagtgcacca   5460
tatgcggtgt gaaataccgc acagatgcgt aaggagaaaa taccgcatca ggcgctcttc   5520
cgcttcctcg ctcactgact cgctgcgctc ggtcgttcgg ctgcggcgag cggtatcagc   5580
tcactcaaag gcggtaatac ggttatccac agaatcaggg gataacgcag gaaagaacat   5640
gtgagcaaaa ggccagcaaa aggccaggaa ccgtaaaaag gccgcgttgc tggcgttttt   5700
ccataggctc cgcccccctg acgagcatca caaaaatcga cgctcaagtc agaggtggcg   5760
aaacccgaca ggactataaa gataccaggc gtttccccct ggaagctccc tcgtgcgctc   5820
tcctgttccg accctgccgc ttaccggata cctgtccgcc tttctccctt cgggaagcgt   5880
ggcgctttct catagctcac gctgtaggta tctcagttcg gtgtaggtcg ttcgctccaa   5940
gctgggctgt gtgcacgaac ccccgttca gcccgaccgc tgcgccttat ccggtaacta   6000
tcgtcttgag tccaacccgg taagacacga cttatcgcca ctggcagcag ccactggtaa   6060
caggattagc agagcgaggt atgtaggcgg tgctacagag ttcttgaagt ggtggcctaa   6120
ctacggctac actagaagga cagtatttgg tatctgcgct ctgctgaagc cagttacctt   6180
cggaaaaaga gttggtagct cttgatccgg caaacaaacc accgctggta gcggtggttt   6240
ttttgtttgc aagcagcaga ttacgcgcag aaaaaaaggga tctcaagaag atcctttgat   6300
cttttctacg gggtctgacg ctcagtggaa cgaaaactca cgttaaggga ttttggtcat   6360
gcattctagg tactaaaaca attcatccag taaaatataa tattttattt tctcccaatc   6420
aggcttgatc cccagtaagt caaaaaatag ctcgacatac tgttcttccc cgatatcctc   6480
cctgatcgac cggacgcaga aggcaatgtc ataccacttg tccgccctgc cgcttctccc   6540
aagatcaata aagccactta ctttgccatc tttcacaaag atgttgctgt ctcccaggtc   6600
gccgtgggaa aagacaagtt cctcttcggg ctttttccgtc tttaaaaat catacagctc   6660
gcgcggatct taaatggag tgtcttcttc ccagttttcg caatccacat cggccagatc   6720
gttattcagt aagtaatcca attcggctaa gcggctgtct aagctattcg tatagggaca   6780
atccgatatg tcgatggagt gaaagagcct gatgcactcc gcatacagct cgataatctt   6840
ttcagggctt tgttcatctt cactctcttc cgagcaaagg acgccatcgg cctcactcat   6900
gagcagattg ctccagccat catgccgttc aaagtgcagg acctttggaa caggcagctt   6960
tccttccagc catagcatca tgtccttttc ccgttccaca tcataggtgg tcccttttata   7020
ccggctgtcc gtcatttta aatataggtt ttcatttct cccaccagct tatatacctt   7080
agcaggagac attccttccg tatctttttac gcagcggtat ttttcgatca gtttttttcaa   7140
ttccggtgat attctcattt tagccatttta ttattttcctt cctctttctt acagtatttta  7200
aagatacccc aagaagctaa tttaacaag acgaactcca attcactgtt ccttgcattc   7260
taaaacctta aataccagaa aacagctttt tcaaagttgt tttcaaagtt gcgtataac   7320
atagtatcga cggagccgat tttgaaaccg cggtgatcac aggcagcaac gctctgtcat   7380
cgttacaatc aacatgctac cctccgcgag atcatccgtg tttcaaaccc ggcagcttag   7440
ttgccgttct tccgaatagc atcggtaaca tgagcaaagt ctgccgcctt acaacggctc   7500
tcccgtcgac gccgtcccgg actgatgggc tgcctgtatc gagtggtgat tttgtgccga   7560
gctgccggtc ggggagctgt tggctggctg gtgcaggat atattgtggt gtaaacaaat   7620
tgacgcttag acaacttaat aacacattgc ggacgttttt aatgtagagc tcaaagttta   7680
acgcgttagc agaaggcatg ttgttgtgac tccgaggggg tgcctcaaac tctatcttat   7740
aaccggcgtg gaggcatgga ggcaggggta ttttggtcat tttaatagat agtgaaaat   7800
gacgtggaat ttacttaaag acgaagtctt tgcgacaagg gggggcccac gccgaattta   7860
atattaccgg cgtggccccc ccttatcgcg agtgctttag cacgagcggt ccagatttaa   7920
agtagaaaat ttcccgccca ctaggttaa aggtgttcac actataaaag catatacgat   7980
gtgatggtat ttgatggagc gtatattgta tcaggtattt ccgttggata cgaattattc   8040
gtacgaccct cggtaccgat cggcgcgcca gatttgcctt ttcaatttca gaaagaatgc   8100
taacccacag atggttagag aggcttacgc agcaggtatc atcaagacga tctacccgag   8160
caataatctc caggaaatca aataccttcc caagaaggtt aaagatgcag tcaaaagatt   8220
caggactaac tgcatcaaga acacagagaa agatatattt ctcaagatca gaagtactat   8280
tccagtatgg acgattcaag gcttgcttca caaaccaagg caagtaatag agattggagt   8340
ctctaaaaag gtagttccca ctgaatcaaa ggccatggag tcaaagattc aaatagagga   8400
cctaacagaa ctcgccgtaa agactggcga acagttcata cagagtctct tacgactcaa   8460
tgacaagaag aaaatcttcg tcaacatggt ggagcacgac acacttgtct actccaaaaa   8520
tatcaaagat acagtctcag aagaccaaag ggcaattgag acttttcaac aaagggtaat   8580
atccggaaac ctcctcggat tccattgccc agctatctgt cactttattg tgaagatagt   8640
ggaaaggaa ggtggctcct acaaatgcca tcattgcgat aaaggaaagg ccatcgttga   8700
agatgcctct gccgacagtg gtcccaaaga tggacccccaa cccacgagga gcatcgtgga   8760
aaaagaagac gttccaacca cgtcttcaaa gcaagtggat tgatgtgata tctccatgga   8820
cgtaagggat gacgcacaat cccactatcc ttcgcaagac ccttcctcta tataaggaag   8880
ttcatttcat ttggagagaa cacggggac tcctgcagga tggaagacgc caaaaacata   8940
aagaaaggcc cggcgccatt ctatccgctg aagatggaa ccgctggaga caactgcat   9000
aaggctatga agagatacgc cctggttcct ggaacaattg cttttacaga tgcacatatc   9060
gaggtggaca tcacttacgc tgagtactc gaaatgtccg ttcggttggc agaagctatg   9120
aaacgatatg ggctgaatac aaatcacaga atcgtcgtat gcagtgaaaa ctctcttcaa   9180
ttctttatgc cggtgttggg cgcgttattt atcggagttg cagttgcgcc cgcgaacgac   9240
atttataatg aacgtgaatt gctcaacagt atgggcattt cgcagcctac cgtggtgttc   9300
gtttccaaaa aggggttgca aaaaattttg aacgtgcaaa aaaagctccc aatcatccaa   9360
aaaattatta tcatggattc taaaacggat taccagggat ttcagtcgat gtacacgttc   9420
gtcacatctc atctacctcc cggttttaat gaatacgatt ttgtgccaga gtccttcgat   9480
agggacaaga caattgcact gatcatgaac tcctctggat ctactggtct gcctaaaggt   9540
gtcgctctgc tcatagaac tgcctgcgtg agattctcgc atgccagaga tcctattttt   9600
ggcaatcaaa tcattccgga tactgcgatt ttaagtgttg ttccattcca tcacggtttt   9660
ggaatgttta ctacactcgg atatttgata tgtggatttc gagtcgtctt aatgtataga   9720
```

```
tttgaagaag agctgtttct gaggagcctt caggattaca agattcaaag tgcgctgctg   9780
gtgccaaccc tattctcctt cttcgccaaa agcactctga ttgacaaata cgatttatct   9840
aatttacacg aaattgcttc tggtggcgct cccctctcta aggaagtcgg ggaagcggtt   9900
gccaagaggt tccatctgcc aggtatcagg caaggatatg ggctcactga gactacatca   9960
gctattctga ttacacccga gggggatgat aaaccggcgc cggtcggtaa agttgttcca  10020
ttttttgaag cgaaggttgt ggatctggat accgggaaaa cgctgggcgt taatcaaaga  10080
ggcgaactgt gtgtgagagg tcctatgatt atgtccggtt atgtaaacaa tccggaagcg  10140
accaacgcct tgattgacaa ggatggatgg ctacattctg gagacatagc ttactgggac  10200
gaagcgaac  acttcttcat cgttgaccgc ctgaagtctc tgattaagta caaaggctat  10260
caggtcgctc ccgctgaatt ggaatccatc ttgctccaac accccaacat cttcgacgct  10320
ggtgtcgcag gtcttcccga cgatgacgcc ggtgaacttc ccgccgccgt tgttgttttg  10380
gagcacggaa agacgatgac ggaaaaagag atcgtggatt acgtcgccag tcaagtaaca  10440
accgcgaaaa agttgcgcgg aggagttgtg tttgtggacg aagtaccgaa aggtcttacc  10500
ggaaaactcg acgcaagaaa aatcagagag atcctcagcc aggccaagaa gggcggaaag  10560
atcgccgtgt gacgtcgacg atatgaagat gaagatgaaa tatttggtgt gtcaaataaa  10620
aagcttgtgt gcttaagttt gtgtttttttt cttggcttgt tgtgttatga atttgtggct  10680
ttttctaata ttaaatgaat gtaagatcac attataatga ataaacaaat gtttctataa  10740
tccattgtga atgttttgtt ggatctcttc tgcagcatat aactactgta tgtgctatgg  10800
tatggactat ggaatatgat taaagataag ccagagctct ggtgacggac ccatggcttc  10860
gttgaacaac ggaaactcga cttgccttcc gcacaataca tcatttcttc ttagcttttt  10920
ttcttcttct tcgttcatac agtttttttt tgtttatcag cttacatttt cttgaaccgt  10980
agctttcgtt ttcttctttt taactttcca ttcggagtttt ttgtatcttg ttccatagtt  11040
tgtcccagga ttagaatgat taggcatcga accttcaaga atttgattga ataaaacatc  11100
ttcattctta agatatgaag ataatcttca aaaggcccct gggaatctga agaagagaa  11160
gcaggcccat ttatatggga agaacaata gtatttctta tataggccca tttaagttga  11220
aaacaatctt caaaagtccc acatcgctta gataagaaca cgaagctgag tttatataca  11280
gctagagtcg aagtagtgat tgttggtagt agcgactcca tggttttaga gctagaaata  11340
gcaagttaaa ataaggctag tccgttatca acttgaaaaa gtggcaccga gtcggtgctt  11400
ttttttccgg ggcgcgccga tatcgagctc tcccggcgcg ccgatatcga gctcagtgtt  11460
tgatcgccgg cggtaccgag tgtacttcaa gtcagtggga aatcaataaa atgattattt  11520
tatgaatata tttcattgtg caagtagata gaaattacat atgttacata acacacgaaa  11580
taaacaaaaa aagacaatcc aaaaacaaac ccccaaaaa aataatcac tttagataaa  11640
ctcgtatgag gagaggcacg ttcagtgact cgacgattcc cgagcaaaaa aagtctcccc  11700
gtcacacatg tagtgggtga cgcaattatc tttaaagtaa tccttctgtt gacttgtcat  11760
tgataacatc cagtcttcgt caggattgca aagaattata gaagggatcc ca           11812

SEQ ID NO: 99          moltype = DNA  length = 62
FEATURE                Location/Qualifiers
source                 1..62
                       mol_type = other DNA
                       organism = Nicotiana benthamiana
SEQUENCE: 99
ggaatttgtt atgttttggt agtagcgact ccatggggca taagtttaga attcgtactc    60
cc                                                                   62

SEQ ID NO: 100         moltype = DNA  length = 61
FEATURE                Location/Qualifiers
source                 1..61
                       mol_type = other DNA
                       organism = synthetic construct
SEQUENCE: 100
ggaatttgtt atgttttggt agtagcgact catggggcat aagtttagaa ttcgtactcc    60
c                                                                    61

SEQ ID NO: 101         moltype = DNA  length = 52
FEATURE                Location/Qualifiers
source                 1..52
                       mol_type = other DNA
                       organism = synthetic construct
SEQUENCE: 101
ggaatttgtt atgttttggt agatggggca taagtttaga attcgtactc cc            52

SEQ ID NO: 102         moltype = DNA  length = 33
FEATURE                Location/Qualifiers
source                 1..33
                       mol_type = other DNA
                       organism = synthetic construct
SEQUENCE: 102
ggaatttgtt atgttttggt agtagcgact ccc                                 33

SEQ ID NO: 103         moltype = DNA  length = 58
FEATURE                Location/Qualifiers
source                 1..58
                       mol_type = other DNA
                       organism = synthetic construct
SEQUENCE: 103
ggaatttgtt atgttttggt agtagcgcat ggggcataag tttagaattc gtactccc      58

SEQ ID NO: 104         moltype = DNA  length = 59
```

```
FEATURE                 Location/Qualifiers
source                  1..59
                        mol_type = other DNA
                        organism = synthetic construct
SEQUENCE: 104
ggaatttgtt atgttttggt agtagcgaca tgggcataa gtttagaatt cgtactccc        59

SEQ ID NO: 105          moltype = DNA   length = 63
FEATURE                 Location/Qualifiers
source                  1..63
                        mol_type = other DNA
                        organism = synthetic construct
SEQUENCE: 105
ggaatttgtt atgttttggt agtagcgact cccatggggc ataagtttag aattcgtact      60
ccc                                                                    63

SEQ ID NO: 106          moltype = DNA   length = 58
FEATURE                 Location/Qualifiers
source                  1..58
                        mol_type = other DNA
                        organism = synthetic construct
SEQUENCE: 106
ggaatttgtt atgttttggt agtagcgaat gggcataag tttagaattc gtactccc         58

SEQ ID NO: 107          moltype = DNA   length = 56
FEATURE                 Location/Qualifiers
source                  1..56
                        mol_type = other DNA
                        organism = synthetic construct
SEQUENCE: 107
ggaatttgtt atgttttggt agtagcatgg ggcataagtt tagaattcgt actccc          56

SEQ ID NO: 108          moltype = DNA   length = 33
FEATURE                 Location/Qualifiers
source                  1..33
                        mol_type = other DNA
                        organism = synthetic construct
SEQUENCE: 108
ggaatttgtt atgttttggt agtagcgact ccc                                   33

SEQ ID NO: 109          moltype = DNA   length = 50
FEATURE                 Location/Qualifiers
source                  1..50
                        mol_type = other DNA
                        organism = synthetic construct
SEQUENCE: 109
ggaatttgtt atgttttggt atggggcata agtttagaat tcgtactccc                 50

SEQ ID NO: 110          moltype = DNA   length = 53
FEATURE                 Location/Qualifiers
source                  1..53
                        mol_type = other DNA
                        organism = synthetic construct
SEQUENCE: 110
ggaatttgtt atgttttggt agtatggggc ataagtttag aattcgtact ccc             53

SEQ ID NO: 111          moltype = DNA   length = 55
FEATURE                 Location/Qualifiers
source                  1..55
                        mol_type = other DNA
                        organism = synthetic construct
SEQUENCE: 111
ggaatttgtt atgttttggt agtagatggg gcataagttt agaattcgta ctccc           55

SEQ ID NO: 112          moltype = DNA   length = 51
FEATURE                 Location/Qualifiers
source                  1..51
                        mol_type = other DNA
                        organism = synthetic construct
SEQUENCE: 112
ggaatttgtt atgttttggt agtagggcat aagtttagaa ttcgtactcc c               51

SEQ ID NO: 113          moltype = DNA   length = 30
FEATURE                 Location/Qualifiers
source                  1..30
                        mol_type = other DNA
                        organism = synthetic construct
SEQUENCE: 113
atggggcata agtttagaat tcgtactccc                                       30
```

| SEQ ID NO: 114 | moltype = DNA length = 40 |
| --- | --- |
| FEATURE | Location/Qualifiers |
| source | 1..40 |
| | mol_type = other DNA |
| | organism = Nicotiana benthamiana |

SEQUENCE: 114
ggaatttgtt atgttttggt agtagcgact ccatggggca                40

| SEQ ID NO: 115 | moltype = DNA length = 41 |
| --- | --- |
| FEATURE | Location/Qualifiers |
| source | 1..41 |
| | mol_type = other DNA |
| | organism = synthetic construct |

SEQUENCE: 115
ggaatttgtt atgttttggt agtagcgact cccatggggc a              41

| SEQ ID NO: 116 | moltype = DNA length = 38 |
| --- | --- |
| FEATURE | Location/Qualifiers |
| source | 1..38 |
| | mol_type = other DNA |
| | organism = synthetic construct |

SEQUENCE: 116
ggaatttgtt atgttttggt agtagcgacc atggggca                  38

| SEQ ID NO: 117 | moltype = DNA length = 39 |
| --- | --- |
| FEATURE | Location/Qualifiers |
| source | 1..39 |
| | mol_type = other DNA |
| | organism = synthetic construct |

SEQUENCE: 117
ggaatttgtt atgttttggt agtagcgact catggggca                 39

| SEQ ID NO: 118 | moltype = AA length = 302 |
| --- | --- |
| FEATURE | Location/Qualifiers |
| source | 1..302 |
| | mol_type = protein |
| | organism = Zea Mays |

SEQUENCE: 118
MAANAGGGGA GGGSGSGSVA APAVCRPSGS RWTPTPEQIR MLKELYYGCG IRSPSSEQIQ   60
RITAMLRQHG KIEGKNVFYW FQNHKARERQ KRRLTSLDVN VPAAGAADAT TSQLGVLSLS  120
SPPPSGAAPP SPTLGFYAAG NGGGSAVLLD TSSDWGSSGA AMATETCFLQ DYMGVTDTGS  180
SSQWPRFSSS DTIMAAAAAR AATTRAPETL PLFPTCGDDG GSGSSSYLPF WGAASTTAGA  240
TSSVAIQQQH QLQEQYSFYS NSNSTQLAGT GNQDVSATAA AAAALELSLS SWCSPYPAAG  300
SM                                                                302

| SEQ ID NO: 119 | moltype = AA length = 382 |
| --- | --- |
| FEATURE | Location/Qualifiers |
| source | 1..382 |
| | mol_type = protein |
| | organism = Arabidopsis thaliana |

SEQUENCE: 119
MESGSNSTSC PMAFAGDNSD GPMCPMMMMM PPIMTSHQHH GHDHQHQQQE HDGYAYQSHH   60
QQSSSLFLQS LAPPQGTKNK VASSSSPSSC APAYSLMEIH HNEIVAGGIN PCSSSSSSAS  120
VKAKIMAHPH YHRLLAAYVN CQKVGAPPEV VARLEEACSS AAAAAASMGP TGCLGEDPGL  180
DQFMEAYCEM LVKYEQELSK PFKEAMVFLQ RVECQFKSLS LSSPSSFSGY GETAIDRNNN  240
GSSEEEVDMN NEFVDPQAED RELKGQLLRK YSGYLGSLKQ EPMKKRKKGK LPKEARQQLL  300
DWWSRHYKWP YPSEQQKLAL AESTGLDQKQ INNWFINQRK RHWKPSEDMQ FVVMDATHPH  360
HYFMDNVLGN PFPMDHISST ML                                          382

| SEQ ID NO: 120 | moltype = AA length = 794 |
| --- | --- |
| FEATURE | Location/Qualifiers |
| source | 1..794 |
| | mol_type = protein |
| | organism = Arabidopsis thaliana |

SEQUENCE: 120
MMASLSCVED KMKTSCLVNG GGTITTTTSQ STLLEEMKLL KDQSGTRKPV INSELWHACA   60
GPLVCLPQVG SLVYYFSQGH SEQVAVSTRR SATTQVPNYP NLPSQLMCQV HNVTLHADKD  120
SDEIYAQMSL QPVHSERDVF PVPDFGMLRG SKHPTEFFCK TLTASDTSTH GGFSVPRRAA  180
EKLFPPLDYS AQPPTQELVV RDLHENTWTF RHIYRGQPKR HLLTTGWSLF VGSKRLRAGD  240
SVLFIRDEKS QLMVGVRRAN RQQTALPSSV LSADSMHIGV LAAAAHATAN RTPFLIFYNP  300
RACPAEFVIP LAKYRKAICG SQLSVGMRFG MMFETEDSGK RRYMGTIVGI SDLDPLRWPG  360
SKWRNLQVEW DEPGCNDKPT RVSPWDIETP ESLFIFPSLT SGLKRQLHPS YFAGETEWGS  420
LIKRPLIRVP DSANGIMPYA SFPSMASEQL MKMMMRPHNN QNVPSFMSEM QQNIVMGNGG  480
LLGDMKMQQP LMMNQKSEMV QPQNKLTVNP SASNTSGQEQ NLSQSMSAPA KPENSTLSGC  540
SSGRVQHGLE QSMEQASQVT TSTVCNEEKV NQLLQKPGAS SPVQADQCLD ITHQIYQPQS  600
DPINGFSFLE TDELTSQVSS FQSLAGSYKQ PFILSSQDSS AVVLPDSTNS PLFHDVWDTQ  660
LNGLKFDQFS PLMQQDLYAS QNICMSNSTT SNILDPPLSN TVLDDFCAIK DTDFQNHPSG  720
CLVGNNNTSF AQDVQSQITS ASFADSQAFS RQDFPDNSGG TGTSSSNVDF DDCSLRQNSK  780

```
-continued
GSSWQKIATP RVRT                                                           794

SEQ ID NO: 121          moltype = AA  length = 584
FEATURE                 Location/Qualifiers
source                  1..584
                        mol_type = protein
                        organism = Arabidopsis thaliana
SEQUENCE: 121
MNSMNNWLGF SLSPHDQNHH RTDVDSSTTR TAVDVAGGYC FDLAAPSDES SAVQTSFLSP           60
FGVTLEAFTR DNNSHSRDWD INGGACNNIN NNEQNGPKLE NFLGRTTTIY NTNETVVDGN          120
GDCGGGDGGG GGSLGLSMIK TWLSNHSVAN ANHQDNGNGA RGLSLSMNSS TSDSNNYNNN          180
DDVVQEKTIV DVVETTPKKT IESFGQRTSI YRGVTRHRWT GRYEAHLWDN SCKREGQTRK          240
GRQVYLGGYD KEEKAARAYD LAALKYWGTT TTTNFPLSEY EKEVEEMKHM TRQEYVASLR          300
RKSSGFSRGA SIYRGVTRHH QHGRWQARIG RVAGNKDLYL GTFGTQEEAA EAYDIAAIKF          360
RGLSAVTNFD MNRYNVKAIL ESPSLPIGSS AKRLKDVNNP VPAMMISNNV SESANNVSGW          420
QNTAFQHHQG MDLSLLQQQQ ERYVGYYNGG NLSTESTRVC FKQEEEQQHF LRNSPSHMTN          480
VDHHSSTSDD SVTVCGNVVS YGGYQGFAIP VGTSVNYDPF TAAEIAYNAR NHYYYAQHQQ          540
QQQIQQSPGG DFPVAISNNH SSNMYFHGEG GGEGAPTFSV WNDT                          584

SEQ ID NO: 122          moltype = AA  length = 240
FEATURE                 Location/Qualifiers
source                  1..240
                        mol_type = protein
                        organism = Agrobacterium tumefaciens
SEQUENCE: 122
MDLRLIFGPT CTGKTSTAIR LAQQTGLPVL SLDRVQCCPQ LSTGSGRPTV EELKGTTRLY           60
LEDRPLVKGI IAAKQAHERL IGEVYNYEAH GGLILEGGSI SLLRCMAQSS YWSTDFRWHI          120
IRHKLADEET FMNAAKARVR QMLRPAVGPS IIQELVHLWN EPRLRPILKE IDGYRYAMLF          180
ASQNQITPDM LLQLDPDMEG ELIHGIAQEY LIHARRQEQE FPPVSVVAFE GFEGPPFGMC          240
```

DELIVERY OF DEVELOPMENTAL REGULATORS TO PLANTS FOR THE INDUCTION OF MERISTEMATIC TISSUE WITH GENETIC ALTERATIONS

CROSS-REFERENCE TO RELATED APPLICATIONS

This application is a continuation of U.S. application Ser. No. 17/255,305, filed on Dec. 22, 2020, now U.S. Pat. No. 11,608,506, which is a National Stage application under 35 U.S.C. § 371 of International Application No. PCT/US2019/039297 having an International Filing Date of Jun. 26, 2019, which claims priority from U.S. Provisional Application Ser. No. 62/690,165, filed Jun. 26, 2018. The disclosures of the prior applications are considered part of (and are incorporated by reference in) the disclosure of this application.

STATEMENT OF FEDERALLY SPONSORED RESEARCH

This invention was made with government support under IOS-1339209 awarded by the National Science Foundation. The government has certain rights in the invention.

SEQUENCE LISTING

This application contains a Sequence Listing that has been submitted electronically as an XML file named 09531-0418002_SL_ST26.xml. The XML file, created on Nov. 6, 2023, is 552,379 bytes in size. The material in the XML file is hereby incorporated by reference in its entirety.

TECHNICAL FIELD

This document relates to materials and methods for inducing genetic alterations in meristematic plant tissue.

BACKGROUND

The ability to generate plants with a desired genetic makeup, whether commercially or for basic research, is limited by two facets—the delivery of genetic engineering (GE) reagents and the subsequent generation of edited tissues. Procedures for delivery of GE reagents typically utilize the gene transferring bacterium *Agrobacterium tumefaciens*, or physical means such as particle bombardment. After delivery of reagents, many protocols require subsequent regeneration of the edited somatic tissue into whole plants. Transformed somatic tissue often is pushed to de-differentiate (into callus) and then re-differentiate using tissue culture media containing specific hormone ratios required to drive shoot or root formation. Tissue culture techniques can be complicated by the fact that a majority of agriculturally relevant crop lines are recalcitrant to tissue culture regeneration. Additionally, this process can be time consuming and technically demanding, requires sterile conditions, and may be subject to undesired genetic alterations due to prolonged exposure to hormones. Efforts also may be confounded because resulting tissues can present non-specific chimerism for the transgene, requiring more than one generation to fix the genetic event of interest. All of these limitations render current practices for plant genetic engineering non-ideal for large scale generation of edited plants in a high throughput manner.

Developmental regulatory genes have been employed to generate tissues with modifications of interest. For example, controlled expression of the maize regulatory genes WUSCHEL (WUS) and BABY BOOM (BBM) induced somatic embryogenesis from immature maize embryos, as well as other somatic tissues (Lowe et al., *Plant Cell* 28(9): 1998-2015, 2016; and Mookkan et al., *Plant Cell Reports* 36(9): 1477-1491, 2017). Hundreds of plantlets were recovered from these somatic embryos even in lines previously recalcitrant to tissue culture, and the generated somatic embryos were capable of developing into full plants with the transgene cassette of interest. Despite this improvement to standard monocot regeneration practices, however, the generation of full plants still required tissue culture steps, sterile technique, and explant handling. In addition, these techniques were only demonstrated in monocot species and have not been implemented in any dicot species.

SUMMARY

This document provides new techniques that avoid the constraints noted above and provide a boon for both basic research and commercial germplasm production. The combination of developmental regulators WUS and SHOOT MERISTEMLESS (STM), as well as other regulator combinations, can have an impact on patterning and formation of shoot meristems (Gallois et al., *Development* 129:3207-3217, 2002), and these developmental regulators have been ectopically expressed in *Arabidopsis thaliana* and other species to create meristem-like tissue. The methods described herein are based, at least in part, on the discovery that such genes can be combined with GE reagents to promote the formation of edited meristematic tissue that can flower and produce seed. The resultant seed is derived from a single meristematic cell, and therefore represents a clonal genetic editing event that provides an abundance of edited seed after one generation. The direct delivery method described herein also provides the advantage of avoiding tissue culture, which reduces the time needed to regenerate tissues and considerably simplifies the process of generating GE events. Thus, the methods described herein can circumvent the limitations of current plant regeneration protocols, and greatly enhance the potential for development of GE plant lines for both commercial use and basic research.

Thus, this document is based, at least in part, on the development of methods for delivery of developmental regulators to whole plants to induce the transdifferentiation of somatic plant cells in vivo for the production of meristems. These meristems can carry transgenic insertions or genetic editing events to the next generation, creating seed with a GE event of interest in a fraction of the time needed using current standard protocols. The techniques described herein can simplify protocols for transformation, remove requirements for tissue culture, and be accessible to labs with diverse skill sets.

In a first aspect, this document features a method for generating plant tissue having one or more genetic modifications of interest. The method can include (a) introducing into plant cells (i) nucleic acid encoding one or more developmental regulators that, when expressed in the plant cells, induce meristem formation from the plant cells, and (ii) nucleic acid comprising one or more sequences that, when expressed, modify a plant cell to achieve one or more genetic modifications of interest; and (b) deriving de novo tissue from plant cells identified as having the one or more genetic modifications of interest. The one or more developmental regulators can include one or more of Baby Boom, Isopentenyl Transferase, Irrepressible Variants of Monopteros, Shoot Meristemless, and Wuschel. The introducing can be by *Agrobacterium*, and the nucleic acid encoding one or more developmental regulators and the nucleic acid comprising one or more sequences that modify a plant cell can be included on the same T-DNA or on separate T-DNAs. The method can include introducing nucleic acid encoding two or more developmental regulators into the plant cells by *Agrobacterium*, where the two or more developmental regulators are encoded by a single T-DNA or are encoded by separate T-DNAs. The method can include introducing nucleic acid encoding two or more developmental regulators into the plant cells by *Agrobacterium*, where the two or more developmental regulators are encoded by two or more strains of *Agrobacterium*. The introducing can include electroporation, biolistics, particle bombardment, chemical transfection, nanoparticle delivery, or viral infection. The introducing can include transient transformation or stable transgenesis. The plant cells into which the nucleic acids are introduced can be within a differentiated tissue, within an undifferentiated tissue, within a whole plant, within a germinating seedling, or within a plant part taken from a plant. The plant cells can be cells of a monocotyledonous plant, or cells of a dicotyledonous plant. The one or more sequences that modify a plant cell can include a transgene that, when expressed in the plant cells, achieves an agriculturally relevant trait (e.g., herbicide tolerance). The one or more sequences that modify a plant cell can include a transgene that, when expressed, edits the plant DNA. For example, the one or more sequences that modify a plant cell can include a nucleotide sequence encoding a targeted endonuclease (e.g., a meganuclease, zinc finger nuclease, transcription activator-like effector nuclease, or Clustered Regularly-Interspaced Short Palindromic Repeats-associated nuclease). The one or more sequences that modify a plant cell can encode a targeted enzyme that modifies plant DNA (e.g., a cytosine deaminase or an adenosine deaminase, such as BE3 or ABE). The one or more sequences that modify a plant cell can encode a targeted endonuclease and can include a repair template to introduce one or more specific modifications into the plant genome. The de novo tissue can be meristematic and can be capable of deriving new tissue carrying the one or more genetic modifications of interest. The new tissue can include a branch, a flower, or a root.

In some cases, the method can include (a) using *Agrobacterium*, introducing into cells of a germinating seedling or a portion thereof nucleic acid encoding the one or more developmental regulators, wherein expression of the one or more developmental regulators induces meristem formation in the germinating seedling or portion thereof; (b) introducing into the cells, via the *Agrobacterium*, the nucleic acid comprising one or more sequences that, when expressed, modify the cells to achieve the one or more genetic modifications of interest; and (c) culturing the meristem induced by the one or more developmental regulators, to obtain modified plant tissue comprising the one or more genetic modifications of interest. The method can include introducing nucleic acid encoding two or more developmental regulators, wherein the two or more developmental regulators are encoded by one T-DNA or by separate T-DNAs. The method can include introducing nucleic acid encoding two or more developmental regulators, where the two or more developmental regulators are encoded by separate strains of *Agrobacterium*. The germinating seedling or portion thereof can be from a monocotyledonous plant or from a dicotyledonous plant. The one or more genetic modifications can include insertion of a transgene that, when expressed, achieves an agriculturally relevant trait (e.g., herbicide tolerance). The one or more genetic modifications can include insertion of a transgene that, when expressed, edits the plant cell DNA. The nucleic acid that modifies a plant cell can encode a targeted endonuclease (e.g., a meganuclease, zinc finger nuclease, transcription activator-like effector nuclease, or Clustered Regularly-Interspaced Short Palindromic Repeats-associated nuclease). The nucleic acid that modifies a plant cell can encode a targeted enzyme that modifies plant DNA (e.g., a cytosine deaminase or an adenosine deaminase, such as BE3 or ABE). The nucleic acid that modifies a plant cell can encode a targeted endonuclease and can include a repair template to introduce a specific modification into the genetic material of the plant cell. The method can further include assaying the meristem induced by the one or more developmental regulators for the one or more genetic modifications of interest, and subsequently generating a whole plant from the meristem induced by the one or more developmental regulators. The method also can include placing the meristem induced by the one or more developmental regulators directly into culture and inducing the meristem in culture to form a plant.

In another aspect, this document features a method for generating plant tissue containing one or more genetic modifications of interest. The method can include (a) using *Agrobacterium*, introducing into cells of a germinating seedling or a portion thereof nucleic acid encoding one or more developmental regulators, wherein expression of the one or more developmental regulators induces meristem formation in the germinating seedling or portion thereof; (b) simultaneously introducing into the cells, via the *Agrobacterium*, nucleic acid that modifies genetic material within the cells to achieve one or more targeted genetic modifications of interest; and (c) culturing the meristem induced by the one or more developmental regulators, to obtain modified plant tissue containing the one or more genetic modifications of interest. The one or more developmental regulators can include, for example, one or more of Baby Boom, Isopentenyl Transferase, Irrepressible Variants of Monopteros, Shoot Meristemless, and Wuschel. The method can include introducing two or more developmental regulators into cells of the germinating seedling or portion thereof, where the two or more developmental regulators are encoded by one T-DNA, or where the two or more developmental regulators are encoded on separate T-DNAs. The method can include introducing two or more developmental regulators into cells of the germinating seedling or portion thereof, where the two or more developmental regulators are encoded by two or more strains of *Agrobacterium*.

The germinating seedling or portion thereof can be from a monocotyledonous plant or from a dicotyledonous plant. The one or more targeted genetic modifications can include insertion of a transgene that, when expressed, achieves an agriculturally relevant trait (e.g., herbicide tolerance). The one or more targeted genetic modifications can include insertion of a transgene that, when expressed, edits the plant cell DNA. The nucleic acid that modifies a plant cell can encode a targeted endonuclease, such as a meganuclease, zinc finger nuclease (ZFN), transcription activator-like effector (TALE) nuclease, or clustered regularly-interspaced short palindromic repeats (CRISPR)/CRISPR associated (Cas) nuclease. The nucleic acid that modifies a plant cell can encode a targeted enzyme that modifies plant DNA. The targeted enzyme can be a cytosine deaminase or an adenosine deaminase (e.g., BE3 or ABE). The nucleic acid that modifies a plant cell can encode a targeted endonuclease and can contain a repair template to introduce a specific modification into the genetic material of the plant cell. The method can further include assaying meristem induced by the one or more developmental regulators for the one or more genetic modifications of interest, and subsequently generating a whole plant from the meristem induced by the one or more developmental regulators. The method can further include placing the meristem induced by the one or more developmental regulators directly into culture and inducing the meristem in culture to form a plant.

In another aspect, this document features a method for generating plant tissue containing one or more genetic modifications of interest. The method can include (a) introducing into plant cells (i) nucleic acid encoding one or more developmental regulators that, when expressed in the plant cells, induce meristem formation from the plant cells, and (ii) nucleic acid comprising one or more sequences that modify a plant cell to achieve one or more genetic modifications of interest; and (b) deriving de novo tissue from plant cells identified as having the one or more genetic modifications of interest. The one or more developmental regulators can include one or more of Baby Boom, Isopentenyl Transferase, Irrepressible Variants of Monopteros, Shoot Meristemless, and Wuschel. The introducing can be by *Agrobacterium*, and the nucleic acid encoding one or more developmental regulators and the nucleic acid comprising one or more sequences that modify a plant cell can be included on the same T-DNA. Alternatively, the nucleic acid encoding one or more developmental regulators and the nucleic acid comprising one or more sequences that modify a plant cell can be included on separate T-DNAs. The method can include introducing nucleic acid encoding two or more developmental regulators into the plant cells by *Agrobacterium*, where the two or more developmental regulators are encoded by a single T-DNA, or where the two or more developmental regulators are encoded by separate T-DNAs. The method can include introducing nucleic acid encoding two or more developmental regulators into the plant cells by *Agrobacterium*, where the two or more developmental regulators are encoded by two or more strains of *Agrobacterium*. The introducing can include electroporation, nanoparticle delivery, biolistics, particle bombardment, chemical transfection, or viral infection. The method can include transient delivery of the one or more developmental regulators or stable integration of genes encoding the one or more developmental regulators into the plant genome by any of the above means of delivery.

The plant cells into which the nucleic acids are introduced can be within a differentiated tissue, or within an undifferentiated tissue. The plant cells into which the nucleic acids are introduced can be within a whole plant, or within a plant part taken from a plant. The plant cells can be of a monocotyledonous plant or a dicotyledonous plant.

The one or more sequences that modify a plant cell can include a transgene that, when expressed in the plant cells, achieves an agriculturally relevant trait (e.g., herbicide tolerance). The one or more sequences that modify a plant cell can include a transgene that, when expressed, edits the plant DNA. The one or more sequences that modify a plant cell can include a nucleotide sequence encoding a targeted endonuclease, such as a meganuclease, ZFN, TALE nuclease, or CRISPR/Cas nuclease. The one or more sequences that modify a plant cell can encode a targeted enzyme that modifies plant DNA (e.g., a cytosine deaminase or an adenosine deaminase, such as BE3 or ABE). The one or more sequences that modify a plant cell can encode a targeted endonuclease and can include a repair template to introduce one or more specific modifications into the plant genome. The de novo tissue can be meristematic and capable of deriving new tissue carrying the one or more genetic modifications of interest. The new tissue can include a branch, a flower, or a root.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A-2F show the generation of de novo tissues from injection sites.

Reagents for the induction of de novo shoot meristems were delivered to *Nicotiana benthamiana* as outlined in FIG. 1. For this experiment, *Agrobacterium* was injected into somatic tissues. The delivered T-DNA contained a geminiviral replicon (GVR) designed to circularize and replicate within a plant cell. The replicon contained a luciferase reporter (SEQ ID NO:14) for visualization of vector presence, as well as the developmental regulators WUS (SEQ ID NO:6) and STM (SEQ ID NO:7). FIGS. 2A, 2B, 2C, and 2D are representative of induced de novo growth observed for multiple plants. FIGS. 2E and 2F are images providing visual confirmation that in some cases, newly formed tissues contained the reporter gene, as evidenced by imaging in bright field (FIG. 2E) and bioluminescence (FIG. 2F).

FIGS. 3A to 3G show the results of molecular analyses to assess the delivery of developmental regulators and editing of de novo tissue. *Agrobacterium* was used to deliver a T-DNA containing sequences encoding developmental regulators, a luciferase reporter gene, and a guide RNA (gRNA) targeting an endogenous site in the genome of *N. benthamiana* plants transgenic for 35S:Cas9. The *Agrobacterium* solution was delivered to somatic tissues by injection (FIGS. 3C and 3F; injection sites are indicated by boxes). Sample tissues were harvested at distal sites of tissue generated from the injection sites (FIGS. 3C and 3F; harvest sites are indicated by circles). Tissue samples were treated with luciferin and imaged for bioluminescence (FIGS. 3A and 3D, bright field; FIGS. 3B and 3E, luminescence). Genomic DNA was isolated from the harvested tissue by cetyl trimethylammonium bromide (CTAB) extraction, and the genomic region targeted by the gRNA was amplified by PCR and subjected to NcoI endonuclease digestion prior to electrophoresis (FIG. 3G). The Cas9 endonuclease could induce mutations to destroy the NcoI site at the gRNA target. Thus, the WT "un-edited" genomic sequence produced a lower molecular weight band upon NcoI digestion (FIG. 3G, solid arrow), while undigested "edited" DNA produces a higher molecular weight band (dashed arrow). Samples 114-2 and 155-1 showed complete cutting (lanes 3 and 5) and therefore do not have induced mutations. Samples 114-1 and 115-2 (lanes 1 and 7) demonstrated incomplete cutting by NcoI, denoting gRNA-induced mutations. The positive control (Pos) was obtained by leaf infiltration followed by leaf DNA isolation 7 days post infection.

FIGS. 4A to 4G show that edited shoots are discernable by phenotype due to targeted editing. Transgenic *N. benthamiana* plants expressing 35S:Cas9 were exposed to developmental regulators to induce de novo tissue formation. The developmental regulators were delivered either as a coinfection of *Agrobacterium* strains containing WUS or STM on separate T-DNA vectors (FIG. 4A) or as a single T-DNA vector containing WUS and IPT (FIG. 4B). All vectors included a gRNA targeting both NbPDS homologs present in the genome (SEQ ID NOS:16 and 17). A PDS knock-out phenotype was observed as white sectoring (FIG. 4A) or as completely white de novo meristems (FIGS. 4B and 4C) formed from the injection site. To molecularly characterize targeted mutation of both PDS homologs, genomic DNA was isolated from select tissues (white arrows), and was amplified by PCR and visualized for induced mutations at the gRNA target sites. As two homologs of the NbPDS gene exist in the *N. benthamiana* genome, primers were used that selectively amplify either homolog 1 (Niben101Scf14708g00023.1; FIG. 4D) or homolog 2 (Niben101Scf01283g02002.1; FIG. 4E). Incomplete digestion of PCR amplicons by the restriction enzyme NcoI denoted a mutation within the restriction recognition site. Amplification of Scf14708g00023.1 provided a band of 712 bp, while a NcoI digested band was visible at 648 bp. Amplification of Scf01283g02002.1 provided a band of 755 bp, and a corresponding cleaved 691 bp band after NcoI digest. Tissue samples assayed for the split vector system were completely modified at the Scf14708g00023.1 locus as observed by undigested restriction bands in the digest assay (FIG. 4D, lane 2), but appeared unedited (completely digested) at the Scf01283g02002.1 locus (FIG. 4E, lane 2). This pattern was reversed for the combination vector. Positive control ("Editing Cont.") was acquired by infiltrating vectors into leaf tissue and harvesting DNA 7 days post infection, and was expected to demonstrate chimerism (both cleaved and uncleaved bands; FIGS. 4D and 4E, lane 6). Negative control ("Digest Cont.") utilized genomic DNA isolated from an uninoculated plant (FIGS. 4D and 4E, lane 8). While restriction digest assays did not show editing for some samples (FIG. 4D, lane 4; FIG. 4E, lane 2), Illumina sequencing performed on genomic amplifications of Scf14708g00023.1 validated the presence of genomic edits when WUS or STM were delivered on separate T-DNA vectors (FIG. 4F; from top to bottom, SEQ ID NOS:38, 39, 40, and 38) or when WUS and IPT were delivered via a single T-DNA vector (FIG. 4G; from top to bottom, SEQ ID NOS:38, 40, and 39). The frequency of edits inferred the tissues present were non-chimeric as compared to negative controls. In addition, edits that could not be visualized by restriction digest were confirmed as edited for both alleles of both homologs of PDS (targeted mutations involved a 'C' insertion that did not destroy the CCATGG NcoI site).

FIGS. 5A and 5B further demonstrate the ability to create targeted mutations in the *N. benthamiana* PDS2 locus (SEQ ID NO:17). Constructs introduced included a single vector containing WUS and STM (WUS/STM, SEQ ID NO:30) a single vector containing WUS and IPT (WUS/IPT; SEQ ID NO:31) a combination of co-inoculated vectors each containing a single DR (STM, IPT, WUS, MPΔ, and BBM; SEQ ID NOS:33, 34, 35, 36, and 37, respectively). FIG. 5A is a table providing results from these studies. Derived shoots were given individual designators to facilitate tracking of samples (FIG. 5A, column 2). Purified genomic DNA was amplified for the PDS2 locus. Amplicons were pooled and submitted for next generation sequencing. The observed number of sequences containing the expected forward and reverse barcodes (column 3), the number of sequences observed to have non-specific DNA insertions at the sgRNA target site (column 4), the number of sequences observed to have targeted mutations at the sgRNA target site (column 5), and the total number of sequences that were observed to have targeted modifications (column 6) are provided. Mutations observed at a frequency >30% of the total are denoted in column 7. "Seed produced" (column 8) indicates whether sampled shoots were identified that produced seed. It was observed that one sample (5-14-1-08) produced seed capable of transmitting genomic modifications to the next generation. FIG. 5B shows the sequences of mutations observed by next generation sequencing for plants listed in FIG. 5A.

FIG. 6 is a graph plotting results from an injection study in *N. benthamiana*. Constructs introduced included WUS and IPT as either a single vector (WUS/IPT; SEQ ID NO:31), or a combination of co-inoculated vectors each containing a single DR (SEQ ID NOS:34 and 35), or a vector containing editing reagents but no DRs (No Dev Reg, SEQ ID NO:98). The total number of sites injected, as well as the number of shooting sites, was monitored across all plants within each group. Groups were additionally observed for the number of shoots with distorted morphology, likely induced by developmental regulators, and photobleaching due to simultaneous targeted mutations in both PDS homologs.

FIG. 8A is a table listing observed mutations for white tissues shown in FIG. 7 and for the resulting progeny. Genomic DNA was extracted from parental tissue and seedlings and submitted for Sanger sequencing. Sequences were assessed for mutations by TIDE sequence trace analysis.

FIG. 8A). Genomic DNA also was extracted from plants that did not receive the vector (Neg Ctrl1 and Neg Ctrl2), as well as from leaf tissue infiltrated with the target vector (Pos Ctrl). DNA was amplified using primers specific to the U6 promoter present on the T-DNA (expected 448 bp). Ladder=NEB 2 log.

FIG. 10A is a table listing observed mutations for green tissues shown in FIG. 7 and the resulting progeny. Genomic DNA was extracted from parental tissue and seedlings and submitted for Sanger sequencing. Sequences were assessed for mutations by TIDE sequence trace analysis.

FIG. 11 is a table listing observed phenotypes and genotypes for PDS mutations in a TO plant (plant designator 5-14-1-08; FIGS. 5A and 5B) induced to form meristems and next generation progeny. The parent plant was trimmed and co-inoculated with *agrobacterium* strains individually carrying T-DNAs harboring DRs STM (pMM131; SEQ ID NO:33), IPT (pMM134; SEQ ID NO:34), WUS (pMM135; SEQ ID NO:35), MPΔ (pMM136; SEQ ID NO:36), or BBM (pMM146; SEQ ID NO:37). Resulting induced de novo shoots were screened for PDS phenotype and genotype. Shoots were allowed to flower and set seed. Next generation progeny seed was germinated and assessed for phenotype and genotype. FIG. 11 provides information for parental shoot tissue from 5-14-1-8 and ten screened seedlings. The parent tissue was observed to harbor a −3 bp mutation in PDS1 in a heterozygous state. Progeny from this event were observed to segregate this −3 bp mutation.

FIGS. 12A-12I depict induced transgenic shooting for vectors containing a luciferase reporter in *Solanum tuberosum* (potato) and *Vitis vinifera* (grape). *Agrobacterium* strains expressing either IPT (FIGS. 12A, 12B, and 12C; SEQ ID NO:96) or co-expressing WUS and IPT (FIGS. 12D, 12E, 12F, and 12G; SEQ ID NO:94) were delivered to potato plants along with a luciferase expression cassette (SEQ ID NO:14). FIGS. 12A and 12D show abnormal shooting phenotypes induced by DRs 95 days post infection (p.i.). Transgenic shoot formation was confirmed by imaging bioluminescence of de novo shoots formed after injection (FIGS. 12B, 12C, 12E, 12F, and 12G) at 97 days p.i. Fully transgenic shoots were detected upon trimming away several wild-type shoots (FIGS. 12C and 12G), signifying stable T-DNA integration in those induced shoots (highlighted in FIG. 12C by white arrowheads). FIGS. 12H and 12I demonstrate that delivery of DRs to grape plants (Pixie Pinnot cultivar) induced transgenic shoot formation with normal growth phenotypes. FIG. 12H is an image showing an exemplary grape plant 40 days after co-inoculation of *agrobacterium* strains individually carrying T-DNA vectors with DRs (WUS, IPT, MPΔ, STM, and BBM; SEQ ID NOs: 88, 89, 90, 91, and 92, respectively). Newly formed shoots were generated at *Agrobacterium* inoculation sites. FIG. 12I shows that newly formed shoots removed from the grape plant of FIG. 12H panel were transgenic, as determined by a bioluminescence assay. Shoots were removed, exposed to luciferin substrate, and imaged for bioluminescence. The presence of bioluminescent-positive tissues indicated that the newly formed tissues were transgenic and expressed the luciferase reporter.

FIGS. 16A to 16H show confirmation of editing occurring in generated growths. Using the Fast-TrACC method, gene editing reagents were delivered along with the developmental regulators WUS and STM to promote the formation of edited growths. Five out of twenty-four seedlings had growths (FIG. 16A) that were candidates for molecular analysis. Using primers in NbPDS (Niben101Scf14708g00023.1), the target locus was amplified and tested for edits via a RFLP assay (FIG. 16B). The growths also were tested for amplification of Rep (FIG. 16C) to indicate the presence of the T-DNA. The isolated DNA samples were submitted for next generation sequencing (NGS; FIGS. 16D to 16H) for the NbPDS locus of interest to determine the frequency and scope of edits made. A variety of different edits were detected at the target site, with a single cytosine insertion and a single base deletion being the most consistently observed edits. Sequences that likely were the product of PCR induced mutation (asterisks) also were observed; these are not likely to have been caused by the delivered editing reagents. FIG. 16D, top to bottom: SEQ ID NOS:38, 40, 41, 39, 42, 43, 44, 45, 46, 47, 48, and 49. FIG. 16E, top to bottom: SEQ ID NOS:38, 40, 39, 50, 51, N/A, 52, 45, N/A, 53, 43, 54, 41, 44, 55, 56, 57, and 58. FIG. 16F, top to bottom: SEQ ID NOS:38, 40, 44, 39, 59, N/A, 45, 49, 41, 60, 50, 48, 61, and 62. FIG. 16G, top to bottom: SEQ ID NOS:38, 40, 39, 44, 45, 42, 50, 63, 41, 64, 54, N/A, 65, and 66. FIG. 16H, top to bottom: SEQ ID NOS:38, 40, 39, 45, 67, 41, N/A, 49, 44, N/A, 50, 68, 69, 57, and 48. N/A, no sequence identifier if less than 10 nucleotides in length.

FIGS. 17A to 17I show results for mosaic plantlets derived from growths.

Plantlets were regenerated from developmental regulator derived growths that received gene editing components (Cas9 and NbPDS gRNA). These plantlets exhibited a range of phenotypes, with individuals that appeared mostly wild type (FIGS. 17A and 17B) as well as individuals exhibiting abnormal leaf or branch phenotypes (FIG. 17C), or generally disorganized states. DNA isolated from leaves using CTAB was pooled and submitted for NGS sequencing at the NbPDS (Niben101Scf14708g00023.1) locus. The resulting spectrum of edited reads indicated that the derived plantlets were mosaics of different edits. The proportion of reads isolated that contained edits was fairly low (FIGS. 17D, 17E, and 17F), but clearly detectable. The most commonly induced mutations of those observed (FIGS. 17G, 17H, and 17I) were single base insertions and deletions, as expected. FIG. 17G, top to bottom: SEQ ID NOS:38, 38, 40, 39, 70, N/A, and 71. FIG. 17H, top to bottom: SEQ ID NOS:38, 38, 40, 39, 52, N/A, 47, 50, N/A, 44, 58, N/A, 72, 60, 73, 68, 45, 74, 48, and 75. FIG. 17I, top to bottom: SEQ ID NOS:38, 38, 40, 71, 39, 76, 51, N/A, 77, 45, 44, 54, 43, and 48. N/A, no sequence identifier if less than 10 nucleotides in length.

FIG. 19A is a table listing characteristics for plants that received various combinations of DRs. To determine combinations of DRs that were most effective in creating de novo meristems, *A. tumefaciens* strains each carrying a single DR delivered individually or in various pools to *N. benthamiana* seedlings, which were monitored for de novo growth formation. Out of twelve tested options, five combinations produced de novo meristems and subsequent plants. The number of seedlings, growths, shoot-like growths, white shoot-like growths, and full plants for these five combinations are plotted in FIG. 19B.

FIGS. 22A-22J demonstrate results for tomato. To induce de novo meristems in tomato, combinations of developmental regulators that effectively induced meristems in *N. benthamiana* were tested (WUS+IPT and two combinations of WUS+STM). For both combinations of WUS and STM, no shoot-like growths were formed (FIGS. 21A and 21C), and substantial tissue necrosis was observed after delivery. In contrast, the combination of WUS and IPT promoted shoot-like growths (FIGS. 21A and 21C), which ultimately formed fully rooted plants (FIG. 21B). WUS and IPT were then delivered to tomato seedlings on either a single vector (WUS/IPT) or on separate vectors in two different *Agrobacterium* strains (WUS&IPT). Both WUS/IPT and WUS&IPT showed an increase in the frequency of average growths per plant over the background level of growths that developed on plants that did not receive developmental regulators (FIGS. 22D and 22J). Shoot-like growths form from the WUS and IPT derived growths (FIGS. 22E and 22J), and luciferase positive, meristem-like structures were observed (FIG. 22F (boxed) and 22G, arrowhead). These structures progressed to form shoot-like growths (FIG. 22H) that were excised and assessed for luminescence (FIG. 22I). Four out of 15 shoot-like growths showed evidence of luminescence (FIGS. 22I and 22J).

DETAILED DESCRIPTION

A principle goal of GE techniques is the creation of an editing event in the germline of an organism so that the modification can be transmitted to the next generation. For plants, the germline is produced by reproductive tissues derived from the meristem, instead of from isolated gametophyte cells. Plant meristems are the developmental centers of the plant from which all ensuing plant growth is derived. If these stem cells are edited, all tissues subsequently derived from the meristem should contain the GE event(s) of interest, leading to transmission to the next generation. Direct modification of existing meristematic tissue has proven challenging, as it is a highly regulated tissue type that has historically been recalcitrant to genetic modification. This little understood barrier, among other factors, has necessitated the use of suboptimal tissue culture procedures for most agriculturally relevant crops.

The present document is based, at least in part, on the discovery that developmental regulators can be combined with GE reagents to promote the formation of edited meristematic tissue that can flower and produce seed. The methods described herein include steps for delivery of developmental regulators to whole plants to induce the transdifferentiation of somatic plant cells in vivo, leading to the production of meristems. These meristems can carry transgenic insertions or genetic editing events to the next generation, creating seed with a GE event of interest in a fraction of the time needed using current standard protocols. Because the seed is derived from a single meristematic cell, it represents a clonal genetic editing event that provides an abundance of edited seed after a single generation. The direct delivery methods described herein also provide the advantage of avoiding tissue culture, which can reduce the time needed to regenerate tissues and considerably simplifies the process of generating GE events. Thus, the methods provided herein can circumvent the limitations of current plant regeneration protocols, and greatly enhance the potential for development of GE plant lines for both commercial use and basic research.

Figure 1:
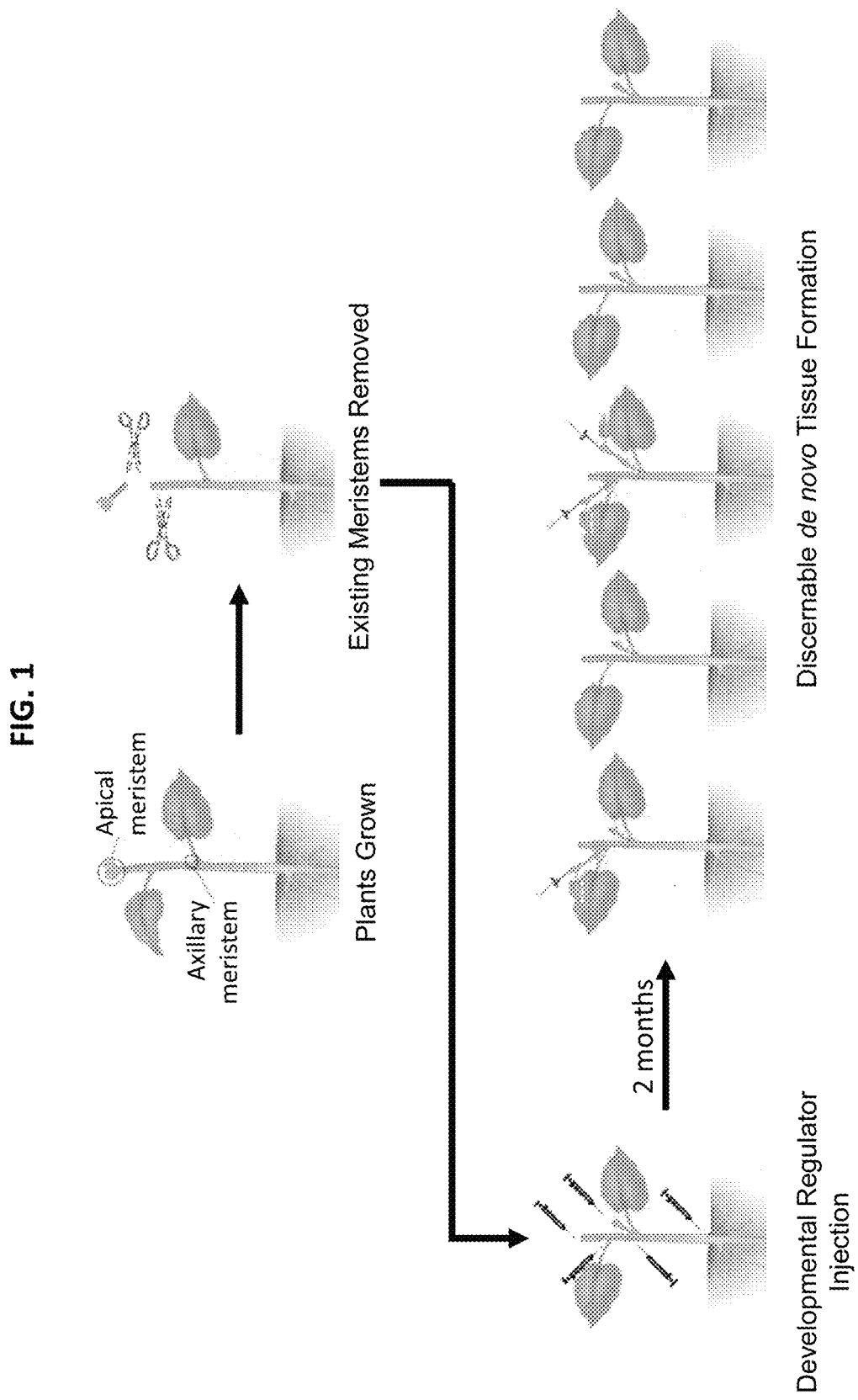
FIG. 1 is a diagram depicting an experimental procedure for a direct injection method as provided herein. Plants can be grown to a developmental stage at which axillary shoot meristems are visualized. Removal of existing shoot meristem tissue (shoot apical meristem and axillary meristems) can be performed to increase the potential for de novo shoot formation. Reagents to create a genetic change and to stimulate growth of de novo tissue can be delivered to plant tissues by various means, including direct injection as depicted in FIG. 1. The delivered reagents can result in induction of de novo shoots, as well as other somatic tissues, and the newly formed tissue(s) can contain the genetic change of interest.

In some embodiments, this document provides methods in which plants can be grown to a desired stage in either sterile or non-sterile conditions (e.g., soil). In these methods, one or more developmental regulators can be delivered to select tissues, either by *Agrobacterium* or through ectopic means such as direct injection, electroporation, particle bombardment, biolistics, chemical transfection, viral infection, nanoparticle delivery, or any other suitable means for transient transfection or stable integration (exemplified in FIG. 1). In some cases, pre-existing meristems can be removed prior to delivery of the one or more developmental regulators. The tissues can summarily be induced to produce meristematic tissues containing a GE event of interest. Importantly, this method can obviate the need for sterile tissue culture and advanced equipment, significantly reducing the cost and level of expertise necessary to carry out experiments.

Non-limiting examples of developmental regulators that can be used in the methods provided herein are listed in TABLE 1. As used herein, a "developmental regulator" (DR) is an agent (e.g., a transcription factor, an enzyme, or a hormone) that directs or influences a plant's development, and may guide the differentiation of plant cells, organs, or tissues. For example, a DR can be a transcription factor (e.g., Baby Boom, Irrepressible Variants of Monopteros, Shoot Meristemless, or Wuschel) that can stimulate plant hormone biosynthesis or plant susceptibility to/sensing of cytokinins or other plant hormones that affect plant development and lead to de novo meristem development. In some cases, a DR can lead to increased cytokinin levels. Therefore, a DR also can be a means of increasing one or more cytokinins through ectopic application or through endogenous biogenesis, such as by increasing the expression of one or more enzymes involved in the synthesis of plant hormones. Thus, in some cases, a DR can be an enzyme involved in synthesis of plant hormones, such as Isopentenyl Transferase, which is in the cytokinin biosynthesis pathway. Other examples of enzymes that can lead to increased cytokinin levels and may be useful as DRs include, without limitation, tRNA-isopentenyltransferase, cytochrome P450 monooxygenase, LONELY GUY, adenosine kinase, and adenine phosphoribosyltransferase. A nucleic acid encoding a DR also is considered to be a DR for the purposes of this document, since the nucleic acid can be delivered to plant cells (e.g., in a whole plant or plant part) in order to increase the level of the encoded DR. The DR coding sequence can be operably linked to a promoter (e.g., Nos, 35S, CmYLCV, AtUBQ10, or any other appropriate promoter) that drives expression of the DR in plant cells. Moreover, in some cases, a DR can be a means of increasing expression of genes downstream of the DRs listed in TABLE 1.

Thus, in some embodiments of the methods provided herein, one or more of the DRs listed in TABLE 1 can be delivered to a plant or a plant part.

TABLE 1

| Developmental Regulators | |
| --- | --- |
| Name | Abbreviation |
| Baby Boom | BBM |
| Isopentenyl Transferase | IPT |
| Irrepressible Variants of Monopteros | MPΔ |
| Shoot Meristemless | STM |
| Wuschel | WUS |
| Leafy Cotyledon 1 | LEC1 |
| Wound Induced Dedifferentiation 1 | WIND1 |

Exemplary sequences for at least some of the above-referenced DRs and promoters are provided in the attached sequence listing. It is to be noted, however, that homologs of these DRs exist in numerous plant species, and the methods provided herein are not limited to use of the listed DRs or to DRs having 100% identity to the provided sequences. In some cases, for example, a DR coding sequence can have at least 80% (e.g., at least 85%, at least 90%, or at least 95%) identity to the WUS sequence set forth in SEQ ID NO:6, the STM sequence set forth in SEQ ID NO:7, the MPΔ sequence set forth in SEQ ID NO:8, the BBM sequence set forth in SEQ ID NO:9 or SEQ ID NO:10, or the IPT sequence set forth in SEQ ID NO: 11. Further, in some cases, a DR can have an amino acid sequence that is at least 80% (e.g., at least 85%, at least 90%, or at least 95%) identical to the WUS sequence set forth in SEQ ID NO: 118, the STM sequence set forth in SEQ ID NO:119, the MPΔ sequence set forth in SEQ ID NO:120, the BBM sequence set forth in SEQ ID NO:121, or the IPT sequence set forth in SEQ ID NO:122.

The terms "percent identity" or "identity" in the context of two or more nucleic acids or polypeptides refer to two or more sequences that are the same or have a specified percentage of nucleotides or amino acid residues that are the same. The percent identity can be measured using sequence comparison software or algorithms or by visual inspection.

In general, percent sequence identity is calculated by determining the number of matched positions in aligned nucleic acid or polypeptide sequences, dividing the number of matched positions by the total number of aligned nucleotides or amino acids, respectively, and multiplying by 100. A matched position refers to a position in which identical nucleotides or amino acids occur at the same position in aligned sequences. With regard to DR sequences, the total number of aligned nucleotides or amino acids refers to the minimum number of DR nucleotides or amino acids that are necessary to align the second sequence, and does not include alignment (e.g., forced alignment) with non-DR sequences. The total number of aligned nucleotides or amino acids may correspond to the entire DR sequence or may correspond to fragments of a full-length DR sequence.

Sequences can be aligned using the algorithm described by Altschul et al. (*Nucleic Acids Res*, 25:3389-3402, 1997) as incorporated into BLAST® (basic local alignment search tool) programs, available at ncbi.nlm.nih.gov on the World Wide Web. BLAST® searches or alignments can be performed to determine percent sequence identity between a DR nucleic acid or amino acid sequence and any other sequence or portion thereof using the Altschul et al. algorithm. BLASTN is the program used to align and compare the identity between nucleic acid sequences, while BLASTP is the program used to align and compare the identity between amino acid sequences. When utilizing BLAST® programs to calculate the percent identity between a NOTCH sequence and another sequence, the default parameters of the respective programs are used.

Figure 13:
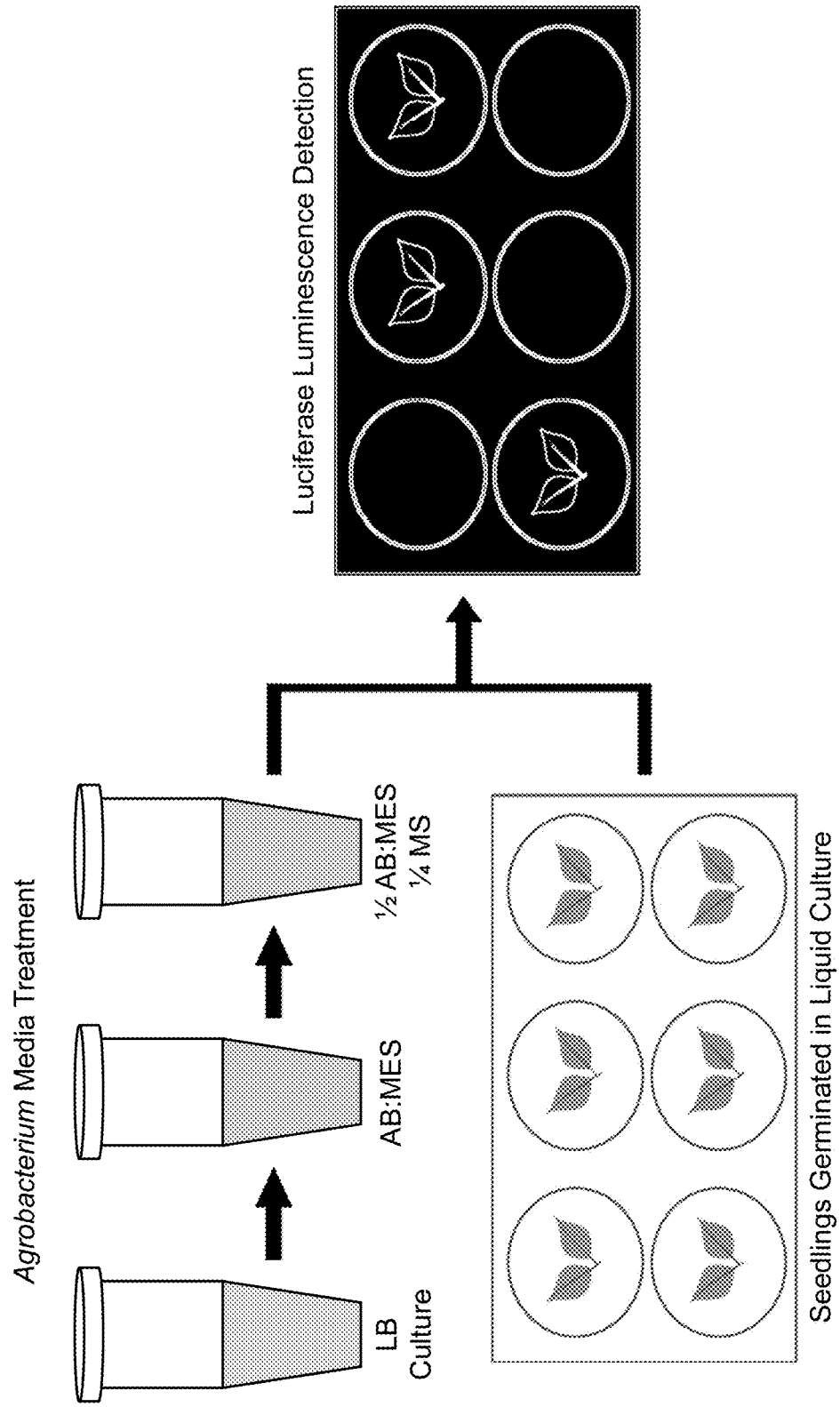
FIG. 13 is a diagram showing the steps of a Fast-TrACC delivery method as provided herein. As depicted, Fast-TrACC delivery involves three days of treatment with an *Agrobacterium tumefaciens* culture of interest, where the Agrobacteria contain one or more T-DNAs that encode one, two, or more developmental regulators, and also contain nucleic acid sequences that can result in a genetic change within a plant. The T-DNA also can include a reporter such as a luciferase gene. In the first step, Agrobacteria cultures are grown overnight to achieve confluency. Next, cultures are resuspended in AB:MES salts to increase the expression of vir genes, and grown overnight again. The final treatment involves combining AB:MES salts with plant growth media (½ MS) to promote the activity of both the bacteria and the seedlings being co-cultured. After the final treatment, the Agrobacteria are combined with seedlings roughly 2-3 days post germination. The co-culture is incubated for two days before the seedlings are washed free of the Agrobacteria. The washed seedlings are returned to liquid ½ MS containing the antibiotic Timentin to kill off any residual Agrobacteria. Using a reporter such as luciferase, seedlings can be analyzed for delivery of the T-DNA construct.

This document also provides methods that are referred to herein as "Fast-TrACC" (Treated *Agrobacterium* Co-Culture) methods (exemplified in FIG. 13). Fast-TrACC methods involve the co-culture of germinating seedlings with treated *Agrobacterium* to deliver gene cassettes encoding developmental regulators. The developmental regulators can be broadly delivered to somatic cells in a variety of tissue types within the germinating seedlings. Cells expressing the developmental regulators, and their surrounding neighbors, can then be induced into a meristematic growth pattern that subsequently derives plant tissues of interest (e.g., shoots). In addition to the cassettes encoding the developmental regulators that promote shoot formation, one or more transgenes can be co-delivered. In some cases, the one or more transgenes themselves can create a GE event of interest. Alternatively, the transgene(s) can encode one or more gene editing reagents that can make precise alterations to the developing meristem, or to somatic cells prior to transdifferentiation, to create the desired GE event.

Both types of methods described herein can offer new and broadly applicable approaches to solve current bottlenecks in delivery of GE reagents, as well as the regeneration of tissues carrying GE events of interest. Inherently, in vivo delivery of developmental regulators provides a means to easily deliver reagents to somatic tissues, and also provides positive selection for cells receiving GE reagents. By inducing transdifferentiation of somatic cells and subsequent growth on existing tissues, the significant periods of time that otherwise would be necessary for regeneration and development of whole plant tissues can be avoided. Additionally, as these developmental regulators are evolutionarily conserved, these method are amenable to use across a variety of species. Finally, the methods may avoid regulatory hurdles in the development of agricultural crops, as there is potential for transient delivery of reagents and subsequent recovery of non-transgenic progeny carrying a GE event of interest.

Thus, in some embodiments, this document provides methods for generating plant cells, plant parts, plant tissues, or plants that contain one or more genetic modifications of interest, where the methods can include removing existing meristems from a plant, and then introducing nucleic acids into cells of the remaining plant. The introduced nucleic acid sequences can (1) encode one or more (e.g., two, three, four, or more) developmental regulators such as WUS, BBM, IPT, MPΔ, and/or STM to induce meristem formation, and (2) edit endogenous sequences within the plant cells, or encode polypeptides that act to edit endogenous sequences within the plant cells, to result in a genetic modification of interest. As a result of introducing these nucleic acid sequences, de novo tissue subsequently derived from the plant can carry the genetic modification of interest. In some cases, the de novo tissue can be meristematic, and capable of deriving new tissue (e.g., branch, flower, or root tissue) carrying the genetic modification(s) of interest.

The nucleic acids provided to the plant (e.g., after removal of existing meristems) can be delivered by any suitable method, including by *Agrobacterium*—in which case the developmental regulator(s) and the editing sequence(s) can be delivered on the same T-DNA or on separate T-DNAs. In some cases, the nucleic acids can be delivered by direct injection, electroporation, biolistics, nanoparticle delivery, particle bombardment, chemical transfection, viral infection, or any other useful method that can result in transient expression or stable integration of the delivered nucleic acid sequences. When two or more developmental regulators are delivered by *Agrobacterium*, they can be present on the same T-DNA or on separate T-DNAs. In some cases, different strains of *Agrobacterium* can be used to deliver the developmental regulator(s) and the gene editing component(s). In addition, it is to be noted that the T-DNA(s) used in the methods provided herein can include any suitable replicon. In some cases, for example, a T-DNA can include a viral replicon (e.g., a geminivirus replicon), which can include any appropriate virus component (e.g., RepA) to enable the generation of meristems.

In some embodiments, this document also provides methods for generating plant cells, plant parts, plant tissues, or plants that contain a genetic modifications of interest, where the methods include using *Agrobacterium* to introduce nucleic acids into germinating seedlings. The nucleic acids can (1) encode one or more (e.g., two, three, four, or more) developmental regulators such as WUS, BBM, IPT, MPΔ, and/or STM to induce meristem formation in the germinating seedling, and (2) edit endogenous sequences within cells of the seedlings, or encode polypeptides that act to edit endogenous sequences within cells of the seedlings, to result in a genetic modification of interest. The methods can further include culturing meristem generated as a result of expression of the developmental regulator(s), to yield modified plant cells, plant tissue, plant parts, and/or plants that contain the genetic modification of interest.

The developmental regulator(s) and the editing nucleic acid(s) can be introduced into the seedling via the same T-DNA or via separate T-DNAs, or even via different strains of *Agrobacterium*. Similarly, when two or more developmental regulators are used, they can be introduced into the seedling via the same T-DNA, or via separate T-DNAs or different strains of *Agrobacterium*.

The methods provided herein can be used with monocotyledonous plants, plant cells, plant tissues, and plant parts (e.g., banana, grasses such as Brachypodium distachyon), wheat, oats, barley, maize, *Haynaldia villosa*, millet, palms, orchids, onions, pineapple, rice, rye, sorghum, and sugarcane) and dicotyledonous plants, plant cells, plant tissues, and plant parts (e.g., alfalfa, amaranth, *Arabidopsis*, beans, *Brassica*, carnations, chrysanthemums, citrus plants, coffee, cotton, *eucalyptus*, grape, *impatiens*, melons, peanuts, peas, peppers, *Petunia*, poplars, potatoes, rapeseed, roses, safflower, soybeans, squash, strawberry, sugar beets, sunflower, tobacco, tomatoes, and woody tree species).

In some cases, the methods provided herein can be used to obtain plants, plant tissues, plant parts, and plant cells having a desired trait, such as an agriculturally relevant trait. Agriculturally relevant traits can include, without limitation, herbicide tolerance, resistance to diseases and pests, growth rate, size, shape, color, and flavor of harvested products. For example, the methods provided herein can be used to insert a transgene into the genomic sequence of a plant cell, where expression of the transgene yields the desired trait. In some cases, expression of an inserted transgene can produce a polypeptide that edits the plant DNA. Examples of such polypeptides include targeted rare-cutting endonucleases (e.g., meganucleases, zinc finger nucleases (ZFNs), transcription activator-like effector (TALE) endonucleases, and RNA-guided endonucleases such as clustered regularly-interspaced short palindromic repeats (CRISPR)/CRISPR associated (Cas) endonucleases), as well as targeted cytosine or adenosine deaminases (e.g., apolipoprotein B mRNA editing enzyme, catalytic polypeptide-like (APOBEC)-CRISPR/Cas fusions such as BE3, and ABE). Methods for making and using such targeted DNA modifying enzymes are described elsewhere. See, e.g., Sander et al., *Nature Methods*, 8:67-69, 2011; Jacoby et al., *Nucl. Acids Res.*, 10.1093/nar/gkr1303, 2012); Christian et al., *Genetics*, 186: 757-761, 2010; U.S. Publication No. 2011/0145940; Cong et al., *Science* 339:819-823, 2013; and Mali et al., *Science* 339:823-826, 2013. For example, CRISPR/Cas systems use RNA base pairing to direct DNA or RNA cleavage by a Cas endonuclease. CRISPR RNA (crRNA) and transactivating crRNA (tracrRNA) sequences direct the Cas enzyme to a specific target DNA sequence (Makarova et al., *Nat Rev Microbiol*, 9(6):467-477, 2011). The modification of a single targeting RNA can be sufficient to alter the nucleotide target of a Cas protein. In some cases, crRNA and tracrRNA can be engineered as a single cr/tracrRNA hybrid to direct Cas9 cleavage activity (Jinek et al., *Science*, 337(6096):816-821, 2012).

In some embodiments, a repair template also can be delivered to plant cells along with a targeted endonuclease. When the endonuclease cleaves the plant cell DNA, the repair template can become integrated into the plant cell's genomic DNA, thus introducing a specific modification into the plant genome.

The methods provided herein also can include culturing the meristem induced by the developmental regulator(s) to give rise to a plant. In some cases, before a plant is generated from the new meristem, de novo derived tissue resulting from expression of the developmental regulator(s) can be assessed to determine whether it includes the genetic modification of interest. For example, DNA from newly derived tissue can be isolated and assessed by restriction digest, hybridization methods (e.g., Southern blotting), or sequencing to determine whether a genetic modification has occurred at the target site. In some embodiments, the expression of a reporter delivered with the developmental regulator(s) and the editing sequence(s) can first be detected, to identify tissues that are likely to carry the genetic modification.

The invention will be further described in the following examples, which do not limit the scope of the invention described in the claims.

EXAMPLES

Example 1—Vectors for Expressing Developmental Regulators

To facilitate the expression of developmental regulators in plants, T-DNA vectors encoding different arrangements of developmental regulators were generated (SEQ ID NOS:6-11. These T-DNA vectors were designed to have two developmental regulators combined on one T-DNA (SEQ ID NOS:26-32) or to contain a single developmental regulator (SEQ ID NOS:33-37). Construct descriptions are provided in TABLE 2. Developmental regulators were expressed using the 35S (SEQ ID NO:1), CmYLCV (SEQ ID NO:3), AtUBQ10 (SEQ ID NO:2), or Nos (SEQ ID NO:5) promoter. For Fast-TrACC experiments, these vectors often coexpressed the RNA guided endonuclease Cas9 (SEQ ID NO:24) driven by the 35S promoter. For many of the experiments, a gRNA was expressed under the control of an AtU6 promoter (SEQ ID NO:4) targeting both of the duplicated PDS1 homologs (Niben101Scf14708g00023.1, SEQ ID NO:16; and Niben101Scf01283g02002.1, SEQ ID NO: 17) in the *N. benthamiana* genome. A luciferase reporter gene (SEQ ID NO:14) driven by either the 35S or the CmYLCV promoter was used as a visual confirmation of construct delivery. These constructs were cloned into the T-DNA backbone of pTRANS_201 (SEQ ID NO:18) or pTRANS_221 (SEQ ID NO:19) as described elsewhere (Cermak et al., *Plant Cell* 29(6):1196-1217, 2017). This *Agrobacterium* vector was designed to deliver a T-DNA containing a modified bean yellow dwarf virus (BeYDV) capable of circularization and replication upon delivery and expression of the encoded replication protein (Rep; SEQ ID NO:25) in vivo. Replication of the replicon can enable an increased copy number of the vector, and consequently high levels of gene expression. Additionally, this vector has the potential to replicate regardless of whether it integrates into the genome, enabling transient high copy delivery of vector constructs.

TABLE 2

Construct descriptions

| Construct | Promoter: Reporter | Promoter: gRNA | Promoter: 1$^{st}$ DR | Promoter: 2$^{nd}$ DR | Base Vector | SEQ ID: |
|---|---|---|---|---|---|---|
| pRN114 | 35S: Luc+ | — | Nos: WUS | CmCLYV: STM | T-DNA w/ BeYDV Replicon, Kan Resistance | 26 |
| pRN119 | CmYLCV: Luc+ | — | Nos: WUS | 35S: STM | T-DNA w/ BeYDV Replicon, Kan Resistance | 27 |
| PRN120 | CmYLCV: Luc+ | — | Nos: WUS | AtUBQ10: STM | T-DNA w/ BeYDV Replicon, Kan Resistance | 28 |
| pRN227 | 35S: Cas9 | AtU6: NbPDS gRNA1 | Nos: WUS | CmCLYV: STM | T-DNA w/ BeYDV Replicon, Kan Resistance | 29 |

TABLE 2-continued

Construct descriptions

| Construct | Promoter: Reporter | Promoter: gRNA | Promoter: 1st DR | Promoter: 2nd DR | Base Vector | SEQ ID: |
|---|---|---|---|---|---|---|
| pMM113 | 35S: Luc+ | AtU6: NbPDS gRNA1 | Nos: WUS | CmCLYV: STM | T-DNA w/ BeYDV Replicon, Kan Resistance | 30 |
| pMM114 | CmYLCV: Luc+ | AtU6: NbPDS gRNA1 | Nos: WUS | 35S: IPT | T-DNA w/ BeYDV Replicon, Kan Resistance | 31 |
| pMM115 | CmYLCV: Luc+ | AtU6: NbPDS gRNA1 | Nos: WUS | 35S: MPΔ | T-DNA w/ BeYDV Replicon, Kan Resistance | 32 |
| pMM131 | 35S: Luc+ | AtU6: NbPDS gRNA1 | — | CmCLYV: STM | T-DNA w/ BeYDV Replicon | 33 |
| pMM134 | CmYLCV: Luc+ | AtU6: NbPDS gRNA1 | 35S: IPT | — | T-DNA w/ BeYDV Replicon | 34 |
| pMM135 | CmYLCV: Luc+ | AtU6: NbPDS gRNA1 | Nos: WUS | — | T-DNA w/ BeYDV Replicon | 35 |
| pMM136 | CmYLCV: Luc+ | AtU6: NbPDS gRNA1 | — | 35S: MPΔ | T-DNA w/ BeYDV Replicon | 36 |
| pMM146 | CmYLCV: Luc+ | AtU6: NbPDS gRNA1 | — | Ubi1: BBM | T-DNA w/ BeYDV Replicon | 37 |
| pMM230 | 35S: AtCas9 | AtU6: gRNA (VvMLO) | Nos: ZmWUS2 | AtUbi10: LUC | pCambia T-DNA w/ BeYDV Replicon, Kan Resistance | 88 |
| pMM231 | 35S: AtCas9 | AtU6: gRNA (VvMLO) | 35S: IPT | AtUbi10: LUC | pCambia T-DNA w/ BeYDV Replicon, Kan Resistance | 89 |
| pMM232 | 35S: AtCas9 | AtU6: gRNA (VvMLO) | AtUbi10: LUC | 35S: MPΔ | pCambia T-DNA w/ BeYDV Replicon, Kan Resistance | 90 |
| pMM233 | 35S: AtCas9 | AtU6: gRNA (VvMLO) | AtUbi10: LUC | 35S: STM | pCambia T-DNA w/ BeYDV Replicon, Kan Resistance | 91 |
| pMM234 | 35S: AtCas9 | AtU6: gRNA (VvMLO) | AtUbi10: LUC | AtUbi10: BBM | pCambia T-DNA w/ BeYDV Replicon, Kan Resistance | 92 |

TABLE 2-continued

Construct descriptions

| Construct | Promoter: Reporter | Promoter: gRNA | Promoter: 1st DR | Promoter: 2nd DR | Base Vector | SEQ ID: |
|---|---|---|---|---|---|---|
| pMM235 | 35S: AtCas9 | AtU6: gRNA (VvMLO) | AtUbi10: LUC | — | pCambia T-DNA w/ BeYDV Replicon, Kan Resistance | 93 |
| pMVK057 | — | AtUbi10: Luc | Nos: ZmWUS2 | 35S: IPT | pCambia T-DNA w/ BeYDV Replicon, Kan Resistance | 94 |
| pMVK058 | — | AtUbi10: Luc | Nos: ZmWUS2 | — | pCambia T-DNA w/ BeYDV Replicon, Kan Resistance | 95 |
| PMVK059 | — | AtUbi10: Luc | — | 35S: IPT | pCambia T-DNA w/ BeYDV Replicon, Kan Resistance | 96 |
| pMVK060 | — | AtUbi10: Luc | — | — | pCambia T-DNA w/ BeYDV Replicon, Kan Resistance | 97 |

Example 2—Generation of Transgenic Branches from Direct Injection

Plant cells are inherently totipotent and can be transdifferentiated into other cell types. Thus, studies were conducted to determine whether de novo meristems could be induced in vivo by ectopically expressing DRs in plant somatic cells, and by co-delivering gene editing reagents with the DRs, whether it might be possible to create edited meristems that ultimately produce seed and transmit induced genetic changes to the next generation.

Young (10-12 week-old) transgenic *N. benthamiana* plants that constitutively expressed Cas9 were pruned to remove all visibly discernible shoot meristems (FIG. 1). *Agrobacterium* strains with vectors encoding various DR combinations and a luciferase reporter were grown overnight and resuspended in infiltration buffer (150 μM acetosyringone, 10 mM MgCl$_2$, pH 5.6) to an OD600 of 0.2. Selected meristematic tissues (shoot apical and axillary) were removed from plants using a razor blade. *Agrobacterium* cultures were injected into wound sites created by the removal of meristematic tissue, and also into other tissues such as nodes and internodes. Plants were monitored for 2 weeks to remove residual unerupted premature axillary meristems, as well as those that spontaneously developed from the stem base. After 3-5 weeks, various tissue types developed. Some shoots appeared phenotypically normal (FIGS. 2A and 3F), whereas others displayed abnormal and/or adverse phenotypes, such as an abundance of leaves or other developmental abnormalities, likely due to persistent expression of the DRs (FIGS. 2B-2D and 3C).

To demonstrate that transgenic tissues were generated de novo from injected tissues, samples were visualized for luciferase activity. Tissues were isolated from newly formed shoots arising from *Agrobacterium* injection sites. To visualize luciferase expression, tissues were immersed in water containing 5 mM luciferin for 5 minutes prior to bright field imaging or imaging in the dark using a CCD camera. Some tissues demonstrated luciferase expression, indicating that the newly formed tissues were derived from cells that had received the T-DNA from *Agrobacterium* (FIGS. 2E, and 2F, 3A, 3B, 3D, and 3E). Thus, direct injection of *Agrobacterium* strains delivering DRs was able to induce transgenic shoots.

In subsequent studies, transgenic shoots are allowed to develop and produce flowers. At some frequency, transgenes are transmitted to progeny, thereby creating stably transgenic plants.

Example 3—Generation of Tissues with Gene Edits from Direct Injection

Figure 3G:
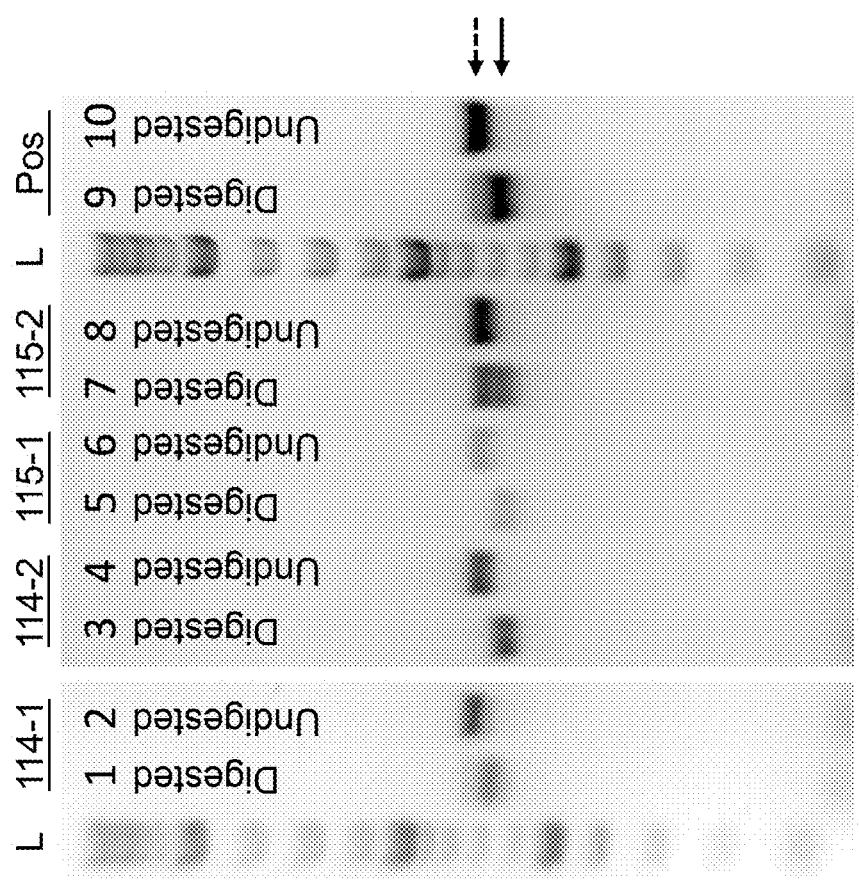
Figure 4C:
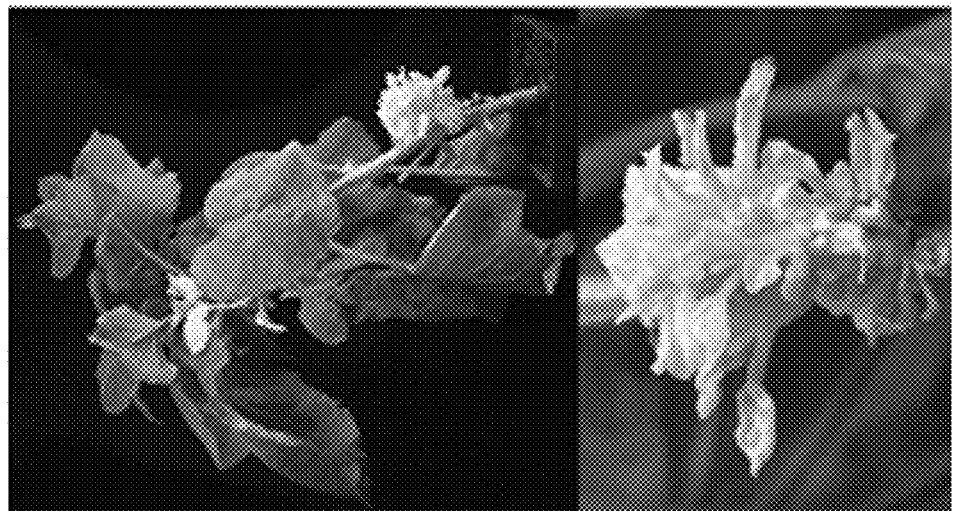
Figure 4B:
Figure 4A:
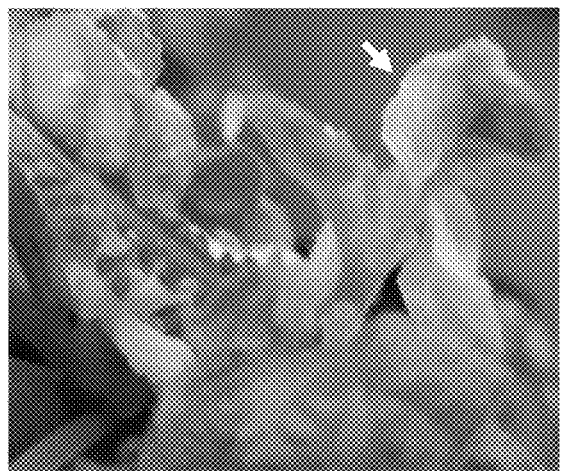
Figure 4D:
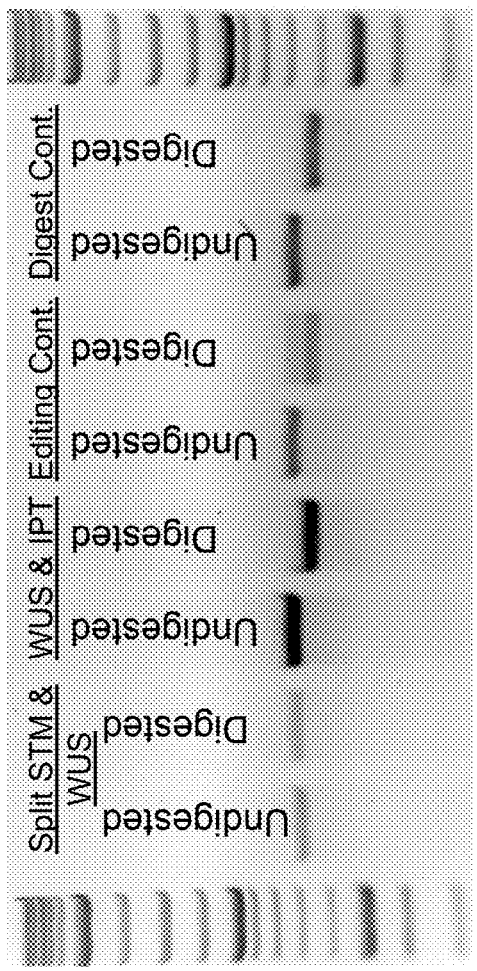
Figure 4E:
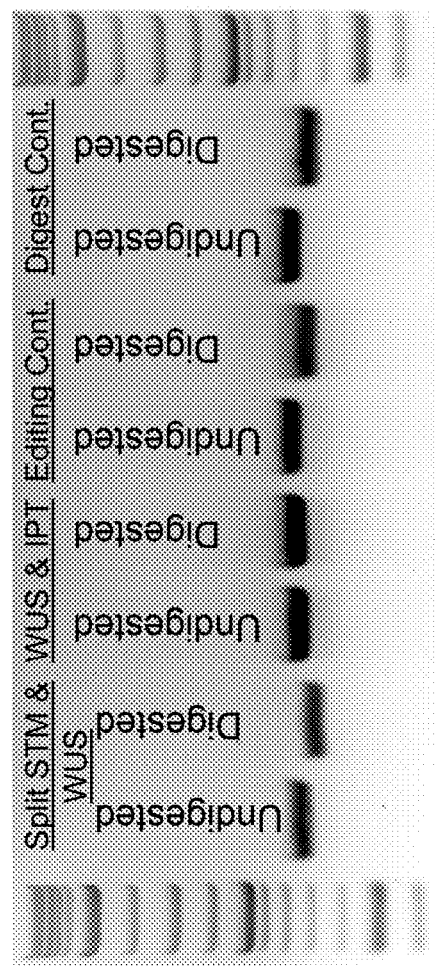

The T-DNA delivered to the transgenic Cas9 plants also expressed a gRNA targeting *N. benthamiana* phytoene desaturase (PDS) genes. There are two PDS homologs in *N. benthamiana* (NbPDS1; Niben101Scf14708g00023.1 and NbPDS2; Niben101Scf01283g02002.1). The gRNA was selected to target conserved sequences in both genes. In the absence of PDS, photobleaching occurs due to lack of photoprotective carotenoids, giving rise to a readily discernible phenotype (Qin et al., *Cell Res* 17:471-482, 2007). A subset of the shoots that emerged in the experiments described in Example 2 were white, suggesting biallelic inactivation of the two PDS homologs (FIGS. 4A-4C). To assess gene editing, genomic DNA was isolated from white tissue samples, amplified by PCR, and analyzed for NHEJ induced mutations at the gRNA target sites. Primers were used to selectively amplify either gene: TGGGAACT-GAAAGTCAAGATGGTC (oCS1200; SEQ ID NO:20) and ACAATAAATGGGATGGGCCTGG (oCS1202; SEQ ID NO:21) for Niben101Scf14708g00023.1, and TGGGAACT-GAAAGTCAAGATGTTT (oMM299; SEQ ID NO:22) and CAAAAGCTAGCTTATGAGGTGAAGC (oMM300; SEQ ID NO:23) for Niben101Scf01283g02002.1). Incomplete digestion of PCR amplicons by the restriction enzyme NcoI indicated that mutations had occurred within the restriction recognition site as a result of gRNA-directed cutting and error prone NHEJ mediated repair (FIGS. 3G, 4D, and 4E). These results indicated that de novo derived tissues received the expression cassettes containing the developmental regulators and gene editing reagents.

To confirm the creation of non-chimeric, genetically modified de novo tissue, genomic DNA was isolated from tissues exhibiting the PDS phenotype. NGS primers specific to the Scf14708g00023.1 homolog (NbPDS1, SEQ ID NOS: 78-87) were used to amplify the locus in the genomic DNA sample, and the resulting amplicon was submitted for Illumina sequencing. The results demonstrated a mutation profile consistent with a single editing event at the target locus as compared to negative controls (FIGS. 4F and 4G). Thus, the activity of developmental regulators strongly increased the potential for deriving editing events in de novo meristems.

Example 4—Vertical Transmission of GE from De Novo Derived Tissues

It was desired to determine whether GE in induced shoots could transmit the edits to the next generation. However, none of the shoots with developmental abnormalities or the PDS phenotype set seed. Because all shoots were molecularly surveyed for mutations at the PDS targets, however, one green shoot that produced viable seed and had a 3 bp deletion in one PDS allele was identified (FIG. 5A, shaded row; FIG. 5B). To determine if additional gene edited shoots could be obtained, a second experiment was performed in which WUS and IPT were delivered on the same T-DNA or on separate T-DNAs (again, a mixed infection with separate strains). Rather than monitoring the total number of shoots produced, the number of shoots that emerged from each injection site was monitored. Previous experiments had suggested that initial shoots were often not transgenic and, as such, shoots appearing in the first 20 days were removed and discarded. Abundant shoots emerged regardless of whether the developmental regulators were on the same T-DNA or on T-DNAs in different strains (FIG. 6). When on the same T-DNA, for example, 46 shoots were recovered from 76 injection sites. Of these, 16 shoots had a distorted phenotype and four were white or had white sectors, indicative of transgene overexpression and PDS targeting, respectively. In contrast, the negative control produced no white shoots, although some shoots were initially distorted due to trimming but then progressed with a WT growth pattern.

Figure 7:
FIG. 7 is a representative image of an induced chimeric shoot with a WT growth pattern and sectored green and photobleached tissue, both of which produced seed (inner two circles). Below the image are the genotypes of the parental green and white tissues (outer two circles) observed by Tracking of Indels by Decomposition (TIDE) analysis of Sanger sequencing and phenotypes of the resulting progeny (see, also, FIGS. 8A and 10A for the resulting genotypes of individual seedlings). The −48 bp mutation constituted an in-frame deletion that may have maintained a functional PDS protein, retaining the green phenotype for green sectors.
Figure 8B:
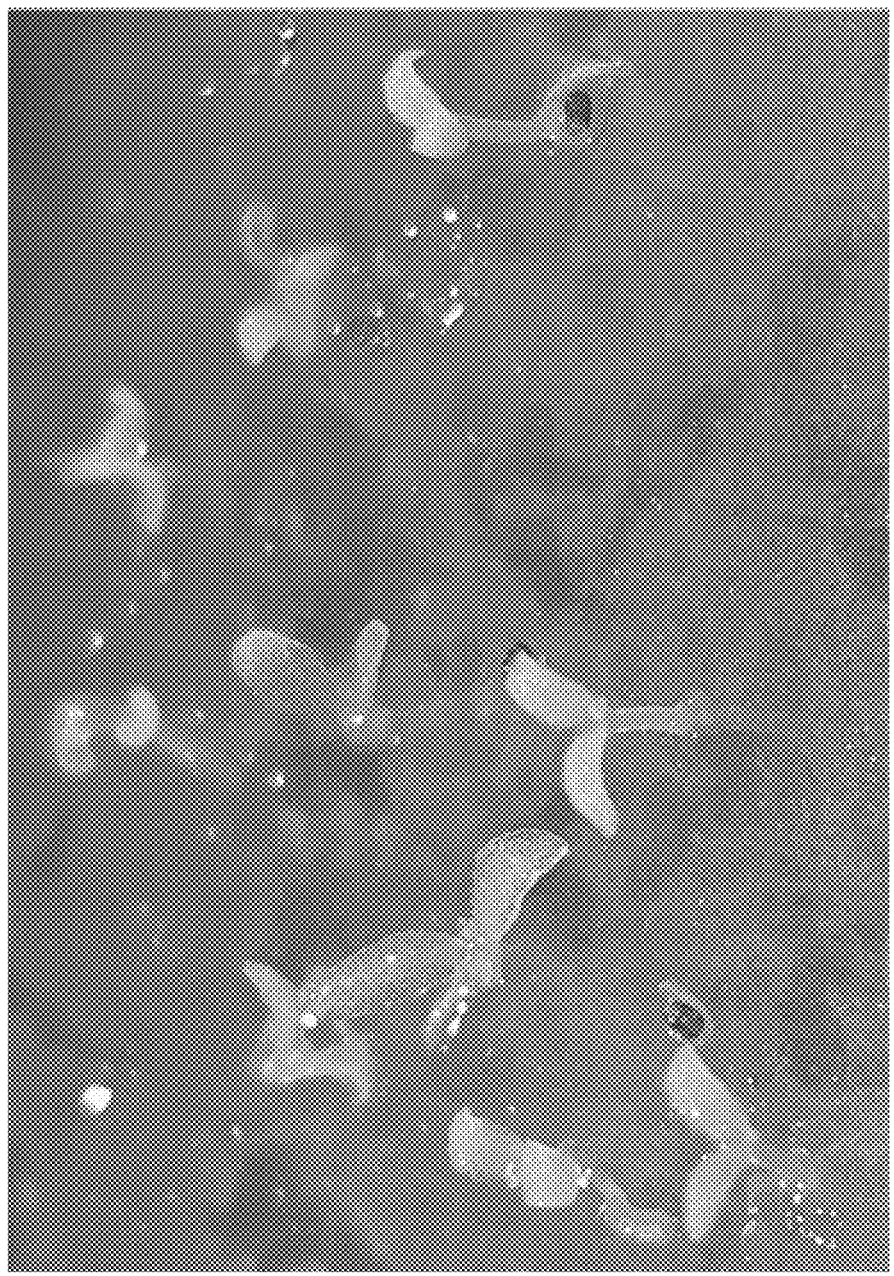
FIG. 8B is an image showing seedlings exhibiting the PDS KO phenotype.
Figure 9:
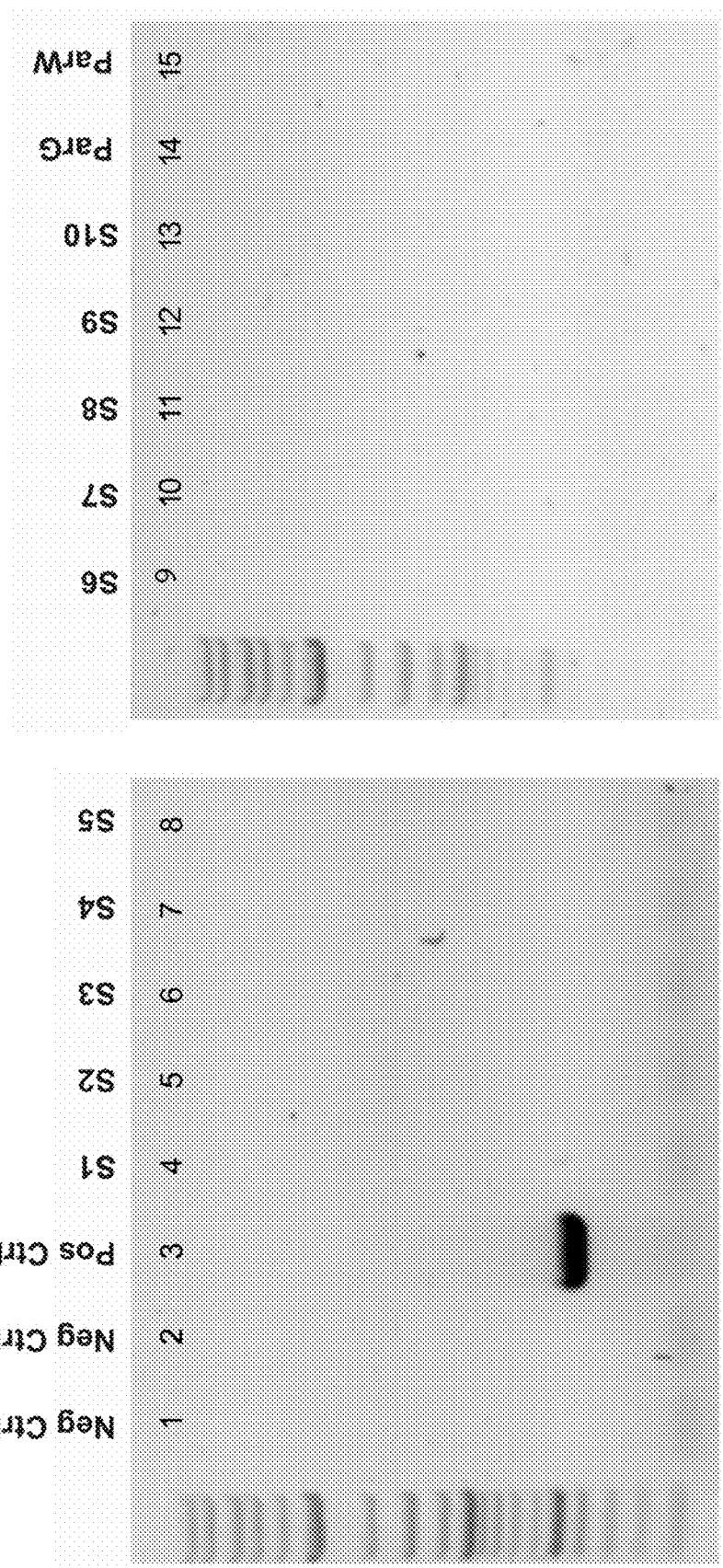
FIG. 9 is a pair of images confirming that the plants shown FIGS. 7 and 8B were transgene-free. Genomic DNA (gDNA) was extracted from parental white (ParW) and green (ParG) tissues of a plant demonstrating targeted editing (shown in FIG. 7), as well as from ten seedlings derived from the white flower (S1-S10.
Figure 10B:
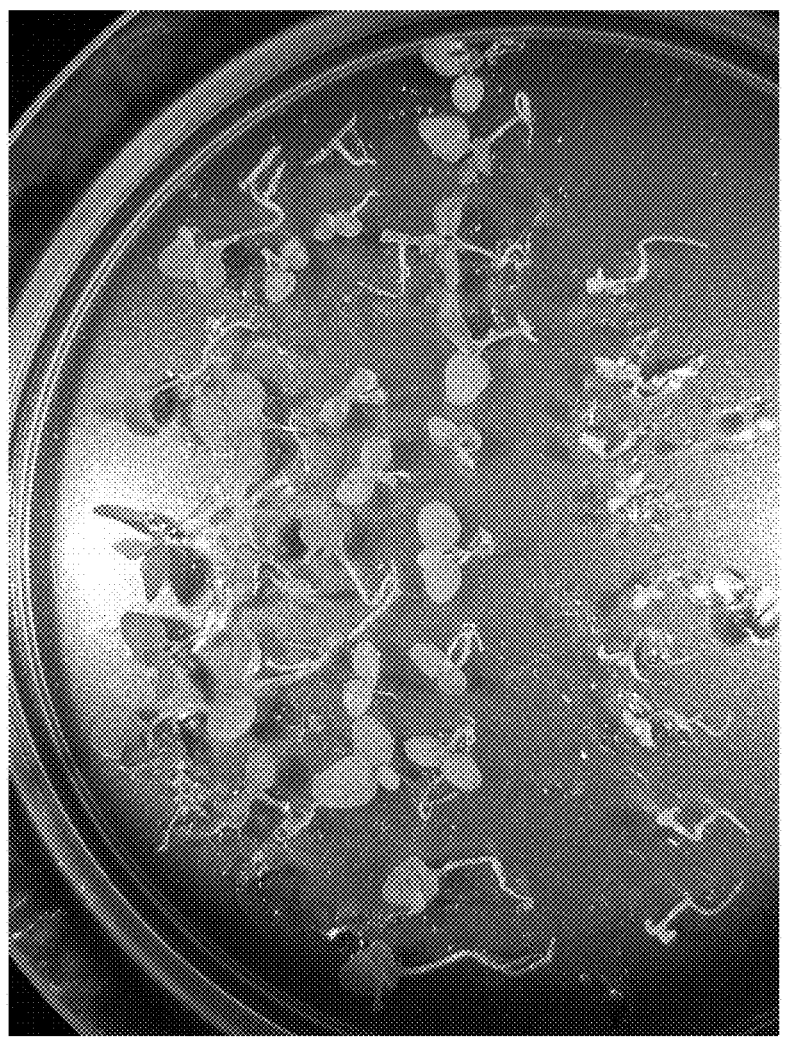
FIG. 10B is an image demonstrating segregation of the PDS KO phenotype in a 3:1 ratio observed for the seedlings listed in FIG. 8A.

One shoot emerged that was chimeric for white and green tissue, but otherwise was phenotypically normal and non-bioluminescent (FIG. 7). From the white tissue, a flower was produced that set seed, which produced completely white seedlings when germinated (FIGS. 8A and 8B). The seedlings had biallelic mutations in both PDS homologs, and the frameshift mutations transmitted to the progeny were present in the parental white tissue. Neither the parental tissues nor the seedlings were transgenic, as indicated by the lack of luciferase expression and the inability to detect the transgene cassette by PCR (FIG. 9). Seed and tissue also were harvested from the associated green chimeric sector. Germinated seed segregated in an approximately 3:1 ratio for the PDS phenotype (FIGS. 10A and 10B). The mutations in the seedlings were the same as those observed in the parental green tissue, but they were distinct from those observed in white sectors. The green shoot that was produced in the initial experiment also was shown to transmit mutations to progeny (FIG. 11). Thus, in three independent studies, non-transgenic tissues were produced in N. benthamiana with multiple targeted mutations and within a single generation, without the use of plant selection. Importantly, gene edited plants that lacked a transgene were recovered, obviating the need to segregate away the transgene in subsequent generations.

Figure 12I:
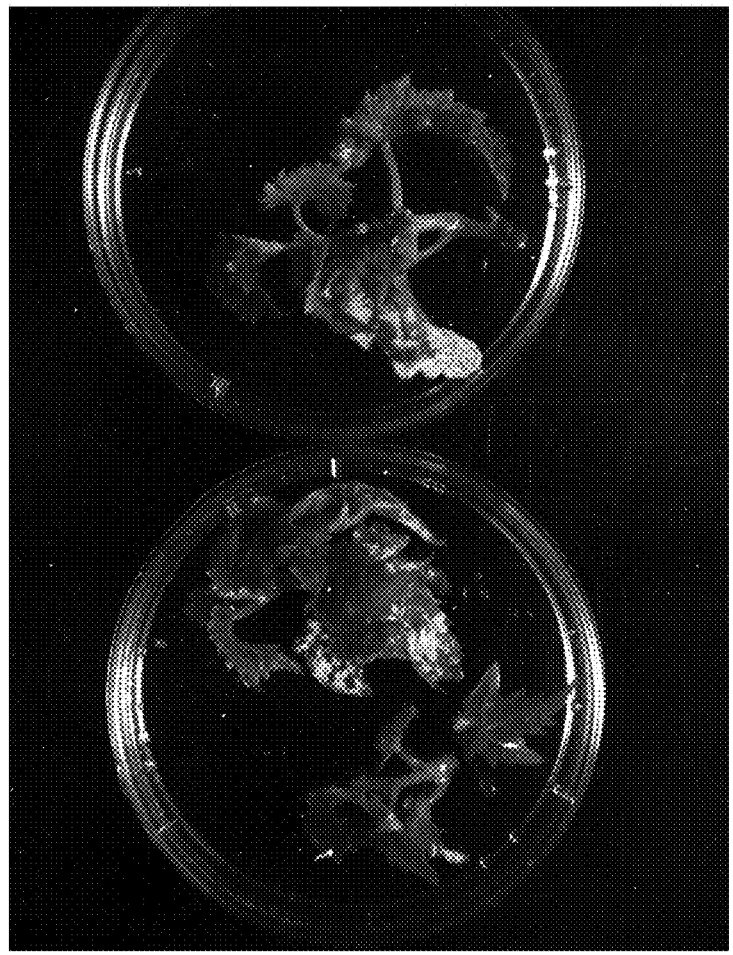
Figure 12H:
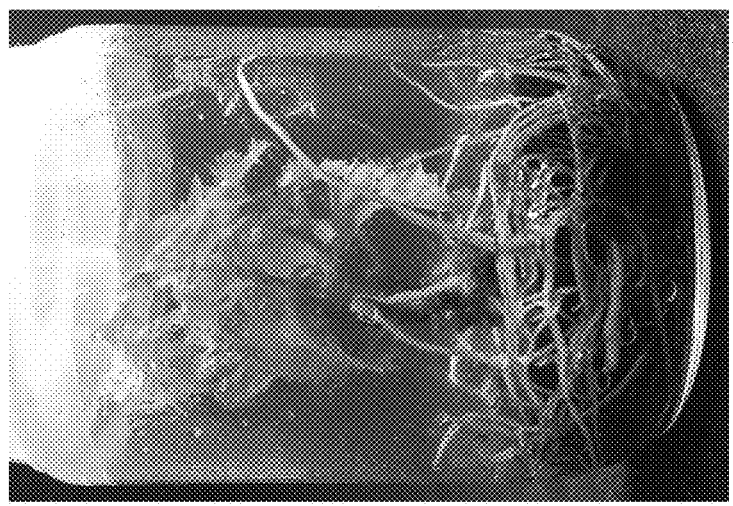

Example 5—Generation of Transgenic Tissues in Grape and Potato after Direct Injection of Developmental Regulators To determine if de novo meristems could be induced on agronomically important species, additional experiments were performed in Vitis vinifera (grape) and Solanum tuberosum (potato). Cuttings from asexually propagated potato (FIGS. 12A and 12D) and grape (FIG. 12H) were injected in sterile culture jars with Agrobacterium strains delivering individual or a combination of DRs. Vectors in both experiments contained a luciferase reporter. For both grape and potato, a subset of plants produced bioluminescent shoots (FIGS. 12B, 12C, 12E, 12F, 12G, and 12I). In grape, the shoots were produced after combined delivery of vectors expressing WUS, IPT, STM, MPΔ, and BBM (pMM230 through 234), as well as after individual delivery of Agrobacterium expressing IPT (pMM231). In potato, shoots were induced after delivery of WUS and IPT (pMKV057) or IPT alone (pMVK059). These results demonstrated that DRs can induce transgenic shoots on diverse dicot species.

In further studies, transgenic shoots are created in potato, grape, or other species that express Cas9 and a gRNA targeting an endogenous gene. Cas9 and the gRNA create mutations in somatic cells, which are induced by the DRs to form meristems and shoots. Some shoots have edited genes that produce flowers and transmit gene edits to the next generation. Other shoots have edited genes but lack the transgene and produce edited, transgene-free progeny (as described in Example 4 for N. benthamiana, for example).

Example 6—Generation of Growths from Sites of Delivery after Fast-TrACC

Examples 1-5 describe studies using methods to generate de novo meristems in whole plants that either carry transgenes or have GE events. This Example and the following Examples describe studies showing that de novo meristem-like tissue can be generated out of somatic tissue via Fast-TrACC delivery of developmental regulators (FIG. 13).

Fast-TrACC involves treating A. tumefaciens cultures (GV3101 was used in the studies described herein, but any other suitable strain can be used) for three days prior to a two day co-culture with newly germinated seedlings. The first step is to grow the cultures overnight (8-12 hours) at 28° C.

Next, cells are harvested by centrifugation and re-suspended to an $OD_{600}$ of 0.3 in AB:MES salts (17.2 mM $K_2HPO_4$, 8.3 mM $NaH_2PO_4$, 18.7 mM NH+C1, 2 mM KCl, 1.25 mM $MgSO_4$, 100 μM $CaCl_2$), 10 μM $FeSO_4$, 50 mM MES, 2% glucose (w/v), 200 μM acetosyringone, pH 5.5) (Wu et al., Plant Methods 10:19, 2014), with the intent to increase the expression of vir genes, and then grown overnight. The culture is again centrifuged and resuspended to $OD_{600}$ within the range of 0.10 to 0.18 in a 50:50 (v/v) mix of AB:MES salts and ½ MS liquid plant growth medium (½ MS salt supplemented with 0.5% sucrose (w/v), pH 5.5). The A. tumefaciens culture is now ready for incubating with seedlings.

Seeds are sterilized using 70% ethanol for 1 minute and 50% bleach (v/v) for 5 minutes. The seeds are then rinsed 5 times with sterile water, and transferred to 6-well plates (~5 seeds per well in 2 mL ½ MS), where they are subsequently germinated and maintained in growth chambers for 2-3 days at 24° C. under a 16 hour/8 hour light/dark cycle. A. tumefaciens is added and the co-culture is incubated for two days before the seedlings are washed free of A. tumefaciens using sterile water. The washed seedlings are returned to liquid ½ MS containing 100 μM of antibiotic timentin to effectively counter-select against residual A. tumefaciens.

The Fast-TrACC method was used to deliver Agrobacterium tumefaciens T-DNA constructs (SEQ ID NOS:26 and 27) encoding developmental regulators into the cotyledons of N. benthamiana seedlings. These constructs contained a luciferase reporter (CmYLCV:Luc, SEQ ID NO:3:SEQ ID NO:14) and the developmental regulators WUS (Nos:WUS, SEQ ID NO:5:SEQ ID NO:6) and STM (SEQ ID NO:7). STM was expressed using three different promoters (35S, SEQ ID NO:1; AtUBQ10, SEQ ID NO:2; and CmYLCV, SEQ ID NO:3) to determine if one had optimal meristem patterning potential. All three promoters formed growths but at slightly different frequencies.

Figure 14B:
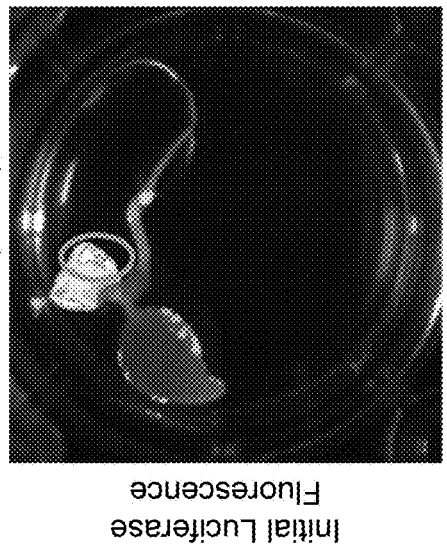
FIGS. 14A to 14D illustrate the generation of growths from sites of delivery for the Fast-TrACC method. T-DNAs with GVRs containing luciferase and the developmental regulators WUS and STM were incorporated into *N. benthamiana* seedlings. The sites of delivery were approximated by observing luminescence from the luciferase reporter (FIGS. 14A and 14B). De novo tissue growth occurred from the sites with the highest expression of luciferase (circles in FIGS. 14A and 14B). This presumably was due to high levels of developmental regulator expression coinciding with the reporter expression. The de novo tissues that were generated developed into different tissue types. Many remained in an undifferentiated callus-like state (FIG. 14C, arrow), while others progressed into meristem-like tissues (FIG. 14D, circle). The meristem-like growths developed defined structures such as leaflets (FIG. 14D, arrows).
Figure 14D:
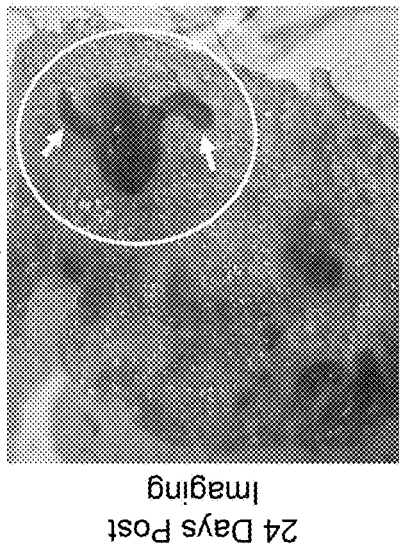
Figure 14A:
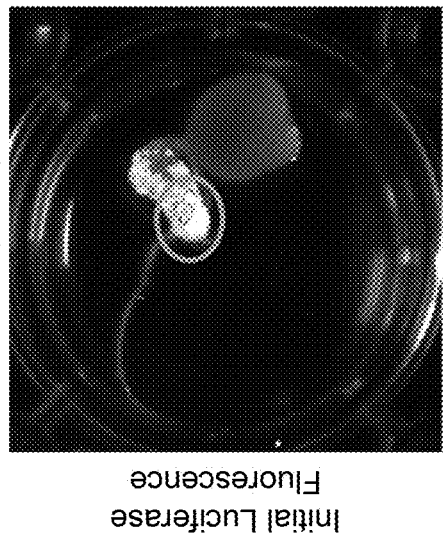
Figure 14C:
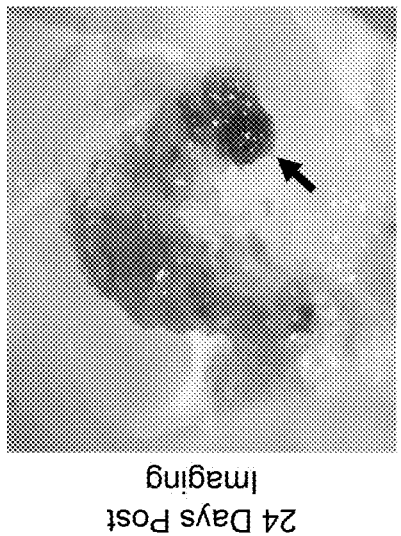

Using the luciferase reporter expression as a proxy for T-DNA delivery, sectors of the plant that received the developmental regulators were identified. From regions exhibiting high levels of localized luciferase expression (FIGS. 14A and 14B, circled) developmental regulator-derived growths were formed. The derived growths appeared to be of two types: one subset included globular callus-like growths (FIG. 14C, arrow), while others formed into meristem-like structures (FIG. 14D, circled). The globular growths continued as undifferentiated tissue, but the meristem-like growths formed structures such as leaflets (FIG. 14D, arrows) that indicated differentiation of the tissue. Observing de novo formation of meristem-like tissues suggested that developmental regulators can be implemented to generate new plant tissues out of entirely separate tissue types, which allows for the potential to be used for the generation of whole plants.

Example 7—Generation of Transgenic Plants from Fast-TrACC Treatment

Figure 15B:
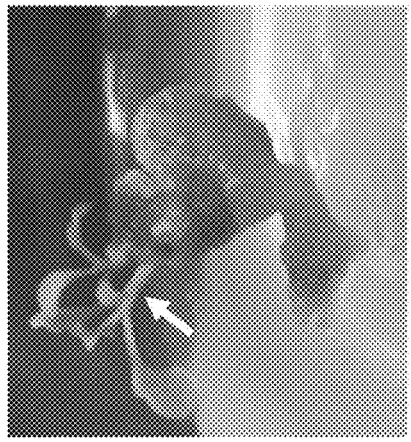
FIGS. 15A to 15E show regeneration of plantlets from developmental regulator derived shoots. Using the developmental regulator combination WUS and STM, shoot-like growths (FIGS. 15A and 15B) were formed on the cotyledons of *N. benthamiana* seedlings. These growths were transferred to auxin-rich rooting media to promote root system formation. Once full plantlets were generated, they were moved to soil (FIGS. 15C and 15D) to promote further growth. The generated plantlets exhibited a variety of whole plant phenotypes. For example, certain plantlets exhibited close to wild type appearance (FIG. 15D) while others had a far more disorganized phenotype (FIG. 15C). Three leaves from each of six generated plantlets were tested for expression of luciferase (FIG. 15E) from the original delivered T-DNA. Five of the six tested plantlets were luciferase positive in at least one leaf sample, indicating some chimeric level of transgene integration and maintenance.
Figure 15D:
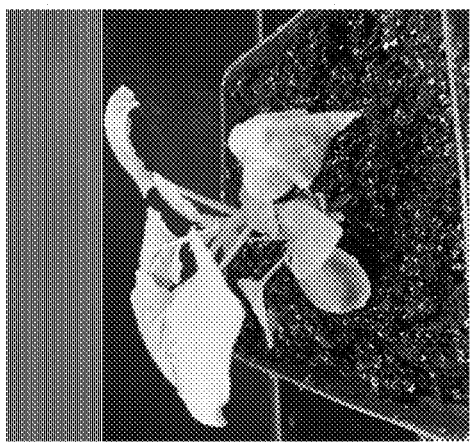
Figure 15A:
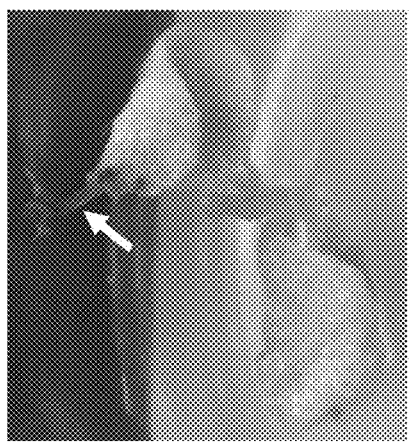
Figure 15C:
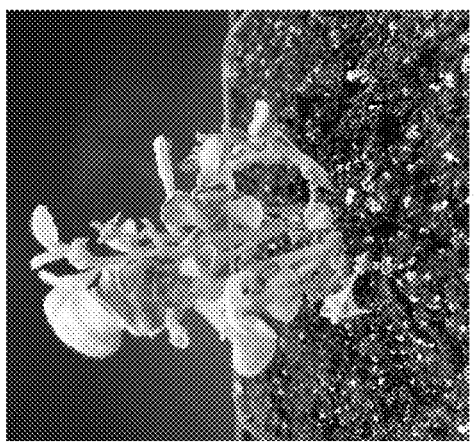
Figure 15E:
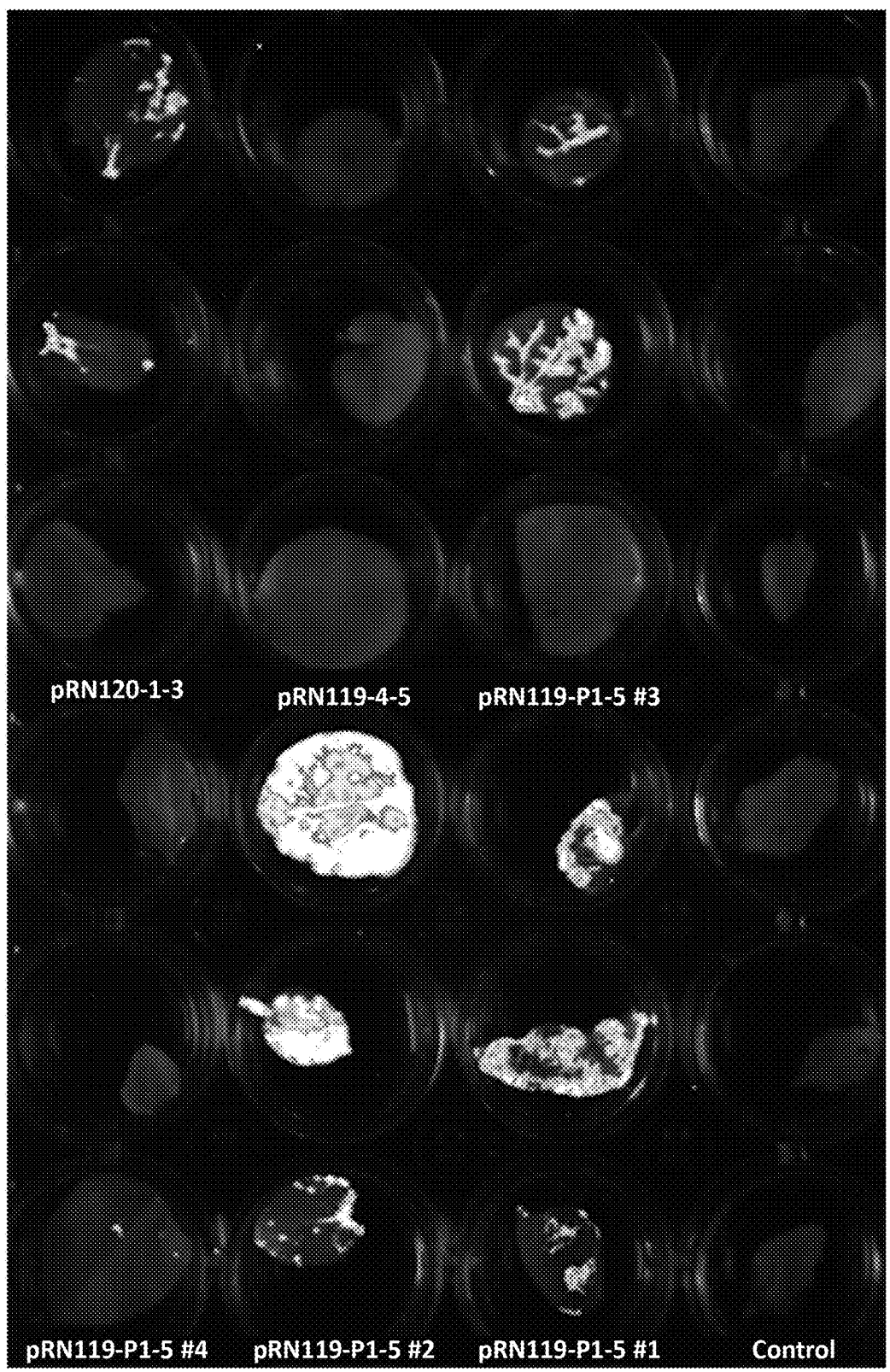

To determine the ability to produce plants from de novo growths, N. benthamiana seedlings with meristem-like growths were selected as candidates for the generation of transgenic plants. The meristem-like growths were derived using the developmental regulator combination WUS and STM. Efforts were made to ensure that the newly formed meristem-like tissue could be propagated. The meristem-like tissues were grown for about 3 weeks, until they started to form secondary leaves (FIGS. 15A and 15B). The shoot-like growths were then transferred to auxin-rich media to establish a root network. Once roots formed (about 1.5 weeks later), the plantlets were transferred to soil (FIGS. 15C and 15D). Among the derived plants, some looked essentially wild type (FIG. 15D), some exhibited excessive shooting and slight leaf abnormalities (FIG. 15C), and others were completely disfigured (not shown). To assess transgenesis, leaf punches were taken from each recovered plant and tested for luciferase expression (FIG. 15E). Varying levels of luciferase expression were observed, ranging from completely luciferase positive to specific sectoring of expression, to overall absence of luciferase.

One purpose of generating transgenic plants, whether of mosaic or uniform genetic constitution, was to produce flowers. These flowers can be derived from the same tissues that lead to the formation of luciferase positive leaves, implying that at some frequency, the flowers have the T-DNA and therefore will be transgenic themselves. The transgenic flowers will produce seed, some of which will be transgenic. Seeds from transgene-positive plants can be collected and tested for luciferase expression (i.e., presence of the transgene) and for the presence of GE events. Demonstration of heritable transmission of transgenes is described below in Example 10; demonstration of heritable transmission of GE events is described below in Example 12.

Example 8—Confirmation of Gene Editing in Developmental Regulator-Derived Growths To demonstrate that GE events can occur in de novo growths, gene editing reagents were combined with developmental regulators and delivered to seedlings. The construct that was used (SEQ ID NO:29) contained 35S:Cas9 (SEQ ID NO:1:SEQ ID NO:24), AtU6:gRNA (SEQ ID NO:4:SEQ ID NO:12), Nos: WUS (SEQ ID NO:5:SEQ ID NO:6), and CmYLCV:STM (SEQ ID NO:3:SEQ ID NO:7). Limits on construct size prevented the inclusion of luciferase as a delivery reporter. Seedlings were screened for production of growths. Out of twenty-four seedlings, five seedlings exhibited growth formations (FIG. 16A) suitable to test for edits.

Figure 16B:
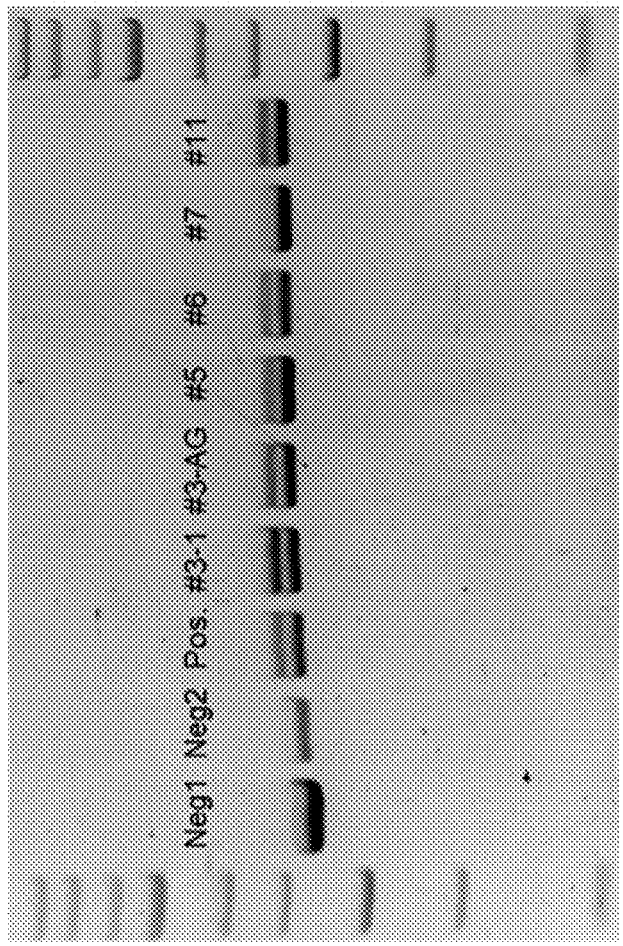
Figure 16C:
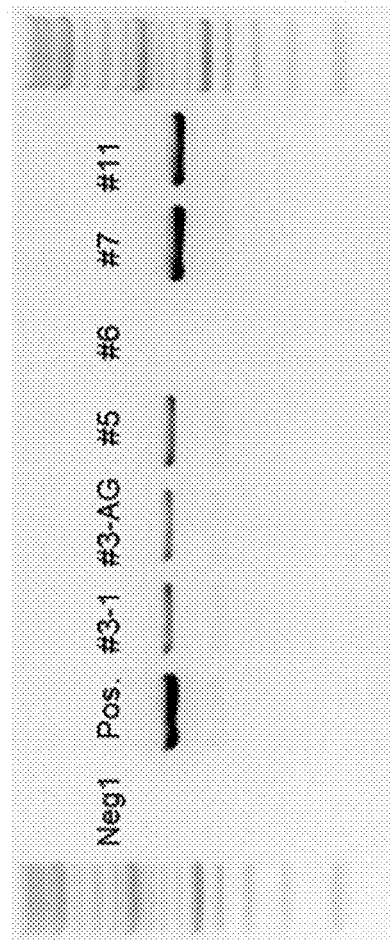
Figure 16A:
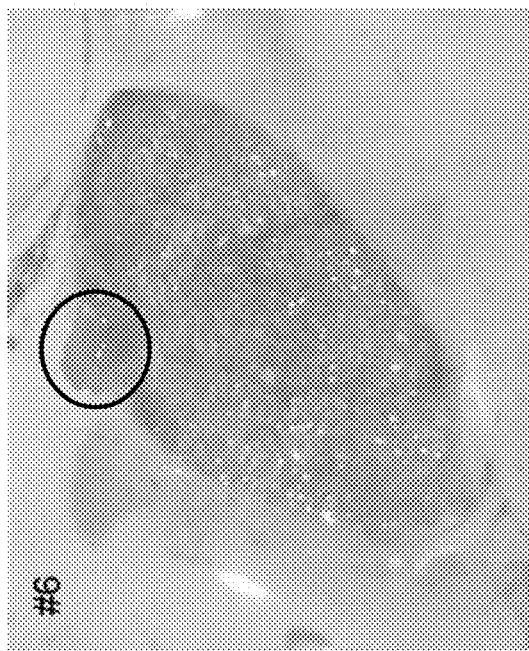
Figure 16D:
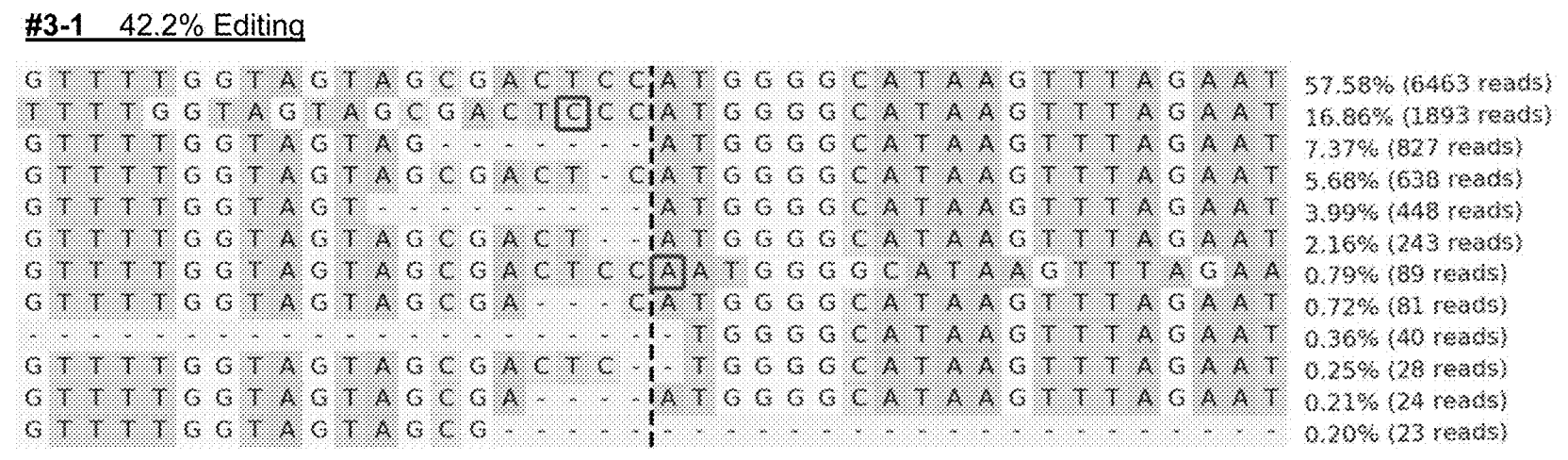
Figure 16E:
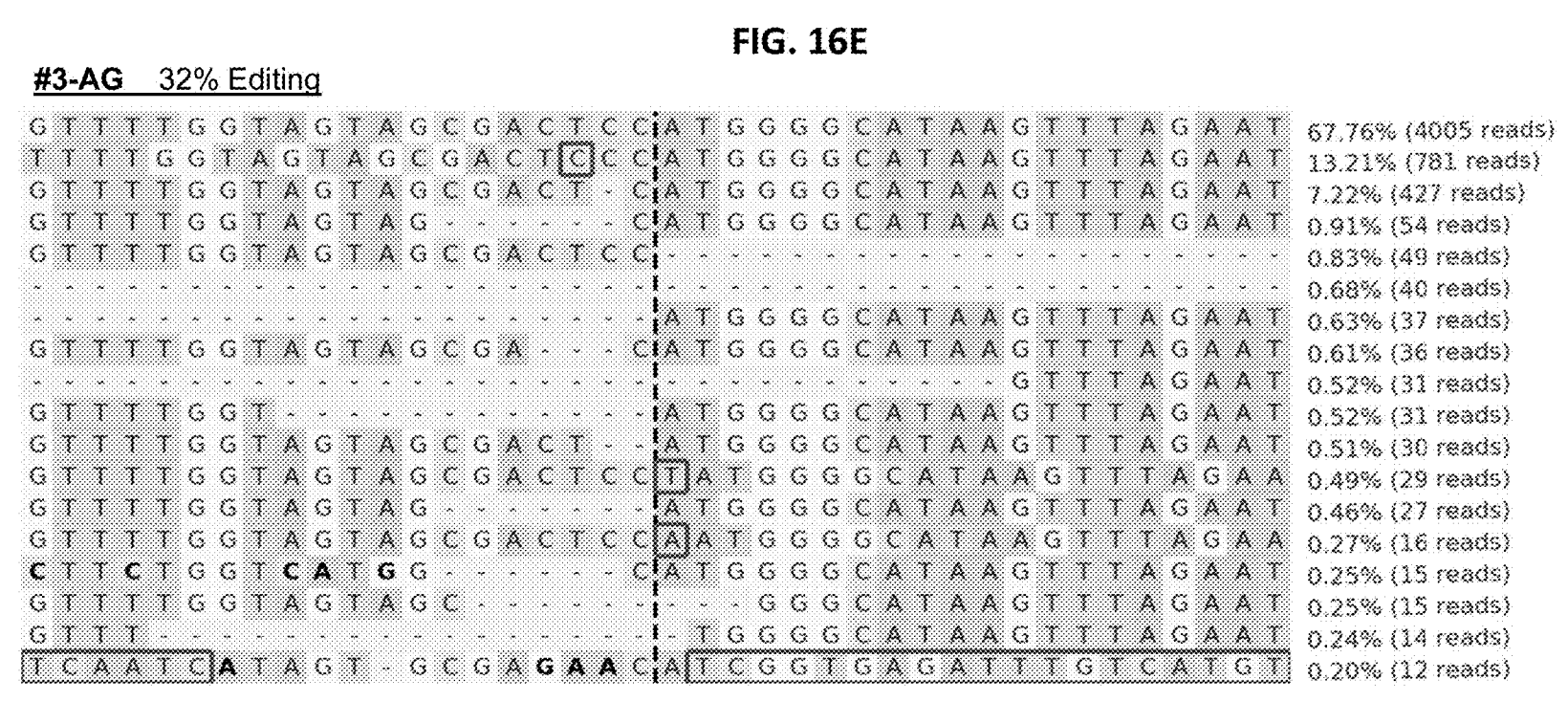
Figure 16F:
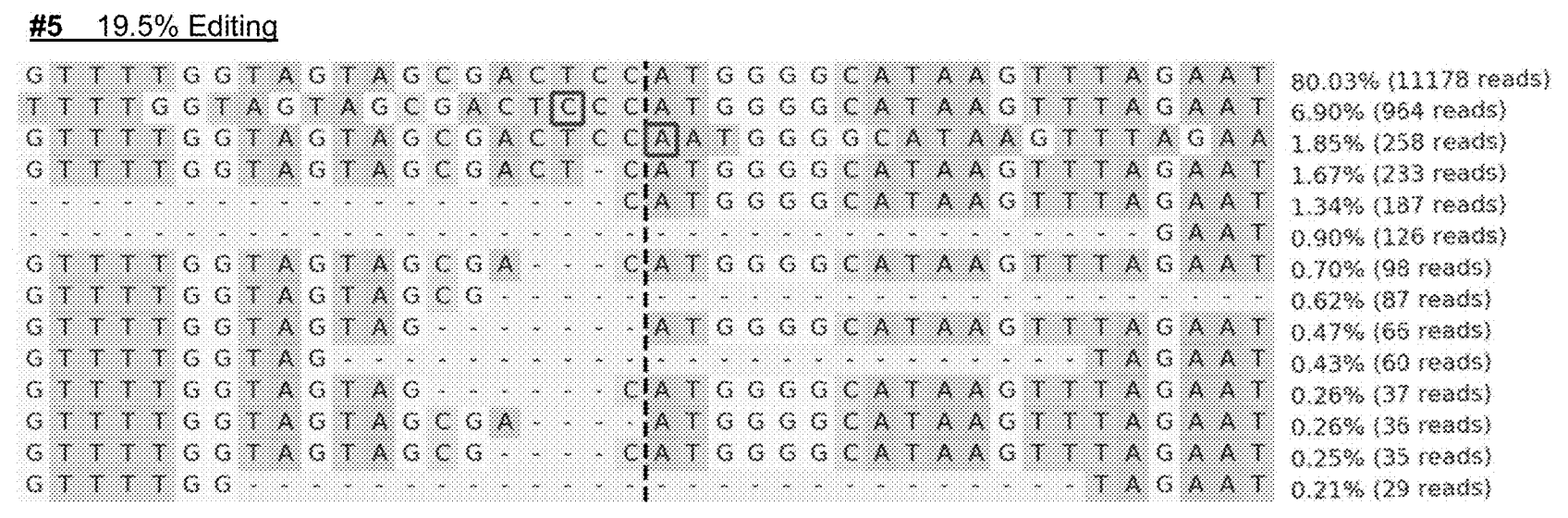
Figure 16G:
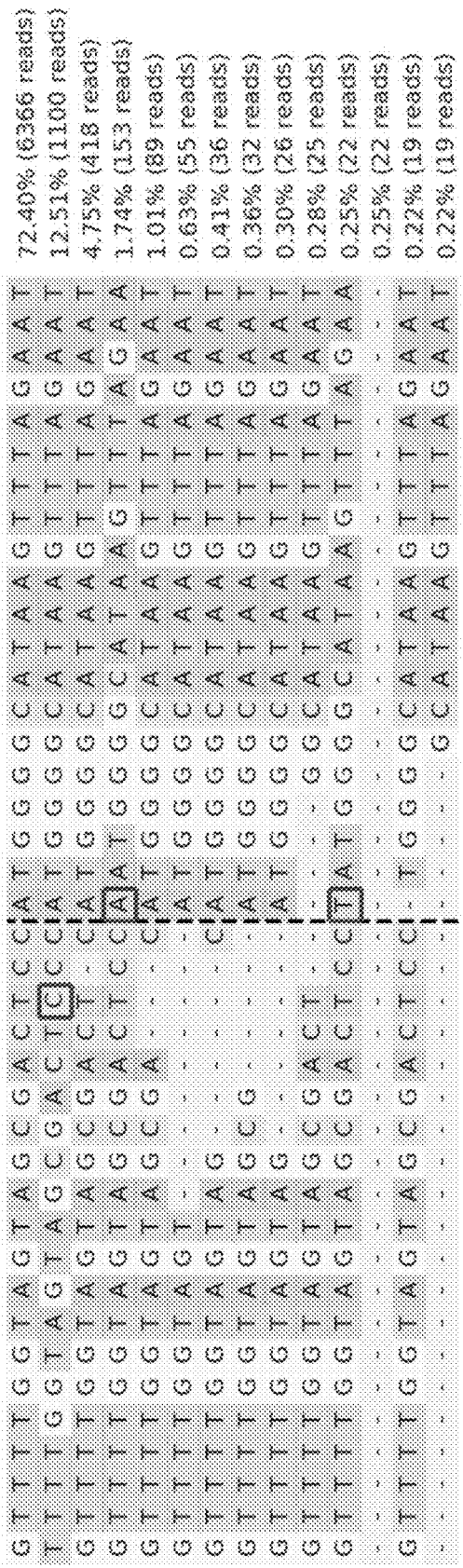
Figure 16H:
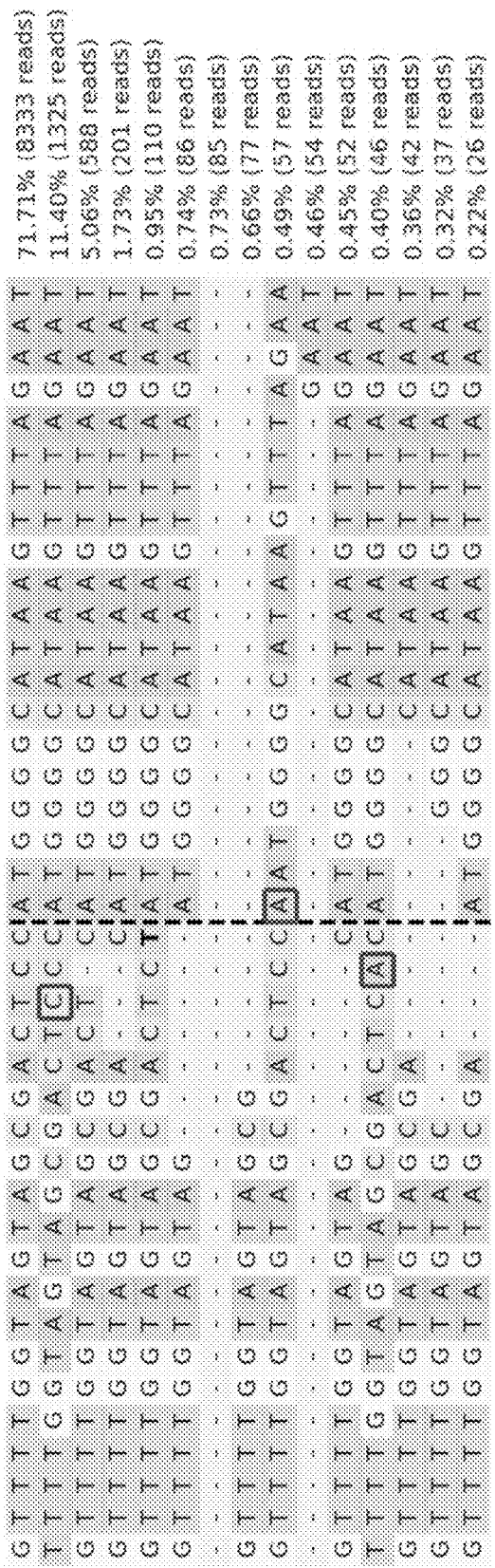

The growths were excised and DNA was isolated from each. From the isolated DNA, the target region in NbPDS1 was PCR amplified. The gRNA used in these studies targeted a locus with a NcoI restriction site that, when edited, will not allow for digestion in a RFLP assay. Four of the five tested samples contained the "protected" band indicative of editing (FIG. 16B). These same samples contained the T-DNA, as indicated by the presence of Rep (FIG. 16C). The samples were then submitted for NGS. The resulting sequences (FIGS. 16D-16H) indicated that the tissues were considerably edited, with as high as 42% of reads from a given growth being edited. This observation indicated that the delivery of gene editing reagents with developmental regulators allowed for editing within the tissues generated by developmental regulators.

Example 9—Generation of Edited Plants after Fast-TrACC Treatment

Figure 17C:
Figure 17B:
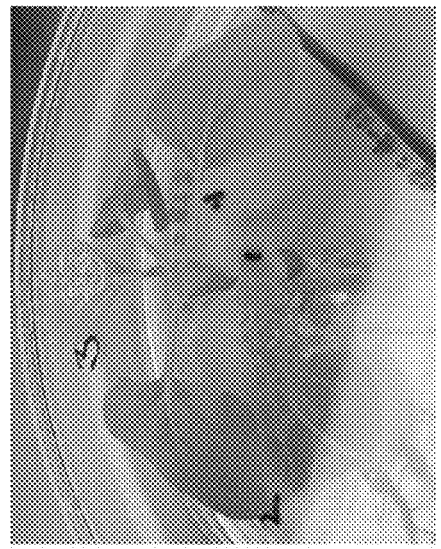
Figure 17A:
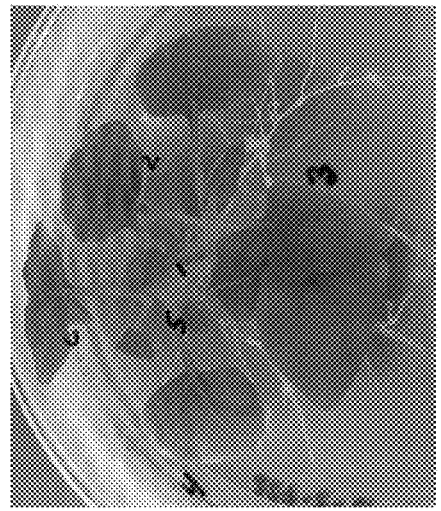

To illustrate the capability to regenerate edited plants in a fashion similar to the generation of transgenic plants, whole plants were derived from edited growths. The same construct (SEQ ID NO:29) used to generate edits within undifferentiated growths was used to promote the formation of plantlets with edits. A new set of growths were developed on N. benthamiana cotyledons that then formed meristem-like growths. Once the growths established a shoot-like structure, they were transferred to rooting medium to initiate a root network. Full plants were considered formed once the root system was established (FIGS. 17A-17C), and the plants were subsequently moved to soil.

Figure 17E:
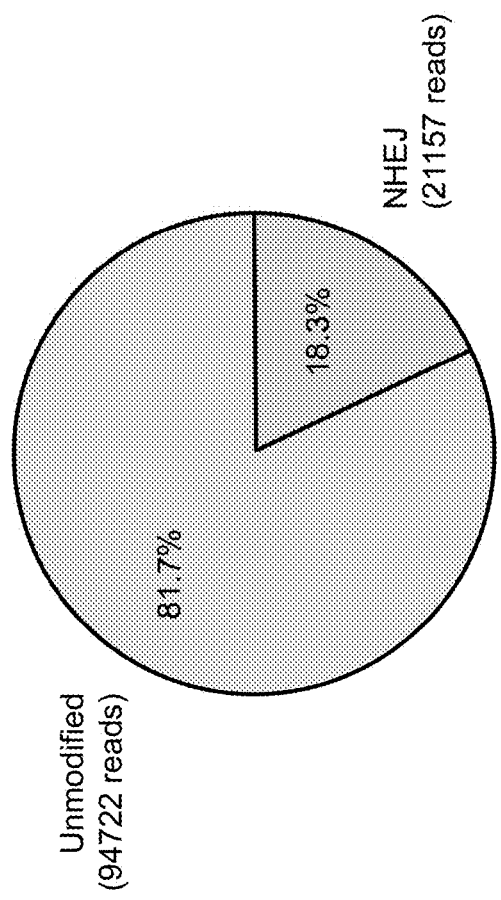
Figure 17G:
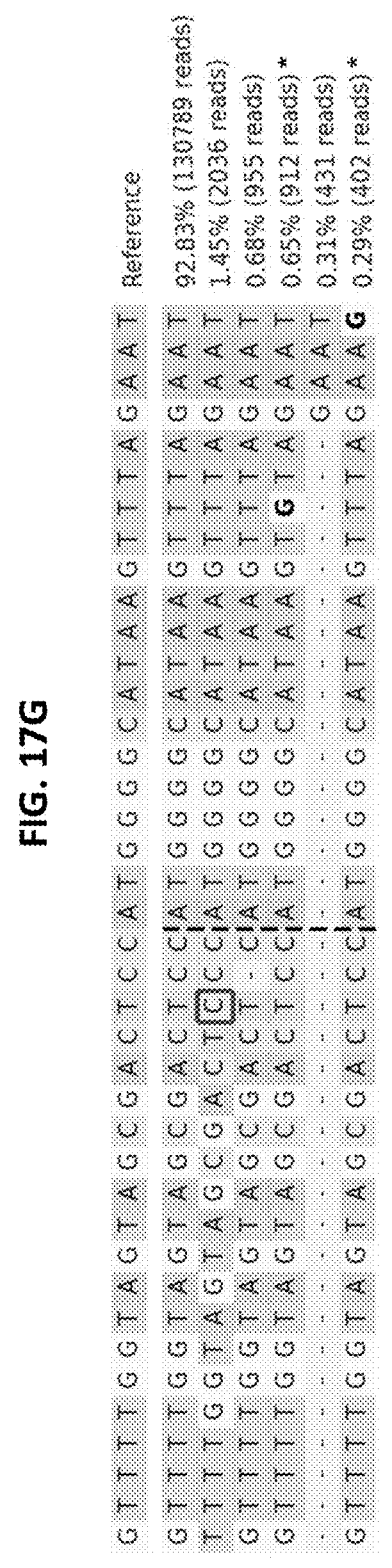
Figure 17H:
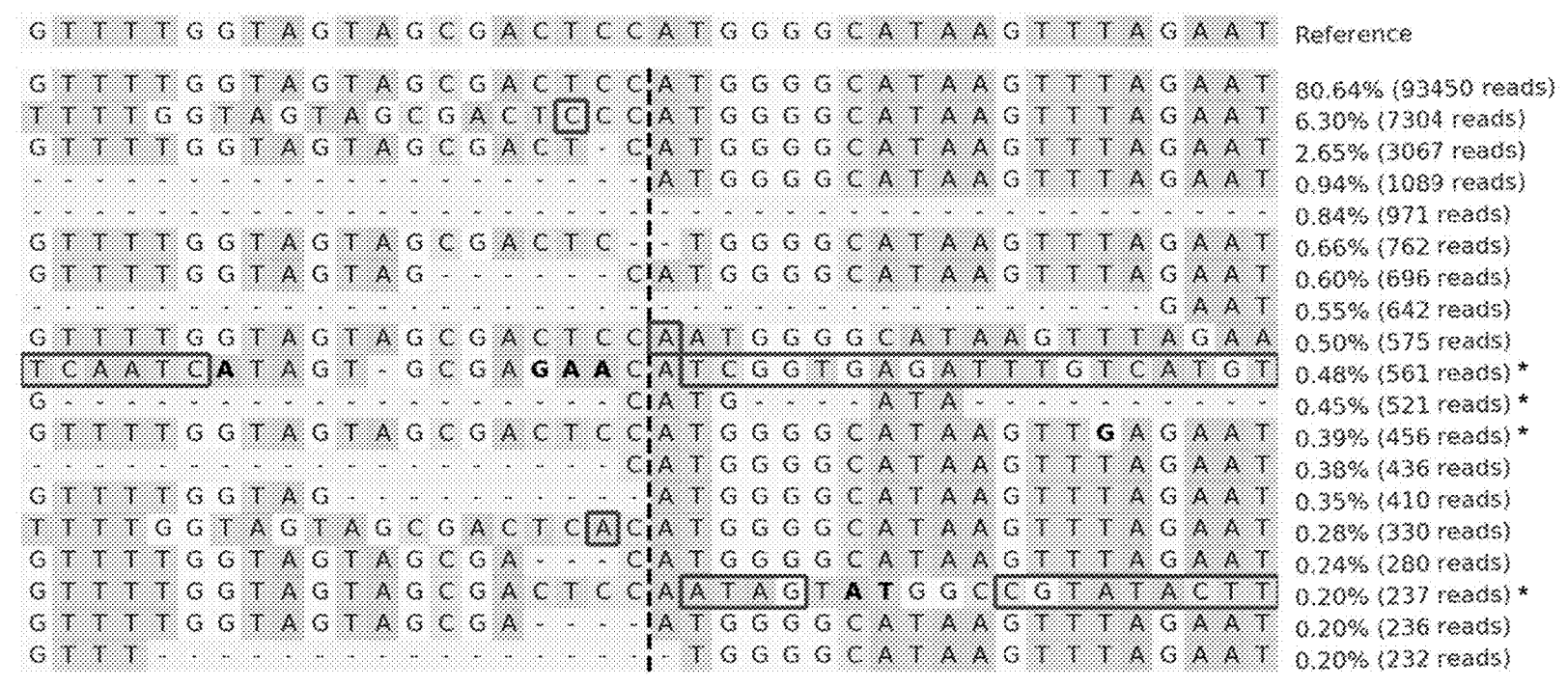
Figure 17I:
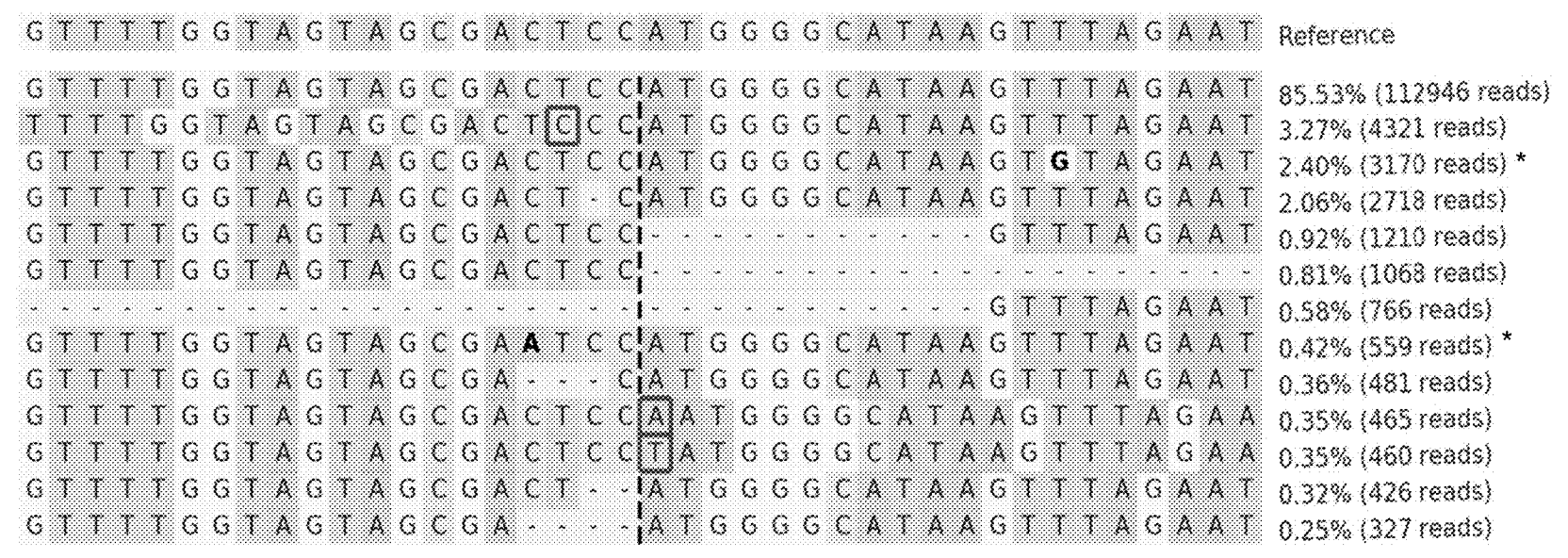

Leaf tissue samples were taken from the generated plants and submitted for NGS. The sequencing results from individual tissue samples resulted in a small proportion of edited reads (FIGS. 17D-17F), revealing that the generated plantlets were chimeric but did contain edits derived from the gene editing reagents. Since the plants were chimeric, a variety of different mutations were isolated from the NGS reads (FIGS. 17G-17I). The most common mutations were single base insertions or deletions. Reads that were likely due to aberrant mutations from PCR amplification (denoted with asterisks) were also isolated, indicating that the overall editing frequencies highlighted (FIGS. 17D-17F) were over estimates. The amount of mosaicism differed between plants, with the presence of the most common two edits ranging from 9% (FIG. 17H) to as low as 2% (FIG. 17G).

Ideally, these chimeric plants will contain mutations within a floral meristem, which would cause the flower to produce edited seeds at some frequency. As described below in Example 12, plants are grown and seeds are collected and tested for gene editing. The isolation of edited plants derived from these seeds demonstrates that edited plants can be obtained in a single generation through the creation of developmental regulator-derived plants.

Example 10—Vertical Transmission of Transgenes from Fast-TrACC Derived Plants

Figure 18B:
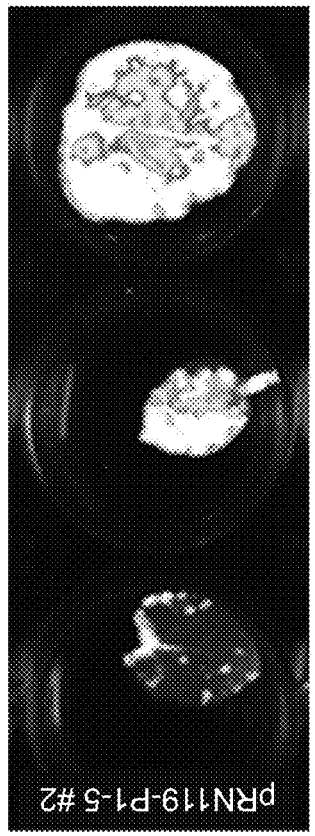
FIGS. 18A to 18D show vertical transmission of integrated T-DNA. Plants were derived after delivery of developmental regulators using the Fast-TrACC method. The original construct delivered to the progenitor plant via *Agrobacterium* contained 35S:Luciferase, Nos: WUS, and CmYLCV:STM on the T-DNA (pRN119, SEQ ID NO:27). Candidate plants (FIG. 18A) exhibiting high luciferase expression from leaf punches (FIG. 18B) were monitored for vertical transmission; after the plants flowered and set seed, the seeds themselves were tested for luminescence. The seedlings were found to maintain high levels of reporter expression (FIG. 18C), and luminescence was observed in the positive seedlings at a Mendelian ratio, consistent with inheritance from a heterozygote (FIG. 18D, 119-P1-5-2).
Figure 18C:
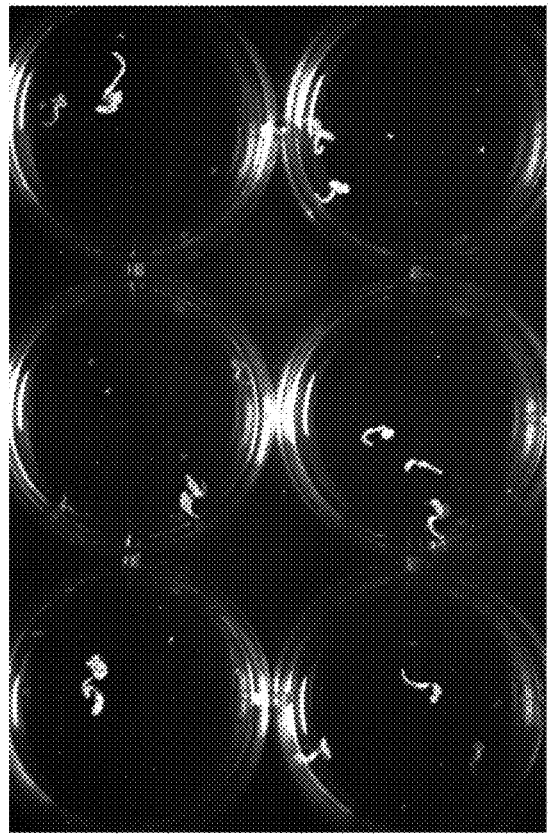
Figure 18A:
Figure 18D:
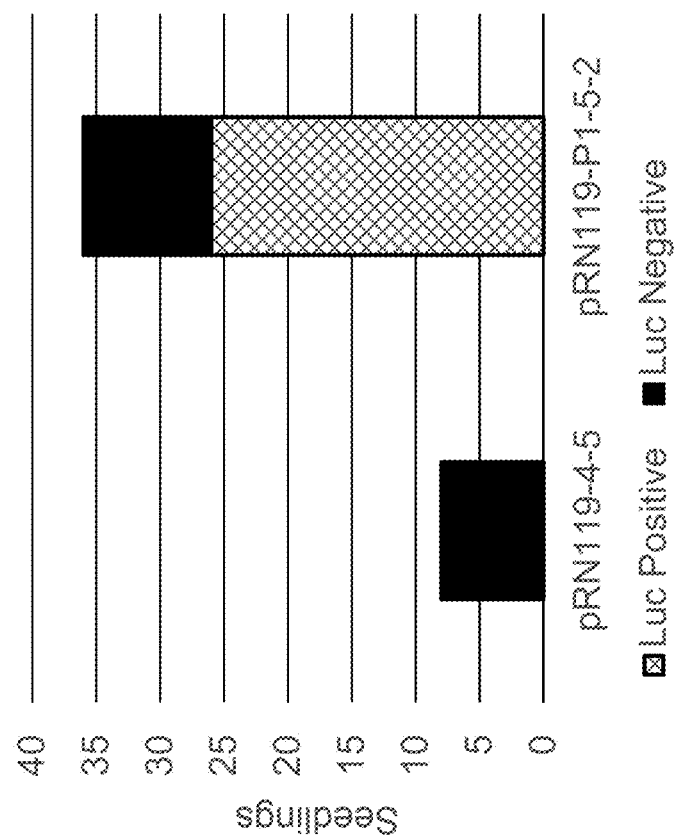

The ultimate goal for DR-based plant generation is to create genetic changes that can be transmitted to subsequent generations. Several of the DR-derived *N. benthamiana* plants grew seed-bearing flowers. These plants were created using the constructs pRN114, pRN119 and pRN120 (SEQ ID NOS:26-28) and exhibited different levels of luciferase expression (FIG. 15E). Seeds from the most luciferase-positive plant, RN119-P1-5-2 (FIG. 18A), were collected and tested for luminescence (FIG. 18B). A large proportion of the seeds from this plant were positive for luciferase (FIG. 18C). The inheritance pattern of luciferase (~75% of seedlings) was in line with the expected Mendelian inheritance pattern of a hemizygous transgene insertion (FIG. 18D). Not all plants tested had a luciferase-positive signal in their derived seeds (FIG. 18D, RN119-4-5), which could be due to mosaicism in the parent, segregation of the transgene, or silencing of the T-DNA. It also is possible that transient delivery of the developmental regulators primed a microenvironment that promoted meristem formation without transgene integration. Regardless, the observation that transgenes could be transmitted to the next generation demonstrated that a heritable transgenic event was created through de novo induction of a meristem.

Example 11—Optimizing Combinations of Developmental Regulators for Meristem Induction and the Recovery of Plants Fast-TrACC was used to test different combinations of developmental regulators in order to identify those that could best induce growths that give rise to full plants. Separate *A. tumefaciens* strains, each carrying expression cassettes for a unique DR, were pooled for seedling co-culture. Twelve combinations of DRs were tested, and five of those combinations resulted in growths from which plants could be derived (FIGS. 19A and 19B). Two combinations, WUS & STM and WUS & IPT, produced up to five times as many shoot-like growths and roughly four times more full plants than the other treatments. Thus, Fast-TrACC can be used to determine the best combination of developmental regulators for meristem induction in a given plant species.

Example 12—Vertical Transmission of GE Events from Fast-TrACC Derived Plants

Figure 20:
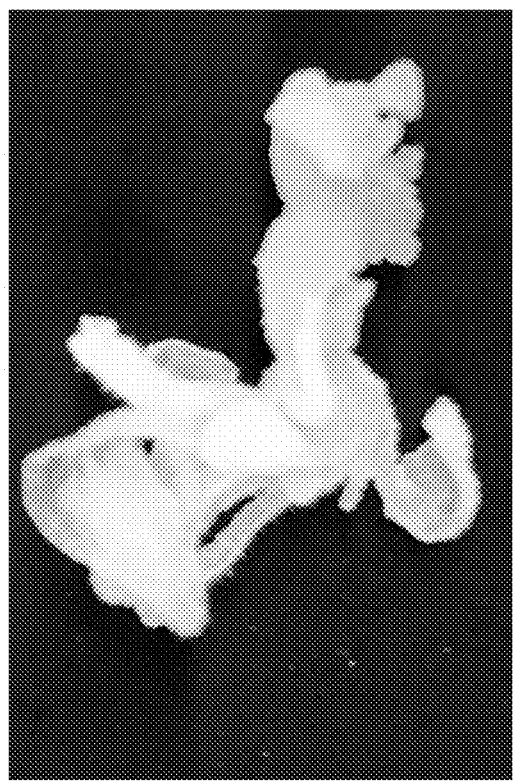
FIG. 20 is an image showing a seedling that resulted from Fast-TrACC delivery of T-DNAs with developmental regulators and a gRNA that targeted the two homologs of phytoene desaturase (PDS1 and PDS2) to *N. benthamiana* seedlings constitutively expressing Cas9. When the alleles of both homologs are fully knocked-out, plants exhibited a white phenotype due to photobleaching. About 15% of the shoots were white, but could not be grown into full plants due to lack of chlorophyll.

Studies were conducted to determine if Fast-TrACC could be used to generate meristems with gene edits and subsequently plants that transmit mutations to progeny. In the experiment described in Example 11, transgenic *N. benthamiana* seedlings constitutively expressing Cas9 were treated with Fast-TrACC. In addition to a DR, the T-DNAs carried a cassette that expressed a gRNA targeting NbPDS1 and NbPDS2. Biallelic knockouts of both PDS homologs are expected to result in a white phenotype due to chlorophyll photobleaching (Qin et al., supra). About 15% of the generated shoots showed evidence of photobleaching, but these shoots did not form full plants; they were likely compromised by lack of chlorophyll (FIG. 20). Nonetheless, white shoots were evaluated molecularly and found to have biallelic mutations in both PDS homologs. Thus Fast-TrACC can generate meristems with gene edits.

Figure 21A:
FIG. 21A is an image showing green plants that were chimeric for edits at the PDS loci. Seedlings derived from some of these plants possessed the expected white phenotype (arrowheads). In plant 1-7, two separate flowers (designated as F4 and F6) produced white seedlings. Mutations were observed in the alleles of both PDS loci, and are listed in FIG. 21B. The sgRNA sequence is underlined, and the predicted cut site is represented as a vertical line.

Of 27 total plants recovered in the experiment described in Example 11, five phenotypically normal green plants were found to show considerable amounts of editing in somatic cells (FIG. 19A). For one of these plants, seed collected from two flowers (F4 and F6) produced green and white seedlings (FIG. 21A). gRNA target sites for both PDS homologs were assessed molecularly for two white seedlings derived from each flower, and mutations were observed in both alleles of each PDS gene (FIG. 21B). Based on this data, it was concluded that co-delivery of DRs and gene editing reagents can produce shoots with mutations, and these shoots can transmit mutations to the next generation.

Example 13—Generation of Transgenic Tomato Shoots Using Fast-TrACC

Figure 22A:
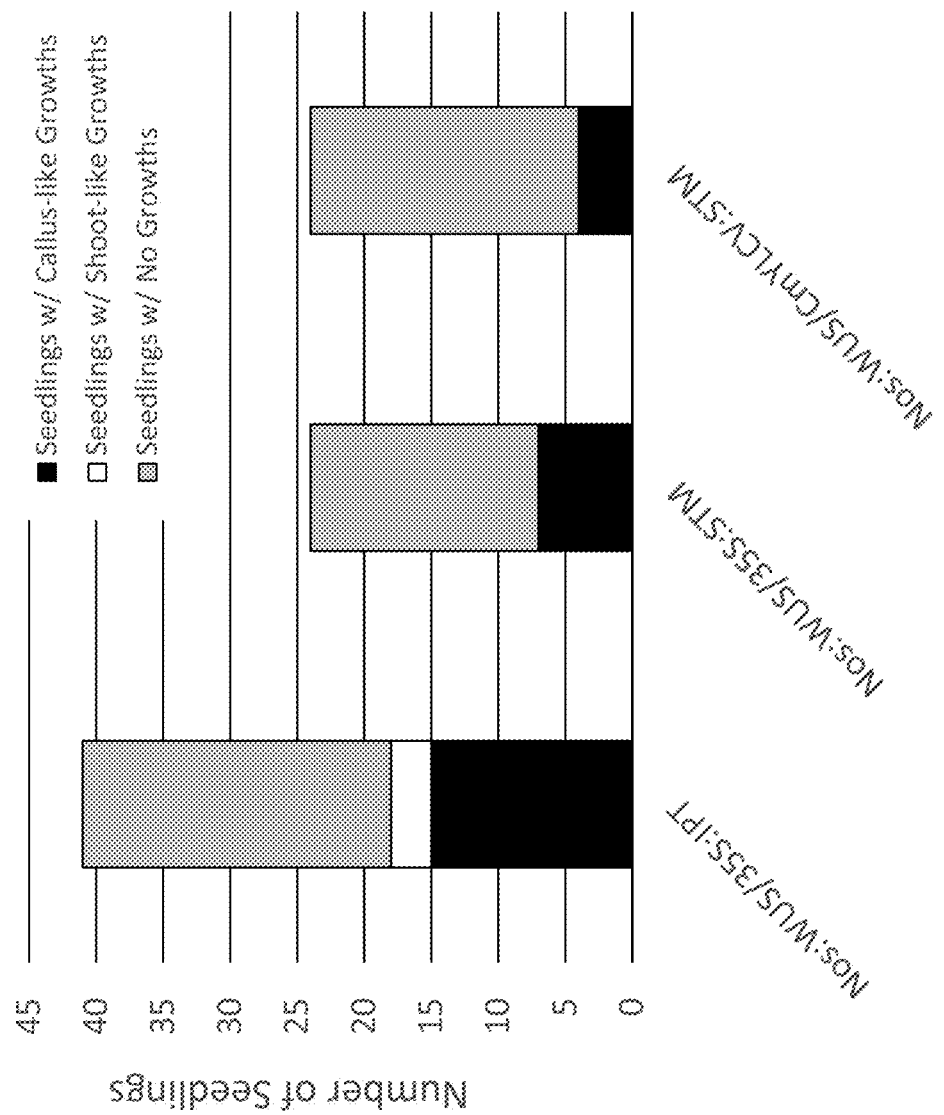
Figure 22B:

As DRs are evolutionarily conserved, studies were conducted to determine whether the approach for seedling transformation would be applicable to other plant species. Combinations of DRs that generated de novo meristems on *N. benthamiana* seedlings were therefore tested to determine whether they could induce shoots on other dicots, such as tomato. In particular, Fast-TrACC was used to deliver three combinations of developmental regulators (Nos:WUS&35S: STM, Nos:WUS&CmYLCV:STM, and Nos:WUS&35S: IPT) to tomato seedlings. For both combinations of WUS & STM, no shoot-like growths formed (FIGS. 22A and 22C). In contrast, WUS & IPT promoted shoot-like growths (FIGS. 22A and 22C), which ultimately formed fully rooted plants (FIG. 22B).

Figure 22E:
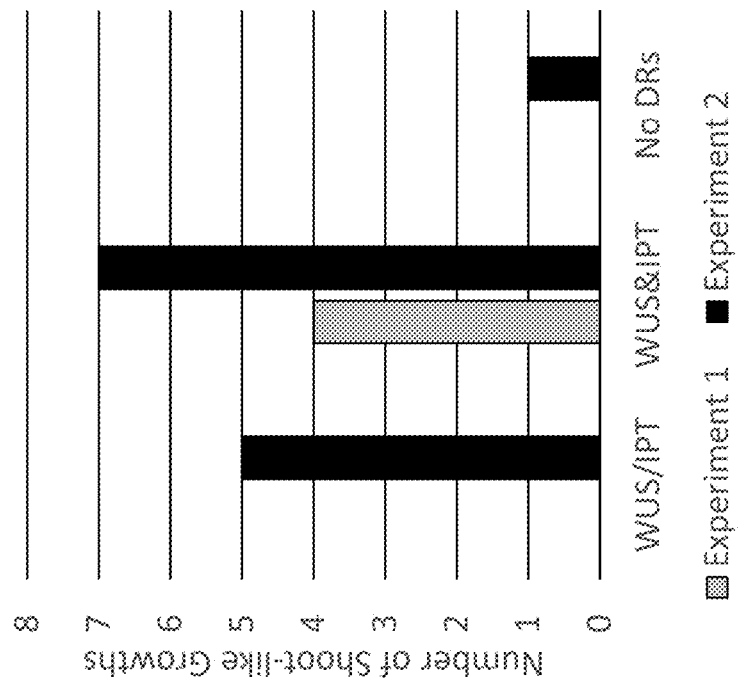
Figure 22D:
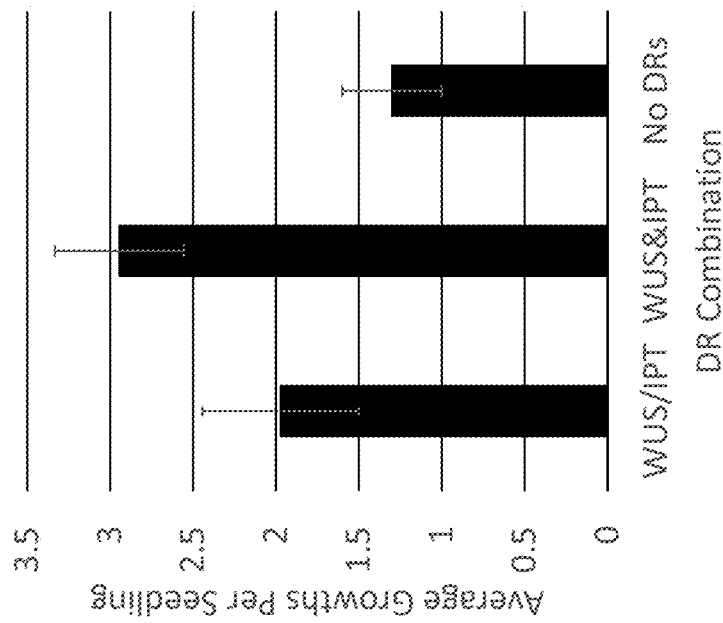
Figure 22G:
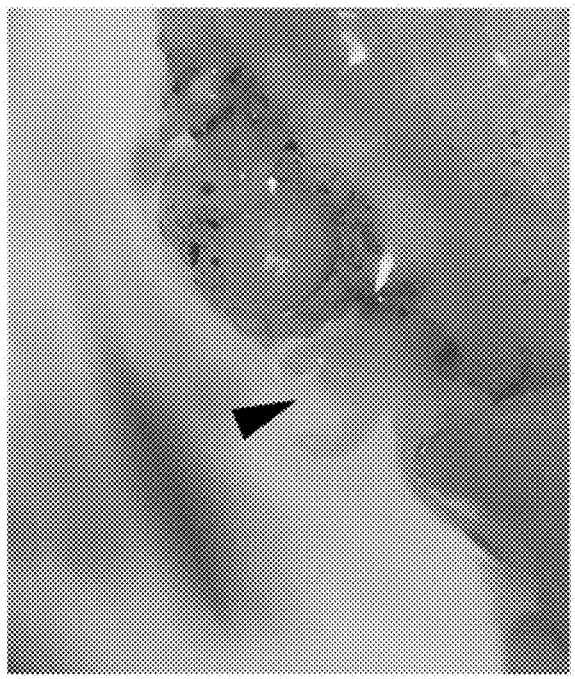
Figure 22F:
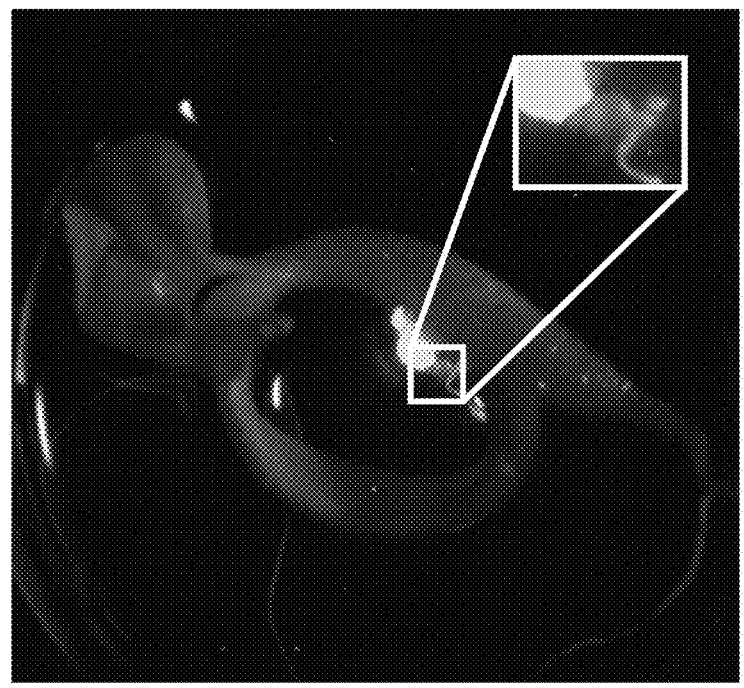
Figure 22I:
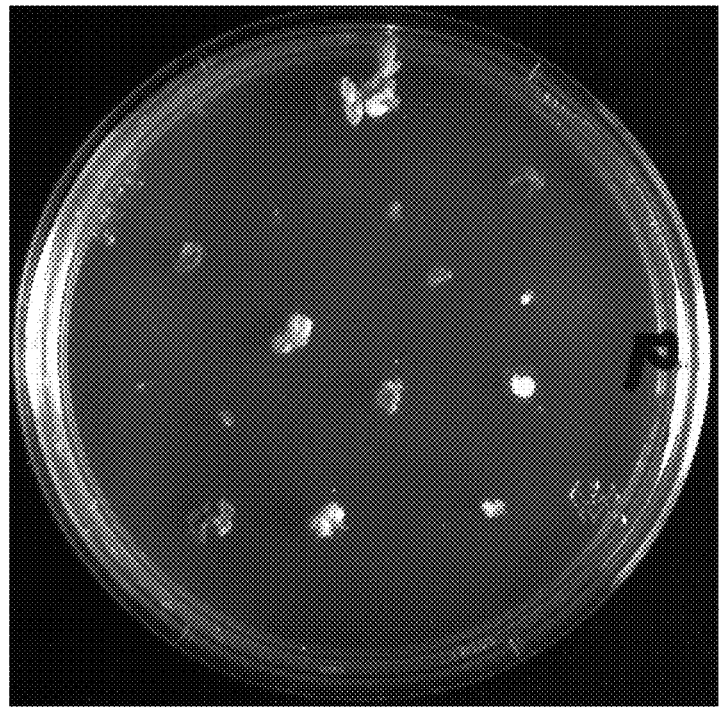
Figure 22H:
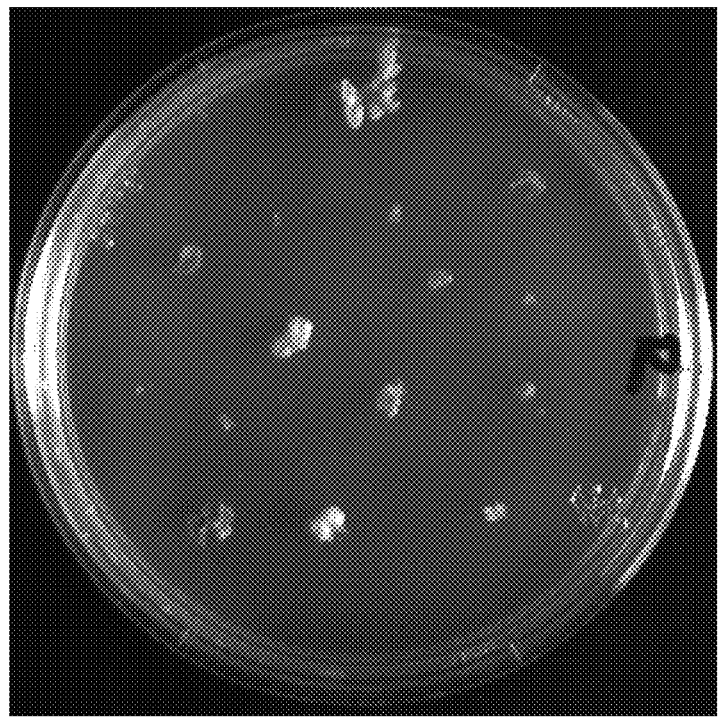

Next, WUS and IPT were delivered to tomato seedlings on either a single vector (WUS/IPT) or on separate vectors in two different *Agrobacterium* strains (WUS&IPT). Both WUS/IPT and WUS&IPT showed an increase in the frequency of average growths per plant over the background level of callus-like growths that developed on plants that did not receive developmental regulators (FIG. 22D). From the WUS and IPT derived growths, shoot-like growths formed that were luciferase positive (FIGS. 22E, 22F, and 22G). These structures progressed to form shoots (FIG. 22H), which were excised and assessed for luminescence (FIG. 22I). Four out of 15 shoots showed evidence of luminescence (FIG. 22J). Thus FAST-TrACC can be used to determine the optimal combination of developmental regulators for meristem induction in other plant species, which indicates that Fast-TrACC has utility outside of the *N. benthamiana* model to induce transgenic shoots.

In subsequent experiments, transgenic shoots are placed on root-inducing medium to promote root formation. Resulting plantlets are transferred to soil where they continue to grow, flower, and produce fruit and seed. Progeny are assessed to for transmission of the transgene, as demonstrated in Example 10. Gene edited tomato plants are generated and assessed through an approach similar to that described in detail in Example 12 for *N. benthamiana*.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for generating plant tissue comprising one or more genetic modifications of interest, the method comprising:
   (a) introducing into plant cells (i) a nucleic acid construct encoding one or more developmental regulators that, when expressed in the plant cells, induce meristem formation from the plant cells, and (ii) a nucleic acid construct comprising one or more sequences that, when expressed, edit the plant cell DNA to introduce one or more genetic modifications of interest, wherein the introducing comprises viral infection; and
   (b) deriving de novo tissue from plant cells identified as having the one or more genetic modifications of interest.

2. The method of claim 1, wherein the one or more developmental regulators comprise one or more of Baby Boom, Isopentenyl Transferase, Irrepressible Variants of Monopteros, Shoot Meristemless, and Wuschel.

3. The method of claim 1, wherein the introducing comprises transient transformation.

4. The method of claim 1, wherein the introducing comprises stable transgenesis.

5. The method of claim 1, wherein the plant cells into which the nucleic acids are introduced are within a differentiated tissue.

6. The method of claim 1, wherein the plant cells into which the nucleic acids are introduced are within an undifferentiated tissue.

7. The method of claim 1, wherein the plant cells into which the nucleic acids are introduced are within a whole plant.

8. The method of claim 1, wherein the plant cells into which the nucleic acids are introduced are within a germinating seedling.

9. The method of claim 1, wherein the plant cells into which the nucleic acids are introduced are within a plant part taken from a plant.

10. The method of claim 1, wherein the plant cells are of a monocotyledonous plant.

11. The method of claim 1, wherein the plant cells are of a dicotyledonous plant.

12. The method of claim 1, wherein the one or more sequences that modify a plant cell comprise a transgene that, when expressed in the plant cells, achieves an agriculturally relevant trait.

13. The method of claim 12, wherein the agriculturally relevant trait is herbicide tolerance.

14. The method of claim 1, wherein the one or more sequences that edit the plant cell DNA comprise a nucleotide sequence encoding a targeted endonuclease, and wherein the targeted endonuclease comprises a meganuclease, zinc finger nuclease, transcription activator-like effector nuclease, or Clustered Regularly-Interspaced Short Palindromic Repeats-associated nuclease.

15. The method of claim 1, wherein the one or more sequences that edit the plant cell DNA encode a targeted enzyme that, when expressed, edits plant DNA, and wherein the targeted enzyme is a cytosine deaminase or an adenosine deaminase.

16. The method of claim 15, wherein the cytosine deaminase or adenosine deaminase is BE3 or ABE.

17. The method of claim 1, wherein the one or more sequences that edit the plant cell DNA comprise (1) a nucleotide sequence encoding a targeted endonuclease and (2) a repair template.

18. The method of claim 1, wherein the de novo tissue is meristematic and is capable of deriving new tissue carrying the one or more genetic modifications of interest.

19. The method of claim 18, wherein the new tissue comprises a branch, a flower, or a root.

* * * * *